US012522837B2

(12) United States Patent
Mattanovich et al.

(10) Patent No.: US 12,522,837 B2
(45) Date of Patent: *Jan. 13, 2026

(54) PROMOTER VARIANTS

(71) Applicant: LONZA LTD, Visp (CH)

(72) Inventors: Diethard Mattanovich, Vienna (AT); Brigitte Gasser, Vienna (AT); Roland Prielhofer, Vienna (AT)

(73) Assignee: LONZA LTD, Visp (CH)

( * ) Notice: Subject to any disclaimer, the term of this patent is extended or adjusted under 35 U.S.C. 154(b) by 1599 days.

This patent is subject to a terminal disclaimer.

(21) Appl. No.: 16/914,866

(22) Filed: Jun. 29, 2020

(65) Prior Publication Data

US 2020/0347391 A1 Nov. 5, 2020

Related U.S. Application Data

(63) Continuation of application No. 15/750,334, filed as application No. PCT/EP2016/068784 on Aug. 5, 2016, now Pat. No. 10,752,907.

(30) Foreign Application Priority Data

Aug. 5, 2015 (WO) ................ PCT/EP2015/068024
Apr. 5, 2016 (EP) .................................... 16163932

(51) Int. Cl.
*C12N 15/81* (2006.01)
*C12N 1/16* (2006.01)
*C12P 21/00* (2006.01)
*C12P 21/02* (2006.01)

(52) U.S. Cl.
CPC ............. *C12N 15/815* (2013.01); *C12N 1/16* (2013.01); *C12P 21/00* (2013.01); *C12P 21/02* (2013.01); *C12N 2830/001* (2013.01)

(58) Field of Classification Search
CPC .. C12N 15/815; C12N 1/16; C12N 2830/001; C12P 21/00; C12P 21/02
See application file for complete search history.

(56) References Cited

U.S. PATENT DOCUMENTS

2013/0011875 A1* 1/2013 Meehl .................. C12P 21/005 435/254.23

FOREIGN PATENT DOCUMENTS

WO WO-2013050551 A1 * 4/2013 ............. C07K 14/39

* cited by examiner

*Primary Examiner* — Paul J Holland
(74) *Attorney, Agent, or Firm* — MEDLER FERRO WOODHOUSE & MILLS PLLC

(57) ABSTRACT

An isolated and/or artificial pG1-x promoter, which is a functional variant of the carbon source regulatable pG1 promoter of *Pichia pastoris* identified by SEQ ID 1, which pG1-x promoter consists of or comprises at least a part of SEQ ID 1 with a length of at least 293 bp, characterized by the following promoter regions:

Figure 1:
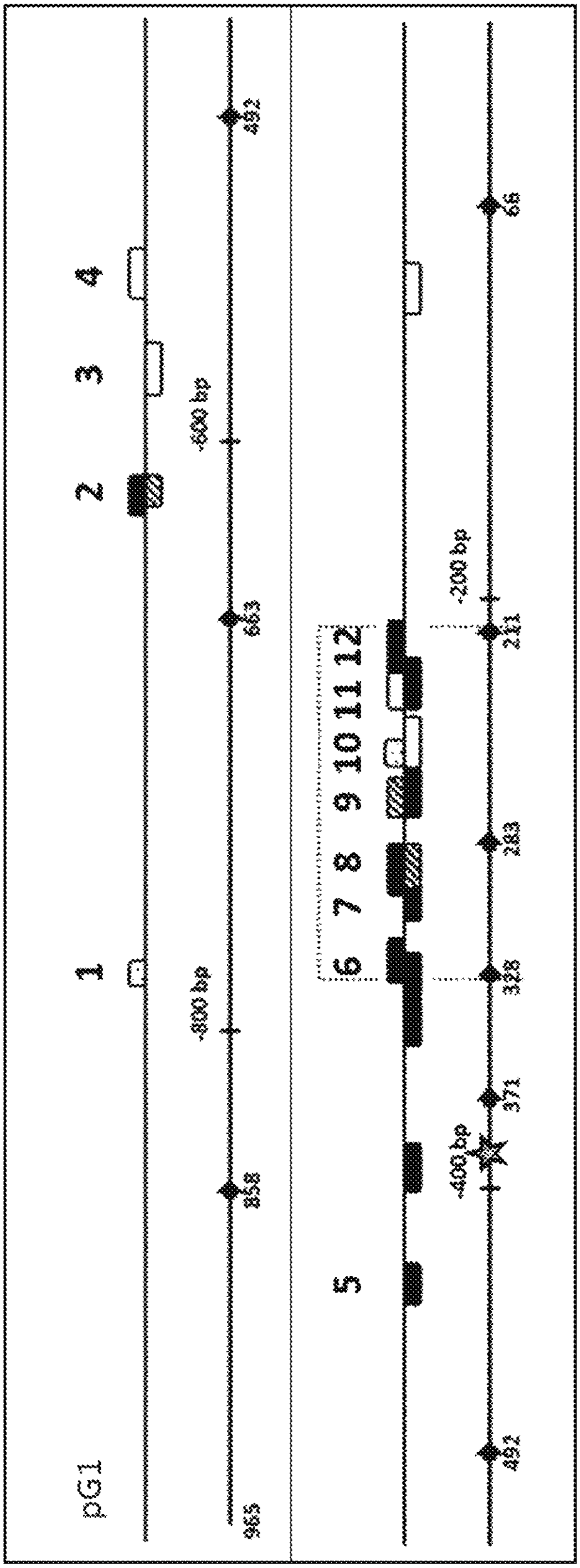

a) at least one core regulatory region comprising the nucleotide sequences SEQ ID 2 and SEQ ID 3; and
b) a non-core regulatory region, which is any region within the pG1-x promoter sequence other than the core regulatory region;

wherein the pG1-x promoter comprises at least one mutation in any of the promoter regions and a sequence identity of at least 80% in SEQ ID 2 and SEQ ID 3, and a sequence identity of at least 50% in any region other than SEQ ID 2 or SEQ ID 3; and further wherein the pG1-x promoter is characterized by the same or an increased promoter strength and induction ratio as compared to the pG1 promoter, wherein the promoter strength is at least 1.1-fold increased in the induced state as compared to the pG1 promoter, and/or the induction ratio is at least 1.1-fold increased as compared to the pG1 promoter.

13 Claims, 147 Drawing Sheets

Specification includes a Sequence Listing.

Indications in sequences:

- Main regulatory region: bold
- Core regulatory region: *bold, italic and underlined*, SEQ ID 2 and 3 *double underlined*
- T motif: *italic and underlined*, may be optionally extended (at the 5'-terminal end of the T motif) by a preceding TA sequence, or (at the 3'-terminal end of the T motif) by a succeeding AT sequence
- 3'-terminal region: underlined with dotted line
- Region less relevant for promoter activity in the reference pG1 ($P_{GTH1}$) sequences: underlined with a dash-dot line; one or more nucleotides up to all nucleotides within the region ranging from the 5'-terminal end to -328 (region underlined in Fig. 6a with a dash-dot line) may be substituted, or deleted, or further nucleotides may be inserted within such region, however, preferred embodiments still comprise at least one T motif which is (T)n (n=13-20) with or without preceding preceding A or TA nucleotides; or with or without succeeding A or AT nucleotides
- Deletion: del (underlined)

FIG.6A-1 pG1 ($P_{GTH1}$) comprising the TA(T)$_n$ motif, n=14-16:

SEQ ID 1

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TA(T)$_n$*GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTT*ATTACCCCACCTGGAAGTGCCCAGAATTTTCCGGGGATTACGGATAATAC**GGTGGTCTGGATTA
ATTAATACGCCAAGTCTTACATTTTGTTGCAGTCTCGTGCGAGTATGTGCAATAATAAACAAGATGAGCCAATTTA
TTGGATTAGTTGCAGCTTGACCCCGCCATAGCTAGGCATAGCCAAGTGCTATGGGTGTTAGATGATGCACTTGGA
TGCAGTGAGTTTTGGAGTATAAAAGATCCTTAAAATTCCACCCTT

Sequence without indications (SEQ ID 1):

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGCTAXGATGACCCCGTTTTCGTGACAAATTAATT
TCCAACGGGGTCTTGTCCGGATAAGAGAATTTTGTTTGATTATCCGTTCGGATAAATGGACGCCTGCTCCATATTT
TTCCGGTTATTACCCCACCTGGAAGTGCCCAGAATTTTCCGGGGATTACGGATAATACGGTGGTCTGGATTAATT
AATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTT

X...(T)n wherein n is 14-16

FIG.6A-2

Position 8 (SEQ ID 2): *ATAAATGGA* (e.g. position -293 to -285 in SEQ ID 9):

Position 9 (SEQ ID 3): *CATATTTTTCCGGTT* (e.g. position -275 to-261 in SEQ ID 9)

Core region: (SEQ ID 4): *ATAAATGGACGCCTGCTCCATATTTTTCCGGTT* (e.g. position -293 to -261 in SEQ ID 9)

Main regulatory region: (SEQ ID 5): (e.g. position -328 to -211 in SEQ ID 9):

CCGGATAAGAGAATTTTGTTTGATTATCCGTTCGG*ATAAATGGACGCCTGCTCCATATTTTTCCGGTT*ATTACCC CACCTGGAAGTGCCCAGAATTTTCCGGGGATTACGGATAATAC

3'-terminal nucleotide sequence (SEQ ID 6): TTCCACCCTT

FIG.6A-3 pG1 ($P_{GTH1}$) comprising the $TA(T)_{14}$ motif

SEQ ID 7

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTT*GATGACCCCGTTTTCGT
GACAAATTAATTTCCAACGGGGTCTTGTCCGGATAAGAGAATTTTGTTTGATTATCCGTTCGG*ATAAATGGACG*
*CCTGCTCCATATTTTTCCGGTT*ATTACCCCACCTGGAAGTGCCCAGAATTTTCCGGGGATTACGGATAATACGGT
GGTCTGGATTAATTAATACGCCAAGTCTTACATTTTGTTGCAGTCTCGTGCGAGTATGTGCAATAATAAACAAGAT
GAGCCAATTTATTGGATTAGTTGCAGCTTGACCCCGCCATAGCTAGGCATAGCCAAGTGCTATGGGTGTTAGATG
ATGCACTTGGATGCAGTGAGTTTTGGAGTATAAAAGATCCTTAAAATTCCACCCTT pG1 ($P_{GTH1}$) comprising the $TA(T)_{14}$ motif SEQ ID 7 sequence as above, indicating the position numbering from -964 to -1

```
-964 CAAACATTTG CTCCCCCTAG TCTCCAGGGA AATGTAAAAT ATACTGCTAA
-914 TAGAAAACAG TAAGACGCTC AGTTGTCAGG ATAATTACGT TCGACTGTAG
-864 TAAAACAGGA ATCTGTATTG TTAGAAAGAA CGAGAGTTTT TTACGGCGCC
-814 GCCATATTGG GCCGTGTGAA AACAGCTTGA AACCCCACTA CTTTCAAAGG
-764 TTCTGTTGCT ATACACGAAC CATGTTTAAC CAACCTCGCT TTTGACTTGA
-714 CTGAAGTCAT CGGTTAACAA TCAAGTACCC TAGTCTGTCT GAATGCTCCT
-664 TTCCATATTC AGTAGGTGTT TCTTGCACTT TTGCATGCAC TGCGGAAGAA
-614 TTAGCCAATA GCGCGTTTCA TATGCGCTTT TACCCCCTCT TTTGTCAAGC
-564 GCAAAATGCC TGTAAGATTT GGTGGGGGTG TGAGCCGTTA GCTGAAGTAC
-514 AACAGGCTAA TTCCCTGAAA AAACTGCAGA TAGACTTCAA GATCTCAGGG
-464 ATTCCCACTA TTTGGTATTC TGATATGTTT TTCCTGATAT GCATCAAAAC
-414 TCTAATCTAA AACCTGAATC TCCGCTATTT TTTTTTTTTT TGATGACCCC
-364 GTTTTCGTGA CAAATTAATT TCCAACGGGG TCTTGTCCGG ATAAGAGAAT
-314 TTTGTTTGAT TATCCGTTCG GATAAATGGA CGCCTGCTCC ATATTTTTCC
-264 GGTTATTACC CCACCTGGAA GTGCCCAGAA TTTTCCGGGG ATTACGGATA
-214 ATACGGTGGT CTGGATTAAT TAATACGCCA AGTCTTACAT TTTGTTGCAG
-164 TCTCGTGCGA GTATGTGCAA TAATAAACAA GATGAGCCAA TTTATTGGAT
-114 TAGTTGCAGC TTGACCCCGC CATAGCTAGG CATAGCCAAG TGCTATGGGT
 -64 GTTAGATGAT GCACTTGGAT GCAGTGAGTT TTGGAGTATA AAAGATCCTT
 -14 AAAATTCCAC CCTT
```

FIG.6A-4 pG1 ($P_{GTH1}$) comprising the $TA(T)_{15}$ motif

SEQ ID 8

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTCCGGTT*ATTACCCCACCTGGAAGTGCCCAGAATTTTCCGGGGATTACGGATAATACGG**
TGGTCTGGATTAATTAATACGCCAAGTCTTACATTTTGTTGCAGTCTCGTGCGAGTATGTGCAATAATAAACAAGA
TGAGCCAATTTATTGGATTAGTTGCAGCTTGACCCCGCCATAGCTAGGCATAGCCAAGTGCTATGGGTGTTAGAT
GATGCACTTGGATGCAGTGAGTTTTGGAGTATAAAAGATCCTTAAAATTCCACCCTT pG1 ($P_{GTH1}$) comprising the $TA(T)_{15}$ motif SEQ ID 8 sequence as above, indicating the position numbering from -965 to -1

```
 -965 CAAACATTTG CTCCCCCTAG TCTCCAGGGA AATGTAAAAT ATACTGCTAA
 -915 TAGAAAACAG TAAGACGCTC AGTTGTCAGG ATAATTACGT TCGACTGTAG
 -865 TAAAACAGGA ATCTGTATTG TTAGAAAGAA CGAGAGTTTT TTACGGCGCC
 -815 GCCATATTGG GCCGTGTGAA AACAGCTTGA AACCCCACTA CTTTCAAAGG
 -765 TTCTGTTGCT ATACACGAAC CATGTTTAAC CAACCTCGCT TTTGACTTGA
 -715 CTGAAGTCAT CGGTTAACAA TCAAGTACCC TAGTCTGTCT GAATGCTCCT
 -665 TTCCATATTC AGTAGGTGTT TCTTGCACTT TTGCATGCAC TGCGGAAGAA
 -615 TTAGCCAATA GCGCGTTTCA TATGCGCTTT TACCCCCTCT TTTGTCAAGC
 -565 GCAAAATGCC TGTAAGATTT GGTGGGGGTG TGAGCCGTTA GCTGAAGTAC
 -515 AACAGGCTAA TTCCCTGAAA AAACTGCAGA TAGACTTCAA GATCTCAGGG
 -465 ATTCCCACTA TTTGGTATTC TGATATGTTT TTCCTGATAT GCATCAAAAC
 -415 TCTAATCTAA AACCTGAATC TCCGCTATTT TTTTTTTTTT TTGATGACCC
 -365 CGTTTTCGTG ACAAATTAAT TTCCAACGGG GTCTTGTCCG GATAAGAGAA
 -315 TTTTGTTTGA TTATCCGTTC GGATAAATGG ACGCCTGCTC CATATTTTTC
 -265 CGGTTATTAC CCCACCTGGA AGTGCCCAGA ATTTTCCGGG GATTACGGAT
 -215 AATACGGTGG TCTGGATTAA TTAATACGCC AAGTCTTACA TTTTGTTGCA
 -165 GTCTCGTGCG AGTATGTGCA ATAATAAACA AGATGAGCCA ATTTATTGGA
 -115 TTAGTTGCAG CTTGACCCCG CCATAGCTAG GCATAGCCAA GTGCTATGGG
 -65 TGTTAGATGA TGCACTTGGA TGCAGTGAGT TTTGGAGTAT AAAAGATCCT
 -15 TAAAATTCCA CCCTT
```

FIG.6A-5 pG1 ($P_{GTH1}$) comprising the $TA(T)_{16}$ motif

SEQ ID 9

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATACG**
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT pG1 ($P_{GTH1}$) comprising the $TA(T)_{16}$ motif SEQ ID 9 sequence as above, indicating the position numbering from -966 to -1

```
-966 CAAACATTTG CTCCCCCTAG TCTCCAGGGA AATGTAAAAT ATACTGCTAA
-916 TAGAAAACAG TAAGACGCTC AGTTGTCAGG ATAATTACGT TCGACTGTAG
-866 TAAAACAGGA ATCTGTATTG TTAGAAAGAA CGAGAGTTTT TTACGGCGCC
-816 GCCATATTGG GCCGTGTGAA AACAGCTTGA AACCCCACTA CTTTCAAAGG
-766 TTCTGTTGCT ATACACGAAC CATGTTTAAC CAACCTCGCT TTTGACTTGA
-716 CTGAAGTCAT CGGTTAACAA TCAAGTACCC TAGTCTGTCT GAATGCTCCT
-666 TTCCATATTC AGTAGGTGTT TCTTGCACTT TTGCATGCAC TGCGGAAGAA
-616 TTAGCCAATA GCGCGTTTCA TATGCGCTTT TACCCCCTCT TTTGTCAAGC
-566 GCAAAATGCC TGTAAGATTT GGTGGGGGTG TGAGCCGTTA GCTGAAGTAC
-516 AACAGGCTAA TTCCCTGAAA AAACTGCAGA TAGACTTCAA GATCTCAGGG
-466 ATTCCCACTA TTTGGTATTC TGATATGTTT TTCCTGATAT GCATCAAAAC
-416 TCTAATCTAA AACCTGAATC TCCGCTATTT TTTTTTTTTT TTTGATGACC
-366 CCGTTTTCGT GACAAATTAA TTTCCAACGG GGTCTTGTCC GGATAAGAGA
-316 ATTTTGTTTG ATTATCCGTT CGGATAAATG GACGCCTGCT CCATATTTTT
-266 CCGGTTATTA CCCCACCTGG AAGTGCCCAG AATTTTCCGG GGATTACGGA
-216 TAATACGGTG GTCTGGATTA ATTAATACGC CAAGTCTTAC ATTTTGTTGC
-166 AGTCTCGTGC GAGTATGTGC AATAATAAAC AAGATGAGCC AATTTATTGG
-116 ATTAGTTGCA GCTTGACCCC GCCATAGCTA GGCATAGCCA AGTGCTATGG
 -66 GTGTTAGATG ATGCACTTGG ATGCAGTGAG TTTTGGAGTA TAAAAGATCC
 -16 TTAAAATTCC ACCCTT
```

FIG.6A-6 pG1-10 (PG1-s328) Fragment

SEQ ID 10

**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT pG1-11 (PG1-s370) Fragment

SEQ ID 11

GACCCCGTTTTCGTGACAAATTAATTTCCAACGGGGTCTTGTCCGGATAAGAGAATTTTGTTTGATTATCCGTTC
**GG*ATAAATGGACGCCTGCTCCATATTTTTCCGGTT*ATTACCCCACCTGGAAGTGCCCAGAATTTTCCGGGGATTA**
CGGATAATACGGTGGTCTGGATTAATTAATACGCCAAGTCTTACATTTTGTTGCAGTCTCGTGCGAGTATGTGCA
ATAATAAACAAGATGAGCCAATTTATTGGATTAGTTGCAGCTTGACCCCGCCATAGCTAGGCATAGCCAAGTGCT
ATGGGTGTTAGATGATGCACTTGGATGCAGTGAGTTTTGGAGTATAAAAGATCCTTAAAATTCCACCCTT pG1-1 (PG1-Δ8, PG1-delta8): Comparable example comprising the $TA(T)_{15}$ motif

SEQ ID 30

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTT*GATGACCCCGTTTTCG
TGACAAATTAATTTCCAACGGGGTCTTGTCCGGATAAGAGAATTTTGTTTGATTATCCGTTCGGdelCGCCTGCTC*C*
*ATATTTTTCCGGTT*ATTACCCCACCTGGAAGTGCCCAGAATTTTCCGGGGATTACGGATAATACGGTGGTCTGGA
TTAATTAATACGCCAAGTCTTACATTTTGTTGCAGTCTCGTGCGAGTATGTGCAATAATAAACAAGATGAGCCAAT
TTATTGGATTAGTTGCAGCTTGACCCCGCCATAGCTAGGCATAGCCAAGTGCTATGGGTGTTAGATGATGCACTT
GGATGCAGTGAGTTTTGGAGTATAAAAGATCCTTAAAATTCCACCCTT

FIG.6A-7 pG1-2 (PG1-Δ9, PG1-delta9): Comparable example comprising the $TA(T)_{15}$ motif

SEQ ID 31

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTT*GATGACCCCGTTTTCG
TGACAAATTAATTTCCAACGGGGTCTTGTCCGGATAAGAGAATTTTGTTTGATTATCCGTTCGG*ATAAATGGA*CG
CCTGCTCdelATTACCCCACCTGGAAGTGCCCAGAATTTTCCGGGGATTACGGATAATACGGTGGTCTGGATTAAT
TAATACGCCAAGTCTTACATTTTGTTGCAGTCTCGTGCGAGTATGTGCAATAATAAACAAGATGAGCCAATTTATT
GGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTT

FIG.6A-8

$(T)_n$ $(n=13\text{-}20)$ motifs, may be optionally extended at its 5′ end by "A" or "TA"; or at its 3′ end by "A" or "AT"

- $(T)_{13}$: SEQ ID 12: *TTTTTTTTTTTTT*
- $(T)_{14}$: SEQ ID 13: *TTTTTTTTTTTTTT*
- $(T)_{15}$: SEQ ID 14: *TTTTTTTTTTTTTTT*
- $(T)_{16}$: SEQ ID 15: *TTTTTTTTTTTTTTTT*
- $(T)_{17}$: SEQ ID 16: *TTTTTTTTTTTTTTTTT*
- $(T)_{18}$: SEQ ID 17: *TTTTTTTTTTTTTTTTTT*
- $(T)_{19}$: SEQ ID 18: *TTTTTTTTTTTTTTTTTTT*
- $(T)_{20}$: SEQ ID 19: *TTTTTTTTTTTTTTTTTTTT*

FIG.6B-1

TA(T)$_n$ (n=13-20) motifs, may be optionally mutated to substitute the "A" at position 2 for a "T" (A/T)

- TA(T)$_{13}$: SEQ ID 20: *TATTTTTTTTTTTTT*
- TA(T)$_{13}$ (substituted A/T), SEQ ID 14 (see (T)$_{15}$): *TTTTTTTTTTTTTTT*
- TA(T)$_{14}$: SEQ ID 21: *TATTTTTTTTTTTTTT*
- TA(T)$_{14}$ (substituted A/T), SEQ ID 15 (see (T)$_{16}$): *TTTTTTTTTTTTTTTT*
- TA(T)$_{15}$: SEQ ID 22: *TATTTTTTTTTTTTTTT*
- TA(T)$_{15}$ (substituted A/T), SEQ ID 16 (see (T)$_{17}$): *TTTTTTTTTTTTTTTTT*
- TA(T)$_{16}$: SEQ ID 23: *TATTTTTTTTTTTTTTTT*
- TA(T)$_{16}$ (substituted A/T), SEQ ID 17 (see (T)$_{18}$): *TTTTTTTTTTTTTTTTTT*
- TA(T)$_{17}$: SEQ ID 24: *TATTTTTTTTTTTTTTTTT*
- TA(T)$_{17}$ (substituted A/T), SEQ ID 18 (see (T)$_{19}$): *TTTTTTTTTTTTTTTTTTT*
- TA(T)$_{18}$: SEQ ID 25: *TATTTTTTTTTTTTTTTTTT*
- TA(T)$_{18}$ (substituted A/T), SEQ ID 19 (see (T)$_{20}$): *TTTTTTTTTTTTTTTTTTTT*
- TA(T)$_{19}$: SEQ ID 26: *TATTTTTTTTTTTTTTTTTTT*
- TA(T)$_{19}$ (substituted A/T), SEQ ID 28 (i.e. (T)$_{21}$): *TTTTTTTTTTTTTTTTTTTTT*
- TA(T)$_{20}$: SEQ ID 27: *TATTTTTTTTTTTTTTTTTTTT*
- TA(T)$_{20}$ (substituted A/T), SEQ ID 29 (i.e. (T)$_{22}$): *TTTTTTTTTTTTTTTTTTTTTT* pG1-x ($P_{GTH1-x}$) comprising the shortened TAT motif which is TA(T)$_{13}$

SEQ ID 32 (position numbering from -963 to -1)

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTCCGGTT*ATTACCCCACCTGGAAGTGCCCAGAATTTTCCGGGGATTACGGATAATAC**GGTGG
TCTGGATTAATTAATACGCCAAGTCTTACATTTTGTTGCAGTCTCGTGCGAGTATGTGCAATAATAAACAAGATGA
GCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT

FIG.6B-2 pG1-x ($P_{GTH1\text{-}x}$) comprising the extended TAT motif which is $TA(T)_{17}$

SEQ ID 33

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATAC**G
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT pG1-x ($P_{GTH1\text{-}x}$) comprising the extended TAT motif which is $TA(T)_{17}$ SEQ ID 33 sequence as above, indicating the position numbering from -967 to -1

```
-967 CAAACATTTG CTCCCCCTAG TCTCCAGGGA AATGTAAAAT ATACTGCTAA
-917 TAGAAAACAG TAAGACGCTC AGTTGTCAGG ATAATTACGT TCGACTGTAG
-867 TAAAACAGGA ATCTGTATTG TTAGAAAGAA CGAGAGTTTT TTACGGCGCC
-817 GCCATATTGG GCCGTGTGAA AACAGCTTGA AACCCCACTA CTTTCAAAGG
-767 TTCTGTTGCT ATACACGAAC CATGTTTAAC CAACCTCGCT TTTGACTTGA
-717 CTGAAGTCAT CGGTTAACAA TCAAGTACCC TAGTCTGTCT GAATGCTCCT
-667 TTCCATATTC AGTAGGTGTT TCTTGCACTT TTGCATGCAC TGCGGAAGAA
-617 TTAGCCAATA GCGCGTTTCA TATGCGCTTT TACCCCCTCT TTTGTCAAGC
-567 GCAAAATGCC TGTAAGATTT GGTGGGGGTG TGAGCCGTTA GCTGAAGTAC
-517 AACAGGCTAA TTCCCTGAAA AAACTGCAGA TAGACTTCAA GATCTCAGGG
-467 ATTCCCACTA TTTGGTATTC TGATATGTTT TTCCTGATAT GCATCAAAAC
-417 TCTAATCTAA AACCTGAATC TCCGCTATTT TTTTTTTTTT TTTTGATGAC
-367 CCCGTTTTCG TGACAAATTA ATTTCCAACG GGGTCTTGTC CGGATAAGAG
-317 AATTTTGTTT GATTATCCGT TCGGATAAAT GGACGCCTGC TCCATATTTT
-267 TCCGGTTATT ACCCCACCTG GAAGTGCCCA GAATTTTCCG GGGATTACGG
-217 ATAATACGGT GGTCTGGATT AATTAATACG CCAAGTCTTA CATTTTGTTG
-167 CAGTCTCGTG CGAGTATGTG CAATAATAAA CAAGATGAGC CAATTTATTG
-117 GATTAGTTGC AGCTTGACCC CGCCATAGCT AGGCATAGCC AAGTGCTATG
 -67 GGTGTTAGAT GATGCACTTG GATGCAGTGA GTTTTGGAGT ATAAAAGATC
 -17 CTTAAAATTC CACCCTT
```

FIG.6B-3 pG1-x ($P_{GTH1-x}$) comprising the extended TAT motif which is $TA(T)_{18}$

SEQ ID 34

CAAACATTTGCTCCCCCTAGTCTCCAGGGAAATGTAAAATATACTGCTAATAGAAAACAGTAAGACGCTCAGTTG

TCAGGATAATTACGTTCGACTGTAGTAAAACAGGAATCTGTATTGTTAGAAAGAACGAGAGTTTTTTACGGCGCC

GCCATATTGGGCCGTGTGAAAACAGCTTGAAACCCCACTACTTTCAAAGGTTCTGTTGCTATACACGAACCATGTT

TAACCAACCTCGCTTTTGACTTGACTGAAGTCATCGGTTAACAATCAAGTACCCTAGTCTGTCTGAATGCTCCTTTC

CATATTCAGTAGGTGTTTCTTGCACTTTTGCATGCACTGCGGAAGAATTAGCCAATAGCGCGTTTCATATGCGCTT

TTACCCCCTCTTTTGTCAAGCGCAAAATGCCTGTAAGATTTGGTGGGGGTGTGAGCCGTTAGCTGAAGTACAACA

GGCTAATTCCCTGAAAAAACTGCAGATAGACTTCAAGATCTCAGGGATTCCCACTATTTGGTATTCTGATATGTTT

TTCCTGATATGCATCAAAACTCTAATCTAAAACCTGAATCTCCGC*TATTTTTTTTTTTTTTTTTT*GATGACCCCGTTTT

CGTGACAAATTAATTTCCAACGGGGTCTTGT**CCGGATAAGAGAATTTTGTTTGATTATCCGTTCGG*ATAAATGG***

***ACGCCTGCTCCATATTTTTCCGGTT*ATTACCCCACCTGGAAGTGCCCAGAATTTTCCGGGGATTACGGATAATAC**

GGTGGTCTGGATTAATTAATACGCCAAGTCTTACATTTTGTTGCAGTCTCGTGCGAGTATGTGCAATAATAAACA

AGATGAGCCAATTTATTGGATTAGTTGCAGCTTGACCCCGCCATAGCTAGGCATAGCCAAGTGCTATGGGTGTTA

GATGATGCACTTGGATGCAGTGAGTTTTGGAGTATAAAAGATCCTTAAAATTCCACCCTT pG1-x ($P_{GTH1-x}$) comprising the extended TAT motif which is $TA(T)_{18}$ SEQ ID 34 sequence as above, indicating the position numbering from -968 to -1

```
-968  CAAACATTTG  CTCCCCCTAG  TCTCCAGGGA  AATGTAAAAT  ATACTGCTAA
-918  TAGAAAACAG  TAAGACGCTC  AGTTGTCAGG  ATAATTACGT  TCGACTGTAG
-868  TAAAACAGGA  ATCTGTATTG  TTAGAAAGAA  CGAGAGTTTT  TTACGGCGCC
-818  GCCATATTGG  GCCGTGTGAA  AACAGCTTGA  AACCCCACTA  CTTTCAAAGG
-768  TTCTGTTGCT  ATACACGAAC  CATGTTTAAC  CAACCTCGCT  TTTGACTTGA
-718  CTGAAGTCAT  CGGTTAACAA  TCAAGTACCC  TAGTCTGTCT  GAATGCTCCT
-668  TTCCATATTC  AGTAGGTGTT  TCTTGCACTT  TTGCATGCAC  TGCGGAAGAA
-618  TTAGCCAATA  GCGCGTTTCA  TATGCGCTTT  TACCCCCTCT  TTTGTCAAGC
-568  GCAAAATGCC  TGTAAGATTT  GGTGGGGGTG  TGAGCCGTTA  GCTGAAGTAC
-518  AACAGGCTAA  TTCCCTGAAA  AAACTGCAGA  TAGACTTCAA  GATCTCAGGG
-468  ATTCCCACTA  TTTGGTATTC  TGATATGTTT  TTCCTGATAT  GCATCAAAAC
-418  TCTAATCTAA  AACCTGAATC  TCCGCTATTT  TTTTTTTTTT  TTTTTGATGA
-368  CCCCGTTTTC  GTGACAAATT  AATTTCCAAC  GGGGTCTTGT  CCGGATAAGA
-318  GAATTTTGTT  TGATTATCCG  TTCGGATAAA  TGGACGCCTG  CTCCATATTT
-268  TTCCGGTTAT  TACCCCACCT  GGAAGTGCCC  AGAATTTTCC  GGGGATTACG
-218  GATAATACGG  TGGTCTGGAT  TAATTAATAC  GCCAAGTCTT  ACATTTTGTT
-168  GCAGTCTCGT  GCGAGTATGT  GCAATAATAA  ACAAGATGAG  CCAATTTATT
-118  GGATTAGTTG  CAGCTTGACC  CCGCCATAGC  TAGGCATAGC  CAAGTGCTAT
 -68  GGGTGTTAGA  TGATGCACTT  GGATGCAGTG  AGTTTTGGAG  TATAAAAGAT
 -18  CCTTAAAATT  CCACCCTT
```

FIG.6B-4 pG1-x ($P_{GTH1-x}$) comprising the extended TAT motif which is $TA(T)_{19}$

SEQ ID 35

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTTCCGGTT*ATTACCCCACCTGGAAGTGCCCAGAATTTTCCGGGGATTACGGATAATAC**
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT pG1-x ($P_{GTH1-x}$) comprising the extended TAT motif which is $TA(T)_{19}$ SEQ ID 35 sequence as above, indicating the position numbering from -969 to -1

| | | | | | |
|---|---|---|---|---|---|
| -969 | CAAACATTTG | CTCCCCCTAG | TCTCCAGGGA | AATGTAAAAT | ATACTGCTAA |
| -919 | TAGAAAACAG | TAAGACGCTC | AGTTGTCAGG | ATAATTACGT | TCGACTGTAG |
| -869 | TAAAACAGGA | ATCTGTATTG | TTAGAAAGAA | CGAGAGTTTT | TTACGGCGCC |
| -819 | GCCATATTGG | GCCGTGTGAA | AACAGCTTGA | AACCCCACTA | CTTTCAAAGG |
| -769 | TTCTGTTGCT | ATACACGAAC | CATGTTTAAC | CAACCTCGCT | TTTGACTTGA |
| -719 | CTGAAGTCAT | CGGTTAACAA | TCAAGTACCC | TAGTCTGTCT | GAATGCTCCT |
| -669 | TTCCATATTC | AGTAGGTGTT | TCTTGCACTT | TTGCATGCAC | TGCGGAAGAA |
| -619 | TTAGCCAATA | GCGCGTTTCA | TATGCGCTTT | TACCCCCTCT | TTTGTCAAGC |
| -569 | GCAAAATGCC | TGTAAGATTT | GGTGGGGGTG | TGAGCCGTTA | GCTGAAGTAC |
| -519 | AACAGGCTAA | TTCCCTGAAA | AAACTGCAGA | TAGACTTCAA | GATCTCAGGG |
| -469 | ATTCCCACTA | TTTGGTATTC | TGATATGTTT | TTCCTGATAT | GCATCAAAAC |
| -419 | TCTAATCTAA | AACCTGAATC | TCCGCTATTT | TTTTTTTTTT | TTTTTTGATG |
| -369 | ACCCCGTTTT | CGTGACAAAT | TAATTTCCAA | CGGGGTCTTG | TCCGGATAAG |
| -319 | AGAATTTTGT | TTGATTATCC | GTTCGGATAA | ATGGACGCCT | GCTCCATATT |
| -269 | TTTCCGGTTA | TTACCCCACC | TGGAAGTGCC | CAGAATTTTC | CGGGGATTAC |
| -219 | GGATAATACG | GTGGTCTGGA | TTAATTAATA | CGCCAAGTCT | TACATTTTGT |
| -169 | TGCAGTCTCG | TGCGAGTATG | TGCAATAATA | AACAAGATGA | GCCAATTTAT |
| -119 | TGGATTAGTT | GCAGCTTGAC | CCCGCCATAG | CTAGGCATAG | CCAAGTGCTA |
| -69 | TGGGTGTTAG | ATGATGCACT | TGGATGCAGT | GAGTTTTGGA | GTATAAAAGA |
| -19 | TCCTTAAAAT | TCCACCCTT | | | |

FIG.6B-5 pG1-x ($P_{GTH1-x}$) comprising the extended TAT motif which is TA(T)$_{20}$
SEQ ID 36

CAAACATTTGCTCCCCCTAGTCTCCAGGGAAATGTAAAATATACTGCTAATAGAAAACAGTAAGACGCTCAGTTG

TCAGGATAATTACGTTCGACTGTAGTAAAACAGGAATCTGTATTGTTAGAAAGAACGAGAGTTTTTTACGGCGCC

GCCATATTGGGCCGTGTGAAAACAGCTTGAAACCCCACTACTTTCAAAGGTTCTGTTGCTATACACGAACCATGTT

TAACCAACCTCGCTTTTGACTTGACTGAAGTCATCGGTTAACAATCAAGTACCCTAGTCTGTCTGAATGCTCCTTTC

CATATTCAGTAGGTGTTTCTTGCACTTTTGCATGCACTGCGGAAGAATTAGCCAATAGCGCGTTTCATATGCGCTT

TTACCCCCTCTTTTGTCAAGCGCAAAATGCCTGTAAGATTTGGTGGGGGTGTGAGCCGTTAGCTGAAGTACAACA

GGCTAATTCCCTGAAAAAACTGCAGATAGACTTCAAGATCTCAGGGATTCCCACTATTTGGTATTCTGATATGTTT

TTCCTGATATGCATCAAAACTCTAATCTAAAACCTGAATCTCCGC*TATTTTTTTTTTTTTTTTTTTT*GATGACCCCGTT

TTCGTGACAAATTAATTTCCAACGGGGTCTTGT**CCGGATAAGAGAATTTTGTTTGATTATCCGTTCGG*ATAAATG***

***GACGCCTGCTCCATATTTTTCCGGTT*ATTACCCCACCTGGAAGTGCCCAGAATTTTCCGGGGATTACGGATAATA**

CGGTGGTCTGGATTAATTAATACGCCAAGTCTTACATTTTGTTGCAGTCTCGTGCGAGTATGTGCAATAATAAACA

AGATGAGCCAATTTATTGGATTAGTTGCAGCTTGACCCCGCCATAGCTAGGCATAGCCAAGTGCTATGGGTGTTA

GATGATGCACTTGGATGCAGTGAGTTTTGGAGTATAAAAGATCCTTAAAATTCCACCCTT pG1-x ($P_{GTH1-x}$) comprising the extended TAT motif which is TA(T)$_{20}$
SEQ ID 36 sequence as above, indicating the position numbering from -970 to -1

```
-970 CAAACATTTG CTCCCCCTAG TCTCCAGGGA AATGTAAAAT ATACTGCTAA
-920 TAGAAAACAG TAAGACGCTC AGTTGTCAGG ATAATTACGT TCGACTGTAG
-870 TAAAACAGGA ATCTGTATTG TTAGAAAGAA CGAGAGTTTT TTACGGCGCC
-820 GCCATATTGG GCCGTGTGAA AACAGCTTGA AACCCCACTA CTTTCAAAGG
-770 TTCTGTTGCT ATACACGAAC CATGTTTAAC CAACCTCGCT TTTGACTTGA
-720 CTGAAGTCAT CGGTTAACAA TCAAGTACCC TAGTCTGTCT GAATGCTCCT
-670 TTCCATATTC AGTAGGTGTT TCTTGCACTT TTGCATGCAC TGCGGAAGAA
-620 TTAGCCAATA GCGCGTTTCA TATGCGCTTT TACCCCCTCT TTTGTCAAGC
-570 GCAAAATGCC TGTAAGATTT GGTGGGGGTG TGAGCCGTTA GCTGAAGTAC
-520 AACAGGCTAA TTCCCTGAAA AAACTGCAGA TAGACTTCAA GATCTCAGGG
-470 ATTCCCACTA TTTGGTATTC TGATATGTTT TTCCTGATAT GCATCAAAAC
-420 TCTAATCTAA AACCTGAATC TCCGCTATTT TTTTTTTTTT TTTTTTTGAT
-370 GACCCCGTTT TCGTGACAAA TTAATTTCCA ACGGGGTCTT GTCCGGATAA
-320 GAGAATTTTG TTTGATTATC CGTTCGGATA AATGGACGCC TGCTCCATAT
-270 TTTTCCGGTT ATTACCCCAC CTGGAAGTGC CCAGAATTTT CCGGGGATTA
-220 CGGATAATAC GGTGGTCTGG ATTAATTAAT ACGCCAAGTC TTACATTTTG
-170 TTGCAGTCTC GTGCGAGTAT GTGCAATAAT AAACAAGATG AGCCAATTTA
-120 TTGGATTAGT TGCAGCTTGA CCCCGCCATA GCTAGGCATA GCCAAGTGCT
 -70 ATGGGTGTTA GATGATGCAC TTGGATGCAG TGAGTTTTGG AGTATAAAAG
 -20 ATCCTTAAAA TTCCACCCTT
```

FIG.6B-6 pG1-3 (PG1-D1240-2xTA(T)$_n$): Example comprising two T motifs which are (T)$_n$ (n=13-20), each extended by preceding TA (extending the T motif at its 5′-end to become a TA(T)$_n$ motif)

SEQ ID 37

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TA(T)$_n$*GATGACCCCGTTTTCGTGACAAATTAATTTCCAACGGGGT
CTTGT**CCGGATAAGAGAATTTTGTTTGATTATCCGTTCGGATAAATGGA*CGCCTGCTC*CATATTTTTCCGGTTAT**
TACCCCACCTGGAAGTGCCCAGAATTTTCCGGGGATTACGGATAATACGGTGGTCTGGATTAATTAATACGAGA
TCTCAGGGATTCCCACTATTTGGTATTCTGATATGTTTTTCCTGATATGCATCAAAACTCTAATCTAAAACCTGAAT
CTCCGC*TA(T)$_n$*GATGACCCCGTTTTCGTGACAAATTAATTTCCAACGGGGTCTTGTCCGGATAAGAGAATTTTGTT
**TGATTATCCGTTCGG*ATAAATGGACGCCTGCTCCATATTTTTCCGGTT*ATTACCCCACCTGGAAGTGCCCAGAAT**
TTTCCGGGGATTACGGATAATACGGTGGTCTGGATTAATTAATACGCCAAGTCTTACATTTTGTTGCAGTCTCGT
GCGAGTATGTGCAATAATAAACAAGATGAGCCAATTTATTGGATTAGTTGCAGCTTGACCCCGCCATAGCTAGGC
ATAGCCAAGTGCTATGGGTGTTAGATGATGCACTTGGATGCAGTGAGTTTTGGAGTATAAAAGATCCTTAAAATT
CCACCCTT pG1-3 (PG1-D1240-TA(T)$_n$-(T)$_n$): Example comprising a first T motif which is (T)$_n$ (n=13-20) extended by preceding TA (extending the T motif at its 5′-end to become a TA(T)$_n$ motif; and a second T motif which is (T)$_n$ (n=13-20) without a TA extension

SEQ ID 38

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TA(T)$_n$*GATGACCCCGTTTTCGTGACAAATTAATTTCCAACGGGGT
CTTGT**CCGGATAAGAGAATTTTGTTTGATTATCCGTTCGGATAAATGGA*CGCCTGCTC*CATATTTTTCCGGTTAT**
TACCCCACCTGGAAGTGCCCAGAATTTTCCGGGGATTACGGATAATACGGTGGTCTGGATTAATTAATACGAGA
TCTCAGGGATTCCCACTATTTGGTATTCTGATATGTTTTTCCTGATATGCATCAAAACTCTAATCTAAAACCTGAAT
CTCCGC*(T)$_n$*GATGACCCCGTTTTCGTGACAAATTAATTTCCAACGGGGTCTTGTCCGGATAAGAGAATTTTGTTTG
**ATTATCCGTTCGG*ATAAATGGACGCCTGCTCCATATTTTTCCGGTT*ATTACCCCACCTGGAAGTGCCCAGAATTT**
TCCGGGGATTACGGATAATACGGTGGTCTGGATTAATTAATACGCCAAGTCTTACATTTTGTTGCAGTCTCGTGC
GAGTATGTGCAATAATAAACAAGATGAGCCAATTTATTGGATTAGTTGCAGCTTGACCCCGCCATAGCTAGGCAT
AGCCAAGTGCTATGGGTGTTAGATGATGCACTTGGATGCAGTGAGTTTTGGAGTATAAAAGATCCTTAAAATTCC
ACCCTT

FIG.6B-7 pG1-3 (PG1-D1240-$(T)_n$-TA$(T)_n$): Example comprising a first T motif which is $(T)_n$ (n=13-20) without a TA extension; and a second T motif which is $(T)_n$ (n=13-20) extended by preceding TA (extending the T motif at its 5′-end to become a TA$(T)_n$ motif

SEQ ID 39

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC$(T)_n$GATGACCCCGTTTTCGTGACAAATTAATTTCCAACGGGGTCTT
GT**CCGGATAAGAGAATTTTGTTTGATTATCCGTTCGGATAAATGGA*CGCCTGCTC*CATATTTTTCCGGTTATTAC**
CCCACCTGGAAGTGCCCAGAATTTTCCGGGGATTACGGATAATACGGTGGTCTGGATTAATTAATACGAGATCT
CAGGGATTCCCACTATTTGGTATTCTGATATGTTTTTCCTGATATGCATCAAAACTCTAATCTAAAACCTGAATCTC
CGC*TA*$(T)_n$GATGACCCCGTTTTCGTGACAAATTAATTTCCAACGGGGTCTTGTCCGGATAAGAGAATTTTGTTTG
**ATTATCCGTTCGG*ATAAATGGACGCCTGCTCCATATTTTTCCGGTT*ATTACCCCACCTGGAAGTGCCCAGAATTT**
TCCGGGGATTACGGATAATACGGTGGTCTGGATTAATTAATACGCCAAGTCTTACATTTTGTTGCAGTCTCGTGC
GAGTATGTGCAATAATAAACAAGATGAGCCAATTTATTGGATTAGTTGCAGCTTGACCCCGCCATAGCTAGGCAT
AGCCAAGTGCTATGGGTGTTAGATGATGCACTTGGATGCAGTGAGTTTTGGAGTATAAAAGATCCTTAAAATTCC
ACCCTT pG1-3 (PG1-D1240-T(A/T)$(T)_n$-TA$(T)_n$): Example comprising a first T motif which is T(A/T)$(T)_n$ (n=13-20) which comprises the A/T substitution (extending the $(T)_n$ motif at its 5′-end by two additional "T" to become a TT$(T)_n$ motif); and a second T motif which is TA$(T)_n$ (n=13-20)

SEQ ID 40

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TT*$(T)_n$GATGACCCCGTTTTCGTGACAAATTAATTTCCAACGGGGTC
TTGT**CCGGATAAGAGAATTTTGTTTGATTATCCGTTCGGATAAATGGA*CGCCTGCTC*CATATTTTTCCGGTTATT**
ACCCCACCTGGAAGTGCCCAGAATTTTCCGGGGATTACGGATAATACGGTGGTCTGGATTAATTAATACGAGAT
CTCAGGGATTCCCACTATTTGGTATTCTGATATGTTTTTCCTGATATGCATCAAAACTCTAATCTAAAACCTGAATC
TCCGC*TA*$(T)_n$GATGACCCCGTTTTCGTGACAAATTAATTTCCAACGGGGTCTTGTCCGGATAAGAGAATTTTGTTT
**GATTATCCGTTCGG*ATAAATGGACGCCTGCTCCATATTTTTCCGGTT*ATTACCCCACCTGGAAGTGCCCAGAATT**
TTCCGGGGATTACGGATAATACGGTGGTCTGGATTAATTAATACGCCAAGTCTTACATTTTGTTGCAGTCTCGTG
CGAGTATGTGCAATAATAAACAAGATGAGCCAATTTATTGGATTAGTTGCAGCTTGACCCCGCCATAGCTAGGCA
TAGCCAAGTGCTATGGGTGTTAGATGATGCACTTGGATGCAGTGAGTTTTGGAGTATAAAAGATCCTTAAAATTC
CACCCTT

FIG.6B-8 pG1-3 (PG1-D1240-TA$(T)_n$-T(A/T)$(T)_n$): Example comprising a first T motif which is TA$(T)_n$ (n=13-20); and a second T motif which is T(A/T)$(T)_n$ (n=13-20) which comprises the A/T substitution (extending the $(T)_n$ motif at its 5′-end by two additional "T" to become a TT$(T)_n$ motif);

SEQ ID 41

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TA(T)*$_n$GATGACCCCGTTTTCGTGACAAATTAATTTCCAACGGGGT
CTTGT**CCGGATAAGAGAATTTTGTTTGATTATCCGTTCGGATAAATGGA*CGCCTGCTC*CATATTTTTCCGGTTAT**
TACCCCACCTGGAAGTGCCCAGAATTTTCCGGGGATTACGGATAATACGGTGGTCTGGATTAATTAATACGAGA
TCTCAGGGATTCCCACTATTTGGTATTCTGATATGTTTTTCCTGATATGCATCAAAACTCTAATCTAAAACCTGAAT
CTCCGC*TT(T)*$_n$GATGACCCCGTTTTCGTGACAAATTAATTTCCAACGGGGTCTTGTCCGGATAAGAGAATTTTGTT
**TGATTATCCGTTCGG*ATAAATGGACGCCTGCTCCATATTTTTCCGGTT*ATTACCCCACCTGGAAGTGCCCAGAAT**
TTTCCGGGGATTACGGATAATACGGTGGTCTGGATTAATTAATACGCCAAGTCTTACATTTTGTTGCAGTCTCGT
GCGAGTATGTGCAATAATAAACAAGATGAGCCAATTTATTGGATTAGTTGCAGCTTGACCCCGCCATAGCTAGGC
ATAGCCAAGTGCTATGGGTGTTAGATGATGCACTTGGATGCAGTGAGTTTTGGAGTATAAAAGATCCTTAAAATT
CCACCCTT pG1-3 (PG1-D1240-T(A/T)$(T)_n$-$(T)_n$): Example comprising a first T motif which is T(A/T)$(T)_n$ (n=13-20) which comprises the A/T substitution (extending the $(T)_n$ motif at its 5′-end by two additional "T" to become a TT$(T)_n$ motif); and a second T motif which is $(T)_n$ (n=13-20)

SEQ ID 42

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TT(T)*$_n$GATGACCCCGTTTTCGTGACAAATTAATTTCCAACGGGGTC
TTGT**CCGGATAAGAGAATTTTGTTTGATTATCCGTTCGGATAAATGGA*CGCCTGCTC*CATATTTTTCCGGTTATT**
ACCCCACCTGGAAGTGCCCAGAATTTTCCGGGGATTACGGATAATACGGTGGTCTGGATTAATTAATACGAGAT
CTCAGGGATTCCCACTATTTGGTATTCTGATATGTTTTTCCTGATATGCATCAAAACTCTAATCTAAAACCTGAATC
TCCGC*(T)*$_n$GATGACCCCGTTTTCGTGACAAATTAATTTCCAACGGGGTCTTGTCCGGATAAGAGAATTTTGTTTGA
**TTATCCGTTCGG*ATAAATGGACGCCTGCTCCATATTTTTCCGGTT*ATTACCCCACCTGGAAGTGCCCAGAATTTT**
CCGGGGATTACGGATAATACGGTGGTCTGGATTAATTAATACGCCAAGTCTTACATTTTGTTGCAGTCTCGTGCG
AGTATGTGCAATAATAAACAAGATGAGCCAATTTATTGGATTAGTTGCAGCTTGACCCCGCCATAGCTAGGCATA
GCCAAGTGCTATGGGTGTTAGATGATGCACTTGGATGCAGTGAGTTTTGGAGTATAAAAGATCCTTAAAATTCCA
CCCTT

FIG. 6B-9 pG1-3 (PG1-D1240-$(T)_n$-$T(A/T)(T)_n$): Example comprising a first T motif which is $(T)_n$ (n=13-20); and a second T motif which is $T(A/T)(T)_n$ (n=13-20) which comprises the A/T substitution (extending the $(T)_n$ motif at its 5′-end by two additional "T" to become a $TT(T)_n$ motif);

SEQ ID 43

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC$(T)_n$GATGACCCCGTTTTCGTGACAAATTAATTTCCAACGGGGTCTT
GT**CCGGATAAGAGAATTTTGTTTGATTATCCGTTCGGATAAATGGA*CGCCTGCTC*CATATTTTTCCGGTTATTAC**
CCCACCTGGAAGTGCCCAGAATTTTCCGGGGATTACGGATAATACGGTGGTCTGGATTAATTAATACGAGATCT
CAGGGATTCCCACTATTTGGTATTCTGATATGTTTTTCCTGATATGCATCAAAACTCTAATCTAAAACCTGAATCTC
CGC$TT(T)_n$GATGACCCCGTTTTCGTGACAAATTAATTTCCAACGGGGTCTTGTCCGGATAAGAGAATTTTGTTTGA
**TTATCCGTTCGG*ATAAATGGACGCCTGCTCCATATTTTTCCGGTT*ATTACCCCACCTGGAAGTGCCCAGAATTTT**
CCGGGGATTACGGATAATACGGTGGTCTGGATTAATTAATACGCCAAGTCTTACATTTTGTTGCAGTCTCGTGCG
AGTATGTGCAATAATAAACAAGATGAGCCAATTTATTGGATTAGTTGCAGCTTGACCCCGCCATAGCTAGGCATA
GCCAAGTGCTATGGGTGTTAGATGATGCACTTGGATGCAGTGAGTTTTGGAGTATAAAAGATCCTTAAAATTCCA
CCCTT pG1-3 (PG1-D1240-2x$(T)_n$): Example comprising two T motifs which are $(T)_n$ (n=13-20), each without a TA extension

SEQ ID 44

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC$(T)_n$GATGACCCCGTTTTCGTGACAAATTAATTTCCAACGGGGTCTT
GT**CCGGATAAGAGAATTTTGTTTGATTATCCGTTCGGATAAATGGA*CGCCTGCTC*CATATTTTTCCGGTTATTAC**
CCCACCTGGAAGTGCCCAGAATTTTCCGGGGATTACGGATAATACGGTGGTCTGGATTAATTAATACGAGATCT
CAGGGATTCCCACTATTTGGTATTCTGATATGTTTTTCCTGATATGCATCAAAACTCTAATCTAAAACCTGAATCTC
CGC$(T)_n$GATGACCCCGTTTTCGTGACAAATTAATTTCCAACGGGGTCTTGTCCGGATAAGAGAATTTTGTTTGATT
**ATCCGTTCGG*ATAAATGGACGCCTGCTCCATATTTTTCCGGTT*ATTACCCCACCTGGAAGTGCCCAGAATTTTCC**
GGGGATTACGGATAATACGGTGGTCTGGATTAATTAATACGCCAAGTCTTACATTTTGTTGCAGTCTCGTGCGAG
TATGTGCAATAATAAACAAGATGAGCCAATTTATTGGATTAGTTGCAGCTTGACCCCGCCATAGCTAGGCATAGC
CAAGTGCTATGGGTGTTAGATGATGCACTTGGATGCAGTGAGTTTTGGAGTATAAAAGATCCTTAAAATTCCACC
CTT

FIG.6B-10 pG1-3 (PG1-D1240-2xTA$(T)_{13}$): Example comprising two T motifs which are $(T)_n$ (n=13), each extended by preceding TA (extending the T motif at its 5'-end to become a TA$(T)_n$ motif)

SEQ ID 45

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTT*GATGACCCCGTTTTCGTGACAAATTAATTTCC
AACGGGGTCTTGT**CCGGATAAGAGAATTTTGTTTGATTATCCGTTCGGATAAATGGA*CGCCTGCTC*CATATTTTT**
CCGGTTATTACCCCACCTGGAAGTGCCCAGAATTTTCCGGGGATTACGGATAATACGGTGGTCTGGATTAATTA
ATACGAGATCTCAGGGATTCCCACTATTTGGTATTCTGATATGTTTTTCCTGATATGCATCAAAACTCTAATCTAAA
ACCTGAATCTCCGC*TATTTTTTTTTTTTT*GATGACCCCGTTTTCGTGACAAATTAATTTCCAACGGGGTCTTGTCCG
**GATAAGAGAATTTTGTTTGATTATCCGTTCGG*ATAAATGGACGCCTGCTCCATATTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT pG1-3 (PG1-D1240-TA$(T)_{13}$-$(T)_{13}$): Example comprising a first T motif which is $(T)_n$ (n=13) extended by preceding TA (extending the T motif at its 5'-end to become a TA$(T)_n$ motif; and a second T motif which is $(T)_n$ (n=13) without a TA extension

SEQ ID 46

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTT*GATGACCCCGTTTTCGTGACAAATTAATTTCC
AACGGGGTCTTGT**CCGGATAAGAGAATTTTGTTTGATTATCCGTTCGGATAAATGGA*CGCCTGCTC*CATATTTTT**
CCGGTTATTACCCCACCTGGAAGTGCCCAGAATTTTCCGGGGATTACGGATAATACGGTGGTCTGGATTAATTA
ATACGAGATCTCAGGGATTCCCACTATTTGGTATTCTGATATGTTTTTCCTGATATGCATCAAAACTCTAATCTAAA
ACCTGAATCTCCGC*TTTTTTTTTTTTT*GATGACCCCGTTTTCGTGACAAATTAATTTCCAACGGGGTCTTGTCCGGA
**TAAGAGAATTTTGTTTGATTATCCGTTCGG*ATAAATGGACGCCTGCTCCATATTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT

FIG.6B-11 pG1-3 (PG1-D1240-$(T)_{13}$-TA$(T)_{13}$): Example comprising a first T motif which is $(T)_n$ (n=13) without a TA extension; and a second T motif which is $(T)_n$ (n=13) extended by preceding TA (extending the T motif at its 5′-end to become a TA$(T)_n$ motif

SEQ ID 47

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTT*GATGACCCCGTTTTCGTGACAAATTAATTTCCAA
CGGGGTCTTGT**CCGGATAAGAGAATTTTGTTTGATTATCCGTTCGGATAAATGGA*CGCCTGCTC*CATATTTTTCC**
GGTTATTACCCCACCTGGAAGTGCCCAGAATTTTCCGGGGATTACGGATAATACGGTGGTCTGGATTAATTAAT
ACGAGATCTCAGGGATTCCCACTATTTGGTATTCTGATATGTTTTTCCTGATATGCATCAAAACTCTAATCTAAAAC
CTGAATCTCCGC*TATTTTTTTTTTTTT*GATGACCCCGTTTTCGTGACAAATTAATTTCCAACGGGGTCTTGTCCGGA
**TAAGAGAATTTTGTTTGATTATCCGTTCGG*ATAAATGGACGCCTGCTCCATATTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT pG1-3 (PG1-D1240-2x$(T)_{13}$): Example comprising two T motifs which are $(T)_n$ (n=13), each without a TA extension

SEQ ID 48

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTT*GATGACCCCGTTTTCGTGACAAATTAATTTCCAA
CGGGGTCTTGT**CCGGATAAGAGAATTTTGTTTGATTATCCGTTCGGATAAATGGA*CGCCTGCTC*CATATTTTTCC**
GGTTATTACCCCACCTGGAAGTGCCCAGAATTTTCCGGGGATTACGGATAATACGGTGGTCTGGATTAATTAAT
ACGAGATCTCAGGGATTCCCACTATTTGGTATTCTGATATGTTTTTCCTGATATGCATCAAAACTCTAATCTAAAAC
CTGAATCTCCGC*TTTTTTTTTTTTT*GATGACCCCGTTTTCGTGACAAATTAATTTCCAACGGGGTCTTGTCCGGATA
**AGAGAATTTTGTTTGATTATCCGTTCGG*ATAAATGGACGCCTGCTCCATATTTTTCCGGTT*ATTACCCCACCTGG**
AAGTGCCCAGAATTTTCCGGGGATTACGGATAATACGGTGGTCTGGATTAATTAATACGCCAAGTCTTACATTTT
GTTGCAGTCTCGTGCGAGTATGTGCAATAATAAACAAGATGAGCCAATTTATTGGATTAGTTGCAGCTTGACCCC
GCCATAGCTAGGCATAGCCAAGTGCTATGGGTGTTAGATGATGCACTTGGATGCAGTGAGTTTTGGAGTATAAA
AGATCCTTAAAATTCCACCCTT

FIG.6B-12 pG1-3 (PG1-D1240-2xTA$(T)_{14}$): Example comprising two T motifs which are $(T)_n$ (n=14), each extended by preceding TA (extending the T motif at its 5'-end to become a TA$(T)_n$ motif)

SEQ ID 49

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTT*GATGACCCCGTTTTCGTGACAAATTAATTTC
CAACGGGGTCTTGT**CCGGATAAGAGAATTTTGTTTGATTATCCGTTCGGATAAATGGA*CGCCTGCTC*CATATTTT**
TCCGGTTATTACCCCACCTGGAAGTGCCCAGAATTTTCCGGGGATTACGGATAATACGGTGGTCTGGATTAATT
AATACGAGATCTCAGGGATTCCCACTATTTGGTATTCTGATATGTTTTTCCTGATATGCATCAAAACTCTAATCTAA
AACCTGAATCTCCGC*TATTTTTTTTTTTTTT*GATGACCCCGTTTTCGTGACAAATTAATTTCCAACGGGGTCTTGTCC
**GGATAAGAGAATTTTGTTTGATTATCCGTTCGG*ATAAATGGACGCCTGCTCCATATTTTTCCGGTT*ATTACCCCA**
CCTGGAAGTGCCCAGAATTTTCCGGGGATTACGGATAATACGGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1-3 (PG1-D1240-TA$(T)_{14}$-$(T)_{14}$): Example comprising a first T motif which is $(T)_n$ (n=14) extended by preceding TA (extending the T motif at its 5'-end to become a TA$(T)_n$ motif; and a second T motif which is $(T)_n$ (n=14) without a TA extension

SEQ ID 50

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTT*GATGACCCCGTTTTCGTGACAAATTAATTTC
CAACGGGGTCTTGT**CCGGATAAGAGAATTTTGTTTGATTATCCGTTCGGATAAATGGA*CGCCTGCTC*CATATTTT**
TCCGGTTATTACCCCACCTGGAAGTGCCCAGAATTTTCCGGGGATTACGGATAATACGGTGGTCTGGATTAATT
AATACGAGATCTCAGGGATTCCCACTATTTGGTATTCTGATATGTTTTTCCTGATATGCATCAAAACTCTAATCTAA
AACCTGAATCTCCGC*TTTTTTTTTTTTTT*GATGACCCCGTTTTCGTGACAAATTAATTTCCAACGGGGTCTTGTCCG
**GATAAGAGAATTTTGTTTGATTATCCGTTCGG*ATAAATGGACGCCTGCTCCATATTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT

FIG.6B-13 pG1-3 (PG1-D1240-$(T)_{14}$-$TA(T)_{14}$): Example comprising a first T motif which is $(T)_n$ (n=14) without a TA extension; and a second T motif which is $(T)_n$ (n=14) extended by preceding TA (extending the T motif at its 5'-end to become a $TA(T)_n$ motif

SEQ ID 51

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTT*GATGACCCCGTTTTCGTGACAAATTAATTTCCA
ACGGGGTCTTGT**CCGGATAAGAGAATTTTGTTTGATTATCCGTTCGGATAAATGGA*CGCCTGCTC*CATATTTTTC**
CGGTTATTACCCCACCTGGAAGTGCCCAGAATTTTCCGGGGATTACGGATAATACGGTGGTCTGGATTAATTAA
TACGAGATCTCAGGGATTCCCACTATTTGGTATTCTGATATGTTTTTCCTGATATGCATCAAAACTCTAATCTAAAA
CCTGAATCTCCGC*TATTTTTTTTTTTTTT*GATGACCCCGTTTTCGTGACAAATTAATTTCCAACGGGGTCTTGTCCG
**GATAAGAGAATTTTGTTTGATTATCCGTTCGG*ATAAATGGACGCCTGCTCCATATTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT pG1-3 (PG1-D1240-2x$(T)_{14}$): Example comprising two T motifs which are $(T)_n$ (n=14), each without a TA extension

SEQ ID 52

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTT*GATGACCCCGTTTTCGTGACAAATTAATTTCCA
ACGGGGTCTTGT**CCGGATAAGAGAATTTTGTTTGATTATCCGTTCGGATAAATGGA*CGCCTGCTC*CATATTTTTC**
CGGTTATTACCCCACCTGGAAGTGCCCAGAATTTTCCGGGGATTACGGATAATACGGTGGTCTGGATTAATTAA
TACGAGATCTCAGGGATTCCCACTATTTGGTATTCTGATATGTTTTTCCTGATATGCATCAAAACTCTAATCTAAAA
CCTGAATCTCCGC*TTTTTTTTTTTTTT*GATGACCCCGTTTTCGTGACAAATTAATTTCCAACGGGGTCTTGTCCGGA
**TAAGAGAATTTTGTTTGATTATCCGTTCGG*ATAAATGGACGCCTGCTCCATATTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT

FIG.6B-14 pG1-3 (PG1-D1240-2xTA$(T)_{15}$): Example comprising two T motifs which are $(T)_n$ (n=15), each extended by preceding TA (extending the T motif at its 5′-end to become a TA$(T)_n$ motif)

SEQ ID 53

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTT*GATGACCCCGTTTTCGTGACAAATTAATTT
CCAACGGGGTCTTGT**CCGGATAAGAGAATTTTGTTTGATTATCCGTTCGGATAAATGGA*CGCCTGCTC*CATATTT**
TTCCGGTTATTACCCCACCTGGAAGTGCCCAGAATTTTCCGGGGATTACGGATAATACGGTGGTCTGGATTAAT
TAATACGAGATCTCAGGGATTCCCACTATTTGGTATTCTGATATGTTTTTCCTGATATGCATCAAAACTCTAATCTA
AAACCTGAATCTCCGC*TATTTTTTTTTTTTTTT*GATGACCCCGTTTTCGTGACAAATTAATTTCCAACGGGGTCTTGT
**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT pG1-3 (PG1-D1240-TA$(T)_{15}$-$(T)_{15}$): Example comprising a first T motif which is $(T)_n$ (n=15) extended by preceding TA (extending the T motif at its 5′-end to become a TA$(T)_n$ motif; and a second T motif which is $(T)_n$ (n=15) without a TA extension

SEQ ID 54

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTT*GATGACCCCGTTTTCGTGACAAATTAATTT
CCAACGGGGTCTTGT**CCGGATAAGAGAATTTTGTTTGATTATCCGTTCGGATAAATGGA*CGCCTGCTC*CATATTT**
TTCCGGTTATTACCCCACCTGGAAGTGCCCAGAATTTTCCGGGGATTACGGATAATACGGTGGTCTGGATTAAT
TAATACGAGATCTCAGGGATTCCCACTATTTGGTATTCTGATATGTTTTTCCTGATATGCATCAAAACTCTAATCTA
AAACCTGAATCTCCGC*TTTTTTTTTTTTTTT*GATGACCCCGTTTTCGTGACAAATTAATTTCCAACGGGGTCTTGTCC
**GGATAAGAGAATTTTGTTTGATTATCCGTTCGG*ATAAATGGACGCCTGCTCCATATTTTTCCGGTT*ATTACCCCA**
CCTGGAAGTGCCCAGAATTTTCCGGGGATTACGGATAATACGGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT

FIG.6B-15 pG1-3 (PG1-D1240-$(T)_{15}$-TA$(T)_{15}$): Example comprising a first T motif which is $(T)_n$ (n=15) without a TA extension; and a second T motif which is $(T)_n$ (n=15) extended by preceding TA (extending the T motif at its 5'-end to become a TA$(T)_n$ motif

SEQ ID 55

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTT*GATGACCCCGTTTTCGTGACAAATTAATTTCC
AACGGGGTCTTGT**CCGGATAAGAGAATTTTGTTTGATTATCCGTTCGGATAAATGGA*CGCCTGCTC*CATATTTTT**
CCGGTTATTACCCCACCTGGAAGTGCCCAGAATTTTCCGGGGATTACGGATAATACGGTGGTCTGGATTAATTA
ATACGAGATCTCAGGGATTCCCACTATTTGGTATTCTGATATGTTTTTCCTGATATGCATCAAAACTCTAATCTAAA
ACCTGAATCTCCGC*TATTTTTTTTTTTTTTT*GATGACCCCGTTTTCGTGACAAATTAATTTCCAACGGGGTCTTGTCC
**GGATAAGAGAATTTTGTTTGATTATCCGTTCGG*ATAAATGGACGCCTGCTCCATATTTTTCCGGTT*ATTACCCCA**
CCTGGAAGTGCCCAGAATTTTCCGGGGATTACGGATAATACGGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1-3 (PG1-D1240-2x$(T)_{15}$): Example comprising two T motifs which are $(T)_n$ (n=15), each without a TA extension

SEQ ID 56

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTT*GATGACCCCGTTTTCGTGACAAATTAATTTCC
AACGGGGTCTTGT**CCGGATAAGAGAATTTTGTTTGATTATCCGTTCGGATAAATGGA*CGCCTGCTC*CATATTTTT**
CCGGTTATTACCCCACCTGGAAGTGCCCAGAATTTTCCGGGGATTACGGATAATACGGTGGTCTGGATTAATTA
ATACGAGATCTCAGGGATTCCCACTATTTGGTATTCTGATATGTTTTTCCTGATATGCATCAAAACTCTAATCTAAA
ACCTGAATCTCCGC*TTTTTTTTTTTTTTT*GATGACCCCGTTTTCGTGACAAATTAATTTCCAACGGGGTCTTGTCCG
**GATAAGAGAATTTTGTTTGATTATCCGTTCGG*ATAAATGGACGCCTGCTCCATATTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT

FIG.6B-16 pG1-3 (PG1-D1240-2xTA$(T)_{16}$): Example comprising two T motifs which are $(T)_n$ (n=16), each extended by preceding TA (extending the T motif at its 5′-end to become a TA$(T)_n$ motif)

SEQ ID 57

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTT*GATGACCCCGTTTTCGTGACAAATTAATT
TCCAACGGGGTCTTGT**CCGGATAAGAGAATTTTGTTTGATTATCCGTTCGGATAAATGGA*CGCCTGCTC*CATATT**
TTTCCGGTTATTACCCCACCTGGAAGTGCCCAGAATTTTCCGGGGATTACGGATAATACGGTGGTCTGGATTAA
TTAATACGAGATCTCAGGGATTCCCACTATTTGGTATTCTGATATGTTTTTCCTGATATGCATCAAAACTCTAATCT
AAAACCTGAATCTCCGC*TATTTTTTTTTTTTTTTT*GATGACCCCGTTTTCGTGACAAATTAATTTCCAACGGGGTCTT
GT**CCGGATAAGAGAATTTTGTTTGATTATCCGTTCGG*ATAAATGGACGCCTGCTCCATATTTTTCCGGTT*ATTAC**
CCCACCTGGAAGTGCCCAGAATTTTCCGGGGATTACGGATAATACGGTGGTCTGGATTAATTAATACGCCAAGT
CTTACATTTTGTTGCAGTCTCGTGCGAGTATGTGCAATAATAAACAAGATGAGCCAATTTATTGGATTAGTTGCAG
CTTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTT pG1-3 (PG1-D1240-TA$(T)_{16}$-$(T)_{16}$): Example comprising a first T motif which is $(T)_n$ (n=16) extended by preceding TA (extending the T motif at its 5′-end to become a TA$(T)_n$ motif; and a second T motif which is $(T)_n$ (n=16) without a TA extension

SEQ ID 58

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTT*GATGACCCCGTTTTCGTGACAAATTAATT
TCCAACGGGGTCTTGT**CCGGATAAGAGAATTTTGTTTGATTATCCGTTCGGATAAATGGA*CGCCTGCTC*CATATT**
TTTCCGGTTATTACCCCACCTGGAAGTGCCCAGAATTTTCCGGGGATTACGGATAATACGGTGGTCTGGATTAA
TTAATACGAGATCTCAGGGATTCCCACTATTTGGTATTCTGATATGTTTTTCCTGATATGCATCAAAACTCTAATCT
AAAACCTGAATCTCCGC*TTTTTTTTTTTTTTTT*GATGACCCCGTTTTCGTGACAAATTAATTTCCAACGGGGTCTTGT
**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT

FIG.6B-17 pG1-3 (PG1-D1240-$(T)_{16}$-TA$(T)_{16}$): Example comprising a first T motif which is $(T)_n$ (n=16) without a TA extension; and a second T motif which is $(T)_n$ (n=16) extended by preceding TA (extending the T motif at its 5'-end to become a TA$(T)_n$ motif

SEQ ID 59

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTT*GATGACCCCGTTTTCGTGACAAATTAATTTC
CAACGGGGTCTTGT**CCGGATAAGAGAATTTTGTTTGATTATCCGTTCGGATAAATGGA*CGCCTGCTC*CATATTTT**
TCCGGTTATTACCCCACCTGGAAGTGCCCAGAATTTTCCGGGGATTACGGATAATACGGTGGTCTGGATTAATT
AATACGAGATCTCAGGGATTCCCACTATTTGGTATTCTGATATGTTTTTCCTGATATGCATCAAAACTCTAATCTAA
AACCTGAATCTCCGC*TATTTTTTTTTTTTTTTT*GATGACCCCGTTTTCGTGACAAATTAATTTCCAACGGGGTCTTGT
**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT pG1-3 (PG1-D1240-2x$(T)_{16}$): Example comprising two T motifs which are $(T)_n$ (n=16), each without a TA extension

SEQ ID 60

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTT*GATGACCCCGTTTTCGTGACAAATTAATTTC
CAACGGGGTCTTGT**CCGGATAAGAGAATTTTGTTTGATTATCCGTTCGGATAAATGGA*CGCCTGCTC*CATATTTT**
TCCGGTTATTACCCCACCTGGAAGTGCCCAGAATTTTCCGGGGATTACGGATAATACGGTGGTCTGGATTAATT
AATACGAGATCTCAGGGATTCCCACTATTTGGTATTCTGATATGTTTTTCCTGATATGCATCAAAACTCTAATCTAA
AACCTGAATCTCCGC*TTTTTTTTTTTTTTTT*GATGACCCCGTTTTCGTGACAAATTAATTTCCAACGGGGTCTTGTCC
**GGATAAGAGAATTTTGTTTGATTATCCGTTCGG*ATAAATGGACGCCTGCTCCATATTTTTCCGGTT*ATTACCCCA**
CCTGGAAGTGCCCAGAATTTTCCGGGGATTACGGATAATACGGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT

FIG.6B-18 pG1-3 (PG1-D1240-2xTA$(T)_{17}$): Example comprising two T motifs which are $(T)_n$ (n=17), each extended by preceding TA (extending the T motif at its 5'-end to become a TA$(T)_n$ motif)

SEQ ID 61

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTT*GATGACCCCGTTTTCGTGACAAATTAAT
TTCCAACGGGGTCTTGT**CCGGATAAGAGAATTTTGTTTGATTATCCGTTCGGATAAATGGA*CGCCTGCTC*CATAT**
TTTTCCGGTTATTACCCCACCTGGAAGTGCCCAGAATTTTCCGGGGATTACGGATAATACGGTGGTCTGGATTA
ATTAATACGAGATCTCAGGGATTCCCACTATTTGGTATTCTGATATGTTTTTCCTGATATGCATCAAAACTCTAATC
TAAAACCTGAATCTCCGC*TATTTTTTTTTTTTTTTTT*GATGACCCCGTTTTCGTGACAAATTAATTTCCAACGGGGTC
TTGT**CCGGATAAGAGAATTTTGTTTGATTATCCGTTCGG*ATAAATGGACGCCTGCTCCATATTTTTCCGGTT*ATT**
ACCCCACCTGGAAGTGCCCAGAATTTTCCGGGGATTACGGATAATACGGTGGTCTGGATTAATTAATACGCCAA
GTCTTACATTTTGTTGCAGTCTCGTGCGAGTATGTGCAATAATAAACAAGATGAGCCAATTTATTGGATTAGTTGC
AGCTTGACCCCGCCATAGCTAGGCATAGCCAAGTGCTATGGGTGTTAGATGATGCACTTGGATGCAGTGAGTTTT
GGAGTATAAAAGATCCTTAAAATTCCACCCTT pG1-3 (PG1-D1240-TA$(T)_{17}$-$(T)_{17}$): Example comprising a first T motif which is $(T)_n$ (n=17) extended by preceding TA (extending the T motif at its 5'-end to become a TA$(T)_n$ motif; and a second T motif which is $(T)_n$ (n=17) without a TA extension

SEQ ID 62

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTT*GATGACCCCGTTTTCGTGACAAATTAAT
TTCCAACGGGGTCTTGT**CCGGATAAGAGAATTTTGTTTGATTATCCGTTCGGATAAATGGA*CGCCTGCTC*CATAT**
TTTTCCGGTTATTACCCCACCTGGAAGTGCCCAGAATTTTCCGGGGATTACGGATAATACGGTGGTCTGGATTA
ATTAATACGAGATCTCAGGGATTCCCACTATTTGGTATTCTGATATGTTTTTCCTGATATGCATCAAAACTCTAATC
TAAAACCTGAATCTCCGC*TTTTTTTTTTTTTTTTT*GATGACCCCGTTTTCGTGACAAATTAATTTCCAACGGGGTCTT
GT**CCGGATAAGAGAATTTTGTTTGATTATCCGTTCGG*ATAAATGGACGCCTGCTCCATATTTTTCCGGTT*ATTAC**
CCCACCTGGAAGTGCCCAGAATTTTCCGGGGATTACGGATAATACGGTGGTCTGGATTAATTAATACGCCAAGT
CTTACATTTTGTTGCAGTCTCGTGCGAGTATGTGCAATAATAAACAAGATGAGCCAATTTATTGGATTAGTTGCAG
CTTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTT

FIG.6B-19 pG1-3 (PG1-D1240-$(T)_{17}$-TA$(T)_{17}$): Example comprising a first T motif which is $(T)_n$ (n=17) without a TA extension; and a second T motif which is $(T)_n$ (n=17) extended by preceding TA (extending the T motif at its 5'-end to become a TA$(T)_n$ motif

SEQ ID 63

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTT*GATGACCCCGTTTTCGTGACAAATTAATTT
CCAACGGGGTCTTGT**CCGGATAAGAGAATTTTGTTTGATTATCCGTTCGGATAAATGGA*CGCCTGCTC*CATATTT**
TTCCGGTTATTACCCCACCTGGAAGTGCCCAGAATTTTCCGGGGATTACGGATAATACGGTGGTCTGGATTAAT
TAATACGAGATCTCAGGGATTCCCACTATTTGGTATTCTGATATGTTTTTCCTGATATGCATCAAAACTCTAATCTA
AAACCTGAATCTCCGC*TATTTTTTTTTTTTTTTTT*GATGACCCCGTTTTCGTGACAAATTAATTTCCAACGGGGTCTT
GT**CCGGATAAGAGAATTTTGTTTGATTATCCGTTCGG*ATAAATGGACGCCTGCTCCATATTTTTCCGGTT*ATTAC**
CCCACCTGGAAGTGCCCAGAATTTTCCGGGGATTACGGATAATACGGTGGTCTGGATTAATTAATACGCCAAGT
CTTACATTTTGTTGCAGTCTCGTGCGAGTATGTGCAATAATAAACAAGATGAGCCAATTTATTGGATTAGTTGCAG
CTTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTT pG1-3 (PG1-D1240-2x$(T)_{17}$): Example comprising two T motifs which are $(T)_n$ (n=17), each without a TA extension

SEQ ID 64

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTT*GATGACCCCGTTTTCGTGACAAATTAATTT
CCAACGGGGTCTTGT**CCGGATAAGAGAATTTTGTTTGATTATCCGTTCGGATAAATGGA*CGCCTGCTC*CATATTT**
TTCCGGTTATTACCCCACCTGGAAGTGCCCAGAATTTTCCGGGGATTACGGATAATACGGTGGTCTGGATTAAT
TAATACGAGATCTCAGGGATTCCCACTATTTGGTATTCTGATATGTTTTTCCTGATATGCATCAAAACTCTAATCTA
AAACCTGAATCTCCGC*TTTTTTTTTTTTTTTTT*GATGACCCCGTTTTCGTGACAAATTAATTTCCAACGGGGTCTTGT
**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT

FIG.6B-20 pG1-3 (PG1-D1240-2xTA(T)$_{18}$): Example comprising two T motifs which are (T)$_n$ (n=18), each extended by preceding TA (extending the T motif at its 5'-end to become a TA(T)$_n$ motif)

SEQ ID 65

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTT*GATGACCCCGTTTTCGTGACAAATTAA
TTTCCAACGGGGTCTTGT**CCGGATAAGAGAATTTTGTTTGATTATCCGTTCGGATAAATGGA*CGCCTGCTC*CATA**
TTTTTCCGGTTATTACCCCACCTGGAAGTGCCCAGAATTTTCCGGGGATTACGGATAATACGGTGGTCTGGATT
AATTAATACGAGATCTCAGGGATTCCCACTATTTGGTATTCTGATATGTTTTTCCTGATATGCATCAAAACTCTAAT
CTAAAACCTGAATCTCCGC*TATTTTTTTTTTTTTTTTTT*GATGACCCCGTTTTCGTGACAAATTAATTTCCAACGGGG
TCTTGT**CCGGATAAGAGAATTTTGTTTGATTATCCGTTCGG*ATAAATGGACGCCTGCTCCATATTTTTCCGGTT*A**
TTACCCCACCTGGAAGTGCCCAGAATTTTCCGGGGATTACGGATAATACGGTGGTCTGGATTAATTAATACGCC
AAGTCTTACATTTTGTTGCAGTCTCGTGCGAGTATGTGCAATAATAAACAAGATGAGCCAATTTATTGGATTAGTT
GCAGCTTGACCCCGCCATAGCTAGGCATAGCCAAGTGCTATGGGTGTTAGATGATGCACTTGGATGCAGTGAGT
TTTGGAGTATAAAAGATCCTTAAAATTCCACCCTT pG1-3 (PG1-D1240-TA(T)$_{18}$-(T)$_{18}$): Example comprising a first T motif which is (T)$_n$ (n=18) extended by preceding TA (extending the T motif at its 5'-end to become a TA(T)$_n$ motif; and a second T motif which is (T)$_n$ (n=18) without a TA extension

SEQ ID 66

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTT*GATGACCCCGTTTTCGTGACAAATTAA
TTTCCAACGGGGTCTTGT**CCGGATAAGAGAATTTTGTTTGATTATCCGTTCGGATAAATGGA*CGCCTGCTC*CATA**
TTTTTCCGGTTATTACCCCACCTGGAAGTGCCCAGAATTTTCCGGGGATTACGGATAATACGGTGGTCTGGATT
AATTAATACGAGATCTCAGGGATTCCCACTATTTGGTATTCTGATATGTTTTTCCTGATATGCATCAAAACTCTAAT
CTAAAACCTGAATCTCCGC*TTTTTTTTTTTTTTTTTT*GATGACCCCGTTTTCGTGACAAATTAATTTCCAACGGGGTC
TTGT**CCGGATAAGAGAATTTTGTTTGATTATCCGTTCGG*ATAAATGGACGCCTGCTCCATATTTTTCCGGTT*ATT**
ACCCCACCTGGAAGTGCCCAGAATTTTCCGGGGATTACGGATAATACGGTGGTCTGGATTAATTAATACGCCAA
GTCTTACATTTTGTTGCAGTCTCGTGCGAGTATGTGCAATAATAAACAAGATGAGCCAATTTATTGGATTAGTTGC
AGCTTGACCCCGCCATAGCTAGGCATAGCCAAGTGCTATGGGTGTTAGATGATGCACTTGGATGCAGTGAGTTTT
GGAGTATAAAAGATCCTTAAAATTCCACCCTT

FIG.6B-21 pG1-3 (PG1-D1240-$(T)_{18}$-TA$(T)_{18}$): Example comprising a first T motif which is $(T)_n$ (n=18) without a TA extension; and a second T motif which is $(T)_n$ (n=18) extended by preceding TA (extending the T motif at its 5'-end to become a TA$(T)_n$ motif

SEQ ID 67

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTT*GATGACCCCGTTTTCGTGACAAATTAATT
TCCAACGGGGTCTTGT**CCGGATAAGAGAATTTTGTTTGATTATCCGTTCGGATAAATGGA*CGCCTGCTC*CATATT**
TTTCCGGTTATTACCCCACCTGGAAGTGCCCAGAATTTTCCGGGGATTACGGATAATACGGTGGTCTGGATTAA
TTAATACGAGATCTCAGGGATTCCCACTATTTGGTATTCTGATATGTTTTTCCTGATATGCATCAAAACTCTAATCT
AAAACCTGAATCTCCGC*TATTTTTTTTTTTTTTTTTT*GATGACCCCGTTTTCGTGACAAATTAATTTCCAACGGGGTC
TTGT**CCGGATAAGAGAATTTTGTTTGATTATCCGTTCGG*ATAAATGGACGCCTGCTCCATATTTTTCCGGTT*ATT**
ACCCCACCTGGAAGTGCCCAGAATTTTCCGGGGATTACGGATAATACGGTGGTCTGGATTAATTAATACGCCAA
GTCTTACATTTTGTTGCAGTCTCGTGCGAGTATGTGCAATAATAAACAAGATGAGCCAATTTATTGGATTAGTTGC
AGCTTGACCCCGCCATAGCTAGGCATAGCCAAGTGCTATGGGTGTTAGATGATGCACTTGGATGCAGTGAGTTTT
GGAGTATAAAAGATCCTTAAAATTCCACCCTT pG1-3 (PG1-D1240-2x$(T)_{18}$): Example comprising two T motifs which are $(T)_n$ (n=18), each without a TA extension

SEQ ID 68

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTT*GATGACCCCGTTTTCGTGACAAATTAATT
TCCAACGGGGTCTTGT**CCGGATAAGAGAATTTTGTTTGATTATCCGTTCGGATAAATGGA*CGCCTGCTC*CATATT**
TTTCCGGTTATTACCCCACCTGGAAGTGCCCAGAATTTTCCGGGGATTACGGATAATACGGTGGTCTGGATTAA
TTAATACGAGATCTCAGGGATTCCCACTATTTGGTATTCTGATATGTTTTTCCTGATATGCATCAAAACTCTAATCT
AAAACCTGAATCTCCGC*TTTTTTTTTTTTTTTTTT*GATGACCCCGTTTTCGTGACAAATTAATTTCCAACGGGGTCTT
GT**CCGGATAAGAGAATTTTGTTTGATTATCCGTTCGG*ATAAATGGACGCCTGCTCCATATTTTTCCGGTT*ATTAC**
CCCACCTGGAAGTGCCCAGAATTTTCCGGGGATTACGGATAATACGGTGGTCTGGATTAATTAATACGCCAAGT
CTTACATTTTGTTGCAGTCTCGTGCGAGTATGTGCAATAATAAACAAGATGAGCCAATTTATTGGATTAGTTGCAG
CTTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTT

FIG.6B-22 pG1-3 (PG1-D1240-2xTA(T)$_{19}$): Example comprising two T motifs which are (T)$_n$ (n=19), each extended by preceding TA (extending the T motif at its 5'-end to become a TA(T)$_n$ motif)

SEQ ID 69

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTTT*GATGACCCCGTTTTCGTGACAAATTA
ATTTCCAACGGGGTCTTGTCCGGATAAGAGAATTTTGTTTGATTATCCGTTCGGATAAATGGACGCCTGCTCCAT
ATTTTTCCGGTTATTACCCCACCTGGAAGTGCCCAGAATTTTCCGGGGATTACGGATAATACGGTGGTCTGGAT
TAATTAATACGAGATCTCAGGGATTCCCACTATTTGGTATTCTGATATGTTTTTCCTGATATGCATCAAAACTCTAA
TCTAAAACCTGAATCTCCGC*TATTTTTTTTTTTTTTTTTTT*GATGACCCCGTTTTCGTGACAAATTAATTTCCAACGG
GGTCTTGTCCGGATAAGAGAATTTTGTTTGATTATCCGTTCGGATAAATGGACGCCTGCTCCATATTTTTCCGGT
TATTACCCCACCTGGAAGTGCCCAGAATTTTCCGGGGATTACGGATAATACGGTGGTCTGGATTAATTAATACG
CCAAGTCTTACATTTTGTTGCAGTCTCGTGCGAGTATGTGCAATAATAAACAAGATGAGCCAATTTATTGGATTAG
TTGCAGCTTGACCCCGCCATAGCTAGGCATAGCCAAGTGCTATGGGTGTTAGATGATGCACTTGGATGCAGTGA
GTTTTGGAGTATAAAAGATCCTTAAAATTCCACCCTT pG1-3 (PG1-D1240-TA(T)$_{19}$-(T)$_{19}$): Example comprising a first T motif which is (T)$_n$ (n=19) extended by preceding TA (extending the T motif at its 5'-end to become a TA(T)$_n$ motif; and a second T motif which is (T)$_n$ (n=19) without a TA extension

SEQ ID 70

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTTT*GATGACCCCGTTTTCGTGACAAATTA
ATTTCCAACGGGGTCTTGTCCGGATAAGAGAATTTTGTTTGATTATCCGTTCGGATAAATGGACGCCTGCTCCAT
ATTTTTCCGGTTATTACCCCACCTGGAAGTGCCCAGAATTTTCCGGGGATTACGGATAATACGGTGGTCTGGAT
TAATTAATACGAGATCTCAGGGATTCCCACTATTTGGTATTCTGATATGTTTTTCCTGATATGCATCAAAACTCTAA
TCTAAAACCTGAATCTCCGC*TTTTTTTTTTTTTTTTTTT*GATGACCCCGTTTTCGTGACAAATTAATTTCCAACGGGG
TCTTGTCCGGATAAGAGAATTTTGTTTGATTATCCGTTCGGATAAATGGACGCCTGCTCCATATTTTTCCGGTTA
TTACCCCACCTGGAAGTGCCCAGAATTTTCCGGGGATTACGGATAATACGGTGGTCTGGATTAATTAATACGCC
AAGTCTTACATTTTGTTGCAGTCTCGTGCGAGTATGTGCAATAATAAACAAGATGAGCCAATTTATTGGATTAGTT
GCAGCTTGACCCCGCCATAGCTAGGCATAGCCAAGTGCTATGGGTGTTAGATGATGCACTTGGATGCAGTGAGT
TTTGGAGTATAAAAGATCCTTAAAATTCCACCCTT

FIG.6B-23 pG1-3 (PG1-D1240-$(T)_{19}$-TA$(T)_{19}$): Example comprising a first T motif which is $(T)_n$ (n=19) without a TA extension; and a second T motif which is $(T)_n$ (n=19) extended by preceding TA (extending the T motif at its 5'-end to become a TA$(T)_n$ motif

SEQ ID 71

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTTT*GATGACCCCGTTTTCGTGACAAATTAAT
TTCCAACGGGGTCTTGT**CCGGATAAGAGAATTTTGTTTGATTATCCGTTCGGATAAATGGA*CGCCTGCTC*CATAT**
TTTTCCGGTTATTACCCCACCTGGAAGTGCCCAGAATTTTCCGGGGATTACGGATAATACGGTGGTCTGGATTA
ATTAATACGAGATCTCAGGGATTCCCACTATTTGGTATTCTGATATGTTTTTCCTGATATGCATCAAAACTCTAATC
TAAAACCTGAATCTCCGC*TATTTTTTTTTTTTTTTTTTT*GATGACCCCGTTTTCGTGACAAATTAATTTCCAACGGGG
TCTTGT**CCGGATAAGAGAATTTTGTTTGATTATCCGTTCGG*ATAAATGGACGCCTGCTCCATATTTTTCCGGTT*A**
TTACCCCACCTGGAAGTGCCCAGAATTTTCCGGGGATTACGGATAATACGGTGGTCTGGATTAATTAATACGCC
AAGTCTTACATTTTGTTGCAGTCTCGTGCGAGTATGTGCAATAATAAACAAGATGAGCCAATTTATTGGATTAGTT
GCAGCTTGACCCCGCCATAGCTAGGCATAGCCAAGTGCTATGGGTGTTAGATGATGCACTTGGATGCAGTGAGT
TTTGGAGTATAAAAGATCCTTAAAATTCCACCCTT pG1-3 (PG1-D1240-2x$(T)_{19}$): Example comprising two T motifs which are $(T)_n$ (n=19), each without a TA extension

SEQ ID 72

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTTT*GATGACCCCGTTTTCGTGACAAATTAAT
TTCCAACGGGGTCTTGT**CCGGATAAGAGAATTTTGTTTGATTATCCGTTCGGATAAATGGA*CGCCTGCTC*CATAT**
TTTTCCGGTTATTACCCCACCTGGAAGTGCCCAGAATTTTCCGGGGATTACGGATAATACGGTGGTCTGGATTA
ATTAATACGAGATCTCAGGGATTCCCACTATTTGGTATTCTGATATGTTTTTCCTGATATGCATCAAAACTCTAATC
TAAAACCTGAATCTCCGC*TTTTTTTTTTTTTTTTTTT*GATGACCCCGTTTTCGTGACAAATTAATTTCCAACGGGGTC
TTGT**CCGGATAAGAGAATTTTGTTTGATTATCCGTTCGG*ATAAATGGACGCCTGCTCCATATTTTTCCGGTT*ATT**
ACCCCACCTGGAAGTGCCCAGAATTTTCCGGGGATTACGGATAATACGGTGGTCTGGATTAATTAATACGCCAA
GTCTTACATTTTGTTGCAGTCTCGTGCGAGTATGTGCAATAATAAACAAGATGAGCCAATTTATTGGATTAGTTGC
AGCTTGACCCCGCCATAGCTAGGCATAGCCAAGTGCTATGGGTGTTAGATGATGCACTTGGATGCAGTGAGTTTT
GGAGTATAAAAGATCCTTAAAATTCCACCCTT

FIG. 6B-24 pG1-3 (PG1-D1240-2xTA$(T)_{20}$): Example comprising two T motifs which are $(T)_n$ (n=20), each extended by preceding TA (extending the T motif at its 5'-end to become a TA$(T)_n$ motif)

SEQ ID 73

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTTTT*GATGACCCCGTTTTCGTGACAAATT
AATTTCCAACGGGGTCTTGT**CCGGATAAGAGAATTTTGTTTGATTATCCGTTCGGATAAATGGA*CGCCTGCTCCA***
***TATTTTTCCGGTT*ATTACCCCACCTGGAAGTGCCCAGAATTTTCCGGGGATTACGGATAATA**CGGTGGTCTGGA
TTAATTAATACGAGATCTCAGGGATTCCCACTATTTGGTATTCTGATATGTTTTTCCTGATATGCATCAAAACTCTA
ATCTAAAACCTGAATCTCCGC*TATTTTTTTTTTTTTTTTTTTT*GATGACCCCGTTTTCGTGACAAATTAATTTCCAAC
GGGGTCTTGT**CCGGATAAGAGAATTTTGTTTGATTATCCGTTCGG*ATAAATGGACGCCTGCTCCATATTTTTCCG***
***GTT*ATTACCCCACCTGGAAGTGCCCAGAATTTTCCGGGGATTACGGATAATAC**GGTGGTCTGGATTAATTAATA
CGCCAAGTCTTACATTTTGTTGCAGTCTCGTGCGAGTATGTGCAATAATAAACAAGATGAGCCAATTTATTGGATT
AGTTGCAGCTTGACCCCGCCATAGCTAGGCATAGCCAAGTGCTATGGGTGTTAGATGATGCACTTGGATGCAGT
GAGTTTTGGAGTATAAAAGATCCTTAAAATTCCACCCTT pG1-3 (PG1-D1240-TA$(T)_{20}$-$(T)_{20}$): Example comprising a first T motif which is $(T)_n$ (n=20) extended by preceding TA (extending the T motif at its 5'-end to become a TA$(T)_n$ motif; and a second T motif which is $(T)_n$ (n=20) without a TA extension

SEQ ID 74

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTTTT*GATGACCCCGTTTTCGTGACAAATT
AATTTCCAACGGGGTCTTGT**CCGGATAAGAGAATTTTGTTTGATTATCCGTTCGGATAAATGGA*CGCCTGCTCCA***
***TATTTTTCCGGTT*ATTACCCCACCTGGAAGTGCCCAGAATTTTCCGGGGATTACGGATAATA**CGGTGGTCTGGA
TTAATTAATACGAGATCTCAGGGATTCCCACTATTTGGTATTCTGATATGTTTTTCCTGATATGCATCAAAACTCTA
ATCTAAAACCTGAATCTCCGC*TTTTTTTTTTTTTTTTTTTT*GATGACCCCGTTTTCGTGACAAATTAATTTCCAACGG
GGTCTTGT**CCGGATAAGAGAATTTTGTTTGATTATCCGTTCGG*ATAAATGGACGCCTGCTCCATATTTTTCCGGT***
***T*ATTACCCCACCTGGAAGTGCCCAGAATTTTCCGGGGATTACGGATAATAC**GGTGGTCTGGATTAATTAATACG
CCAAGTCTTACATTTTGTTGCAGTCTCGTGCGAGTATGTGCAATAATAAACAAGATGAGCCAATTTATTGGATTAG
TTGCAGCTTGACCCCGCCATAGCTAGGCATAGCCAAGTGCTATGGGTGTTAGATGATGCACTTGGATGCAGTGA
GTTTTGGAGTATAAAAGATCCTTAAAATTCCACCCTT

FIG.6B-25 pG1-3 (PG1-D1240-$(T)_{20}$-TA$(T)_{20}$): Example comprising a first T motif which is $(T)_n$ (n=20) without a TA extension; and a second T motif which is $(T)_n$ (n=20) extended by preceding TA (extending the T motif at its 5'-end to become a TA$(T)_n$ motif

SEQ ID 75

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTTTT*GATGACCCCGTTTTCGTGACAAATTAA
TTTCCAACGGGGTCTTGTCCGGATAAGAGAATTTTGTTTGATTATCCGTTCGGATAAATGGACGCCTGCTCCATA
TTTTTCCGGTTATTACCCCACCTGGAAGTGCCCAGAATTTTCCGGGGATTACGGATAATACGGTGGTCTGGATT
AATTAATACGAGATCTCAGGGATTCCCACTATTTGGTATTCTGATATGTTTTTCCTGATATGCATCAAAACTCTAAT
CTAAAACCTGAATCTCCGC*TATTTTTTTTTTTTTTTTTTTT*GATGACCCCGTTTTCGTGACAAATTAATTTCCAACGG
GGTCTTGTCCGGATAAGAGAATTTTGTTTGATTATCCGTTCGGATAAATGGACGCCTGCTCCATATTTTTCCGGT
TATTACCCCACCTGGAAGTGCCCAGAATTTTCCGGGGATTACGGATAATACGGTGGTCTGGATTAATTAATACG
CCAAGTCTTACATTTTGTTGCAGTCTCGTGCGAGTATGTGCAATAATAAACAAGATGAGCCAATTTATTGGATTAG
TTGCAGCTTGACCCCGCCATAGCTAGGCATAGCCAAGTGCTATGGGTGTTAGATGATGCACTTGGATGCAGTGA
GTTTTGGAGTATAAAAGATCCTTAAAATTCCACCCTT pG1-3 (PG1-D1240-2x$(T)_{20}$): Example comprising two T motifs which are $(T)_n$ (n=20), each without a TA extension

SEQ ID 76

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTTTT*GATGACCCCGTTTTCGTGACAAATTAA
TTTCCAACGGGGTCTTGTCCGGATAAGAGAATTTTGTTTGATTATCCGTTCGGATAAATGGACGCCTGCTCCATA
TTTTTCCGGTTATTACCCCACCTGGAAGTGCCCAGAATTTTCCGGGGATTACGGATAATACGGTGGTCTGGATT
AATTAATACGAGATCTCAGGGATTCCCACTATTTGGTATTCTGATATGTTTTTCCTGATATGCATCAAAACTCTAAT
CTAAAACCTGAATCTCCGC*TTTTTTTTTTTTTTTTTTTT*GATGACCCCGTTTTCGTGACAAATTAATTTCCAACGGGG
TCTTGTCCGGATAAGAGAATTTTGTTTGATTATCCGTTCGGATAAATGGACGCCTGCTCCATATTTTTCCGGTTA
TTACCCCACCTGGAAGTGCCCAGAATTTTCCGGGGATTACGGATAATACGGTGGTCTGGATTAATTAATACGCC
AAGTCTTACATTTTGTTGCAGTCTCGTGCGAGTATGTGCAATAATAAACAAGATGAGCCAATTTATTGGATTAGTT
GCAGCTTGACCCCGCCATAGCTAGGCATAGCCAAGTGCTATGGGTGTTAGATGATGCACTTGGATGCAGTGAGT
TTTGGAGTATAAAAGATCCTTAAAATTCCACCCTT

FIG.6B-26 pG1-4 (PG1-D1427-2xTA(T)$_n$): Example comprising two T motifs which are (T)$_n$ (n=13-20), each extended by preceding TA (extending the T motif at its 5'-end to become a TA(T)$_n$ motif)

SEQ ID 77

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TA(T)*$_n$GATGACCCCGTTTTCGTGACAAATTAATTTCCAACGGGGT
CTTGT**CCGGATAAGAGAATTTTGTTTGATTATCCGTTCGG*ATAAATGGACGCCTGCTCCATATTTTTCCGGTT*AT**
TACCCCACCTGGAAGTGCCCAGAATTTTCCGGGGATTACGGATAATACGGTGGTCTGGATTAATTAATACGCCA
AGTCTTACATTTTGTTGCAGTCTCGTGCGAGTATGTGCAATAATAAACAAGATGAGCCAATTTATTGGATTAGTTG
CAGCTTGACCCCGCCATAGCTAGGCATAGCCAAGTGCTATGGGTGTTAGATGATGCACTTGGATGCAGTGAGTTT
TGGAGTATAAAAGATCCTTAAAATTCCACCCTTAGATCTCAGGGATTCCCACTATTTGGTATTCTGATATGTTTTTC
CTGATATGCATCAAAACTCTAATCTAAAACCTGAATCTCCGC*TA(T)*$_n$GATGACCCCGTTTTCGTGACAAATTAATTT
CCAACGGGGTCTTGT**CCGGATAAGAGAATTTTGTTTGATTATCCGTTCGG*ATAAATGGACGCCTGCTCCATATTT***
***TTCCGGTT*ATTACCCCACCTGGAAGTGCCCAGAATTTTCCGGGGATTACGGATAATAC**GGTGGTCTGGATTAAT
TAATACGCCAAGTCTTACATTTTGTTGCAGTCTCGTGCGAGTATGTGCAATAATAAACAAGATGAGCCAATTTATT
GGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTT

FIG.6B-27 pG1-4 (PG1-D1427-$TA(T)_n$-$(T)_n$): Example comprising a first T motif which is $(T)_n$ (n=13-20) extended by preceding TA (extending the T motif at its 5'-end to become a $TA(T)_n$ motif; and a second T motif which is $(T)_n$ (n=13-20) without a TA extension

SEQ ID 78

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*$TA(T)_n$*GATGACCCCGTTTTCGTGACAAATTAATTTCCAACGGGGT
CTTGT**CCGGATAAGAGAATTTTGTTTGATTATCCGTTCGG*ATAAATGGACGCCTGCTCCATATTTTTCCGGTT*AT**
TACCCCACCTGGAAGTGCCCAGAATTTTCCGGGGATTACGGATAATACGGTGGTCTGGATTAATTAATACGCCA
AGTCTTACATTTTGTTGCAGTCTCGTGCGAGTATGTGCAATAATAAACAAGATGAGCCAATTTATTGGATTAGTTG
CAGCTTGACCCCGCCATAGCTAGGCATAGCCAAGTGCTATGGGTGTTAGATGATGCACTTGGATGCAGTGAGTTT
TGGAGTATAAAAGATCCTTAAAATTCCACCCTTAGATCTCAGGGATTCCCACTATTTGGTATTCTGATATGTTTTTC
CTGATATGCATCAAAACTCTAATCTAAAACCTGAATCTCCGC*$(T)_n$*GATGACCCCGTTTTCGTGACAAATTAATTTCC
AACGGGGTCTTGT**CCGGATAAGAGAATTTTGTTTGATTATCCGTTCGG*ATAAATGGACGCCTGCTCCATATTTTT***
***CCGGTT*ATTACCCCACCTGGAAGTGCCCAGAATTTTCCGGGGATTACGGATAATAC**GGTGGTCTGGATTAATTA
ATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTT

FIG.6B-28 pG1-4 (PG1-D1427-$(T)_n$-TA$(T)_n$): Example comprising a first T motif which is $(T)_n$ (n=13-20) without a TA extension; and a second T motif which is $(T)_n$ (n=13-20) extended by preceding TA (extending the T motif at its 5'-end to become a TA$(T)_n$ motif

SEQ ID 79

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*$(T)_n$*GATGACCCCGTTTTCGTGACAAATTAATTTCCAACGGGGTCTT
GT**CCGGATAAGAGAATTTTGTTTGATTATCCGTTCGG*ATAAATGGACGCCTGCTCCATATTTTTCCGGTT*ATTAC**
CCCACCTGGAAGTGCCCAGAATTTTCCGGGGATTACGGATAATACGGTGGTCTGGATTAATTAATACGCCAAGT
CTTACATTTTGTTGCAGTCTCGTGCGAGTATGTGCAATAATAAACAAGATGAGCCAATTTATTGGATTAGTTGCAG
CTTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTTAGATCTCAGGGATTCCCACTATTTGGTATTCTGATATGTTTTTCCTG
ATATGCATCAAAACTCTAATCTAAAACCTGAATCTCCGC*TA$(T)_n$*GATGACCCCGTTTTCGTGACAAATTAATTTCCA
ACGGGGTCTTGT**CCGGATAAGAGAATTTTGTTTGATTATCCGTTCGG*ATAAATGGACGCCTGCTCCATATTTTTC***
***CGGTT*ATTACCCCACCTGGAAGTGCCCAGAATTTTCCGGGGATTACGGATAATAC**GGTGGTCTGGATTAATTAA
TACGCCAAGTCTTACATTTTGTTGCAGTCTCGTGCGAGTATGTGCAATAATAAACAAGATGAGCCAATTTATTGG
ATTAGTTGCAGCTTGACCCCGCCATAGCTAGGCATAGCCAAGTGCTATGGGTGTTAGATGATGCACTTGGATGCA
GTGAGTTTTGGAGTATAAAAGATCCTTAAAATTCCACCCTT

FIG.6B-29 pG1-4 (PG1-D1427-2x$(T)_n$): Example comprising two T motifs which are $(T)_n$ (n=13-20), each without a TA extension

SEQ ID 80

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*$(T)_n$*GATGACCCCGTTTTCGTGACAAATTAATTTCCAACGGGGTCTT
GT**CCGGATAAGAGAATTTTGTTTGATTATCCGTTCGG*ATAAATGGACGCCTGCTCCATATTTTTCCGGTT*ATTAC**
CCCACCTGGAAGTGCCCAGAATTTTCCGGGGATTACGGATAATACGGTGGTCTGGATTAATTAATACGCCAAGT
CTTACATTTTGTTGCAGTCTCGTGCGAGTATGTGCAATAATAAACAAGATGAGCCAATTTATTGGATTAGTTGCAG
CTTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTTAGATCTCAGGGATTCCCACTATTTGGTATTCTGATATGTTTTTCCTG
ATATGCATCAAAACTCTAATCTAAAACCTGAATCTCCGC*$(T)_n$*GATGACCCCGTTTTCGTGACAAATTAATTTCCAAC
GGGGTCTTGT**CCGGATAAGAGAATTTTGTTTGATTATCCGTTCGG*ATAAATGGACGCCTGCTCCATATTTTTCCG***
***GTT*ATTACCCCACCTGGAAGTGCCCAGAATTTTCCGGGGATTACGGATAATAC**GGTGGTCTGGATTAATTAATA
CGCCAAGTCTTACATTTTGTTGCAGTCTCGTGCGAGTATGTGCAATAATAAACAAGATGAGCCAATTTATTGGATT
AGTTGCAGCTTGACCCCGCCATAGCTAGGCATAGCCAAGTGCTATGGGTGTTAGATGATGCACTTGGATGCAGT
GAGTTTTGGAGTATAAAAGATCCTTAAAATTCCACCCTT

FIG.6B-30 pG1-4 (PG1-D1427-2xTA$(T)_{13}$): Example comprising two T motifs which are $(T)_n$ (n=13), each extended by preceding TA (extending the T motif at its 5'-end to become a TA$(T)_n$ motif)

SEQ ID 81

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTT*GATGACCCCGTTTTCGTGACAAATTAATTTCC
AACGGGGTCTTGT**CCGGATAAGAGAATTTTGTTTGATTATCCGTTCGG*ATAAATGGACGCCTGCTCCATATTTTT***
***CCGGTT*ATTACCCCACCTGGAAGTGCCCAGAATTTTCCGGGGATTACGGATAATA**CGGTGGTCTGGATTAATTA
ATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTTAGATCTCAGGGATTCCCACTATTTGGTATTCTGA
TATGTTTTTCCTGATATGCATCAAAACTCTAATCTAAAACCTGAATCTCCGC*TATTTTTTTTTTTTT*GATGACCCCGT
TTTCGTGACAAATTAATTTCCAACGGGGTCTTGT**CCGGATAAGAGAATTTTGTTTGATTATCCGTTCGG*ATAAAT***
***GGACGCCTGCTCCATATTTTTCCGGTT*ATTACCCCACCTGGAAGTGCCCAGAATTTTCCGGGGATTACGGATAAT**
ACGGTGGTCTGGATTAATTAATACGCCAAGTCTTACATTTTGTTGCAGTCTCGTGCGAGTATGTGCAATAATAAA
CAAGATGAGCCAATTTATTGGATTAGTTGCAGCTTGACCCCGCCATAGCTAGGCATAGCCAAGTGCTATGGGTGT
TAGATGATGCACTTGGATGCAGTGAGTTTTGGAGTATAAAAGATCCTTAAAATTCCACCCTT

FIG.6B-31 pG1-4 (PG1-D1427-TA$(T)_{13}$-$(T)_{13}$): Example comprising a first T motif which is $(T)_n$ (n=13) extended by preceding TA (extending the T motif at its 5'-end to become a TA$(T)_n$ motif; and a second T motif which is $(T)_n$ (n=13) without a TA extension

SEQ ID 82

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTT*GATGACCCCGTTTTCGTGACAAATTAATTTCC
AACGGGGTCTTGT**CCGGATAAGAGAATTTTGTTTGATTATCCGTTCGG*ATAAATGGACGCCTGCTCCATATTTTT***
***CCGGTT*ATTACCCCACCTGGAAGTGCCCAGAATTTTCCGGGGATTACGGATAATA**CGGTGGTCTGGATTAATTA
ATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTTAGATCTCAGGGATTCCCACTATTTGGTATTCTGA
TATGTTTTTCCTGATATGCATCAAAACTCTAATCTAAAACCTGAATCTCCGC*TTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT

FIG.6B-32 pG1-4 (PG1-D1427-$(T)_{13}$-TA$(T)_{13}$): Example comprising a first T motif which is $(T)_n$ (n=13) without a TA extension; and a second T motif which is $(T)_n$ (n=13) extended by preceding TA (extending the T motif at its 5′-end to become a TA$(T)_n$ motif

SEQ ID 83

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTT*GATGACCCCGTTTTCGTGACAAATTAATTTCCAA
CGGGGTCTTGT**CCGGATAAGAGAATTTTGTTTGATTATCCGTTCGG*ATAAATGGACGCCTGCTCCATATTTTTCC***
***GGTT*ATTACCCCACCTGGAAGTGCCCAGAATTTTCCGGGGATTACGGATAATA**CGGTGGTCTGGATTAATTAAT
ACGCCAAGTCTTACATTTTGTTGCAGTCTCGTGCGAGTATGTGCAATAATAAACAAGATGAGCCAATTTATTGGA
TTAGTTGCAGCTTGACCCCGCCATAGCTAGGCATAGCCAAGTGCTATGGGTGTTAGATGATGCACTTGGATGCAG
TGAGTTTTGGAGTATAAAAGATCCTTAAAATTCCACCCTTAGATCTCAGGGATTCCCACTATTTGGTATTCTGATA
TGTTTTTCCTGATATGCATCAAAACTCTAATCTAAAACCTGAATCTCCGC*TATTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT

FIG.6B-33 pG1-4 (PG1-D1427-2x(T)$_{13}$): Example comprising two T motifs which are (T)$_n$ (n=13), each without a TA extension

SEQ ID 84

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTT*GATGACCCCGTTTTCGTGACAAATTAATTTCCAA
CGGGGTCTTGT**CCGGATAAGAGAATTTTGTTTGATTATCCGTTCGG*ATAAATGGACGCCTGCTCCATATTTTTCC***
***GGTT*ATTACCCCACCTGGAAGTGCCCAGAATTTTCCGGGGATTACGGATAATA**CGGTGGTCTGGATTAATTAAT
ACGCCAAGTCTTACATTTTGTTGCAGTCTCGTGCGAGTATGTGCAATAATAAACAAGATGAGCCAATTTATTGGA
TTAGTTGCAGCTTGACCCCGCCATAGCTAGGCATAGCCAAGTGCTATGGGTGTTAGATGATGCACTTGGATGCAG
TGAGTTTTGGAGTATAAAAGATCCTTAAAATTCCACCCTTAGATCTCAGGGATTCCCACTATTTGGTATTCTGATA
TGTTTTTCCTGATATGCATCAAAACTCTAATCTAAAACCTGAATCTCCGC*TTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATAC**G
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT

FIG.6B-34 pG1-4 (PG1-D1427-2xTA$(T)_{14}$): Example comprising two T motifs which are $(T)_n$ (n=14), each extended by preceding TA (extending the T motif at its 5′-end to become a TA$(T)_n$ motif)

SEQ ID 85

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTT*GATGACCCCGTTTTCGTGACAAATTAATTTC
CAACGGGGTCTTGT**CCGGATAAGAGAATTTTGTTTGATTATCCGTTCGG*ATAAATGGACGCCTGCTCCATATTTT***
***TCCGGTT*ATTACCCCACCTGGAAGTGCCCAGAATTTTCCGGGGATTACGGATAATA**CGGTGGTCTGGATTAATT
AATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTTAGATCTCAGGGATTCCCACTATTTGGTATTCTGA
TATGTTTTTCCTGATATGCATCAAAACTCTAATCTAAAACCTGAATCTCCGC*TATTTTTTTTTTTTTT*GATGACCCCG
TTTTCGTGACAAATTAATTTCCAACGGGGTCTTGT**CCGGATAAGAGAATTTTGTTTGATTATCCGTTCGG*ATAAA***
***TGGACGCCTGCTCCATATTTTTCCGGTT*ATTACCCCACCTGGAAGTGCCCAGAATTTTCCGGGGATTACGGATAA**
TACGGTGGTCTGGATTAATTAATACGCCAAGTCTTACATTTTGTTGCAGTCTCGTGCGAGTATGTGCAATAATAAA
CAAGATGAGCCAATTTATTGGATTAGTTGCAGCTTGACCCCGCCATAGCTAGGCATAGCCAAGTGCTATGGGTGT
TAGATGATGCACTTGGATGCAGTGAGTTTTGGAGTATAAAAGATCCTTAAAATTCCACCCTT

FIG.6B-35 pG1-4 (PG1-D1427-TA$(T)_{14}$-$(T)_{14}$): Example comprising a first T motif which is $(T)_n$ (n=14) extended by preceding TA (extending the T motif at its 5'-end to become a TA$(T)_n$ motif; and a second T motif which is $(T)_n$ (n=14) without a TA extension

SEQ ID 86

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTT*GATGACCCCGTTTTCGTGACAAATTAATTTC
CAACGGGGTCTTGT**CCGGATAAGAGAATTTTGTTTGATTATCCGTTCGG*ATAAATGGACGCCTGCTCCATATTTT***
***TCCGGTT*ATTACCCCACCTGGAAGTGCCCAGAATTTTCCGGGGATTACGGATAATA**CGGTGGTCTGGATTAATT
AATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTTAGATCTCAGGGATTCCCACTATTTGGTATTCTGA
TATGTTTTTCCTGATATGCATCAAAACTCTAATCTAAAACCTGAATCTCCGC*TTTTTTTTTTTTTT*GATGACCCCGTT
TTCGTGACAAATTAATTTCCAACGGGGTCTTGT**CCGGATAAGAGAATTTTGTTTGATTATCCGTTCGG*ATAAATG***
***GACGCCTGCTCCATATTTTTCCGGTT*ATTACCCCACCTGGAAGTGCCCAGAATTTTCCGGGGATTACGGATAATA**
CGGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT

FIG.6B-36 pG1-4 (PG1-D1427-$(T)_{14}$-TA$(T)_{14}$): Example comprising a first T motif which is $(T)_n$ (n=14) without a TA extension; and a second T motif which is $(T)_n$ (n=14) extended by preceding TA (extending the T motif at its 5′-end to become a TA$(T)_n$ motif

SEQ ID 87

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTT*GATGACCCCGTTTTCGTGACAAATTAATTTCCA
ACGGGGTCTTGT**CCGGATAAGAGAATTTTGTTTGATTATCCGTTCGG*ATAAATGGACGCCTGCTCCATATTTTTC***
***CGGTT*ATTACCCCACCTGGAAGTGCCCAGAATTTTCCGGGGATTACGGATAATA**CGGTGGTCTGGATTAATTAA
TACGCCAAGTCTTACATTTTGTTGCAGTCTCGTGCGAGTATGTGCAATAATAAACAAGATGAGCCAATTTATTGG
ATTAGTTGCAGCTTGACCCCGCCATAGCTAGGCATAGCCAAGTGCTATGGGTGTTAGATGATGCACTTGGATGCA
GTGAGTTTTGGAGTATAAAAGATCCTTAAAATTCCACCCTTAGATCTCAGGGATTCCCACTATTTGGTATTCTGAT
ATGTTTTTCCTGATATGCATCAAAACTCTAATCTAAAACCTGAATCTCCGC*TATTTTTTTTTTTTTT*GATGACCCCGT
TTTCGTGACAAATTAATTTCCAACGGGGTCTTGT**CCGGATAAGAGAATTTTGTTTGATTATCCGTTCGG*ATAAAT***
***GGACGCCTGCTCCATATTTTTCCGGTT*ATTACCCCACCTGGAAGTGCCCAGAATTTTCCGGGGATTACGGATAAT**
ACGGTGGTCTGGATTAATTAATACGCCAAGTCTTACATTTTGTTGCAGTCTCGTGCGAGTATGTGCAATAATAAA
CAAGATGAGCCAATTTATTGGATTAGTTGCAGCTTGACCCCGCCATAGCTAGGCATAGCCAAGTGCTATGGGTGT
TAGATGATGCACTTGGATGCAGTGAGTTTTGGAGTATAAAAGATCCTTAAAATTCCACCCTT

FIG. 6B-37 pG1-4 (PG1-D1427-2x$(T)_{14}$): Example comprising two T motifs which are $(T)_n$ (n=14), each without a TA extension

SEQ ID 88

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTT*GATGACCCCGTTTTCGTGACAAATTAATTTCCA
ACGGGGTCTTGT**CCGGATAAGAGAATTTTGTTTGATTATCCGTTCGG*ATAAATGGACGCCTGCTCCATATTTTTC***
***CGGTT*ATTACCCCACCTGGAAGTGCCCAGAATTTTCCGGGGATTACGGATAATA**CGGTGGTCTGGATTAATTAA
TACGCCAAGTCTTACATTTTGTTGCAGTCTCGTGCGAGTATGTGCAATAATAAACAAGATGAGCCAATTTATTGG
ATTAGTTGCAGCTTGACCCCGCCATAGCTAGGCATAGCCAAGTGCTATGGGTGTTAGATGATGCACTTGGATGCA
GTGAGTTTTGGAGTATAAAAGATCCTTAAAATTCCACCCTTAGATCTCAGGGATTCCCACTATTTGGTATTCTGAT
ATGTTTTTCCTGATATGCATCAAAACTCTAATCTAAAACCTGAATCTCCGC*TTTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT

FIG.6B-38 pG1-4 (PG1-D1427-2xTA$(T)_{15}$): Example comprising two T motifs which are $(T)_n$ (n=15), each extended by preceding TA (extending the T motif at its 5'-end to become a TA$(T)_n$ motif)

SEQ ID 89

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTT*GATGACCCCGTTTTCGTGACAAATTAATTT
CCAACGGGGTCTTGT**CCGGATAAGAGAATTTTGTTTGATTATCCGTTCGG*ATAAATGGACGCCTGCTCCATATTT***
***TTCCGGTT*ATTACCCCACCTGGAAGTGCCCAGAATTTTCCGGGGATTACGGATAATA**CGGTGGTCTGGATTAAT
TAATACGCCAAGTCTTACATTTTGTTGCAGTCTCGTGCGAGTATGTGCAATAATAAACAAGATGAGCCAATTTATT
GGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTTAGATCTCAGGGATTCCCACTATTTGGTATTCT
GATATGTTTTTCCTGATATGCATCAAAACTCTAATCTAAAACCTGAATCTCCGC*TATTTTTTTTTTTTTTT*GATGACC
CCGTTTTCGTGACAAATTAATTTCCAACGGGGTCTTGT**CCGGATAAGAGAATTTTGTTTGATTATCCGTTCGG*AT***
***AAATGGACGCCTGCTCCATATTTTTCCGGTT*ATTACCCCACCTGGAAGTGCCCAGAATTTTCCGGGGATTACGG**
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT

FIG.6B-39 pG1-4 (PG1-D1427-TA$(T)_{15}$-$(T)_{15}$): Example comprising a first T motif which is $(T)_n$ (n=15) extended by preceding TA (extending the T motif at its 5'-end to become a TA$(T)_n$ motif; and a second T motif which is $(T)_n$ (n=15) without a TA extension

SEQ ID 90

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTT*GATGACCCCGTTTTCGTGACAAATTAATTT
CCAACGGGGTCTTGTCCGGATAAGAGAATTTTGTTTGATTATCCGTTCGG*ATAAATGGACGCCTGCTCCATATTT*
*TTCCGGTT*ATTACCCCACCTGGAAGTGCCCAGAATTTTCCGGGGATTACGGATAATACGGTGGTCTGGATTAAT
TAATACGCCAAGTCTTACATTTTGTTGCAGTCTCGTGCGAGTATGTGCAATAATAAACAAGATGAGCCAATTTATT
GGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTTAGATCTCAGGGATTCCCACTATTTGGTATTCT
GATATGTTTTTCCTGATATGCATCAAAACTCTAATCTAAAACCTGAATCTCCGC*TTTTTTTTTTTTTTT*GATGACCCC
GTTTTCGTGACAAATTAATTTCCAACGGGGTCTTGTCCGGATAAGAGAATTTTGTTTGATTATCCGTTCGG*ATAA*
*ATGGACGCCTGCTCCATATTTTTCCGGTT*ATTACCCCACCTGGAAGTGCCCAGAATTTTCCGGGGATTACGGATA
ATACGGTGGTCTGGATTAATTAATACGCCAAGTCTTACATTTTGTTGCAGTCTCGTGCGAGTATGTGCAATAATAA
ACAAGATGAGCCAATTTATTGGATTAGTTGCAGCTTGACCCCGCCATAGCTAGGCATAGCCAAGTGCTATGGGTG
TTAGATGATGCACTTGGATGCAGTGAGTTTTGGAGTATAAAAGATCCTTAAAATTCCACCCTT

FIG.6B-40 pG1-4 (PG1-D1427-$(T)_{15}$-TA$(T)_{15}$): Example comprising a first T motif which is $(T)_n$ (n=15) without a TA extension; and a second T motif which is $(T)_n$ (n=15) extended by preceding TA (extending the T motif at its 5′-end to become a TA$(T)_n$ motif

SEQ ID 91

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTT*GATGACCCCGTTTTCGTGACAAATTAATTTCC
AACGGGGTCTTGT**CCGGATAAGAGAATTTTGTTTGATTATCCGTTCGG*ATAAATGGACGCCTGCTCCATATTTTT***
***CCGGTT*ATTACCCCACCTGGAAGTGCCCAGAATTTTCCGGGGATTACGGATAATA**CGGTGGTCTGGATTAATTA
ATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTTAGATCTCAGGGATTCCCACTATTTGGTATTCTGA
TATGTTTTTCCTGATATGCATCAAAACTCTAATCTAAAACCTGAATCTCCGC*TATTTTTTTTTTTTTTT*GATGACCCC
GTTTTCGTGACAAATTAATTTCCAACGGGGTCTTGT**CCGGATAAGAGAATTTTGTTTGATTATCCGTTCGG*ATAA***
***ATGGACGCCTGCTCCATATTTTTCCGGTT*ATTACCCCACCTGGAAGTGCCCAGAATTTTCCGGGGATTACGGATA**
ATACGGTGGTCTGGATTAATTAATACGCCAAGTCTTACATTTTGTTGCAGTCTCGTGCGAGTATGTGCAATAATAA
ACAAGATGAGCCAATTTATTGGATTAGTTGCAGCTTGACCCCGCCATAGCTAGGCATAGCCAAGTGCTATGGGTG
TTAGATGATGCACTTGGATGCAGTGAGTTTTGGAGTATAAAAGATCCTTAAAATTCCACCCTT

FIG.6B-41 pG1-4 (PG1-D1427-2x(T)$_{15}$): Example comprising two T motifs which are (T)$_n$ (n=15), each without a TA extension

SEQ ID 92

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTT*GATGACCCCGTTTTCGTGACAAATTAATTTCC
AACGGGGTCTTGT**CCGGATAAGAGAATTTTGTTTGATTATCCGTTCGG*ATAAATGGACGCCTGCTCCATATTTTT***
***CCGGTT*ATTACCCCACCTGGAAGTGCCCAGAATTTTCCGGGGATTACGGATAATA**CGGTGGTCTGGATTAATTA
ATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTTAGATCTCAGGGATTCCCACTATTTGGTATTCTGA
TATGTTTTTCCTGATATGCATCAAAACTCTAATCTAAAACCTGAATCTCCGC*TTTTTTTTTTTTTTT*GATGACCCCGT
TTTCGTGACAAATTAATTTCCAACGGGGTCTTGT**CCGGATAAGAGAATTTTGTTTGATTATCCGTTCGG*ATAAAT***
***GGACGCCTGCTCCATATTTTTCCGGTT*ATTACCCCACCTGGAAGTGCCCAGAATTTTCCGGGGATTACGGATAAT**
ACGGTGGTCTGGATTAATTAATACGCCAAGTCTTACATTTTGTTGCAGTCTCGTGCGAGTATGTGCAATAATAAA
CAAGATGAGCCAATTTATTGGATTAGTTGCAGCTTGACCCCGCCATAGCTAGGCATAGCCAAGTGCTATGGGTGT
TAGATGATGCACTTGGATGCAGTGAGTTTTGGAGTATAAAAGATCCTTAAAATTCCACCCTT

FIG.6B-42 pG1-4 (PG1-D1427-2xTA$(T)_{16}$): Example comprising two T motifs which are $(T)_n$ (n=16), each extended by preceding TA (extending the T motif at its 5'-end to become a TA$(T)_n$ motif)

SEQ ID 93

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTT*GATGACCCCGTTTTCGTGACAAATTAATT
TCCAACGGGGTCTTGT**CCGGATAAGAGAATTTTGTTTGATTATCCGTTCGG*ATAAATGGACGCCTGCTCCATATT***
***TTTCCGGTT*ATTACCCCACCTGGAAGTGCCCAGAATTTTCCGGGGATTACGGATAATA**CGGTGGTCTGGATTAA
TTAATACGCCAAGTCTTACATTTTGTTGCAGTCTCGTGCGAGTATGTGCAATAATAAACAAGATGAGCCAATTTAT
TGGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTTAGATCTCAGGGATTCCCACTATTTGGTATTCT
GATATGTTTTTCCTGATATGCATCAAAACTCTAATCTAAAACCTGAATCTCCGC*TATTTTTTTTTTTTTTTT*GATGAC
CCCGTTTTCGTGACAAATTAATTTCCAACGGGGTCTTGT**CCGGATAAGAGAATTTTGTTTGATTATCCGTTCGG*A***
***TAAATGGACGCCTGCTCCATATTTTTCCGGTT*ATTACCCCACCTGGAAGTGCCCAGAATTTTCCGGGGATTACGG**
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT

FIG.6B-43 pG1-4 (PG1-D1427-TA$(T)_{16}$-$(T)_{16}$): Example comprising a first T motif which is $(T)_n$ (n=16) extended by preceding TA (extending the T motif at its 5'-end to become a TA$(T)_n$ motif; and a second T motif which is $(T)_n$ (n=16) without a TA extension

SEQ ID 94

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTT*GATGACCCCGTTTTCGTGACAAATTAATT
TCCAACGGGGTCTTGT**CCGGATAAGAGAATTTTGTTTGATTATCCGTTCGG*ATAAATGGACGCCTGCTCCATATT***
***TTTCCGGTT*ATTACCCCACCTGGAAGTGCCCAGAATTTTCCGGGGATTACGGATAATA**CGGTGGTCTGGATTAA
TTAATACGCCAAGTCTTACATTTTGTTGCAGTCTCGTGCGAGTATGTGCAATAATAAACAAGATGAGCCAATTTAT
TGGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTTAGATCTCAGGGATTCCCACTATTTGGTATTCT
GATATGTTTTTCCTGATATGCATCAAAACTCTAATCTAAAACCTGAATCTCCGC*TTTTTTTTTTTTTTTT*GATGACCC
CGTTTTCGTGACAAATTAATTTCCAACGGGGTCTTGT**CCGGATAAGAGAATTTTGTTTGATTATCCGTTCGG*ATA***
***AATGGACGCCTGCTCCATATTTTTCCGGTT*ATTACCCCACCTGGAAGTGCCCAGAATTTTCCGGGGATTACGGAT**
AATACGGTGGTCTGGATTAATTAATACGCCAAGTCTTACATTTTGTTGCAGTCTCGTGCGAGTATGTGCAATAAT
AAACAAGATGAGCCAATTTATTGGATTAGTTGCAGCTTGACCCCGCCATAGCTAGGCATAGCCAAGTGCTATGG
GTGTTAGATGATGCACTTGGATGCAGTGAGTTTTGGAGTATAAAAGATCCTTAAAATTCCACCCTT

FIG.6B-44 pG1-4 (PG1-D1427-$(T)_{16}$-TA$(T)_{16}$): Example comprising a first T motif which is $(T)_n$ (n=16) without a TA extension; and a second T motif which is $(T)_n$ (n=16) extended by preceding TA (extending the T motif at its 5'-end to become a TA$(T)_n$ motif

SEQ ID 95

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTT*GATGACCCCGTTTTCGTGACAAATTAATTTC
CAACGGGGTCTTGT**CCGGATAAGAGAATTTTGTTTGATTATCCGTTCGG*ATAAATGGACGCCTGCTCCATATTTT***
***TCCGGTT*ATTACCCCACCTGGAAGTGCCCAGAATTTTCCGGGGATTACGGATAATA**CGGTGGTCTGGATTAATT
AATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTTAGATCTCAGGGATTCCCACTATTTGGTATTCTGA
TATGTTTTTCCTGATATGCATCAAAACTCTAATCTAAAACCTGAATCTCCGC*TATTTTTTTTTTTTTTTT*GATGACCC
CGTTTTCGTGACAAATTAATTTCCAACGGGGTCTTGT**CCGGATAAGAGAATTTTGTTTGATTATCCGTTCGG*ATA***
***AATGGACGCCTGCTCCATATTTTTCCGGTT*ATTACCCCACCTGGAAGTGCCCAGAATTTTCCGGGGATTACGGAT**
AATACGGTGGTCTGGATTAATTAATACGCCAAGTCTTACATTTTGTTGCAGTCTCGTGCGAGTATGTGCAATAAT
AAACAAGATGAGCCAATTTATTGGATTAGTTGCAGCTTGACCCCGCCATAGCTAGGCATAGCCAAGTGCTATGG
GTGTTAGATGATGCACTTGGATGCAGTGAGTTTTGGAGTATAAAAGATCCTTAAAATTCCACCCTT

FIG.6B-45 pG1-4 (PG1-D1427-2x$(T)_{16}$): Example comprising two T motifs which are $(T)_n$ (n=16), each without a TA extension

SEQ ID 96

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTT*GATGACCCCGTTTTCGTGACAAATTAATTTC
CAACGGGGTCTTGT**CCGGATAAGAGAATTTTGTTTGATTATCCGTTCGG*ATAAATGGACGCCTGCTCCATATTTT***
***TCCGGTT*ATTACCCCACCTGGAAGTGCCCAGAATTTTCCGGGGATTACGGATAATA**CGGTGGTCTGGATTAATT
AATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTTAGATCTCAGGGATTCCCACTATTTGGTATTCTGA
TATGTTTTTCCTGATATGCATCAAAACTCTAATCTAAAACCTGAATCTCCGC*TTTTTTTTTTTTTTTT*GATGACCCCG
TTTTCGTGACAAATTAATTTCCAACGGGGTCTTGT**CCGGATAAGAGAATTTTGTTTGATTATCCGTTCGG*ATAAA***
***TGGACGCCTGCTCCATATTTTTCCGGTT*ATTACCCCACCTGGAAGTGCCCAGAATTTTCCGGGGATTACGGATAA**
TACGGTGGTCTGGATTAATTAATACGCCAAGTCTTACATTTTGTTGCAGTCTCGTGCGAGTATGTGCAATAATAAA
CAAGATGAGCCAATTTATTGGATTAGTTGCAGCTTGACCCCGCCATAGCTAGGCATAGCCAAGTGCTATGGGTGT
TAGATGATGCACTTGGATGCAGTGAGTTTTGGAGTATAAAAGATCCTTAAAATTCCACCCTT

FIG.6B-46 pG1-4 (PG1-D1427-2xTA(T)$_{17}$): Example comprising two T motifs which are $(T)_n$ (n=17), each extended by preceding TA (extending the T motif at its 5'-end to become a $TA(T)_n$ motif)

SEQ ID 97

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTT*GATGACCCCGTTTTCGTGACAAATTAAT
TTCCAACGGGGTCTTGT**CCGGATAAGAGAATTTTGTTTGATTATCCGTTCGG*ATAAATGGACGCCTGCTCCATAT***
***TTTTCCGGTT*ATTACCCCACCTGGAAGTGCCCAGAATTTTCCGGGGATTACGGATAATA**CGGTGGTCTGGATTA
ATTAATACGCCAAGTCTTACATTTTGTTGCAGTCTCGTGCGAGTATGTGCAATAATAAACAAGATGAGCCAATTTA
TTGGATTAGTTGCAGCTTGACCCCGCCATAGCTAGGCATAGCCAAGTGCTATGGGTGTTAGATGATGCACTTGGA
TGCAGTGAGTTTTGGAGTATAAAAGATCCTTAAAATTCCACCCTTAGATCTCAGGGATTCCCACTATTTGGTATTC
TGATATGTTTTTCCTGATATGCATCAAAACTCTAATCTAAAACCTGAATCTCCGC*TATTTTTTTTTTTTTTTTT*GATG
ACCCCGTTTTCGTGACAAATTAATTTCCAACGGGGTCTTGTCCGGATAAGAGAATTTTGTTTGATTATCCGTTCG
**G*ATAAATGGACGCCTGCTCCATATTTTTCCGGTT*ATTACCCCACCTGGAAGTGCCCAGAATTTTCCGGGGATTAC**
GGATAATACGGTGGTCTGGATTAATTAATACGCCAAGTCTTACATTTTGTTGCAGTCTCGTGCGAGTATGTGCAA
TAATAAACAAGATGAGCCAATTTATTGGATTAGTTGCAGCTTGACCCCGCCATAGCTAGGCATAGCCAAGTGCTA
TGGGTGTTAGATGATGCACTTGGATGCAGTGAGTTTTGGAGTATAAAAGATCCTTAAAATTCCACCCTT

FIG.6B-47 pG1-4 (PG1-D1427-TA$(T)_{17}$-$(T)_{17}$): Example comprising a first T motif which is $(T)_n$ (n=17) extended by preceding TA (extending the T motif at its 5'-end to become a TA$(T)_n$ motif; and a second T motif which is $(T)_n$ (n=17) without a TA extension

SEQ ID 98

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTT*GATGACCCCGTTTTCGTGACAAATTAAT
TTCCAACGGGGTCTTGTCCGGATAAGAGAATTTTGTTTGATTATCCGTTCGGATAAATGGACGCCTGCTCCATAT
TTTTCCGGTTATTACCCCACCTGGAAGTGCCCAGAATTTTCCGGGGATTACGGATAATACGGTGGTCTGGATTA
ATTAATACGCCAAGTCTTACATTTTGTTGCAGTCTCGTGCGAGTATGTGCAATAATAAACAAGATGAGCCAATTTA
TTGGATTAGTTGCAGCTTGACCCCGCCATAGCTAGGCATAGCCAAGTGCTATGGGTGTTAGATGATGCACTTGGA
TGCAGTGAGTTTTGGAGTATAAAAGATCCTTAAAATTCCACCCTTAGATCTCAGGGATTCCCACTATTTGGTATTC
TGATATGTTTTTCCTGATATGCATCAAAACTCTAATCTAAAACCTGAATCTCCGC*TTTTTTTTTTTTTTTTT*GATGAC
CCCGTTTTCGTGACAAATTAATTTCCAACGGGGTCTTGTCCGGATAAGAGAATTTTGTTTGATTATCCGTTCGGA
TAAATGGACGCCTGCTCCATATTTTTCCGGTTATTACCCCACCTGGAAGTGCCCAGAATTTTCCGGGGATTACGG
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT

FIG.6B-48 pG1-4 (PG1-D1427-$(T)_{17}$-$TA(T)_{17}$): Example comprising a first T motif which is $(T)_n$ (n=17) without a TA extension; and a second T motif which is $(T)_n$ (n=17) extended by preceding TA (extending the T motif at its 5′-end to become a $TA(T)_n$ motif

SEQ ID 99

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTT*GATGACCCCGTTTTCGTGACAAATTAATTT
CCAACGGGGTCTTGT**CCGGATAAGAGAATTTTGTTTGATTATCCGTTCGG*ATAAATGGACGCCTGCTCCATATTT***
***TTCCGGTT*ATTACCCCACCTGGAAGTGCCCAGAATTTTCCGGGGATTACGGATAATA**CGGTGGTCTGGATTAAT
TAATACGCCAAGTCTTACATTTTGTTGCAGTCTCGTGCGAGTATGTGCAATAATAAACAAGATGAGCCAATTTATT
GGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTTAGATCTCAGGGATTCCCACTATTTGGTATTCT
GATATGTTTTTCCTGATATGCATCAAAACTCTAATCTAAAACCTGAATCTCCGC*TATTTTTTTTTTTTTTTTT*GATGA
CCCCGTTTTCGTGACAAATTAATTTCCAACGGGGTCTTGTCCGGATAAGAGAATTTTGTTTGATTATCCGTTCGG
***ATAAATGGACGCCTGCTCCATATTTTTCCGGTT*ATTACCCCACCTGGAAGTGCCCAGAATTTTCCGGGGATTACG**
GATAATACGGTGGTCTGGATTAATTAATACGCCAAGTCTTACATTTTGTTGCAGTCTCGTGCGAGTATGTGCAAT
AATAAACAAGATGAGCCAATTTATTGGATTAGTTGCAGCTTGACCCCGCCATAGCTAGGCATAGCCAAGTGCTAT
GGGTGTTAGATGATGCACTTGGATGCAGTGAGTTTTGGAGTATAAAAGATCCTTAAAATTCCACCCTT

FIG.6B-49 pG1-4 (PG1-D1427-2x$(T)_{17}$): Example comprising two T motifs which are $(T)_n$ (n=17), each without a TA extension

SEQ ID 100

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTT*GATGACCCCGTTTTCGTGACAAATTAATTT
CCAACGGGGTCTTGTCCGGATAAGAGAATTTTGTTTGATTATCCGTTCGG *ATAAATGGACGCCTGCTCCATATTT*
*TTCCGGTT* ATTACCCCACCTGGAAGTGCCCAGAATTTTCCGGGGATTACGGATAATACGGTGGTCTGGATTAAT
TAATACGCCAAGTCTTACATTTTGTTGCAGTCTCGTGCGAGTATGTGCAATAATAAACAAGATGAGCCAATTTATT
GGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTTAGATCTCAGGGATTCCCACTATTTGGTATTCT
GATATGTTTTTCCTGATATGCATCAAAACTCTAATCTAAAACCTGAATCTCCGC*TTTTTTTTTTTTTTTTT*GATGACC
CCGTTTTCGTGACAAATTAATTTCCAACGGGGTCTTGTCCGGATAAGAGAATTTTGTTTGATTATCCGTTCGG *AT*
*AAATGGACGCCTGCTCCATATTTTTCCGGTT* ATTACCCCACCTGGAAGTGCCCAGAATTTTCCGGGGATTACGG
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT

FIG.6B-50 pG1-4 (PG1-D1427-2xTA$(T)_{18}$): Example comprising two T motifs which are $(T)_n$ (n=18), each extended by preceding TA (extending the T motif at its 5′-end to become a TA$(T)_n$ motif)

SEQ ID 101

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTT*GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTT*ATTACCCCACCTGGAAGTGCCCAGAATTTTCCGGGGATTACGGATAATA**CGGTGGTCTGGATT
AATTAATACGCCAAGTCTTACATTTTGTTGCAGTCTCGTGCGAGTATGTGCAATAATAAACAAGATGAGCCAATTT
ATTGGATTAGTTGCAGCTTGACCCCGCCATAGCTAGGCATAGCCAAGTGCTATGGGTGTTAGATGATGCACTTGG
ATGCAGTGAGTTTTGGAGTATAAAAGATCCTTAAAATTCCACCCTTAGATCTCAGGGATTCCCACTATTTGGTATT
CTGATATGTTTTTCCTGATATGCATCAAAACTCTAATCTAAAACCTGAATCTCCGC*TATTTTTTTTTTTTTTTTTT*GAT
GACCCCGTTTTCGTGACAAATTAATTTCCAACGGGGTCTTGTCCGGATAAGAGAATTTTGTTTGATTATCCGTTC
**GG*ATAAATGGACGCCTGCTCCATATTTTTCCGGTT*ATTACCCCACCTGGAAGTGCCCAGAATTTTCCGGGGATTA**
CGGATAATACGGTGGTCTGGATTAATTAATACGCCAAGTCTTACATTTTGTTGCAGTCTCGTGCGAGTATGTGCA
ATAATAAACAAGATGAGCCAATTTATTGGATTAGTTGCAGCTTGACCCCGCCATAGCTAGGCATAGCCAAGTGCT
ATGGGTGTTAGATGATGCACTTGGATGCAGTGAGTTTTGGAGTATAAAAGATCCTTAAAATTCCACCCTT

FIG.6B-51 pG1-4 (PG1-D1427-TA$(T)_{18}$-$(T)_{18}$): Example comprising a first T motif which is $(T)_n$ (n=18) extended by preceding TA (extending the T motif at its 5′-end to become a TA$(T)_n$ motif; and a second T motif which is $(T)_n$ (n=18) without a TA extension

SEQ ID 102

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTT*GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTT*ATTACCCCACCTGGAAGTGCCCAGAATTTTCCGGGGATTACGGATAATA**CGGTGGTCTGGATT
AATTAATACGCCAAGTCTTACATTTTGTTGCAGTCTCGTGCGAGTATGTGCAATAATAAACAAGATGAGCCAATTT
ATTGGATTAGTTGCAGCTTGACCCCGCCATAGCTAGGCATAGCCAAGTGCTATGGGTGTTAGATGATGCACTTGG
ATGCAGTGAGTTTTGGAGTATAAAAGATCCTTAAAATTCCACCCTTAGATCTCAGGGATTCCCACTATTTGGTATT
CTGATATGTTTTTCCTGATATGCATCAAAACTCTAATCTAAAACCTGAATCTCCGC*TTTTTTTTTTTTTTTTTT*GATG
ACCCCGTTTTCGTGACAAATTAATTTCCAACGGGGTCTTGTCCGGATAAGAGAATTTTGTTTGATTATCCGTTCG
**G*ATAAATGGACGCCTGCTCCATATTTTTCCGGTT*ATTACCCCACCTGGAAGTGCCCAGAATTTTCCGGGGATTAC**
GGATAATACGGTGGTCTGGATTAATTAATACGCCAAGTCTTACATTTTGTTGCAGTCTCGTGCGAGTATGTGCAA
TAATAAACAAGATGAGCCAATTTATTGGATTAGTTGCAGCTTGACCCCGCCATAGCTAGGCATAGCCAAGTGCTA
TGGGTGTTAGATGATGCACTTGGATGCAGTGAGTTTTGGAGTATAAAAGATCCTTAAAATTCCACCCTT

FIG. 6B-52 pG1-4 (PG1-D1427-(T)$_{18}$-TA(T)$_{18}$): Example comprising a first T motif which is (T)$_n$ (n=18) without a TA extension; and a second T motif which is (T)$_n$ (n=18) extended by preceding TA (extending the T motif at its 5′-end to become a TA(T)$_n$ motif

SEQ ID 103

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTT*GATGACCCCGTTTTCGTGACAAATTAATT
TCCAACGGGGTCTTGT**CCGGATAAGAGAATTTTGTTTGATTATCCGTTCGG*ATAAATGGACGCCTGCTCCATATT***
***TTTCCGGTT*ATTACCCCACCTGGAAGTGCCCAGAATTTTCCGGGGATTACGGATAATA**CGGTGGTCTGGATTAA
TTAATACGCCAAGTCTTACATTTTGTTGCAGTCTCGTGCGAGTATGTGCAATAATAAACAAGATGAGCCAATTTAT
TGGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTTAGATCTCAGGGATTCCCACTATTTGGTATTCT
GATATGTTTTTCCTGATATGCATCAAAACTCTAATCTAAAACCTGAATCTCCGC*TATTTTTTTTTTTTTTTTTT*GATG
ACCCCGTTTTCGTGACAAATTAATTTCCAACGGGGTCTTGTCCGGATAAGAGAATTTTGTTTGATTATCCGTTCG
**G*ATAAATGGACGCCTGCTCCATATTTTTCCGGTT*ATTACCCCACCTGGAAGTGCCCAGAATTTTCCGGGGATTAC**
GGATAATACGGTGGTCTGGATTAATTAATACGCCAAGTCTTACATTTTGTTGCAGTCTCGTGCGAGTATGTGCAA
TAATAAACAAGATGAGCCAATTTATTGGATTAGTTGCAGCTTGACCCCGCCATAGCTAGGCATAGCCAAGTGCTA
TGGGTGTTAGATGATGCACTTGGATGCAGTGAGTTTTGGAGTATAAAAGATCCTTAAAATTCCACCCTT

FIG.6B-53 pG1-4 (PG1-D1427-2x$(T)_{18}$): Example comprising two T motifs which are $(T)_n$ (n=18), each without a TA extension

SEQ ID 104

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTT*GATGACCCCGTTTTCGTGACAAATTAATT
TCCAACGGGGTCTTGTCCGGATAAGAGAATTTTGTTTGATTATCCGTTCGG*ATAAATGGACGCCTGCTCCATATT*
*TTTCCGGTT*ATTACCCCACCTGGAAGTGCCCAGAATTTTCCGGGGATTACGGATAATACGGTGGTCTGGATTAA
TTAATACGCCAAGTCTTACATTTTGTTGCAGTCTCGTGCGAGTATGTGCAATAATAAACAAGATGAGCCAATTTAT
TGGATTAGTTGCAGCTTGACCCCGCCATAGCTAGGCATAGCCAAGTGCTATGGGTGTTAGATGATGCACTTGGAT
GCAGTGAGTTTTGGAGTATAAAAGATCCTTAAAATTCCACCCTTAGATCTCAGGGATTCCCACTATTTGGTATTCT
GATATGTTTTTCCTGATATGCATCAAAACTCTAATCTAAAACCTGAATCTCCGC*TTTTTTTTTTTTTTTTTT*GATGAC
CCCGTTTTCGTGACAAATTAATTTCCAACGGGGTCTTGTCCGGATAAGAGAATTTTGTTTGATTATCCGTTCGG*A*
*TAAATGGACGCCTGCTCCATATTTTTCCGGTT*ATTACCCCACCTGGAAGTGCCCAGAATTTTCCGGGGATTACGG
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT

FIG.6B-54 pG1-4 (PG1-D1427-2xTA(T)$_{19}$): Example comprising two T motifs which are (T)$_n$ (n=19), each extended by preceding TA (extending the T motif at its 5'-end to become a TA(T)$_n$ motif)

SEQ ID 105

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTTT*GATGACCCCGTTTTCGTGACAAATTA
ATTTCCAACGGGGTCTTGT**CCGGATAAGAGAATTTTGTTTGATTATCCGTTCGG*ATAAATGGACGCCTGCTCCAT***
***ATTTTTCCGGTT*ATTACCCCACCTGGAAGTGCCCAGAATTTTCCGGGGATTACGGATAATA**CGGTGGTCTGGAT
TAATTAATACGCCAAGTCTTACATTTTGTTGCAGTCTCGTGCGAGTATGTGCAATAATAAACAAGATGAGCCAATT
TATTGGATTAGTTGCAGCTTGACCCCGCCATAGCTAGGCATAGCCAAGTGCTATGGGTGTTAGATGATGCACTTG
GATGCAGTGAGTTTTGGAGTATAAAAGATCCTTAAAATTCCACCCTTAGATCTCAGGGATTCCCACTATTTGGTAT
TCTGATATGTTTTTCCTGATATGCATCAAAACTCTAATCTAAAACCTGAATCTCCGC*TATTTTTTTTTTTTTTTTTTT*G
ATGACCCCGTTTTCGTGACAAATTAATTTCCAACGGGGTCTTGTCCGGATAAGAGAATTTTGTTTGATTATCCGTT
**CGG*ATAAATGGACGCCTGCTCCATATTTTTCCGGTT*ATTACCCCACCTGGAAGTGCCCAGAATTTTCCGGGGATT**
ACGGATAATACGGTGGTCTGGATTAATTAATACGCCAAGTCTTACATTTTGTTGCAGTCTCGTGCGAGTATGTGC
AATAATAAACAAGATGAGCCAATTTATTGGATTAGTTGCAGCTTGACCCCGCCATAGCTAGGCATAGCCAAGTGC
TATGGGTGTTAGATGATGCACTTGGATGCAGTGAGTTTTGGAGTATAAAAGATCCTTAAAATTCCACCCTT

FIG.6B-55 pG1-4 (PG1-D1427-TA$(T)_{19}$-$(T)_{19}$): Example comprising a first T motif which is $(T)_n$ (n=19) extended by preceding TA (extending the T motif at its 5'-end to become a TA$(T)_n$ motif; and a second T motif which is $(T)_n$ (n=19) without a TA extension

SEQ ID 106

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTTT*GATGACCCCGTTTTCGTGACAAATTA
ATTTCCAACGGGGTCTTGT**CCGGATAAGAGAATTTTGTTTGATTATCCGTTCGG*ATAAATGGACGCCTGCTCCAT***
***ATTTTTCCGGTT*ATTACCCCACCTGGAAGTGCCCAGAATTTTCCGGGGATTACGGATAATA**CGGTGGTCTGGAT
TAATTAATACGCCAAGTCTTACATTTTGTTGCAGTCTCGTGCGAGTATGTGCAATAATAAACAAGATGAGCCAATT
TATTGGATTAGTTGCAGCTTGACCCCGCCATAGCTAGGCATAGCCAAGTGCTATGGGTGTTAGATGATGCACTTG
GATGCAGTGAGTTTTGGAGTATAAAAGATCCTTAAAATTCCACCCTTAGATCTCAGGGATTCCCACTATTTGGTAT
TCTGATATGTTTTTCCTGATATGCATCAAAACTCTAATCTAAAACCTGAATCTCCGC*TTTTTTTTTTTTTTTTTTT*GAT
GACCCCGTTTTCGTGACAAATTAATTTCCAACGGGGTCTTGTCCGGATAAGAGAATTTTGTTTGATTATCCGTTC
**GG*ATAAATGGACGCCTGCTCCATATTTTTCCGGTT*ATTACCCCACCTGGAAGTGCCCAGAATTTTCCGGGGATTA**
CGGATAATACGGTGGTCTGGATTAATTAATACGCCAAGTCTTACATTTTGTTGCAGTCTCGTGCGAGTATGTGCA
ATAATAAACAAGATGAGCCAATTTATTGGATTAGTTGCAGCTTGACCCCGCCATAGCTAGGCATAGCCAAGTGCT
ATGGGTGTTAGATGATGCACTTGGATGCAGTGAGTTTTGGAGTATAAAAGATCCTTAAAATTCCACCCTT

FIG.6B-56 pG1-4 (PG1-D1427-$(T)_{19}$-TA$(T)_{19}$): Example comprising a first T motif which is $(T)_n$ (n=19) without a TA extension; and a second T motif which is $(T)_n$ (n=19) extended by preceding TA (extending the T motif at its 5'-end to become a TA$(T)_n$ motif

SEQ ID 107

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTTT*GATGACCCCGTTTTCGTGACAAATTAAT
TTCCAACGGGGTCTTGT**CCGGATAAGAGAATTTTGTTTGATTATCCGTTCGG*ATAAATGGACGCCTGCTCCATAT***
***TTTTCCGGTT*ATTACCCCACCTGGAAGTGCCCAGAATTTTCCGGGGATTACGGATAATA**CGGTGGTCTGGATTA
ATTAATACGCCAAGTCTTACATTTTGTTGCAGTCTCGTGCGAGTATGTGCAATAATAAACAAGATGAGCCAATTTA
TTGGATTAGTTGCAGCTTGACCCCGCCATAGCTAGGCATAGCCAAGTGCTATGGGTGTTAGATGATGCACTTGGA
TGCAGTGAGTTTTGGAGTATAAAAGATCCTTAAAATTCCACCCTTAGATCTCAGGGATTCCCACTATTTGGTATTC
TGATATGTTTTTCCTGATATGCATCAAAACTCTAATCTAAAACCTGAATCTCCGC*TATTTTTTTTTTTTTTTTTTT*GAT
GACCCCGTTTTCGTGACAAATTAATTTCCAACGGGGTCTTGTCCGGATAAGAGAATTTTGTTTGATTATCCGTTC
**GG*ATAAATGGACGCCTGCTCCATATTTTTCCGGTT*ATTACCCCACCTGGAAGTGCCCAGAATTTTCCGGGGATTA**
CGGATAATACGGTGGTCTGGATTAATTAATACGCCAAGTCTTACATTTTGTTGCAGTCTCGTGCGAGTATGTGCA
ATAATAAACAAGATGAGCCAATTTATTGGATTAGTTGCAGCTTGACCCCGCCATAGCTAGGCATAGCCAAGTGCT
ATGGGTGTTAGATGATGCACTTGGATGCAGTGAGTTTTGGAGTATAAAAGATCCTTAAAATTCCACCCTT

FIG. 6B-57 pG1-4 (PG1-D1427-2x(T)$_{19}$): Example comprising two T motifs which are (T)$_n$ (n=19), each without a TA extension

SEQ ID 108

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTTT*GATGACCCCGTTTTCGTGACAAATTAAT
TTCCAACGGGGTCTTGTCCGGATAAGAGAATTTTGTTTGATTATCCGTTCGG*ATAAATGGACGCCTGCTCCATAT*
*TTTTCCGGTT*ATTACCCCACCTGGAAGTGCCCAGAATTTTCCGGGGATTACGGATAATACGGTGGTCTGGATTA
ATTAATACGCCAAGTCTTACATTTTGTTGCAGTCTCGTGCGAGTATGTGCAATAATAAACAAGATGAGCCAATTTA
TTGGATTAGTTGCAGCTTGACCCCGCCATAGCTAGGCATAGCCAAGTGCTATGGGTGTTAGATGATGCACTTGGA
TGCAGTGAGTTTTGGAGTATAAAAGATCCTTAAAATTCCACCCTTAGATCTCAGGGATTCCCACTATTTGGTATTC
TGATATGTTTTTCCTGATATGCATCAAAACTCTAATCTAAAACCTGAATCTCCGC*TTTTTTTTTTTTTTTTTTT*GATGA
CCCCGTTTTCGTGACAAATTAATTTCCAACGGGGTCTTGTCCGGATAAGAGAATTTTGTTTGATTATCCGTTCGG
*ATAAATGGACGCCTGCTCCATATTTTTCCGGTT*ATTACCCCACCTGGAAGTGCCCAGAATTTTCCGGGGATTACG
GATAATACGGTGGTCTGGATTAATTAATACGCCAAGTCTTACATTTTGTTGCAGTCTCGTGCGAGTATGTGCAAT
AATAAACAAGATGAGCCAATTTATTGGATTAGTTGCAGCTTGACCCCGCCATAGCTAGGCATAGCCAAGTGCTAT
GGGTGTTAGATGATGCACTTGGATGCAGTGAGTTTTGGAGTATAAAAGATCCTTAAAATTCCACCCTT

FIG.6B-58 pG1-4 (PG1-D1427-2xTA$(T)_{20}$): Example comprising two T motifs which are $(T)_n$ (n=20), each extended by preceding TA (extending the T motif at its 5′-end to become a TA$(T)_n$ motif)

SEQ ID 109

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTTTT*GATGACCCCGTTTTCGTGACAAATT
AATTTCCAACGGGGTCTTGT**CCGGATAAGAGAATTTTGTTTGATTATCCGTTCGG*ATAAATGGACGCCTGCTCCA***
***TATTTTTCCGGTT*ATTACCCCACCTGGAAGTGCCCAGAATTTTCCGGGGATTACGGATAATA**CGGTGGTCTGGA
TTAATTAATACGCCAAGTCTTACATTTTGTTGCAGTCTCGTGCGAGTATGTGCAATAATAAACAAGATGAGCCAAT
TTATTGGATTAGTTGCAGCTTGACCCCGCCATAGCTAGGCATAGCCAAGTGCTATGGGTGTTAGATGATGCACTT
GGATGCAGTGAGTTTTGGAGTATAAAAGATCCTTAAAATTCCACCCTTAGATCTCAGGGATTCCCACTATTTGGTA
TTCTGATATGTTTTTCCTGATATGCATCAAAACTCTAATCTAAAACCTGAATCTCCGC*TATTTTTTTTTTTTTTTTTTT*
*T*GATGACCCCGTTTTCGTGACAAATTAATTTCCAACGGGGTCTTGTCCGGATAAGAGAATTTTGTTTGATTATCC
**GTTCGG*ATAAATGGACGCCTGCTCCATATTTTTCCGGTT*ATTACCCCACCTGGAAGTGCCCAGAATTTTCCGGGG**
ATTACGGATAATACGGTGGTCTGGATTAATTAATACGCCAAGTCTTACATTTTGTTGCAGTCTCGTGCGAGTATG
TGCAATAATAAACAAGATGAGCCAATTTATTGGATTAGTTGCAGCTTGACCCCGCCATAGCTAGGCATAGCCAAG
TGCTATGGGTGTTAGATGATGCACTTGGATGCAGTGAGTTTTGGAGTATAAAAGATCCTTAAAATTCCACCCTT

FIG.6B-59 pG1-4 (PG1-D1427-TA$(T)_{20}$-$(T)_{20}$): Example comprising a first T motif which is $(T)_n$ (n=20) extended by preceding TA (extending the T motif at its 5'-end to become a TA$(T)_n$ motif; and a second T motif which is $(T)_n$ (n=20) without a TA extension

SEQ ID 110

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TATTTTTTTTTTTTTTTTTTTT*GATGACCCCGTTTTCGTGACAAATT
AATTTCCAACGGGGTCTTGT**CCGGATAAGAGAATTTTGTTTGATTATCCGTTCGG*ATAAATGGACGCCTGCTCCA***
***TATTTTTCCGGTT*ATTACCCCACCTGGAAGTGCCCAGAATTTTCCGGGGATTACGGATAATA**CGGTGGTCTGGA
TTAATTAATACGCCAAGTCTTACATTTTGTTGCAGTCTCGTGCGAGTATGTGCAATAATAAACAAGATGAGCCAAT
TTATTGGATTAGTTGCAGCTTGACCCCGCCATAGCTAGGCATAGCCAAGTGCTATGGGTGTTAGATGATGCACTT
GGATGCAGTGAGTTTTGGAGTATAAAAGATCCTTAAAATTCCACCCTTAGATCTCAGGGATTCCCACTATTTGGTA
TTCTGATATGTTTTTCCTGATATGCATCAAAACTCTAATCTAAAACCTGAATCTCCGC*TTTTTTTTTTTTTTTTTTTT*G
ATGACCCCGTTTTCGTGACAAATTAATTTCCAACGGGGTCTTGTCCGGATAAGAGAATTTTGTTTGATTATCCGTT
**CGG*ATAAATGGACGCCTGCTCCATATTTTTCCGGTT*ATTACCCCACCTGGAAGTGCCCAGAATTTTCCGGGGATT**
ACGGATAATACGGTGGTCTGGATTAATTAATACGCCAAGTCTTACATTTTGTTGCAGTCTCGTGCGAGTATGTGC
AATAATAAACAAGATGAGCCAATTTATTGGATTAGTTGCAGCTTGACCCCGCCATAGCTAGGCATAGCCAAGTGC
TATGGGTGTTAGATGATGCACTTGGATGCAGTGAGTTTTGGAGTATAAAAGATCCTTAAAATTCCACCCTT

FIG.6B-60 pG1-4 (PG1-D1427-$(T)_{20}$-TA$(T)_{20}$): Example comprising a first T motif which is $(T)_n$ (n=20) without a TA extension; and a second T motif which is $(T)_n$ (n=20) extended by preceding TA (extending the T motif at its 5'-end to become a TA$(T)_n$ motif

SEQ ID 111

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTTTT*GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTT*ATTACCCCACCTGGAAGTGCCCAGAATTTTCCGGGGATTACGGATAATA**CGGTGGTCTGGATT
AATTAATACGCCAAGTCTTACATTTTGTTGCAGTCTCGTGCGAGTATGTGCAATAATAAACAAGATGAGCCAATTT
ATTGGATTAGTTGCAGCTTGACCCCGCCATAGCTAGGCATAGCCAAGTGCTATGGGTGTTAGATGATGCACTTGG
ATGCAGTGAGTTTTGGAGTATAAAAGATCCTTAAAATTCCACCCTTAGATCTCAGGGATTCCCACTATTTGGTATT
CTGATATGTTTTTCCTGATATGCATCAAAACTCTAATCTAAAACCTGAATCTCCGC*TATTTTTTTTTTTTTTTTTTTT*G
ATGACCCCGTTTTCGTGACAAATTAATTTCCAACGGGGTCTTGTCCGGATAAGAGAATTTTGTTTGATTATCCGTT
**CGG*ATAAATGGACGCCTGCTCCATATTTTTCCGGTT*ATTACCCCACCTGGAAGTGCCCAGAATTTTCCGGGGATT**
ACGGATAATACGGTGGTCTGGATTAATTAATACGCCAAGTCTTACATTTTGTTGCAGTCTCGTGCGAGTATGTGC
AATAATAAACAAGATGAGCCAATTTATTGGATTAGTTGCAGCTTGACCCCGCCATAGCTAGGCATAGCCAAGTGC
TATGGGTGTTAGATGATGCACTTGGATGCAGTGAGTTTTGGAGTATAAAAGATCCTTAAAATTCCACCCTT

FIG.6B-61 pG1-4 (PG1-D1427-2x(T)$_{20}$): Example comprising two T motifs which are (T)$_n$ (n=20), each without a TA extension

SEQ ID 112

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGCTCAGGGATTCCCACTATTTGGTATTCTGATATGTTTTTCCTGATATGCAT
CAAAACTCTAATCTAAAACCTGAATCTCCGC*TTTTTTTTTTTTTTTTTTTT*GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTT*ATTACCCCACCTGGAAGTGCCCAGAATTTTCCGGGGATTACGGATAATA**CGGTGGTCTGGATT
AATTAATACGCCAAGTCTTACATTTTGTTGCAGTCTCGTGCGAGTATGTGCAATAATAAACAAGATGAGCCAATTT
ATTGGATTAGTTGCAGCTTGACCCCGCCATAGCTAGGCATAGCCAAGTGCTATGGGTGTTAGATGATGCACTTGG
ATGCAGTGAGTTTTGGAGTATAAAAGATCCTTAAAATTCCACCCTTAGATCTCAGGGATTCCCACTATTTGGTATT
CTGATATGTTTTTCCTGATATGCATCAAAACTCTAATCTAAAACCTGAATCTCCGC*TTTTTTTTTTTTTTTTTTTT*GAT
GACCCCGTTTTCGTGACAAATTAATTTCCAACGGGGTCTTGTCCGGATAAGAGAATTTTGTTTGATTATCCGTTC
**GG*ATAAATGGACGCCTGCTCCATATTTTTCCGGTT*ATTACCCCACCTGGAAGTGCCCAGAATTTTCCGGGGATTA**
CGGATAATACGGTGGTCTGGATTAATTAATACGCCAAGTCTTACATTTTGTTGCAGTCTCGTGCGAGTATGTGCA
ATAATAAACAAGATGAGCCAATTTATTGGATTAGTTGCAGCTTGACCCCGCCATAGCTAGGCATAGCCAAGTGCT
ATGGGTGTTAGATGATGCACTTGGATGCAGTGAGTTTTGGAGTATAAAAGATCCTTAAAATTCCACCCTT

FIG.6B-62 pG1-5 (PG1-D1083-TA$(T)_n$): Example comprising one T motif which is $(T)_n$ (n=13-20), extended by preceding TA (extending the T motif at its 5'-end to become a TA$(T)_n$ motif); (Duplication of main regulatory region -328 to -211, inserted between -211/-210)

SEQ ID 113

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TA(T)*$_n$GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTT*ATTACCCCACCTGGAAGTGCCCAGAATTTTCCGGGGATTACGGATAATACCCGGATAAGAGAA**
**TTTTGTTTGATTATCCGTTCGG*ATAAATGGACGCCTGCTCCATATTTTTCCGGTT*ATTACCCCACCTGGAAGTGCC**
CAGAATTTTCCGGGGATTACGGATAATACGGTGGTCTGGATTAATTAATACGCCAAGTCTTACATTTTGTTGCAG
TCTCGTGCGAGTATGTGCAATAATAAACAAGATGAGCCAATTTATTGGATTAGTTGCAGCTTGACCCCGCCATAG
CTAGGCATAGCCAAGTGCTATGGGTGTTAGATGATGCACTTGGATGCAGTGAGTTTTGGAGTATAAAAGATCCTT
AAAATTCCACCCTT pG1-5 (PG1-D1083-$(T)_n$): Example comprising one T motif which is $(T)_n$ (n=13-20) without a TA extension; (Duplication of main regulatory region -328 to -211, inserted between -211/-210)

SEQ ID 114

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*(T)*$_n$GATGACCCCGTTTTCGTGACAAATTAATT
TCCAACGGGGTCTTGT**CCGGATAAGAGAATTTTGTTTGATTATCCGTTCGG*ATAAATGGACGCCTGCTCCATATT***
***TTTCCGGTT*ATTACCCCACCTGGAAGTGCCCAGAATTTTCCGGGGATTACGGATAATACCCGGATAAGAGAATT**
**TTGTTTGATTATCCGTTCGG*ATAAATGGACGCCTGCTCCATATTTTTCCGGTT*ATTACCCCACCTGGAAGTGCCC**
AGAATTTTCCGGGGATTACGGATAATACGGTGGTCTGGATTAATTAATACGCCAAGTCTTACATTTTGTTGCAGT
CTCGTGCGAGTATGTGCAATAATAAACAAGATGAGCCAATTTATTGGATTAGTTGCAGCTTGACCCCGCCATAGC
TAGGCATAGCCAAGTGCTATGGGTGTTAGATGATGCACTTGGATGCAGTGAGTTTTGGAGTATAAAAGATCCTT
AAAATTCCACCCTT

FIG.6B-63 pG1-5 (PG1-D1083-TA(T)$_{13}$): Example comprising one T motif which is (T)$_n$ (n=13), extended by preceding TA (extending the T motif at its 5'-end to become a TA(T)$_n$ motif); (Duplication of main regulatory region -328 to -211, inserted between -211/-210)

SEQ ID 115

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTCCGGTT*ATTACCCCACCTGGAAGTGCCCAGAATTTTCCGGGGATTACGGATAATACCCGGA**
**TAAGAGAATTTTGTTTGATTATCCGTTCGG*ATAAATGGACGCCTGCTCCATATTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT pG1-5 (PG1-D1083-(T)$_{13}$): Example comprising one T motif which is (T)$_n$ (n=13) without a TA extension; (Duplication of main regulatory region -328 to -211, inserted between -211/-210)

SEQ ID 116

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTT*GATGACCCCGTTTTCGTGAC
AAATTAATTTCCAACGGGGTCTTGT**CCGGATAAGAGAATTTTGTTTGATTATCCGTTCGG*ATAAATGGACGCCT***
***GCTCCATATTTTTCCGGTT*ATTACCCCACCTGGAAGTGCCCAGAATTTTCCGGGGATTACGGATAATACCCGGAT**
**AAGAGAATTTTGTTTGATTATCCGTTCGG*ATAAATGGACGCCTGCTCCATATTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT

FIG.6B-64 pG1-5 (PG1-D1083-TA$(T)_{14}$): Example comprising one T motif which is $(T)_n$ (n=14), extended by preceding TA (extending the T motif at its 5'-end to become a TA$(T)_n$ motif); (Duplication of main regulatory region -328 to -211, inserted between -211/-210)

SEQ ID 117

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTT*ATTACCCCACCTGGAAGTGCCCAGAATTTTCCGGGGATTACGGATAATACCCG**
**GATAAGAGAATTTTGTTTGATTATCCGTTCGG*ATAAATGGACGCCTGCTCCATATTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT pG1-5 (PG1-D1083-$(T)_{14}$): Example comprising one T motif which is $(T)_n$ (n=14) without a TA extension; (Duplication of main regulatory region -328 to -211, inserted between -211/-210)

SEQ ID 118

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTT*GATGACCCCGTTTTCGTGA
CAAATTAATTTCCAACGGGGTCTTGT**CCGGATAAGAGAATTTTGTTTGATTATCCGTTCGG*ATAAATGGACGCCT***
***GCTCCATATTTTTCCGGTT*ATTACCCCACCTGGAAGTGCCCAGAATTTTCCGGGGATTACGGATAATACCCGGAT**
**AAGAGAATTTTGTTTGATTATCCGTTCGG*ATAAATGGACGCCTGCTCCATATTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT

FIG.6B-65 pG1-5 (PG1-D1083-TA(T)$_{15}$): Example comprising one T motif which is (T)$_n$ (n=15), extended by preceding TA (extending the T motif at its 5'-end to become a TA(T)$_n$ motif); (Duplication of main regulatory region -328 to -211, inserted between -211/-210)

SEQ ID 119

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTCCGGTT*ATTACCCCACCTGGAAGTGCCCAGAATTTTCCGGGGATTACGGATAATACCC**
**GGATAAGAGAATTTTGTTTGATTATCCGTTCGG*ATAAATGGACGCCTGCTCCATATTTTTCCGGTT*ATTACCCCA**
CCTGGAAGTGCCCAGAATTTTCCGGGGATTACGGATAATACGGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1-5 (PG1-D1083-(T)$_{15}$): Example comprising one T motif which is (T)$_n$ (n=15) without a TA extension; (Duplication of main regulatory region -328 to -211, inserted between -211/-210)

SEQ ID 120

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTCCGGTT*ATTACCCCACCTGGAAGTGCCCAGAATTTTCCGGGGATTACGGATAATACCCGGA**
**TAAGAGAATTTTGTTTGATTATCCGTTCGG*ATAAATGGACGCCTGCTCCATATTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT

FIG.6B-66 pG1-5 (PG1-D1083-TA$(T)_{16}$): Example comprising one T motif which is $(T)_n$ (n=16), extended by preceding TA (extending the T motif at its 5'-end to become a TA$(T)_n$ motif); (Duplication of main regulatory region -328 to -211, inserted between -211/-210)

SEQ ID 121

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTT*GATGACCCCGTTTTC
GTGACAAATTAATTTCCAACGGGGTCTTGTCCGGATAAGAGAATTTTGTTTGATTATCCGTTCGG*ATAAATGGA*
*CGCCTGCTCCATATTTTTCCGGTT*ATTACCCCACCTGGAAGTGCCCAGAATTTTCCGGGGATTACGGATAATACC
CGGATAAGAGAATTTTGTTTGATTATCCGTTCGG*ATAAATGGACGCCTGCTCCATATTTTTCCGGTT*ATTACCCC
ACCTGGAAGTGCCCAGAATTTTCCGGGGATTACGGATAATACGGTGGTCTGGATTAATTAATACGCCAAGTCTT
ACATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1-5 (PG1-D1083-$(T)_{16}$): Example comprising one T motif which is $(T)_n$ (n=16) without a TA extension; (Duplication of main regulatory region -328 to -211, inserted between -211/-210)

SEQ ID 122

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTT*GATGACCCCGTTTTCGT
GACAAATTAATTTCCAACGGGGTCTTGTCCGGATAAGAGAATTTTGTTTGATTATCCGTTCGG*ATAAATGGACG*
*CCTGCTCCATATTTTTCCGGTT*ATTACCCCACCTGGAAGTGCCCAGAATTTTCCGGGGATTACGGATAATACCCG
GATAAGAGAATTTTGTTTGATTATCCGTTCGG*ATAAATGGACGCCTGCTCCATATTTTTCCGGTT*ATTACCCCAC
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT

FIG.6B-67 pG1-5 (PG1-D1083-TA(T)$_{17}$): Example comprising one T motif which is (T)$_n$ (n=17), extended by preceding TA (extending the T motif at its 5'-end to become a TA(T)$_n$ motif); (Duplication of main regulatory region -328 to -211, inserted between -211/-210)

SEQ ID 123

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATACC**
**CGGATAAGAGAATTTTGTTTGATTATCCGTTCGG*ATAAATGGACGCCTGCTCCATATTTTTCCGGTT*ATTACCCC**
ACCTGGAAGTGCCCAGAATTTTCCGGGGATTACGGATAATACGGTGGTCTGGATTAATTAATACGCCAAGTCTT
ACATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1-5 (PG1-D1083-(T)$_{17}$): Example comprising one T motif which is (T)$_n$ (n=17) without a TA extension; (Duplication of main regulatory region -328 to -211, inserted between -211/-210)

SEQ ID 124

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTCCGGTT*ATTACCCCACCTGGAAGTGCCCAGAATTTTCCGGGGATTACGGATAATACCC**
**GGATAAGAGAATTTTGTTTGATTATCCGTTCGG*ATAAATGGACGCCTGCTCCATATTTTTCCGGTT*ATTACCCCA**
CCTGGAAGTGCCCAGAATTTTCCGGGGATTACGGATAATACGGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT

FIG.6B-68 pG1-5 (PG1-D1083-TA$(T)_{18}$): Example comprising one T motif which is $(T)_n$ (n=18), extended by preceding TA (extending the T motif at its 5′-end to become a TA$(T)_n$ motif); (Duplication of main regulatory region -328 to -211, inserted between -211/-210)

SEQ ID 125

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT pG1-5 (PG1-D1083-$(T)_{18}$): Example comprising one T motif which is $(T)_n$ (n=18) without a TA extension; (Duplication of main regulatory region -328 to -211, inserted between -211/-210)

SEQ ID 126

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATACC**
**CGGATAAGAGAATTTTGTTTGATTATCCGTTCGG*ATAAATGGACGCCTGCTCCATATTTTTCCGGTT*ATTACCCC**
ACCTGGAAGTGCCCAGAATTTTCCGGGGATTACGGATAATACGGTGGTCTGGATTAATTAATACGCCAAGTCTT
ACATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT

FIG.6B-69 pG1-5 (PG1-D1083-TA(T)$_{19}$): Example comprising one T motif which is (T)$_n$ (n=19), extended by preceding TA (extending the T motif at its 5'-end to become a TA(T)$_n$ motif); (Duplication of main regulatory region -328 to -211, inserted between -211/-210)

SEQ ID 127

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT pG1-5 (PG1-D1083-(T)$_{19}$): Example comprising one T motif which is (T)$_n$ (n=19) without a TA extension; (Duplication of main regulatory region -328 to -211, inserted between -211/-210)

SEQ ID 128

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATACC**
**CGGATAAGAGAATTTTGTTTGATTATCCGTTCGG*ATAAATGGACGCCTGCTCCATATTTTTCCGGTT*ATTACCCC**
ACCTGGAAGTGCCCAGAATTTTCCGGGGATTACGGATAATACGGTGGTCTGGATTAATTAATACGCCAAGTCTT
ACATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT

FIG.6B-70 pG1-5 (PG1-D1083-TA$(T)_{20}$): Example comprising one T motif which is $(T)_n$ (n=20), extended by preceding TA (extending the T motif at its 5′-end to become a TA$(T)_n$ motif); (Duplication of main regulatory region -328 to -211, inserted between -211/-210)

SEQ ID 129

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTTT*GATGACCCCGTT
TTCGTGACAAATTAATTTCCAACGGGGTCTTGTCCGGATAAGAGAATTTTGTTTGATTATCCGTTCGG*ATAAATG*
*GACGCCTGCTCCATATTTTTCCGGTT*ATTACCCCACCTGGAAGTGCCCAGAATTTTCCGGGGATTACGGATAATA
CCCGGATAAGAGAATTTTGTTTGATTATCCGTTCGG*ATAAATGGACGCCTGCTCCATATTTTTCCGGTT*ATTACC
CCACCTGGAAGTGCCCAGAATTTTCCGGGGATTACGGATAATACGGTGGTCTGGATTAATTAATACGCCAAGTC
TTACATTTTGTTGCAGTCTCGTGCGAGTATGTGCAATAATAAACAAGATGAGCCAATTTATTGGATTAGTTGCAGC
TTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTT pG1-5 (PG1-D1083-$(T)_{20}$): Example comprising one T motif which is $(T)_n$ (n=20) without a TA extension; (Duplication of main regulatory region -328 to -211, inserted between -211/-210)

SEQ ID 130

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTTT*GATGACCCCGTTTT
CGTGACAAATTAATTTCCAACGGGGTCTTGTCCGGATAAGAGAATTTTGTTTGATTATCCGTTCGG*ATAAATGG*
*ACGCCTGCTCCATATTTTTCCGGTT*ATTACCCCACCTGGAAGTGCCCAGAATTTTCCGGGGATTACGGATAATAC
CCGGATAAGAGAATTTTGTTTGATTATCCGTTCGG*ATAAATGGACGCCTGCTCCATATTTTTCCGGTT*ATTACCC
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT

FIG.6B-71 pG1-6 PE-d998 (PG1-D998-TA(T)$_n$): Example comprising one T motif which is (T)$_n$ (n=13-20), extended by preceding TA (extending the T motif at its 5'-end to become a TA(T)$_n$ motif); (Duplication of core region -293 to -261, inserted between -261/-260)

SEQ ID 131

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TA(T)$_n$*GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTTATAAATGGACGCCTGCTCCATATTTTTCCGGTT*ATTACCCCACCTGGAAGTGCCCAGAATTTTCC**
GGGGATTACGGATAATACGGTGGTCTGGATTAATTAATACGCCAAGTCTTACATTTTGTTGCAGTCTCGTGCGAG
TATGTGCAATAATAAACAAGATGAGCCAATTTATTGGATTAGTTGCAGCTTGACCCCGCCATAGCTAGGCATAGC
CAAGTGCTATGGGTGTTAGATGATGCACTTGGATGCAGTGAGTTTTGGAGTATAAAAGATCCTTAAAATTCCACC
CTT pG1-6 PE-d998 (PG1-D998-(T)$_n$): Example comprising one T motif which is (T)$_n$ (n=13-20) without a TA extension; (Duplication of core region -293 to -261, inserted between -261/-260)

SEQ ID 132

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*(T)$_n$*GATGACCCCGTTTTCGTGACAAATTAATT
TCCAACGGGGTCTTGT**CCGGATAAGAGAATTTTGTTTGATTATCCGTTCGG*ATAAATGGACGCCTGCTCCATATT***
***TTTCCGGTTATAAATGGACGCCTGCTCCATATTTTTCCGGTT*ATTACCCCACCTGGAAGTGCCCAGAATTTTCCG**
GGGATTACGGATAATACGGTGGTCTGGATTAATTAATACGCCAAGTCTTACATTTTGTTGCAGTCTCGTGCGAGT
ATGTGCAATAATAAACAAGATGAGCCAATTTATTGGATTAGTTGCAGCTTGACCCCGCCATAGCTAGGCATAGCC
AAGTGCTATGGGTGTTAGATGATGCACTTGGATGCAGTGAGTTTTGGAGTATAAAAGATCCTTAAAATTCCACCC
TT

FIG.6B-72 pG1-6 PE-d998 (PG1-D998-TA$(T)_{13}$): Example comprising one T motif which is $(T)_n$ (n=13), extended by preceding TA (extending the T motif at its 5'-end to become a TA$(T)_n$ motif); (Duplication of core region -293 to -261, inserted between -261/-260)

SEQ ID 133

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTTCCGGTTATAAATGGACGCCTGCTCCATATTTTTTCCGGTT*ATTACCCCACCTGGAAGTGCCCA**
GAATTTTCCGGGGATTACGGATAATACGGTGGTCTGGATTAATTAATACGCCAAGTCTTACATTTTGTTGCAGTC
TCGTGCGAGTATGTGCAATAATAAACAAGATGAGCCAATTTATTGGATTAGTTGCAGCTTGACCCCGCCATAGCT
AGGCATAGCCAAGTGCTATGGGTGTTAGATGATGCACTTGGATGCAGTGAGTTTTGGAGTATAAAAGATCCTTA
AAATTCCACCCTT pG1-6 PE-d998 (PG1-D998-$(T)_{13}$): Example comprising one T motif which is $(T)_n$ (n=13) without a TA extension; (Duplication of core region -293 to -261, inserted between -261/-260)

SEQ ID 134

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTT*GATGACCCCGTTTTCGTGAC
AAATTAATTTCCAACGGGGTCTTGT**CCGGATAAGAGAATTTTGTTTGATTATCCGTTCGG*ATAAATGGACGCCT***
***GCTCCATATTTTTTCCGGTTATAAATGGACGCCTGCTCCATATTTTTTCCGGTT*ATTACCCCACCTGGAAGTGCCCAG**
AATTTTCCGGGGATTACGGATAATACGGTGGTCTGGATTAATTAATACGCCAAGTCTTACATTTTGTTGCAGTCT
CGTGCGAGTATGTGCAATAATAAACAAGATGAGCCAATTTATTGGATTAGTTGCAGCTTGACCCCGCCATAGCTA
GGCATAGCCAAGTGCTATGGGTGTTAGATGATGCACTTGGATGCAGTGAGTTTTGGAGTATAAAAGATCCTTAA
AATTCCACCCTT

FIG.6B-73 pG1-6 PE-d998 (PG1-D998-TA$(T)_{14}$): Example comprising one T motif which is $(T)_n$ (n=14), extended by preceding TA (extending the T motif at its 5'-end to become a TA$(T)_n$ motif); (Duplication of core region -293 to -261, inserted between -261/-260)

SEQ ID 135

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTTATAAATGGACGCCTGCTCCATATTTTTCCGGTT*ATTACCCCACCTGGAAGTGCC**
CAGAATTTTCCGGGGATTACGGATAATACGGTGGTCTGGATTAATTAATACGCCAAGTCTTACATTTTGTTGCAG
TCTCGTGCGAGTATGTGCAATAATAAACAAGATGAGCCAATTTATTGGATTAGTTGCAGCTTGACCCCGCCATAG
CTAGGCATAGCCAAGTGCTATGGGTGTTAGATGATGCACTTGGATGCAGTGAGTTTTGGAGTATAAAAGATCCTT
AAAATTCCACCCTT pG1-6 PE-d998 (PG1-D998-$(T)_{14}$): Example comprising one T motif which is $(T)_n$ (n=14) without a TA extension; (Duplication of core region -293 to -261, inserted between -261/-260)

SEQ ID 136

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTT*GATGACCCCGTTTTCGTGA
CAAATTAATTTCCAACGGGGTCTTGT**CCGGATAAGAGAATTTTGTTTGATTATCCGTTCGG*ATAAATGGACGCCT***
***GCTCCATATTTTTCCGGTTATAAATGGACGCCTGCTCCATATTTTTCCGGTT*ATTACCCCACCTGGAAGTGCCCAG**
AATTTTCCGGGGATTACGGATAATACGGTGGTCTGGATTAATTAATACGCCAAGTCTTACATTTTGTTGCAGTCT
CGTGCGAGTATGTGCAATAATAAACAAGATGAGCCAATTTATTGGATTAGTTGCAGCTTGACCCCGCCATAGCTA
GGCATAGCCAAGTGCTATGGGTGTTAGATGATGCACTTGGATGCAGTGAGTTTTGGAGTATAAAAGATCCTTAA
AATTCCACCCTT

FIG.6B-74 pG1-6 PE-d998 (PG1-D998-TA(T)$_{15}$): Example comprising one T motif which is (T)$_n$ (n=15), extended by preceding TA (extending the T motif at its 5'-end to become a TA(T)$_n$ motif); (Duplication of core region -293 to -261, inserted between -261/-260)

SEQ ID 137

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTCCGGTTATAAATGGACGCCTGCTCCATATTTTTCCGGTT*ATTACCCCACCTGGAAGTGC**
CCAGAATTTTCCGGGGATTACGGATAATACGGTGGTCTGGATTAATTAATACGCCAAGTCTTACATTTTGTTGCA
GTCTCGTGCGAGTATGTGCAATAATAAACAAGATGAGCCAATTTATTGGATTAGTTGCAGCTTGACCCCGCCATA
GCTAGGCATAGCCAAGTGCTATGGGTGTTAGATGATGCACTTGGATGCAGTGAGTTTTGGAGTATAAAAGATCC
TTAAAATTCCACCCTT pG1-6 PE-d998 (PG1-D998-(T)$_{15}$): Example comprising one T motif which is (T)$_n$ (n=15) without a TA extension; (Duplication of core region -293 to -261, inserted between -261/-260)

SEQ ID 138

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTCCGGTTATAAATGGACGCCTGCTCCATATTTTTCCGGTT*ATTACCCCACCTGGAAGTGCCCA**
GAATTTTCCGGGGATTACGGATAATACGGTGGTCTGGATTAATTAATACGCCAAGTCTTACATTTTGTTGCAGTC
TCGTGCGAGTATGTGCAATAATAAACAAGATGAGCCAATTTATTGGATTAGTTGCAGCTTGACCCCGCCATAGCT
AGGCATAGCCAAGTGCTATGGGTGTTAGATGATGCACTTGGATGCAGTGAGTTTTGGAGTATAAAAGATCCTTA
AAATTCCACCCTT

FIG.6B-75 pG1-6 PE-d998 (PG1-D998-TA(T)$_{16}$): Example comprising one T motif which is (T)$_n$ (n=16), extended by preceding TA (extending the T motif at its 5'-end to become a TA(T)$_n$ motif); (Duplication of core region -293 to -261, inserted between -261/-260)

SEQ ID 139

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTTATAAATGGACGCCTGCTCCATATTTTTCCGGTT*ATTACCCCACCTGGAAGTG**
CCCAGAATTTTCCGGGGATTACGGATAATACGGTGGTCTGGATTAATTAATACGCCAAGTCTTACATTTTGTTGC
AGTCTCGTGCGAGTATGTGCAATAATAAACAAGATGAGCCAATTTATTGGATTAGTTGCAGCTTGACCCCGCCAT
AGCTAGGCATAGCCAAGTGCTATGGGTGTTAGATGATGCACTTGGATGCAGTGAGTTTTGGAGTATAAAAGATC
CTTAAAATTCCACCCTT pG1-6 PE-d998 (PG1-D998-(T)$_{16}$): Example comprising one T motif which is (T)$_n$ (n=16) without a TA extension; (Duplication of core region -293 to -261, inserted between -261/-260)

SEQ ID 140

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTTATAAATGGACGCCTGCTCCATATTTTTCCGGTT*ATTACCCCACCTGGAAGTGCC**
CAGAATTTTCCGGGGATTACGGATAATACGGTGGTCTGGATTAATTAATACGCCAAGTCTTACATTTTGTTGCAG
TCTCGTGCGAGTATGTGCAATAATAAACAAGATGAGCCAATTTATTGGATTAGTTGCAGCTTGACCCCGCCATAG
CTAGGCATAGCCAAGTGCTATGGGTGTTAGATGATGCACTTGGATGCAGTGAGTTTTGGAGTATAAAAGATCCTT
AAAATTCCACCCTT

FIG.6B-76 pG1-6 PE-d998 (PG1-D998-TA(T)$_{17}$): Example comprising one T motif which is (T)$_n$ (n=17), extended by preceding TA (extending the T motif at its 5'-end to become a TA(T)$_n$ motif); (Duplication of core region -293 to -261, inserted between -261/-260)

SEQ ID 141

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTTCCGGTTATAAATGGACGCCTGCTCCATATTTTTTCCGGTT*ATTACCCCACCTGGAAGTG**
CCCAGAATTTTCCGGGGATTACGGATAATACGGTGGTCTGGATTAATTAATACGCCAAGTCTTACATTTTGTTGC
AGTCTCGTGCGAGTATGTGCAATAATAAACAAGATGAGCCAATTTATTGGATTAGTTGCAGCTTGACCCCGCCAT
AGCTAGGCATAGCCAAGTGCTATGGGTGTTAGATGATGCACTTGGATGCAGTGAGTTTTGGAGTATAAAAGATC
CTTAAAATTCCACCCTT pG1-6 PE-d998 (PG1-D998-(T)$_{17}$): Example comprising one T motif which is (T)$_n$ (n=17) without a TA extension; (Duplication of core region -293 to -261, inserted between -261/-260)

SEQ ID 142

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTTCCGGTTATAAATGGACGCCTGCTCCATATTTTTTCCGGTT*ATTACCCCACCTGGAAGTGC**
CCAGAATTTTCCGGGGATTACGGATAATACGGTGGTCTGGATTAATTAATACGCCAAGTCTTACATTTTGTTGCA
GTCTCGTGCGAGTATGTGCAATAATAAACAAGATGAGCCAATTTATTGGATTAGTTGCAGCTTGACCCCGCCATA
GCTAGGCATAGCCAAGTGCTATGGGTGTTAGATGATGCACTTGGATGCAGTGAGTTTTGGAGTATAAAAGATCC
TTAAAATTCCACCCTT

FIG.6B-77 pG1-6 PE-d998 (PG1-D998-TA(T)$_{18}$): Example comprising one T motif which is (T)$_n$ (n=18), extended by preceding TA (extending the T motif at its 5'-end to become a TA(T)$_n$ motif); (Duplication of core region -293 to -261, inserted between -261/-260)

SEQ ID 143

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTTCCGGTTATAAATGGACGCCTGCTCCATATTTTTTCCGGTT*ATTACCCCACCTGGAAGT**
GCCCAGAATTTTCCGGGGATTACGGATAATACGGTGGTCTGGATTAATTAATACGCCAAGTCTTACATTTTGTTG
CAGTCTCGTGCGAGTATGTGCAATAATAAACAAGATGAGCCAATTTATTGGATTAGTTGCAGCTTGACCCCGCCA
TAGCTAGGCATAGCCAAGTGCTATGGGTGTTAGATGATGCACTTGGATGCAGTGAGTTTTGGAGTATAAAAGAT
CCTTAAAATTCCACCCTT pG1-6 PE-d998 (PG1-D998-(T)$_{18}$): Example comprising one T motif which is (T)$_n$ (n=18) without a TA extension; (Duplication of core region -293 to -261, inserted between -261/-260)

SEQ ID 144

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTTCCGGTTATAAATGGACGCCTGCTCCATATTTTTTCCGGTT*ATTACCCCACCTGGAAGTG**
CCCAGAATTTTCCGGGGATTACGGATAATACGGTGGTCTGGATTAATTAATACGCCAAGTCTTACATTTTGTTGC
AGTCTCGTGCGAGTATGTGCAATAATAAACAAGATGAGCCAATTTATTGGATTAGTTGCAGCTTGACCCCGCCAT
AGCTAGGCATAGCCAAGTGCTATGGGTGTTAGATGATGCACTTGGATGCAGTGAGTTTTGGAGTATAAAAGATC
CTTAAAATTCCACCCTT

FIG.6B-78 pG1-6 PE-d998 (PG1-D998-TA(T)$_{19}$): Example comprising one T motif which is (T)$_n$ (n=19), extended by preceding TA (extending the T motif at its 5'-end to become a TA(T)$_n$ motif); (Duplication of core region -293 to -261, inserted between -261/-260)

SEQ ID 145

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTTCCGGTTATAAATGGACGCCTGCTCCATATTTTTTCCGGTT*ATTACCCCACCTGGAAGT**
GCCCAGAATTTTCCGGGGATTACGGATAATACGGTGGTCTGGATTAATTAATACGCCAAGTCTTACATTTTGTTG
CAGTCTCGTGCGAGTATGTGCAATAATAAACAAGATGAGCCAATTTATTGGATTAGTTGCAGCTTGACCCCGCCA
TAGCTAGGCATAGCCAAGTGCTATGGGTGTTAGATGATGCACTTGGATGCAGTGAGTTTTGGAGTATAAAAGAT
CCTTAAAATTCCACCCTT pG1-6 PE-d998 (PG1-D998-(T)$_{19}$): Example comprising one T motif which is (T)$_n$ (n=19) without a TA extension; (Duplication of core region -293 to -261, inserted between -261/-260)

SEQ ID 146

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTTCCGGTTATAAATGGACGCCTGCTCCATATTTTTTCCGGTT*ATTACCCCACCTGGAAGTG**
CCCAGAATTTTCCGGGGATTACGGATAATACGGTGGTCTGGATTAATTAATACGCCAAGTCTTACATTTTGTTGC
AGTCTCGTGCGAGTATGTGCAATAATAAACAAGATGAGCCAATTTATTGGATTAGTTGCAGCTTGACCCCGCCAT
AGCTAGGCATAGCCAAGTGCTATGGGTGTTAGATGATGCACTTGGATGCAGTGAGTTTTGGAGTATAAAAGATC
CTTAAAATTCCACCCTT

FIG.6B-79 pG1-6 PE-d998 (PG1-D998-TA$(T)_{20}$): Example comprising one T motif which is $(T)_n$ (n=20), extended by preceding TA (extending the T motif at its 5'-end to become a TA$(T)_n$ motif); (Duplication of core region -293 to -261, inserted between -261/-260)

SEQ ID 147

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTTT*GATGACCCCGTT
TTCGTGACAAATTAATTTCCAACGGGGTCTTGT**CCGGATAAGAGAATTTTGTTTGATTATCCGTTCGG*ATAAATG***
***GACGCCTGCTCCATATTTTTCCGGTTATAAATGGACGCCTGCTCCATATTTTTCCGGTT*ATTACCCCACCTGGAAG**
TGCCCAGAATTTTCCGGGGATTACGGATAATACGGTGGTCTGGATTAATTAATACGCCAAGTCTTACATTTTGTT
GCAGTCTCGTGCGAGTATGTGCAATAATAAACAAGATGAGCCAATTTATTGGATTAGTTGCAGCTTGACCCCGCC
ATAGCTAGGCATAGCCAAGTGCTATGGGTGTTAGATGATGCACTTGGATGCAGTGAGTTTTGGAGTATAAAAGA
TCCTTAAAATTCCACCCTT pG1-6 PE-d998 (PG1-D998-$(T)_{20}$): Example comprising one T motif which is $(T)_n$ (n=20) without a TA extension; (Duplication of core region -293 to -261, inserted between -261/-260)

SEQ ID 148

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTTATAAATGGACGCCTGCTCCATATTTTTCCGGTT*ATTACCCCACCTGGAAGT**
GCCCAGAATTTTCCGGGGATTACGGATAATACGGTGGTCTGGATTAATTAATACGCCAAGTCTTACATTTTGTTG
CAGTCTCGTGCGAGTATGTGCAATAATAAACAAGATGAGCCAATTTATTGGATTAGTTGCAGCTTGACCCCGCCA
TAGCTAGGCATAGCCAAGTGCTATGGGTGTTAGATGATGCACTTGGATGCAGTGAGTTTTGGAGTATAAAAGAT
CCTTAAAATTCCACCCTT

FIG.6B-80 pG1-7 (PG1-D974-TA$(T)_n$): Example comprising one T motif which is $(T)_n$ (n=13-20), extended by preceding TA (extending the T motif at its 5'-end to become a TA$(T)_n$ motif); (Duplication of delta8 [SEQ ID 2] region -293 to -285, inserted between -285/-284)

SEQ ID 149

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TA$(T)_n$*GATGACCCCGTTTTCGTGACAAATTAA
TTTCCAACGGGGTCTTGT**CCGGATAAGAGAATTTTGTTTGATTATCCGTTCGG*ATAAATGGAATAAATGGACGC***
***CTGCTCCATATTTTTTCCGGTT*ATTACCCCACCTGGAAGTGCCCAGAATTTTCCGGGGATTACGGATAATAC**GGTG
GTCTGGATTAATTAATACGCCAAGTCTTACATTTTGTTGCAGTCTCGTGCGAGTATGTGCAATAATAAACAAGATG
AGCCAATTTATTGGATTAGTTGCAGCTTGACCCCGCCATAGCTAGGCATAGCCAAGTGCTATGGGTGTTAGATGA
TGCACTTGGATGCAGTGAGTTTTGGAGTATAAAAGATCCTTAAAATTCCACCCTT pG1-7 (PG1-D974-$(T)_n$): Example comprising one T motif which is $(T)_n$ (n=13-20) without a TA extension; (Duplication of delta8 [SEQ ID 2] region -293 to -285, inserted between -285/-284)

SEQ ID 150

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*$(T)_n$*GATGACCCCGTTTTCGTGACAAATTAATT
TCCAACGGGGTCTTGT**CCGGATAAGAGAATTTTGTTTGATTATCCGTTCGG*ATAAATGGAATAAATGGACGCCT***
***GCTCCATATTTTTTCCGGTT*ATTACCCCACCTGGAAGTGCCCAGAATTTTCCGGGGATTACGGATAATAC**GGTGGT
CTGGATTAATTAATACGCCAAGTCTTACATTTTGTTGCAGTCTCGTGCGAGTATGTGCAATAATAAACAAGATGA
GCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT

FIG.6B-81 pG1-7 (PG1-D974-TA(T)$_{13}$): Example comprising one T motif which is (T)$_n$ (n=13), extended by preceding TA (extending the T motif at its 5'-end to become a TA(T)$_n$ motif); (Duplication of delta8 [SEQ ID 2] region -293 to -285, inserted between -285/-284)

SEQ ID 151

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGAATA***
***AATGGACGCCTGCTCCATATTTTTCCGGTT*ATTACCCCACCTGGAAGTGCCCAGAATTTTCCGGGGATTACGGAT**
AATACGGTGGTCTGGATTAATTAATACGCCAAGTCTTACATTTTGTTGCAGTCTCGTGCGAGTATGTGCAATAAT
AAACAAGATGAGCCAATTTATTGGATTAGTTGCAGCTTGACCCCGCCATAGCTAGGCATAGCCAAGTGCTATGG
GTGTTAGATGATGCACTTGGATGCAGTGAGTTTTGGAGTATAAAAGATCCTTAAAATTCCACCCTT pG1-7 (PG1-D974-(T)$_{13}$): Example comprising one T motif which is (T)$_n$ (n=13) without a TA extension;

(Duplication of delta8 [SEQ ID 2] region -293 to -285, inserted between -285/-284)

SEQ ID 152

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTT*GATGACCCCGTTTTCGTGAC
AAATTAATTTCCAACGGGGTCTTGT**CCGGATAAGAGAATTTTGTTTGATTATCCGTTCGG*ATAAATGGAATAAA***
***TGGACGCCTGCTCCATATTTTTCCGGTT*ATTACCCCACCTGGAAGTGCCCAGAATTTTCCGGGGATTACGGATAA**
TACGGTGGTCTGGATTAATTAATACGCCAAGTCTTACATTTTGTTGCAGTCTCGTGCGAGTATGTGCAATAATAAA
CAAGATGAGCCAATTTATTGGATTAGTTGCAGCTTGACCCCGCCATAGCTAGGCATAGCCAAGTGCTATGGGTGT
TAGATGATGCACTTGGATGCAGTGAGTTTTGGAGTATAAAAGATCCTTAAAATTCCACCCTT

FIG.6B-82 pG1-7 (PG1-D974-TA$(T)_{14}$): Example comprising one T motif which is $(T)_n$ (n=14), extended by preceding TA (extending the T motif at its 5'-end to become a TA$(T)_n$ motif); (Duplication of delta8 [SEQ ID 2] region -293 to -285, inserted between -285/-284)

SEQ ID 153

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGAAT***
***AAATGGACGCCTGCTCCATATTTTTTCCGGTT*ATTACCCCACCTGGAAGTGCCCAGAATTTTCCGGGGATTACGG**
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT pG1-7 (PG1-D974-$(T)_{14}$): Example comprising one T motif which is $(T)_n$ (n=14) without a TA extension;

(Duplication of delta8 [SEQ ID 2] region -293 to -285, inserted between -285/-284)

SEQ ID 154

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTT*GATGACCCCGTTTTCGTGA
CAAATTAATTTCCAACGGGGTCTTGT**CCGGATAAGAGAATTTTGTTTGATTATCCGTTCGG*ATAAATGGAATAA***
***ATGGACGCCTGCTCCATATTTTTTCCGGTT*ATTACCCCACCTGGAAGTGCCCAGAATTTTCCGGGGATTACGGATA**
ATACGGTGGTCTGGATTAATTAATACGCCAAGTCTTACATTTTGTTGCAGTCTCGTGCGAGTATGTGCAATAATAA
ACAAGATGAGCCAATTTATTGGATTAGTTGCAGCTTGACCCCGCCATAGCTAGGCATAGCCAAGTGCTATGGGTG
TTAGATGATGCACTTGGATGCAGTGAGTTTTGGAGTATAAAAGATCCTTAAAATTCCACCCTT

FIG.6B-83 pG1-7 (PG1-D974-TA(T)$_{15}$): Example comprising one T motif which is (T)$_n$ (n=15), extended by preceding TA (extending the T motif at its 5'-end to become a TA(T)$_n$ motif); (Duplication of delta8 [SEQ ID 2] region -293 to -285, inserted between -285/-284)

SEQ ID 155

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAA***
***TAAATGGACGCCTGCTCCATATTTTTCCGGTT*ATTACCCCACCTGGAAGTGCCCAGAATTTTCCGGGGATTACGG**
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT pG1-7 (PG1-D974-(T)$_{15}$): Example comprising one T motif which is (T)$_n$ (n=15) without a TA extension;

(Duplication of delta8 [SEQ ID 2] region -293 to -285, inserted between -285/-284)

SEQ ID 156

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGAATA***
***AATGGACGCCTGCTCCATATTTTTCCGGTT*ATTACCCCACCTGGAAGTGCCCAGAATTTTCCGGGGATTACGGAT**
AATACGGTGGTCTGGATTAATTAATACGCCAAGTCTTACATTTTGTTGCAGTCTCGTGCGAGTATGTGCAATAAT
AAACAAGATGAGCCAATTTATTGGATTAGTTGCAGCTTGACCCCGCCATAGCTAGGCATAGCCAAGTGCTATGG
GTGTTAGATGATGCACTTGGATGCAGTGAGTTTTGGAGTATAAAAGATCCTTAAAATTCCACCCTT

FIG.6B-84 pG1-7 (PG1-D974-TA$(T)_{16}$): Example comprising one T motif which is $(T)_n$ (n=16), extended by preceding TA (extending the T motif at its 5'-end to become a TA$(T)_n$ motif); (Duplication of delta8 [SEQ ID 2] region -293 to -285, inserted between -285/-284)

SEQ ID 157

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***ATAAATGGACGCCTGCTCCATATTTTTCCGGTT*ATTACCCCACCTGGAAGTGCCCAGAATTTTCCGGGGATTACG**
GATAATACGGTGGTCTGGATTAATTAATACGCCAAGTCTTACATTTTGTTGCAGTCTCGTGCGAGTATGTGCAAT
AATAAACAAGATGAGCCAATTTATTGGATTAGTTGCAGCTTGACCCCGCCATAGCTAGGCATAGCCAAGTGCTAT
GGGTGTTAGATGATGCACTTGGATGCAGTGAGTTTTGGAGTATAAAAGATCCTTAAAATTCCACCCTT pG1-7 (PG1-D974-$(T)_{16}$): Example comprising one T motif which is $(T)_n$ (n=16) without a TA extension;

(Duplication of delta8 [SEQ ID 2] region -293 to -285, inserted between -285/-284)

SEQ ID 158

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGAAT***
***AAATGGACGCCTGCTCCATATTTTTCCGGTT*ATTACCCCACCTGGAAGTGCCCAGAATTTTCCGGGGATTACGG**
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT

FIG.6B-85 pG1-7 (PG1-D974-TA(T)$_{17}$): Example comprising one T motif which is (T)$_n$ (n=17), extended by preceding TA (extending the T motif at its 5′-end to become a TA(T)$_n$ motif); (Duplication of delta8 [SEQ ID 2] region -293 to -285, inserted between -285/-284)

SEQ ID 159

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***ATAAATGGACGCCTGCTCCATATTTTTCCGGTT*ATTACCCCACCTGGAAGTGCCCAGAATTTTCCGGGGATTACG**
GATAATACGGTGGTCTGGATTAATTAATACGCCAAGTCTTACATTTTGTTGCAGTCTCGTGCGAGTATGTGCAAT
AATAAACAAGATGAGCCAATTTATTGGATTAGTTGCAGCTTGACCCCGCCATAGCTAGGCATAGCCAAGTGCTAT
GGGTGTTAGATGATGCACTTGGATGCAGTGAGTTTTGGAGTATAAAAGATCCTTAAAATTCCACCCTT pG1-7 (PG1-D974-(T)$_{17}$): Example comprising one T motif which is (T)$_n$ (n=17) without a TA extension;

(Duplication of delta8 [SEQ ID 2] region -293 to -285, inserted between -285/-284)

SEQ ID 160

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAA***
***TAAATGGACGCCTGCTCCATATTTTTCCGGTT*ATTACCCCACCTGGAAGTGCCCAGAATTTTCCGGGGATTACGG**
ATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT

FIG.6B-86 pG1-7 (PG1-D974-TA(T)$_{18}$): Example comprising one T motif which is (T)$_n$ (n=18), extended by preceding TA (extending the T motif at its 5′-end to become a TA(T)$_n$ motif); (Duplication of delta8 [SEQ ID 2] region -293 to -285, inserted between -285/-284)

SEQ ID 161

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***AATAAATGGACGCCTGCTCCATATTTTTCCGGTT*ATTACCCCACCTGGAAGTGCCCAGAATTTTCCGGGGATTAC**
GGATAATACGGTGGTCTGGATTAATTAATACGCCAAGTCTTACATTTTGTTGCAGTCTCGTGCGAGTATGTGCAA
TAATAAACAAGATGAGCCAATTTATTGGATTAGTTGCAGCTTGACCCCGCCATAGCTAGGCATAGCCAAGTGCTA
TGGGTGTTAGATGATGCACTTGGATGCAGTGAGTTTTGGAGTATAAAAGATCCTTAAAATTCCACCCTT pG1-7 (PG1-D974-(T)$_{18}$): Example comprising one T motif which is (T)$_n$ (n=18) without a TA extension;

(Duplication of delta8 [SEQ ID 2] region -293 to -285, inserted between -285/-284)

SEQ ID 162

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***ATAAATGGACGCCTGCTCCATATTTTTCCGGTT*ATTACCCCACCTGGAAGTGCCCAGAATTTTCCGGGGATTACG**
GATAATACGGTGGTCTGGATTAATTAATACGCCAAGTCTTACATTTTGTTGCAGTCTCGTGCGAGTATGTGCAAT
AATAAACAAGATGAGCCAATTTATTGGATTAGTTGCAGCTTGACCCCGCCATAGCTAGGCATAGCCAAGTGCTAT
GGGTGTTAGATGATGCACTTGGATGCAGTGAGTTTTGGAGTATAAAAGATCCTTAAAATTCCACCCTT

FIG.6B-87 pG1-7 (PG1-D974-TA(T)$_{19}$): Example comprising one T motif which is (T)$_n$ (n=19), extended by preceding TA (extending the T motif at its 5'-end to become a TA(T)$_n$ motif); (Duplication of delta8 [SEQ ID 2] region -293 to -285, inserted between -285/-284)

SEQ ID 163

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTT*GATGACCCCGTTT
TCGTGACAAATTAATTTCCAACGGGGTCTTGTCCGGATAAGAGAATTTTGTTTGATTATCCGTTCGG*ATAAATGG*
*AATAAATGGACGCCTGCTCCATATTTTTCCGGTT*ATTACCCCACCTGGAAGTGCCCAGAATTTTCCGGGGATTAC
GGATAATACGGTGGTCTGGATTAATTAATACGCCAAGTCTTACATTTTGTTGCAGTCTCGTGCGAGTATGTGCAA
TAATAAACAAGATGAGCCAATTTATTGGATTAGTTGCAGCTTGACCCCGCCATAGCTAGGCATAGCCAAGTGCTA
TGGGTGTTAGATGATGCACTTGGATGCAGTGAGTTTTGGAGTATAAAAGATCCTTAAAATTCCACCCTT pG1-7 (PG1-D974-(T)$_{19}$): Example comprising one T motif which is (T)$_n$ (n=19) without a TA extension;

(Duplication of delta8 [SEQ ID 2] region -293 to -285, inserted between -285/-284)

SEQ ID 164

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTT*GATGACCCCGTTTTC
GTGACAAATTAATTTCCAACGGGGTCTTGTCCGGATAAGAGAATTTTGTTTGATTATCCGTTCGG*ATAAATGGA*
*ATAAATGGACGCCTGCTCCATATTTTTCCGGTT*ATTACCCCACCTGGAAGTGCCCAGAATTTTCCGGGGATTACG
GATAATACGGTGGTCTGGATTAATTAATACGCCAAGTCTTACATTTTGTTGCAGTCTCGTGCGAGTATGTGCAAT
AATAAACAAGATGAGCCAATTTATTGGATTAGTTGCAGCTTGACCCCGCCATAGCTAGGCATAGCCAAGTGCTAT
GGGTGTTAGATGATGCACTTGGATGCAGTGAGTTTTGGAGTATAAAAGATCCTTAAAATTCCACCCTT

FIG.6B-88 pG1-7 (PG1-D974-TA(T)$_{20}$): Example comprising one T motif which is (T)$_n$ (n=20), extended by preceding TA (extending the T motif at its 5'-end to become a TA(T)$_n$ motif); (Duplication of delta8 [SEQ ID 2] region -293 to -285, inserted between -285/-284)

SEQ ID 165

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTTT*GATGACCCCGTT
TTCGTGACAAATTAATTTCCAACGGGGTCTTGT**CCGGATAAGAGAATTTTGTTTGATTATCCGTTCGG*ATAAATG
GAATAAATGGACGCCTGCTCCATATTTTTCCGGTT*ATTACCCCACCTGGAAGTGCCCAGAATTTTCCGGGGATTA
CGGATAATAC**GGTGGTCTGGATTAATTAATACGCCAAGTCTTACATTTTGTTGCAGTCTCGTGCGAGTATGTGCA
ATAATAAACAAGATGAGCCAATTTATTGGATTAGTTGCAGCTTGACCCCGCCATAGCTAGGCATAGCCAAGTGCT
ATGGGTGTTAGATGATGCACTTGGATGCAGTGAGTTTTGGAGTATAAAAGATCCTTAAAATTCCACCCTT pG1-7 (PG1-D974-(T)$_{20}$): Example comprising one T motif which is (T)$_n$ (n=20) without a TA extension;

(Duplication of delta8 [SEQ ID 2] region -293 to -285, inserted between -285/-284)

SEQ ID 166

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG
AATAAATGGACGCCTGCTCCATATTTTTCCGGTT*ATTACCCCACCTGGAAGTGCCCAGAATTTTCCGGGGATTAC
GGATAATAC**GGTGGTCTGGATTAATTAATACGCCAAGTCTTACATTTTGTTGCAGTCTCGTGCGAGTATGTGCAA
TAATAAACAAGATGAGCCAATTTATTGGATTAGTTGCAGCTTGACCCCGCCATAGCTAGGCATAGCCAAGTGCTA
TGGGTGTTAGATGATGCACTTGGATGCAGTGAGTTTTGGAGTATAAAAGATCCTTAAAATTCCACCCTT

FIG.6B-89 pG1-8 (PG1-D980-TA(T)$_n$): Example comprising one T motif which is (T)$_n$ (n=13-20), extended by preceding TA (extending the T motif at its 5'-end to become a TA(T)$_n$ motif); (Duplication of delta9 region -275 to-261, inserted between -261/-260)

SEQ ID 167

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TA(T)$_n$*GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTTCATATTTTTTCCGGTT*ATTACCCCACCTGGAAGTGCCCAGAATTTTCCGGGGATTACGGATAATA**
CGGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT pG1-8 (PG1-D980-(T)$_n$): Example comprising one T motif which is (T)$_n$ (n=13-20) without a TA extension;

(Duplication of delta9 region -275 to-261, inserted between -261/-260)

SEQ ID 168

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*(T)$_n$*GATGACCCCGTTTTCGTGACAAATTAATT
TCCAACGGGGTCTTGT**CCGGATAAGAGAATTTTGTTTGATTATCCGTTCGG*ATAAATGGACGCCTGCTCCATATT***
***TTTCCGGTTCATATTTTTTCCGGTT*ATTACCCCACCTGGAAGTGCCCAGAATTTTCCGGGGATTACGGATAATACG**
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT

FIG.6B-90 pG1-8 (PG1-D980-TA$(T)_{13}$): Example comprising one T motif which is $(T)_n$ (n=13), extended by preceding TA (extending the T motif at its 5'-end to become a TA$(T)_n$ motif); (Duplication of delta9 [SEQ ID 3] region -275 to-261, inserted between -261/-260)

SEQ ID 169

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTCCGGTTCATATTTTTCCGGTT*ATTACCCCACCTGGAAGTGCCCAGAATTTTCCGGGGATTAC**
GGATAATACGGTGGTCTGGATTAATTAATACGCCAAGTCTTACATTTTGTTGCAGTCTCGTGCGAGTATGTGCAA
TAATAAACAAGATGAGCCAATTTATTGGATTAGTTGCAGCTTGACCCCGCCATAGCTAGGCATAGCCAAGTGCTA
TGGGTGTTAGATGATGCACTTGGATGCAGTGAGTTTTGGAGTATAAAAGATCCTTAAAATTCCACCCTT pG1-8 (PG1-D980-$(T)_{13}$): Example comprising one T motif which is $(T)_n$ (n=13) without a TA extension;

(Duplication of delta9 [SEQ ID 3] region -275 to-261, inserted between -261/-260)

SEQ ID 170

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTT*GATGACCCCGTTTTCGTGAC
AAATTAATTTCCAACGGGGTCTTGT**CCGGATAAGAGAATTTTGTTTGATTATCCGTTCGG*ATAAATGGACGCCT***
***GCTCCATATTTTTCCGGTTCATATTTTTCCGGTT*ATTACCCCACCTGGAAGTGCCCAGAATTTTCCGGGGATTACG**
GATAATACGGTGGTCTGGATTAATTAATACGCCAAGTCTTACATTTTGTTGCAGTCTCGTGCGAGTATGTGCAAT
AATAAACAAGATGAGCCAATTTATTGGATTAGTTGCAGCTTGACCCCGCCATAGCTAGGCATAGCCAAGTGCTAT
GGGTGTTAGATGATGCACTTGGATGCAGTGAGTTTTGGAGTATAAAAGATCCTTAAAATTCCACCCTT

FIG.6B-91 pG1-8 (PG1-D980-TA$(T)_{14}$): Example comprising one T motif which is $(T)_n$ (n=14), extended by preceding TA (extending the T motif at its 5'-end to become a TA$(T)_n$ motif); (Duplication of delta9 [SEQ ID 3] region -275 to-261, inserted between -261/-260)

SEQ ID 171

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTTCATATTTTTCCGGTT*ATTACCCCACCTGGAAGTGCCCAGAATTTTCCGGGGATT**
ACGGATAATACGGTGGTCTGGATTAATTAATACGCCAAGTCTTACATTTTGTTGCAGTCTCGTGCGAGTATGTGC
AATAATAAACAAGATGAGCCAATTTATTGGATTAGTTGCAGCTTGACCCCGCCATAGCTAGGCATAGCCAAGTGC
TATGGGTGTTAGATGATGCACTTGGATGCAGTGAGTTTTGGAGTATAAAAGATCCTTAAAATTCCACCCTT pG1-8 (PG1-D980-$(T)_{14}$): Example comprising one T motif which is $(T)_n$ (n=14) without a TA extension;

(Duplication of delta9 [SEQ ID 3] region -275 to-261, inserted between -261/-260)

SEQ ID 172

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTT*GATGACCCCGTTTTCGTGA
CAAATTAATTTCCAACGGGGTCTTGT**CCGGATAAGAGAATTTTGTTTGATTATCCGTTCGG*ATAAATGGACGCCT***
***GCTCCATATTTTTCCGGTTCATATTTTTCCGGTT*ATTACCCCACCTGGAAGTGCCCAGAATTTTCCGGGGATTACG**
GATAATACGGTGGTCTGGATTAATTAATACGCCAAGTCTTACATTTTGTTGCAGTCTCGTGCGAGTATGTGCAAT
AATAAACAAGATGAGCCAATTTATTGGATTAGTTGCAGCTTGACCCCGCCATAGCTAGGCATAGCCAAGTGCTAT
GGGTGTTAGATGATGCACTTGGATGCAGTGAGTTTTGGAGTATAAAAGATCCTTAAAATTCCACCCTT

FIG.6B-92 pG1-8 (PG1-D980-TA(T)$_{15}$): Example comprising one T motif which is (T)$_n$ (n=15), extended by preceding TA (extending the T motif at its 5'-end to become a TA(T)$_n$ motif); (Duplication of delta9 [SEQ ID 3] region -275 to-261, inserted between -261/-260)

SEQ ID 173

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTTCCGGTTCATATTTTTTCCGGTT*ATTACCCCACCTGGAAGTGCCCAGAATTTTCCGGGGAT**
TACGGATAATACGGTGGTCTGGATTAATTAATACGCCAAGTCTTACATTTTGTTGCAGTCTCGTGCGAGTATGTG
CAATAATAAACAAGATGAGCCAATTTATTGGATTAGTTGCAGCTTGACCCCGCCATAGCTAGGCATAGCCAAGTG
CTATGGGTGTTAGATGATGCACTTGGATGCAGTGAGTTTTGGAGTATAAAAGATCCTTAAAATTCCACCCTT pG1-8 (PG1-D980-(T)$_{15}$): Example comprising one T motif which is (T)$_n$ (n=15) without a TA extension; (Duplication of delta9 [SEQ ID 3] region -275 to-261, inserted between -261/-260)

SEQ ID 174

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTTCCGGTTCATATTTTTTCCGGTT*ATTACCCCACCTGGAAGTGCCCAGAATTTTCCGGGGATTAC**
GGATAATACGGTGGTCTGGATTAATTAATACGCCAAGTCTTACATTTTGTTGCAGTCTCGTGCGAGTATGTGCAA
TAATAAACAAGATGAGCCAATTTATTGGATTAGTTGCAGCTTGACCCCGCCATAGCTAGGCATAGCCAAGTGCTA
TGGGTGTTAGATGATGCACTTGGATGCAGTGAGTTTTGGAGTATAAAAGATCCTTAAAATTCCACCCTT

FIG.6B-93 pG1-8 (PG1-D980-TA(T)$_{16}$): Example comprising one T motif which is (T)$_n$ (n=16), extended by preceding TA (extending the T motif at its 5'-end to become a TA(T)$_n$ motif); (Duplication of delta9 [SEQ ID 3] region -275 to-261, inserted between -261/-260)

SEQ ID 175

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTTCATATTTTTCCGGTT*ATTACCCCACCTGGAAGTGCCCAGAATTTTCCGGGGA**
TTACGGATAATACGGTGGTCTGGATTAATTAATACGCCAAGTCTTACATTTTGTTGCAGTCTCGTGCGAGTATGT
GCAATAATAAACAAGATGAGCCAATTTATTGGATTAGTTGCAGCTTGACCCCGCCATAGCTAGGCATAGCCAAGT
GCTATGGGTGTTAGATGATGCACTTGGATGCAGTGAGTTTTGGAGTATAAAAGATCCTTAAAATTCCACCCTT pG1-8 (PG1-D980-(T)$_{16}$): Example comprising one T motif which is (T)$_n$ (n=16) without a TA extension;

(Duplication of delta9 [SEQ ID 3] region -275 to-261, inserted between -261/-260)

SEQ ID 176

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTTCATATTTTTCCGGTT*ATTACCCCACCTGGAAGTGCCCAGAATTTTCCGGGGATT**
ACGGATAATACGGTGGTCTGGATTAATTAATACGCCAAGTCTTACATTTTGTTGCAGTCTCGTGCGAGTATGTGC
AATAATAAACAAGATGAGCCAATTTATTGGATTAGTTGCAGCTTGACCCCGCCATAGCTAGGCATAGCCAAGTGC
TATGGGTGTTAGATGATGCACTTGGATGCAGTGAGTTTTGGAGTATAAAAGATCCTTAAAATTCCACCCTT

FIG.6B-94 pG1-8 (PG1-D980-TA$(T)_{17}$): Example comprising one T motif which is $(T)_n$ (n=17), extended by preceding TA (extending the T motif at its 5'-end to become a TA$(T)_n$ motif); (Duplication of delta9 [SEQ ID 3] region -275 to-261, inserted between -261/-260)

SEQ ID 177

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTTCATATTTTTCCGGTT*ATTACCCCACCTGGAAGTGCCCAGAATTTTCCGGGGA**
TTACGGATAATACGGTGGTCTGGATTAATTAATACGCCAAGTCTTACATTTTGTTGCAGTCTCGTGCGAGTATGT
GCAATAATAAACAAGATGAGCCAATTTATTGGATTAGTTGCAGCTTGACCCCGCCATAGCTAGGCATAGCCAAGT
GCTATGGGTGTTAGATGATGCACTTGGATGCAGTGAGTTTTGGAGTATAAAAGATCCTTAAAATTCCACCCTT pG1-8 (PG1-D980-$(T)_{17}$): Example comprising one T motif which is $(T)_n$ (n=17) without a TA extension;

(Duplication of delta9 [SEQ ID 3] region -275 to-261, inserted between -261/-260)

SEQ ID 178

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTCCGGTTCATATTTTTCCGGTT*ATTACCCCACCTGGAAGTGCCCAGAATTTTCCGGGGAT**
TACGGATAATACGGTGGTCTGGATTAATTAATACGCCAAGTCTTACATTTTGTTGCAGTCTCGTGCGAGTATGTG
CAATAATAAACAAGATGAGCCAATTTATTGGATTAGTTGCAGCTTGACCCCGCCATAGCTAGGCATAGCCAAGTG
CTATGGGTGTTAGATGATGCACTTGGATGCAGTGAGTTTTGGAGTATAAAAGATCCTTAAAATTCCACCCTT

FIG.6B-95 pG1-8 (PG1-D980-TA$(T)_{18}$): Example comprising one T motif which is $(T)_n$ (n=18), extended by preceding TA (extending the T motif at its 5'-end to become a TA$(T)_n$ motif); (Duplication of delta9 [SEQ ID 3] region -275 to-261, inserted between -261/-260)

SEQ ID 179

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTTCATATTTTTCCGGTT*ATTACCCCACCTGGAAGTGCCCAGAATTTTCCGGGG**
ATTACGGATAATACGGTGGTCTGGATTAATTAATACGCCAAGTCTTACATTTTGTTGCAGTCTCGTGCGAGTATG
TGCAATAATAAACAAGATGAGCCAATTTATTGGATTAGTTGCAGCTTGACCCCGCCATAGCTAGGCATAGCCAAG
TGCTATGGGTGTTAGATGATGCACTTGGATGCAGTGAGTTTTGGAGTATAAAAGATCCTTAAAATTCCACCCTT pG1-8 (PG1-D980-$(T)_{18}$): Example comprising one T motif which is $(T)_n$ (n=18) without a TA extension; (Duplication of delta9 [SEQ ID 3] region -275 to-261, inserted between -261/-260)

SEQ ID 180

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTTCATATTTTTCCGGTT*ATTACCCCACCTGGAAGTGCCCAGAATTTTCCGGGGA**
TTACGGATAATACGGTGGTCTGGATTAATTAATACGCCAAGTCTTACATTTTGTTGCAGTCTCGTGCGAGTATGT
GCAATAATAAACAAGATGAGCCAATTTATTGGATTAGTTGCAGCTTGACCCCGCCATAGCTAGGCATAGCCAAGT
GCTATGGGTGTTAGATGATGCACTTGGATGCAGTGAGTTTTGGAGTATAAAAGATCCTTAAAATTCCACCCTT

FIG.6B-96 pG1-8 (PG1-D980-TA$(T)_{19}$): Example comprising one T motif which is $(T)_n$ (n=19), extended by preceding TA (extending the T motif at its 5'-end to become a TA$(T)_n$ motif); (Duplication of delta9 [SEQ ID 3] region -275 to-261, inserted between -261/-260)

SEQ ID 181

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTTCATATTTTTCCGGTT*ATTACCCCACCTGGAAGTGCCCAGAATTTTCCGGGG**
ATTACGGATAATACGGTGGTCTGGATTAATTAATACGCCAAGTCTTACATTTTGTTGCAGTCTCGTGCGAGTATG
TGCAATAATAAACAAGATGAGCCAATTTATTGGATTAGTTGCAGCTTGACCCCGCCATAGCTAGGCATAGCCAAG
TGCTATGGGTGTTAGATGATGCACTTGGATGCAGTGAGTTTTGGAGTATAAAAGATCCTTAAAATTCCACCCTT pG1-8 (PG1-D980-$(T)_{19}$): Example comprising one T motif which is $(T)_n$ (n=19) without a TA extension;

(Duplication of delta9 [SEQ ID 3] region -275 to-261, inserted between -261/-260)

SEQ ID 182

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTTCATATTTTTCCGGTT*ATTACCCCACCTGGAAGTGCCCAGAATTTTCCGGGGA**
TTACGGATAATACGGTGGTCTGGATTAATTAATACGCCAAGTCTTACATTTTGTTGCAGTCTCGTGCGAGTATGT
GCAATAATAAACAAGATGAGCCAATTTATTGGATTAGTTGCAGCTTGACCCCGCCATAGCTAGGCATAGCCAAGT
GCTATGGGTGTTAGATGATGCACTTGGATGCAGTGAGTTTTGGAGTATAAAAGATCCTTAAAATTCCACCCTT

FIG.6B-97 pG1-8 (PG1-D980-TA$(T)_{20}$): Example comprising one T motif which is $(T)_n$ (n=20), extended by preceding TA (extending the T motif at its 5'-end to become a TA$(T)_n$ motif); (Duplication of delta9 [SEQ ID 3] region -275 to-261, inserted between -261/-260)

SEQ ID 183

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTTT*GATGACCCCGTT
TTCGTGACAAATTAATTTCCAACGGGGTCTTGT**CCGGATAAGAGAATTTTGTTTGATTATCCGTTCGG*ATAAATG***
***GACGCCTGCTCCATATTTTTCCGGTTCATATTTTTCCGGTT*ATTACCCCACCTGGAAGTGCCCAGAATTTTCCGGG**
GATTACGGATAATACGGTGGTCTGGATTAATTAATACGCCAAGTCTTACATTTTGTTGCAGTCTCGTGCGAGTAT
GTGCAATAATAAACAAGATGAGCCAATTTATTGGATTAGTTGCAGCTTGACCCCGCCATAGCTAGGCATAGCCAA
GTGCTATGGGTGTTAGATGATGCACTTGGATGCAGTGAGTTTTGGAGTATAAAAGATCCTTAAAATTCCACCCTT pG1-8 (PG1-D980-$(T)_{20}$): Example comprising one T motif which is $(T)_n$ (n=20) without a TA extension;

(Duplication of delta9 [SEQ ID 3] region -275 to-261, inserted between -261/-260)

SEQ ID 184

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTTCATATTTTTCCGGTT*ATTACCCCACCTGGAAGTGCCCAGAATTTTCCGGGG**
ATTACGGATAATACGGTGGTCTGGATTAATTAATACGCCAAGTCTTACATTTTGTTGCAGTCTCGTGCGAGTATG
TGCAATAATAAACAAGATGAGCCAATTTATTGGATTAGTTGCAGCTTGACCCCGCCATAGCTAGGCATAGCCAAG
TGCTATGGGTGTTAGATGATGCACTTGGATGCAGTGAGTTTTGGAGTATAAAAGATCCTTAAAATTCCACCCTT

FIG.6B-98 pG1-9 (PG1-D1034-TA$(T)_n$): Example comprising one T motif which is $(T)_n$ (n=13-20), extended by preceding TA (extending the T motif at its 5'-end to become a TA$(T)_n$ motif); (Duplication of delta7 to delta 10 region -310 to -242, inserted between -242/-241)

SEQ ID 185

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TA$(T)_n$*GATGACCCCGTTTTCGTGACAAATTAA
TTTCCAACGGGGTCTTGT**CCGGATAAGAGAATTTTGTTTGATTATCCGTTCGG*ATAAATGGACGCCTGCTCCATA***
***TTTTTCCGGTT*ATTACCCCACCTGGAAGTGTTTGATTATCCGTTCGG*ATAAATGGACGCCTGCTCCATATTTTTCC***
***GGTT*ATTACCCCACCTGGAAGTGCCCAGAATTTTCCGGGGATTACGGATAATAC**GGTGGTCTGGATTAATTAAT
ACGCCAAGTCTTACATTTTGTTGCAGTCTCGTGCGAGTATGTGCAATAATAAACAAGATGAGCCAATTTATTGGA
TTAGTTGCAGCTTGACCCCGCCATAGCTAGGCATAGCCAAGTGCTATGGGTGTTAGATGATGCACTTGGATGCAG
TGAGTTTTGGAGTATAAAAGATCCTTAAAA*TTCCACCCTT* pG1-9 (PG1-D1034-$(T)_n$): Example comprising one T motif which is $(T)_n$ (n=13-20) without a TA extension; (Duplication of delta7 to delta 10 region -310 to -242, inserted between -242/-241)

SEQ ID 186

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*$(T)_n$*GATGACCCCGTTTTCGTGACAAATTAATT
TCCAACGGGGTCTTGT**CCGGATAAGAGAATTTTGTTTGATTATCCGTTCGG*ATAAATGGACGCCTGCTCCATATT***
***TTTCCGGTT*ATTACCCCACCTGGAAGTGTTTGATTATCCGTTCGG*ATAAATGGACGCCTGCTCCATATTTTTCCGG***
***TT*ATTACCCCACCTGGAAGTGCCCAGAATTTTCCGGGGATTACGGATAATAC**GGTGGTCTGGATTAATTAATAC
GCCAAGTCTTACATTTTGTTGCAGTCTCGTGCGAGTATGTGCAATAATAAACAAGATGAGCCAATTTATTGGATTA
GTTGCAGCTTGACCCCGCCATAGCTAGGCATAGCCAAGTGCTATGGGTGTTAGATGATGCACTTGGATGCAGTG
AGTTTTGGAGTATAAAAGATCCTTAAAA*TTCCACCCTT*

FIG.6B-99 pG1-9 (PG1-D1034-TA$(T)_{13}$): Example comprising one T motif which is $(T)_n$ (n=13), extended by preceding TA (extending the T motif at its 5'-end to become a TA$(T)_n$ motif); (Duplication of delta7 to delta 10 region -310 to -242, inserted between -242/-241)

SEQ ID 187

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTCCGGTT*ATTACCCCACCTGGAAGTGTTTGATTATCCGTTCGG*ATAAATGGACGCCTGCTCCA***
***TATTTTTCCGGTT*ATTACCCCACCTGGAAGTGCCCAGAATTTTCCGGGGATTACGGATAATAC**GGTGGTCTGGA
TTAATTAATACGCCAAGTCTTACATTTTGTTGCAGTCTCGTGCGAGTATGTGCAATAATAAACAAGATGAGCCAAT
TTATTGGATTAGTTGCAGCTTGACCCCGCCATAGCTAGGCATAGCCAAGTGCTATGGGTGTTAGATGATGCACTT
GGATGCAGTGAGTTTTGGAGTATAAAAGATCCTTAAAATTCCACCCTT pG1-9 (PG1-D1034-$(T)_{13}$): Example comprising one T motif which is $(T)_n$ (n=13) without a TA extension;

(Duplication of delta7 to delta 10 region -310 to -242, inserted between -242/-241)

SEQ ID 188

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTT*GATGACCCCGTTTTCGTGAC
AAATTAATTTCCAACGGGGTCTTGT**CCGGATAAGAGAATTTTGTTTGATTATCCGTTCGG*ATAAATGGACGCCT***
***GCTCCATATTTTTCCGGTT*ATTACCCCACCTGGAAGTGTTTGATTATCCGTTCGG*ATAAATGGACGCCTGCTCCAT***
***ATTTTTCCGGTT*ATTACCCCACCTGGAAGTGCCCAGAATTTTCCGGGGATTACGGATAATAC**GGTGGTCTGGAT
TAATTAATACGCCAAGTCTTACATTTTGTTGCAGTCTCGTGCGAGTATGTGCAATAATAAACAAGATGAGCCAATT
TATTGGATTAGTTGCAGCTTGACCCCGCCATAGCTAGGCATAGCCAAGTGCTATGGGTGTTAGATGATGCACTTG
GATGCAGTGAGTTTTGGAGTATAAAAGATCCTTAAAATTCCACCCTT

FIG.6B-100 pG1-9 (PG1-D1034-TA(T)$_{14}$): Example comprising one T motif which is $(T)_n$ (n=14), extended by preceding TA (extending the T motif at its 5'-end to become a $TA(T)_n$ motif); (Duplication of delta7 to delta 10 region -310 to -242, inserted between -242/-241)

SEQ ID 189

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTT*ATTACCCCACCTGGAAGTGTTTGATTATCCGTTCGG*ATAAATGGACGCCTGCTC***
***CATATTTTTCCGGTT*ATTACCCCACCTGGAAGTGCCCAGAATTTTCCGGGGATTACGGATAATAC**GGTGGTCTG
GATTAATTAATACGCCAAGTCTTACATTTTGTTGCAGTCTCGTGCGAGTATGTGCAATAATAAACAAGATGAGCC
AATTTATTGGATTAGTTGCAGCTTGACCCCGCCATAGCTAGGCATAGCCAAGTGCTATGGGTGTTAGATGATGCA
CTTGGATGCAGTGAGTTTTGGAGTATAAAAGATCCTTAAAATTCCACCCTT pG1-9 (PG1-D1034-(T)$_{14}$): Example comprising one T motif which is $(T)_n$ (n=14) without a TA extension;

(Duplication of delta7 to delta 10 region -310 to -242, inserted between -242/-241)

SEQ ID 190

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTT*GATGACCCCGTTTTCGTGA
CAAATTAATTTCCAACGGGGTCTTGT**CCGGATAAGAGAATTTTGTTTGATTATCCGTTCGG*ATAAATGGACGCCT***
***GCTCCATATTTTTCCGGTT*ATTACCCCACCTGGAAGTGTTTGATTATCCGTTCGG*ATAAATGGACGCCTGCTCCAT***
***ATTTTTCCGGTT*ATTACCCCACCTGGAAGTGCCCAGAATTTTCCGGGGATTACGGATAATAC**GGTGGTCTGGAT
TAATTAATACGCCAAGTCTTACATTTTGTTGCAGTCTCGTGCGAGTATGTGCAATAATAAACAAGATGAGCCAATT
TATTGGATTAGTTGCAGCTTGACCCCGCCATAGCTAGGCATAGCCAAGTGCTATGGGTGTTAGATGATGCACTTG
GATGCAGTGAGTTTTGGAGTATAAAAGATCCTTAAAATTCCACCCTT

FIG.6B-101 pG1-9 (PG1-D1034-TA(T)$_{15}$): Example comprising one T motif which is (T)$_n$ (n=15), extended by preceding TA (extending the T motif at its 5'-end to become a TA(T)$_n$ motif); (Duplication of delta7 to delta 10 region -310 to -242, inserted between -242/-241)

SEQ ID 191

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTCCGGTT*ATTACCCCACCTGGAAGTGTTTGATTATCCGTTCGG*ATAAATGGACGCCTGC***
***TCCATATTTTTCCGGTT*ATTACCCCACCTGGAAGTGCCCAGAATTTTCCGGGGATTACGGATAATAC**GGTGGTCT
GGATTAATTAATACGCCAAGTCTTACATTTTGTTGCAGTCTCGTGCGAGTATGTGCAATAATAAACAAGATGAGC
CAATTTATTGGATTAGTTGCAGCTTGACCCCGCCATAGCTAGGCATAGCCAAGTGCTATGGGTGTTAGATGATGC
ACTTGGATGCAGTGAGTTTTGGAGTATAAAAGATCCTTAAAATTCCACCCTT pG1-9 (PG1-D1034-(T)$_{15}$): Example comprising one T motif which is (T)$_n$ (n=15) without a TA extension;

(Duplication of delta7 to delta 10 region -310 to -242, inserted between -242/-241)

SEQ ID 192

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTCCGGTT*ATTACCCCACCTGGAAGTGTTTGATTATCCGTTCGG*ATAAATGGACGCCTGCTCCA***
***TATTTTTCCGGTT*ATTACCCCACCTGGAAGTGCCCAGAATTTTCCGGGGATTACGGATAATAC**GGTGGTCTGGA
TTAATTAATACGCCAAGTCTTACATTTTGTTGCAGTCTCGTGCGAGTATGTGCAATAATAAACAAGATGAGCCAAT
TTATTGGATTAGTTGCAGCTTGACCCCGCCATAGCTAGGCATAGCCAAGTGCTATGGGTGTTAGATGATGCACTT
GGATGCAGTGAGTTTTGGAGTATAAAAGATCCTTAAAATTCCACCCTT

FIG.6B-102 pG1-9 (PG1-D1034-TA(T)$_{16}$): Example comprising one T motif which is $(T)_n$ (n=16), extended by preceding TA (extending the T motif at its 5'-end to become a TA$(T)_n$ motif); (Duplication of delta7 to delta 10 region -310 to -242, inserted between -242/-241)

SEQ ID 193

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGTTTGATTATCCGTTCGG*ATAAATGGACGCCTG***
***CTCCATATTTTTCCGGTT*ATTACCCCACCTGGAAGTGCCCAGAATTTTCCGGGGATTACGGATAATAC**GGTGGTC
TGGATTAATTAATACGCCAAGTCTTACATTTTGTTGCAGTCTCGTGCGAGTATGTGCAATAATAAACAAGATGAG
CCAATTTATTGGATTAGTTGCAGCTTGACCCCGCCATAGCTAGGCATAGCCAAGTGCTATGGGTGTTAGATGATG
CACTTGGATGCAGTGAGTTTTGGAGTATAAAAGATCCTTAAAA*TTCCACCCTT* pG1-9 (PG1-D1034-(T)$_{16}$): Example comprising one T motif which is $(T)_n$ (n=16) without a TA extension;

(Duplication of delta7 to delta 10 region -310 to -242, inserted between -242/-241)

SEQ ID 194

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTT*ATTACCCCACCTGGAAGTGTTTGATTATCCGTTCGG*ATAAATGGACGCCTGCTC***
***CATATTTTTCCGGTT*ATTACCCCACCTGGAAGTGCCCAGAATTTTCCGGGGATTACGGATAATAC**GGTGGTCTG
GATTAATTAATACGCCAAGTCTTACATTTTGTTGCAGTCTCGTGCGAGTATGTGCAATAATAAACAAGATGAGCC
AATTTATTGGATTAGTTGCAGCTTGACCCCGCCATAGCTAGGCATAGCCAAGTGCTATGGGTGTTAGATGATGCA
CTTGGATGCAGTGAGTTTTGGAGTATAAAAGATCCTTAAAA*TTCCACCCTT*

FIG.6B-103 pG1-9 (PG1-D1034-TA$(T)_{17}$): Example comprising one T motif which is $(T)_n$ (n=17), extended by preceding TA (extending the T motif at its 5'-end to become a TA$(T)_n$ motif); (Duplication of delta7 to delta 10 region -310 to -242, inserted between -242/-241)

SEQ ID 195

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGTTTGATTATCCGTTCGG*ATAAATGGACGCCTG***
***CTCCATATTTTTCCGGTT*ATTACCCCACCTGGAAGTGCCCAGAATTTTCCGGGGATTACGGATAATAC**GGTGGTC
TGGATTAATTAATACGCCAAGTCTTACATTTTGTTGCAGTCTCGTGCGAGTATGTGCAATAATAAACAAGATGAG
CCAATTTATTGGATTAGTTGCAGCTTGACCCCGCCATAGCTAGGCATAGCCAAGTGCTATGGGTGTTAGATGATG
CACTTGGATGCAGTGAGTTTTGGAGTATAAAAGATCCTTAAAATTCCACCCTT pG1-9 (PG1-D1034-$(T)_{17}$): Example comprising one T motif which is $(T)_n$ (n=17) without a TA extension;

(Duplication of delta7 to delta 10 region -310 to -242, inserted between -242/-241)

SEQ ID 196

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTCCGGTT*ATTACCCCACCTGGAAGTGTTTGATTATCCGTTCGG*ATAAATGGACGCCTGC***
***TCCATATTTTTCCGGTT*ATTACCCCACCTGGAAGTGCCCAGAATTTTCCGGGGATTACGGATAATAC**GGTGGTCT
GGATTAATTAATACGCCAAGTCTTACATTTTGTTGCAGTCTCGTGCGAGTATGTGCAATAATAAACAAGATGAGC
CAATTTATTGGATTAGTTGCAGCTTGACCCCGCCATAGCTAGGCATAGCCAAGTGCTATGGGTGTTAGATGATGC
ACTTGGATGCAGTGAGTTTTGGAGTATAAAAGATCCTTAAAATTCCACCCTT

FIG.6B-104 pG1-9 (PG1-D1034-TA$(T)_{18}$): Example comprising one T motif which is $(T)_n$ (n=18), extended by preceding TA (extending the T motif at its 5'-end to become a TA$(T)_n$ motif); (Duplication of delta7 to delta 10 region -310 to -242, inserted between -242/-241)

SEQ ID 197

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGTTTGATTATCCGTTCGG*ATAAATGGACGCCT***
***GCTCCATATTTTTCCGGTT*ATTACCCCACCTGGAAGTGCCCAGAATTTTCCGGGGATTACGGATAATAC**GGTGGT
CTGGATTAATTAATACGCCAAGTCTTACATTTTGTTGCAGTCTCGTGCGAGTATGTGCAATAATAAACAAGATGA
GCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT pG1-9 (PG1-D1034-$(T)_{18}$): Example comprising one T motif which is $(T)_n$ (n=18) without a TA extension;

(Duplication of delta7 to delta 10 region -310 to -242, inserted between -242/-241)

SEQ ID 198

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGTTTGATTATCCGTTCGG*ATAAATGGACGCCTG***
***CTCCATATTTTTCCGGTT*ATTACCCCACCTGGAAGTGCCCAGAATTTTCCGGGGATTACGGATAATAC**GGTGGTC
TGGATTAATTAATACGCCAAGTCTTACATTTTGTTGCAGTCTCGTGCGAGTATGTGCAATAATAAACAAGATGAG
CCAATTTATTGGATTAGTTGCAGCTTGACCCCGCCATAGCTAGGCATAGCCAAGTGCTATGGGTGTTAGATGATG
CACTTGGATGCAGTGAGTTTTGGAGTATAAAAGATCCTTAAAATTCCACCCTT

FIG.6B-105 pG1-9 (PG1-D1034-TA$(T)_{19}$): Example comprising one T motif which is $(T)_n$ (n=19), extended by preceding TA (extending the T motif at its 5′-end to become a TA$(T)_n$ motif); (Duplication of delta7 to delta 10 region -310 to -242, inserted between -242/-241)

SEQ ID 199

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGTTTGATTATCCGTTCGG*ATAAATGGACGCCT***
***GCTCCATATTTTTCCGGTT*ATTACCCCACCTGGAAGTGCCCAGAATTTTCCGGGGATTACGGATAATAC**GGTGGT
CTGGATTAATTAATACGCCAAGTCTTACATTTTGTTGCAGTCTCGTGCGAGTATGTGCAATAATAAACAAGATGA
GCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT pG1-9 (PG1-D1034-$(T)_{19}$): Example comprising one T motif which is $(T)_n$ (n=19) without a TA extension;

(Duplication of delta7 to delta 10 region -310 to -242, inserted between -242/-241)

SEQ ID 200

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGTTTGATTATCCGTTCGG*ATAAATGGACGCCTG***
***CTCCATATTTTTCCGGTT*ATTACCCCACCTGGAAGTGCCCAGAATTTTCCGGGGATTACGGATAATAC**GGTGGTC
TGGATTAATTAATACGCCAAGTCTTACATTTTGTTGCAGTCTCGTGCGAGTATGTGCAATAATAAACAAGATGAG
CCAATTTATTGGATTAGTTGCAGCTTGACCCCGCCATAGCTAGGCATAGCCAAGTGCTATGGGTGTTAGATGATG
CACTTGGATGCAGTGAGTTTTGGAGTATAAAAGATCCTTAAAATTCCACCCTT

FIG.6B-106 pG1-9 (PG1-D1034-TA$(T)_{20}$): Example comprising one T motif which is $(T)_n$ (n=20), extended by preceding TA (extending the T motif at its 5′-end to become a TA$(T)_n$ motif); (Duplication of delta7 to delta 10 region -310 to -242, inserted between -242/-241)

SEQ ID 201

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TATTTTTTTTTTTTTTTTTTTT*GATGACCCCGTT
TTCGTGACAAATTAATTTCCAACGGGGTCTTGT**CCGGATAAGAGAATTTTGTTTGATTATCCGTTCGG*ATAAATG***
***GACGCCTGCTCCATATTTTTCCGGTT*ATTACCCCACCTGGAAGTGTTTGATTATCCGTTCGG*ATAAATGGACGCC***
***TGCTCCATATTTTTCCGGTT*ATTACCCCACCTGGAAGTGCCCAGAATTTTCCGGGGATTACGGATAATAC**GGTGG
TCTGGATTAATTAATACGCCAAGTCTTACATTTTGTTGCAGTCTCGTGCGAGTATGTGCAATAATAAACAAGATGA
GCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT pG1-9 (PG1-D1034-$(T)_{20}$): Example comprising one T motif which is $(T)_n$ (n=20) without a TA extension;

(Duplication of delta7 to delta 10 region -310 to -242, inserted between -242/-241)

SEQ ID 202

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGTTTGATTATCCGTTCGG*ATAAATGGACGCCT***
***GCTCCATATTTTTCCGGTT*ATTACCCCACCTGGAAGTGCCCAGAATTTTCCGGGGATTACGGATAATAC**GGTGGT
CTGGATTAATTAATACGCCAAGTCTTACATTTTGTTGCAGTCTCGTGCGAGTATGTGCAATAATAAACAAGATGA
GCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT

FIG.6B-107 pG1-12 (PG1-s492-$TA(T)_n$): Example comprising a fragment of pG1 containing one T motif which is $(T)_n$ (n=13-20), extended by preceding TA (extending the T motif at its 5'-end to become a $TA(T)_n$ motif);

SEQ ID 203

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*$TA(T)_n$*GATGACCCCGTTTTCGTGACAAATTAATTTCCAACGGGGTCTTGTC
**CGGATAAGAGAATTTTGTTTGATTATCCGTTCGG*ATAAATGGACGCCTGCTCCATATTTTTCCGGTT*ATTACCCC**
ACCTGGAAGTGCCCAGAATTTTCCGGGGATTACGGATAATACGGTGGTCTGGATTAATTAATACGCCAAGTCTT
ACATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1-12 (PG1-s492-$(T)_n$): Example comprising a fragment of pG1 containing one T motif which is $(T)_n$ (n=13-20) without a TA extension;

SEQ ID 204

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*$(T)_n$*GATGACCCCGTTTTCGTGACAAATTAATTTCCAACGGGGTCTTGTCCG
**GATAAGAGAATTTTGTTTGATTATCCGTTCGG*ATAAATGGACGCCTGCTCCATATTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT pG1-12 (PG1-s492-$TA(T)_{13}$): Example comprising a fragment of pG1 containing one T motif which is $(T)_n$ (n=13), extended by preceding TA (extending the T motif at its 5'-end to become a $TA(T)_n$ motif);

SEQ ID 205

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TATTTTTTTTTTTTT*GATGACCCCGTTTTCGTGACAAATTAATTTCCAACGG
GGTCTTGT**CCGGATAAGAGAATTTTGTTTGATTATCCGTTCGG*ATAAATGGACGCCTGCTCCATATTTTTCCGGT***
***T*ATTACCCCACCTGGAAGTGCCCAGAATTTTCCGGGGATTACGGATAATAC**GGTGGTCTGGATTAATTAATACG
CCAAGTCTTACATTTTGTTGCAGTCTCGTGCGAGTATGTGCAATAATAAACAAGATGAGCCAATTTATTGGATTAG
TTGCAGCTTGACCCCGCCATAGCTAGGCATAGCCAAGTGCTATGGGTGTTAGATGATGCACTTGGATGCAGTGA
GTTTTGGAGTATAAAAGATCCTTAAAATTCCACCCTT

FIG.6B-108 pG1-12 (PG1-s492-$(T)_{13}$): Example comprising a fragment of pG1 containing one T motif which is $(T)_n$ (n=13) without a TA extension;

SEQ ID 206

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TTTTTTTTTTTTT*GATGACCCCGTTTTCGTGACAAATTAATTTCCAACGGG
GTCTTGT**CCGGATAAGAGAATTTTGTTTGATTATCCGTTCGG*ATAAATGGACGCCTGCTCCATATTTTTCCGGTT***
ATTACCCCACCTGGAAGTGCCCAGAATTTTCCGGGGATTACGGATAATACGGTGGTCTGGATTAATTAATACGC
CAAGTCTTACATTTTGTTGCAGTCTCGTGCGAGTATGTGCAATAATAAACAAGATGAGCCAATTTATTGGATTAGT
TGCAGCTTGACCCCGCCATAGCTAGGCATAGCCAAGTGCTATGGGTGTTAGATGATGCACTTGGATGCAGTGAG
TTTTGGAGTATAAAAGATCCTTAAAATTCCACCCTT pG1-12 (PG1-s492-TA$(T)_{14}$): Example comprising a fragment of pG1 containing one T motif which is $(T)_n$ (n=14), extended by preceding TA (extending the T motif at its 5'-end to become a TA$(T)_n$ motif);

SEQ ID 207

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TATTTTTTTTTTTTTT*GATGACCCCGTTTTCGTGACAAATTAATTTCCAACG
GGGTCTTGT**CCGGATAAGAGAATTTTGTTTGATTATCCGTTCGG*ATAAATGGACGCCTGCTCCATATTTTTCCGG***
***TT*ATTACCCCACCTGGAAGTGCCCAGAATTTTCCGGGGATTACGGATAATAC**GGTGGTCTGGATTAATTAATAC
GCCAAGTCTTACATTTTGTTGCAGTCTCGTGCGAGTATGTGCAATAATAAACAAGATGAGCCAATTTATTGGATTA
GTTGCAGCTTGACCCCGCCATAGCTAGGCATAGCCAAGTGCTATGGGTGTTAGATGATGCACTTGGATGCAGTG
AGTTTTGGAGTATAAAAGATCCTTAAAATTCCACCCTT pG1-12 (PG1-s492-$(T)_{14}$): Example comprising a fragment of pG1 containing one T motif which is $(T)_n$ (n=14) without a TA extension;

SEQ ID 208

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TTTTTTTTTTTTTT*GATGACCCCGTTTTCGTGACAAATTAATTTCCAACGGG
GTCTTGT**CCGGATAAGAGAATTTTGTTTGATTATCCGTTCGG*ATAAATGGACGCCTGCTCCATATTTTTCCGGTT***
ATTACCCCACCTGGAAGTGCCCAGAATTTTCCGGGGATTACGGATAATACGGTGGTCTGGATTAATTAATACGC
CAAGTCTTACATTTTGTTGCAGTCTCGTGCGAGTATGTGCAATAATAAACAAGATGAGCCAATTTATTGGATTAGT
TGCAGCTTGACCCCGCCATAGCTAGGCATAGCCAAGTGCTATGGGTGTTAGATGATGCACTTGGATGCAGTGAG
TTTTGGAGTATAAAAGATCCTTAAAATTCCACCCTT

FIG.6B-109 pG1-12 (PG1-s492-TA(T)$_{15}$): Example comprising a fragment of pG1 containing one T motif which is (T)$_n$ (n=15), extended by preceding TA (extending the T motif at its 5'-end to become a TA(T)$_n$ motif);

SEQ ID 209

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TATTTTTTTTTTTTTTT*GATGACCCCGTTTTCGTGACAAATTAATTTCCAAC
GGGGTCTTGT**CCGGATAAGAGAATTTTGTTTGATTATCCGTTCGG*ATAAATGGACGCCTGCTCCATATTTTTCCG***
***GTT*ATTACCCCACCTGGAAGTGCCCAGAATTTTCCGGGGATTACGGATAATAC**GGTGGTCTGGATTAATTAATA
CGCCAAGTCTTACATTTTGTTGCAGTCTCGTGCGAGTATGTGCAATAATAAACAAGATGAGCCAATTTATTGGATT
AGTTGCAGCTTGACCCCGCCATAGCTAGGCATAGCCAAGTGCTATGGGTGTTAGATGATGCACTTGGATGCAGT
GAGTTTTGGAGTATAAAAGATCCTTAAAATTCCACCCTT pG1-12 (PG1-s492-(T)$_{15}$): Example comprising a fragment of pG1 containing one T motif which is (T)$_n$ (n=15) without a TA extension;

SEQ ID 210

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TTTTTTTTTTTTTTT*GATGACCCCGTTTTCGTGACAAATTAATTTCCAACGG
GGTCTTGT**CCGGATAAGAGAATTTTGTTTGATTATCCGTTCGG*ATAAATGGACGCCTGCTCCATATTTTTCCGGT***
***T*ATTACCCCACCTGGAAGTGCCCAGAATTTTCCGGGGATTACGGATAATAC**GGTGGTCTGGATTAATTAATACG
CCAAGTCTTACATTTTGTTGCAGTCTCGTGCGAGTATGTGCAATAATAAACAAGATGAGCCAATTTATTGGATTAG
TTGCAGCTTGACCCCGCCATAGCTAGGCATAGCCAAGTGCTATGGGTGTTAGATGATGCACTTGGATGCAGTGA
GTTTTGGAGTATAAAAGATCCTTAAAATTCCACCCTT pG1-Δ2 comprising the TA(T)$_{14}$ motif with deletion of -628 to -612, at the position indicated with "del" (underlined)

SEQ ID 211

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGdelCCAATAGCGCGTTTCATATGCGCTTTTACCCCCTCTTTTGT
CAAGCGCAAAATGCCTGTAAGATTTGGTGGGGGTGTGAGCCGTTAGCTGAAGTACAACAGGCTAATTCCCTGAA
AAAACTGCAGATAGACTTCAAGATCTCAGGGATTCCCACTATTTGGTATTCTGATATGTTTTTCCTGATATGCATC
AAAACTCTAATCTAAAACCTGAATCTCCGC*TATTTTTTTTTTTTTT*GATGACCCCGTTTTCGTGACAAATTAATTTCC
AACGGGGTCTTGT**CCGGATAAGAGAATTTTGTTTGATTATCCGTTCGG*ATAAATGGACGCCTGCTCCATATTTTT***
***CCGGTT*ATTACCCCACCTGGAAGTGCCCAGAATTTTCCGGGGATTACGGATAATAC**GGTGGTCTGGATTAATTA
ATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTT

FIG.6B-110 pG1-12 (PG1-s492-$(T)_{16}$): Example comprising a fragment of pG1 containing one T motif which is $(T)_n$ (n=16) without a TA extension;

SEQ ID 212

CTGCAGATAGACTTCAAGATCTCAGGGATTCCCACTATTTGGTATTCTGATATGTTTTTCCTGATATGCATCAAAA
CTCTAATCTAAAACCTGAATCTCCGCTTTTTTTTTTTTTTTTGATGACCCCGTTTTCGTGACAAATTAATTTCCAACG
GGGTCTTGTCCGGATAAGAGAATTTTGTTTGATTATCCGTTCGGATAAATGGACGCCTGCTCCATATTTTTCCGG
TTATTACCCCACCTGGAAGTGCCCAGAATTTTCCGGGGATTACGGATAATACGGTGGTCTGGATTAATTAATAC
GCCAAGTCTTACATTTTGTTGCAGTCTCGTGCGAGTATGTGCAATAATAAACAAGATGAGCCAATTTATTGGATTA
GTTGCAGCTTGACCCCGCCATAGCTAGGCATAGCCAAGTGCTATGGGTGTTAGATGATGCACTTGGATGCAGTG
AGTTTTGGAGTATAAAAGATCCTTAAAATTCCACCCTT pG1-12 (PG1-s492-TA$(T)_{17}$): Example comprising a fragment of pG1 containing one T motif which is $(T)_n$ (n=17), extended by preceding TA (extending the T motif at its 5'-end to become a TA$(T)_n$ motif);

SEQ ID 213

CTGCAGATAGACTTCAAGATCTCAGGGATTCCCACTATTTGGTATTCTGATATGTTTTTCCTGATATGCATCAAAA
CTCTAATCTAAAACCTGAATCTCCGCTATTTTTTTTTTTTTTTTTGATGACCCCGTTTTCGTGACAAATTAATTTCCA
ACGGGGTCTTGTCCGGATAAGAGAATTTTGTTTGATTATCCGTTCGGATAAATGGACGCCTGCTCCATATTTTTC
CGGTTATTACCCCACCTGGAAGTGCCCAGAATTTTCCGGGGATTACGGATAATACGGTGGTCTGGATTAATTAA
TACGCCAAGTCTTACATTTTGTTGCAGTCTCGTGCGAGTATGTGCAATAATAAACAAGATGAGCCAATTTATTGG
ATTAGTTGCAGCTTGACCCCGCCATAGCTAGGCATAGCCAAGTGCTATGGGTGTTAGATGATGCACTTGGATGCA
GTGAGTTTTGGAGTATAAAAGATCCTTAAAATTCCACCCTT pG1-12 (PG1-s492-$(T)_{17}$): Example comprising a fragment of pG1 containing one T motif which is $(T)_n$ (n=17) without a TA extension;

SEQ ID 214

CTGCAGATAGACTTCAAGATCTCAGGGATTCCCACTATTTGGTATTCTGATATGTTTTTCCTGATATGCATCAAAA
CTCTAATCTAAAACCTGAATCTCCGCTTTTTTTTTTTTTTTTTGATGACCCCGTTTTCGTGACAAATTAATTTCCAAC
GGGGTCTTGTCCGGATAAGAGAATTTTGTTTGATTATCCGTTCGGATAAATGGACGCCTGCTCCATATTTTTCCG
GTTATTACCCCACCTGGAAGTGCCCAGAATTTTCCGGGGATTACGGATAATACGGTGGTCTGGATTAATTAATA
CGCCAAGTCTTACATTTTGTTGCAGTCTCGTGCGAGTATGTGCAATAATAAACAAGATGAGCCAATTTATTGGATT
AGTTGCAGCTTGACCCCGCCATAGCTAGGCATAGCCAAGTGCTATGGGTGTTAGATGATGCACTTGGATGCAGT
GAGTTTTGGAGTATAAAAGATCCTTAAAATTCCACCCTT

FIG.6B-111 pG1-12 (PG1-s492-TA(T)$_{18}$): Example comprising a fragment of pG1 containing one T motif which is (T)$_n$ (n=18), extended by preceding TA (extending the T motif at its 5'-end to become a TA(T)$_n$ motif);

SEQ ID 215

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TATTTTTTTTTTTTTTTTTT*GATGACCCCGTTTTCGTGACAAATTAATTTCCA
ACGGGGTCTTGT**CCGGATAAGAGAATTTTGTTTGATTATCCGTTCGG*ATAAATGGACGCCTGCTCCATATTTTTC*
*CGGTT*ATTACCCCACCTGGAAGTGCCCAGAATTTTCCGGGGATTACGGATAATAC**GGTGGTCTGGATTAATTAA
TACGCCAAGTCTTACATTTTGTTGCAGTCTCGTGCGAGTATGTGCAATAATAAACAAGATGAGCCAATTTATTGG
ATTAGTTGCAGCTTGACCCCGCCATAGCTAGGCATAGCCAAGTGCTATGGGTGTTAGATGATGCACTTGGATGCA
GTGAGTTTTGGAGTATAAAAGATCCTTAAAATTCCACCCTT pG1-12 (PG1-s492-(T)$_{18}$): Example comprising a fragment of pG1 containing one T motif which is (T)$_n$ (n=18) without a TA extension;

SEQ ID 216

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TTTTTTTTTTTTTTTTTT*GATGACCCCGTTTTCGTGACAAATTAATTTCCAAC
GGGGTCTTGT**CCGGATAAGAGAATTTTGTTTGATTATCCGTTCGG*ATAAATGGACGCCTGCTCCATATTTTTCCG*
*GTT*ATTACCCCACCTGGAAGTGCCCAGAATTTTCCGGGGATTACGGATAATAC**GGTGGTCTGGATTAATTAATA
CGCCAAGTCTTACATTTTGTTGCAGTCTCGTGCGAGTATGTGCAATAATAAACAAGATGAGCCAATTTATTGGATT
AGTTGCAGCTTGACCCCGCCATAGCTAGGCATAGCCAAGTGCTATGGGTGTTAGATGATGCACTTGGATGCAGT
GAGTTTTGGAGTATAAAAGATCCTTAAAATTCCACCCTT pG1-12 (PG1-s492-TA(T)$_{19}$): Example comprising a fragment of pG1 containing one T motif which is (T)$_n$ (n=19), extended by preceding TA (extending the T motif at its 5'-end to become a TA(T)$_n$ motif);

SEQ ID 217

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TATTTTTTTTTTTTTTTTTTT*GATGACCCCGTTTTCGTGACAAATTAATTTCC
AACGGGGTCTTGT**CCGGATAAGAGAATTTTGTTTGATTATCCGTTCGG*ATAAATGGACGCCTGCTCCATATTTTTT*
*CCGGTT*ATTACCCCACCTGGAAGTGCCCAGAATTTTCCGGGGATTACGGATAATAC**GGTGGTCTGGATTAATTA
ATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTT

FIG.6B-112 pG1-12 (PG1-s492-(T)$_{19}$): Example comprising a fragment of pG1 containing one T motif which is (T)$_n$ (n=19) without a TA extension;

SEQ ID 218

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TTTTTTTTTTTTTTTTTTT*GATGACCCCGTTTTCGTGACAAATTAATTTCCAA
CGGGGTCTTGT**CCGGATAAGAGAATTTTGTTTGATTATCCGTTCGG*ATAAATGGACGCCTGCTCCATATTTTTCC***
***GGTT*ATTACCCCACCTGGAAGTGCCCAGAATTTTCCGGGGATTACGGATAATAC**GGTGGTCTGGATTAATTAAT
ACGCCAAGTCTTACATTTTGTTGCAGTCTCGTGCGAGTATGTGCAATAATAAACAAGATGAGCCAATTTATTGGA
TTAGTTGCAGCTTGACCCCGCCATAGCTAGGCATAGCCAAGTGCTATGGGTGTTAGATGATGCACTTGGATGCAG
TGAGTTTTGGAGTATAAAAGATCCTTAAAATTCCACCCTT pG1-12 (PG1-s492-TA(T)$_{20}$): Example comprising a fragment of pG1 containing one T motif which is (T)$_n$ (n=20), extended by preceding TA (extending the T motif at its 5′-end to become a TA(T)$_n$ motif);

SEQ ID 219

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TATTTTTTTTTTTTTTTTTTTT*GATGACCCCGTTTTCGTGACAAATTAATTTC
CAACGGGGTCTTGT**CCGGATAAGAGAATTTTGTTTGATTATCCGTTCGG*ATAAATGGACGCCTGCTCCATATTTT***
***TCCGGTT*ATTACCCCACCTGGAAGTGCCCAGAATTTTCCGGGGATTACGGATAATAC**GGTGGTCTGGATTAATT
AATACGCCAAGTCTTACATTTTGTTGCAGTCTCGTGCGAGTATGTGCAATAATAAACAAGATGAGCCAATTTATTG
GATTAGTTGCAGCTTGACCCCGCCATAGCTAGGCATAGCCAAGTGCTATGGGTGTTAGATGATGCACTTGGATGC
AGTGAGTTTTGGAGTATAAAAGATCCTTAAAATTCCACCCTT pG1-12 (PG1-s492-(T)$_{20}$): Example comprising a fragment of pG1 containing one T motif which is (T)$_n$ (n=20) without a TA extension;

SEQ ID 220

CTGCAGATAGACTTCAAGATCTCAGGGATTCCCACTATTTGGTATTCTGATATGTTTTTCCTGATATGCATCAAAA
CTCTAATCTAAAACCTGAATCTCCGC*TTTTTTTTTTTTTTTTTTTT*GATGACCCCGTTTTCGTGACAAATTAATTTCCA
ACGGGGTCTTGT**CCGGATAAGAGAATTTTGTTTGATTATCCGTTCGG*ATAAATGGACGCCTGCTCCATATTTTTC***
***CGGTT*ATTACCCCACCTGGAAGTGCCCAGAATTTTCCGGGGATTACGGATAATAC**GGTGGTCTGGATTAATTAA
TACGCCAAGTCTTACATTTTGTTGCAGTCTCGTGCGAGTATGTGCAATAATAAACAAGATGAGCCAATTTATTGG
ATTAGTTGCAGCTTGACCCCGCCATAGCTAGGCATAGCCAAGTGCTATGGGTGTTAGATGATGCACTTGGATGCA
GTGAGTTTTGGAGTATAAAAGATCCTTAAAATTCCACCCTT

FIG.6B-113 pG1-13 (PG1--s663-TA(T)$_n$): Example comprising a fragment of pG1 containing one T motif which is (T)$_n$ (n=13-20), extended by preceding TA (extending the T motif at its 5'-end to become a TA(T)$_n$ motif);

SEQ ID 221

CCATATTCAGTAGGTGTTTCTTGCACTTTTGCATGCACTGCGGAAGAATTAGCCAATAGCGCGTTTCATATGCGCT TTTACCCCCTCTTTTGTCAAGCGCAAAATGCCTGTAAGATTTGGTGGGGGTGTGAGCCGTTAGCTGAAGTACAAC AGGCTAATTCCCTGAAAAAACTGCAGATAGACTTCAAGATCTCAGGGATTCCCACTATTTGGTATTCTGATATGTT TTTCCTGATATGCATCAAAACTCTAATCTAAAACCTGAATCTCCGC*TA(T)$_n$*GATGACCCCGTTTTCGTGACAAATTA ATTTCCAACGGGGTCTTGT**CCGGATAAGAGAATTTTGTTTGATTATCCGTTCGG*ATAAATGGACGCCTGCTCCAT ATTTTTCCGGTT*ATTACCCCACCTGGAAGTGCCCAGAATTTTCCGGGGATTACGGATAATAC**GGTGGTCTGGAT TAATTAATACGCCAAGTCTTACATTTTGTTGCAGTCTCGTGCGAGTATGTGCAATAATAAACAAGATGAGCCAATT TATTGGATTAGTTGCAGCTTGACCCCGCCATAGCTAGGCATAGCCAAGTGCTATGGGTGTTAGATGATGCACTTG GATGCAGTGAGTTTTGGAGTATAAAAGATCCTTAAAATTCCACCCTT pG1-13 (PG1--s663-(T)$_n$): Example comprising a fragment of pG1 containing one T motif which is (T)$_n$ (n=13-20) without a TA extension;

SEQ ID 222

CCATATTCAGTAGGTGTTTCTTGCACTTTTGCATGCACTGCGGAAGAATTAGCCAATAGCGCGTTTCATATGCGCT TTTACCCCCTCTTTTGTCAAGCGCAAAATGCCTGTAAGATTTGGTGGGGGTGTGAGCCGTTAGCTGAAGTACAAC AGGCTAATTCCCTGAAAAAACTGCAGATAGACTTCAAGATCTCAGGGATTCCCACTATTTGGTATTCTGATATGTT TTTCCTGATATGCATCAAAACTCTAATCTAAAACCTGAATCTCCGC*(T)$_n$*GATGACCCCGTTTTCGTGACAAATTAAT TTCCAACGGGGTCTTGT**CCGGATAAGAGAATTTTGTTTGATTATCCGTTCGG*ATAAATGGACGCCTGCTCCATAT TTTTCCGGTT*ATTACCCCACCTGGAAGTGCCCAGAATTTTCCGGGGATTACGGATAATAC**GGTGGTCTGGATTA ATTAATACGCCAAGTCTTACATTTTGTTGCAGTCTCGTGCGAGTATGTGCAATAATAAACAAGATGAGCCAATTTA TTGGATTAGTTGCAGCTTGACCCCGCCATAGCTAGGCATAGCCAAGTGCTATGGGTGTTAGATGATGCACTTGGA TGCAGTGAGTTTTGGAGTATAAAAGATCCTTAAAATTCCACCCTT pG1-13 (PG1--s663-TA(T)$_{13}$): Example comprising a fragment of pG1 containing one T motif which is (T)$_n$ (n=13), extended by preceding TA (extending the T motif at its 5'-end to become a TA(T)$_n$ motif);

SEQ ID 223

CCATATTCAGTAGGTGTTTCTTGCACTTTTGCATGCACTGCGGAAGAATTAGCCAATAGCGCGTTTCATATGCGCT TTTACCCCCTCTTTTGTCAAGCGCAAAATGCCTGTAAGATTTGGTGGGGGTGTGAGCCGTTAGCTGAAGTACAAC AGGCTAATTCCCTGAAAAAACTGCAGATAGACTTCAAGATCTCAGGGATTCCCACTATTTGGTATTCTGATATGTT TTTCCTGATATGCATCAAAACTCTAATCTAAAACCTGAATCTCCGC*TATTTTTTTTTTTTT*GATGACCCCGTTTTCGT GACAAATTAATTTCCAACGGGGTCTTGT**CCGGATAAGAGAATTTTGTTTGATTATCCGTTCGG*ATAAATGGACG CCTGCTCCATATTTTTCCGGTT*ATTACCCCACCTGGAAGTGCCCAGAATTTTCCGGGGATTACGGATAATAC**GGT GGTCTGGATTAATTAATACGCCAAGTCTTACATTTTGTTGCAGTCTCGTGCGAGTATGTGCAATAATAAACAAGAT GAGCCAATTTATTGGATTAGTTGCAGCTTGACCCCGCCATAGCTAGGCATAGCCAAGTGCTATGGGTGTTAGATG ATGCACTTGGATGCAGTGAGTTTTGGAGTATAAAAGATCCTTAAAATTCCACCCTT

FIG.6B-114 pG1-13 (PG1--s663-$(T)_{13}$): Example comprising a fragment of pG1 containing one T motif which is $(T)_n$ (n=13) without a TA extension;

SEQ ID 224

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TTTTTTTTTTTTT*GATGACCCCGTTTTCGTGA
CAAATTAATTTCCAACGGGGTCTTGT**CCGGATAAGAGAATTTTGTTTGATTATCCGTTCGG*ATAAATGGACGCCT***
***GCTCCATATTTTTTCCGGTT*ATTACCCCACCTGGAAGTGCCCAGAATTTTCCGGGGATTACGGATAATAC**GGTGGT
CTGGATTAATTAATACGCCAAGTCTTACATTTTGTTGCAGTCTCGTGCGAGTATGTGCAATAATAAACAAGATGA
GCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT pG1-13 (PG1--s663-TA$(T)_{14}$): Example comprising a fragment of pG1 containing one T motif which is $(T)_n$ (n=14), extended by preceding TA (extending the T motif at its 5′-end to become a TA$(T)_n$ motif);

SEQ ID 225

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TATTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTTCCGGTT*ATTACCCCACCTGGAAGTGCCCAGAATTTTCCGGGGATTACGGATAATAC**GG
TGGTCTGGATTAATTAATACGCCAAGTCTTACATTTTGTTGCAGTCTCGTGCGAGTATGTGCAATAATAAACAAGA
TGAGCCAATTTATTGGATTAGTTGCAGCTTGACCCCGCCATAGCTAGGCATAGCCAAGTGCTATGGGTGTTAGAT
GATGCACTTGGATGCAGTGAGTTTTGGAGTATAAAAGATCCTTAAAATTCCACCCTT pG1-13 (PG1--s663-$(T)_{14}$): Example comprising a fragment of pG1 containing one T motif which is $(T)_n$ (n=14) without a TA extension;

SEQ ID 226

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TTTTTTTTTTTTTT*GATGACCCCGTTTTCGTG
ACAAATTAATTTCCAACGGGGTCTTGT**CCGGATAAGAGAATTTTGTTTGATTATCCGTTCGG*ATAAATGGACGCC***
***TGCTCCATATTTTTTCCGGTT*ATTACCCCACCTGGAAGTGCCCAGAATTTTCCGGGGATTACGGATAATAC**GGTGG
TCTGGATTAATTAATACGCCAAGTCTTACATTTTGTTGCAGTCTCGTGCGAGTATGTGCAATAATAAACAAGATGA
GCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT

FIG.6B-115 pG1-13 (PG1--s663-TA(T)$_{15}$): Example comprising a fragment of pG1 containing one T motif which is (T)$_n$ (n=15), extended by preceding TA (extending the T motif at its 5'-end to become a TA(T)$_n$ motif);

SEQ ID 227

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TATTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATACG**
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT pG1-13 (PG1--s663-(T)$_{15}$): Example comprising a fragment of pG1 containing one T motif which is (T)$_n$ (n=15) without a TA extension;

SEQ ID 228

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TTTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTT*ATTACCCCACCTGGAAGTGCCCAGAATTTTCCGGGGATTACGGATAATAC**GGT
GGTCTGGATTAATTAATACGCCAAGTCTTACATTTTGTTGCAGTCTCGTGCGAGTATGTGCAATAATAAACAAGAT
GAGCCAATTTATTGGATTAGTTGCAGCTTGACCCCGCCATAGCTAGGCATAGCCAAGTGCTATGGGTGTTAGATG
ATGCACTTGGATGCAGTGAGTTTTGGAGTATAAAAGATCCTTAAAATTCCACCCTT pG1-13 (PG1--s663-TA(T)$_{16}$): Example comprising a fragment of pG1 containing one T motif which is (T)$_n$ (n=16), extended by preceding TA (extending the T motif at its 5'-end to become a TA(T)$_n$ motif);

SEQ ID 229

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TATTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATACG**
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT

FIG.6B-116 pG1-13 (PG1--s663-$(T)_{16}$): Example comprising a fragment of pG1 containing one T motif which is $(T)_n$ (n=16) without a TA extension;

SEQ ID 230

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TTTTTTTTTTTTTTTT*GATGACCCCGTTTTCG
TGACAAATTAATTTCCAACGGGGTCTTGT**CCGGATAAGAGAATTTTGTTTGATTATCCGTTCGG*ATAAATGGAC***
***GCCTGCTCCATATTTTTCCGGTT*ATTACCCCACCTGGAAGTGCCCAGAATTTTCCGGGGATTACGGATAATAC**GG
TGGTCTGGATTAATTAATACGCCAAGTCTTACATTTTGTTGCAGTCTCGTGCGAGTATGTGCAATAATAAACAAGA
TGAGCCAATTTATTGGATTAGTTGCAGCTTGACCCCGCCATAGCTAGGCATAGCCAAGTGCTATGGGTGTTAGAT
GATGCACTTGGATGCAGTGAGTTTTGGAGTATAAAAGATCCTTAAAATTCCACCCTT pG1-13 (PG1--s663-TA$(T)_{17}$): Example comprising a fragment of pG1 containing one T motif which is $(T)_n$ (n=17), extended by preceding TA (extending the T motif at its 5'-end to become a TA$(T)_n$ motif);

SEQ ID 231

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TATTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT pG1-13 (PG1--s663-$(T)_{17}$): Example comprising a fragment of pG1 containing one T motif which is $(T)_n$ (n=17) without a TA extension;

SEQ ID 232

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATACG**
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT

FIG.6B-117 pG1-13 (PG1--s663-TA(T)$_{18}$): Example comprising a fragment of pG1 containing one T motif which is $(T)_n$ (n=18), extended by preceding TA (extending the T motif at its 5'-end to become a $TA(T)_n$ motif);

SEQ ID 233

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TATTTTTTTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT pG1-13 (PG1--s663-(T)$_{18}$): Example comprising a fragment of pG1 containing one T motif which is $(T)_n$ (n=18) without a TA extension;

SEQ ID 234

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATAC**G
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT pG1-13 (PG1--s663-TA(T)$_{19}$): Example comprising a fragment of pG1 containing one T motif which is $(T)_n$ (n=19), extended by preceding TA (extending the T motif at its 5'-end to become a $TA(T)_n$ motif);

SEQ ID 235

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TATTTTTTTTTTTTTTTTTTT*GATGACCCCGTT
TTCGTGACAAATTAATTTCCAACGGGGTCTTGT**CCGGATAAGAGAATTTTGTTTGATTATCCGTTCGG*ATAAATG***
***GACGCCTGCTCCATATTTTTCCGGTT*ATTACCCCACCTGGAAGTGCCCAGAATTTTCCGGGGATTACGGATAATA**
CGGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT

FIG.6B-118 pG1-13 (PG1--s663-$(T)_{19}$): Example comprising a fragment of pG1 containing one T motif which is $(T)_n$ (n=19) without a TA extension;

SEQ ID 236

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TTTTTTTTTTTTTTTTTTT*GATGACCCCGTTTT
CGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT pG1-13 (PG1--s663-TA$(T)_{20}$): Example comprising a fragment of pG1 containing one T motif which is $(T)_n$ (n=20), extended by preceding TA (extending the T motif at its 5'-end to become a TA$(T)_n$ motif);

SEQ ID 237

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TATTTTTTTTTTTTTTTTTTTT*GATGACCCCGT
TTTCGTGACAAATTAATTTCCAACGGGGTCTTGT**CCGGATAAGAGAATTTTGTTTGATTATCCGTTCGG*ATAAAT***
***GGACGCCTGCTCCATATTTTTCCGGTT*ATTACCCCACCTGGAAGTGCCCAGAATTTTCCGGGGATTACGGATAAT**
ACGGTGGTCTGGATTAATTAATACGCCAAGTCTTACATTTTGTTGCAGTCTCGTGCGAGTATGTGCAATAATAAA
CAAGATGAGCCAATTTATTGGATTAGTTGCAGCTTGACCCCGCCATAGCTAGGCATAGCCAAGTGCTATGGGTGT
TAGATGATGCACTTGGATGCAGTGAGTTTTGGAGTATAAAAGATCCTTAAAATTCCACCCTT pG1-13 (PG1--s663-$(T)_{20}$): Example comprising a fragment of pG1 containing one T motif which is $(T)_n$ (n=20) without a TA extension;

SEQ ID 238

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGC*TTTTTTTTTTTTTTTTTTTT*GATGACCCCGTTT
TCGTGACAAATTAATTTCCAACGGGGTCTTGT**CCGGATAAGAGAATTTTGTTTGATTATCCGTTCGG*ATAAATGG***
***ACGCCTGCTCCATATTTTTCCGGTT*ATTACCCCACCTGGAAGTGCCCAGAATTTTCCGGGGATTACGGATAATAC**
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT

FIG.6B-119 pG1-14 (PG1--s858-TA$(T)_n$): Example comprising a fragment of pG1 containing one T motif which is $(T)_n$ (n=13-20), extended by preceding TA (extending the T motif at its 5′-end to become a TA$(T)_n$ motif);

SEQ ID 239

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TA(T)*$_n$GATGACCCCGTTTTCGTGACAAATTAATTTCCAACGGGGTCTTGTCCGGATAAGAGA
**ATTTTGTTTGATTATCCGTTCGG*ATAAATGGACGCCTGCTCCATATTTTTCCGGTT*ATTACCCCACCTGGAAGTGC**
CCAGAATTTTCCGGGGATTACGGATAATACGGTGGTCTGGATTAATTAATACGCCAAGTCTTACATTTTGTTGCA
GTCTCGTGCGAGTATGTGCAATAATAAACAAGATGAGCCAATTTATTGGATTAGTTGCAGCTTGACCCCGCCATA
GCTAGGCATAGCCAAGTGCTATGGGTGTTAGATGATGCACTTGGATGCAGTGAGTTTTGGAGTATAAAAGATCC
TTAAAATTCCACCCTT pG1-14 (PG1--s858-$(T)_n$): Example comprising a fragment of pG1 containing one T motif which is $(T)_n$ (n=13-20) without a TA extension;

SEQ ID 240

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*(T)*$_n$GATGACCCCGTTTTCGTGACAAATTAATTTCCAACGGGGTCTTGTCCGGATAAGAGAATT
**TTGTTTGATTATCCGTTCGG*ATAAATGGACGCCTGCTCCATATTTTTCCGGTT*ATTACCCCACCTGGAAGTGCCC**
AGAATTTTCCGGGGATTACGGATAATACGGTGGTCTGGATTAATTAATACGCCAAGTCTTACATTTTGTTGCAGT
CTCGTGCGAGTATGTGCAATAATAAACAAGATGAGCCAATTTATTGGATTAGTTGCAGCTTGACCCCGCCATAGC
TAGGCATAGCCAAGTGCTATGGGTGTTAGATGATGCACTTGGATGCAGTGAGTTTTGGAGTATAAAAGATCCTT
AAAATTCCACCCTT

FIG.6B-120 pG1-14 (PG1--s858-TA$(T)_{13}$): Example comprising a fragment of pG1 containing one T motif which is $(T)_n$ (n=13), extended by preceding TA (extending the T motif at its 5'-end to become a TA$(T)_n$ motif);

SEQ ID 241

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TATTTTTTTTTTTTT*GATGACCCCGTTTTCGTGACAAATTAATTTCCAACGGGGTCTTGTCCGG
**ATAAGAGAATTTTGTTTGATTATCCGTTCGG*ATAAATGGACGCCTGCTCCATATTTTTCCGGTT*ATTACCCCACCT**
GGAAGTGCCCAGAATTTTCCGGGGATTACGGATAATACGGTGGTCTGGATTAATTAATACGCCAAGTCTTACAT
TTTGTTGCAGTCTCGTGCGAGTATGTGCAATAATAAACAAGATGAGCCAATTTATTGGATTAGTTGCAGCTTGAC
CCCGCCATAGCTAGGCATAGCCAAGTGCTATGGGTGTTAGATGATGCACTTGGATGCAGTGAGTTTTGGAGTAT
AAAAGATCCTTAAAATTCCACCCTT pG1-14 (PG1--s858-$(T)_{13}$): Example comprising a fragment of pG1 containing one T motif which is $(T)_n$ (n=13) without a TA extension;

SEQ ID 242

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TTTTTTTTTTTTT*GATGACCCCGTTTTCGTGACAAATTAATTTCCAACGGGGTCTTGTCCGGAT
**AAGAGAATTTTGTTTGATTATCCGTTCGG*ATAAATGGACGCCTGCTCCATATTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT

FIG.6B-121 pG1-14 (PG1--s858-TA$(T)_{14}$): Example comprising a fragment of pG1 containing one T motif which is $(T)_n$ (n=14), extended by preceding TA (extending the T motif at its 5'-end to become a TA$(T)_n$ motif);

SEQ ID 243

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TATTTTTTTTTTTTTT*GATGACCCCGTTTTCGTGACAAATTAATTTCCAACGGGGTCTTGTCCG
**GATAAGAGAATTTTGTTTGATTATCCGTTCGG*ATAAATGGACGCCTGCTCCATATTTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT pG1-14 (PG1--s858-$(T)_{14}$): Example comprising a fragment of pG1 containing one T motif which is $(T)_n$ (n=14) without a TA extension;

SEQ ID 244

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TTTTTTTTTTTTTT*GATGACCCCGTTTTCGTGACAAATTAATTTCCAACGGGGTCTTGTCCGGA
**TAAGAGAATTTTGTTTGATTATCCGTTCGG*ATAAATGGACGCCTGCTCCATATTTTTTCCGGTT*ATTACCCCACCTG**
GAAGTGCCCAGAATTTTCCGGGGATTACGGATAATACGGTGGTCTGGATTAATTAATACGCCAAGTCTTACATT
TTGTTGCAGTCTCGTGCGAGTATGTGCAATAATAAACAAGATGAGCCAATTTATTGGATTAGTTGCAGCTTGACC
CCGCCATAGCTAGGCATAGCCAAGTGCTATGGGTGTTAGATGATGCACTTGGATGCAGTGAGTTTTGGAGTATA
AAAGATCCTTAAAATTCCACCCTT

FIG.6B-122 pG1-14 (PG1--s858-TA$(T)_{15}$): Example comprising a fragment of pG1 containing one T motif which is $(T)_n$ (n=15), extended by preceding TA (extending the T motif at its 5'-end to become a TA$(T)_n$ motif);

SEQ ID 245

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TATTTTTTTTTTTTTTT*GATGACCCCGTTTTCGTGACAAATTAATTTCCAACGGGGTCTTGTCCG
**GATAAGAGAATTTTGTTTGATTATCCGTTCGG*ATAAATGGACGCCTGCTCCATATTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT pG1-14 (PG1--s858-$(T)_{15}$): Example comprising a fragment of pG1 containing one T motif which is $(T)_n$ (n=15) without a TA extension;

SEQ ID 246

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TTTTTTTTTTTTTTT*GATGACCCCGTTTTCGTGACAAATTAATTTCCAACGGGGTCTTGTCCGG
**ATAAGAGAATTTTGTTTGATTATCCGTTCGG*ATAAATGGACGCCTGCTCCATATTTTTCCGGTT*ATTACCCCACCT**
GGAAGTGCCCAGAATTTTCCGGGGATTACGGATAATACGGTGGTCTGGATTAATTAATACGCCAAGTCTTACAT
TTTGTTGCAGTCTCGTGCGAGTATGTGCAATAATAAACAAGATGAGCCAATTTATTGGATTAGTTGCAGCTTGAC
CCCGCCATAGCTAGGCATAGCCAAGTGCTATGGGTGTTAGATGATGCACTTGGATGCAGTGAGTTTTGGAGTAT
AAAAGATCCTTAAAATTCCACCCTT

FIG.6B-123 pG1-14 (PG1--s858-TA(T)$_{16}$): Example comprising a fragment of pG1 containing one T motif which is $(T)_n$ (n=16), extended by preceding TA (extending the T motif at its 5'-end to become a TA$(T)_n$ motif);

SEQ ID 247

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TATTTTTTTTTTTTTTTT*GATGACCCCGTTTTCGTGACAAATTAATTTCCAACGGGGTCTTGT**CC
GGATAAGAGAATTTTGTTTGATTATCCGTTCGG*ATAAATGGACGCCTGCTCCATATTTTTCCGGTT*ATTACCCCA
CCTGGAAGTGCCCAGAATTTTCCGGGGATTACGGATAATAC**GGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1-14 (PG1--s858-(T)$_{16}$): Example comprising a fragment of pG1 containing one T motif which is $(T)_n$ (n=16) without a TA extension;

SEQ ID 248

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TTTTTTTTTTTTTTTT*GATGACCCCGTTTTCGTGACAAATTAATTTCCAACGGGGTCTTGT**CCGG
ATAAGAGAATTTTGTTTGATTATCCGTTCGG*ATAAATGGACGCCTGCTCCATATTTTTCCGGTT*ATTACCCCACCT
GGAAGTGCCCAGAATTTTCCGGGGATTACGGATAATAC**GGTGGTCTGGATTAATTAATACGCCAAGTCTTACAT
TTTGTTGCAGTCTCGTGCGAGTATGTGCAATAATAAACAAGATGAGCCAATTTATTGGATTAGTTGCAGCTTGAC
CCCGCCATAGCTAGGCATAGCCAAGTGCTATGGGTGTTAGATGATGCACTTGGATGCAGTGAGTTTTGGAGTAT
AAAAGATCCTTAAAATTCCACCCTT

FIG.6B-124 pG1-14 (PG1--s858-TA$(T)_{17}$): Example comprising a fragment of pG1 containing one T motif which is $(T)_n$ (n=17), extended by preceding TA (extending the T motif at its 5′-end to become a TA$(T)_n$ motif);

SEQ ID 249

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TATTTTTTTTTTTTTTTTT*GATGACCCCGTTTTCGTGACAAATTAATTTCCAACGGGGTCTTGTC
**CGGATAAGAGAATTTTGTTTGATTATCCGTTCGG*ATAAATGGACGCCTGCTCCATATTTTTCCGGTT*ATTACCCC**
ACCTGGAAGTGCCCAGAATTTTCCGGGGATTACGGATAATACGGTGGTCTGGATTAATTAATACGCCAAGTCTT
ACATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1-14 (PG1--s858-$(T)_{17}$): Example comprising a fragment of pG1 containing one T motif which is $(T)_n$ (n=17) without a TA extension;

SEQ ID 250

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TTTTTTTTTTTTTTTTT*GATGACCCCGTTTTCGTGACAAATTAATTTCCAACGGGGTCTTGTCCG
**GATAAGAGAATTTTGTTTGATTATCCGTTCGG*ATAAATGGACGCCTGCTCCATATTTTTCCGGTT*ATTACCCCAC**
CTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTG
ACCCCGCCATAGCTAGGCATAGCCAAGTGCTATGGGTGTTAGATGATGCACTTGGATGCAGTGAGTTTTGGAGT
ATAAAAGATCCTTAAAATTCCACCCTT

FIG.6B-125 pG1-14 (PG1--s858-TA(T)$_{18}$): Example comprising a fragment of pG1 containing one T motif which is (T)$_n$ (n=18), extended by preceding TA (extending the T motif at its 5'-end to become a TA(T)$_n$ motif);

SEQ ID 251

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TATTTTTTTTTTTTTTTTTT*GATGACCCCGTTTTCGTGACAAATTAATTTCCAACGGGGTCTTGT
**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT pG1-14 (PG1--s858-(T)$_{18}$): Example comprising a fragment of pG1 containing one T motif which is (T)$_n$ (n=18) without a TA extension;

SEQ ID 252

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TTTTTTTTTTTTTTTTTT*GATGACCCCGTTTTCGTGACAAATTAATTTCCAACGGGGTCTTGTCC
**GGATAAGAGAATTTTGTTTGATTATCCGTTCGG*ATAAATGGACGCCTGCTCCATATTTTTCCGGTT*ATTACCCCA**
CCTGGAAGTGCCCAGAATTTTCCGGGGATTACGGATAATACGGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT

FIG.6B-126 pG1-14 (PG1--s858-TA$(T)_{19}$): Example comprising a fragment of pG1 containing one T motif which is $(T)_n$ (n=19), extended by preceding TA (extending the T motif at its 5'-end to become a TA$(T)_n$ motif);

SEQ ID 253

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TATTTTTTTTTTTTTTTTTTT*GATGACCCCGTTTTCGTGACAAATTAATTTCCAACGGGGTCTTG
**TCCGGATAAGAGAATTTTGTTTGATTATCCGTTCGG*ATAAATGGACGCCTGCTCCATATTTTTCCGGTT*ATTACC**
CCACCTGGAAGTGCCCAGAATTTTCCGGGGATTACGGATAATACGGTGGTCTGGATTAATTAATACGCCAAGTC
TTACATTTTGTTGCAGTCTCGTGCGAGTATGTGCAATAATAAACAAGATGAGCCAATTTATTGGATTAGTTGCAGC
TTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTT pG1-14 (PG1--s858-$(T)_{19}$): Example comprising a fragment of pG1 containing one T motif which is $(T)_n$ (n=19) without a TA extension;

SEQ ID 254

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TTTTTTTTTTTTTTTTTTT*GATGACCCCGTTTTCGTGACAAATTAATTTCCAACGGGGTCTTGTC
**CGGATAAGAGAATTTTGTTTGATTATCCGTTCGG*ATAAATGGACGCCTGCTCCATATTTTTCCGGTT*ATTACCCC**
ACCTGGAAGTGCCCAGAATTTTCCGGGGATTACGGATAATACGGTGGTCTGGATTAATTAATACGCCAAGTCTT
ACATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT

FIG.6B-127 pG1-14 (PG1--s858-TA(T)$_{20}$): Example comprising a fragment of pG1 containing one T motif which is (T)$_n$ (n=20), extended by preceding TA (extending the T motif at its 5'-end to become a TA(T)$_n$ motif);

SEQ ID 255

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TATTTTTTTTTTTTTTTTTTTT*GATGACCCCGTTTTCGTGACAAATTAATTTCCAACGGGGTCTT
GT**CCGGATAAGAGAATTTTGTTTGATTATCCGTTCGG*ATAAATGGACGCCTGCTCCATATTTTTCCGGTT*ATTAC**
CCCACCTGGAAGTGCCCAGAATTTTCCGGGGATTACGGATAATACGGTGGTCTGGATTAATTAATACGCCAAGT
CTTACATTTTGTTGCAGTCTCGTGCGAGTATGTGCAATAATAAACAAGATGAGCCAATTTATTGGATTAGTTGCAG
CTTGACCCCGCCATAGCTAGGCATAGCCAAGTGCTATGGGTGTTAGATGATGCACTTGGATGCAGTGAGTTTTGG
AGTATAAAAGATCCTTAAAATTCCACCCTT pG1-14 (PG1--s858-(T)$_{20}$): Example comprising a fragment of pG1 containing one T motif which is (T)$_n$ (n=20) without a TA extension;

SEQ ID 256

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGC*TTTTTTTTTTTTTTTTTTTT*GATGACCCCGTTTTCGTGACAAATTAATTTCCAACGGGGTCTTGT
**CCGGATAAGAGAATTTTGTTTGATTATCCGTTCGG*ATAAATGGACGCCTGCTCCATATTTTTCCGGTT*ATTACCC**
CACCTGGAAGTGCCCAGAATTTTCCGGGGATTACGGATAATACGGTGGTCTGGATTAATTAATACGCCAAGTCT
TACATTTTGTTGCAGTCTCGTGCGAGTATGTGCAATAATAAACAAGATGAGCCAATTTATTGGATTAGTTGCAGCT
TGACCCCGCCATAGCTAGGCATAGCCAAGTGCTATGGGTGTTAGATGATGCACTTGGATGCAGTGAGTTTTGGA
GTATAAAAGATCCTTAAAATTCCACCCTT

FIG.6B-128 pG1-15 (PG1-(T)$_{16}$)

SEQ ID 257

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTT*GATGACCCCGTTTTCGT
GACAAATTAATTTCCAACGGGGTCTTGT**CCGGATAAGAGAATTTTGTTTGATTATCCGTTCGG*ATAAATGGACG***
***CCTGCTCCATATTTTTCCGGTT*ATTACCCCACCTGGAAGTGCCCAGAATTTTCCGGGGATTACGGATAATAC**GGT
GGTCTGGATTAATTAATACGCCAAGTCTTACATTTTGTTGCAGTCTCGTGCGAGTATGTGCAATAATAAACAAGAT
GAGCCAATTTATTGGATTAGTTGCAGCTTGACCCCGCCATAGCTAGGCATAGCCAAGTGCTATGGGTGTTAGATG
ATGCACTTGGATGCAGTGAGTTTTGGAGTATAAAAGATCCTTAAAATTCCACCCTT pG1-16 (PG1-(T)$_{18}$)

SEQ ID 258

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTT*GATGACCCCGTTTTC
GTGACAAATTAATTTCCAACGGGGTCTTGT**CCGGATAAGAGAATTTTGTTTGATTATCCGTTCGG*ATAAATGGA***
***CGCCTGCTCCATATTTTTCCGGTT*ATTACCCCACCTGGAAGTGCCCAGAATTTTCCGGGGATTACGGATAATAC**G
GTGGTCTGGATTAATTAATACGCCAAGTCTTACATTTTGTTGCAGTCTCGTGCGAGTATGTGCAATAATAAACAA
GATGAGCCAATTTATTGGATTAGTTGCAGCTTGACCCCGCCATAGCTAGGCATAGCCAAGTGCTATGGGTGTTAG
ATGATGCACTTGGATGCAGTGAGTTTTGGAGTATAAAAGATCCTTAAAATTCCACCCTT

FIG.6B-129 pG1-17 (PG1-(T)$_{20}$)

SEQ ID 259

CAAACATTTGCTCCCCCTAGTCTCCAGGGAAATGTAAAATATACTGCTAATAGAAAACAGTAAGACGCTCAGTTG
TCAGGATAATTACGTTCGACTGTAGTAAAACAGGAATCTGTATTGTTAGAAAGAACGAGAGTTTTTTACGGCGCC
GCCATATTGGGCCGTGTGAAAACAGCTTGAAACCCCACTACTTTCAAAGGTTCTGTTGCTATACACGAACCATGTT
TAACCAACCTCGCTTTTGACTTGACTGAAGTCATCGGTTAACAATCAAGTACCCTAGTCTGTCTGAATGCTCCTTTC
CATATTCAGTAGGTGTTTCTTGCACTTTTGCATGCACTGCGGAAGAATTAGCCAATAGCGCGTTTCATATGCGCTT
TTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TTCCTGATATGCATCAAAACTCTAATCTAAAACCTGAATCTCCGC*TTTTTTTTTTTTTTTTTTTT*GATGACCCCGTTTT
CGTGACAAATTAATTTCCAACGGGGTCTTGTCCGGATAAGAGAATTTTGTTTGATTATCCGTTCGG*ATAAATGG*
*ACGCCTGCTCCATATTTTTCCGGTT*ATTACCCCACCTGGAAGTGCCCAGAATTTTCCGGGGATTACGGATAATAC
GGTGGTCTGGATTAATTAATACGCCAAGTCTTACATTTTGTTGCAGTCTCGTGCGAGTATGTGCAATAATAAACA
AGATGAGCCAATTTATTGGATTAGTTGCAGCTTGACCCCGCCATAGCTAGGCATAGCCAAGTGCTATGGGTGTTA
GATGATGCACTTGGATGCAGTGAGTTTTGGAGTATAAAAGATCCTTAAAATTCCACCCTT

FIG.6B-130

Fig. 7 native pGAP promoter sequence of P. pastoris (GS115) (SEQ ID 260)

CTGCTACTCTGGTCCCAAGTGAACCACCTTTTGGACCCTATTGACCGGACCTTAACTTGCCAAACCTAAACGCTTA
ATGCCTCAGACGTTTTAATGCCTCTCAACACCTCCAAGGTTGCTTTCTTGAGCATGCCTACTAGGAACTTTAACGA
ACTGTGGGGTTGCAGACAGTTTCAGGCGTGTCCCGACCAATATGGCCTACTAGACTCTCTGAAAAATCACAGTTT
TCCAGTAGTTCCGATCAAATTACCATCGAAATGGTCCCATAAACGGACATTTGACATCCGTTCCTGAATTATAGTC
TTCCACCGTGGATCATGGTGTTCCTTTTTTTCCCAAAGAATATCAGCATCCCTTAACTACGTTAGGTCAGTGATGA
CAATGGACCAAATTGTTGCAAGGTTTTTCTTTTTCTTTCATCGGCACATTTCAGCCTCACATGCGACTATTATCGAT
CAATGAAATCCATCAAGATTGAAATCTTAAAATTGCCCCTTTCACTTGACAGGATCCTTTTTTGTAGAAATGTCTTG
GTGTCCTCGTCCAATCAGGTAGCCATCTCTGAAATATCTGGCTCCGTTGCAACTCCGAACGACCTGCTGGCAACG
TAAAATTCTCCGGGGTAAAACTTAAATGTGGAGTAATGGAACCAGAAACGTCTCTTCCCTTCTCTCTCCTTCCACC
GCCCGTTACCGTCCCTAGGAAATTTTACTCTGCTGGAGAGCTTCTTCTACGGCCCCCTTGCAGCAATGCTCTTCCC
AGCATTACGTTGCGGGTAAAACGGAGGTCGTGTACCCGACCTAGCAGCCCAGGGATGGAAAAGTCCCGGCCGT
CGCTGGCAATAATAGCGGGCGGACGCATGTCATGAGATTATTGGAAACCACCAGAATCGAATATAAAAGGCGA
ACACCTTTCCCAATTTTGGTTTCTCCTGACCCAAAGACTTTAAATTTAATTTATTTGTCCCTATTTCAATCAATTGAA
CAACTATCAAAACACA

Rgt1 (PAS_chr1-3_0233) (SEQ ID 261)

MIPTIDPKDPELVSEDTAQSASARKRSKVSRACDECRRKKIKCDATFLANSNTLLKPCTNCYKYNCSCSFTRVPLKRGPS
KGFARDGSGYERRRSSSVHSVSSSQSVTSPVPSHASLPIPPANPVSLPRLNVPGDGLLSPKAVPPTNLFWKVPYELPSFS
DRRSSVASADSFRRPSIYQSDSEDDFYSATGSQRNSISQAPRQRNLSPALSVSSTSSLNNRIKSLNMVASTLESNIHNYY
SQGFNSSLPILPLDERILSTLLSNVSNGSSSASWDAIRSPILELFDKSILMLLRSYESQFNFNDLLDHVTEMQSIYPRIRSHL
LSDELLKLIFLMSGVLTDYALILTGQPYSTGLSITVSVFNDWKTYENVQRVLVINRAGSLDLDYDSLPFLFARCYLSLATLD
LIYSLSFSSPRLISSFANLPILDIVQKCGITKDAKLDETPLPVLDQFLNCFLPGDTYPTALNTLKTGLVLLDFTNNRSTTLRFP
FINIHDDNHMTGLSHLLSNVSDFMSQFTEVHSDSKDSQLLFLRCIWAFWEIGSVLSELIDHFISSSANSQVGDKDASFF
YEHQLKVTTLLGTFSNIASAFLTSSTTAASHPPPSISPFHIISMVESFKMVQFLNKLIASFISLNEKLEKRELEDELSKCKEEL
NNLNERFQAVSSVQTLPVVHVLFRDLVFSSNRLDTQRDRASSVVSATTTTSTATTTATTKKSSFGNLLHSDEENILPTVI
DWCKEQKHSAEMFLNKNDLNGWLY

Cat8-1 (PAS_chr2-1_0757) (SEQ ID 262)

MMPEEQVTSPQRKHQKSKAKTIRAPGSSIERVAQACDRCRSKKTRCDGKRPQCSQCAAVGFECKISDKLSRRAFPRG
YTETLEERIRELEFENKKLHKLIDLKNEQVEIKNRIDQESTLTNENLTLLNKEQEVSHSGNIHHHADGEPCNCANSVSARP
VSIAGSVDIDTTDLSDEDDSLYSAASYNAKYHQTGTSGPEMVRLSQRYSSGNFNDPLSFEQSNAPGAAAAISIQNKMR
TQTFVNLANLVAMSIPRTTEETLFIASLLAKICNVHGFQSKAPILTAKSIALLKDKYNYGNDEVFANITLKNVNFNKLTSQ
QSQQFFQSLNLPNQVNLDLFITTFFNTWNNFIPIINRHIFMSSYIKFNKSRETMFTDNSMFGNEKFGEILLLITTMVMLS
QERNNNREAVPSSSYKKDSTPHPHRPDASSQSNVEILQYYDHLIHEFIKSNISDDCSLPTLESLSLQLLYCLAIGDLTTSYE
LRGKIITMGQQLRLHRCPSAVLGTNGSKVSQMQQGERRILFWCIYILDTFSALILGVPRLLKDYEIECALPFSNESNNAN
VKGSIENTTNTVIINNIKLSLAGKVSDCALAVMRYSKVLGNILDSIFQRSSINNPSVVSKSTNITEETCLLHEHALDLWRRE
LSPHINVDLDKSPGGVEYERLSDNQLTILFLYYHAKILIYLPLMANESSQSRSSASYINIQQSTTSILAIANTLATKERNFYFL
PLPVNLSREKVRLAFLSAKGSLEYARGGALFQESKILLASVINELKIETSIGMLGCLSVPCMEAVDNAMEQIMALPGKVS
SVNGSNSEMKRSSSKRKSSPLRQDISGDERKSHNIEVSDSRTPSVQSSLYPQPNQMHHPNIIKSENNEQMIPENDTPG
AINDIFTSHSPPGTVTSMKEEDLPIKVPILLQTQQRQIYNNNPNHSLFSQQPGTQVLSGQQMPGPSSTDQQFKRITTP
DGLDSLMMQDFGVDASLGLPMLDFDFNFDFENVQNNYSQSNVSPPNSESVPSSIQGTHSNDPKDSQVSAGSLFGL

Fig. 7 (continued)

Cat8-2 (PAS_chr4_0540) (SEQ ID 263)

MKENQASNKFNLIKNPITGKPRISQACDRCRIKKIKCDGTLPSCTNCSKIGFVCKISDRLTRSSFPKGYTKNLEQKLIDME
LDRNRLMLELNRIKKEGFDGTNNNIAMASSVSSSENLKSDDSSECQSVTVSLSSTSGPSLSPEPKQDDFRFRVGMDGS
FVLNQFLQSPLMDYIKSLNVLQFNGCANFDQSFNDDPLVLNKYHMNLNRFLNLIFYKLLLPLIHRNSNTLNEKFAEDNN
SLDSLIWKFFTNYNKLIPILEFDSFYKDYLQFIHKYYSNNQVFVDGFRKYFEFSEFEQCFIVKLILILKFTLPVIHDTSVPSEIY
RLISMDSLQRLFGNIDFLKPSTDKVSILLLVLHYMVLYESPKSLLDTQDEAQKYDEFIGNLLSTAVHHITSLRLHIDPRKLQ
FPRPLPSNGNRLRIKLSWCYKLISKLFRVIYNIDNDSLYSLDDSHLPELQSISILHEELDVTIQFNNLLNLIPNNFHSLRDKQ
SLSKIKTQLLEWHKNFNTEFVEHFNLNDTDSDELSAEKINVLRSKLISLNRLNCYNSYFQLVIELQLKENLDSVVSGIFGLS
NEMLIDNKSSTELLNTLQQTPIIHQSSILVSLCYRIQTGNLQDEICSILVNNYEKLLQCNDAGLPIKILPQLVHYFKGKISTN
LSNSAAHEDLMNMFTLNDNLSTTTTDLDSFIIPPKRKQDQTLPIGTKRSKSASTSSVISSDDCSLFSNSLSVPTTFSGSSIS
VGMDNPPSSLFGSYKRPSSIVKQEPTINPRSNGTNTDSNLFDTFNDSIKGSLNNGLKKLKDIRCNSVVERSHSSQRNDF
LMDQEDSITKETINFSELFTCGTPTASQSIDRSPKSLLLNDLAIAPDTLVIKPDAEDLDRLKNKIRSVKSTVH

Fig. 8: Prior art sequences pG1 (SEQ ID 264) DNA; Pichia pastoris

ATTTCCACCCCCATCCCAGTAGAATGTAGGGTCCCCAAACATTTGCTCCCCCTAGTCTCCAGGGAAATGTAAAATA
TACTGCTAATAGAAAACAGTAAGACGCTCAGTTGTCAGGATAATTACGTTCGACTGTAGTAAAACAGGAATCTGT
ATTGTTAGAAAGAACGAGAGTTTTTTACGGCGCCGCCATATTGGGCCGTGTGAAAACAGCTTGAAACCCCACTAC
TTTCAAAGGTTCTGTTGCTATACACGAACCATGTTTAACCAACCTCGCTTTTGACTTGACTGAAGTCATCGGTTAA
CAATCAAGTACCCTAGTCTGTCTGAATGCTCCTTTCCATATTCAGTAGGTGTTTCTTGCACTTTTGCATGCACTGCG
GAAGAATTAGCCAATAGCGCGTTTCATATGCGCTTTTACCCCCTCTTTTGTCAAGCGCAAAATGCCTGTAAGATTT
GGTGGGGGTGTGAGCCGTTAGCTGAAGTACAACAGGCTAATTCCCTGAAAAAACTGCAGATAGACTTCAAGATC
TCAGGGATTCCCACTATTTGGTATTCTGATATGTTTTTCCTGATATGCATCAAAACTCTAATCTAAAACCTGAATCT
CCGCTATTTTTTTTTTTTTTTTTTGATGACCCCGTTTTCGTGACAAATTAATTTCCAACGGGGTCTTGTCCGGATAAGA
GAATTTTGTTTGATTATCCGTTCGGATAAATGGACGCCTGCTCCATATTTTTCCGGTTATTACCCCACCTGGAAGT
GCCCAGAATTTTCCGGGGATTACGGATAATACGGTGGTCTGGATTAATTAATACGCCAAGTCTTACATTTTGTTGC
AGTCTCGTGCGAGTATGTGCAATAATAAACAAGATGAGCCAATTTATTGGATTAGTTGCAGCTTGACCCCGCCAT
AGCTAGGCATAGCCAAGTGCTATGGGTGTTAGATGATGCACTTGGATGCAGTGAGTTTTGGAGTATAAAAGATC
CTTAAAATTCCACCCTT pG1a (SEQ ID 265)

GGAATCTGTATTGTTAGAAAGAACGAGAGTTTTTTACGGCGCCGCCATATTGGGCCGTGTGAAAACAGCTTGAA
ACCCCACTACTTTCAAAGGTTCTGTTGCTATACACGAACCATGTTTAACCAACCTCGCTTTTGACTTGACTGAAGTC
ATCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGAC
TTCAAGATCTCAGGGATTCCCACTATTTGGTATTCTGATATGTTTTTCCTGATATGCATCAAAACTCTAATCTAAAA
CCTGAATCTCCGCTATTTTTTTTTTTTTTTTTTGATGACCCCGTTTTCGTGACAAATTAATTTCCAACGGGGTCTTGTCC
GGATAAGAGAATTTTGTTTGATTATCCGTTCGGATAAATGGACGCCTGCTCCATATTTTTCCGGTTATTACCCCAC
CTGGAAGTGCCCAGAATTTTCCGGGGATTACGGATAATACGGTGGTCTGGATTAATTAATACGCCAAGTCTTACA
TTTTGTTGCAGTCTCGTGCGAGTATGTGCAATAATAAACAAGATGAGCCAATTTATTGGATTAGTTGCAGCTTGA
CCCCGCCATAGCTAGGCATAGCCAAGTGCTATGGGTGTTAGATGATGCACTTGGATGCAGTGAGTTTTGGAGTA
TAAAAGATCCTTAAAATTCCACCCTT

Fig. 8 (continued)

pG1b (SEQ ID 266)

CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAAC
AGGCTAATTCCCTGAAAAAACTGCAGATAGACTTCAAGATCTCAGGGATTCCCACTATTTGGTATTCTGATATGTT
TTTCCTGATATGCATCAAAACTCTAATCTAAAACCTGAATCTCCGCTATTTTTTTTTTTTTTTTGATGACCCCGTTTTC
GTGACAAATTAATTTCCAACGGGGTCTTGTCCGGATAAGAGAATTTTGTTTGATTATCCGTTCGGATAAATGGAC
GCCTGCTCCATATTTTTCCGGTTATTACCCCACCTGGAAGTGCCCAGAATTTTCCGGGGATTACGGATAATACGGT
GGTCTGGATTAATTAATACGCCAAGTCTTACATTTTGTTGCAGTCTCGTGCGAGTATGTGCAATAATAAACAAGAT
GAGCCAATTTATTGGATTAGTTGCAGCTTGACCCCGCCATAGCTAGGCATAGCCAAGTGCTATGGGTGTTAGATG
ATGCACTTGGATGCAGTGAGTTTTGGAGTATAAAAGATCCTTAAAATTCCACCCTT pG1c (SEQ ID 267)

CTGCAGATAGACTTCAAGATCTCAGGGATTCCCACTATTTGGTATTCTGATATGTTTTTCCTGATATGCATCAAAA
CTCTAATCTAAAACCTGAATCTCCGCTATTTTTTTTTTTTTTTTGATGACCCCGTTTTCGTGACAAATTAATTTCCAA
CGGGGTCTTGTCCGGATAAGAGAATTTTGTTTGATTATCCGTTCGGATAAATGGACGCCTGCTCCATATTTTTCCG
GTTATTACCCCACCTGGAAGTGCCCAGAATTTTCCGGGGATTACGGATAATACGGTGGTCTGGATTAATTAATAC
GCCAAGTCTTACATTTTGTTGCAGTCTCGTGCGAGTATGTGCAATAATAAACAAGATGAGCCAATTTATTGGATTA
GTTGCAGCTTGACCCCGCCATAGCTAGGCATAGCCAAGTGCTATGGGTGTTAGATGATGCACTTGGATGCAGTG
AGTTTTGGAGTATAAAAGATCCTTAAAATTCCACCCTT pG1d (SEQ ID 268)

GACCCCGTTTTCGTGACAAATTAATTTCCAACGGGGTCTTGTCCGGATAAGAGAATTTTGTTTGATTATCCGTTCG
GATAAATGGACGCCTGCTCCATATTTTTCCGGTTATTACCCCACCTGGAAGTGCCCAGAATTTTCCGGGGATTACG
GATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATG
GGTGTTAGATGATGCACTTGGATGCAGTGAGTTTTGGAGTATAAAAGATCCTTAAAATTCCACCCTT pG1e (SEQ ID 269)

CCGGATAAGAGAATTTTGTTTGATTATCCGTTCGGATAAATGGACGCCTGCTCCATATTTTTCCGGTTATTACCCC
ACCTGGAAGTGCCCAGAATTTTCCGGGGATTACGGATAATACGGTGGTCTGGATTAATTAATACGCCAAGTCTTA
CATTTTGTTGCAGTCTCGTGCGAGTATGTGCAATAATAAACAAGATGAGCCAATTTATTGGATTAGTTGCAGCTT
GACCCCGCCATAGCTAGGCATAGCCAAGTGCTATGGGTGTTAGATGATGCACTTGGATGCAGTGAGTTTTGGAG
TATAAAAGATCCTTAAAATTCCACCCTT pG1f (SEQ ID 270)

GCCTGCTCCATATTTTTCCGGTTATTACCCCACCTGGAAGTGCCCAGAATTTTCCGGGGATTACGGATAATACGGT
GGTCTGGATTAATTAATACGCCAAGTCTTACATTTTGTTGCAGTCTCGTGCGAGTATGTGCAATAATAAACAAGAT
GAGCCAATTTATTGGATTAGTTGCAGCTTGACCCCGCCATAGCTAGGCATAGCCAAGTGCTATGGGTGTTAGATG
ATGCACTTGGATGCAGTGAGTTTTGGAGTATAAAAGATCCTTAAAATTCCACCCTT

Fig. 9
(A)
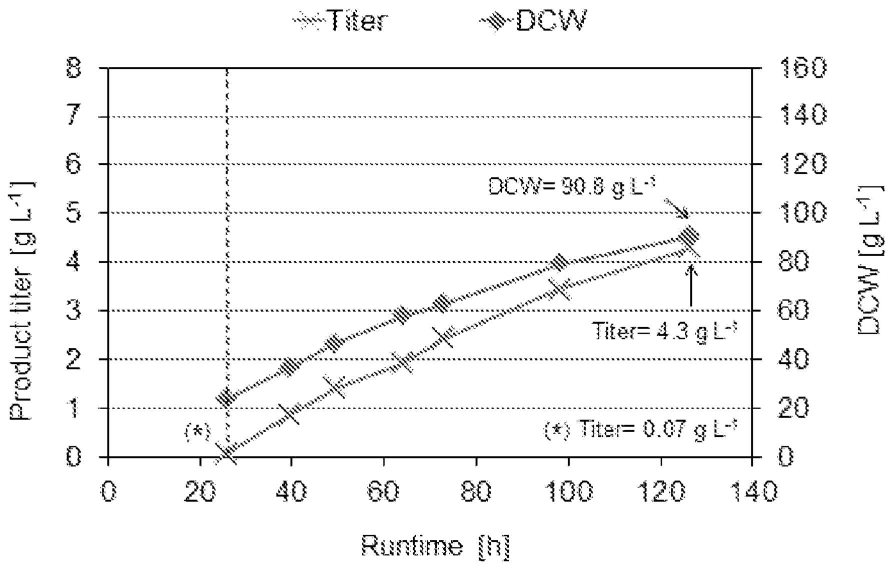
(B)
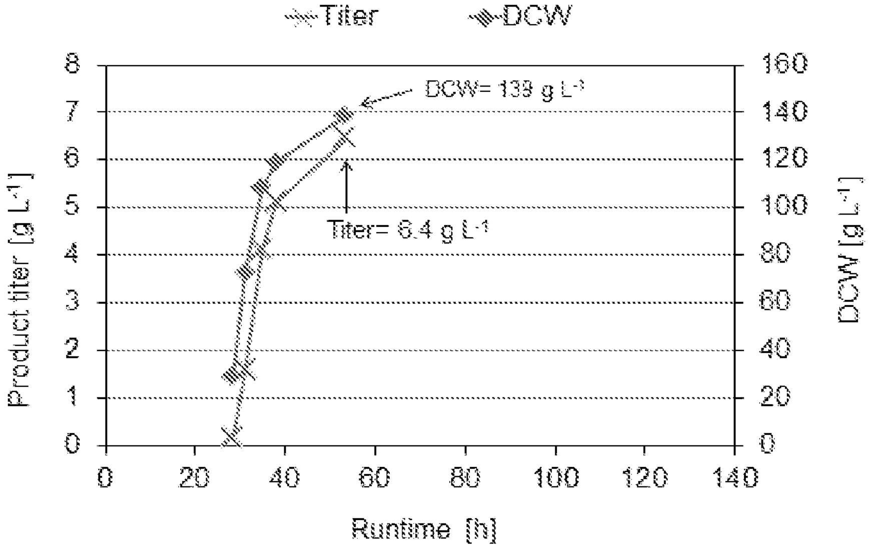

PROMOTER VARIANTS

REFERENCE TO AN ELECTRONIC SEQUENCE LISTING

The content of the electronic sequence listing (02020002US2_SequenceListing_Corrected.txt; Size: 421,888 bytes; and Date of Creation Jul. 10, 2020) is herein incorporated by reference in its entirety.

TECHNICAL FIELD

The invention refers to an isolated artificial promoter, which is a functional variant or derivative of the carbon source regulatable pG1 promoter of *Pichia pastoris* identified by SEQ ID 1, which promoter is herein referred to as pG1-x that is characterized by specific promoter elements and features.

BACKGROUND

The methylotrophic yeast *Pichia pastoris* (syn. *Komagataella* sp.) is a well-established protein production host. Numerous strain engineering approaches for *P. pastoris* improved the productivity for various products and effort was also dedicated to promoters for production purposes (Prielhofer, R., M. Maurer, J. Klein, J. Wenger, C. Kiziak, B. Gasser & D. Mattanovich, (2013) Induction without methanol: novel regulated promoters enable high-level expression in *Pichia pastoris*. Microb Cell Fact 12: 5). Gene promoters are key features for the expression of a gene of interest (GOI): transcription of RNA of a downstream (3') GOI is driven by the upstream (5') promoter sequence. RNA polymerase II (RNAPII) is responsible for transcription of mRNA in eukaryotes. RNAPII promoters consist of a core promoter and several cis-acting DNA elements: proximal promoter, enhancers, silencers and boundary/insulator elements. Yeast core promoters are typically located close (−75/+50 bp) to the main transcription initiation site, they frequently contain improper TATA boxes (up to 2 bases difference to the TATA consensus sequence) and lack promoter elements which are typically found in other organisms. Transcriptional regulation responds to different conditions and is conducted through by cis-acting elements and corresponding regulatory proteins (transcription factors (TFs)).

For biotechnological applications, promoters allowing either constitutive or regulated/inducible gene expression are used. Production processes utilizing *P. pastoris* favorably apply carbon source dependent promoters such as the methanol-inducible $P_{AOX}$. Thereby, the growth phase can be separated from the potentially burdening protein production phase. A set of promoters was recently reported (Prielhofer et al., 2013), which is also controlled by the carbon source, but does not rely on methanol for induction: These promoters share the feature of repression by excess glycerol and induction by limiting glucose. pG1 (SEQ ID 1), the strongest out of these promoters, is fully induced below 0.05 g/L glucose; it natively controls the expression of a high-affinity glucose transporter gene GTH1. Glucose uptake characteristics are dependent on the presence of high and low affinity glucose transporters. Seventeen hexose transport (HXT) genes in *S. cerevisiae* (HXT1-17) are expressed depending on the glucose concentration, but only two HXT homologs are found in *P. pastoris* (PAS_chr1-4_0570 and PAS_chr2-1_0054, named PpHxt1 and PpHxt2). PpHxt1 was identified to be the major low-affinity transporter in *P. pastoris*, while high affinity glucose transport is facilitated by two other genes, namely PAS_chr3_0023 and PAS_chr1-3_0011 (GTH1, the gene controlled by pG1) Prielhofer et al., 2013).

While *S. cerevisiae* features a huge capacity of glucose uptake and (fermentative) glucose metabolism, *P. pastoris* has a lower glucose uptake rate and a respiratory metabolism of glucose. Furthermore, *P. pastoris* is able to take glucose at much lower extracellular concentrations than *S. cerevisiae* ($K_M$ of high-affinity transporters in the μM range in *P. pastoris* vs. mM range in *S. cerevisiae*). The fundamental difference in glucose uptake behavior is also displayed at the transcriptional control of related genes and can also be seen in the evolved functions of transcriptional regulators e. g. PpAft1 and PpMxr1 (homolog of ScAdr1).

*P. pastoris* promoter studies and random mutagenesis of $P_{AOX1}$ and of the promoter of glyceraldehyde-3-phosphate dehydrogenase $P_{GAP}$ resulted in libraries with promoter variants possessing different activities, altered induction behavior compared to the wild-type promoter and in the identification of several important transcription factor binding sites (TFBS) of $P_{AOX1}$ (WO2006/089329 A2).

The pG1 promoter and fragments thereof are further described in WO2013/050551 A1.

WO2014067926A1 discloses the expression of a protein of interest employing specific leader sequences. The leader were used with various promoter. As an exemplary promoter, the pG1 promoter is used.

Struhl K. (Proceedings of the National Academy of Sciences of the United States of America 1982, 78(7):4461-4465) describes deletion mapping of the yeast his3 promoter region. He concludes that the T-A-T-A box, a sequence in front of most eukaryotic genes is not sufficient for wild-type promoter function and suggests that the yeast promoter appears to be more complex than a simple site of interaction between RNA polymerase and DNA.

Quandt et al. (Nucleic Acids Research 1995, 23(23)4878-4884) describe tools for detection of consensus matches in nucleotide sequence data to identify regulatory motifs based on sequence data analysis. A library of consensus patterns was created and potential sequence matches were detected using a software tool (MatInspector).

SUMMARY OF THE INVENTION

It is the object of the invention to provide improved regulatable promoters with respect to carbon source regulation and promoter strength. It is the further object to provide such promoter for enhanced POI production and/or POI production within a reduced time period.

The object is solved by the subject matter as claimed.

According to the invention there is provided an isolated and/or artificial pG1-x promoter, which is a functional variant of the carbon source regulatable pG1 promoter of *Pichia pastoris* identified by SEQ ID 1, which pG1-x promoter consists of or comprises at least a part of SEQ ID 1 with a length of at least 293 bp, characterized by the following promoter regions:

a) at least one core regulatory region comprising the nucleotide sequences SEQ ID 2 and SEQ ID 3; and b) a non-core regulatory region, which is any region within the pG1-x promoter sequence other than the core regulatory region;

wherein the pG1-x promoter comprises at least one mutation in any of the promoter regions and a sequence identity of at least 80% in SEQ ID 2 and SEQ ID 3, and a sequence identity of at least 50% in any region other than SEQ ID 2 or SEQ ID 3; and further wherein the pG1-x promoter is characterized by the same or an increased promoter strength and induction ratio as compared to the pG1 promoter, wherein the promoter strength is at least 1.1-fold increased in the induced state as compared to the pG1 promoter, and/or the induction ratio is at least 1.1-fold increased as compared to the pG1 promoter.

Specifically, the pG1 promoter of *Pichia pastoris* identified by SEQ ID 1 is any of SEQ ID 7, 8, or 9, more specifically SEQ ID 9 as used herein as a reference in the Examples.

Specifically, the pG1-x promoter is not any of the prior art promoter named pG1 (SEQ ID 264), or any of pG1a (SEQ ID 265), pG1b (SEQ ID 266), pG1c (SEQ ID 267), pG1d (SEQ ID 268), pG1e (SEQ ID 269), or pG1f (SEQ ID 270), as described in WO2013050551 A1.

According to a specific embodiment, the pG1-x promoter according to the invention is a carbon source regulatable promoter which is characterized by an at least 1.1-fold, or at least 1.2-fold, or at least 1.3-fold, or at least 1.4-fold, or at least 1.5-fold, or at least 1.6-fold, or at least 1.7-fold, or at least 1.8-fold, or at least 1.9-fold, or at least 2-fold, or at least 2.1-fold, or at least 2.2-fold, or at least 2.3-fold, or at least 2.4-fold, or at least 2.5-fold, or at least 2.6-fold, or at least 2.7-fold, or at least 2.8-fold increased, or at least 2.9-fold, or at least 3-fold, or at least 3.3-fold, or at least 3.5-fold, or at least 3.8-fold, or at least 4-fold, or at least 4.5-fold, or at least 5-fold, or at least 5.5-fold, or at least 6-fold increased promoter strength in the induced state as compared to the pG1 promoter, and the capability of being carbon source regulated as determined by an induction ratio which is the same or higher as compared to the induction ratio achieved with the pG1 promoter.

According to a specific further embodiment, the pG1-x promoter according to the invention is a carbon source regulatable promoter which is characterized by the same or higher promoter strength in the induced state as compared to the pG1 promoter, and the capability of being carbon source regulated as determined by an induction ratio which is at least 1.1-fold, or at least 1.2-fold, or at least 1.3-fold, or at least 1.4-fold, or at least 1.5-fold, or at least 1.6-fold, or at least 1.7-fold, or at least 1.8-fold, or at least 1.9-fold, or at least 2-fold, or at least 2.1-fold, or at least 2.2-fold, or at least 2.3-fold, or at least 2.4-fold, or at least 2.5-fold, or at least 2.6-fold, or at least 2.7-fold, or at least 2.8-fold increased, or at least 2.9-fold, or at least 3-fold, or at least 3.3-fold, or at least 3.5-fold, or at least 3.8-fold, or at least 4-fold, or at least 4.5-fold, or at least 5-fold, or at least 5.5-fold, or at least 6-fold increased as compared to the induction ratio achieved with the pG1 promoter.

According to a specific further embodiment, the pG1-x promoter according to the invention is a carbon source regulatable promoter which is characterized by an at least 1.1-fold, or at least 1.2-fold, or at least 1.3-fold, or at least 1.4-fold, or at least 1.5-fold, or at least 1.6-fold, or at least 1.7-fold, or at least 1.8-fold, or at least 1.9-fold, or at least 2-fold, or at least 2.1-fold, or at least 2.2-fold, or at least 2.3-fold, or at least 2.4-fold, or at least 2.5-fold, or at least 2.6-fold, or at least 2.7-fold, or at least 2.8-fold increased, or at least 2.9-fold, or at least 3-fold, or at least 3.3-fold, or at least 3.5-fold, or at least 3.8-fold, or at least 4-fold, or at least 4.5-fold, or at least 5-fold, or at least 5.5-fold, or at least 6-fold increased promoter strength in the induced state as compared to the pG1 promoter, and the capability of being carbon source regulated as determined by an induction ratio which is at least 1.1-fold, or at least 1.2-fold, or at least 1.3-fold, or at least 1.4-fold, or at least 1.5-fold, or at least 1.6-fold, or at least 1.7-fold, or at least 1.8-fold, or at least 1.9-fold, or at least 2-fold, or at least 2.1-fold, or at least 2.2-fold, or at least 2.3-fold, or at least 2.4-fold, or at least 2.5-fold, or at least 2.6-fold, or at least 2.7-fold, or at least 2.8-fold increased, or at least 2.9-fold, or at least 3-fold, or at least 3.3-fold, or at least 3.5-fold, or at least 3.8-fold, or at least 4-fold, or at least 4.5-fold, or at least 5-fold, or at least 5.5-fold, or at least 6-fold increased as compared to the induction ratio achieved with the pG1 promoter.

Specifically, the promoter strength is determined by the expression level of a protein of interest (POI), such as a model protein (e.g., Green Fluorescence Protein, GFP, including e.g., enhanced GFP, eGFP, Gene Bank Accession no. U57607), and/or the transcription rate, as compared to the pG1 promoter. The promoter strength of pG1-x is specifically at least 1.2-fold, or at least 1.3-fold, or at least 1.4-fold, or 1.5-fold, or at least 1.6-fold, or at least 1.7-fold, or at least 1.8-fold, or at least 1.9-fold, or at least 2-fold, or at least 2.1-fold, or at least 2.2-fold, or at least 2.3-fold, or at least 2.4-fold, or at least 2.5-fold, or at least 2.6-fold, or at least 2.7-fold, or at least 2.8-fold increased, or at least 2.9-fold, or at least 3-fold, or at least 3.5-fold, or at least 4-fold, or at least 4.5-fold, or at least 5-fold, or at least 5.5-fold, or at least 6-fold, or at least 6.5-fold, or at least 7-fold, or at least 7.5-fold, or at least 8-fold, or at least 8.5-fold, or at least 9-fold, or at least 9.5-fold, or at least 10-fold increased as compared for example to the pG1 promoter.

Herein, the pG1 promoter may serve as a reference or control to determine the improved promoter function. Such control pG1 promoter may be used in parallel control experiments using the same host cell and expression system, or as internal control within the same host cell culture. Such control experiments to qualify the promoter function as compared to the pG1 promoter are preferably carried out in *P. pastoris* host cell cultures, in particular recombinant *P. pastoris* expressing a model protein, such as GFP or eGFP.

The pG1-x promoter induction specifically refers to induction of transcription, specifically including further translation and optional expression of said POI.

Said transcription rate is determined as a measure of the promoter strength and specifically refers to the amount of transcripts obtained upon fully inducing said promoter.

Said transcription rate may be determined by the transcription strength in the fully induced state, which is e.g., obtained under conditions of glucose-limited chemostat cultivations and expressed relative to the transcription rate of the pG1 promoter.

Preferably the transcription analysis is quantitative or semi-quantitative, preferably employing qRT-PCR, DNA microarrays, RNA sequencing and transcriptome analysis.

The promoter strength as compared to the pG1 promoter strength can be determined by the following standard assay: *P. pastoris* strains expressing eGFP under the control of the promoter to be tested are screened in 24-deep well plates at 25° C. with shaking at 280 rpm with 2 mL culture per well. Glucose feed beads (6 mm, Kuhner, CH) are used to generate glucose-limiting growth conditions. Cells are analysed for eGFP expression in the induced state (YP+1 feed bead, for 20-28 hours).

Said promoter is considered as de-repressed and fully induced, if the culture conditions provide for about maximum induction, e.g. at glucose concentrations of less than 0.4 g/L, preferably less than 0.04 g/L, specifically less than 0.02 g/L. The fully induced promoter preferably shows a transcription rate of at least 20%, more preferred at least 30%, 40%, 50%, 60%, 70%, 80%, 90% and at least 100% or even higher transcription rate of at least 150% or at least 200% as compared to the native pGAP promoter. The transcription rate may, for example, be determined by the amount of transcripts of a reporter gene, such as eGFP, such as described in the Example section below, upon cultivating a clone in liquid culture. Alternatively, the transcription rate may be determined by the transcription strength on a microarray, where microarray data show the difference of expression level between repressed and de-repressed state and a high signal intensity in the fully induced state as compared to a control.

Said native pGAP promoter specifically of is a promoter endogenous or homologous to the eukaryotic cell which may be used as a host cell to determine the expression of a POI, and serves as a standard or reference promoter for comparison purposes.

For example, a native pGAP promoter of *P. pastoris* is the unmodified, endogenous promoter sequence in *P. pastoris*, as used to control the expression of GAPDH in *P. pastoris*, e.g. having the sequence shown in FIG. 7: native pGAP promoter sequence of *P. pastoris* (GS115) (SEQ ID 260). If *P. pastoris* is used as a host for producing a POI according to the invention, the transcription strength or rate of the pG1-x promoter according to the invention is compared to such native pGAP promoter of *P. pastoris*, and/or compared to the native pG1 promoter.

As another example, a native pGAP promoter of *S. cerevisiae* is the unmodified, endogenous promoter sequence in *S. cerevisiae*, as used to control the expression of GAPDH in *S. cerevisiae*. If *S. cerevisiae* is used as a host for producing a POI, the transcription strength or rate of the pG1-x promoter is compared to such native pGAP promoter of *S. cerevisiae*.

Therefore, the relative transcription strength or rate of a promoter according to the invention is usually compared to the native pGAP promoter of a cell of the same species or strain that is used as a host for producing a POI.

The induction ratio is a key parameter to determine the regulation of the present pG1-x promoter, and sets the promoter activity or strength in the induced state in relation to the promoter activity or strength in the repressed state. For example, the expression level of a model protein (e.g., GFP or eGFP) and/or the transcription rate in the repressed state is determined upon repression by excess glycerol, and the expression level of the model protein and/or the transcription rate is determined in the induced state upon induction by limiting glucose feeding.

Specifically, the induction ratio is determined by the ratio of expression level (e.g. GFP or eGFP) in the induced vs. the repressed state. The induction ratio of the pG1-x promoter is specifically the same or higher as compared to the pG1 promoter. In specific cases, the induction ratio is at least 2-fold, or at least 3-fold, or at least 4-fold, at least 5-fold, or at least 6-fold, or at least 7-fold, at least 8-fold, or at least 9-fold, or at least 10-fold increased, as compared to the pG1 promoter.

The induction ratio as compared to the pG1 promoter strength can be determined by the following standard assay: *P. pastoris* strains expressing eGFP under the control of the promoter to be tested are screened in 24-deep well plates at 25° C. with shaking at 280 rpm with 2 mL culture per well. Glucose feed beads (6 mm, Kuhner, CH) are used to generate glucose-limiting growth conditions. Cells are analyzed for eGFP expression during repression (YP+1% glycerol, exponential phase) and induction (YP+1 feed bead, for 20-28 hours).

Specifically, the pG1-x promoter has a promoter activity or strength (e.g., transcriptional activity or transcription strength) in the de-repressed (induced) state, which is at least 2.5-fold, or at least 3 fold, or at least 4-fold, at least 5-fold, or at least 6-fold, or at least 7-fold, at least 8-fold, or at least 9-fold, or at least 10-fold higher than in the repressed state.

Specifically, the core regulatory region incorporates the nucleotide sequences SEQ ID 2 and SEQ ID 3, meaning that the sequences SEQ ID 2 and 3 are comprised in the pG1-x promoter sequence in any order, preferably in close proximity to each other, e.g. with up to 10, 20, 50 or 100 bp between the sequences SEQ ID 2 and 3.

Specifically, the SEQ ID 2 and/or SEQ ID 3 contain one or more transcription factor binding sites (TFBS).

Specifically, the SEQ ID 2 and SEQ ID 3 nucleotide sequences, each of which or both sequences together represents a TFBS or at least a part thereof which is considered functional being recognized by the respective transcription factor. Such SEQ ID 2 or SEQ ID 3 nucleotide sequence (or a functional variant thereof) is considered essential and is incorporated in the pG1-x promoter either in unmodified form or as a functional variant thereof with at least 80% sequence identity, or at least 85%, or at least 90%, or at least 95%, up to 100% sequence identity.

Specifically, the pG1-x promoter comprises a nucleotide sequence other than SEQ ID 2 and SEQ ID 3, which has at least 50% sequence identity to a corresponding region in the pG1 promoter, specifically, at least 60%, or at least 70%, or at least 80%, or at least 90% sequence identity in the core regulatory region or in the non-core regulatory region. Specifically, the nucleotide sequence within the core-regulatory region which is any other than SEQ ID 2 and SEQ ID 3 has at least at least 60%, or at least 70%, or at least 80%, or at least 90%, or at least 95%, or at least 98% sequence identity to the corresponding region in the pG1 promoter. Specifically, the nucleotide sequence in the non-core regulatory region can have less than 90%, or less than 80%, or less than 70%, or less than 60% sequence identity to a corresponding region in the pG1 promoter.

Specifically, the core regulatory region comprises or consists of the nucleotide sequence SEQ ID 4, or a functional variant thereof comprising the TFBS, preferably a functional variant with at least 80%, or at least 90%, or at least 95%, or at least 98% sequence identity.

Specifically, the core regulatory region is incorporated into a main regulatory region represented by SEQ ID 5, or a functional variant thereof comprising the TFBS, preferably a functional variant with at least 80%, or at least 90%, or at least 95%, or at least 98% sequence identity.

Specifically, the one or more TFBS is a TFBS for any of the transcription factors selected from the group consisting of Rgt1, Cat8-1 and Cat8-2.

Specifically, the TFBS are recognized by the transcription factors Rgt1 and/or Cat8-1 and/or Cat8-2. TFBS are characterized by certain consensus sequences, which can vary for the same factor. The specific transcription factors are identified as follows:

Rgt1 is a glucose-responsive transcriptional activator and repressor and it regulates the expression of several glucose transporter (HXT) genes. Rgt1 of *P. pastoris* is characterized by the amino acid sequence SEQ ID 261 (FIG. 7).

Cat8-1 and Cat8-2 are zinc cluster transcriptional activators binding to carbon source response elements, necessary for derepression of a variety of genes under non-fermentative growth conditions. Cat8-1 and Cat8-2 of *P. pastoris* are characterized by the amino acid sequences SEQ ID 262 and 263, respectively (FIG. 7).

Specifically, the core regulatory region comprises a deletion of one or more nucleotides between the nucleotide sequences SEQ ID 2 and SEQ ID 3. The deletion may be one or more point mutations, and refer to 1, 2, 3, 4, 5, 6, 7, 8, or all 9 nucleotides positioned between SEQ ID 2 and SEQ ID 3.

Specifically, the core regulatory region comprises an insertion of one or more nucleotides between the nucleotide sequences SEQ ID 2 and SEQ ID 3. The insertion may be one or more point mutations, and refer to at least 1, 2, 3, 4, 5, 6, 7, 8, 9, or 10 nucleotides positioned between SEQ ID 2 and SEQ ID 3.

Specifically, the core regulatory region comprises a substitution of one or more nucleotides between the nucleotide sequences SEQ ID 2 and SEQ ID 3. The substitution may be one or more point mutations, and refer to 1, 2, 3, 4, 5, 6, 7, 8, or all 9 nucleotides positioned between SEQ ID 2 and SEQ ID 3.

Any of the specific deletions, insertions or substitutions may be combined to obtain the pG1-x promoter.

According to a specific aspect, the pG1-x promoter comprises at least two copies of the core regulatory region or the main regulatory region, either the original core regulatory region or the functional variant comprising at least one mutation. Specifically, the pG1-x promoter may comprise at least two, three or four copies of the core regulatory region and/or at least two, three or four copies of the main regulatory region.

According to a another specific aspect, the pG1-x promoter comprises at least two, three, four, five, six, seven or eight copies of the one or more TFBS selected from the group consisting of Rgt1, Cat8-1 and Cat8-2.

Specifically, the pG1-x promoter is an improved functional variant of the pG1 promoter comprising a deletion of one or more nucleotides at the 5'-end of the pG1 sequence, preferably leaving at least 280 nucleotides of the 3' region of the pG1 sequence or a functional variant of the 3' region.

According to a specific embodiment, the pG1-x promoter comprises at least one or at least two T motifs identified by any of SEQ ID 12-29. The T motif specifically consists of any of a) a sequence of contiguous T (thymine) which is herein referred to as $T_n$ or $(T)_n$, preferably wherein n=13-20, preferably wherein the T motif is T14, T15, or T16;
b) a sequence characterized by A (adenine) at the first position, followed by a sequence of contiguous T (thymine), which is herein referred to as ATn or $A(T)_n$, preferably wherein n=13-20, in some cases preferably wherein n=13-22;
c) a sequence characterized by T (thymine) at the first position, and A (adenine) at the second position, followed by a sequence of contiguous T (thymine), which is herein referred to as TATn or $TA(T)_n$, preferably wherein n=13-20;
d) a sequence characterized by a sequence of contiguous T (thymine) and A (adenine) at the last position, which is herein referred to as TnA or $(T)_nA$, preferably wherein n=13-20;
e) a sequence characterized by a sequence of contiguous T (thymine) followed by A (adenine) at the last but one position, and T (thymine) at the last position, which is herein referred to as TnAT or $(T)_nAT$, preferably wherein n=13-20; or
d) a sequence of c) or e) wherein the A (adenine) is substituted by T (thymine), which is herein referred to as TTTn or TnTT or T(A/T)Tn or $T(A/T)(T)_n$, or Tn(A/T)T or $(T)_n(A/T)T$, preferably wherein n=13-20, e.g. resulting in a T motif which consists of a sequence of $(T)_n$ wherein n=15-22.

Any of the T motifs specified under a) to d) above may be combined in one promoter sequence e.g., such that the promoter sequence comprises one T motif which is a $TA(T)_n$ motif wherein n=13-20, and another T motif which is a $(T)_n$ motif, wherein n=13-22.

The T motif optionally comprises an extension, such that it is extended by one or more "A" (e.g., 1, 2, or 3 adenine) and optionally further extended by "T" (e.g., 1, 2, or 3 thymine) at the 3'-end and/or at the 5'-end of the T motif, which extension is herein also referred to as an extended T motif.

Herein the term "T motif" shall always include the T motif which is extended or not, thus, the term specifically includes both, the T motif that does not comprise the extension, or the extended T motif.

Specifically, the T motif comprises or consists of the nucleotide sequence which is any of SEQ ID 12-29. Any one, two, or more of the T motifs may be incorporated into the pG1-x promoter with or without the motif extension.

According to one specific aspect, the T motif extension is a "TA" sequence elongation at its 5'-end, to obtain a "TAT" 5'-end.

According to another specific aspect, the T motif extension is a "TAA" sequence elongation at its 5'-end, to obtain a "TAAT" 5'-end.

According to another specific aspect, the T motif extension is a "AT" sequence elongation at its 3'-end, to obtain a "TAT" 3'-end.

According to another specific aspect, the T motif extension is a "AAT" sequence elongation at its 3'-end, to obtain a "TAAT" 3'-end.

According to a specific aspect, the T motif is located upstream the core regulatory region, and optionally upstream the main regulatory region.

According to another specific aspect, the T motif is located downstream the core regulatory region, and optionally downstream the main regulatory region.

Specifically, the pG1-x promoter comprises a 3'-terminal nucleotide sequence incorporating at least part of a translation initiation site. A translation initiation site is specifically known as Kozak consensus sequence in eukaryotes, and a suitable sequence to support gene expression.

Specifically, the translation initiation site is a) originating from the pG1 promoter and consists of or comprises the nucleotide sequence SEQ ID 6, or a functional variant thereof with at least 90% sequence identity; or
b) originating from any other promoter of *Pichia pastoris*, or a functional variant thereof with at least 90% sequence identity.

Exemplary alternative 3'-terminal promoter regions which can be used instead of the 3'-terminal region of the pG1 promoter, or instead of the nucleotide sequence SEQ ID 6, are e.g., derived from any of the following promoter: pAOX1, pAOX2, pDAS1, pDAS2, pFLD, pGAP, or pTEF2.

According to a specific embodiment, the promoter has a length up to 2000 bp. Specific pG1-x promoter have a length which is shorter than the pG1 promoter, such as with a length of at least 293 bp or 300 bp, or of at least 328 bp, or at least 350 bp or at least 400 bp, or at least 500 bp.

Specifically, the pG1-x promoter may comprise a sequence originating from a fragment of the pG1 promoter. According to a specific aspect, the pG1-x promoter is a variant or derivative of a parent fragment of pG1, which comprises at least the 3'-region of SEQ ID 1 which extends to at least 50%, or 60%, or 70%, or 80%, or at least 90% of the pG1 sequence.

Specifically, the pG1-x nucleotide sequence is derived from the pG1 promoter nucleotide sequence which comprises a deletion of or in the 5' terminal region, e.g. a cut-off of the nucleotide sequence at the 5' end, so to obtain a specific length with a range from the 3' end to a varying 5' end, such as with a length of the nucleotide sequence length of at least 293 bp or 300 bp, or of at least 328 bp, or at least 350 bp, or at least 400 bp, or at least 500 bp up to the length of the pG1 promoter fragment which comprises a deletion of at least 1, or at least 10, or at least 100 bp.

However, the promoter length can as well be increased, such as to obtain a length which is longer than the length of the pG1 promoter, specifically a length of up to 1500 bp, or up to 2000 bp. Specifically, the length may be within any of the ranges: 293 bp-1500 bp, 293 bp-2000 bp, 328 bp-1500 bp, or 328-2000 bp.

According to a specific aspect, the invention provides for an isolated and/or artificial pG1-x promoter, comprising or consisting of the nucleotide sequence selected from the group consisting of any of a) SEQ ID 37-44, preferably any of SEQ ID 45-76;
b) SEQ ID 77-80, preferably any of SEQ ID 81-112;
c) SEQ ID 113-114, preferably any of SEQ ID 115-130;
d) SEQ ID 131-132, preferably any of SEQ ID 133-148;
e) SEQ ID 149-150, preferably any of SEQ ID 151-166;
f) SEQ ID 167-168, preferably any of SEQ ID 169-184;
g) SEQ ID 185-186, preferably any of SEQ ID 187-202;
h) SEQ ID 203-204, preferably any of SEQ ID 205-220;
i) SEQ ID 221-222, preferably any of SEQ ID 223-238;
j) SEQ ID 239-240, preferably any of SEQ ID 241-256; and
k) SEQ ID 32-36 or SEQ ID 257-259;

or l) a functional variant of any of a)-k) above, preferably, wherein the pG1-x promoter is characterized by the same or an increased promoter strength and induction ratio as compared to the pG1 promoter, wherein the promoter strength is at least 1.1-fold increased in the induced state as compared to the pG1 promoter, and/or the induction ratio is at least 1.1-fold increased as compared to the pG1 promoter.

A functional variant of such pG1-x promoter of a)-k) above is preferably characterized by any of the specific features as described for the functional variant of the pG1 promoter as described herein.

Specifically, the functional variant of any of the pG1-x promoter of a)-k) above, preferably a functional variant of any of SEQ ID 45-76, is characterized by one or more of the following features a) the sequence is a functional variant of the promoter sequence of any of the pG1-x promoter of a)-k) above comprising a deletion of one or more nucleotides at the 5'-end of the promoter sequence, preferably leaving at least 280 nucleotides of the 3' region of the promoter sequence or a functional variant of the 3' region, preferably comprising a 5' deletion of the promoter sequence of 50, 100, 150, 200, 250, or 300 nucleotides up to but not including the main regulatory region together with any sequence downstream or 3' of said main regulatory region, in case of more than 1 main regulatory regions the 5'-end deletion of the promoter sequence is up to but not including the first or most 5' main regulatory region;
b) the sequence comprises one or more TFBS, preferably wherein the TFBS is for any of the transcription factors selected from the group consisting of Rgt1, Cat8-1, and Cat8-2;
c) the core regulatory region comprises the nucleotide sequence SEQ ID 4, or a functional variant thereof comprising one or more TFBS, preferably a functional variant with at least 80% sequence identity,
d) the core regulatory region is incorporated into a main regulatory region represented by SEQ ID 5, or a functional variant thereof comprising the TFBS, preferably a functional variant with at least 80% sequence identity;
e) the core regulatory region comprises a deletion of one or more nucleotides between the nucleotide sequences SEQ ID 2 and SEQ ID 3;
f) the sequence comprises at least two copies of the core regulatory region or of the main regulatory region;
g) the sequence further comprises at least one or at least two T motifs identified by any of SEQ ID 12-29; preferably wherein the T motif is located either upstream or downstream the core regulatory region, and optionally upstream or downstream the main regulatory region;
h) the sequence comprises a 3'-terminal nucleotide sequence comprising at least part of a translation initiation site;
i) the sequence is elongated to a length up to 2000 bp.

The invention further provides for the pG1-x promoter in the isolated form.

Specifically, the isolated pG1-x promoter nucleic acid is provided which comprises the pG1-x promoter as described herein, or a nucleic acid comprising the complementary sequence. Specifically, the complementary sequence is a sequence which hybridizes under stringent conditions to the pG1-x promoter.

Specifically, the nucleic acid is operably linked to a nucleotide sequence encoding a protein of interest (POI), which nucleic acid is not natively associated with the nucleotide sequence encoding the POI. The POI is specifically a heterologous polypeptide or protein.

Specifically, the nucleotide sequence further comprises a nucleotide sequence encoding a signal peptide enabling the secretion of the POI, preferably wherein nucleotide sequence encoding the signal peptide is located adjacent to the 5'-end of the nucleotide sequence encoding the POI.

Specifically, the signal peptide is selected from the group consisting of signal sequences from *S. cerevisiae* alpha-mating factor prepro peptide, the signal peptides from the *P. pastoris* acid phosphatase gene (PHO1) and the extracellular protein X (EPX1) (Heiss, S., V. Puxbaum, C. Gruber, F. Altmann, D. Mattanovich & B. Gasser, (2015) Multistep processing of the secretion leader of the extracellular protein Epx1 in *Pichia pastoris* and implications on protein localization. Microbiology).

Specifically, the POI is a eukaryotic protein, preferably a mammalian protein.

In specific cases, a POI is a multimeric protein, specifically a dimer or tetramer.

According to specific embodiments, the POI is a heterologous protein, preferably selected from therapeutic proteins, including antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI, specifically including a cell metabolite of the recombinant cell culture that expresses a gene of interest under the transcriptional control of a promoter of the invention.

A specific POI is an antigen-binding molecule such as an antibody, or a fragment thereof. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH or VHH or V-NAR. Further antigen-binding molecules may be selected from (alternative) scaffold proteins such as e.g. engineered Kunitz domains, Adnectins, Affibodies, Anticalins, and DARPins. The term "scaffold" describes a multifaceted group of compact and stably folded proteins—differing in size, structure, and origin—that serve as a starting point for the generation of antigen-binding molecules. Inspired by the structure-function relationships of antibodies (immunoglobulins), such an alternative protein scaffold provides a robust, conserved structural framework that supports an interaction site which can be reshaped for the tight and specific recognition of a given (bio)molecular target.

According to a specific embodiment, a fermentation product is manufactured using the POI, a metabolite or a derivative thereof.

The invention further provides for an expression construct comprising the nucleic acid as described herein, preferably an autonomously replicating vector or plasmid, or a vector or plasmid which integrates into the chromosomal DNA of a host cell.

Specifically, the expression construct comprises the pG1-x promoter, operably linked to a nucleotide sequence encoding a POI under the transcriptional control of said promoter, which promoter is not natively associated with the coding sequence of the POI. Specifically, the expression construct is a vector.

The invention further provides for a recombinant host cell which comprises the expression construct as described herein, preferably a eukaryotic cell, such as a mammalian, insect, yeast, filamentous fungi or plant cells, preferably a yeast or filamentous fungal cell, more preferably a yeast cell of the *Saccharomyces* or *Pichia* genus.

Specifically, the yeast is selected from the group consisting of *Pichia, Candida, Torulopsis, Arxula, Hansenula, Yarrowia, Kluyveromyces, Saccharomyces, Komagataella*, preferably a methylotrophic yeast.

A specifically preferred yeast is *Pichia pastoris, Komagataella pastoris, K. phaffii*, or *K. pseudopastoris*, such as e.g., any of the *P. pastoris* strains CBS 704, CBS 2612, CBS 7435, CBS 9173-9189, DSMZ 70877, X-33, GS115, KM71 and SMD1168.

According to a specific aspect, the recombinant host cell comprises multiple copies of the nucleic acid sequence, and/or multiple copies of the expression construct. For example, the recombinant cell comprises 2, 3, 4, or more copies (gene copy number, GCN).

The invention further provides for a stable culture of the recombinant host cell as described herein.

According to a specific embodiment, a cell is employed, which has a higher specific growth rate in the presence of a surplus of carbon source relative to conditions of limited carbon source.

The invention further provides for a method of producing a POI by culturing a recombinant host cell line as described herein, comprising the steps of a) cultivating the cell line under conditions to express said POI, and
b) recovering the POI.

Specifically, said method is carried out under the transcriptional control of the carbon source regulatable pG1-x promoter, wherein said pG1-x promoter has at least one of the promoter strength and regulatable features improved as compared to the pG1 promoter.

According to a specific embodiment, the cell line is cultivated under batch, fed-batch or continuous cultivation conditions, and/or in media containing limited carbon substrate.

Specifically, the cultivation is performed in a bioreactor starting with a batch phase as the first step, followed by a fed-batch phase or a continuous cultivation phase as the second step.

Specifically, the host cells are grown in a carbon source rich medium during the phase of high growth rate (e.g. at least 50%, or at least 60%, at least 70%, at least 80%, at least 90%, at least 95%, at least 98%, at least 99%, or up to the maximum growth rate) and producing the POI during a phase of low growth rate (e.g. less than 90%, preferably less than 80%, less than 70%, less than 60%, less than 50%, or less than 40%, less than 30%, less than 20%, less than 10%, less than 5%, less than 3%, less than 2%, less than 1%, less than 0.5%, less than 0.4%, less than 0.3%, or less than 0.2% of the maximum growth rate) e.g. while limiting the carbon source, preferably by feeding a defined minimal medium.

Specifically, the POI is expressed under growth-limiting conditions, e.g. by cultivating the cell line at a growth rate of less than the maximal growth rate, typically less than 90%, preferably less than 80%, less than 70%, less than 60%, less than 50%, less than 40%, less than 30%, less than 20%, less than 10%, less than 5%, less than 3%, less than 2%, less than 1%, less than 0.5%, less than 0.4%, less than 0.3%, or less than 0.2% of the maximum growth rate of the cells. Typically the maximum growth rate is individually determined for a specific host cell.

Specifically, the cultivation method comprises a) a first step using a basal carbon source repressing the pG1-x promoter, followed by
b) a second step using no or a limited amount of a supplemental carbon source de-repressing or inducing the pG1-x promoter to induce production of the POI.

Specifically, the batch phase is performed until the basal carbon source that is initially added to the cell culture is consumed by the cell line. The dissolved oxygen (DO) spike method can be used to determine basal carbon source consumption during batch phase.

According to a specific embodiment, the batch phase is characterized by a continuous decrease in oxygen partial pressure (pO2) signal and wherein the end of the batch phase is characterized by an increase of pO2. Typically, while consuming the basal carbon source during the batch phase and without adding further carbon sources as typical for batch phases, the oxygen partial pressure (pO2) signal will continuously decrease until for example below 65% such as for example 30%. Upon consumption of the basal carbon source, the pO2 may increase to e.g. above 30% such as for example above 65%, or more indicating the appropriate time point to switch to the fed-batch system using feed medium to add further carbon source under carbon source limited conditions.

Specifically, the pO2 is decreased to less than 65% or less saturation during batch phase followed by an increase of above 65% or more saturation at the end of the batch. Specifically, the batch phase is performed until an increase of the oxygen partial pressure (pO2) signal above 65% saturation, specifically above any of 70%, 75%, 80%, or 85%.

Specifically, the batch phase is performed for around 20 to 36 h.

The term "around" with respect to cultivation time shall mean+/−5% or +/−10%.

For example, the specific batch performance time of around 20 to 36 h means a duration of 18 to 39.6 h, specifically 19 to 37.8 h.

According to a specific embodiment, the batch phase is performed using 40 to 50 g/L glycerol, specifically 45 g/L glycerol as a basal carbon source in batch media, and cultivation is performed at 25° C. for around 27 to 30 h, or at 30° C. for around 23 to 36 h, or at any temperature between 25° C. and 30° C. during a cultivation time of 23 to 36 h. Lowering the glycerol concentration in the batch medium would decrease the length of the batch phase, while increasing the glycerol in the batch medium would even prolong the batch phase. As an alternative to glycerol, glucose can be used, e.g. in about the same amounts.

In a typical system of cell culture and POI expression, wherein a batch phase is followed by a fed-batch phase, specifically, the cultivation in the fed-batch phase is performed for any of, around 15 to 80 h, around 15 to 70 h, around 15 to 60 h, around 15 to 50 h, around 15 to 45 h, around 15 to 40 h, around 15 to 35 h, around 15 to 30 h, around 15 to 35 h, around 15 to 25 h, or around 15 to 20 h; preferably around 20 to 40 h. Specifically, the cultivation in the fed-batch phase is performed for any of around 80 h, around 70 h, around 60 h, around 55 h, around 50 h, around 45 h, around 40 h, around 35 h, around 33 h, around 30 h, around 25 h, around 20 h, or around 15 h.

Any such fed-batch cultivation of less than 120 h or less than 100 h or up to 80 h, which results in a successful POI production thereby obtaining a high yield is herein referred to as "speed fermentation". Specifically, the volume specific product formation rate (rP) is the amount of product (mg) formed per Unit Volume (L) and Unit time (h) (mg $(L\ h)^{-1}$). Volume specific product formation rate is also called space time yield (STY) or volumetric productivity.

Specifically, the fed-batch cultivation is performed such that a space time yield of around 30 mg $(L\ h)^{-1}$ (meaning 30 mg $(L\ h)^{-1}$+/−5% or +/−10%). Specifically a space time yield of around 30 mg $(L\ h)^{-1}$ is achieved within around 30 h fed batch, specifically at least any of 27, 28, 29, 30, 31, 32, or 33 mg $(L\ h)^{-1}$ within less than any of 33 h, 32 h, 31 h, 30 h, 29 h, 28 h, 27 h, 26 h, or 25 h fed batch time can be achieved.

Specifically, the batch phase is performed as a first step a), and the fed-batch phase is performed as a second step b).

Specifically, the second step b) employs a feed medium in a fed-batch phase that provides for the supplemental carbon source in a growth limiting amount to keep the specific growth rate within the range of 0.04 $h^{-1}$ to 0.2 $h^{-1}$, preferably less than any of 0.2, 0.15, 0.1 $h^{-1}$ or 0.15 $h^{-1}$.

Specifically, the method of batch and fed-batch cultivation employs a yeast host cell, e.g. a yeast of any of the *Saccharomyces* genus or *Pichia* genus or *Komagataella* genus, or yeast from a genus other than *Pichia*, such as from *K. lactis, Z. rouxii, P. stipitis, H. polymorpha*, or *Y. lipolytica*, preferably *Pichia pastoris* or *Komagataella pastoris*. Specifically, the yeast is used in a speed fermentation.

Specifically, the method of batch and fed-batch cultivation employs the pG1-x promoter which is any of SEQ ID 37-44, preferably any of SEQ ID 45-76. In particular, the pG1-x promoter is characterized by SEQ ID 39, preferably SEQ ID 49.

Specifically, the POI is produced at a transcription rate of at least 15% as compared to the native pGAP promoter of the cell.

According to a specific embodiment, the basal carbon source is different from the supplemental carbon source, e.g. quantitatively and/or qualitatively different. The quantitative difference may provide for the different conditions to repress or de-repress the promoter activity.

According to a further specific embodiment the basal and the supplemental carbon sources comprise the same type of molecules or carbohydrates, preferably in different concentrations. According to a further specific embodiment, the carbon source is a mixture of two or more different carbon sources.

Any type of organic carbon suitable used for eukaryotic cell culture may be used. According to a specific embodiment, the carbon source is a hexose, such as glucose, fructose, galactose or mannose, a disaccharide, such as saccharose, an alcohol, such as glycerol or ethanol, or a mixture thereof.

According to a specifically preferred embodiment, the basal carbon source is selected from the group consisting of glucose, glycerol, ethanol, or mixtures thereof, and complex nutrient material. According to a preferred embodiment, the basal carbon source is glycerol.

According to a further specific embodiment, the supplemental carbon source is a hexose such as glucose, fructose, galactose and mannose, a disaccharide, such as saccharose, an alcohol, such as glycerol or ethanol, or a mixture thereof. According to a preferred embodiment, the supplemental carbon source is glucose.

Specifically, a) the basal carbon source is selected from the group consisting of glucose, glycerol, ethanol, a mixture thereof, and complex nutrient material; and b) the supplemental carbon source is a hexose such as glucose, fructose, galactose or mannose, a disaccharide, such as saccharose, an alcohol, such as glycerol or ethanol, or a mixture of any of the foregoing.

Said cultivating steps specifically comprise cultivating the cell line in the presence of said carbon sources, thus, in a culture medium comprising said carbon sources, or in step b) also in the absence of a supplemental carbon source.

The de-repressing (or inducing) conditions suitably may be achieved by specific means. The second step b) optionally employs a feed medium that provides for no or the supplemental carbon source in a limited amount.

Specifically, the feed medium is chemically defined and methanol-free.

The feed medium may be added to the culture medium in the liquid form or else in an alternative form, such as a solid, e.g. as a tablet or other sustained release means, or a gas, e.g. carbon dioxide. Yet, according to a preferred embodiment the limited amount of a supplemental carbon source added to the cell culture medium, may even be zero. Preferably, under conditions of a limited carbon substrate, the concentration of a supplemental carbon source in the culture medium is 0-1 g/L, preferably less than 0.6 g/L, more preferred less than 0.3 g/L, more preferred less than 0.1 g/L, preferably 1-50 mg/L, more preferred 1-10 mg/L, specifically preferred 1 mg/L or even below, such as below the detection limit as measured with a suitable standard assay, e.g. determined as a residual concentration in the culture medium upon consumption by the growing cell culture.

In a preferred method, the limited amount of the supplemental source provides for a residual amount in the cell culture which is below the detection limit as determined in the fermentation broth at the end of a production phase or in the output of a fermentation process, preferably upon harvesting the fermentation product.

Specifically, the second step b) employs a feed medium that provides for the supplemental carbon source in a growth limiting amount to keep the specific growth rate within the range of 0.001 $h^{-1}$ to 0.2 $h^{-1}$, preferably 0.005 $h^{-1}$ to 0.15 $h^{-1}$.

FIGURES

FIG. 1: pG1 sequence analysis for carbon source-related TFBS using Matinspector. pG1 (also referred to as $P_{GTH1}$), was initially amplified and cloned from position −965 to −1 (length of 965 bp, sequence is provided in FIG. 6 (SEQ ID 1, in particular SEQ ID 9 has been used). Numbers indicate TFBS which were selected for deletion (listed in Table 2). Associated matrix families are F$CSRE (carbon source response elements, striped boxes), F$ADR (Yeast metabolic regulator, dotted boxes), F$MGCM (Monomeric Gal4-class motifs, filled boxes) and F$YMIG (Yeast GC-Box Proteins, white boxes). Other TFBS might be affected by the deletions (matrix match detail information is given in Table 1). The black dashed box indicates the main regulatory region of pG1 which was identified by the screening of shortened pG1 variants. The asterisk indicates the position of the prominent TAT (position −390 to −374) motif which was also selected for deletion and for mutation. Alternative 5'-starts of the shortened pG1 promoter variants are labeled with arrows and the length of the corresponding variant.

Figure 2:
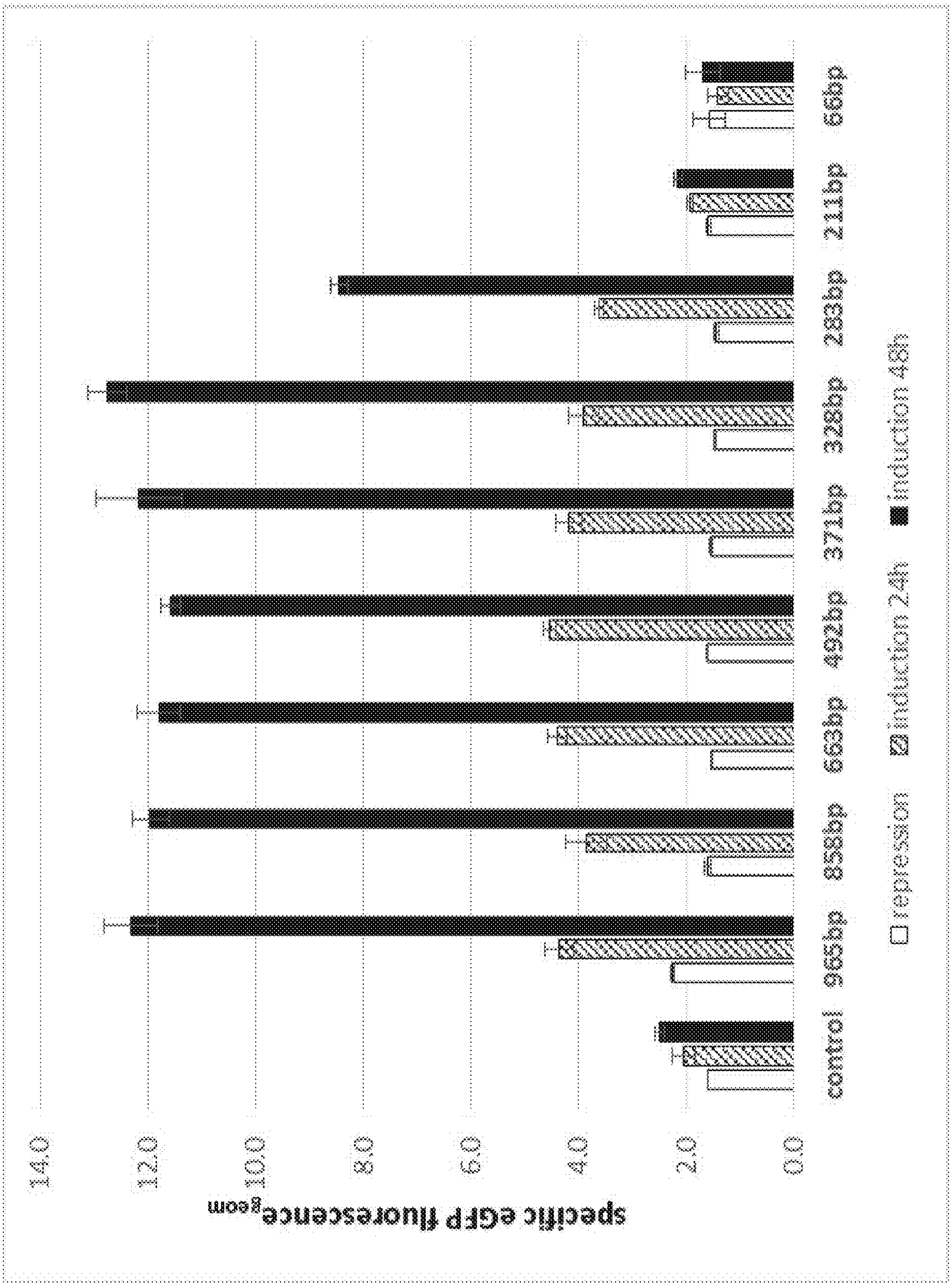

FIG. 2: Screening data of the shortened pG1 promoter variants The geometric mean of the population's specific eGFP fluorescence (fluorescence related to cell volume) is shown for clones expressing eGFP under control of pG1 (clone #8, verified GCN of 1) or a shortened pG1 variant (each 2 clones cultivated in triplicates, selected in prescreenings) in repressing and inducing growth conditions. Non-expressing wild type *P. pastoris* cells were used as negative control. Samples were taken during the repressing pre-culture and after 24 and 48 hours induction with feed beads.

Figure 3:
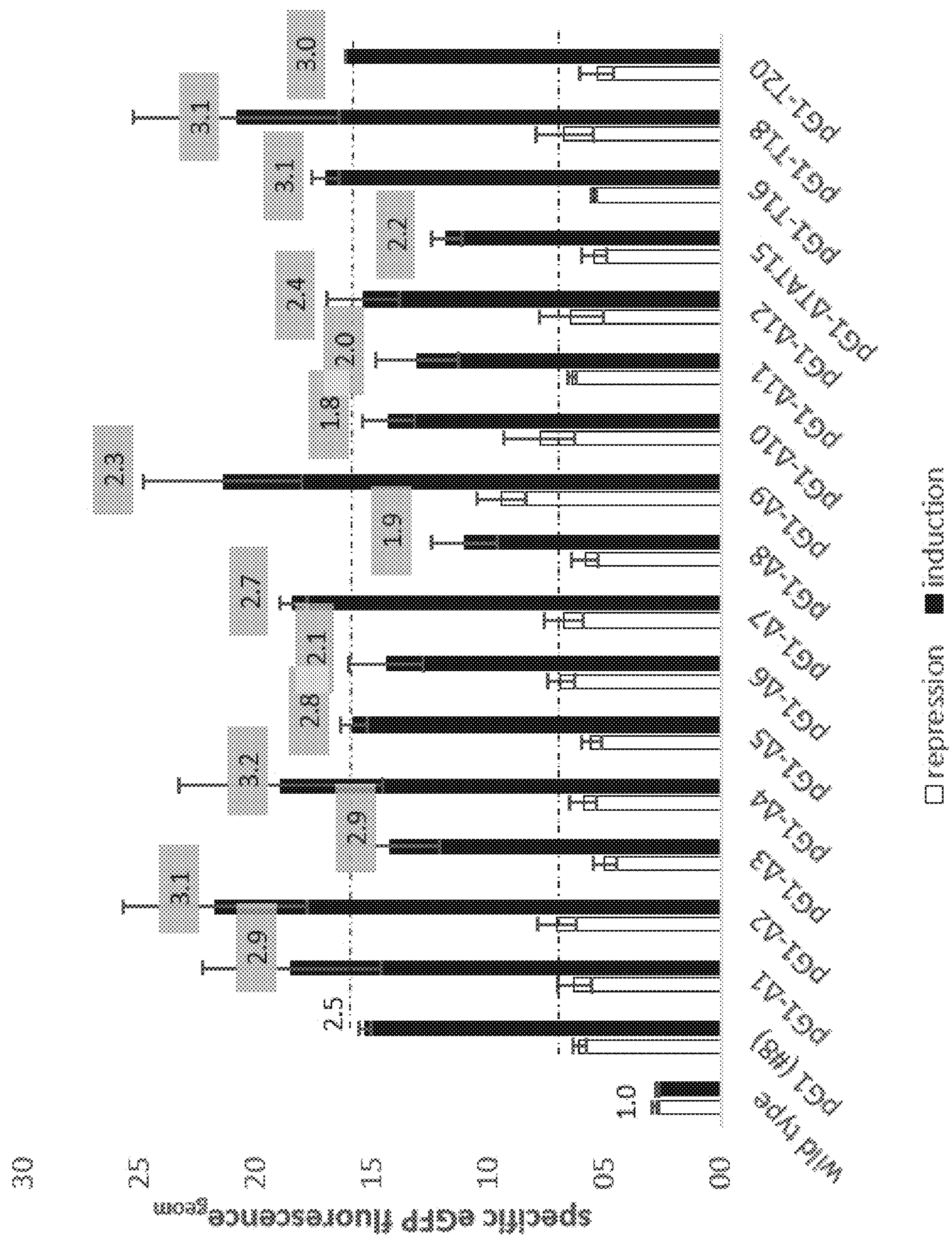

FIG. 3: Screening data of the TFBS deletion and -TAT mutation variants

The geometric mean of the population's specific eGFP fluorescence (fluorescence related to cell volume) is shown for clones expressing eGFP under the control of pG1 (clone #8, verified GCN of 1) or a pG1 variant (up to 9 clones were pool cultivated in 3 wells) in repressing and inducing growth conditions. Wild type *P. pastoris* cells were used as negative control.

Figure 4:
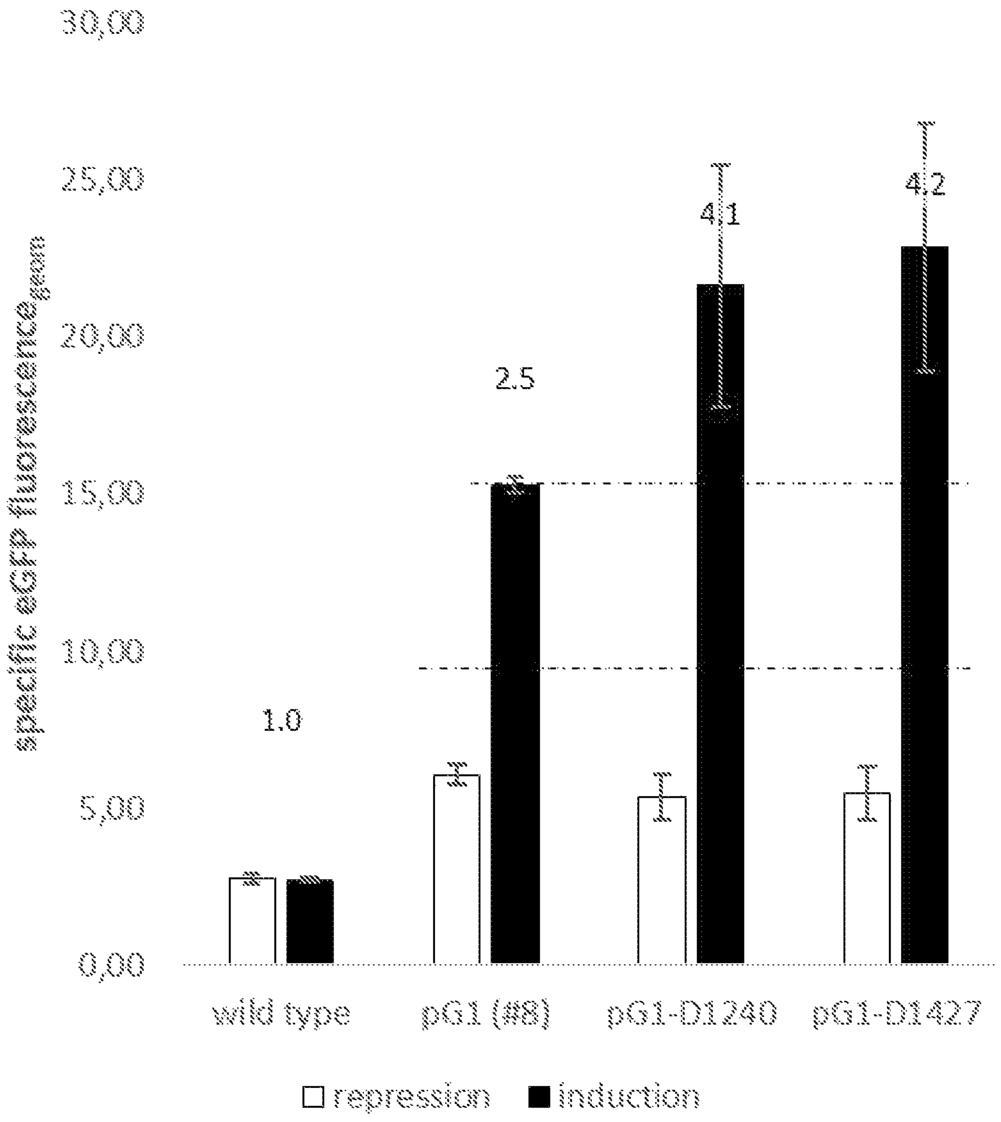

FIG. 4: Screening data of the pG1 duplication variants

The geometric mean of the population's specific eGFP fluorescence (fluorescence related to cell volume) is shown for clones expressing eGFP under the control of pG1 (clone #8, verified GCN of 1) or a pG1 variant (up to 9 clones were pool cultivated in 3 wells, selected in pre-screenings) in repressing and inducing growth conditions. Wild type *P. pastoris* cells were used as negative control.

Figure 5:
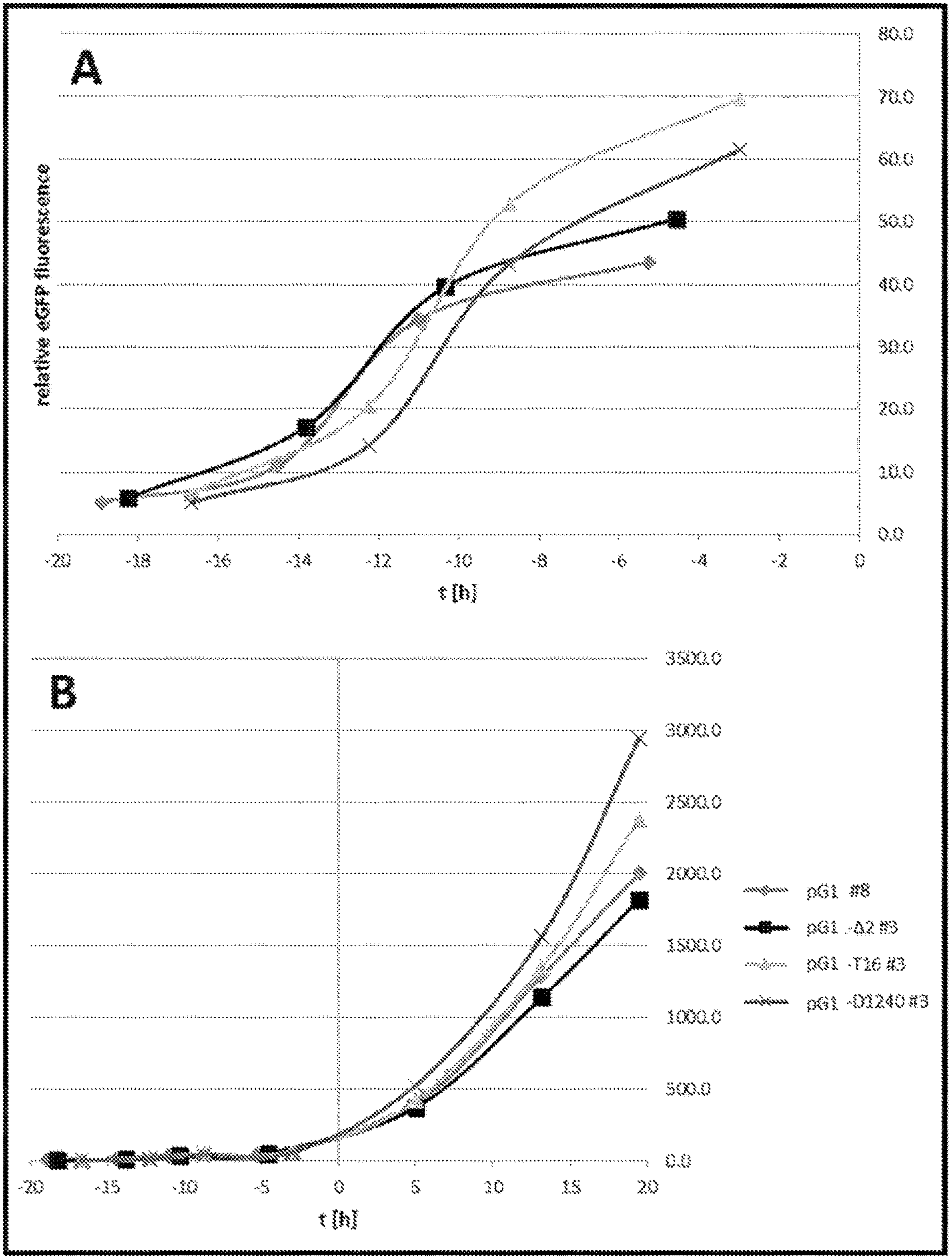

FIG. 5: Fed batch cultivation of pG1 and pG1 variants expressing eGFP Relative eGFP fluorescence was measured from bioreactor samples (diluted to similar biomass densities) using a plate reader and is shown over the feed time (batch end set to 0) in batch (A) and fed batch cultivation (B). A clone expressing eGFP under control of pG1 (#8) was compared to clones expressing under control of a pG1 deletion variant (pG1-Δ2, SEQ ID 211), a TAT mutation (pG1-T16, SEQ ID 257, and a duplication (pG1-D1240) variant (SEQ ID 49).

FIG. 6: pG1 and pG1-x promoter sequences

FIG. 6*a*: Reference sequences

FIG. 6*b*: Sequences of pG1-x promoter

Individual Sequence Elements:

Position 8 (SEQ ID 2):

*ATAAATGGA*

(e.g. position −293 to −285 in SEQ ID 8):

Position 9 (SEQ ID 3):

*CATATTTTTCCGGTT*

(e.g. position −275 to −261 in SEQ ID 8)

Core region: (SEQ ID 4):

*ATAAATGGACGCCTGCTCCATATTTTTCCGGTT*

(e.g. position −293 to −261 in SEQ ID 8)

Main regulatory region: (SEQ ID 5):

CCGGATAAGAGAATTTTGTTTGATTATCCGTTCGG*ATAAATGGACG*

*CCTGCTCCATATTTTTCCGGTT*ATTACCCCACCTGGAAGTGCCCAG

AATTTTCCGGGGATTACGGATAATAC (e.g. position −328 to −211 in SEQ ID 8):

3'-terminal nucleotide sequence (SEQ ID 6):

TTCCACCCTT

Indications in Sequences:

Main regulatory region: bold

Core regulatory region: bold, italic and underlined, SEQ ID 2 and 3 double underlined T motif: italic and underlined, may be optionally extended (at the 5'-terminal end of the T motif) by a preceding TA sequence, or (at the 3'-terminal end of the T motif) by a succeeding AT sequence 3'-terminal region: underlined with dotted line Region less relevant for promoter activity in the reference pG1 ($P_{GTH1}$) sequences: underlined with a dash-dot line: one or more nucleotides up to all nucleotides within the region ranging from the 5'-terminal end to −328 (region underlined in FIG. 6*a* with a dash-dot line) may be substituted, or deleted, or further nucleotides may be inserted within such region, however, preferred embodiments still comprise at least one T motif which is (T)n (n=13-20) with or without preceding A or TA nucleotides; or with or without succeeding A or AT nucleotides. Such a less relevant region which can be partially or fully deleted is the region ranging from the 5'-terminal end to the first or 5' main regulatory region (bold) in any one of SEQ ID 37 to SEQ ID 202; preferably, up to 50, 100, 150, 200, 250, 300, 320, or 325 nucleotides of the 5'-terminal end of any one of SEQ ID 37 to SEQ ID 202 can be deleted.

Deletion: del (underlined)

(T)$_n$ (n = 13-20) motifs: may be optionally extended at its 5' end, e.g. by "A" or "TA"; or at its 3' end, e.g. by "A" or "AT"

(T)$_{13}$: SEQ ID 12: TTTTTTTTTTTTT (T)$_{14}$: SEQ ID 13: TTTTTTTTTTTTTT (T)$_{15}$: SEQ ID 14: TTTTTTTTTTTTTTT (T)$_{16}$: SEQ ID 15: TTTTTTTTTTTTTTTT (T)$_{17}$: SEQ ID 16: TTTTTTTTTTTTTTTTT (T)$_{18}$: SEQ ID 17: TTTTTTTTTTTTTTTTTT (T)$_{19}$: SEQ ID 18: TTTTTTTTTTTTTTTTTTT (T)$_{20}$: SEQ ID 19: TTTTTTTTTTTTTTTTTTTT

TA(T)$_n$ (n = 13-20) motifs, may be optionally mutated to substitute the "A" at position 2 for a "T" (A/T)

TA(T)$_{13}$: SEQ ID 20: TATTTTTTTTTTTTT

TA(T)$_{13}$ (substituted A/T), SEQ ID 14 (see (T)$_{15}$): TTTTTTTTTTTTTTT

TA(T)$_{14}$: SEQ ID 21: TATTTTTTTTTTTTTT

TA(T)$_{14}$ (substituted A/T), SEQ ID 15 (see (T)$_{16}$): TTTTTTTTTTTTTTTT

TA(T)$_{15}$: SEQ ID 22: TATTTTTTTTTTTTTTT

TA(T)$_{15}$ (substituted A/T), SEQ ID 16 (see (T)$_{17}$): TTTTTTTTTTTTTTTTT

TA(T)$_{16}$: SEQ ID 23: TATTTTTTTTTTTTTTTT

TA(T)$_{16}$ (substituted A/T), SEQ ID 17 (see (T)$_{18}$): TTTTTTTTTTTTTTTTTT

TA(T)$_{17}$: SEQ ID 24: TATTTTTTTTTTTTTTTTT

TA(T)$_{17}$ (substituted A/T), SEQ ID 18 (see (T)$_{19}$): TTTTTTTTTTTTTTTTTTT

TA(T)$_{18}$: SEQ ID 25: TATTTTTTTTTTTTTTTTTT

TA(T)$_{18}$ (substituted A/T), SEQ ID 19 (see (T)$_{20}$): TTTTTTTTTTTTTTTTTTTT

TA(T)$_{19}$: SEQ ID 26: TATTTTTTTTTTTTTTTTTTT

TA(T)$_{19}$ (substituted A/T), SEQ ID 28 (i.e. (T)$_{21}$): TTTTTTTTTTTTTTTTTTTTT

TA(T)$_{20}$: SEQ ID 27: TATTTTTTTTTTTTTTTTTTTT

TA(T)$_{20}$ (substituted A/T), SEQ ID 29 (i.e. (T)$_{22}$): TTTTTTTTTTTTTTTTTTTTTT

FIG. 7:

Native pGAP promoter sequence of *P. pastoris* (GS115) (SEQ ID 260)

| # | Name | PAS* | PIPA* | GS115 description |
|---|---|---|---|---|
| pGAP | TDH3 | PAS_chr2-1_0437 | PIPA02510 | Glyceraldehyde-3-phosphate dehydrogenase |

*PAS: ORF name in *P. pastoris* GS115; PIPA: ORF name in *P. pastoris* type strain DSMZ70382

FIG. 7 continued: Transcription factor sequences

Rgt1 (PAS_chr1-3_0233) (SEQ ID 261)

Cat8-2(PAS_chr4_0540) (SEQ ID 262)

Cat8-1(PAS_chr2-1_0757) (SEQ ID 263)

FIG. 8: Prior art sequences pG1 (SEQ ID 264), pG1a (SEQ ID 265), pG1b (SEQ ID 266), pG1c (SEQ ID 267), pG1d (SEQ ID 268), pG1e (SEQ ID 269), or pG1f (SEQ ID 270), as described in WO2013050551 A1

FIG. 9: Fed batch cultivation of the selected pG1-3 embodiment of SEQ ID 39 (pG1-D1240 (SEQ ID 49)) expressing an alternative scaffold protein as a model protein using (A) the standard fed batch protocol, (B) the space-time yield optimized fed batch protocol ("speed fermentation") adapted from Maurer et al. (Microbial Cell Factories, 2006, 5:37)

DETAILED DESCRIPTION OF THE INVENTION

Specific terms as used throughout the specification have the following meaning.

The term "carbon source" also referred as "carbon substrate" as used herein shall mean a fermentable carbon substrate, typically a source carbohydrate, suitable as an energy source for microorganisms, such as those capable of being metabolized by host organisms or production cell lines, in particular sources selected from the group consisting of monosaccharides, oligosaccharides, polysaccharides, alcohols including glycerol, in the purified form, in minimal media or provided in raw materials, such as a complex nutrient material. The carbon source may be used according to the invention as a single carbon source or as a mixture of different carbon sources.

A "basal carbon source" such as used according to the invention typically is a carbon source suitable for cell growth, such as a nutrient for eukaryotic cells. The basal carbon source may be provided in a medium, such as a basal medium or complex medium, but also in a chemically defined medium containing a purified carbon source. The basal carbon source typically is provided in an amount to provide for cell growth, in particular during the growth phase in a cultivation process, for example to obtain cell densities of at least 5 g/L cell dry mass, preferably at least 10 g/L cell dry mass, or at least 15 g/L cell dry mass, e.g. exhibiting viabilities of more than 90% during standard sub-culture steps, preferably more than 95%.

According to the invention the basal carbon source is typically used in an excess or surplus amount, which is understood as an excess providing energy to increase the biomass, e.g. during the cultivation of a cell line with a high specific growth rate, such as during the growth phase of a cell line in a batch or fed-batch cultivation process. This surplus amount is particularly in excess of the limited amount of a supplemental carbon source (as used under growth-limited conditions) to achieve a residual concentration in the fermentation broth that is measurable and typically at least 10 fold higher, preferably at least 50 fold or at least 100 fold higher than during feeding the limited amount of the supplemental carbon source.

A "supplemental carbon source" such as used according to the invention typically is a supplemental substrate facilitating the production of fermentation products by production cell lines, in particular in the production phase of a cultivation process. The production phase specifically follows a growth phase, e.g. in batch, fed-batch and continuous cultivation process. The supplemental carbon source specifically may be contained in the feed of a fed-batch process. The supplemental carbon source is typically employed in a cell culture under carbon substrate limited conditions, i.e. using the carbon source in a limited amount.

A "limited amount" of a carbon source or a "limited carbon source" is herein understood to specifically refer to the type and amount of a carbon substrate facilitating the production of fermentation products by production cell lines, in particular in a cultivation process with controlled growth rates of less than the maximum growth rate. The production phase specifically follows a growth phase, e.g. in batch, fed-batch and continuous cultivation process. Cell culture processes may employ batch culture, continuous culture, and fed-batch culture. Batch culture is a culture process by which a small amount of a seed culture solution is added to a medium and cells are grown without adding an additional medium or discharging a culture solution during culture. Continuous culture is a culture process by which a medium is continuously added and discharged during culture. The continuous culture also includes perfusion culture. Fed-batch culture, which is an intermediate between the batch culture and the continuous culture and also referred to as semi-batch culture, is a culture process by which a medium is continuously or sequentially added during culture but, unlike the continuous culture, a culture solution is not continuously discharged.

Specifically preferred is a fed-batch process which is based on feeding of a growth limiting nutrient substrate to a culture. The fed-batch strategy, including single fed-batch or repeated fed-batch fermentation, is typically used in bio-industrial processes to reach a high cell density in the bioreactor. The controlled addition of the carbon substrate directly affects the growth rate of the culture and helps to avoid overflow metabolism or the formation of unwanted metabolic byproducts. Under carbon source limited conditions, the carbon source specifically may be contained in the feed of a fed-batch process. Thereby, the carbon substrate is provided in a limited amount.

Also in chemostat or continuous culture as described herein, the growth rate can be tightly controlled.

The limited amount of a carbon source is herein particularly understood as the amount of a carbon source necessary to keep a production cell line under growth-limited conditions, e.g. in a production phase or production mode. Such a limited amount may be employed in a fed-batch process, where the carbon source is contained in a feed medium and supplied to the culture at low feed rates for sustained energy delivery, e.g. to produce a POI, while keeping the biomass at low specific growth rates. A feed medium is typically added to a fermentation broth during the production phase of a cell culture.

The limited amount of a carbon source may, for example, be determined by the residual amount of the carbon source in the cell culture broth, which is below a predetermined threshold or even below the detection limit as measured in a standard (carbohydrate) assay. The residual amount typically would be determined in the fermentation broth upon harvesting a fermentation product.

The limited amount of a carbon source may as well be determined by defining the average feed rate of the carbon source to the fermenter, e.g. as determined by the amount added over the full cultivation process, e.g. the fed-batch phase, per cultivation time, to determine a calculated average amount per time. This average feed rate is kept low to ensure complete usage of the supplemental carbon source by the cell culture, e.g. between 0.6 g $L^{-1}$ $h^{-1}$ (g carbon source per L initial fermentation volume and h time) and 25 g $L^{-1}$ $h^{-1}$, preferably between 1.6 g $L^{-1}$ $h^{-1}$ and 20 g $L^{-1}$ $h^{-1}$.

The limited amount of a carbon source may also be determined by measuring the specific growth rate, which specific growth rate is kept low, e.g. lower than the maximum specific growth rate, during the production phase, e.g. within a predetermined range, such as in the range of 0.001 $h^{-1}$ to 0.20 $h^{-1}$, or 0.005 $h^{-1}$ to 0.20 $h^{-1}$, preferably between 0.01 $h^{-1}$ and 0.15 $h^{-1}$.

Specifically, a feed medium is used which is chemically defined and methanol-free.

The term "chemically defined" with respect to cell culture medium, such as a minimal medium or feed medium in a fed-batch process, shall mean a cultivation medium suitable for the in vitro cell culture of a production cell line, in which all of the chemical components and (poly)peptides are known. Typically, a chemically defined medium is entirely free of animal-derived components and represents a pure and consistent cell culture environment.

The term "cell line" as used herein refers to an established clone of a particular cell type that has acquired the ability to proliferate over a prolonged period of time. The term "host cell line" refers to a cell line as used for expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process, such as a POI. The term "eukaryotic host" or "eukaryotic cell line" shall mean any eukaryotic cell or organism, which may be cultivated to produce a POI or a host cell metabolite. It is well understood that the term does not include human beings.

The term "cell culture" or "cultivation", also termed "fermentation", with respect to a host cell line is meant the maintenance of cells in an artificial, e.g., an in vitro environment, under conditions favoring growth, differentiation or continued viability, in an active or quiescent state, of the cells, specifically in a controlled bioreactor according to methods known in the industry.

When cultivating a cell culture using the culture media of the present invention, the cell culture is brought into contact with the media in a culture vessel or with substrate under conditions suitable to support cultivation of the cell culture. In certain embodiments, a culture medium as described herein is used to culture cells according to standard cell culture techniques that are well-known in the art. In various aspects of the invention, a culture medium is provided that can be used for the growth of eukaryotic cells, specifically yeast or filamentous fungi.

Cell culture media provide the nutrients necessary to maintain and grow cells in a controlled, artificial and in vitro environment. Characteristics and compositions of the cell culture media vary depending on the particular cellular requirements. Important parameters include osmolality, pH, and nutrient formulations. Feeding of nutrients may be done in a continuous or discontinuous mode according to methods known in the art. The culture media used according to the invention are particularly useful for producing recombinant proteins.

Whereas a batch process is a cultivation mode in which all the nutrients necessary for cultivation of the cells are contained in the initial culture medium, without additional supply of further nutrients during fermentation, in a fed-batch process, after a batch phase, a feeding phase takes place in which one or more nutrients are supplied to the culture by feeding. The purpose of nutrient feeding is to increase the amount of biomass in order to increase the amount of recombinant protein as well. Although in most cultivation processes the mode of feeding is critical and important, the present invention employing the promoter of the invention is not restricted with regard to a certain mode of cultivation.

In certain embodiments, the method of the invention is a fed-batch process. Specifically, a host cell transformed with a nucleic acid construct encoding a desired recombinant POI, is cultured in a growth phase medium and transitioned to a production phase medium in order to produce a desired recombinant POI.

In another embodiment, host cells of the present invention are cultivated in continuous mode, e.g. a chemostat. A continuous fermentation process is characterized by a defined, constant and continuous rate of feeding of fresh culture medium into the bioreactor, whereby culture broth is at the same time removed from the bioreactor at the same defined, constant and continuous removal rate. By keeping culture medium, feeding rate and removal rate at the same constant level, the cultivation parameters and conditions in the bioreactor remain constant.

A stable cell culture as described herein is specifically understood to refer to a cell culture maintaining the genetic properties, specifically keeping the POI production level high, e.g. at least at a μg level, even after about 20 generations of cultivation, preferably at least 30 generations, more preferably at least 40 generations, most preferred of at least 50 generations. Specifically, a stable recombinant host cell line is provided which is considered a great advantage when used for industrial scale production.

The cell culture of the invention is particularly advantageous for methods on an industrial manufacturing scale, e.g. with respect to both the volume and the technical system, in combination with a cultivation mode that is based on feeding of nutrients, in particular a fed-batch or batch process, or a continuous or semi-continuous process (e.g. chemostat).

The term "expression" or "expression system" or "expression cassette" refers to nucleic acid molecules containing a desired coding sequence and control sequences in operable linkage, so that hosts transformed or transfected with these sequences are capable of producing the encoded proteins or host cell metabolites. In order to effect transformation, the expression system may be included in a vector; however, the relevant DNA may also be integrated into the host chromosome. Expression may refer to secreted or non-secreted expression products, including polypeptides or metabolites.

"Expression constructs" or "vectors" or "plasmid" used herein are defined as DNA sequences that are required for the transcription of cloned recombinant nucleotide sequences, i.e. of recombinant genes and the translation of their mRNA in a suitable host organism. Expression vectors or plasmids usually comprise an origin for autonomous replication in the host cells, selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences.

The expression construct of the invention specifically comprises a promoter of the invention, operably linked to a nucleotide sequence encoding a POI under the transcriptional control of said promoter, which promoter is not natively associated with the coding sequence of the POI.

The term "heterologous" as used herein with respect to a nucleotide or amino acid sequence or protein, refers to a compound which is either foreign, i.e. "exogenous", such as not found in nature, to a given host cell; or that is naturally found in a given host cell, e.g., is "endogenous", however, in the context of a heterologous construct, e.g. employing a heterologous nucleic acid. The heterologous nucleotide sequence as found endogenously may also be produced in an unnatural, e.g. greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a nucleotide sequence not natively associated with the promoter according to the invention, e.g. to obtain a hybrid promoter, or operably linked to a coding sequence, as described herein. As a result, a hybrid or chimeric polynucleotide may be obtained. A further example of a heterologous compound is a POI encoding polynucleotide operably linked to a transcriptional control element, e.g., a promoter of the invention, to which an endogenous, naturally-occurring POI coding sequence is not normally operably linked.

The term "variant" as used herein in the context of the present invention shall refer to any sequence with a specific sequence identity or homology to a comparable parent sequence. A variant is specifically any sequence derived from a parent sequence e.g., by size variation, such as (terminal or non-terminal, such as "interstitional" i.e. with deletions or insertions within the nucleotide sequence) elongation, or fragmentation, mutation, hybridization (including combination of sequences).

The pG1-x promoter as described herein is specifically an artificial variant of the native (wild-type) pG1 promoter. Though there is a certain degree of sequence identity to the native structure, it is well understood that the materials, methods and uses of the invention, e.g. specifically referring to isolated nucleic acid sequences, amino acid sequences, expression constructs, transformed host cells and recombinant proteins, are "man-made" or synthetic, and are therefore not considered as a result of "law of nature".

The promoter herein referred to as "pG1-x promoter" is a variant of the pG1 promoter and its nucleotide sequence may be produced by mutagenesis of the pG1 promoter which is used as a "parent" sequence for producing a variant. A pG1-x promoter includes a promoter comprising two, three, four or more copies of SEQ ID 2, SEQ ID 3, SEQ ID 4 or SEQ ID 5.

A series of pG1-x promoters is e.g., exemplified by the promoter comprising or consisting of any of the sequences exemplified in FIG. 6*b*, in particular any of the following sequences:

a) SEQ ID 37-44, preferably any of SEQ ID 45-76;
b) SEQ ID 77-80, preferably any of SEQ ID 81-112;
c) SEQ ID 113-114, preferably any of SEQ ID 115-130;
d) SEQ ID 131-132, preferably any of SEQ ID 133-148;
e) SEQ ID 149-150, preferably any of SEQ ID 151-166;
f) SEQ ID 167-168, preferably any of SEQ ID 169-184;
g) SEQ ID 185-186, preferably any of SEQ ID 187-202;
h) SEQ ID 203-204, preferably any of SEQ ID 205-220;
i) SEQ ID 221-222, preferably any of SEQ ID 223-238;
j) SEQ ID 239-240, preferably any of SEQ ID 241-256; and
k) SEQ ID 32-36 or SEQ ID 257-259.

A pG1-x promoter also includes 3' fragments of any one of SEQ ID 37 to SEQ ID 202 wherein part or all of the 5'-terminal end up to the first or 5' main regulatory region has been deleted; preferably, up to 50, 100, 150, 200, 250, 300, 320, or 325 nucleotides of the 5'-terminal end of any one of SEQ ID 37 to SEQ ID 202 is deleted.

The pG1-x promoter is characterized by having the same or an increased promoter strength and induction ratio as compared to the pG1 promoter, wherein the promoter strength is at least 1.1-fold increased in the induced state as compared to the pG1 promoter, and/or the induction ratio is at least 1.1-fold increased as compared to the pG1 promoter.

Further pG1-x variants are feasible e.g., using the exemplified pG1-x promoter of FIG. 6*b*, or size variants, in particular elongated variants or fragments thereof, as "parent" sequences to produce variants by mutagenesis of certain regions, in particular such, that the essential elements and functions of the promoter be maintained or even improved. The pG1-x promoter variants may e.g., be derived from any of the exemplified pG1-x promoter sequences by mutagenesis to produce sequences suitable for use as a promoter in recombinant cell lines. Such variant promoter may be obtained from a library of mutant sequences by selecting those library members with predetermined properties. Variant promoters may have the same or even improved properties, e.g. improved in the promoter strength, the induction of POI production, with increased differential effect under repressing and de-repressing conditions (in particular the induction ratio). The variant promoter may also comprise a nucleotide sequence from analogous sequences, e.g. from eukaryotic species other than *Pichia pastoris* or from a genus other than *Pichia*, such as from *K. lactis, Z. rouxii, P. stipitis, H. polymorpha.*

The term "functionally active" as used herein with respect to e.g., a promoter variant, the pG1-x promoter or variant of a pG1-x promoter as described herein or variant of the pG1 promoter, means a variant sequence resulting from modification of a parent sequence by mutagenesis, specifically by insertion, deletion or substitution of one or more nucleotides within the sequence or at either or both of the distal ends of the sequence, and which modification does not affect (in particular impair) the activity of this sequence. Regarding the pG1-x promoter as described herein, the function and activity is specifically characterized by the promoter activity and strength as well as the induction ratio.

Functionally active promoter variants as described herein are specifically characterized by exhibiting substantially the same promoter activity as the pG1 promoter (+1-10%, or +1-5%), or even higher.

Functionally active promoter variants as described herein are specifically characterized by exhibiting substantially the same regulatable properties as the pG1 promoter e.g., measured by the induction ratio (+/−10%, or +1-5%), or an even higher induction ratio.

The term "promoter" as used herein refers to a DNA sequence capable of controlling the expression of a coding sequence or functional RNA. Promoter activity may be assessed by its transcriptional efficiency. This may be determined directly by measurement of the amount of mRNA transcription from the promoter, e.g. by Northern Blotting or indirectly by measurement of the amount of gene product expressed from the promoter.

The pG1-x promoter as described herein specifically initiates, regulates, or otherwise mediates or controls the expression of a coding DNA. Promoter DNA and coding DNA may be from the same gene or from different genes, and may be from the same or different organisms.

The pG1-x promoter as described herein is specifically understood as a regulatable promoter, in particular a carbon source regulatable promoter with different promoter strength in the repressed and induced state.

The strength of the promoter of the invention specifically refers to its transcription strength, represented by the efficiency of initiation of transcription occurring at that promoter with high or low frequency. The higher transcription strength the more frequently transcription will occur at that promoter. Promoter strength is important, because it determines how often a given mRNA sequence is transcribed, effectively giving higher priority for transcription to some genes over others, leading to a higher concentration of the transcript. A gene that codes for a protein that is required in large quantities, for example, typically has a relatively strong promoter. The RNA polymerase can only perform one transcription task at a time and so must prioritize its work to be efficient. Differences in promoter strength are selected to allow for this prioritization.

According to the invention the regulatable promoter is relatively strong in the fully induced state, which is typically understood as the state of about maximal activity.

The relative strength is commonly determined with respect to a comparable promoter, such as the pG1 promoter, or a standard promoter, such as the respective pGAP promoter of the cell as used as the host cell. The frequency of transcription is commonly understood as the transcription rate, e.g. as determined by the amount of a transcript in a suitable assay, e.g. RT-PCR or Northern blotting. For example, the transcription strength of a promoter according to the invention is determined in the host cell which is *P. pastoris* and compared to the native pGAP promoter of *P. pastoris.*

The strength of a promoter to express a gene of interest is commonly understood as the expression strength or the capability of support a high expression level/rate. For example, the expression and/or transcription strength of a promoter of the invention is determined in the host cell which is *P. pastoris* and compared to the native pGAP promoter of *P. pastoris.*

The comparative transcription strength employing the pGAP promoter as a reference (standard) may be determined by standard means, such as by measuring the quantity of transcripts, e.g. employing a microarray, or else in a cell culture, such as by measuring the quantity of respective gene expression products in recombinant cells. An exemplary test is illustrated in the Examples section.

In particular, the transcription rate may be determined by the transcription strength on a microarray, or with quantitative real time PCR (qRT-PCR) where microarray or qRT-PCR data show the difference of expression level between conditions with high growth rate and conditions with low growth rate, or conditions employing different media composition, and a high signal intensity as compared to the native pGAP promoter.

The expression rate may, for example, be determined by the amount of expression of a reporter gene, such as eGFP.

The pG1-x promoter as described herein exerts a relatively high transcription strength, reflected by a transcription rate or transcription strength of at least 15% as compared to the native pGAP promoter in the host cell, sometimes called "homologous pGAP promoter". Preferably the transcription rate or strength is at least 20%, in specifically preferred cases at least 30%, at least 40%, at least 50%, at least 60%, at least 70%, at least 80%, at least 90% and at least 100% or even higher, such as at least 150% or at least 200% as compared to the native pGAP promoter, e.g. determined in the eukaryotic cell selected as host cell for producing the POI.

The native pGAP promoter typically initiates expression of the gap gene encoding glyceraldehyde-3-phosphate dehydrogenase (GAPDH), which is a constitutive promoter present in most living organisms. GAPDH (EC 1\2\1\12), a key enzyme of glycolysis and gluconeogenesis, plays a crucial role in catabolic and anabolic carbohydrate metabolism.

The native pGAP promoter specifically is active in a recombinant eukaryotic cell in a similar way as in a native eukaryotic cell of the same species or strain, including the unmodified (non-recombinant) or recombinant eukaryotic cell. Such native pGAP promoter is commonly understood to be an endogenous promoter, thus, homologous to the eukaryotic cell, and serves as a standard or reference promoter for comparison purposes.

For example, a native pGAP promoter of *P. pastoris* is the unmodified, endogenous promoter sequence in *P. pastoris*, as used to control the expression of GAPDH in *P. pastoris*, e.g. having the sequence shown in FIG. 13: native pGAP promoter sequence of *P. pastoris* (GS115) (SEQ ID 260). If *P. pastoris* is used as a host for producing a POI according to the invention, the transcription strength or rate of the promoter according to the invention is compared to such native pGAP promoter of *P. pastoris*.

As another example, a native pGAP promoter of *S. cerevisiae* is the unmodified, endogenous promoter sequence in *S. cerevisiae*, as used to control the expression of GAPDH in *S. cerevisiae*. If *S. cerevisiae* is used as a host for producing a POI according to the invention, the transcription strength or rate of the promoter according to the invention is compared to such native pGAP promoter of *S. cerevisiae*.

Therefore, the relative expression or transcription strength of a promoter according to the invention is usually compared to the native pGAP promoter of a cell of the same species or strain that is used as a host for producing a POI.

The term "regulatable" with respect to a pG1-x promoter or pG1 promoter as used herein shall refer to a promoter that is repressed in a eukaryotic cell in the presence of an excess amount of a carbon source (nutrient or basal substrate) in the growth phase of a batch culture, and de-repressed to exert strong promoter activity in the production phase of a production cell line, e.g. upon reduction of the amount of carbon, such as upon feeding of a growth limiting carbon source (nutrient or supplemental substrate) to a culture according to the fed-batch strategy. In this regard, the term "regulatable" is understood as "carbon source-limit regulatable" or "glucose-limit regulatable", referring to the de-repression of a promoter by carbon consumption, reduction, shortcoming or depletion, or by limited addition of the carbon source so that it is readily consumed by the cells.

The functionally active pG1-x promoter as described herein is a relatively strong regulatable promoter that is silenced or repressed under cell growth conditions (growth phase), and activated or de-repressed under production condition (production phase), and therefore suitable for inducing POI production in a production cell line by limiting the carbon source.

Specifically, the promoter as described herein is carbon source regulatable with a differential promoter strength as determined in a test comparing its strength in the presence of glucose and glucose limitation, showing that it is still repressed at relatively high glucose concentrations, preferably at concentrations of at least 10 g/L, preferably at least 20 g/L. Specifically the promoter according to the invention is fully induced at limited glucose concentrations and glucose threshold concentrations fully inducing the promoter, which threshold is less than 20 g/L, preferably less than 10 g/L, less than 1 g/L, even less than 0.1 g/L or less than 50 mg/L, preferably with a full transcription strength of e.g. at least 50% of the native, homologous pGAP promoter, at glucose concentrations of less than 40 mg/L.

Preferably the induction ratio is understood as a differential promoter strength which is determined by the initiation of POI production upon switching to inducing conditions below a predetermined carbon source threshold, and compared to the strength in the repressed state. The transcription strength commonly is understood as the strength in the fully induced state, i.e. showing about maximum activities under de-repressing conditions. The differential promoter strength is, e.g. determined according to the efficiency or yield of POI production in a recombinant host cell line under de-repressing conditions as compared to repressing conditions, or else by the amount of a transcript. The regulatable promoter according to the invention has a preferred differential promoter strength, which is at least 2 fold, more preferably at least 5 fold, even more preferred at least 10 fold, more preferred at least 20 fold, more preferably at least 30, 40, 50, or 100 fold in the de-repressed state compared to the repressed state, also understood as fold induction.

The term "sequence identity" of a variant as compared to a parent sequence indicates the degree of identity (or homology) in that two or more nucleotide sequences have the same or conserved base pairs at a corresponding position, to a certain degree, up to a degree close to 100%. A homologous sequence typically has at least about 50% nucleotide sequence identity, preferably at least about 60% identity, more preferably at least about 70% identity, more preferably at least about 80% identity, more preferably at least about 90% identity, more preferably at least about 95% identity.

"Percent (%) identity" with respect to the nucleotide sequence e.g., of a promoter or a gene, is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. For purposes of the present invention, the sequence identity between two nucleotide sequences is determined using the NCBI BLAST program version 2.2.29 (Jan. 6, 2014) with blastn set at the following exemplary parameters: Word Size: 11; Expect value: 10; Gap costs: Existence=5, Extension=2; Filter=low complexity activated; Match/Mismatch Scores: 2,-3; Filter String: L; m.

The term "mutagenesis" as used in the context of the present invention shall refer to a method of providing mutants of a nucleotide sequence, e.g. through insertion, deletion and/or substitution of one or more nucleotides, so to obtain variants thereof with at least one change in the non-coding or coding region. Mutagenesis may be through random, semi-random or site directed mutation. Specific pG1-x promoter variants are derived from the pG1 promoter sequence by a mutagenesis method using the pG1 nucleotide sequence as a parent sequence. Such mutagenesis method encompass those methods of engineering the nucleic acid or de novo synthesizing a nucleotide sequence using the pG1 promoter sequence information as a template. Specific mutagenesis methods apply rational promoter engineering.

The pG1-x promoter may be produced by mutagenesis of the pG1 promoter, and variants of the pG1-x promoter as described herein may further be produced, including functionally active variants, employing standard techniques. The promoter may e.g. be modified to generate promoter variants with altered expression levels and regulatory properties. For instance, a promoter library may be prepared by mutagenesis of selected promoter sequences, which may be used as parent molecules, e.g. to fine-tune the gene expression in eukaryotic cells by analyzing variants for their expression under different fermentation strategies and selecting suitable variants. A synthetic library of variants may be used, e.g. to select a promoter matching the requirements for producing a selected POI. Such variants may have increased expression efficiency in eukaryotic host cells and differential expression under carbon source rich and limiting conditions. Typically large randomized gene libraries are produced with a high gene diversity, which may be selected according to a specifically desired genotype or phenotype.

Some of the preferred pG1-x promoter as described herein are size variants of the pG1 promoter and comprise more than one copy of certain elements or regions of the promoter, or comprise one or more (the same or different) fragments of the pG1 promoter.

Specific mutagenesis methods provide for point mutations of one or more nucleotides in a sequence, in particular tandem point mutations, such as to change at least 2, 3, 4, 5, 6, 7, 8, 9, 10, or even more continuous nucleotides within the nucleotide sequence of the promoter. Such mutation is typically at least one of a deletion, insertion, and/or substitution of one or more nucleotides. The promoter sequence may be mutated at the distal ends, in particular within the 5'-region which amounts to up to 50% of the nucleotide sequence, which may be highly variable without substantially losing the promoter activity. The promoter sequence may specifically be mutated within the main regulatory region, yet, it is preferred that the sequence identity to the pG1 parent main regulatory region and in particular to the parent core regulatory region is high, such as e.g. at least 80%. Within the main regulatory region, but outside the core regulatory region the variability of the sequence may be higher so to obtain a sequence identity of less than 80%.

The core regulatory region specifically incorporates the SEQ ID 2 and SEQ ID 3, which represent transcription factor binding sites (TFBS) and an interstitional region between SEQ ID 2 and SEQ ID 3.

The nucleotide sequence identified as SEQ ID 2 comprises at least part of the TFBS recognized by Rgt1, Cat8-1 and Cat8-2.

The nucleotide sequence identified as SEQ ID 3 comprises at least part of the TFBS recognized by Rgt1, Cat8-1 and Cat8-2.

Specifically, the nucleotide sequence between SEQ ID 2 and SEQ ID 3 (the interstitional sequence) may be mutated to a non-homologous sequence (e.g., with a sequence identity of less than 50%) or even be deleted.

Any mutations within the SEQ ID 2 and SEQ ID 3 are specifically conservative, i.e. such as to maintain (or improve) the recognition by the respective transcription factor. Upon engineering such conservative mutants, the sequence identity within the SEQ ID 2 and/or SEQ ID 3 nucleotide sequence is at least 90%, preferably at least 95%.

The main regulatory region comprises or consists of the nucleotide sequence identified by SEQ ID 5. Such region comprises the core regulatory region and further non-core regulatory region, which comprises essential elements of the pG1 promoter and which may be mutated to a certain extent to produce the pG1-x promoter as described herein.

Specific regions of site directed mutagenesis are e.g., the non-core regulatory region of the pG1 or the pG1-x promoter (inside or outside the main regulatory region). However, specific mutants may as well be prepared by mutagenesis methods directed to the core regulatory region of the promoter, keeping a certain degree of sequence identity to maintain the promoter function. Further specific regions are outside or within the main regulatory region. Specifically, the promoter may comprise a hybrid nucleotide sequence e.g. comprising the core regulatory region of the pG1 promoter and one or more regions or alternative (native or artificial) promoter, such as the translation initiation site at the 3'-region (specifically the 3'-end which comprises at least 10 terminal nucleotides, or at least 15 terminal nucleotides) of a promoter which is any other than the pG1 promoter may be used to substitute the translation initiation site of the pG1 promoter.

Specific mutations refer to the duplication of selected regions (or motifs) of the pG1 promoter e.g., the T motif or the extended T motif. Such selected motifs may be elongated by additional nucleotides or shortened at one or both distal ends of the motif, or within the motif. The native pG1 sequence comprises a TAT motif consisting of the nucleotides "T" followed by "A" followed by T15 (SEQ ID 14). Such TAT motif 5'-TATTTTTTTTTTTTTTTT-3 (SEQ ID 22) has turned out to have a positive effect on the promoter strength, which may even be increased by duplicating the TAT motif, or inserting at least 2, or 3, or 4 copies of the TAT motif, either the same TAT motif or using an alternative T motif, extended T motif (e.g. a TAT motif), which comprises at least the T13 motif (SEQ ID 12).

The invention further encompasses a nucleotide sequence which hybridizes under stringent conditions to the pG1-x promoter.

As used in the present invention, the term "hybridization" or "hybridizing" is intended to mean the process during which two nucleic acid sequences anneal to one another with stable and specific hydrogen bonds so as to form a double strand under appropriate conditions. The hybridization between two complementary sequences or sufficiently complementary sequences depends on the operating conditions that are used, and in particular the stringency. The stringency may be understood to denote the degree of homology; the higher the stringency, the higher percent homology between the sequences. The stringency may be defined in particular by the base composition of the two nucleic sequences, and/or by the degree of mismatching between these two nucleic sequences. By varying the conditions, e.g. salt concentration and temperature, a given nucleic acid sequence may be allowed to hybridize only with its exact complement (high stringency) or with any somewhat related sequences (low stringency). Increasing the temperature or decreasing the salt concentration may tend to increase the selectivity of a hybridization reaction.

As used herein, the phrase "hybridizing under stringent hybridizing conditions" is preferably understood to refer to hybridizing under conditions of certain stringency. In a preferred embodiment the "stringent hybridizing conditions" are conditions where homology of the two nucleic acid sequences is at least 70%, preferably at least 80%, preferably at least 90%, i.e. under conditions where hybridization is only possible if the double strand obtained during this hybridization comprises preferably at least 70%, preferably at least 80%, preferably at least 90% of A-T bonds and C-G bonds.

The stringency may depend on the reaction parameters, such as the concentration and the type of ionic species present in the hybridization solution, the nature and the concentration of denaturing agents and/or the hybridization temperature. The appropriate conditions can be determined by those skilled in the art, e.g. as described in Sambrook et al. (Molecular Cloning: A Laboratory Manual, Cold Spring Harbor, 1989).

The term "isolated" or "isolation" as used herein with respect to a nucleic acid, a POI or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized,", and in particular those not naturally-occurring in *P. pastoris* or any other organism, herein referred to as "artificial". With reference to nucleic acids of the invention, the term "isolated nucleic acid" or "isolated nucleic acid sequence" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. An "isolated nucleic acid" (either DNA or RNA) may further represent a molecule produced directly by biological or synthetic means and separated from other components present during its production.

The term "operably linked" as used herein refers to the association of nucleotide sequences on a single nucleic acid molecule, e.g. a vector, in a way such that the function of one or more nucleotide sequences is affected by at least one other nucleotide sequence present on said nucleic acid molecule. For example, a promoter is operably linked with a coding sequence of a recombinant gene, when it is capable of effecting the expression of that coding sequence. As a further example, a nucleic acid encoding a signal peptide is operably linked to a nucleic acid sequence encoding a POI, when it is capable of expressing a protein in the secreted form, such as a preform of a mature protein or the mature protein. Specifically, such nucleic acids operably linked to each other may be immediately linked, i.e. without further elements or nucleic acid sequences in between the nucleic acid encoding the signal peptide and the nucleic acid sequence encoding a POI.

A promoter sequence is typically understood to be operably linked to a coding sequence, if the promoter controls the transcription of the coding sequence. If a promoter sequence is not natively associated with the coding sequence, its transcription is either not controlled by the promoter in native (wild-type) cells or the sequences are recombined with different contiguous sequences.

The term "protein of interest (POI)" as used herein refers to a polypeptide or a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In some cases the term POI as used herein also refers to any metabolite product by the host cell as mediated by the recombinantly expressed protein.

The POI may specifically be recovered from the cell culture in the purified form, e.g. substantially pure.

The term "substantially pure" or "purified" as used herein shall refer to a preparation comprising at least 50% (w/w), preferably at least 60%, 70%, 80%, 90% or 95% of a compound, such as a nucleic acid molecule or a POI. Purity is measured by methods appropriate for the compound (e.g. chromatographic methods, polyacrylamide gel electrophoresis, HPLC analysis, and the like).

The term "recombinant" as used herein shall mean "being prepared by or the result of genetic engineering". Thus, a "recombinant microorganism" comprises at least one "recombinant nucleic acid". A recombinant microorganism specifically comprises an expression vector or cloning vector, or it has been genetically engineered to contain a recombinant nucleic acid sequence. A "recombinant protein" is produced by expressing a respective recombinant nucleic acid in a host. A "recombinant promoter" is a genetically engineered non-coding nucleotide sequence suitable for its use as a functionally active promoter as described herein.

In general, the recombinant nucleic acids or organisms as referred to herein may be produced by recombination techniques well known to a person skilled in the art. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual, Cold Spring Harbor, (1982).

According to a preferred embodiment of the present invention, a recombinant construct is obtained by ligating the promoter and relevant genes into a vector or expression construct. These genes can be stably integrated into the host cell genome by transforming the host cell using such vectors or expression constructs.

Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector.

Appropriate expression vectors typically comprise further regulatory sequences suitable for expressing DNA encoding a POI in a eukaryotic host cell. Examples of regulatory sequences include operators, enhancers, ribosomal binding sites, and sequences that control transcription and translation initiation and termination. The regulatory sequences may be operably linked to the DNA sequence to be expressed.

To allow expression of a recombinant nucleotide sequence in a host cell, the expression vector may provide the promoter according to the invention adjacent to the 5' end of the coding sequence, e.g. upstream from the gene of interest (GOI) or a signal peptide gene enabling secretion of the POI. The transcription is thereby regulated and initiated by this promoter sequence.

The term "signal peptide" as used herein shall specifically refer to a native signal peptide, a heterologous signal peptide or a hybrid of a native and a heterologous signal peptide, and may specifically be heterologous or homologous to the host organism producing a POI. The function of the signal peptide is to allow the POI to be secreted to enter the endoplasmic reticulum. It is usually a short (3-60 amino acids long) peptide chain that directs the transport of a protein outside the plasma membrane, thereby making it easy to separate and purify a heterologous protein. Some signal peptides are cleaved from the protein by signal peptidase after the proteins are transported.

Exemplary signal peptides are signal sequences from *S. cerevisiae* alpha-mating factor prepro peptide and the signal peptides from the *P. pastoris* acid phosphatase gene (PHO1) and the extracellular protein X (EPX1) (Heiss et al., 2015; WO2014067926A1).

Expression vectors comprising one or more of the regulatory elements (such as the pG1-x promoter and optionally a signal sequence) may be constructed to drive expression of a POI, and the expressed yield is compared to constructs with conventional regulatory elements, such as to prove the function of the relevant sequences. The identified nucleotide sequences may be amplified by PCR using specific nucleotide primers, cloned into an expression vector and transformed into a eukaryotic cell line, e.g. using a yeast vector and a strain of *P. pastoris*, for high level production of various different POI. To estimate the effect of the pG1-x promoter as described herein on the amount of recombinant POI so produced, the eukaryotic cell line may be cultured in shake flask experiments and fedbatch or chemostat fermentations in comparison with strains comprising a conventional pG1 promoter or the pGAP promoter, in the respective cell. In particular, the choice of the promoter has a great impact on the recombinant protein production.

The POI can be produced using the recombinant host cell line by culturing a transformant, thus obtained in an appropriate medium, isolating the expressed product or metabolite from the culture, and optionally purifying it by a suitable method.

Transformants according to the present invention can be obtained by introducing such a vector DNA, e.g. plasmid DNA, into a host and selecting transformants which express the POI or the host cell metabolite with high yields. Host cells are treated to enable them to incorporate foreign DNA by methods conventionally used for transformation of eukaryotic cells, such as the electric pulse method, the protoplast method, the lithium acetate method, and modified methods thereof. *P. pastoris* is preferably transformed by electroporation. Preferred methods of transformation for the uptake of the recombinant DNA fragment by the microorganism include chemical transformation, electroporation or transformation by protoplastation. Transformants according to the present invention can be obtained by introducing such a vector DNA, e.g. plasmid DNA, into a host and selecting transformants which express the relevant protein or host cell metabolite with high yields.

Several different approaches for the production of the POI according to the method of the invention are preferred. Substances may be expressed, processed and optionally secreted by transforming a eukaryotic host cell with an expression vector harboring recombinant DNA encoding a relevant protein and at least one of the regulatory elements as described above, preparing a culture of the transformed cell, growing the culture, inducing transcription and POI production, and recovering the product of the fermentation process.

The host cell according to the invention is preferably tested for its expression capacity or yield by the following test: ELISA, activity assay, HPLC, or other suitable tests.

The invention specifically allows for the fermentation process on a pilot or industrial scale. The industrial process scale would preferably employ volumina of at least 10 L, specifically at least 50 L, preferably at least 1 $m^3$, preferably at least 10 $m^3$, most preferably at least 100 $m^3$.

Production conditions in industrial scale are preferred, which refer to e.g. fed batch cultivation in reactor volumes of 100 L to 10 $m^3$ or larger, employing typical process times of several days, or continuous processes in fermenter volumes of approximately 50-1000 L or larger, with dilution rates of approximately 0.02-0.15 $h^{-1}$.

The suitable cultivation techniques may encompass cultivation in a bioreactor starting with a batch phase, followed by a short exponential fed batch phase at high specific growth rate, further followed by a fed batch phase at a low specific growth rate. Another suitable cultivation technique may encompass a batch phase followed by a continuous cultivation phase at a low dilution rate.

A preferred embodiment includes a batch culture to provide biomass followed by a fed-batch culture for high yields POI production.

It is preferred to cultivate the host cell line as described herein in a bioreactor under growth conditions to obtain a cell density of at least 1 g/L cell dry weight, more preferably at least 10 g/L cell dry weight, preferably at least 20 g/L cell dry weight. It is advantageous to provide for such yields of biomass production on a pilot or industrial scale.

A growth medium allowing the accumulation of biomass, specifically a basal growth medium, typically comprises a carbon source, a nitrogen source, a source for sulphur and a source for phosphate. Typically, such a medium comprises furthermore trace elements and vitamins, and may further comprise amino acids, peptone or yeast extract.

Preferred nitrogen sources include $NH_4H_2PO_4$, or $NH_3$ or $(NH_4)_2SO_4$,

Preferred sulphur sources include $MgSO_4$, or $(NH_4)_2SO_4$ or $K_2SO_4$,

Preferred phosphate sources include $NH_4H_2PO_4$, or $H_3PO_4$ or $NaH_2PO_4$, $KH_2PO_4$, $Na_2HPO_4$ or $K_2HPO_4$;

Further typical medium components include KCl, $CaCl_2$), and Trace elements such as: Fe, Co, Cu, Ni, Zn, Mo, Mn, I, B;

Preferably the medium is supplemented with vitamin $B_7$;

A typical growth medium for *P. pastoris* comprises glycerol, sorbitol or glucose, $NH_4H_2PO_4$, $MgSO_4$, KCl, $CaCl_2$), biotin, and trace elements.

In the production phase a production medium is specifically used with only a limited amount of a supplemental carbon source.

Preferably the host cell line is cultivated in a mineral medium with a suitable carbon source, thereby further simplifying the isolation process significantly. An example of a preferred mineral medium is one containing an utilizable carbon source (e.g. glucose, glycerol, sorbitol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g. to complement auxotrophies.

Specifically, the cells are cultivated under conditions suitable to effect expression of the desired POI, which can be purified from the cells or culture medium, depending on the nature of the expression system and the expressed protein, e.g. whether the protein is fused to a signal peptide and whether the protein is soluble or membrane-bound. As will be understood by the skilled artisan, cultivation conditions will vary according to factors that include the type of host cell and particular expression vector employed.

A typical production medium comprises a supplemental carbon source, and further $NH_4H_2PO_4$, $MgSO_4$, KCl, $CaCl_2$), biotin, and trace elements.

For example the feed of the supplemental carbon source added to the fermentation may comprise a carbon source with up to 50 wt % utilizable sugars. The low feed rate of the supplemental medium will limit the effects of product or byproduct inhibition on the cell growth, thus a high product yield based on substrate provision will be possible.

The fermentation preferably is carried out at a pH ranging from 3 to 7.5.

Typical fermentation times are about 24 to 120 hours with temperatures in the range of 20° C. to 35° C., preferably 22-30° C.

The POI is preferably expressed employing conditions to produce yields of at least 1 mg/L, preferably at least 10 mg/L, preferably at least 100 mg/L, most preferred at least 1 g/L.

It is understood that the methods disclosed herein may further include cultivating said recombinant host cells under conditions permitting the expression of the POI, preferably in the secreted form or else as intracellular product. A recombinantly produced POI or a host cell metabolite can then be isolated from the cell culture medium and further purified by techniques well known to a person skilled in the art.

The POI produced according to the invention typically can be isolated and purified using state of the art techniques, including the increase of the concentration of the desired POI and/or the decrease of the concentration of at least one impurity.

If the POI is secreted from the cells, it can be isolated and purified from the culture medium using state of the art techniques. Secretion of the recombinant expression products from the host cells is generally advantageous for reasons that include facilitating the purification process, since the products are recovered from the culture supernatant rather than from the complex mixture of proteins that results when yeast cells are disrupted to release intracellular proteins.

The cultured transformant cells may also be ruptured sonically or mechanically, enzymatically or chemically to obtain a cell extract containing the desired POI, from which the POI is isolated and purified.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

As isolation and purification methods the following standard methods are preferred: Cell disruption (if the POI is obtained intracellularly), cell (debris) separation and wash by Microfiltration or Tangential Flow Filter (TFF) or centrifugation, POI purification by precipitation or heat treatment, POI activation by enzymatic digest, POI purification by chromatography, such as ion exchange (IEX), hydrophobic interaction chromatography (HIC), Affinity chromatography, size exclusion (SEC) or HPLC Chromatography, POI precipitation of concentration and washing by ultrafiltration steps.

The isolated and purified POI can be identified by conventional methods such as Western blot, HPLC, activity assay, or ELISA.

The POI can be any eukaryotic, prokaryotic or synthetic polypeptide. It can be a secreted protein or an intracellular protein. The present invention also provides for the recombinant production of functional homologs, functional equivalent variants, derivatives and biologically active fragments of naturally occurring proteins. Functional homologs are preferably identical with or correspond to and have the functional characteristics of a sequence.

A POI referred to herein may be a product homologous to the eukaryotic host cell or heterologous, preferably for therapeutic, prophylactic, diagnostic, analytic or industrial use.

The POI is preferably a heterologous recombinant polypeptide or protein, produced in a eukaryotic cell, preferably a yeast cell, preferably as secreted proteins. Examples of preferably produced proteins are immunoglobulins, immunoglobulin fragments, aprotinin, tissue factor pathway inhibitor or other protease inhibitors, and insulin or insulin precursors, insulin analogues, growth hormones, interleukins, tissue plasminogen activator, transforming growth factor a or b, glucagon, glucagon-like peptide 1 (GLP-1), glucagon-like peptide 2 (GLP-2), GRPP, Factor VII, Factor VIII, Factor XIII, platelet-derived growth factor1, serum albumin, enzymes, such as lipases or proteases, or a functional homolog, functional equivalent variant, derivative and biologically active fragment with a similar function as the native protein. The POI may be structurally similar to the native protein and may be derived from the native protein by addition of one or more amino acids to either or both the C- and N-terminal end or the side-chain of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

A POI can also be selected from substrates, enzymes, inhibitors or cofactors that provide for biochemical reactions in the host cell, with the aim to obtain the product of said biochemical reaction or a cascade of several reactions, e.g. to obtain a metabolite of the host cell. Exemplary products can be vitamins, such as riboflavin, organic acids, and alcohols, which can be obtained with increased yields following the expression of a recombinant protein or a POI according to the invention.

In general, the host cell, which expresses a recombinant product, can be any eukaryotic cell suitable for recombinant expression of a POI.

Examples of preferred mammalian cells are BHK, CHO (CHO-DG44, CHO-DUXB11, CHO-DUKX, CHO-K1, CHOK1SV, CHO—S), HeLa, HEK293, MDCK, NIH3T3, NSO, PER.C6, SP2/0 and VERO cells.

Examples of preferred yeast cells used as host cells according to the invention include but are not limited to the *Saccharomyces* genus (e.g. *Saccharomyces cerevisiae*), the *Pichia* genus (e.g. *P. pastoris*, or *P. methanolica*), the *Komagataella* genus (*K. pastoris, K. pseudopastoris* or *K. phaffii*), *Hansenula polymorpha, Yarrowia lipolytica, Schefferomyces stipitis* or *Kluyveromyces lactis.*

Newer literature divides and renames *Pichia pastoris* into *Komagataella pastoris, Komagataella phaffii* and *Komagataella pseudopastoris*. Herein *Pichia pastoris* is used synonymously for all, *Komagataella pastoris, Komagataella phaffii* and *Komagataella pseudopastoris.*

The preferred yeast host cells are derived from methylotrophic yeast, such as from *Pichia* or *Komagataella*, e.g. *Pichia pastoris*, or *Komagataella pastoris*, or *K. phaffii*, or *K. pseudopastoris*. Examples of the host include yeasts such as *P. pastoris*. Examples of *P. pastoris* strains include CBS 704 (=NRRL Y-1603=DSMZ 70382), CBS 2612 (=NRRL Y-7556), CBS 7435 (=NRRL Y-11430), CBS 9173-9189 (CBS strains: CBS-KNAW Fungal Biodiversity Centre, Centraalbureau voor Schimmel-cultures, Utrecht, The Netherlands), and DSMZ 70877 (German Collection of Microorganisms and Cell Cultures), but also strains from Invitrogen, such as X-33, GS115, KM71 and SMD1168. Examples of *S. cerevisiae* strains include W303, CEN.PK and the BY-series (EUROSCARF collection). All of the strains described above have been successfully used to produce transformants and express heterologous genes.

A preferred yeast host cell according to the invention, such as a *P. pastoris* or *S. cerevisiae* host cell, contains a heterologous or recombinant promoter sequences, which may be derived from a *P. pastoris* or *S. cerevisiae* strain, different from the production host. In another specific embodiment the host cell according to the invention comprises a recombinant expression construct according to the invention comprising the promoter originating from the same genus, species or strain as the host cell.

According to the invention it is preferred to provide a *P. pastoris* host cell line comprising a pG1-x promoter sequence as described herein operably linked to the nucleotide sequence coding for the POI.

If the POI is a protein homologous to the host cell, i.e. a protein which is naturally occurring in the host cell, the expression of the POI in the host cell may be modulated by the exchange of its native promoter sequence with a promoter sequence according to the invention.

This purpose may be achieved e.g. by transformation of a host cell with a recombinant DNA molecule comprising homologous sequences of the target gene to allow site specific recombination, the promoter sequence and a selective marker suitable for the host cell. The site specific recombination shall take place in order to operably link the promoter sequence with the nucleotide sequence encoding the POI. This results in the expression of the POI from the promoter sequence according to the invention instead of from the native promoter sequence.

It is specifically preferred that the pG1-x promoter has an increased promoter activity relative to the native promoter sequence of the POI.

According to a specific embodiment, the POI production method employs a recombinant nucleotide sequence encoding the POI, which is provided on a plasmid suitable for integration into the genome of the host cell, in a single copy or in multiple copies per cell. The recombinant nucleotide sequence encoding the POI may also be provided on an autonomously replicating plasmid in a single copy or in multiple copies per cell.

The preferred method as described herein employs a plasmid, which is a eukaryotic expression vector, preferably a yeast expression vector. Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector, such as a yeast vector, which carries a DNA construct according to the invention. A preferred yeast expression vector is for expression in yeast selected from the group consisting of methylotrophic yeasts represented by the genera *Hansenula, Pichia, Candida* and *Torulopsis.*

In the present invention, it is preferred to use plasmids derived from pPICZ, pGAPZ, pPIC9, pPICZalfa, pGAPZalfa, pPIC9K, pGAPHis or pPUZZLE as the vector.

According to a preferred embodiment of the present invention, a recombinant construct is obtained by ligating the relevant genes into a vector. These genes can be stably integrated into the host cell genome by transforming the host cell using such vectors. The polypeptides encoded by the genes can be produced using the recombinant host cell line by culturing a transformant, thus obtained in an appropriate medium, isolating the expressed POI from the culture, and purifying it by a method appropriate for the expressed product, in particular to separate the POI from contaminating proteins.

Expression vectors may comprise one or more phenotypic selectable markers, e.g. a gene encoding a protein that confers antibiotic resistance or that supplies an autotrophic requirement. Yeast vectors commonly contain an origin of replication from a yeast plasmid, an autonomously replicating sequence (ARS), or alternatively, a sequence used for integration into the host genome, a promoter region, sequences for polyadenylation, sequences for transcription termination, and a selectable marker.

The procedures used to ligate the DNA sequences and regulatory elements, e.g. the pG1-x promoter and the gene(s) coding for the POI, the promoter and the terminator, respectively, and to insert them into suitable vectors containing the information necessary for integration or host replication, are well-known to persons skilled in the art, e.g. described by J. Sambrook et al., (A Laboratory Manual, Cold Spring Harbor, 1989).

It will be understood that the vector, which uses the regulatory elements according to the invention and/or the POI as an integration target, may be constructed either by first preparing a DNA construct containing the entire DNA sequence coding for the regulatory elements and/or the POI and subsequently inserting this fragment into a suitable expression vector, or by sequentially inserting DNA fragments containing genetic information for the individual elements, followed by ligation.

Also multicloning vectors, which are vectors having a multicloning site, can be used according to the invention, wherein a desired heterologous gene can be incorporated at a multicloning site to provide an expression vector. In expression vectors, the promoter is placed upstream of the gene of the POI and regulates the expression of the gene. In the case of multicloning vectors, because the gene of the POI is introduced at the multicloning site, the promoter is placed upstream of the multicloning site.

The DNA construct as provided to obtain a recombinant host cell according to the invention may be prepared synthetically by established standard methods, e.g. the phosphoramidite method. The DNA construct may also be of genomic or cDNA origin, for instance obtained by preparing a genomic or cDNA library and screening for DNA sequences coding for all or part of the polypeptide of the invention by hybridization using synthetic oligonucleotide probes in accordance with standard techniques (Sambrook et al., Molecular Cloning: A Laboratory Manual, Cold Spring Harbor, 1989). Finally, the DNA construct may be of mixed synthetic and genomic, mixed synthetic and cDNA or mixed genomic and cDNA origin prepared by annealing fragments of synthetic, genomic or cDNA origin, as appropriate, the fragments corresponding to various parts of the entire DNA construct, in accordance with standard techniques.

In another preferred embodiment, the yeast expression vector is able to stably integrate in the yeast genome, e. g. by homologous recombination.

A transformant host cell according to the invention obtained by transforming the cell with the regulatory elements according to the invention and/or the POI genes may preferably first be cultivated at conditions to grow efficiently to a large cell number. When the cell line is prepared for the POI expression, cultivation techniques are chosen to produce the expression product.

The foregoing description will be more fully understood with reference to the following examples. Such examples are, however, merely representative of methods of practicing one or more embodiments of the present invention and should not be read as limiting the scope of invention.

EXAMPLES

Example 1: 5'-Shortening of pG1 Reveals the Main Regulatory Region of pG1

The native (wild-type) pG1 promoter has been isolated from *P. pastoris* (*Komagatella phaffii*) strain CBS2612 (CBS strains: CBS-KNAW Fungal Biodiversity Centre, Centraalbureau voor Schimmelcultures, Utrecht, The Netherlands). As determined by Sanger sequencing and subsequent BLAST analysis, the pG1 promoter sequence of CBS2612 had more than 95% sequence identity to the respective regions in the genomic sequences of the strains GS115 (Invitrogen) (upstream of PAS_chr1-3_0011) and CBS7435 (upstream of P7435_Chr1-0007) or *K. pastoris* DSMZ 70382 (DSMZ strains: German Collection of Microorganisms and Cell Cultures) (upstream of PIPA00372). During the analysis of the genomic region of pG1, it was realized that its gene GTH1 has a different start annotation in the strains CBS7435 (P7435_Chr1-0007) and DSMZ 70382 (PIPA00372) than in GS115 (PAS_chr1-3_0011). In contrast to GS115 and CBS2612, the coding sequence is annotated to start 36 bp further downstream in the genomic sequences of the other two strains.

In order to identify the relevant regulatory region of pG1 8 shortened pG1 variants were cloned from CBS2612 starting from the alternative 5' positions −858, −663, −492, −371, −328, −283, −211 and −66 to position −1 (see FIG. 1, numbering based on the start of the GTH1 gene locus PAS_chr1-3_0011). These shortened promoter variants were screened for eGFP expression in deep well plates as described in Example 8 to test for the repression-(glycerol) and induction properties (glucose feed beads) in comparison to the original 965 bp version of pG1 (FIG. 2). No difference in eGFP signal was found for all length variants in the repressing condition, showing that promoter repression was not restricted in any of the shortened variants. After 48 hours of induction, the expression capacity remained fully functional for the promoter variants down to a length of 328 bp. The 283 bp-variant was only about two thirds strong compared to the original pG1 promoter. The two shortest length variants (211 and 66 bp) appeared to be almost nonfunctional. These results that the region between position −400 and −200 contains important regulatory features.

Example 2: A High Density of Predicted Carbon Source Related TFBS Marks the Main Regulatory Region of the pG1 Promoter The pG1 promoter sequence (1000 bp upstream of the gene PAS_chr1-3_0011) was searched for matrix families belonging to the matrix groups ‘fungi’ and ‘general core promoter elements’ using the MatInspector from Genomatix. 111 putative TFBS belonging to 46 different matrix families were found (Table 1). The most common matrix families in the analyzed sequence were monomeric Gal4-class motifs (F$MGCM, 12 binding sites), homeodomain-containing transcriptional regulators (F$HOMD, 6 binding sites), fungal basic leucine zipper family (F$BZIP, 5 binding sites) and yeast GC-Box Proteins (F$YMIG, 5 binding sites). A very high TFBS binding site density was noticed between position −400 to −200 with about two thirds of the mentioned TFBS (most common matrix families) occurring there (18 out of 28). Regarding general core promoter elements, no yeast- or fungi-related motifs were identified by the MatInspector, but a TATA box can be found starting at position −26.

A prominent motif was identified e.g. at position −390 to −375, which was termed TAT14 due to its sequence 5"-TATTTTTTTTTTTTT-3' (SEQ ID 21) or TAT15 due to its sequence 5"-TATTTTTTTTTTTTTTT-3 (SEQ ID 22). Such poly(A:T) tracts in promoter regions are known to negatively affect nucleosome binding and to stimulate TF binding at nearby sites in yeast.

Example 3: The Carbon Source-Related Transcription Factors Mxr1, Rgt1, Cat8-1, Cat8-2 and Mig1 were Revealed to be Important for the Regulatory Properties of pG1

Transcription factor binding sites with predicted glucose- or carbon source dependency were selected for further analysis (see FIG. 1 and Table 2). pG1 variants with deletions of the respective regions were generated using overlap-extension PCR. Table 3 lists all selected TFBS and indicates all TFBS which are (partially) affected by the deletion (detailed list in Table 2). For some deletions (e.g. 49 and Δ10), some nucleotides of the respective TFBS were left untouched in order to keep close neighboring TFBS functional and to separately examine their effect.

All TFBS deletion and TAT mutation variants were screened for eGFP expression as described in Example 8 in repressing (glycerol) and inducing conditions (glucose feed bead) (FIG. 3). It is important to consider that individual TF/TFBS are usually not sufficient to fulfill a promoter's regulation. TFBS deletions also imply that the promoter sequence can be affected by the newly formed adjoined sequence, by altered distances between TFBS or by changes of higher order properties (chromatin organization). The same TFBS at different positions of the promoter can have different functions, also because of other adjacent TFBS. At closely neighbouring TFBS, TFs might either act synergistically or restrict binding of other TFs due to steric hindrance.

Four different carbon source-related TF families were deleted in the pG1 promoter variants (see Table 2 and Table 3): Yeast metabolic regulator (F$ADR; matrixes: F$ADR1.01), Monomeric Gal4-class motifs (F$MGCM; matrixes: F$RGT1.01, F$RGT1.02), Carbon source-responsive elements (F$CSRE, matrixes: F$CSRE.01, F$S1P4.01) and Yeast GC-Box Proteins (F$YMIG; matrixes: F$MIG1.01 and F$MIG1.02). The corresponding transcription factors in *S. cerevisiae* are Adr1, Rgt1, Sip4/Cat8 and Mig1, respectively.

Carbon source dependent promoters are controlled by glucose repression and/or induction by carbohydrates or other non-sugar carbon sources. Glucose repression is mainly conducted by the Snf1 protein kinase complex, the transcriptional repressor Mig1 and protein phosphatase 1. Downstream factors regulate e.g. respiratory genes (Hap4), gluconeogenesis genes (Cat8, Sip4) and glucose transporters (Rgt1) in *S. cerevisiae.*

*P. pastoris* has two Mig1 homologs, called Mig1-1 and Mig1-2, the second of which possibly acts as carbon catabolite repressor. When glucose is available, Mig1 acts as a repressor, while Rgt1 acts as transcriptional activator. To fulfill repressor function, Mig1 gets dephosphorylated and imported into the nucleus where it recruits the corepressors Ssn6 and Tup1.

In limiting glucose, Rgt1 gets dephosphorylated and acts as transcriptional repressor. Rgt1 function is controlled by its phosphorylation state (Rgt1 has four phosphorylation sites), and induction of regulatedpromoters does not require Rgt1 dissociation in *S. cerevisiae*, as typically seen for transcriptional repressors.

The carbon source-responsive zinc-finger transcription factor Adr1 is required for transcriptional activation of the glucose-repressible alcohol dehydrogenase (ADH2) gene in *S. cerevisae*. The Adr1 homolog in *P. pastoris* is Mxr1 (PAS_chr4_0487), the key regulator of methanol metabolism, and it was reported to be a positive acting transcription factor being essential for strong $P_{AOX}$ induction on methanol. The reported TFBS core motif 5' CYCC 3' for Mxr1 matches with both F$ADR1.01 sites found in the pG1 promoter sequence.

The carbon source response element (CSRE) is bound by the transcriptional activators Sip4 and Cat8 and functions to induce the expression of gluconeogenesis genes in *S. cerevisiae*. Two *P. pastoris* homologs of ScCat8 can be found: Cat8-1 (PAS_chr2-1_0757) and Cat8-2 (PAS_chr4_0540), both also being the best blastp hits for ScSip4. Cat8-2 is weakly similar to ScCat8, and it potentially plays an important role in derepressing conditions.

Example 4: Deletion Variants of the pG1 Promoter Reveal TFBS Responsible for its Repression and Induction Out of the 5 deletion variants residing upstream (5') of the main regulatory region of pG1 identified before (see dashed box in FIG. 1 and Table 2), the variants pG1-Δ1, -Δ2 and -Δ4 appear to have a beneficial effect on promoter strength while the deletion variants pG1-Δ3 and Δ5 had no effect on GFP expression compared to the original pG1 promoter (SEQ ID 9). This result suggests that 5' shortening of the promoter might be beneficial for the engineering of pG1. TFBS deletions within the main regulatory region of pG1 (pG1-Δ6 to -Δ12, see FIG. 1 and Table 2) had different impacts on eGFP expression, but none showed increased induction without losing the repression properties. Therefore, it is assumed that the main regulatory region of pG1 needs to be maintained in engineered pG1 promoter variants in order to retain its tight regulation. Accordingly, without this region, much lower induction in limiting glucose was observed in Example 1 (pG1-328 and pG1-283, FIG. 2).

Mig1 binding sites were deleted in pG1-Δ3, -Δ4, -Δ10 and -Δ11 (F$MIG1.02 in Δ3, F$MIG1.01 in Δ4, Δ10 and Δ11), whereat pG1-Δ10 and pG1-Δ11 also include F$ADR1.01 and F$RGT1.02 deletions, respectively. Slightly tighter repression was found for Δ3, while Δ4 had unchanged repression but enhanced eGFP levels after induction.

Liberated repression seen for Δ10 and weaker promoter induction of Δ10 and Δ11 could also be connected to F$RGT1 binding sites in this region (F$RGT1.01 and F$RGT1.02 deleted in Δ9 and Δ11). Also, Mig1 could play a bifunctional role in pG1 regulation: two MIG1 genes are found in *P. pastoris* (MIG1-1, MIG1-2) and they were shown to be regulated contrariwise upon glucose availability.

The deletion of F$ADR1.01 increased eGFP levels in the variant pG1-Δ1, although Mxr1 (positive regulator of methanol metabolism in Pp, homolog of ScADR1) binding site deletion would be expected to rather weaken the promoter. Combined deletion of F$ADR1.01 with F$MIG1.01 in pG1-Δ10 liberated promoter repression on glycerol and weakened its induction, which is a conclusive response for Mig1 TFBS deletion.

In the main regulatory region, the binding site F$RGT1.02 was deleted in the variants pG1-Δ6 (two sites), -Δ7, -Δ8, -Δ11 and -Δ12, and F$RGT1.01 was deleted in 49. The variant harboring the deletion of the paired F$RGT1.02 site (Δ6, binding sites on opposite strands with a shift of 7 bp) showed a slightly liberated repression and reduced induction. The variants Δ7 and Δ8 contain very close F$RGT1.02 sites, whereat the first lies on the negative- and the second on the positive strand; also Δ8 contains the deletion of an F$S1P4.01 site. The first (Δ7) showed a slightly liberated repression and increased induction, while the second (Δ8) was much weaker induced (but had unchanged promoter repression). This indicates a strong role for the transcriptional activator Cat8-1 and/or Cat8-2 (strongest homologs for ScSip4) for pG1 induction. The variant 49 was created to delete closely located F$RGT1.01 and F$CSRE.01 TFBS (binding sites on opposite strands) and the drastic loss of repression indicates a strong role of these TFBS to tightly control pG1, most likely through binding of Rgt1, Cat8-1 and/or Cat8-2. The deletion of F$RGT1.02 in the variant pG1-Δ12 did not have an effect on eGFP expression performance. Interestingly, CATS-2 transcription is strongly upregulated in limiting glucose compared to glucose surplus, while RGT1 and CATS-2 were not transcriptionally regulated in the tested conditions.

Example 5: pG1 Promoter Strength is Dependent on the Poly(A:T) Tract TAT14

The TAT motif is located about 80 bp upstream (5', e.g. position-390 to -374) of the main regulatory region of pG1. Repeated sequencing of the 5'-region of GTH1 in *P. pastoris* CBS2612, CBS7435 or GS115 resulted in the detection of 15+/−1 Ts in the TAT motif. To elucidate its impact on promoter performance, the TAT14 motif was selected for deletion (pG1-ΔTAT14) and mutation (to T16, T18 and T20; pG1-T16, pG1-T18, pG1-T20). Primers (see primers #37-42 in Table 4) were initially designed to obtain T18, T20 and T22, but variants with different lengths (T16, T20 and T18, respectively) were obtained and used. Deletion of the TAT14 motif resulted in lower GFP signals, whereas its prolongation increased the expression strength of pG1. This indicates that the use of a prolonged TAT14 motif would be beneficial for pG1 engineering.

Example 6: Partial Sequence Duplications of pG1's Main Regulatory Region Significantly Improve its Expression Strength Two duplication variants (pG1-D1240 (SEQ ID 49) and pG1-D1427 (SEQ ID 85), the numbers state the lengths of the respective promoter variants) of the pG1 promoter were generated by PCR amplification of two sequence fragments (−472 to -188 and -472 to -1) and insertion using the restriction sites PstI and BglII (positions 509-514 and 525-530). The duplication sections start upstream of TFBS deleted in pG1-Δ5 and end after the main regulatory region of pG1 for the first variant (pG1-D1240), while the second duplication (pG1-D1427) reaches until the 3"-end of the pG1 promoter. These variants were screened for eGFP expression in the same way as described for the TFBS deletion and TAT14 mutation variants (see Example 8). Both duplication variants showed more tight repression in excess glycerol and stronger induction upon limiting glucose (FIG. 4).

The post-transformational stability of the duplication variant clone pG1-D1240 #3 was tested by performing three consecutive batch cultivations without selection pressure, which is equal to about 20 generations. eGFP expression was stable over the whole cultivation time (data not shown). In comparison, a typical *P. pastoris* bioreactor process starts with $OD_{600}$=1 (~0.2-0.4 g/L YDM) in the batch phase and ends with ~100 g/L YDM after the fed batch phase and thereby takes about 10 generations.

Example 7: Verification of pG1 Promoter Variant Performance in Fed Batch Bioreactor Cultivation In order to verify the performance of the generated promoter variants in bioprocess conditions, some variants were selected for fed batch cultivation based on their altered eGFP expression performance: pG1-Δ2 (SEQ ID 211) was the most enhanced variant upstream of the main regulatory region, and pG1-T16 (SEQ ID 257) and pG1-D1240 (SEQ ID 49) showed higher eGFP expression levels in limiting glucose without losing promoter repression in the glycerol condition. A bioreactor cultivation, which was started with a glycerol batch phase followed by a space-time yield optimized fed batch (Prielhofer et al., 2013), was performed for one clone each and compared to the control strain pG1 #8 for eGFP expression (see FIG. 5 and Table 5).

Fed batch fermentations were performed in DASGIP reactors with a final working volume of 0.7 L.

Following media were used:

$PTM_1$ Trace Salts Stock Solution Contained Per Liter 6.0 g $CuSO_4·5H_2O$, 0.08 g NaI, 3.36 g $MnSO_4·H_2O$, 0.2 g $Na_2MoO_4·2H_2O$, 0.02 g $H_3BO_3$, 0.82 g $CoCl_2$, 20.0 g $ZnCl_2$, 65.0 g $FeSO_4·7H_2O$, 0.2 g biotin and 5.0 ml $H_2SO_4$ (95%-98%).

Glycerol Batch Medium Contained Per Liter 2 g Citric acid monohydrate ($C_6H_8O_7·H_2O$), 39.2 g Glycerol, 12.6 g $NH_4H_2PO_4$, 0.5 g $MgSO_4·7H_2O$, 0.9 g KCl, 0.022 g $CaCl_2·2H_2O$, 0.4 mg biotin and 4.6 ml PTM1 trace salts stock solution. HCl was added to set the pH to 5.

Glucose Fed Batch Medium Contained Per Liter 464 g glucose monohydrate, 5.2 g $MgSO_4·7H_2O$, 8.4 g KCl, 0.28 g $CaCl_2·2H_2O$, 0.34 mg biotin and 10.1 mL PTM1 trace salts stock solution.

The dissolved oxygen was controlled at DO=20% with the stirrer speed (400-1200 rpm). Aeration rate was 24 L $h^{-1}$ air, the temperature was controlled at 25° C. and the pH setpoint of 5 was controlled with addition of $NH_4OH$ (25%).

To start the fermentation, 400 mL batch medium was sterile filtered into the fermenter and was inoculated from a selective pre-culture of the respective *P. pastoris* clone with a starting optical density (OD600) of 1. The batch phase of approximately 25 h (reaching a dry biomass concentration of approximately 20 g/L) was followed by a glucose-limited fed batch starting with an exponential feed for 7 h and a constant feed rate of 15 g/L for 13 h, leading to a final dry biomass concentration of approximately 100 g/L. Samples were taken during batch and fed batch phase, and analyzed for eGFP expression using a plate reader (Infinite 200, Tecan, CH). Therefore, samples were diluted to an optical density (OD600) of 5. Results are shown in FIG. 5 as relative fluorescence per bioreactor (FL/r).

The gene copy number of these three clones was analyzed using Real-time PCR and resulted in one GCN for all of them (data not shown). All pG1-variants displayed good repression in the batch phase and strong expression in the induced state (Table 5). The strong improvement of the duplication variant pG1-D1240 could be verified in bioreactor conditions, the clone pG1-D1240 #3 showed a 50% increase in GFP fluorescence at the fed batch end compared to pG1. Although the signal was already increased at the batch end, the induction ratio was even a bit higher than for the original pG1 Other than in the screening, the clone pG1-Δ2 #3 had a slightly increased signal at the batch end, and about 10% weakened signal at the fed batch end. The TAT14 mutation variant clone pG1-T16 #3 showed the strongest signal at the batch end, and fell behind the duplication variant at the fed batch end, reaching about 20% improvement over the control pG1 #8, similar to the screening result. The different induction behavior of the clones in the batch phase is explained by derepression due to decreasing glycerol concentration throughout the batch phase (see FIG. 5A). Overall, the fed batch cultivations could largely confirm the results obtained in small scale screening.

ACHIEVEMENTS AND CONCLUSIONS

Gene promoters with carbon source-dependent regulation are favorable for bioprocess application because the production phase can be separated from growth. Potential promoter-based protein production improvement can be accomplished by finding the optimal growth conditions (e. g. growth rate, feeding strategy) or by directly manipulating the promoter sequence (e. g. mutations, deletions).

Several pG1 promoter variants were constructed with shortened length, TFBS deletions, TAT motif mutations and fragment duplications. Thereby, the main regulatory region of pG1, including its important TFBS was identified. The analysis of TFBS deletions indicates that the transcription factors Rgt1 and Cat8-1 and/or Cat8-2 play an essential role for pG1 repression and induction: two motifs consisting of F$RGT1 and F$CSRE binding at the same position on the opposite strands were deleted. Deletion of the first part (pG1-Δ8, position-293 to -285; RGT1: (+)-310 to -299, CSRE: (−)-299 to −285) caused weakened promoter induction, while deletion of the second part (pG1-Δ9, position-275 to -261; RGT1: (−)-275 to -259, CSRE: (+)-276 to -260) lead to decreased promoter repression. Thereby, regulatory motifs were identified which are essential and characteristic for pG1 regulation.

The role of the transcriptional regulators Mig1 (F$MIG1) and Mxr1 (F$ADR1) might be more important in other conditions such as excess glucose or methanol induction. Other transcription factors which bind in or close to that region might also contribute to pG1's regulation.

The poly(A:T) tracts are known to play a role in promoter sequences, and the TAT motif in pG1, which is located upstream (e.g. position-390 to -375) of the main regulator region, could be shown to be essential for its strength. Elongation of this motif to T16, T18 and T20 had a positive effect on promoter performance.

Deletion variants of pG1 revealed that 5"shortening might be beneficial for promoter engineering as well. TFBS for Mxr1, Mig1, Rgt1 and Cat8 deleted upstream of the main regulatory region of pG1 improved eGFP expression, although this effect was not seen for the 5"shortened promoter variants.

Two variants with partial sequence duplications reached greatly enhanced expression capacities compared to the wild type pG1.

Distinct features of pG1 good expression performance could be assigned, which is a solid basis for rational promoter engineering: 5"shortening, TAT motif use and optional mutation/elongation and fragment duplication. pG1 variant performance in small scale screening could successfully be verified in fed batch cultivations.

Abbreviations

CSRE: carbon source response element, F$: fungi specific TF matrix, GCN: gene copy number, GOI: gene of interest, Pp: *Pichia pastoris*, Sc: *Saccharomyces cerevisiae*, TF: transcription factor(s), TFBS: transcription factor binding site(s), YDM: yeast dry mass

Example 8: Determining the Repression, Induction, pG1-x Expression Level (Expression Level Compared to pG1), Induction Ratio The promoter strength as compared to the pG1 promoter and the induction ratio can be determined by the following standard assay: *P. pastoris* strains are screened in 24-deep well plates at 25° C. with shaking at 280 rpm with 2 mL culture per well. Glucose feed beads (6 mm, Kuhner, CH) are used to generate glucose-limiting growth conditions. Cells are analyzed for eGFP expression during repression (YP+1% glycerol, exponential phase) and induction (YP+1 feed bead, for 20-28 hours) using flow cytometry. The specific eGFP fluorescence is calculated from fluorescence intensity and forward scatter for at least 3000 data points of the flow cytometry data. Forward scatter is a relative measure for the cell volume. Specific eGFP fluorescence equals fluorescence intensity (FI) divided by forward scatter (FSC) to the 1.5, that is $FI/FSC^{1.5}$ (Hohenblum, H., N. Borth & D. Mattanovich, (2003) Assessing viability and cell-associated product of recombinant protein producing *Pichia pastoris* with flow cytometry. J Biotechnol 102: 281-290). From this data, the geometric mean of the population's specific fluorescence is used, and normalized by subtracting background signal of non-producing *P. pastoris* wild type cells. The specific eGFP fluorescence of the glycerol condition is termed "Repression", and the specific eGFP fluorescence of the limited glucose condition (glucose feed beads) is termed "Induction". Therefore, only Repression and Induction values of the same screening and flow cytometry measurement can be compared and used for calculations. To determine relative pG1-x promoter strength, the eGFP expression levels in the induced state of the pG1-x promoters were compared to the original pG1 promoter by dividing the Induction value of a strain comprising the pG1-x promoter by the Induction value of a strain comprising the original pG1 promoter. The Induction ratio is calculated by dividing the Induction value by the Repression value of the same strain/promoter. Repression, Induction, relative pG1-x promoter strength and Induction ratio are shown in Table 6 for several promoter variants Further examples have proven that by using a pG1-x promoter comprising or consisting of the nucleotide sequence SEQ ID 49 a model protein (POI) was produced in *P. pastoris* at much higher yields (a fold increase of more than 3.5 fold), fed-batch experiments) as compared to the unmodified pG1 promoter (reference SEQ ID 7).

Example 9: Comparison of "Speed Fermentation" and Standard Fermentation

Summary: Significantly reduced fermentation times could be obtained for the expression of an alternative scaffold protein as model protein under control of a pG1-3 embodiment of SEQ ID 39 (pG1-D1240 (SEQ ID 49)) promoter by employing a space-time yield optimized fed batch protocol instead of using a standard fed batch regime.

A clone expressing a model protein under control of pG1-D1240 (SEQ ID 49) was selected for the fed batch cultivations. Fed batch cultivations were performed in DASGIP reactors (Eppendorf, Germany) with a final working volume of 0.5 L. Media and trace element solution were prepared as previously described in Example 7, except for the glycerol concentration in the glycerol batch medium which was 45 g/L. During cultivation the dissolved oxygen level was controlled at DO=30% with the stirrer speed (400-1200 rpm). Aeration rate was 1 wm air, the temperature was controlled at 25° C. and the pH set-point of 5.0 was controlled with addition of $NH_4OH$ (25%). To start the bioreactor cultivation, 250 mL batch medium were inoculated from a pre-culture of the respective *P. pastoris* clone with a starting optical density (OD600) of 1.0. The batch phase on glycerol took approximately 30 h and reached a dry biomass concentration of 25-29 g/L. The glycerol batch phase was followed by a glucose-limited fed batch. Two different fed batch cultivation modes were compared: (A) a standard fed batch protocol using a constant feed rate, (B) a space-time yield optimized fed batch protocol ("Speed fermentation"), where the glucose feed rate was optimized to maximize the volumetric productivity of the fermentation.

For the standard cultivation, a constant glucose feed rate of 1.25 mL $h^{-1}$ was selected. The fed batch cultivation was maintained for 100 h (126 h total cultivation time) resulting in a final dry biomass concentration of approximately 90 g $L^{-1}$. For the "Speed fermentation", a model-based optimization algorithm (Maurer et al., Microbial Cell Factories, 2006, 5:37) was adopted, where the optimized volumetric glucose feed rate F(t) was approximated by a linearly increasing function: $F(t)\ [mL\ h^{-1}]=0.3234\ mL\ h^{-2}*t+3.3921\ mL\ h^{-1}$. The fed batch phase was maintained for t=33 h (60 h total cultivation time), which resulted in a final dry biomass concentration of approximately 140 g $L^{-1}$.

Samples were taken at the end of the batch and during the fed batch phase. Product titers were analyzed from clarified supernatants using a HT low MW protein express reagent kit and the Caliper LabChip G×I system (Perkin Elmer, USA). As a reference standard for absolute quantification a purified standard of alternative scaffold protein was used.

FIG. 9 shows the product and biomass generation over the total cultivation time for the standard cultivation (A) and the "Speed fermentation" (B). In comparison, final product titers of 6.4 g $L^{-1}$ and 4.3 g $L^{-1}$ could be reached after 60 h and 126 h for the "Speed fermentation" and the standard fermentation, respectively. In other words, a 1.4-fold higher titer (resp. 1.2-fold higher broth titers) could be found in significantly shorter fermentation time (−66 h) when supplementing the glucose feed during expression under the pG1-D1240 (SEQ ID 49) promoter as described for the "Speed fermentation" instead of using the described standard feed regime.

Tables

TABLE 1

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$TEAF | TEA/ATTS DNA binding domain factors | F$ABAA.01 | Aspergillus spore/ developmental regulator | −985 | −969 | − | accctaCAT Tctactgg (SEQ ID 271) |
| F$NRGF | NRG zinc finger factors | F$NRG1.01 | Transcriptional repressor Nrg1 | −976 | −964 | + | tgtAGGGtc ccca (SEQ ID 272) |
| F$YSTR | Yeast stress response elements | F$MSN2.01 | Transcriptional activator for genes in multistress response | −956 | −942 | − | gagactaGG GGgagc (SEQ ID 273) |
| F$PDRE | Pleiotropic drug resistance responsive elements | F$PDRE.01 | Pleiotropic drug resistance responsive element (yeast) | −944 | −936 | − | TCCCtggag (SEQ ID 274) |
| F$YMAT | Yeast mating factors | F$HMRA2.01 | Hidden Mat Right A2, a2 is one of two genes encoded by the a mating type cassette in *S. cerevisiae* | −939 | −927 | + | gggaaaTG TAaaa (SEQ ID 275) |
| F$MADS | Yeast MADS-Box factors | F$RLM1.01 | Yeast MADS-Box RLM1 transcription factor | −926 | −908 | − | gtttTCTAtta gcagtata (SEQ ID 276) |
| O$INRE | Core promoter initiator elements | O$DINR.01 | Drosophila initiator motifs | −899 | −889 | + | gcTCAGttgtc (SEQ ID 277) |
| F$RFXP | Regulatory factor X protein, homologous to mammalian RFX1-5 | F$RFX1.02 | RFX1 (CRT1), acts by recruiting Ssn6 and Tup1, general repressors to the promoters of damage-inducible genes | −896 | −882 | − | ttatcctgaCA ACtg (SEQ ID 278) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$HOMD | Homeodomain-containing transcriptional regulators | F$YOX1.02 | Yeast homeobox 1, homeodomain-containing transcriptional repressor | -889 | -875 | - | aacgtaATTAtcctg (SEQ ID 279) |
| F$HOMD | Homeodomain-containing transcriptional regulators | F$YOX1.02 | Yeast homeobox 1, homeodomain-containing transcriptional repressor | -888 | -874 | + | aggataATTAcgttc (SEQ ID 280) |
| O$MTEN | Core promoter motif ten elements | O$DMTE.01 | Drosophila motif ten element | -888 | -868 | - | acagtcgAACGtaattatcct (SEQ ID 281) |
| F$BZIP | Fungal basic leucine zipper family | F$CST6.01 | Chromosome stability, bZIP transcription factor of the ATF/CREB family (ACA2) | -885 | -865 | - | actacagtcgaACGTaattat (SEQ ID 282) |
| F$MADS | Yeast MADS-Box factors | F$RLM1.01 | Yeast MADS-Box RLM1 transcription factor | -855 | -837 | - | tcttTCTAacaatacagat (SEQ ID 283) |
| F$YMAT | Yeast mating factors | F$MATALPHA2.02 | Homeodomain transcriptional repressor Matalpha2 | -853 | -841 | + | ctgtaTTGTtaga (SEQ ID 284) |
| F$MMAT | M-box interacting with Mat1-Mc | F$MAT1MC.01 | HMG-BOX protein interacts with M-box site, cooperativity with HMG-Box STE11 protein | -852 | -842 | + | tgtATTGttag (SEQ ID 285) |
| F$STPF | STP gene family | F$STP2.01 | Proteolytically activated transcription factor | -828 | -814 | - | gcggcGCCGtaaaaa (SEQ ID 286) |
| F$STPF | STP gene family | F$STP2.01 | Proteolytically activated transcription factor | -823 | -809 | + | acggcGCCGccatat (SEQ ID 287) |
| **F$YADR** | **Yeast metabolic regulator** | **F$ADR1.01** | **Alcohol Dehydrogenase Regulator, carbon source-responsive zinc-finger transcription factor** | **-785** | **-777** | **+** | **aaCCCCact** (SEQ ID 288) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$RFXP | Regulatory factor X protein, homologous to mammalian RFX1-5 | F$RFX1.01 | RFX1 (CRT1) is a DNA-binding protein that acts by recruiting Ssn6 and Tup1, general repressors to the promoters of damage-inducible genes | -763 | -749 | - | cgtgtataGCAAcag (SEQ ID 289) |
| F$YMCB | Yeast Mlu I cell cycle box | F$SWI4.01 | DNA binding component of the SBF(SCB binding factor) complex (Swi4p-Swi6p) | -756 | -744 | + | tatacaCGAAcca (SEQ ID 290) |
| F$CYTO | Activator of cytochrome C | F$HAP1.01 | HAP1, *S. cerevisiae* member of GAL family, regulates heme dependent cytochrome expression | -715 | -701 | + | ctgaagtcATCGgtt (SEQ ID 291) |
| F$FKHD | Fungal fork head transcription factors | F$FKH1.01 | Fork head transcription factor Fkh1 | -709 | -693 | + | tcatcggTTAAcaatca (SEQ ID 292) |
| F$ROX1 | Repressor of hypoxic genes | F$ROX1.01 | Heme-dependent transcriptional repressor of hypoxic genes | -704 | -692 | - | ttgaTTGTtaacc (SEQ ID 293) |
| F$YMAT | Yeast mating factors | F$MATALPHA2.02 | Homeodomain transcriptional repressor Matalpha2 | -703 | -691 | - | cttgaTTGTtaac (SEQ ID 294) |
| F$MMAT | M-box interacting with Mat1-Mc | F$MAT1MC.01 | HMG-BOX protein interacts with M-box site, cooperativity with HMG-Box STE11 protein | -702 | -692 | - | ttgATTGttaa (SEQ ID 295) |
| F$YHSF | Yeast heat shock factors | F$HSF1.01 | Trimeric heat shock transcription factor | -678 | -646 | - | aacacctactgaatatGGAAaggagcattcaga (SEQ ID 296) |
| F$PHD1 | Pseudohyphal determinant 1 | F$PHD1.03 | Transcription factor involved in regulation of filamentous growth | -635 | -623 | - | gcaGTGCatgcaa (SEQ ID 297) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start posi-tion | End posi-tion | Strand | Sequence SEQ ID NO. |
|---|---|---|---|---|---|---|---|
| **F$MGCM** | **Monomeric Gal4-class motifs** | **F$RGT1.02** | **Glucose-responsive transcription factor involved in regulation of glucose transporters** | **-628** | **-612** | **+** | **cactgCGG Aagaattag** (SEQ ID 298) |
| **F$CSRE** | **Carbon source-responsive elements** | **F$CSRE.01** | **Carbon source-responsive element (yeast)** | **-626** | **-612** | **-** | **ctaattctTC CGcag** (SEQ ID 299) |
| F$YRSC | Yeast transcription factors remodeling chromatin structure | F$RSC3.01 | Component of the RSC chromatin remodeling complex | -614 | -594 | + | tagccaatag CGCGtttcata (SEQ ID 300) |
| F$YMCB | Yeast Mlu I cell cycle box | F$STUAP.01 | Aspergillus Stunted protein, (bHLH)-like structure, regulates multicellular complexity during asexual reproduction | -609 | -597 | - | gaaaCGCG ctatt (SEQ ID 301) |
| F$YMCB | Yeast Mlu I cell cycle box | F$MCB.01 | Mlu I cell cycle box, activates G1/S-specific transcription (yeast) | -608 | -596 | + | atagCGCGt ttca (SEQ ID 302) |
| F$DUIS | DAL upstream induction sequence | F$DAL82.01 | Transcriptional activator for allantoin catabolic genes | -597 | -589 | + | cataTGCGc (SEQ ID 303) |
| F$PHD1 | Pseudohyphal determinant 1 | F$PHD1.02 | Transcription factor involved in regulation of filamentous growth | -597 | -585 | + | cataTGCG ctttt (SEQ ID 304) |
| F$RDNA | RDNA binding factor | F$REB1.02 | rDNA enhancer binding protein 1, termination factor for RNA polymerase I and transcription factor for RNA polymerase II | -589 | -577 | + | cttTTACccc ctc (SEQ ID 305) |
| **F$YMIG** | **Yeast GC-Box Proteins** | **F$MIG1.02** | **MIG1, zinc finger protein mediates glucose repression** | **-586** | **-568** | **-** | **ttgacaaaag aGGGGgtaa** (SEQ ID 306) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$YSTR | Yeast stress response elements | F$MSN2.01 | Transcriptional activator for genes in multistress response | -586 | -572 | - | caaaagaG GGGgtaa (SEQ ID 307) |
| F$BZIP | Fungal basic leucine zipper family | F$YAP1.02 | Yeast activator protein of the basic leucine zipper (bZIP) family | -585 | -565 | + | taccccctctttt GTCAagcg (SEQ ID 308) |
| F$TALE | Fungal TALE homeodomain class | F$TOS8.01 | Homeodomain-containing transcription factor | -579 | -567 | + | ctcttttGTCAag (SEQ ID 309) |
| F$DUIS | DAL upstream induction sequence | F$DAL82.01 | Transcriptional activator for allantoin catabolic genes | -567 | -559 | - | atttTGCGc (SEQ ID 310) |
| F$YMIG | **Yeast GC-Box Proteins** | **F$MIG1.01** | **MIG1, zinc finger protein mediates glucose repression** | **-553** | **-535** | **+** | **taagatttggt GGGGgtgt** (SEQ ID 311) |
| F$YRAP | Yeast activator of glycolyse genes/ repressor of mating type 1 | F$RAP1.06 | RAP1 (TUF1), activator or repressor depending on context | -546 | -524 | - | gctaacggct caCACCcc cacca (SEQ ID 312) |
| F$IRTF | Iron-responsive transcriptional activators | F$AFT2.01 | Activator of Fe(iron) transcription 2, iron-regulated transcriptional activator | -543 | -529 | - | cggctcaCA CCcca (SEQ ID 313) |
| O$VTBP | Vertebrate TATA binding protein factor | O$ATATA.01 | Avian C-type LTR TATA box | -530 | -514 | - | ttgtactTCA Gctaacg (SEQ ID 314) |
| F$RRPE | Ribosomal RNA processing element | F$STB3.01 | Ribosomal RNA processing element (RRPE)-binding protein | -504 | -488 | - | tgcagtttTTT Caggga (SEQ ID 315) |
| **F$MGCM** | **Monomeric Gal4-class motifs** | **F$RGT1.02** | **Glucose-responsive transcription factor involved in regulation of glucose transporters** | **-442** | **-426** | - | **atatcAGG Aaaaacata** (SEQ ID 316) |
| F$GATA | Fungal GATA binding factors | F$GZF3.01 | GATA zinc finger protein Gzf3 | -434 | -420 | + | tcctGATAtg catca (SEQ ID 317) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$PHD1 | Pseudohyphal determinant 1 | F$PHD1.01 | Transcription factor involved in regulation of filamentous growth | -430 | -418 | + | gataTGCAt caaa (SEQ ID 318) |
| F$YMAT | Yeast mating factors | F$MATA1.01 | Homeodomain protein mating factor a1 | -429 | -417 | | ttttGATGca tat (SEQ ID 319) |
| F$ICGG | Inverted CGG triplets spaced preferentially by 10 bp | F$CHA4.01 | Fungal zinc cluster transcription factor Cha4, single triplet | -408 | -388 | + | taaaacctga atctCCGCt at (SEQ ID 320) |
| F$MGCM | Monomeric Gal4-class motifs | F$YRR1.01 | Zinc cluster transcription factor, activates genes involved in multidrug resistance (PDR2) | -403 | -387 | - | aatagCGG Agattcagg (SEQ ID 321) |
| F$RDR1 | Repressor of Drug Resistance 1 | F$RDR1.01 | Repressor of Drug Resistance 1 (transcriptional repressor involved in the control of multidrug resistance | -399 | -389 | - | tagCGGAg att (SEQ ID 322) |
| F$RFXP | Regulatory factor X protein, homologous to mammalian RFX1-5 | F$RFX1.02 | RFX1 (CRT1), acts by recruiting Ssn6 and Tup1, general repressors to the promoters of damage-inducible genes | -366 | -352 | - | ttgtcacgaA AACgg (SEQ ID 323) |
| F$YMCB | Yeast Mlu I cell cycle box | F$SWI4.01 | DNA binding component of the SBF(SCB binding factor) complex (Swi4p-Swi6p) | -364 | -352 | - | ttgtcaCGA Aaac (SEQ ID 324) |
| F$BZIP | Fungal basic leucine zipper family | F$YAP1.02 | Yeast activator protein of the basic leucine zipper (bZIP) family | -361 | -345 | - | tggaaattaat ttGTCAcgaa (SEQ ID 325) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$RRPE | Ribosomal RNA processing element | F$STB3.01 | Ribosomal RNA processing element (RRPE)-binding protein | -359 | -347 | - | aattaattTGTCacgaa (SEQ ID 326) |
| F$TALE | Fungal TALE homeodomain class | F$CUP9.01 | Homeodomain transcriptional repressor Cup9 | -361 | -341 | - | ttaattTGTCacg (SEQ ID 327) |
| F$HOMD | Homeodomain-containing transcriptional regulators | F$YOX1.01 | Yeast homeobox 1, homeodomain-containing transcriptional repressor | -358 | -344 | - | aaattAATTtgtcac (SEQ ID 328) |
| F$HOMD | Homeodomain-containing transcriptional regulators | F$YOX1.01 | Yeast homeobox 1, homeodomain-containing transcriptional repressor | -357 | -343 | + | tgacaAATTaatttc (SEQ ID 329) |
| F$ICGG | Inverted CGG triplets spaced preferentially by 10 bp | F$TEA1.01 | Ty1 enhancer activator, zinc cluster DNA-binding protein | -357 | -337 | + | tgacaaaTTAAtttccaacgg (SEQ ID 330) |
| F$MGCM | Monomeric Gal4-class motifs | F$YRR1.01 | Zinc cluster transcription factor, activates genes involved in multidrug resistance (PDR2) | -352 | -336 | - | cccgtTGGAaattaatt (SEQ ID 331) |
| F$ASG1 | Activator of stress genes | F$ASG1.01 | Fungal zinc cluster transcription factor Asg1 | -340 | -324 | - | tCCGGacaagaccccgt (SEQ ID 332) |
| **F$MGCM** | **Monomeric Gal4-class motifs** | **F$RGT1.02** | **Glucose-responsive transcription factor involved in regulation of glucose transporters** | **-337** | **-321** | **-** | **ttatcCGGAcaagaccc** (SEQ ID 333) |
| **F$MGCM** | **Monomeric Gal4-class motifs** | **F$RGT1.02** | **Glucose-responsive transcription factor involved in regulation of glucose transporters** | **-330** | **-320** | **+** | **ttgtcCGGAtaagagaa** (SEQ ID 334) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$RDR1 | Repressor of Drug Resistance 1 | F$RDR1.01 | Repressor of Drug Resistance 1 (transcriptional repressor involved in the control of multidrug resistance | -332 | -316 | + | gtcCGGAtaag (SEQ ID 335) |
| F$GATA | Fungal GATA binding factors | F$GATA.01 | GATA binding factor (yeast) | -329 | -315 | + | tccgGATAagagaat (SEQ ID 336) |
| F$PRES | Pheromone response elements | F$STE12.01 | Transcription factor activated by a MAP kinase signaling cascade, activates genes involved in mating or pseudohyphal/invasive growth pathways | -315 | -303 | - | taatcaAACAaaa (SEQ ID 337) |
| F$GATA | Fungal GATA binding factors | F$GAT1.01 | GATA-type Zn finger protein Gat1 | -311 | -297 | - | aacggATAAtcaaac (SEQ ID 338) |
| **F$MGCM** | **Monomeric Gal4-class motifs** | **F$RGT1.02** | **Glucose-responsive transcription factor involved in regulation of glucose transporters** | **-310** | **-294** | - | **ccgaaCGGAtaatcaaa** (SEQ ID 339) |
| O$MTEN | Core promoter motif ten elements | O$DMTE.01 | Drosophila motif ten element | -310 | -290 | - | ttatccgAACGgataatcaaa (SEQ ID 340) |
| F$YORE | Yeast oleate response elements | F$OAF1.01 | Oleate-activated transcription factor, acts alone and as a heterodimer with Pip2p | -307 | -283 | - | cgtccatttaTCCGaacggataatc (SEQ ID 341) |
| F$MGCM | Monomeric Gal4-class motifs | **F$RGT1.02** | **Glucose-responsive transcription factor involved in regulation of glucose transporters** | **-299** | **-289** | **+** | **ccgttCGGAtaaatgga** (SEQ ID 342) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start posi-tion | End posi-tion | Strand | Sequence SEQ ID NO. |
|---|---|---|---|---|---|---|---|
| F$YGAL | Yeast GAL4 factor | F$GAL4.01 | GAL4 transcriptional activator in response to galactose induction | -301 | -285 | - | agcaggcgtc catttatCCG Aacgg (SEQ ID 343) |
| **F$CSRE** | **Carbon source-responsive elements** | **F$SIP4.01** | **Zinc cluster transcriptional activator, binds to the carbon source-responsive element (CSRE) of gluconeogenic genes** | **-299** | **-285** | - | **tCCATttatc cgaac** (SEQ ID 344) |
| F$RDR1 | Repressor of Drug Resistance 1 | F$RDR1.01 | Repressor of Drug Resistance 1 (transcriptional repressor involved in the control of multidrug resistance | -301 | -277 | + | gttCGGAtaaa (SEQ ID 345) |
| F$YGAL | Yeast GAL4 factor | F$LAC9.01 | LAC9 binding site, homologous to GAL4 of *Saccharomyces cerevisiae* | -299 | -275 | + | gttCGGAta aatggacgcc tgctcc (SEQ ID 346) |
| F$FBAS | Fungi branched amino acid biosynthesis | F$LEU3.02 | LEU3, *S. cerevisiae*, zinc cluster protein | -275 | -261 | - | taaCCGGa aaaatatgg (SEQ ID 347) |
| **F$CSRE** | **Carbon source-responsive elements** | **F$CSRE.01** | **Carbon source-responsive element (yeast)** | **-276** | **-260** | **+** | **catattttTC CGgtt** (SEQ ID 348) |
| **F$MGCM** | **Monomeric Gal4-class motifs** | **F$RGT1.01** | **Glucose-responsive transcription factor involved in regulation of glucose transporters** | **-275** | **-259** | - | **ataacCGG Aaaaatatg** (SEQ ID 349) |
| F$ICGG | Inverted CGG triplets spaced preferentially by 10 bp | F$TEA1.01 | Ty1 enhancer activator, zinc cluster DNA-binding protein | -269 | -249 | - | aggtgggGT AAtaaccgg aaa (SEQ ID 350) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$RDNA | RDNA binding factor | F$REB1.02 | rDNA enhancer binding protein 1, termination factor for RNA polymerase I and transcription factor for RNA polymerase II | -262 | -250 | + | ttaTTACcccacc (SEQ ID 351) |
| F$YMCM | Yeast cell cycle and metabolic regulator | F$MCM1.02 | Yeast factor MCM1 cooperating with MATalpha factors | -258 | -250 | - | cTTCCaggtggggtaat (SEQ ID 352) |
| **F$YMIG** | **Yeast GC-Box Proteins** | **F$MIG1.01** | **MIG1, zinc finger protein mediates glucose repression** | **-260** | **-244** | - | **cacttccaggtGGGGtaat** (SEQ ID 353) |
| **F$YADR** | **Yeast metabolic regulator** | **F$ADR1.01** | **Alcohol Dehydrogenase Regulator, carbon source-responsive zinc-finger transcription factor** | **-260** | **-242** | **+** | **taCCCCacc** (SEQ ID 354) |
| **F$MGCM** | **Monomeric Gal4-class motifs** | **F$RGT1.02** | **Glucose-responsive transcription factor involved in regulation of glucose transporters** | -239 | -223 | - | **atcccCGGAaaattctg** (SEQ ID 355) |
| **F$YMIG** | **Yeast GC-Box Proteins** | **F$MIG1.01** | **MIG1, zinc finger protein mediates glucose repression** | -239 | -221 | **+** | **cagaattttccGGGGatta** (SEQ ID 356) |
| F$ICGG | Inverted CGG triplets spaced preferentially by 10 bp | F$TEA1.01 | Ty1 enhancer activator, zinc cluster DNA-binding protein | -232 | -224 | - | attatccGTAAtccccggaaa (SEQ ID 357) |
| F$ARPU | Regulator of pyrimidine and purine utilization pathway | F$PPR1.01 | Pyrimidine pathway regulator 1 | -231 | -223 | - | atccgtaatccCCGGaa (SEQ ID 358) |
| F$PDRE | Pleiotropic drug resistance responsive elements | F$PDRE.01 | Pleiotropic drug resistance responsive element (yeast) | -232 | -216 | - | TCCCcggaa (SEQ ID 359) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start posi-tion | End posi-tion | Strand | Sequence SEQ ID NO. |
|---|---|---|---|---|---|---|---|
| F$ARPU | Regulator of pyrimidine and purine utilization pathway | F$PPR1.01 | Pyrimidine pathway regulator 1 | -231 | -215 | + | tccggggatta CGGAta (SEQ ID 360) |
| F$PDRE | Pleiotropic drug resistance responsive elements | F$PDRE.01 | Pleiotropic drug resistance responsive element (yeast) | -230 | -216 | + | TCCGgggat (SEQ ID 361) |
| F$CYTO | Activator of cytochrome C | F$HAP1.01 | HAP1, *S. cerevisiae* member of GAL family, regulates heme dependent cytochrome expression | -233 | -213 | + | ccggggatT ACGgat (SEQ ID 362) |
| F$YQA1 | Neurospora crassa QA1 gene activator | F$QA1F.01 | qa-1F, required for quinic acid induction of transcription in the qa gene cluster | -228 | -208 | + | ggggattacg gaTAATac ggt (SEQ ID 363) |
| **F$MGCM** | **Monomeric Gal4-class motifs** | **F$RGT1.02** | **Glucose-responsive transcription factor involved in regulation of glucose transporters** | **-225** | **-209** | **+** | **gattaCGG Ataatacgg** (SEQ ID 364) |
| F$CYTO | Activator of cytochrome C | F$HAP1.01 | HAP1, *S. cerevisiae* member of GAL family, regulates heme dependent cytochrome expression | -221 | -207 | + | acggataaT ACGgtg (SEQ ID 365) |
| F$BZIP | Fungal basic leucine zipper family | F$CIN5.01 | bZIP transcriptional factor of the yAP-1 family that mediates pleiotropic drug resistance and salt tolerance | -208 | -188 | + | tggtctggatta atTAATacg (SEQ ID 366) |
| F$BZIP | Fungal basic leucine zipper family | F$CIN5.01 | bZIP transcriptional factor of the yAP-1 family that mediates pleiotropic drug resistance and salt tolerance | -203 | -189 | - | cttggcgtatta atTAATcca (SEQ ID 367) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start posi-tion | End posi-tion | Strand | Sequence SEQ ID NO. |
|---|---|---|---|---|---|---|---|
| F$HOMD | Homeodomain-containing transcriptional regulators | F$YOX1.02 | Yeast homeobox 1, homeodomain-containing transcriptional repressor | -202 | -188 | - | gtattaATTA atcca (SEQ ID 368) |
| F$HOMD | Homeodomain-containing transcriptional regulators | F$YOX1.02 | Yeast homeobox 1, homeodomain-containing transcriptional repressor | -203 | -183 | + | ggattaATT Aatacg (SEQ ID 369) |
| F$YABF | Yeast ABF factors | F$ABF1.04 | ARS (autonomously replicating sequence)-binding factor I | -202 | -184 | + | ggATTAatt aatacgccaa (SEQ ID 370) |
| F$PHRR | pH responsive regulators | F$RIM101.01 | Transcriptional repressor involved in response to pH and in cell wall construction | -192 | -176 | + | atacGCCA agtcttaca (SEQ ID 371) |
| F$PRES | Pheromone response elements | F$STE12.01 | Transcription factor activated by a MAP kinase signaling cascade, activates genes involved in mating or pseudohyphal/invasive growth pathways | -175 | -163 | - | gactgcAAC Aaaa (SEQ ID 372) |
| F$FKHD | Fungal fork head transcription factors | F$FKH2.01 | Fork head transcription factor Fkh2 | -148 | -132 | + | gcaataaTA AAcaagat (SEQ ID 373) |
| F$YCAT | Yeast CCAAT binding factors | F$HAP234.01 | Yeast factor complex HAP2/3/5, homolog to vertebrate NF-Y/CP1/CBF | -124 | -112 | | ctaatCCAAt aaa (SEQ ID 374) |
| F$YORE | Yeast oleate response elements | F$ORE.01 | Oleate response element, binding motif of Oaf1 homodimers or Oaf1/Pip2 heterodimers | -120 | -96 | - | CGGGgtca agctgcaact aatccaa (SEQ ID 375) |

TABLE 1 -continued

TFBS identified in the pG1 promoter sequence using MatInspector. Targeted carbon source-related TFBS of the pG1 deletion variants are shown in bold.

| Matrix Family | Detailed Family Information | Matrix | Detailed Matrix Information | Start position | End position | Strand | Sequence SEQ ID NO. |
|---|---|---|---|---|---|---|---|
| F$AAAU | *A. nidulans* activator of acetate utilization genes | F$FACBCB.01 | FACB, activator of acetate utilization genes with a GAL4-type Zn(II)2Cys6 zinc binuclear cluster | −109 | −93 | + | GCAGcttga ccccgcca (SEQ ID 376) |
| F$YMIG | Yeast GC-Box Proteins | F$MIG3.01 | Zinc finger transcriptional repressor MIG3 | −104 | −86 | − | ctagctatggc GGGGtcaa (SEQ ID 377) |
| F$YRAP | Yeast activator of glycolyse genes/ repressor of mating type I | F$RAP1.06 | RAP1 (TUF1), activator or repressor depending on context | −74 | −52 | − | tgcatcatcta aCACCcat agca (SEQ ID 378) |
| F$PHD1 | Pseudohyphal determinant 1 | F$PHD1.03 | Transcription factor involved in regulation of filamentous growth | −60 | −48 | − | caaGTGCa tcatc (SEQ ID 379) |
| O$VTBP | Vertebrate TATA binding protein factor | O$VTATA.01 | Cellular and viral TATA box elements | −31 | −15 | + | gagtaTAAA agatcctt (SEQ ID 380) |
| F$MGCM | Monomeric Gal4-class motifs | F$LYS14.01 | Transcriptional activator involved in regulation of genes of the lysine biosynthesis pathway | −17 | −1 | − | aagggtGG AAttttaag (SEQ ID 381) |

TABLE 2

Affected TFBS of the pG1 promoter sequence in the deletion mutants pG1-Δ1 to Δ12. Sequence analysis was done using MatInspector from Genomatix. Glucose- and carbon- related TFBS which were selected for deletion are shown in bold and the corresponding ID (1-12) and deleted positions are stated in column 1 and 2.

| Deletion | Position | Matrix Family | Detailed Family Information | Matrix | Detailed Matrix Information |
|---|---|---|---|---|---|
| **1** | **−785 to −777** | **F$YADR** | **Yeast metabolic regulator** | **F$ADR1.01** | **Alcohol Dehydrogenase Regulator, carbon source-responsive zinc-finger transcription factor** |
| **2** | **−628 to −612** | F$PHD1 | Pseudohyphal determinant 1 | F$PHD1.03 | Transcription factor involved in regulation of filamentous growth |
| | | **F$MGCM** | **Monomeric Gal4-class motifs** | **F$RGT1.02** | **Glucose-responsive transcription factor involved in regulation of glucose transporters** |
| | | **F$CSRE** | **Carbon source-responsive elements** | **F$CSRE.01** | **Carbon source-responsive element (yeast)** |

TABLE 2-continued

Affected TFBS of the pG1 promoter sequence in the deletion mutants pG1-Δ1 to Δ12. Sequence analysis was done using MatInspector from Genomatix. Glucose- and carbon- related TFBS which were selected for deletion are shown in bold and the corresponding ID (1-12) and deleted positions are stated in column 1 and 2.

| Deletion | Position | Matrix Family | Detailed Family Information | Matrix | Detailed Matrix Information |
|---|---|---|---|---|---|
| **3** | **−586 to −568** | F$RDNA | RDNA binding factor | F$REB1.02 | rDNA enhancer binding protein 1, termination factor for RNA polymerase I and transcription factor for RNA polymerase II |
| | | **F$YMIG** | **Yeast GC-Box Proteins** | **F$MIG1.02** | **MIG1, zinc finger protein mediates glucose repression** |
| | | F$YSTR | Yeast stress response elements | F$MSN2.01 | Transcriptional activator for genes in multistress response |
| | | F$BZIP | Fungal basic leucine zipper family | F$YAP1.02 | Yeast activator protein of the basic leucine zipper (bZIP) family |
| | | F$TALE | Fungal TALE homeodomain class | F$TOS8.01 | Homeodomain-containing transcription factor |
| **4** | **−553 to −535** | **F$YMIG** | **Yeast GC-Box Proteins** | **F$MIG1.01** | **MIG1, zinc finger protein mediates glucose repression** |
| | | F$YRAP | Yeast activator of glycolyse genes/ repressor of mating type I | F$RAP1.06 | RAP1 (TUF1), activator or repressor depending on context |
| | | F$IRTF | Iron-responsive transcriptional activators | F$AFT2.01 | Activator of Fe (iron) transcription 2, iron-regulated transcriptional activator |
| **5** | **−442 to −426** | **F$MGCM** | **Monomeric Gal4-class motifs** | **F$RGT1.02** | **Glucose-responsive transcription factor involved in regulation of glucose transporters** |
| | | F$GATA | Fungal GATA binding factors | F$GZF3.01 | GATA zinc finger protein Gzf3 |
| | | F$PHD1 | Pseudoh yphal determinant 1 | F$PHD1.01 | Transcription factor involved in regulation of filamentous growth |
| **6** | **−337 to −316** | F$ASG1 | Activator of stress genes | F$ASG1.01 | Fungal zinc cluster transcription factor Asg1 |
| | | **F$MGCM** | **Monomeric Gal4-class motifs** | **F$RGT1.02** | **Glucose-responsive transcription factor involved in regulation of glucose transporters** |
| | | **F$MGCM** | **Monomeric Gal4-class motifs** | **F$RGT1.02** | **Glucose-responsive transcription factor involved in regulation of glucose transporters** |
| | | F$RDR1 | Repressor of Drug Resistance 1 | F$RDR1.01 | Repressor of Drug Resistance 1 (transcriptional repressor involved in the control of multidrug resistance |
| | | F$GATA | Fungal GATA binding factors | F$GATA.01 | GATA binding factor (yeast) |
| | | F$PRES | Pheromone response elements | F$STE12.01 | Transcription factor activated by a MAP kinase signaling cascade, activates genes involved in mating or pseudohyphal/invasive growth pathways |
| **7** | **−310 to −299** | F$GATA | Fungal GATA binding factors | F$GAT1.01 | GATA-type Zn finger protein Gat1 |
| | | **F$MGCM** | **Monomeric Gal4-class motifs** | **F$RGT1.02** | **Glucose-responsive transcription factor involved in regulation of glucose transporters** |
| | | O$MTEN | Core promoter motif ten elements | O$DMTE.01 | *Drosophila* motif ten element |
| | | F$YORE | Yeast oleate response elements | F$OAF1.01 | Oleate-activated transcription factor, acts alone and as a heterodimer with Pip2p |
| | | **F$MGCM** | **Monomeric Gal4-class motifs** | **F$RGT1.02** | **Glucose-responsive transcription factor involved in regulation of glucose transporters** |
| | | F$YGAL | Yeast GAL4 factor | F$GAL4.01 | GAL4 transcriptional activator in response to galactose induction |

TABLE 2-continued

Affected TFBS of the pG1 promoter sequence in the deletion mutants pG1-Δ1 to Δ12. Sequence analysis was done using MatInspector from Genomatix. Glucose- and carbon- related TFBS which were selected for deletion are shown in bold and the corresponding ID (1-12) and deleted positions are stated in column 1 and 2.

| Deletion | Position | Matrix Family | Detailed Family Information | Matrix | Detailed Matrix Information |
|---|---|---|---|---|---|
| **8** | **−293 to −285** | **F$CSRE** | **Carbon source-responsive elements** | **F$SIP4.01** | **Zinc cluster transcriptional activator, binds to the carbon source-responsive element (CSRE) of gluconeogenic genes** |
| | | F$RDR1 | Repressor of Drug Resistance 1 | F$RDR1.01 | Repressor of Drug Resistance 1 (transcriptional repressor involved in the control of multidrug resistance |
| | | F$YGAL | Yeast GAL4 factor | F$LAC9.01 | LAC9 binding site, homologous to GAL4 of *Saccharomyces cerevisiae* |
| | | F$FBAS | Fungi branched amino acid biosynthesis | F$LEU3.02 | LEU3, *S. cerevisiae*, zinc cluster protein |
| **9** | **−275 to −261** | **F$CSRE** | **Carbon source-responsive elements** | **F$CSRE.01** | **Carbon source-responsive element (yeast)** |
| | | **F$MGCM** | **Monomeric Gal4-class motifs** | **F$RGT1.01** | **Glucose-responsive transcription factor involved in regulation of glucose transporters** |
| | | F$ICGG | Inverted CGG triplets spaced preferentially by 10 bp | F$TEA1.01 | Ty1 enhancer activator, zinc cluster DNA-binding protein |
| | | F$RDNA | RDNA binding factor | F$REB1.02 | rDNA enhancer binding protein 1, termination factor for RNA polymerase I and transcription factor for RNA polymerase II |
| | | F$YMCM | Yeast cell cycle and metabolic regulator | F$MCM1.02 | Yeast factor MCM1 cooperating with MATalpha factors |
| **10** | **−258 to −242** | **F$YMIG** | **Yeast GC-Box Proteins** | **F$MIG1.01** | **MIG1, zinc finger protein mediates glucose repression** |
| | | **F$YADR** | **Yeast metabolic regulator** | **F$ADR1.01** | **Alcohol Dehydrogenase Regulator, carbon source-responsive zinc-finger transcription factor** |
| **11** | **−239 to −221** | **F$MGCM** | **Monomeric Gal4-class motifs** | **F$RGT1.02** | **Glucose-responsive transcription factor involved in regulation of glucose transporters** |
| | | **F$YMIG** | **Yeast GC-Box Proteins** | **F$MIG1.01** | **MIG1, zinc finger protein mediates glucose repression** |
| | | F$ICGG | Inverted CGG triplets spaced preferentially by 10 bp | F$TEA1.01 | Ty1 enhancer activator, zinc cluster DNA-binding protein |
| | | F$ARPU | Regulator of pyrimidine and purine utilization pathway | F$PPR1.01 | Pyrimidine pathway regulator 1 |
| | | F$PDRE | Pleiotropic drug resistance responsive elements | F$PDRE.01 | Pleiotropic drug resistance responsive element (yeast) |
| | | F$ARPU | Regulator of pyrimidine and purine utilization pathway | F$PPR1.01 | Pyrimidine pathway regulator 1 |
| | | F$PDRE | Pleiotropic drug resistance responsive elements | F$PDRE.01 | Pleiotropic drug resistance responsive element (yeast) |
| | | F$CYTO | Activator of cytochrome C | F$HAP1.01 | HAP1, *S. cerevisiae* member of GAL family, regulates heme dependent cytochrome expression |
| | | F$YQA1 | *Neurospora crassa* QA1 gene activator | F$QA1F.01 | qa-1F, required for quinic acid induction of transcription in the qa gene cluster |

TABLE 2-continued

Affected TFBS of the pG1 promoter sequence in the deletion mutants pG1-Δ1 to Δ12. Sequence analysis was done using MatInspector from Genomatix. Glucose- and carbon- related TFBS which were selected for deletion are shown in bold and the corresponding ID (1-12) and deleted positions are stated in column 1 and 2.

| Deletion | Position | Matrix Family | Detailed Family Information | Matrix | Detailed Matrix Information |
|---|---|---|---|---|---|
| **12** | **−220 to −209** | **F$MGCM** | **Monomeric Gal4-class motifs** | **F$RGT1.02** | **Glucose-responsive transcription factor involved in regulation of glucose transporters** |
| | | F$CYTO | Activator of cytochrome C | F$HAP1.01 | HAP1, *S. cerevisiae* member of GAL family, regulates heme dependent cytochrome expression |

TABLE 3

Positions and TFBS deletions of pG1 TFBS deletion variants Targeted and affected TFBS in pG1 TFBS deletion variants (pG1-Δ1 to Δ12) are listed. Targeted carbon source-related TFBS are shown in bold. Detailed information for all TFBS and for the deleted TFBS is provided in Table 1 and Table 2, respectively.

| pG1-Δ | Position | TFBS Deletions (TF Matrices) |
|---|---|---|
| **1** | **−785 to −777** | **F$ADR1.01** |
| **2** | **−628 to −612** | F$PHD1.03, **F$RGT1.02, F$CSRE.01** |
| **3** | **−586 to −568** | F$REB1.02, **F$MIG1.02**, F$MSN2.01, F$YAP1.02, F$TOS8.01 |
| **4** | **−553 to −535** | **F$MIG1.01**, F$RAP1.06, F$AFT2.01 |
| **5** | **−442 to −426** | **F$RGT1.02**, F$GZF3.01, F$PHD1.01 |
| **6** | **−337 to −316** | F$ASG1.01, **F$RGT1.02, F$RGT1.02**, F$RDR1.01, F$GATA.01 |
| **7** | **−310 to −299** | F$STE12.01, F$GAT1.01, **F$RGT1.02**, O$DMTE.01, F$OAF1.01 |

TABLE 3-continued

Positions and TFBS deletions of pG1 TFBS deletion variants Targeted and affected TFBS in pG1 TFBS deletion variants (pG1-Δ1 to Δ12) are listed. Targeted carbon source-related TFBS are shown in bold. Detailed information for all TFBS and for the deleted TFBS is provided in Table 1 and Table 2, respectively.

| pG1-Δ | Position | TFBS Deletions (TF Matrices) |
|---|---|---|
| **8** | **−293 to −285** | F$OAF1.01, **F$RGT1.02**, F$GAL4.01, **F$SIP4.01**, F$RDR1.01, F$LAC9.01 |
| **9** | **−275 to −261** | F$LEU3.02, **F$CSRE.01, F$RGT1.01**, F$TEA1.01 |
| **10** | **−258 to −242** | F$REB1.02, F$MCM1.02, **F$MIG1.01**, F$ADR1.01 |
| **11** | **−239 to −221** | **F$RGT1.02, F$MIG1.01**, F$TEA1.01, F$PPR1.01, F$PDRE.01, F$PPR1.01, F$PDRE.01 |
| **12** | **−220 to −209** | F$HAP1.01, F$QA1F.01, **F$RGT1.02**, F$HAP1.01 |

TABLE 4

| Primer sequences | | | | |
|---|---|---|---|---|
| # | Name | Product | Sequence (SEQ ID NO.) | $T_M$ |
| 1 | pG1_fw | pG1 | GATAGGGCCCCAAACATTTGCTCCCCCTAGTCTC (SEQ ID 382) | 71 |
| 2 | pG1 back | pG1/pG1-s | GATACCTGCAGGAAGGGTGGAATTTTAAGGATCTTTTAT (SEQ ID 383) | 70 |
| 3 | pG1-858_fw | pG1-s858 | GATAGGGCCCGGAATCTGTATTGTTAGAAAGAACGAGAG (SEQ ID 384) | 71 |
| 4 | pG1-663_fw | pG1-s663 | GATAGGGCCCCCATATTCAGTAGGTGTTTCTTGCAC (SEQ ID 385) | 69 |
| 5 | pG1-492_fw | pG1-s492 | GATAGGGCCCCTGCAGATAGACTTCAAGATCTCAGG (SEQ ID 386) | 69 |
| 6 | pG1-371_fw | pG1-s371 | GATAGGGCCCGACCCCGTTTTCGTGACAAATT (SEQ ID 387) | 70 |
| 7 | pG1-328_fw | pG1-s328 | GATAGGGCCCCCGGATAAGAGAATTTTGTTTGATTAT (SEQ ID 388) | 70 |
| 8 | pG1-283_fw | pG1-s283 | GATAGGGCCCGCCTGCTCCATATTTTTCCGG (SEQ ID 389) | 71 |
| 9 | pG1-211_fw | pG1-s211 | GATAGGGCCCCGGTGGTCTGGATTAATTAATACG (SEQ ID 390) | 68 |
| 10 | pG1-66_fw | pG1-s66 | GATAGGGCCCGTGTTAGATGATGCACTTGGATGC (SEQ ID 391) | 68 |

TABLE 4 -continued

| Primer sequences | | | | |
|---|---|---|---|---|
| # | Name | Product | Sequence (SEQ ID NO.) | $T_M$ |
| 11 | pG1-Δ1_fw | pG1-Δ1 | GAAAACAGCTTGAACTTTCAAAGGTTCTGTTGCTATACAC GAAC (SEQ ID 392) | 69 |
| 12 | pG1-Δ1_bw | pG1-Δ1 | GTTCGTGTATAGCAACAGAACCTTTGAAAGTTCAAGCTG TTTTCACACGGCC (SEQ ID 393) | 68 |
| 13 | pG1-Δ2_fw | pG1-Δ2 | GTAGGTGTTTCTTGCACTTTTGCATGCCAATAGCGCGTT TCATATGC (SEQ ID 394) | 67 |
| 14 | pG1-Δ2_bw | pG1-Δ2 | GCATATGAAACGCGCTATTGGCATGCAAAAGTGCAAGAA ACACCTAC (SEQ ID 395) | 68 |
| 15 | pG1-Δ3_fw | pG1-Δ3 | CGCGTTTCATATGCGCTTGCGCAAAATGCCTGTAAGATT TG (SEQ ID 396) | 68 |
| 16 | pG1-Δ3 bw | pG1-Δ3 | CAAATCTTACAGGCATTTTGCGCAAGCGCATATGAAACG CG (SEQ ID 397) | 65 |
| 17 | pG1-Δ4_fw | pG1-Δ4 | GTCAAGCGCAAAATGCCTGGAGCCGTTAGCTGAAGTAC AACAG (SEQ ID 398) | 65 |
| 18 | pG1-Δ4_bw | pG1-Δ4 | CTGTTGTACTTCAGCTAACGGCTCCAGGCATTTTGCGCT TGAC (SEQ ID 399) | 67 |
| 19 | pG1-Δ5_fw | pG1-Δ5 | GGGATTCCCACTATTTGGTATTCTGAGCATCAAAACTCTA ATCTAAAACCTGAATCTC (SEQ ID 400) | 67 |
| 20 | pG1-Δ5_bw | pG1-Δ5 | GAGATTCAGGTTTTAGATTAGAGTTTTGATGCTCAGAATA CCAAATAGTGGGAATCCC (SEQ ID 401) | 68 |
| 21 | pG1-Δ6_fw | pG1-Δ6 | GTTTTCGTGACAAATTAATTTCCAACGTTTTGTTTGATTAT CCGTTCGG (SEQ ID 402) | 65 |
| 22 | PG1-Δ6_bw | pG1-Δ6 | CCGAACGGATAATCAAACAAAACGTTGGAAATTAATTTGT CACGAAAAC (SEQ ID 403) | 68 |
| 23 | pG1-Δ7_fw | pG1-Δ7 | CCGGATAAGAGAATTTTGTTCGGATAAATGGACGCCTG (SEQ ID 404) | 67 |
| 24 | pG1-Δ7_bw | pG1-Δ7 | CAGGCGTCCATTTATCCGAACAAAATTCTCTTATCCGGA CAAGACC (SEQ ID 405) | 68 |
| 25 | pG1-Δ8_fw | pG1-Δ8 | GAATTTTGTTTGATTATCCGTTCGGCGCCTGCTCCATATT TTTCCG (SEQ ID 406) | 70 |
| 26 | pG1-Δ8_bw | pG1-Δ8 | CGGAAAAATATGGAGCAGGCGCCGAACGGATAATCAAA CAAAATTC (SEQ ID 407) | 67 |
| 27 | pG1-Δ9_fw | pG1-Δ9 | CGGATAAATGGACGCCTGCTCATTACCCCACCTGGAAGT GCC (SEQ ID 408) | 68 |
| 28 | PG1-Δ9_bw | pG1-Δ9 | GGCACTTCCAGGTGGGGTAATGAGCAGGCGTCCATTTA TCCG (SEQ ID 409) | 70 |
| 29 | PG1-Δ10_fw | pG1-Δ10 | GCCTGCTCCATATTTTTCCGGTTATCCCAGAATTTTCCG (SEQ ID 410) | 53 |
| 30 | pG1-Δ10_bw | pG1-Δ10 | CGGAAAATTCTGGGATAACCGGAAAAATATGGAGCAGGC (SEQ ID 411) | 69 |

TABLE 4 -continued

| Primer sequences | | | | |
|---|---|---|---|---|
| # Name | Product | Sequence (SEQ ID NO.) | | $T_M$ |
| 31 PG1-Δ11_fw | pG1-Δ11 | TATTACCCCACCTGGAAGTGCCCGGATAATACGGTGGTC TGGATTAAT (SEQ ID 412) | | 67 |
| 32 PG1-Δ11_bw | pG1-Δ11 | ATTAATCCAGACCACCGTATTATCCGGGCACTTCCAGGT GGGGTAATA (SEQ ID 413) | | 68 |
| 33 PG1-Δ12_fw | pG1-Δ12 | CCAGAATTTTCGGGGATTATGGTCTGGATTAATTAATAC GCCAAGTC (SEQ ID 414) | | 68 |
| 34 PG1-Δ12_bw | pG1-Δ12 | GACTTGGCGTATTAATTAATCCAGACCATAATCCCCGGA AAATTCTGG (SEQ ID 415) | | 65 |
| 35 pG1-ATAT14_fw | pG1-ΔT14 | CAAAACTCTAATCTAAAACCTGAATCTCCGCGATGACCC CGTTTTCGTGAC (SEQ ID 416) | | 67 |
| 36 pG1-ATAT14_bw | PG1-ΔT14 | GTCACGAAAACGGGGTCATCGCGGAGATTCAGGTTTTA GATTAGAGTTTTG (SEQ ID 417) | | 69 |
| 37 pG1-TAT18_fw | pG1-T18 | CCTGAATCTCCGCTTTTTTTTTTTTTTTTTTGATGACCCCG (SEQ ID 418) | | 70 |
| 38 pG1-TAT18_bw | PG1-T18 | CGGGGTCATCAAAAAAAAAAAAAAAAAAGCGGAGATTCAGG (SEQ ID 419) | | 70 |
| 39 pG1-TAT20_fw | pG1-T20 | CCTGAATCTCCGCTTTTTTTTTTTTTTTTTTTTGATGACCC CG (SEQ ID 420) | | 70 |
| 40 pG1-TAT20_bw | pG1-T20 | CGGGGTCATCAAAAAAAAAAAAAAAAAAAAGCGGAGATT CAGG (SEQ ID 421) | | 70 |
| 41 pG1-TAT22_fw | pG1-T22 | CCTGAATCTCCGCTTTTTTTTTTTTTTTTTTTTTTGATGAC CCCG (SEQ ID 422) | | 70 |
| 42 pG1-TAT22_bw | pG1-T22 | CGGGGTCATCAAAAAAAAAAAAAAAAAAAAAAGCGGAGATT CAGG (SEQ ID 423) | | 70 |
| 43 pG1-d-472_fw | pG1-d1240/-d1427 | GATACTGCAGCTCAGGGATTCCCACTATTTGGTATTC (SEQ ID 424) | | 68 |
| 44 pG1-d-188_bw | pG1-d1240 | GATAGATCTCGTATTAATTAATCCAGACCACCG (SEQ ID 425) | | 64 |
| 45 pG1-d-1_bw | pG1-d1427 | GATAGATCTAAGGGTGGAATTTTAAGGATCTTTTAT (SEQ ID 426) | | 64 |

TABLE 5

Fed batch cultivation of pG1 (herein referred to as pG1 #8) and pG1-x variants (herein also referred to as pG1-variants) expressing eGFP Relative eGFP fluorescence is shown for the batch end and for the fed batch end. The time points were set to 0 at the batch end. A clone expressing eGFP under control of pG1 (#8) was compared to clones expressing under control of a pG1 deletion (pG1-Δ2), a TAT14 mutation (pG1-T16), and a duplication (pG1-D1240) variant. The biomass concentrations (YDM) in the batch and fed batch were as expected.

| | Batch End | | | | Fed Batch End | | | |
|---|---|---|---|---|---|---|---|---|
| Clone | t [h] | YDM [g/L] | relative eGFP fluorescence | % | t [h] | YDM [g/L] | relative eGFP fluorescence | % |
| pG1 #8 | −5.3 | 9.8 | 44 +/− 1 | 100 | 19.5 | 118.6 | 2005 +/− 36 | 100 |
| PG1-Δ2 #3 | −4.6 | 11.0 | 51 +/− 1 | 116 | 19.5 | 110.6 | 1819 +/− 43 | 91 |

TABLE 5-continued

Fed batch cultivation of pG1 (herein referred to as pG1 #8) and pG1-x variants (herein also referred to as pG1-variants) expressing eGFP Relative eGFP fluorescence is shown for the batch end and for the fed batch end. The time points were set to 0 at the batch end. A clone expressing eGFP under control of pG1 (#8) was compared to clones expressing under control of a pG1 deletion (pG1-Δ2), a TAT14 mutation (pG1-T16), and a duplication (pG1-D1240) variant. The biomass concentrations (YDM) in the batch and fed batch were as expected.

| | Batch End | | | | Fed Batch End | | | |
|---|---|---|---|---|---|---|---|---|
| Clone | t [h] | YDM [g/L] | relative eGFP fluorescence | % | t [h] | YDM [g/L] | relative eGFP fluorescence | % |
| pG1-T16 #3 | −3.0 | 14.2 | 70 +/− 1 | 160 | 19.5 | 113.1 | 2383 +/− 24 | 119 |
| pG1-D1240 #3 | −3.0 | 14.9 | 62 +/− 1 | 141 | 19.5 | 113.3 | 2948 +/− 33 | 147 |

TABLE 6

Promoter strength compared to pG1 and promoter induction ratio of pG1 variants_from a comparative deep-well screening. The expression strength of the pG1-x variants (induced) is related to the eGFP expression level obtained with the original pG1 promoter The induction ratio is calculated from the GFP level in the induced and repressed state.

| | pG1 ($P_{GTH1}$) | pG1-Δ8 | pG1-Δ9 | pG1-T16 | pG1-T18 | pG1-T20 | pG1-D1240 | pG1-D1427 |
|---|---|---|---|---|---|---|---|---|
| Repression | 6.1 | 5.8 | 9.4 | 5.4 | 6.7 | 5.3 | 5.3 | 5.5 |
| Induction | 15.3 | 11.0 | 21.4 | 17.0 | 20.8 | 16.2 | 21.6 | 22.9 |
| Expression level | 1.00 | 0.72 | 1.40 | 1.11 | 1.36 | 1.06 | 1.41 | 1.49 |
| Induction ratio | 2.52 | 1.89 | 2.27 | 3.12 | 3.10 | 3.03 | 4.05 | 4.18 |

The invention claimed is:

1. A method of producing a protein of interest (POI) by culturing a recombinant host cell which comprises an expression construct expressing the POI under the control of a carbon source regulatable promoter, which method is performed according to a speed fermentation protocol starting with a batch phase as the first step, followed by a fed-batch phase as the second step, wherein:

a) in the first step a basal carbon source is used which represses the promoter and the cells are cultured to grow the cells until the basal carbon source is consumed; and b) in the second step no or a growth-limiting amount of a supplemental carbon source is added, thereby de-repressing the promoter to induce production of the POI, wherein the cells are cultured at a specific growth rate within the range of $0.04\ h^{-1}$ to $0.2\ h^{-1}$ for 13.5 to 88 h;

wherein the promoter comprises or consists of the nucleotide sequence selected from any one of SEQ ID NOs: 37-76.

2. The method of claim 1, wherein a) the basal carbon source is selected from the group consisting of glucose, glycerol, ethanol, a mixture thereof, and complex nutrient material; and b) the supplemental carbon source is a hexose selected from glucose, fructose, galactose or mannose, a disaccharide selected from saccharose, an alcohol selected from glycerol or ethanol, or a mixture of any of the foregoing.

3. The method of claim 1, wherein the oxygen partial pressure (pO2) is continuously decreasing during the batch phase and the end of the batch phase is characterized by an increase of pO2.

4. The method of claim 3, wherein the pO2 is decreased to below 65% saturation during the batch phase followed by an increase to above 65% saturation at the end of the batch phase.

5. The method of claim 1, wherein the batch phase is performed for 18 to 39.6 h.

6. The method of claim 1, wherein the batch phase is performed at a temperature between 25° C. and 30° C. for 20.7 to 39.6 h, using 40-50 g/L glycerol or glucose as a basal carbon source.

7. The method of claim 1, wherein the cultivation in the fed-batch phase is performed for 13.5 to 44 h.

8. The method of claim 1, wherein the POI is produced at a space time yield of around 27 to 33 mg (L h)−1.

9. The method of claim 8, wherein the cultivation in the fed-batch phase is performed for 27 to 33 hr.

10. The method of claim 1, wherein the promoter is any one of SEQ ID NOs: 37-44.

11. The method of claim 1, wherein the promoter is any one of SEQ ID NOs: 45-76.

12. The method of claim 1, wherein the promoter is operably linked to a nucleotide sequence encoding the POI, wherein the promoter is not natively associated with the nucleotide sequence encoding the POI.

13. The method of claim 1, wherein the promoter has a strength to produce the POI at a transcription rate of at least 15% as compared to a native pGAP promoter of the cell.

* * * * *

SEQUENCE LISTING

```
<160> NUMBER OF SEQ ID NOS: 426

<210> SEQ ID NO 1
<211> LENGTH: 966
<212> TYPE: DNA
<213> ORGANISM: Pichia pastoris
<220> FEATURE:
<221> NAME/KEY: misc_feature
<222> LOCATION: (592)..(593)
<223> OTHER INFORMATION: n is t or absent

<400> SEQUENCE: 1

caaacatttg ctccccctag tctccaggga aatgtaaaat atactgctaa tagaaaacag      60

taagacgctc agttgtcagg ataattacgt tcgactgtag taaaacagga atctgtattg     120

ttagaaagaa cgagagtttt ttacggcgcc gccatattgg gccgtgtgaa aacagcttga     180

aaccccacta ctttcaaagg ttctgttgct atacacgaac catgtttaac caacctcgct     240

tttgacttga ctgaagtcat cggttaacaa tcaagtaccc tagtctgtct gaatgctcct     300

ttccatattc agtaggtgtt tcttgcactt ttgcatgcac tgcggaagaa ttagccaata     360

gcgcgtttca tatgcgcttt tacccctct tttgtcaagc gcaaaatgcc tgtaagattt     420

ggtgggggtg tgagccgtta gctgaagtac aacaggctaa ttccctgaaa aaactgcaga     480

tagacttcaa gatctcaggg attcccacta tttggtattc tgatatgttt ttcctgatat     540

gcatcaaaac tctaatctaa aacctgaatc tccgctattt tttttttttt tnngatgacc     600

ccgttttcgt gacaaattaa tttccaacgg ggtcttgtcc ggataagaga attttgtttg     660

attatccgtt cggataaatg gacgcctgct ccatattttt ccggttatta ccccacctgg     720

aagtgcccag aattttccgg ggattacgga taatacggtg gtctggatta attaatacgc     780
```

caagtcttac attttgttgc agtctcgtgc gagtatgtgc aataataaac aagatgagcc 840
aatttattgg attagttgca gcttgacccc gccatagcta ggcatagcca agtgctatgg 900
gtgttagatg atgcacttgg atgcagtgag ttttggagta taaaagatcc ttaaaattcc 960
accctt 966

<210> SEQ ID NO 2
<211> LENGTH: 9
<212> TYPE: DNA
<213> ORGANISM: Pichia pastoris

<400> SEQUENCE: 2 ataaatgga 9

<210> SEQ ID NO 3
<211> LENGTH: 15
<212> TYPE: DNA
<213> ORGANISM: Pichia pastoris

<400> SEQUENCE: 3
catatttttc cggtt 15

<210> SEQ ID NO 4
<211> LENGTH: 33
<212> TYPE: DNA
<213> ORGANISM: Pichia pastoris

<400> SEQUENCE: 4
ataaatggac gcctgctcca tatttttccg gtt 33

<210> SEQ ID NO 5
<211> LENGTH: 118
<212> TYPE: DNA
<213> ORGANISM: Pichia pastoris

<400> SEQUENCE: 5
ccggataaga gaattttgtt tgattatccg ttcggataaa tggacgcctg ctccatattt 60
ttccggttat taccccacct ggaagtgccc agaattttcc ggggattacg gataatac 118

<210> SEQ ID NO 6
<211> LENGTH: 10
<212> TYPE: DNA
<213> ORGANISM: Pichia pastoris

<400> SEQUENCE: 6
ttccaccctt 10

<210> SEQ ID NO 7
<211> LENGTH: 964
<212> TYPE: DNA
<213> ORGANISM: Pichia pastoris

<400> SEQUENCE: 7
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tgatgacccc 600
gttttcgtga caaattaatt tccaacgggg tcttgtccgg ataagagaat tttgtttgat 660
tatccgttcg gataaatgga cgcctgctcc atatttttcc ggttattacc ccacctggaa 720
gtgcccagaa ttttccgggg attacggata atacggtggt ctggattaat taatacgcca 780
agtcttacat tttgttgcag tctcgtgcga gtatgtgcaa taataaacaa gatgagccaa 840
tttattggat tagttgcagc ttgaccccgc catagctagg catagccaag tgctatgggt 900
gttagatgat gcacttggat gcagtgagtt ttggagtata aaagatcctt aaaattccac 960
cctt 964

<210> SEQ ID NO 8
<211> LENGTH: 965
<212> TYPE: DNA
<213> ORGANISM: Pichia pastoris

<400> SEQUENCE: 8
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttgatgaccc 600
cgttttcgtg acaaattaat ttccaacggg gtcttgtccg gataagagaa ttttgtttga 660
ttatccgttc ggataaatgg acgcctgctc catatttttc cggttattac cccacctgga 720
agtgcccaga attttccggg gattacggat aatacggtgg tctggattaa ttaatacgcc 780
aagtcttaca ttttgttgca gtctcgtgcg agtatgtgca ataataaaca agatgagcca 840
atttattgga ttagttgcag cttgaccccg ccatagctag gcatagccaa gtgctatggg 900
tgttagatga tgcacttgga tgcagtgagt tttggagtat aaaagatcct taaaattcca 960
ccctt 965

<210> SEQ ID NO 9
<211> LENGTH: 966
<212> TYPE: DNA
<213> ORGANISM: Pichia pastoris

<400> SEQUENCE: 9
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180

-continued

```
aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt ttttttttt tttgatgacc    600

ccgttttcgt gacaaattaa tttccaacgg ggtcttgtcc ggataagaga attttgtttg    660

attatccgtt cggataaatg gacgcctgct ccatattttt ccggttatta ccccacctgg    720

aagtgcccag aattttccgg ggattacgga taatacggtg gtctggatta attaatacgc    780

caagtcttac attttgttgc agtctcgtgc gagtatgtgc aataataaac aagatgagcc    840

aatttattgg attagttgca gcttgacccc gccatagcta ggcatagcca agtgctatgg    900

gtgttagatg atgcacttgg atgcagtgag ttttggagta taaaagatcc ttaaaattcc    960

accctt                                                               966
```

<210> SEQ ID NO 10
<211> LENGTH: 328
<212> TYPE: DNA
<213> ORGANISM: Artificial Sequence
<220> FEATURE:
<223> OTHER INFORMATION: pG1-10 (PG1-s328) Fragment

<400> SEQUENCE: 10

```
ccggataaga gaattttgtt tgattatccg ttcggataaa tggacgcctg ctccatattt     60

ttccggttat taccccacct ggaagtgccc agaattttcc ggggattacg gataatacgg    120

tggtctggat taattaatac gccaagtctt acattttgtt gcagtctcgt gcgagtatgt    180

gcaataataa acaagatgag ccaatttatt ggattagttg cagcttgacc ccgccatagc    240

taggcatagc caagtgctat gggtgttaga tgatgcactt ggatgcagtg agttttggag    300

tataaaagat ccttaaaatt ccaccctt                                       328
```

<210> SEQ ID NO 11
<211> LENGTH: 370
<212> TYPE: DNA
<213> ORGANISM: Artificial Sequence
<220> FEATURE:
<223> OTHER INFORMATION: pG1-11 (PG1-s370) Fragment

<400> SEQUENCE: 11

```
gaccccgttt tcgtgacaaa ttaatttcca acggggtctt gtccggataa gagaattttg     60

tttgattatc cgttcggata aatggacgcc tgctccatat ttttccggtt attaccccac    120

ctggaagtgc ccagaatttt ccggggatta cggataatac ggtggtctgg attaattaat    180

acgccaagtc ttacattttg ttgcagtctc gtgcgagtat gtgcaataat aaacaagatg    240

agccaattta ttggattagt tgcagcttga ccccgccata gctaggcata gccaagtgct    300

atgggtgtta gatgatgcac ttggatgcag tgagttttgg agtataaaag atccttaaaa    360

ttccaccctt                                                           370
```

<210> SEQ ID NO 12
<211> LENGTH: 13
<212> TYPE: DNA
<213> ORGANISM: Artificial Sequence -continued
<220> FEATURE:
<223> OTHER INFORMATION: T motif

<400> SEQUENCE: 12
tttttttttt ttt 13

<210> SEQ ID NO 13
<211> LENGTH: 14
<212> TYPE: DNA
<213> ORGANISM: Artificial Sequence
<220> FEATURE:
<223> OTHER INFORMATION: T motif

<400> SEQUENCE: 13
tttttttttt tttt 14

<210> SEQ ID NO 14
<211> LENGTH: 15
<212> TYPE: DNA
<213> ORGANISM: Artificial Sequence
<220> FEATURE:
<223> OTHER INFORMATION: T motif

<400> SEQUENCE: 14
tttttttttt ttttt 15

<210> SEQ ID NO 15
<211> LENGTH: 16
<212> TYPE: DNA
<213> ORGANISM: Artificial Sequence
<220> FEATURE:
<223> OTHER INFORMATION: T motif

<400> SEQUENCE: 15
tttttttttt tttttt 16

<210> SEQ ID NO 16
<211> LENGTH: 17
<212> TYPE: DNA
<213> ORGANISM: Artificial Sequence
<220> FEATURE:
<223> OTHER INFORMATION: T motif

<400> SEQUENCE: 16
tttttttttt ttttttt 17

<210> SEQ ID NO 17
<211> LENGTH: 18
<212> TYPE: DNA
<213> ORGANISM: Artificial Sequence
<220> FEATURE:
<223> OTHER INFORMATION: T motif

<400> SEQUENCE: 17
tttttttttt tttttttt 18

<210> SEQ ID NO 18
<211> LENGTH: 19
<212> TYPE: DNA
<213> ORGANISM: Artificial Sequence
<220> FEATURE:
<223> OTHER INFORMATION: T motif

<400> SEQUENCE: 18
tttttttttt ttttttttt 19

<210> SEQ ID NO 19
<211> LENGTH: 20
<212> TYPE: DNA
<213> ORGANISM: Artificial Sequence
<220> FEATURE:
<223> OTHER INFORMATION: T motif

<400> SEQUENCE: 19
tttttttttt tttttttttt 20

<210> SEQ ID NO 20
<211> LENGTH: 998
<212> TYPE: DNA
<213> ORGANISM: Artificial Sequence
<220> FEATURE:
<223> OTHER INFORMATION: TA motif

<400> SEQUENCE: 20
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttgatgaccc 600
cgttttcgtg acaaattaat ttccaacggg gtcttgtccg gataagagaa ttttgtttga 660
ttatccgttc ggataaatgg acgcctgctc catatttttc cggttataaa tggacgcctg 720
ctccatattt ttccggttat taccccacct ggaagtgccc agaattttcc ggggattacg 780
gataatacgg tggtctggat taattaatac gccaagtctt acattttgtt gcagtctcgt 840
gcgagtatgt gcaataataa acaagatgag ccaatttatt ggattagttg cagcttgacc 900
ccgccatagc taggcatagc caagtgctat gggtgttaga tgatgcactt ggatgcagtg 960
agttttggag tataaaagat ccttaaaatt ccaccctt 998

<210> SEQ ID NO 21
<211> LENGTH: 16
<212> TYPE: DNA
<213> ORGANISM: Artificial Sequence
<220> FEATURE:
<223> OTHER INFORMATION: TA motif

<400> SEQUENCE: 21 tattttttttt tttttt 16

<210> SEQ ID NO 22
<211> LENGTH: 17
<212> TYPE: DNA
<213> ORGANISM: Artificial Sequence
<220> FEATURE:
<223> OTHER INFORMATION: TA motif

<400> SEQUENCE: 22 tattttttttt ttttttt 17

-continued

<210> SEQ ID NO 23
<211> LENGTH: 18
<212> TYPE: DNA
<213> ORGANISM: Artificial Sequence
<220> FEATURE:
<223> OTHER INFORMATION: TA motif

<400> SEQUENCE: 23
tatttttttt tttttttt 18

<210> SEQ ID NO 24
<211> LENGTH: 19
<212> TYPE: DNA
<213> ORGANISM: Artificial Sequence
<220> FEATURE:
<223> OTHER INFORMATION: TA motif

<400> SEQUENCE: 24
tatttttttt ttttttttt 19

<210> SEQ ID NO 25
<211> LENGTH: 20
<212> TYPE: DNA
<213> ORGANISM: Artificial Sequence
<220> FEATURE:
<223> OTHER INFORMATION: TA motif

<400> SEQUENCE: 25
tatttttttt tttttttttt 20

<210> SEQ ID NO 26
<211> LENGTH: 21
<212> TYPE: DNA
<213> ORGANISM: Artificial Sequence
<220> FEATURE:
<223> OTHER INFORMATION: TA motif

<400> SEQUENCE: 26
tatttttttt tttttttttt t 21

<210> SEQ ID NO 27
<211> LENGTH: 22
<212> TYPE: DNA
<213> ORGANISM: Artificial Sequence
<220> FEATURE:
<223> OTHER INFORMATION: TA motif

<400> SEQUENCE: 27
tatttttttt tttttttttt tt 22

<210> SEQ ID NO 28
<211> LENGTH: 21
<212> TYPE: DNA
<213> ORGANISM: Artificial Sequence
<220> FEATURE:
<223> OTHER INFORMATION: T motif

<400> SEQUENCE: 28
tttttttttt tttttttttt t 21

<210> SEQ ID NO 29
<211> LENGTH: 22
<212> TYPE: DNA
<213> ORGANISM: Artificial Sequence
<220> FEATURE:

<223> OTHER INFORMATION: TA motif

<400> SEQUENCE: 29 ttttttttt ttttttttt tt 22

<210> SEQ ID NO 30
<211> LENGTH: 956
<212> TYPE: DNA
<213> ORGANISM: Artificial Sequence
<220> FEATURE:
<223> OTHER INFORMATION: pG1-1 promotor

<400> SEQUENCE: 30
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttgatgaccc 600
cgttttcgtg acaaattaat ttccaacggg gtcttgtccg gataagagaa ttttgtttga 660
ttatccgttc ggcgcctgct ccatattttt ccggttatta ccccacctgg aagtgcccag 720
aattttccgg ggattacgga taatacggtg gtctggatta attaatacgc caagtcttac 780
attttgttgc agtctcgtgc gagtatgtgc aataataaac aagatgagcc aatttattgg 840
attagttgca gcttgacccc gccatagcta ggcatagcca agtgctatgg gtgttagatg 900
atgcacttgg atgcagtgag ttttggagta taaaagatcc ttaaaattcc accctt 956

<210> SEQ ID NO 31
<211> LENGTH: 950
<212> TYPE: DNA
<213> ORGANISM: Artificial Sequence
<220> FEATURE:
<223> OTHER INFORMATION: pG1-2 promotor

<400> SEQUENCE: 31
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttgatgaccc 600
cgttttcgtg acaaattaat ttccaacggg gtcttgtccg gataagagaa ttttgtttga 660

```
ttatccgttc ggataaatgg acgcctgctc attaccccac ctggaagtgc ccagaatttt    720

ccggggatta cggataatac ggtggtctgg attaattaat acgccaagtc ttacattttg    780

ttgcagtctc gtgcgagtat gtgcaataat aaacaagatg agccaattta ttggattagt    840

tgcagcttga ccccgccata gctaggcata gccaagtgct atgggtgtta gatgatgcac    900

ttggatgcag tgagttttgg agtataaaag atccttaaaa ttccaccctt               950
```

<210> SEQ ID NO 32
<211> LENGTH: 963
<212> TYPE: DNA
<213> ORGANISM: Artificial Sequence
<220> FEATURE:
<223> OTHER INFORMATION: pG1-x promoter

<400> SEQUENCE: 32

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt gatgaccccg    600

ttttcgtgac aaattaattt ccaacggggt cttgtccgga taagagaatt ttgtttgatt    660

atccgttcgg ataaatggac gcctgctcca tatttttccg gttattaccc cacctggaag    720

tgcccagaat tttccgggga ttacggataa tacggtggtc tggattaatt aatacgccaa    780

gtcttacatt ttgttgcagt ctcgtgcgag tatgtgcaat aataaacaag atgagccaat    840

ttattggatt agttgcagct tgaccccgcc atagctaggc atagccaagt gctatgggtg    900

ttagatgatg cacttggatg cagtgagttt tggagtataa aagatcctta aaattccacc    960

ctt                                                                  963
```

<210> SEQ ID NO 33
<211> LENGTH: 967
<212> TYPE: DNA
<213> ORGANISM: Artificial Sequence
<220> FEATURE:
<223> OTHER INFORMATION: pG1-x promoter

<400> SEQUENCE: 33

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420
```

```
ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt ttttgatgac    600

cccgttttcg tgacaaatta atttccaacg gggtcttgtc cggataagag aattttgttt    660

gattatccgt tcggataaat ggacgcctgc tccatatttt tccggttatt accccacctg    720

gaagtgccca gaattttccg gggattacgg ataatacggt ggtctggatt aattaatacg    780

ccaagtctta cattttgttg cagtctcgtg cgagtatgtg caataataaa caagatgagc    840

caatttattg gattagttgc agcttgaccc cgccatagct aggcatagcc aagtgctatg    900

ggtgttagat gatgcacttg gatgcagtga gttttggagt ataaaagatc cttaaaattc    960

caccctt                                                              967
```

<210> SEQ ID NO 34
<211> LENGTH: 968
<212> TYPE: DNA
<213> ORGANISM: Artificial Sequence
<220> FEATURE:
<223> OTHER INFORMATION: pG1-x promoter

<400> SEQUENCE: 34

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt tttttgatga    600

ccccgttttc gtgacaaatt aatttccaac ggggtcttgt ccggataaga gaattttgtt    660

tgattatccg ttcggataaa tggacgcctg ctccatattt ttccggttat taccccacct    720

ggaagtgccc agaattttcc ggggattacg gataatacgg tggtctggat taattaatac    780

gccaagtctt acattttgtt gcagtctcgt gcgagtatgt gcaataataa acaagatgag    840

ccaatttatt ggattagttg cagcttgacc ccgccatagc taggcatagc caagtgctat    900

gggtgttaga tgatgcactt ggatgcagtg agttttggag tataaaagat ccttaaaatt    960

ccaccctt                                                             968
```

<210> SEQ ID NO 35
<211> LENGTH: 969
<212> TYPE: DNA
<213> ORGANISM: Artificial Sequence
<220> FEATURE:
<223> OTHER INFORMATION: pG1-x promoter

<400> SEQUENCE: 35

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180
```

aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttttgatg 600
accccgtttt cgtgacaaat taatttccaa cggggtcttg tccggataag agaattttgt 660
ttgattatcc gttcggataa atggacgcct gctccatatt tttccggtta ttaccccacc 720
tggaagtgcc cagaattttc cggggattac ggataatacg gtggtctgga ttaattaata 780
cgccaagtct tacattttgt tgcagtctcg tgcgagtatg tgcaataata aacaagatga 840
gccaatttat tggattagtt gcagcttgac cccgccatag ctaggcatag ccaagtgcta 900
tgggtgttag atgatgcact tggatgcagt gagttttgga gtataaaaga tccttaaaat 960
tccaccctt 969

<210> SEQ ID NO 36
<211> LENGTH: 970
<212> TYPE: DNA
<213> ORGANISM: Artificial Sequence
<220> FEATURE:
<223> OTHER INFORMATION: pG1-x promoter

<400> SEQUENCE: 36
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttttttgat 600
gaccccgttt tcgtgacaaa ttaatttcca acggggtctt gtccggataa gagaattttg 660
tttgattatc cgttcggata aatggacgcc tgctccatat ttttccggtt attaccccac 720
ctggaagtgc ccagaatttt ccggggatta cggataatac ggtggtctgg attaattaat 780
acgccaagtc ttacattttg ttgcagtctc gtgcgagtat gtgcaataat aaacaagatg 840
agccaattta ttggattagt tgcagcttga ccccgccata gctaggcata gccaagtgct 900
atgggtgtta gatgatgcac ttggatgcag tgagttttgg agtataaaag atccttaaaa 960
ttccaccctt 970

<210> SEQ ID NO 37
<211> LENGTH: 1250
<212> TYPE: DNA
<213> ORGANISM: Artificial Sequence
<220> FEATURE:

<223> OTHER INFORMATION: pG1-3 promoter
<220> FEATURE:
<221> NAME/KEY: misc_feature
<222> LOCATION: (577)..(583)
<223> OTHER INFORMATION: n is t or absent
<220> FEATURE:
<221> NAME/KEY: misc_feature
<222> LOCATION: (871)..(877)
<223> OTHER INFORMATION: n is t or absent

<400> SEQUENCE: 37

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt ttttttnnnn nnngatgacc ccgttttcgt    600

gacaaattaa tttccaacgg ggtcttgtcc ggataagaga attttgtttg attatccgtt    660

cggataaatg gacgcctgct ccatattttt ccggttatta ccccacctgg aagtgcccag    720

aattttccgg ggattacgga taatacggtg gtctggatta attaatacga gatctcaggg    780

attcccacta tttggtattc tgatatgttt ttcctgatat gcatcaaaac tctaatctaa    840

aacctgaatc tccgctattt tttttttttt nnnnnnngat gaccccgttt tcgtgacaaa    900

ttaatttcca acggggtctt gtccggataa gagaattttg tttgattatc cgttcggata    960

aatggacgcc tgctccatat ttttccggtt attaccccac ctggaagtgc ccagaatttt   1020

ccggggatta cggataatac ggtggtctgg attaattaat acgccaagtc ttacattttg   1080

ttgcagtctc gtgcgagtat gtgcaataat aaacaagatg agccaattta ttggattagt   1140

tgcagcttga ccccgccata gctaggcata gccaagtgct atgggtgtta gatgatgcac   1200

ttggatgcag tgagttttgg agtataaaag atccttaaaa ttccaccctt              1250
```

<210> SEQ ID NO 38
<211> LENGTH: 1248
<212> TYPE: DNA
<213> ORGANISM: Artificial Sequence
<220> FEATURE:
<223> OTHER INFORMATION: pG1-3 promoter
<220> FEATURE:
<221> NAME/KEY: misc_feature
<222> LOCATION: (577)..(583)
<223> OTHER INFORMATION: n is t or absent
<220> FEATURE:
<221> NAME/KEY: misc_feature
<222> LOCATION: (869)..(875)
<223> OTHER INFORMATION: n is t or absent

<400> SEQUENCE: 38

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240
```

```
tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt tttttnnnn nnngatgacc ccgttttcgt    600

gacaaattaa tttccaacgg ggtcttgtcc ggataagaga attttgtttg attatccgtt    660

cggataaatg gacgcctgct ccatattttt ccggttatta ccccacctgg aagtgcccag    720

aattttccgg ggattacgga taatacggtg gtctggatta attaatacga gatctcaggg    780

attcccacta tttggtattc tgatatgttt ttcctgatat gcatcaaaac tctaatctaa    840

aacctgaatc tccgcttttt tttttttnn nnnnngatga ccccgttttc gtgacaaatt    900

aatttccaac ggggtcttgt ccggataaga gaattttgtt tgattatccg ttcggataaa    960

tggacgcctg ctccatattt ttccggttat taccccacct ggaagtgccc agaattttcc   1020

ggggattacg gataatacgg tggtctggat taattaatac gccaagtctt acattttgtt   1080

gcagtctcgt gcgagtatgt gcaataataa acaagatgag ccaatttatt ggattagttg   1140

cagcttgacc ccgccatagc taggcatagc caagtgctat gggtgttaga tgatgcactt   1200

ggatgcagtg agttttggag tataaaagat ccttaaaatt ccaccctt                1248


<210> SEQ ID NO 39
<211> LENGTH: 1248
<212> TYPE: DNA
<213> ORGANISM: Artificial Sequence
<220> FEATURE:
<223> OTHER INFORMATION: pG1-3 promoter
<220> FEATURE:
<221> NAME/KEY: misc_feature
<222> LOCATION: (575)..(581)
<223> OTHER INFORMATION: n is t or absent
<220> FEATURE:
<221> NAME/KEY: misc_feature
<222> LOCATION: (869)..(875)
<223> OTHER INFORMATION: n is t or absent

<400> SEQUENCE: 39

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttnnnnnn ngatgacccc gttttcgtga    600

caaattaatt tccaacgggg tcttgtccgg ataagagaat tttgtttgat tatccgttcg    660

gataaatgga cgcctgctcc atatttttcc ggttattacc ccacctggaa gtgcccagaa    720

ttttccgggg attacggata atacggtggt ctggattaat taatacgaga tctcagggat    780
```

```
tcccactatt tggtattctg atatgttttt cctgatatgc atcaaaactc taatctaaaa    840

cctgaatctc cgctattttt tttttttnn nnnnngatga ccccgttttc gtgacaaatt    900

aatttccaac ggggtcttgt ccggataaga gaattttgtt tgattatccg ttcggataaa    960

tggacgcctg ctccatattt ttccggttat taccccacct ggaagtgccc agaattttcc   1020

ggggattacg gataatacgg tggtctggat taattaatac gccaagtctt acattttgtt   1080

gcagtctcgt gcgagtatgt gcaataataa acaagatgag ccaatttatt ggattagttg   1140

cagcttgacc ccgccatagc taggcatagc caagtgctat gggtgttaga tgatgcactt   1200

ggatgcagtg agttttggag tataaaagat ccttaaaatt ccaccctt                1248


<210> SEQ ID NO 40
<211> LENGTH: 1250
<212> TYPE: DNA
<213> ORGANISM: Artificial Sequence
<220> FEATURE:
<223> OTHER INFORMATION: pG1-3 promoter
<220> FEATURE:
<221> NAME/KEY: misc_feature
<222> LOCATION: (577)..(583)
<223> OTHER INFORMATION: n is t or absent
<220> FEATURE:
<221> NAME/KEY: misc_feature
<222> LOCATION: (871)..(877)
<223> OTHER INFORMATION: n is t or absent

<400> SEQUENCE: 40

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttttnnnn nnngatgacc ccgttttcgt    600

gacaaattaa tttccaacgg ggtcttgtcc ggataagaga attttgtttg attatccgtt    660

cggataaatg gacgcctgct ccatattttt ccggttatta ccccacctgg aagtgcccag    720

aattttccgg ggattacgga taatacggtg gtctggatta attaatacga gatctcaggg    780

attcccacta tttggtattc tgatatgttt ttcctgatat gcatcaaaac tctaatctaa    840

aacctgaatc tccgctattt tttttttttt nnnnnnngat gaccccgttt tcgtgacaaa    900

ttaatttcca acggggtctt gtccggataa gagaattttg tttgattatc cgttcggata    960

aatggacgcc tgctccatat ttttccggtt attaccccac ctggaagtgc ccagaatttt   1020

ccggggatta cggataatac ggtggtctgg attaattaat acgccaagtc ttacattttg   1080

ttgcagtctc gtgcgagtat gtgcaataat aaacaagatg agccaattta ttggattagt   1140

tgcagcttga ccccgccata gctaggcata gccaagtgct atgggtgtta gatgatgcac   1200

ttggatgcag tgagttttgg agtataaaag atccttaaaa ttccaccctt              1250


<210> SEQ ID NO 41
<211> LENGTH: 1250
```

<212> TYPE: DNA
<213> ORGANISM: Artificial Sequence
<220> FEATURE:
<223> OTHER INFORMATION: pG1-3 promoter
<220> FEATURE:
<221> NAME/KEY: misc_feature
<222> LOCATION: (577)..(583)
<223> OTHER INFORMATION: n is t or absent
<220> FEATURE:
<221> NAME/KEY: misc_feature
<222> LOCATION: (871)..(877)
<223> OTHER INFORMATION: n is t or absent

<400> SEQUENCE: 41

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt tttttnnnn nnngatgacc ccgttttcgt    600

gacaaattaa tttccaacgg ggtcttgtcc ggataagaga attttgtttg attatccgtt    660

cggataaatg gacgcctgct ccatattttt ccggttatta ccccacctgg aagtgcccag    720

aattttccgg ggattacgga taatacggtg gtctggatta attaatacga gatctcaggg    780

attcccacta tttggtattc tgatatgttt ttcctgatat gcatcaaaac tctaatctaa    840

aacctgaatc tccgcttttt tttttttttt nnnnnnngat gaccccgttt tcgtgacaaa    900

ttaatttcca acggggtctt gtccggataa gagaattttg tttgattatc cgttcggata    960

aatggacgcc tgctccatat ttttccggtt attaccccac ctggaagtgc ccagaatttt   1020

ccggggatta cggataatac ggtggtctgg attaattaat acgccaagtc ttacattttg   1080

ttgcagtctc gtgcgagtat gtgcaataat aaacaagatg agccaattta ttggattagt   1140

tgcagcttga ccccgccata gctaggcata gccaagtgct atgggtgtta gatgatgcac   1200

ttggatgcag tgagttttgg agtataaaag atccttaaaa ttccaccctt              1250
```

<210> SEQ ID NO 42
<211> LENGTH: 1248
<212> TYPE: DNA
<213> ORGANISM: Artificial Sequence
<220> FEATURE:
<223> OTHER INFORMATION: pG1-3 promoter
<220> FEATURE:
<221> NAME/KEY: misc_feature
<222> LOCATION: (577)..(583)
<223> OTHER INFORMATION: n is t or absent
<220> FEATURE:
<221> NAME/KEY: misc_feature
<222> LOCATION: (869)..(875)
<223> OTHER INFORMATION: n is t or absent

<400> SEQUENCE: 42

```
caaacatttg ctccccctag tctccaggga aatgtaaaat atactgctaa tagaaaacag     60

taagacgctc agttgtcagg ataattacgt tcgactgtag taaaacagga atctgtattg    120
```

```
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg cttttttttt ttttttnnnn nnngatgacc ccgttttcgt    600
gacaaattaa tttccaacgg ggtcttgtcc ggataagaga attttgtttg attatccgtt    660
cggataaatg gacgcctgct ccatattttt ccggttatta ccccacctgg aagtgcccag    720
aattttccgg ggattacgga taatacggtg gtctggatta attaatacga gatctcaggg    780
attcccacta tttggtattc tgatatgttt ttcctgatat gcatcaaaac tctaatctaa    840
aacctgaatc tccgcttttt tttttttnn nnnnngatga ccccgttttc gtgacaaatt    900
aatttccaac ggggtcttgt ccggataaga gaattttgtt tgattatccg ttcggataaa    960
tggacgcctg ctccatattt ttccggttat taccccacct ggaagtgccc agaattttcc   1020
ggggattacg gataatacgg tggtctggat taattaatac gccaagtctt acattttgtt   1080
gcagtctcgt gcgagtatgt gcaataataa acaagatgag ccaatttatt ggattagttg   1140
cagcttgacc ccgccatagc taggcatagc caagtgctat gggtgttaga tgatgcactt   1200
ggatgcagtg agttttggag tataaaagat ccttaaaatt ccaccctt                1248
```

```
<210> SEQ ID NO 43
<211> LENGTH: 1248
<212> TYPE: DNA
<213> ORGANISM: Artificial Sequence
<220> FEATURE:
<223> OTHER INFORMATION: pG1-3 promoter
<220> FEATURE:
<221> NAME/KEY: misc_feature
<222> LOCATION: (575)..(581)
<223> OTHER INFORMATION: n is t or absent
<220> FEATURE:
<221> NAME/KEY: misc_feature
<222> LOCATION: (869)..(875)
<223> OTHER INFORMATION: n is t or absent

<400> SEQUENCE: 43
```

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg cttttttttt ttttnnnnnn ngatgacccc gttttcgtga    600
caaattaatt tccaacgggg tcttgtccgg ataagagaat tttgtttgat tatccgttcg    660
gataaatgga cgcctgctcc atatttttcc ggttattacc ccacctggaa gtgcccagaa    720
```

```
ttttccgggg attacggata atacggtggt ctggattaat taatacgaga tctcagggat    780

tcccactatt tggtattctg atatgttttt cctgatatgc atcaaaactc taatctaaaa    840

cctgaatctc cgcttttttt tttttttnn nnnnngatga ccccgttttc gtgacaaatt    900

aatttccaac ggggtcttgt ccggataaga gaattttgtt tgattatccg ttcggataaa    960

tggacgcctg ctccatattt ttccggttat taccccacct ggaagtgccc agaattttcc   1020

ggggattacg gataatacgg tggtctggat taattaatac gccaagtctt acattttgtt   1080

gcagtctcgt gcgagtatgt gcaataataa acaagatgag ccaatttatt ggattagttg   1140

cagcttgacc ccgccatagc taggcatagc caagtgctat gggtgttaga tgatgcactt   1200

ggatgcagtg agttttggag tataaaagat ccttaaaatt ccaccctt               1248
```

<210> SEQ ID NO 44
<211> LENGTH: 1246
<212> TYPE: DNA
<213> ORGANISM: Artificial Sequence
<220> FEATURE:
<223> OTHER INFORMATION: pG1-3 promoter
<220> FEATURE:
<221> NAME/KEY: misc_feature
<222> LOCATION: (575)..(581)
<223> OTHER INFORMATION: n is t or absent
<220> FEATURE:
<221> NAME/KEY: misc_feature
<222> LOCATION: (867)..(873)
<223> OTHER INFORMATION: n is t or absent

<400> SEQUENCE: 44

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttnnnnnn ngatgacccc gttttcgtga    600

caaattaatt tccaacgggg tcttgtccgg ataagagaat tttgtttgat tatccgttcg    660

gataaatgga cgcctgctcc atatttttcc ggttattacc ccacctggaa gtgcccagaa    720

ttttccgggg attacggata atacggtggt ctggattaat taatacgaga tctcagggat    780

tcccactatt tggtattctg atatgttttt cctgatatgc atcaaaactc taatctaaaa    840

cctgaatctc cgcttttttt ttttttnnnn nnngatgacc ccgttttcgt gacaaattaa    900

tttccaacgg ggtcttgtcc ggataagaga attttgtttg attatccgtt cggataaatg    960

gacgcctgct ccatattttt ccggttatta ccccacctgg aagtgcccag aattttccgg   1020

ggattacgga taatacggtg gtctggatta attaatacgc caagtcttac attttgttgc   1080

agtctcgtgc gagtatgtgc aataataaac aagatgagcc aatttattgg attagttgca   1140

gcttgacccc gccatagcta ggcatagcca agtgctatgg gtgttagatg atgcacttgg   1200

atgcagtgag ttttggagta taaaagatcc ttaaaattcc accctt                 1246
```

<210> SEQ ID NO 45
<211> LENGTH: 1236
<212> TYPE: DNA
<213> ORGANISM: Artificial Sequence
<220> FEATURE:
<223> OTHER INFORMATION: pG1-3 promoter

<400> SEQUENCE: 45
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt ttttttgatg accccgtttt cgtgacaaat 600
taatttccaa cggggtcttg tccggataag agaattttgt ttgattatcc gttcggataa 660
atggacgcct gctccatatt tttccggtta ttaccccacc tggaagtgcc cagaattttc 720
cggggattac ggataatacg gtggtctgga ttaattaata cgagatctca gggattccca 780
ctatttggta ttctgatatg tttttcctga tatgcatcaa aactctaatc taaaacctga 840
atctccgcta tttttttttt tttgatgacc ccgttttcgt gacaaattaa tttccaacgg 900
ggtcttgtcc ggataagaga attttgtttg attatccgtt cggataaatg gacgcctgct 960
ccatattttt ccggttatta ccccacctgg aagtgcccag aattttccgg ggattacgga 1020
taatacggtg gtctggatta attaatacgc caagtcttac attttgttgc agtctcgtgc 1080
gagtatgtgc aataataaac aagatgagcc aatttattgg attagttgca gcttgacccc 1140
gccatagcta ggcatagcca agtgctatgg gtgttagatg atgcacttgg atgcagtgag 1200
ttttggagta taaaagatcc ttaaaattcc accctt 1236

<210> SEQ ID NO 46
<211> LENGTH: 1234
<212> TYPE: DNA
<213> ORGANISM: Artificial Sequence
<220> FEATURE:
<223> OTHER INFORMATION: pG1-3 promoter

<400> SEQUENCE: 46
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540

```
atctaaaacc tgaatctccg ctattttttt ttttttgatg accccgtttt cgtgacaaat    600

taatttccaa cggggtcttg tccggataag agaattttgt ttgattatcc gttcggataa    660

atggacgcct gctccatatt tttccggtta ttaccccacc tggaagtgcc cagaattttc    720

cggggattac ggataatacg gtggtctgga ttaattaata cgagatctca gggattccca    780

ctatttggta ttctgatatg tttttcctga tatgcatcaa aactctaatc taaaacctga    840

atctccgctt tttttttttt tgatgacccc gttttcgtga caaattaatt tccaacgggg    900

tcttgtccgg ataagagaat tttgtttgat tatccgttcg gataaatgga cgcctgctcc    960

atatttttcc ggttattacc ccacctggaa gtgcccagaa ttttccgggg attacggata   1020

atacggtggt ctggattaat taatacgcca agtcttacat tttgttgcag tctcgtgcga   1080

gtatgtgcaa taataaacaa gatgagccaa tttattggat tagttgcagc ttgaccccgc   1140

catagctagg catagccaag tgctatgggt gttagatgat gcacttggat gcagtgagtt   1200

ttggagtata aaagatcctt aaaattccac cctt                              1234
```

<210> SEQ ID NO 47
<211> LENGTH: 1234
<212> TYPE: DNA
<213> ORGANISM: Artificial Sequence
<220> FEATURE:
<223> OTHER INFORMATION: pG1-3 promoter

<400> SEQUENCE: 47

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttgatgac cccgttttcg tgacaaatta    600

atttccaacg gggtcttgtc cggataagag aattttgttt gattatccgt tcggataaat    660

ggacgcctgc tccatatttt tccggttatt accccacctg gaagtgccca gaattttccg    720

gggattacgg ataatacggt ggtctggatt aattaatacg agatctcagg gattcccact    780

atttggtatt ctgatatgtt tttcctgata tgcatcaaaa ctctaatcta aaacctgaat    840

ctccgctatt tttttttttt tgatgacccc gttttcgtga caaattaatt tccaacgggg    900

tcttgtccgg ataagagaat tttgtttgat tatccgttcg gataaatgga cgcctgctcc    960

atatttttcc ggttattacc ccacctggaa gtgcccagaa ttttccgggg attacggata   1020

atacggtggt ctggattaat taatacgcca agtcttacat tttgttgcag tctcgtgcga   1080

gtatgtgcaa taataaacaa gatgagccaa tttattggat tagttgcagc ttgaccccgc   1140

catagctagg catagccaag tgctatgggt gttagatgat gcacttggat gcagtgagtt   1200

ttggagtata aaagatcctt aaaattccac cctt                              1234
```

<210> SEQ ID NO 48

<211> LENGTH: 1232
<212> TYPE: DNA
<213> ORGANISM: Artificial Sequence
<220> FEATURE:
<223> OTHER INFORMATION: pG1-3 promoter

<400> SEQUENCE: 48
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt ttttgatgac cccgttttcg tgacaaatta 600
atttccaacg gggtcttgtc cggataagag aattttgttt gattatccgt tcggataaat 660
ggacgcctgc tccatatttt tccggttatt accccacctg gaagtgccca gaattttccg 720
gggattacgg ataatacggt ggtctggatt aattaatacg agatctcagg gattcccact 780
atttggtatt ctgatatgtt tttcctgata tgcatcaaaa ctctaatcta aaacctgaat 840
ctccgctttt tttttttttg atgaccccgt tttcgtgaca aattaatttc caacggggtc 900
ttgtccggat aagagaattt tgtttgatta tccgttcgga taaatggacg cctgctccat 960
atttttccgg ttattacccc acctggaagt gcccagaatt ttccggggat tacggataat 1020
acggtggtct ggattaatta atacgccaag tcttacattt tgttgcagtc tcgtgcgagt 1080
atgtgcaata ataaacaaga tgagccaatt tattggatta gttgcagctt gaccccgcca 1140
tagctaggca tagccaagtg ctatgggtgt tagatgatgc acttggatgc agtgagtttt 1200
ggagtataaa agatccttaa aattccaccc tt 1232

<210> SEQ ID NO 49
<211> LENGTH: 1238
<212> TYPE: DNA
<213> ORGANISM: Artificial Sequence
<220> FEATURE:
<223> OTHER INFORMATION: pG1-3 promoter

<400> SEQUENCE: 49
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt ttttttgat gaccccgttt tcgtgacaaa 600

```
ttaatttcca acggggtctt gtccggataa gagaattttg tttgattatc cgttcggata    660

aatggacgcc tgctccatat ttttccggtt attaccccac ctggaagtgc ccagaatttt    720

ccggggatta cggataatac ggtggtctgg attaattaat acgagatctc agggattccc    780

actatttggt attctgatat gtttttcctg atatgcatca aaactctaat ctaaaacctg    840

aatctccgct attttttttt tttttgatga ccccgttttc gtgacaaatt aatttccaac    900

ggggtcttgt ccggataaga gaattttgtt tgattatccg ttcggataaa tggacgcctg    960

ctccatattt ttccggttat taccccacct ggaagtgccc agaattttcc ggggattacg   1020

gataatacgg tggtctggat taattaatac gccaagtctt acattttgtt gcagtctcgt   1080

gcgagtatgt gcaataataa acaagatgag ccaatttatt ggattagttg cagcttgacc   1140

ccgccatagc taggcatagc caagtgctat gggtgttaga tgatgcactt ggatgcagtg   1200

agttttggag tataaaagat ccttaaaatt ccaccctt                           1238
```

<210> SEQ ID NO 50
<211> LENGTH: 1236
<212> TYPE: DNA
<213> ORGANISM: Artificial Sequence
<220> FEATURE:
<223> OTHER INFORMATION: pG1-3 promoter

<400> SEQUENCE: 50

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt tttttttgat gaccccgttt tcgtgacaaa    600

ttaatttcca acggggtctt gtccggataa gagaattttg tttgattatc cgttcggata    660

aatggacgcc tgctccatat ttttccggtt attaccccac ctggaagtgc ccagaatttt    720

ccggggatta cggataatac ggtggtctgg attaattaat acgagatctc agggattccc    780

actatttggt attctgatat gtttttcctg atatgcatca aaactctaat ctaaaacctg    840

aatctccgct tttttttttt tttgatgacc ccgttttcgt gacaaattaa tttccaacgg    900

ggtcttgtcc ggataagaga attttgtttg attatccgtt cggataaatg gacgcctgct    960

ccatattttt ccggttatta ccccacctgg aagtgcccag aattttccgg ggattacgga   1020

taatacggtg gtctggatta attaatacgc caagtcttac attttgttgc agtctcgtgc   1080

gagtatgtgc aataataaac aagatgagcc aatttattgg attagttgca gcttgacccc   1140

gccatagcta ggcatagcca agtgctatgg gtgttagatg atgcacttgg atgcagtgag   1200

ttttggagta taaaagatcc ttaaaattcc accctt                             1236
```

<210> SEQ ID NO 51
<211> LENGTH: 1236
<212> TYPE: DNA

<213> ORGANISM: Artificial Sequence
<220> FEATURE:
<223> OTHER INFORMATION: pG1-3 promoter

<400> SEQUENCE: 51
caaacatttg ctcccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttgatga ccccgttttc gtgacaaatt 600
aatttccaac ggggtcttgt ccggataaga gaattttgtt tgattatccg ttcggataaa 660
tggacgcctg ctccatattt ttccggttat taccccacct ggaagtgccc agaattttcc 720
ggggattacg gataatacgg tggtctggat taattaatac gagatctcag ggattcccac 780
tatttggtat tctgatatgt ttttcctgat atgcatcaaa actctaatct aaaacctgaa 840
tctccgctat tttttttttt tttgatgacc ccgttttcgt gacaaattaa tttccaacgg 900
ggtcttgtcc ggataagaga attttgtttg attatccgtt cggataaatg gacgcctgct 960
ccatattttt ccggttatta ccccacctgg aagtgcccag aattttccgg ggattacgga 1020
taatacggtg gtctggatta attaatacgc caagtcttac attttgttgc agtctcgtgc 1080
gagtatgtgc aataataaac aagatgagcc aatttattgg attagttgca gcttgacccc 1140
gccatagcta ggcatagcca agtgctatgg gtgttagatg atgcacttgg atgcagtgag 1200
ttttggagta taaaagatcc ttaaaattcc accctt 1236

<210> SEQ ID NO 52
<211> LENGTH: 1234
<212> TYPE: DNA
<213> ORGANISM: Artificial Sequence
<220> FEATURE:
<223> OTHER INFORMATION: pG1-3 promoter

<400> SEQUENCE: 52
caaacatttg ctcccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttgatga ccccgttttc gtgacaaatt 600
aatttccaac ggggtcttgt ccggataaga gaattttgtt tgattatccg ttcggataaa 660
tggacgcctg ctccatattt ttccggttat taccccacct ggaagtgccc agaattttcc 720
ggggattacg gataatacgg tggtctggat taattaatac gagatctcag ggattcccac 780
tatttggtat tctgatatgt ttttcctgat atgcatcaaa actctaatct aaaacctgaa 840
tctccgcttt tttttttttt tgatgacccc gttttcgtga caaattaatt tccaacgggg 900
tcttgtccgg ataagagaat ttgtttgat tatccgttcg gataaatgga cgcctgctcc 960
atatttttcc ggttattacc ccacctggaa gtgcccagaa ttttccgggg attacggata 1020
atacggtggt ctggattaat taatacgcca agtcttacat tttgttgcag tctcgtgcga 1080
gtatgtgcaa taataaacaa gatgagccaa tttattggat tagttgcagc ttgaccccgc 1140
catagctagg catagccaag tgctatgggt gttagatgat gcacttggat gcagtgagtt 1200
ttggagtata aaagatcctt aaaattccac cctt 1234

<210> SEQ ID NO 53
<211> LENGTH: 1240
<212> TYPE: DNA
<213> ORGANISM: Artificial Sequence
<220> FEATURE:
<223> OTHER INFORMATION: pG1-3 promoter

<400> SEQUENCE: 53
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttga tgaccccgtt ttcgtgacaa 600
attaatttcc aacggggtct tgtccggata agagaatttt gtttgattat ccgttcggat 660
aaatggacgc ctgctccata tttttccggt tattacccca cctggaagtg cccagaattt 720
tccggggatt acggataata cggtggtctg gattaattaa tacgagatct cagggattcc 780
cactatttgg tattctgata tgtttttcct gatatgcatc aaaactctaa tctaaaacct 840
gaatctccgc tatttttttt tttttttgat gaccccgttt tcgtgacaaa ttaatttcca 900
acggggtctt gtccggataa gagaattttg tttgattatc cgttcggata aatggacgcc 960
tgctccatat ttttccggtt attaccccac ctggaagtgc ccagaatttt ccggggatta 1020
cggataatac ggtggtctgg attaattaat acgccaagtc ttacattttg ttgcagtctc 1080
gtgcgagtat gtgcaataat aaacaagatg agccaattta ttggattagt tgcagcttga 1140
ccccgccata gctaggcata gccaagtgct atgggtgtta gatgatgcac ttggatgcag 1200
tgagttttgg agtataaaag atccttaaaa ttccaccctt 1240

<210> SEQ ID NO 54
<211> LENGTH: 1238
<212> TYPE: DNA
<213> ORGANISM: Artificial Sequence
<220> FEATURE:

<223> OTHER INFORMATION: pG1-3 promoter

<400> SEQUENCE: 54
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt ttttttttga tgaccccgtt ttcgtgacaa 600
attaatttcc aacggggtct tgtccggata agagaatttt gtttgattat ccgttcggat 660
aaatggacgc ctgctccata tttttccggt tattacccca cctggaagtg cccagaattt 720
tccggggatt acggataata cggtggtctg gattaattaa tacgagatct cagggattcc 780
cactatttgg tattctgata tgtttttcct gatatgcatc aaaactctaa tctaaaacct 840
gaatctccgc tttttttttt tttttgatga ccccgttttc gtgacaaatt aatttccaac 900
ggggtcttgt ccggataaga gaattttgtt tgattatccg ttcggataaa tggacgcctg 960
ctccatattt ttccggttat taccccacct ggaagtgccc agaattttcc ggggattacg 1020
gataatacgg tggtctggat taattaatac gccaagtctt acattttgtt gcagtctcgt 1080
gcgagtatgt gcaataataa acaagatgag ccaatttatt ggattagttg cagcttgacc 1140
ccgccatagc taggcatagc caagtgctat gggtgttaga tgatgcactt ggatgcagtg 1200
agttttggag tataaaagat ccttaaaatt ccaccctt 1238

<210> SEQ ID NO 55
<211> LENGTH: 1238
<212> TYPE: DNA
<213> ORGANISM: Artificial Sequence
<220> FEATURE:
<223> OTHER INFORMATION: pG1-3 promoter

<400> SEQUENCE: 55
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt ttttttgatg accccgtttt cgtgacaaat 600
taatttccaa cggggtcttg tccggataag agaattttgt ttgattatcc gttcggataa 660
atggacgcct gctccatatt tttccggtta ttaccccacc tggaagtgcc cagaattttc 720
cggggattac ggataatacg gtggtctgga ttaattaata cgagatctca gggattccca 780
ctatttggta ttctgatatg tttttcctga tatgcatcaa aactctaatc taaaacctga 840
atctccgcta tttttttttt tttttgatga ccccgttttc gtgacaaatt aatttccaac 900
ggggtcttgt ccggataaga gaattttgtt tgattatccg ttcggataaa tggacgcctg 960
ctccatattt ttccggttat taccccacct ggaagtgccc agaattttcc ggggattacg 1020
gataatacgg tggtctggat taattaatac gccaagtctt acattttgtt gcagtctcgt 1080
gcgagtatgt gcaataataa acaagatgag ccaatttatt ggattagttg cagcttgacc 1140
ccgccatagc taggcatagc caagtgctat gggtgttaga tgatgcactt ggatgcagtg 1200
agttttggag tataaaagat ccttaaaatt ccaccctt 1238

<210> SEQ ID NO 56
<211> LENGTH: 1236
<212> TYPE: DNA
<213> ORGANISM: Artificial Sequence
<220> FEATURE:
<223> OTHER INFORMATION: pG1-3 promoter

<400> SEQUENCE: 56
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt ttttttgatg accccgtttt cgtgacaaat 600
taatttccaa cggggtcttg tccggataag agaattttgt ttgattatcc gttcggataa 660
atggacgcct gctccatatt tttccggtta ttaccccacc tggaagtgcc cagaattttc 720
cggggattac ggataatacg gtggtctgga ttaattaata cgagatctca gggattccca 780
ctatttggta ttctgatatg tttttcctga tatgcatcaa aactctaatc taaaacctga 840
atctccgctt tttttttttt tttgatgacc ccgttttcgt gacaaattaa tttccaacgg 900
ggtcttgtcc ggataagaga attttgtttg attatccgtt cggataaatg gacgcctgct 960
ccatattttt ccggttatta ccccacctgg aagtgcccag aattttccgg ggattacgga 1020
taatacggtg gtctggatta attaatacgc caagtcttac attttgttgc agtctcgtgc 1080
gagtatgtgc aataataaac aagatgagcc aatttattgg attagttgca gcttgacccc 1140
gccatagcta ggcatagcca agtgctatgg gtgttagatg atgcacttgg atgcagtgag 1200
ttttggagta taaaagatcc ttaaaattcc accctt 1236

<210> SEQ ID NO 57
<211> LENGTH: 1242
<212> TYPE: DNA
<213> ORGANISM: Artificial Sequence
<220> FEATURE:
<223> OTHER INFORMATION: pG1-3 promoter -continued

<400> SEQUENCE: 57

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg ctattttttt ttttttttg atgaccccgt tttcgtgaca    600
aattaatttc caacggggtc ttgtccggat aagagaattt tgtttgatta tccgttcgga    660
taaatggacg cctgctccat atttttccgg ttattacccc acctggaagt gcccagaatt    720
ttccggggat tacggataat acggtggtct ggattaatta atacgagatc tcagggattc    780
ccactatttg gtattctgat atgtttttcc tgatatgcat caaaactcta atctaaaacc    840
tgaatctccg ctattttttt ttttttttg atgaccccgt tttcgtgaca aattaatttc    900
caacggggtc ttgtccggat aagagaattt tgtttgatta tccgttcgga taaatggacg    960
cctgctccat atttttccgg ttattacccc acctggaagt gcccagaatt ttccggggat   1020
tacggataat acggtggtct ggattaatta atacgccaag tcttacattt tgttgcagtc   1080
tcgtgcgagt atgtgcaata ataaacaaga tgagccaatt tattggatta gttgcagctt   1140
gaccccgcca tagctaggca tagccaagtg ctatgggtgt tagatgatgc acttggatgc   1200
agtgagtttt ggagtataaa agatccttaa aattccaccc tt                      1242
```

<210> SEQ ID NO 58
<211> LENGTH: 1240
<212> TYPE: DNA
<213> ORGANISM: Artificial Sequence
<220> FEATURE:
<223> OTHER INFORMATION: pG1-3 promoter

<400> SEQUENCE: 58

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg ctattttttt ttttttttg atgaccccgt tttcgtgaca    600
aattaatttc caacggggtc ttgtccggat aagagaattt tgtttgatta tccgttcgga    660
taaatggacg cctgctccat atttttccgg ttattacccc acctggaagt gcccagaatt    720
ttccggggat tacggataat acggtggtct ggattaatta atacgagatc tcagggattc    780
```

-continued

```
ccactatttg gtattctgat atgtttttcc tgatatgcat caaaactcta atctaaaacc    840
tgaatctccg cttttttttt tttttttgat gaccccgttt tcgtgacaaa ttaatttcca    900
acggggtctt gtccggataa gagaattttg tttgattatc cgttcggata aatggacgcc    960
tgctccatat ttttccggtt attaccccac ctggaagtgc ccagaatttt ccggggatta   1020
cggataatac ggtggtctgg attaattaat acgccaagtc ttacattttg ttgcagtctc   1080
gtgcgagtat gtgcaataat aaacaagatg agccaattta ttggattagt tgcagcttga   1140
ccccgccata gctaggcata gccaagtgct atgggtgtta gatgatgcac ttggatgcag   1200
tgagttttgg agtataaaag atccttaaaa ttccaccctt                         1240
```

<210> SEQ ID NO 59
<211> LENGTH: 1240
<212> TYPE: DNA
<213> ORGANISM: Artificial Sequence
<220> FEATURE:
<223> OTHER INFORMATION: pG1-3 promoter

<400> SEQUENCE: 59

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt taccccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg cttttttttt tttttttgat gaccccgttt tcgtgacaaa    600
ttaatttcca acggggtctt gtccggataa gagaattttg tttgattatc cgttcggata    660
aatggacgcc tgctccatat ttttccggtt attaccccac ctggaagtgc ccagaatttt    720
ccggggatta cggataatac ggtggtctgg attaattaat acgagatctc agggattccc    780
actatttggt attctgatat gtttttcctg atatgcatca aaactctaat ctaaaacctg    840
aatctccgct attttttttt tttttttgat gaccccgttt tcgtgacaaa ttaatttcca    900
acggggtctt gtccggataa gagaattttg tttgattatc cgttcggata aatggacgcc    960
tgctccatat ttttccggtt attaccccac ctggaagtgc ccagaatttt ccggggatta   1020
cggataatac ggtggtctgg attaattaat acgccaagtc ttacattttg ttgcagtctc   1080
gtgcgagtat gtgcaataat aaacaagatg agccaattta ttggattagt tgcagcttga   1140
ccccgccata gctaggcata gccaagtgct atgggtgtta gatgatgcac ttggatgcag   1200
tgagttttgg agtataaaag atccttaaaa ttccaccctt                         1240
```

<210> SEQ ID NO 60
<211> LENGTH: 1238
<212> TYPE: DNA
<213> ORGANISM: Artificial Sequence
<220> FEATURE:
<223> OTHER INFORMATION: pG1-3 promoter

<400> SEQUENCE: 60

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg cttttttttt tttttttgat gaccccgttt tcgtgacaaa    600
ttaatttcca acggggtctt gtccggataa gagaattttg tttgattatc cgttcggata    660
aatggacgcc tgctccatat ttttccggtt attaccccac ctggaagtgc ccagaatttt    720
ccggggatta cggataatac ggtggtctgg attaattaat acgagatctc agggattccc    780
actatttggt attctgatat gtttttcctg atatgcatca aaactctaat ctaaaacctg    840
aatctccgct tttttttttt tttttgatga ccccgttttc gtgacaaatt aatttccaac    900
ggggtcttgt ccggataaga gaattttgtt tgattatccg ttcggataaa tggacgcctg    960
ctccatattt ttccggttat taccccacct ggaagtgccc agaattttcc ggggattacg   1020
gataatacgg tggtctggat taattaatac gccaagtctt acattttgtt gcagtctcgt   1080
gcgagtatgt gcaataataa acaagatgag ccaatttatt ggattagttg cagcttgacc   1140
ccgccatagc taggcatagc caagtgctat gggtgttaga tgatgcactt ggatgcagtg   1200
agttttggag tataaaagat ccttaaaatt ccacccctt                          1238
```

<210> SEQ ID NO 61
<211> LENGTH: 1244
<212> TYPE: DNA
<213> ORGANISM: Artificial Sequence
<220> FEATURE:
<223> OTHER INFORMATION: pG1-3 promoter

<400> SEQUENCE: 61

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg ctattttttt tttttttttt gatgaccccg ttttcgtgac    600
aaattaattt ccaacggggt cttgtccgga taagagaatt ttgtttgatt atccgttcgg    660
ataaatggac gcctgctcca tatttttccg gttattaccc cacctggaag tgcccagaat    720
tttccgggga ttacggataa tacggtggtc tggattaatt aatacgagat ctcagggatt    780
cccactattt ggtattctga tatgtttttc ctgatatgca tcaaaactct aatctaaaac    840
```

-continued

```
ctgaatctcc gctatttttt tttttttttt tgatgacccc gttttcgtga caaattaatt    900

tccaacgggg tcttgtccgg ataagagaat tttgtttgat tatccgttcg gataaatgga    960

cgcctgctcc atatttttcc ggttattacc ccacctggaa gtgcccagaa ttttccgggg   1020

attacggata atacggtggt ctggattaat taatacgcca agtcttacat tttgttgcag   1080

tctcgtgcga gtatgtgcaa taataaacaa gatgagccaa tttattggat tagttgcagc   1140

ttgaccccgc catagctagg catagccaag tgctatgggt gttagatgat gcacttggat   1200

gcagtgagtt ttggagtata aaagatcctt aaaattccac cctt                    1244
```

<210> SEQ ID NO 62
<211> LENGTH: 1242
<212> TYPE: DNA
<213> ORGANISM: Artificial Sequence
<220> FEATURE:
<223> OTHER INFORMATION: pG1-3 promoter

<400> SEQUENCE: 62

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt tttttttttt gatgaccccg ttttcgtgac    600

aaattaattt ccaacggggt cttgtccgga taagagaatt ttgtttgatt atccgttcgg    660

ataaatggac gcctgctcca tatttttccg gttattaccc cacctggaag tgcccagaat    720

tttccgggga ttacggataa tacggtggtc tggattaatt aatacgagat ctcagggatt    780

cccactattt ggtattctga tatgtttttc ctgatatgca tcaaaactct aatctaaaac    840

ctgaatctcc gctttttttt tttttttttg atgaccccgt tttcgtgaca aattaatttc    900

caacggggtc ttgtccggat aagagaattt tgtttgatta tccgttcgga taaatggacg    960

cctgctccat atttttccgg ttattacccc acctggaagt gcccagaatt ttccggggat   1020

tacggataat acggtggtct ggattaatta atacgccaag tcttacattt tgttgcagtc   1080

tcgtgcgagt atgtgcaata ataaacaaga tgagccaatt tattggatta gttgcagctt   1140

gaccccgcca tagctaggca tagccaagtg ctatgggtgt tagatgatgc acttggatgc   1200

agtgagtttt ggagtataaa agatccttaa aattccaccc tt                      1242
```

<210> SEQ ID NO 63
<211> LENGTH: 1242
<212> TYPE: DNA
<213> ORGANISM: Artificial Sequence
<220> FEATURE:
<223> OTHER INFORMATION: pG1-3 promoter

<400> SEQUENCE: 63

```
caaacatttg ctccccctag tctccaggga aatgtaaaat atactgctaa tagaaaacag     60
```

-continued taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttga tgaccccgtt ttcgtgacaa 600
attaatttcc aacggggtct tgtccggata agagaatttt gtttgattat ccgttcggat 660
aaatggacgc ctgctccata tttttccggt tattacccca cctggaagtg cccagaattt 720
tccggggatt acggataata cggtggtctg gattaattaa tacgagatct cagggattcc 780
cactatttgg tattctgata tgtttttcct gatatgcatc aaaactctaa tctaaaacct 840
gaatctccgc tatttttttt tttttttttg atgaccccgt tttcgtgaca aattaatttc 900
caacggggtc ttgtccggat aagagaattt tgtttgatta tccgttcgga taaatggacg 960
cctgctccat atttttccgg ttattacccc acctggaagt gcccagaatt ttccggggat 1020
tacggataat acggtggtct ggattaatta atacgccaag tcttacattt tgttgcagtc 1080
tcgtgcgagt atgtgcaata ataaacaaga tgagccaatt tattggatta gttgcagctt 1140
gaccccgcca tagctaggca tagccaagtg ctatgggtgt tagatgatgc acttggatgc 1200
agtgagtttt ggagtataaa agatccttaa aattccaccc tt 1242

<210> SEQ ID NO 64
<211> LENGTH: 1240
<212> TYPE: DNA
<213> ORGANISM: Artificial Sequence
<220> FEATURE:
<223> OTHER INFORMATION: pG1-3 promoter

<400> SEQUENCE: 64
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttga tgaccccgtt ttcgtgacaa 600
attaatttcc aacggggtct tgtccggata agagaatttt gtttgattat ccgttcggat 660
aaatggacgc ctgctccata tttttccggt tattacccca cctggaagtg cccagaattt 720
tccggggatt acggataata cggtggtctg gattaattaa tacgagatct cagggattcc 780
cactatttgg tattctgata tgtttttcct gatatgcatc aaaactctaa tctaaaacct 840
gaatctccgc tttttttttt tttttttgat gaccccgttt tcgtgacaaa ttaatttcca 900

```
acggggtctt gtccggataa gagaattttg tttgattatc cgttcggata aatggacgcc    960

tgctccatat ttttccggtt attaccccac ctggaagtgc ccagaatttt ccggggatta   1020

cggataatac ggtggtctgg attaattaat acgccaagtc ttacattttg ttgcagtctc   1080

gtgcgagtat gtgcaataat aaacaagatg agccaattta ttggattagt tgcagcttga   1140

ccccgccata gctaggcata gccaagtgct atgggtgtta gatgatgcac ttggatgcag   1200

tgagttttgg agtataaaag atccttaaaa ttccaccctt                         1240
```

```
<210> SEQ ID NO 65
<211> LENGTH: 1246
<212> TYPE: DNA
<213> ORGANISM: Artificial Sequence
<220> FEATURE:
<223> OTHER INFORMATION: pG1-3 promoter

<400> SEQUENCE: 65

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt tttttttttt tgatgacccc gttttcgtga    600

caaattaatt tccaacgggg tcttgtccgg ataagagaat tttgtttgat tatccgttcg    660

gataaatgga cgcctgctcc atatttttcc ggttattacc ccacctggaa gtgcccagaa    720

ttttccgggg attacggata atacggtggt ctggattaat taatacgaga tctcagggat    780

tcccactatt tggtattctg atatgttttt cctgatatgc atcaaaactc taatctaaaa    840

cctgaatctc cgctattttt tttttttttt tttgatgacc ccgttttcgt gacaaattaa    900

tttccaacgg ggtcttgtcc ggataagaga attttgtttg attatccgtt cggataaatg    960

gacgcctgct ccatattttt ccggttatta ccccacctgg aagtgcccag aattttccgg   1020

ggattacgga taatacggtg gtctggatta attaatacgc caagtcttac attttgttgc   1080

agtctcgtgc gagtatgtgc aataataaac aagatgagcc aatttattgg attagttgca   1140

gcttgacccc gccatagcta ggcatagcca agtgctatgg gtgttagatg atgcacttgg   1200

atgcagtgag ttttggagta taaaagatcc ttaaaattcc accctt                  1246
```

```
<210> SEQ ID NO 66
<211> LENGTH: 1244
<212> TYPE: DNA
<213> ORGANISM: Artificial Sequence
<220> FEATURE:
<223> OTHER INFORMATION: pG1-3 promoter

<400> SEQUENCE: 66

caaacatttg ctccccctag tctccaggga aatgtaaaat atactgctaa tagaaaacag     60

taagacgctc agttgtcagg ataattacgt tcgactgtag taaaacagga atctgtattg    120
```

ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttttt tgatgacccc gttttcgtga 600
caaattaatt tccaacgggg tcttgtccgg ataagagaat tttgtttgat tatccgttcg 660
gataaatgga cgcctgctcc atatttttcc ggttattacc ccacctggaa gtgcccagaa 720
ttttccgggg attacggata atacggtggt ctggattaat taatacgaga tctcagggat 780
tcccactatt tggtattctg atatgttttt cctgatatgc atcaaaactc taatctaaaa 840
cctgaatctc cgcttttttt tttttttttt tgatgacccc gttttcgtga caaattaatt 900
tccaacgggg tcttgtccgg ataagagaat tttgtttgat tatccgttcg gataaatgga 960
cgcctgctcc atatttttcc ggttattacc ccacctggaa gtgcccagaa ttttccgggg 1020
attacggata atacggtggt ctggattaat taatacgcca agtcttacat tttgttgcag 1080
tctcgtgcga gtatgtgcaa taataaacaa gatgagccaa tttattggat tagttgcagc 1140
ttgaccccgc catagctagg catagccaag tgctatgggt gttagatgat gcacttggat 1200
gcagtgagtt ttggagtata aaagatcctt aaaattccac cctt 1244

<210> SEQ ID NO 67
<211> LENGTH: 1244
<212> TYPE: DNA
<213> ORGANISM: Artificial Sequence
<220> FEATURE:
<223> OTHER INFORMATION: pG1-3 promoter

<400> SEQUENCE: 67
caaacatttg ctcccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttttg atgaccccgt tttcgtgaca 600
aattaatttc caacggggtc ttgtccggat aagagaattt tgtttgatta tccgttcgga 660
taaatggacg cctgctccat atttttccgg ttattacccc acctggaagt gcccagaatt 720
ttccggggat tacggataat acggtggtct ggattaatta atacgagatc tcagggattc 780
ccactatttg gtattctgat atgtttttcc tgatatgcat caaaactcta atctaaaacc 840
tgaatctccg ctattttttt tttttttttt tgatgacccc gttttcgtga caaattaatt 900
tccaacgggg tcttgtccgg ataagagaat tttgtttgat tatccgttcg gataaatgga 960

```
cgcctgctcc atatttttcc ggttattacc ccacctggaa gtgcccagaa ttttccgggg   1020

attacggata atacggtggt ctggattaat taatacgcca agtcttacat tttgttgcag   1080

tctcgtgcga gtatgtgcaa taataaacaa gatgagccaa tttattggat tagttgcagc   1140

ttgaccccgc catagctagg catagccaag tgctatgggt gttagatgat gcacttggat   1200

gcagtgagtt ttggagtata aaagatcctt aaaattccac cctt                     1244
```

<210> SEQ ID NO 68
<211> LENGTH: 1242
<212> TYPE: DNA
<213> ORGANISM: Artificial Sequence
<220> FEATURE:
<223> OTHER INFORMATION: pG1-3 promoter

<400> SEQUENCE: 68

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt tttttttttg atgaccccgt tttcgtgaca    600

aattaatttc caacggggtc ttgtccggat aagagaattt tgtttgatta tccgttcgga    660

taaatggacg cctgctccat atttttccgg ttattacccc acctggaagt gcccagaatt    720

ttccggggat tacggataat acggtggtct ggattaatta atacgagatc tcagggattc    780

ccactatttg gtattctgat atgtttttcc tgatatgcat caaaactcta atctaaaacc    840

tgaatctccg cttttttttt tttttttttg atgaccccgt tttcgtgaca aattaatttc    900

caacggggtc ttgtccggat aagagaattt tgtttgatta tccgttcgga taaatggacg    960

cctgctccat atttttccgg ttattacccc acctggaagt gcccagaatt ttccggggat   1020

tacggataat acggtggtct ggattaatta atacgccaag tcttacattt tgttgcagtc   1080

tcgtgcgagt atgtgcaata ataaacaaga tgagccaatt tattggatta gttgcagctt   1140

gaccccgcca tagctaggca tagccaagtg ctatgggtgt tagatgatgc acttggatgc   1200

agtgagtttt ggagtataaa agatccttaa aattccaccc tt                       1242
```

<210> SEQ ID NO 69
<211> LENGTH: 1248
<212> TYPE: DNA
<213> ORGANISM: Artificial Sequence
<220> FEATURE:
<223> OTHER INFORMATION: pG1-3 promoter

<400> SEQUENCE: 69

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180
```

```
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt     420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg ctattttttt tttttttttt ttgatgaccc cgttttcgtg    600
acaaattaat ttccaacggg gtcttgtccg gataagagaa ttttgtttga ttatccgttc    660
ggataaatgg acgcctgctc catatttttc cggttattac cccacctgga agtgcccaga    720
attttccggg gattacggat aatacggtgg tctggattaa ttaatacgag atctcaggga    780
ttcccactat ttggtattct gatatgtttt tcctgatatg catcaaaact ctaatctaaa    840
acctgaatct ccgctatttt tttttttttt tttttgatga ccccgttttc gtgacaaatt    900
aatttccaac ggggtcttgt ccggataaga gaattttgtt tgattatccg ttcggataaa    960
tggacgcctg ctccatattt ttccggttat taccccacct ggaagtgccc agaattttcc   1020
ggggattacg gataatacgg tggtctggat taattaatac gccaagtctt acattttgtt   1080
gcagtctcgt gcgagtatgt gcaataataa acaagatgag ccaatttatt ggattagttg   1140
cagcttgacc ccgccatagc taggcatagc caagtgctat gggtgttaga tgatgcactt   1200
ggatgcagtg agttttggag tataaaagat ccttaaaatt ccacccctt              1248
```

<210> SEQ ID NO 70
<211> LENGTH: 1246
<212> TYPE: DNA
<213> ORGANISM: Artificial Sequence
<220> FEATURE:
<223> OTHER INFORMATION: pG1-3 promoter

<400> SEQUENCE: 70

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt     420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg ctattttttt tttttttttt ttgatgaccc cgttttcgtg    600
acaaattaat ttccaacggg gtcttgtccg gataagagaa ttttgtttga ttatccgttc    660
ggataaatgg acgcctgctc catatttttc cggttattac cccacctgga agtgcccaga    720
attttccggg gattacggat aatacggtgg tctggattaa ttaatacgag atctcaggga    780
ttcccactat ttggtattct gatatgtttt tcctgatatg catcaaaact ctaatctaaa    840
acctgaatct ccgctttttt tttttttttt tttgatgacc ccgttttcgt gacaaattaa    900
tttccaacgg ggtcttgtcc ggataagaga attttgtttg attatccgtt cggataaatg    960
gacgcctgct ccatattttt ccggttatta ccccacctgg aagtgcccag aattttccgg   1020
```

ggattacgga taatacggtg gtctggatta attaatacgc caagtcttac attttgttgc 1080
agtctcgtgc gagtatgtgc aataataaac aagatgagcc aatttattgg attagttgca 1140
gcttgacccc gccatagcta ggcatagcca agtgctatgg gtgttagatg atgcacttgg 1200
atgcagtgag ttttggagta taaaagatcc ttaaaattcc accctt 1246

<210> SEQ ID NO 71
<211> LENGTH: 1246
<212> TYPE: DNA
<213> ORGANISM: Artificial Sequence
<220> FEATURE:
<223> OTHER INFORMATION: pG1-3 promoter

<400> SEQUENCE: 71
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttttt gatgaccccg ttttcgtgac 600
aaattaattt ccaacggggt cttgtccgga taagagaatt ttgtttgatt atccgttcgg 660
ataaatggac gcctgctcca tatttttccg gttattaccc cacctggaag tgcccagaat 720
tttccgggga ttacggataa tacggtggtc tggattaatt aatacgagat ctcagggatt 780
cccactattt ggtattctga tatgtttttc ctgatatgca tcaaaactct aatctaaaac 840
ctgaatctcc gctatttttt tttttttttt tttgatgacc ccgttttcgt gacaaattaa 900
tttccaacgg ggtcttgtcc ggataagaga attttgtttg attatccgtt cggataaatg 960
gacgcctgct ccatattttt ccggttatta ccccacctgg aagtgcccag aattttccgg 1020
ggattacgga taatacggtg gtctggatta attaatacgc caagtcttac attttgttgc 1080
agtctcgtgc gagtatgtgc aataataaac aagatgagcc aatttattgg attagttgca 1140
gcttgacccc gccatagcta ggcatagcca agtgctatgg gtgttagatg atgcacttgg 1200
atgcagtgag ttttggagta taaaagatcc ttaaaattcc accctt 1246

<210> SEQ ID NO 72
<211> LENGTH: 1244
<212> TYPE: DNA
<213> ORGANISM: Artificial Sequence
<220> FEATURE:
<223> OTHER INFORMATION: pG1-3 promoter

<400> SEQUENCE: 72
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttttt gatgaccccg ttttcgtgac 600
aaattaattt ccaacggggt cttgtccgga taagagaatt ttgtttgatt atccgttcgg 660
ataaatggac gcctgctcca tatttttccg gttattaccc cacctggaag tgcccagaat 720
tttccgggga ttacggataa tacggtggtc tggattaatt aatacgagat ctcagggatt 780
cccactattt ggtattctga tatgtttttc ctgatatgca tcaaaactct aatctaaaac 840
ctgaatctcc gctttttttt tttttttttt tgatgacccc gttttcgtga caaattaatt 900
tccaacgggg tcttgtccgg ataagagaat tttgtttgat tatccgttcg gataaatgga 960
cgcctgctcc atatttttcc ggttattacc ccacctggaa gtgcccagaa ttttccgggg 1020
attacggata atacggtggt ctggattaat taatacgcca agtcttacat tttgttgcag 1080
tctcgtgcga gtatgtgcaa taataaacaa gatgagccaa tttattggat tagttgcagc 1140
ttgaccccgc catagctagg catagccaag tgctatgggt gttagatgat gcacttggat 1200
gcagtgagtt ttggagtata aaagatcctt aaaattccac cctt 1244

<210> SEQ ID NO 73
<211> LENGTH: 1250
<212> TYPE: DNA
<213> ORGANISM: Artificial Sequence
<220> FEATURE:
<223> OTHER INFORMATION: pG1-3 promoter

<400> SEQUENCE: 73
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttttt tttgatgacc ccgttttcgt 600
gacaaattaa tttccaacgg ggtcttgtcc ggataagaga attttgtttg attatccgtt 660
cggataaatg gacgcctgct ccatattttt ccggttatta ccccacctgg aagtgcccag 720
aattttccgg ggattacgga taatacggtg gtctggatta attaatacga gatctcaggg 780
attcccacta tttggtattc tgatatgttt ttcctgatat gcatcaaaac tctaatctaa 840
aacctgaatc tccgctattt tttttttttt ttttttgat gaccccgttt tcgtgacaaa 900
ttaatttcca acggggtctt gtccggataa gagaattttg tttgattatc cgttcggata 960
aatggacgcc tgctccatat ttttccggtt attaccccac ctggaagtgc ccagaatttt 1020
ccggggatta cggataatac ggtggtctgg attaattaat acgccaagtc ttacattttg 1080

```
ttgcagtctc gtgcgagtat gtgcaataat aaacaagatg agccaattta ttggattagt   1140

tgcagcttga ccccgccata gctaggcata gccaagtgct atgggtgtta gatgatgcac   1200

ttggatgcag tgagttttgg agtataaaag atccttaaaa ttccaccctt              1250


<210> SEQ ID NO 74
<211> LENGTH: 1248
<212> TYPE: DNA
<213> ORGANISM: Artificial Sequence
<220> FEATURE:
<223> OTHER INFORMATION: pG1-3 promoter

<400> SEQUENCE: 74

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt ttttttttt tttgatgacc ccgttttcgt     600

gacaaattaa tttccaacgg ggtcttgtcc ggataagaga attttgtttg attatccgtt    660

cggataaatg gacgcctgct ccatattttt ccggttatta ccccacctgg aagtgcccag    720

aattttccgg ggattacgga taatacggtg gtctggatta attaatacga gatctcaggg    780

attcccacta tttggtattc tgatatgttt ttcctgatat gcatcaaaac tctaatctaa    840

aacctgaatc tccgcttttt tttttttttt tttttgatga ccccgttttc gtgacaaatt    900

aatttccaac ggggtcttgt ccggataaga gaattttgtt tgattatccg ttcggataaa    960

tggacgcctg ctccatattt ttccggttat taccccacct ggaagtgccc agaattttcc   1020

ggggattacg gataatacgg tggtctggat taattaatac gccaagtctt acattttgtt   1080

gcagtctcgt gcgagtatgt gcaataataa acaagatgag ccaatttatt ggattagttg   1140

cagcttgacc ccgccatagc taggcatagc caagtgctat gggtgttaga tgatgcactt   1200

ggatgcagtg agttttggag tataaaagat ccttaaaatt ccaccctt                1248


<210> SEQ ID NO 75
<211> LENGTH: 1248
<212> TYPE: DNA
<213> ORGANISM: Artificial Sequence
<220> FEATURE:
<223> OTHER INFORMATION: pG1-3 promoter

<400> SEQUENCE: 75

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300
```

```
ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt tttttttttt tgatgacccc gttttcgtga    600

caaattaatt tccaacgggg tcttgtccgg ataagagaat tttgtttgat tatccgttcg    660

gataaatgga cgcctgctcc atatttttcc ggttattacc ccacctggaa gtgcccagaa    720

ttttccgggg attacggata atacggtggt ctggattaat taatacgaga tctcagggat    780

tcccactatt tggtattctg atatgttttt cctgatatgc atcaaaactc taatctaaaa    840

cctgaatctc cgctattttt tttttttttt tttttgatga ccccgttttc gtgacaaatt    900

aatttccaac ggggtcttgt ccggataaga gaattttgtt tgattatccg ttcggataaa    960

tggacgcctg ctccatattt ttccggttat taccccacct ggaagtgccc agaattttcc   1020

ggggattacg gataatacgg tggtctggat taattaatac gccaagtctt acattttgtt   1080

gcagtctcgt gcgagtatgt gcaataataa acaagatgag ccaatttatt ggattagttg   1140

cagcttgacc ccgccatagc taggcatagc caagtgctat gggtgttaga tgatgcactt   1200

ggatgcagtg agttttggag tataaaagat ccttaaaatt ccacccctt               1248
```

<210> SEQ ID NO 76
<211> LENGTH: 1246
<212> TYPE: DNA
<213> ORGANISM: Artificial Sequence
<220> FEATURE:
<223> OTHER INFORMATION: pG1-3 promoter

<400> SEQUENCE: 76

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt tttttttttt tgatgacccc gttttcgtga    600

caaattaatt tccaacgggg tcttgtccgg ataagagaat tttgtttgat tatccgttcg    660

gataaatgga cgcctgctcc atatttttcc ggttattacc ccacctggaa gtgcccagaa    720

ttttccgggg attacggata atacggtggt ctggattaat taatacgaga tctcagggat    780

tcccactatt tggtattctg atatgttttt cctgatatgc atcaaaactc taatctaaaa    840

cctgaatctc cgcttttttt tttttttttt tttgatgacc ccgttttcgt gacaaattaa    900

tttccaacgg ggtcttgtcc ggataagaga attttgtttg attatccgtt cggataaatg    960

gacgcctgct ccatattttt ccggttatta ccccacctgg aagtgcccag aattttccgg   1020

ggattacgga taatacggtg gtctggatta attaatacgc caagtcttac attttgttgc   1080

agtctcgtgc gagtatgtgc aataataaac aagatgagcc aatttattgg attagttgca   1140
```

-continued

```
gcttgacccc gccatagcta ggcatagcca agtgctatgg gtgttagatg atgcacttgg   1200

atgcagtgag ttttggagta taaaagatcc ttaaaattcc accctt                  1246


<210> SEQ ID NO 77
<211> LENGTH: 1437
<212> TYPE: DNA
<213> ORGANISM: Artificial Sequence
<220> FEATURE:
<223> OTHER INFORMATION: pG1-4 promoter
<220> FEATURE:
<221> NAME/KEY: misc_feature
<222> LOCATION: (577)..(583)
<223> OTHER INFORMATION: n is t or absent
<220> FEATURE:
<221> NAME/KEY: misc_feature
<222> LOCATION: (1058)..(1064)
<223> OTHER INFORMATION: n is t or absent

<400> SEQUENCE: 77

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt ttttttnnnn nnngatgacc ccgttttcgt    600

gacaaattaa tttccaacgg ggtcttgtcc ggataagaga attttgtttg attatccgtt    660

cggataaatg gacgcctgct ccatattttt ccggttatta ccccacctgg aagtgcccag    720

aattttccgg ggattacgga taatacggtg gtctggatta attaatacgc caagtcttac    780

attttgttgc agtctcgtgc gagtatgtgc aataataaac aagatgagcc aatttattgg    840

attagttgca gcttgacccc gccatagcta ggcatagcca agtgctatgg gtgttagatg    900

atgcacttgg atgcagtgag ttttggagta taaaagatcc ttaaaattcc acccttagat    960

ctcagggatt cccactattt ggtattctga tatgtttttc ctgatatgca tcaaaactct   1020

aatctaaaac ctgaatctcc gctatttttt tttttttnnn nnnngatgac cccgttttcg   1080

tgacaaatta atttccaacg gggtcttgtc cggataagag aattttgttt gattatccgt   1140

tcggataaat ggacgcctgc tccatatttt tccggttatt accccacctg gaagtgccca   1200

gaattttccg gggattacgg ataatacggt ggtctggatt aattaatacg ccaagtctta   1260

cattttgttg cagtctcgtg cgagtatgtg caataataaa caagatgagc caatttattg   1320

gattagttgc agcttgaccc cgccatagct aggcatagcc aagtgctatg ggtgttagat   1380

gatgcacttg gatgcagtga gttttggagt ataaaagatc cttaaaattc caccctt      1437


<210> SEQ ID NO 78
<211> LENGTH: 1435
<212> TYPE: DNA
<213> ORGANISM: Artificial Sequence
<220> FEATURE:
<223> OTHER INFORMATION: pG1-4 promoter
<220> FEATURE:
```

<221> NAME/KEY: misc_feature
<222> LOCATION: (577)..(583)
<223> OTHER INFORMATION: n is t or absent
<220> FEATURE:
<221> NAME/KEY: misc_feature
<222> LOCATION: (1056)..(1062)
<223> OTHER INFORMATION: n is t or absent

<400> SEQUENCE: 78

```
caaacatttg ctccccctag tctccaggga aatgtaaaat atactgctaa tagaaaacag      60

taagacgctc agttgtcagg ataattacgt tcgactgtag taaaacagga atctgtattg     120

ttagaaagaa cgagagtttt ttacggcgcc gccatattgg gccgtgtgaa aacagcttga     180

aaccccacta ctttcaaagg ttctgttgct atacacgaac catgtttaac caacctcgct     240

tttgacttga ctgaagtcat cggttaacaa tcaagtaccc tagtctgtct gaatgctcct     300

ttccatattc agtaggtgtt tcttgcactt ttgcatgcac tgcggaagaa ttagccaata     360

gcgcgtttca tatgcgcttt taccccctct tttgtcaagc gcaaaatgcc tgtaagattt     420

ggtgggggtg tgagccgtta gctgaagtac aacaggctaa ttccctgaaa aaactgcagc     480

tcagggattc ccactatttg gtattctgat atgtttttcc tgatatgcat caaaactcta     540

atctaaaacc tgaatctccg ctattttttt tttttnnnnn nnngatgacc ccgttttcgt     600

gacaaattaa tttccaacgg ggtcttgtcc ggataagaga attttgtttg attatccgtt     660

cggataaatg gacgcctgct ccatattttt ccggttatta ccccacctgg aagtgcccag     720

aattttccgg ggattacgga taatacggtg gtctggatta attaatacgc caagtcttac     780

attttgttgc agtctcgtgc gagtatgtgc aataataaac aagatgagcc aatttattgg     840

attagttgca gcttgacccc gccatagcta ggcatagcca agtgctatgg gtgttagatg     900

atgcacttgg atgcagtgag ttttggagta taaaagatcc ttaaaattcc acccttagat     960

ctcagggatt cccactattt ggtattctga tatgtttttc ctgatatgca tcaaaactct    1020

aatctaaaac ctgaatctcc gctttttttt tttttnnnnn nngatgaccc cgttttcgtg    1080

acaaattaat ttccaacggg gtcttgtccg gataagagaa ttttgtttga ttatccgttc    1140

ggataaatgg acgcctgctc catatttttc cggttattac cccacctgga agtgcccaga    1200

attttccggg gattacggat aatacggtgg tctggattaa ttaatacgcc aagtcttaca    1260

ttttgttgca gtctcgtgcg agtatgtgca ataataaaca agatgagcca atttattgga    1320

ttagttgcag cttgaccccg ccatagctag gcatagccaa gtgctatggg tgttagatga    1380

tgcacttgga tgcagtgagt tttggagtat aaaagatcct taaaattcca ccctt         1435
```

<210> SEQ ID NO 79
<211> LENGTH: 1435
<212> TYPE: DNA
<213> ORGANISM: Artificial Sequence
<220> FEATURE:
<223> OTHER INFORMATION: pG1-4 promoter
<220> FEATURE:
<221> NAME/KEY: misc_feature
<222> LOCATION: (575)..(581)
<223> OTHER INFORMATION: n is t or absent
<220> FEATURE:
<221> NAME/KEY: misc_feature
<222> LOCATION: (1056)..(1062)
<223> OTHER INFORMATION: n is t or absent

<400> SEQUENCE: 79

```
caaacatttg ctccccctag tctccaggga aatgtaaaat atactgctaa tagaaaacag      60

taagacgctc agttgtcagg ataattacgt tcgactgtag taaaacagga atctgtattg     120
```

```
ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttnnnnnn ngatgacccc gttttcgtga    600

caaattaatt tccaacgggg tcttgtccgg ataagagaat tttgtttgat tatccgttcg    660

gataaatgga cgcctgctcc atatttttcc ggttattacc ccacctggaa gtgcccagaa    720

ttttccgggg attacggata atacggtggt ctggattaat taatacgcca agtcttacat    780

tttgttgcag tctcgtgcga gtatgtgcaa taataaacaa gatgagccaa tttattggat    840

tagttgcagc ttgaccccgc catagctagg catagccaag tgctatgggt gttagatgat    900

gcacttggat gcagtgagtt ttggagtata aaagatcctt aaaattccac ccttagatct    960

cagggattcc cactatttgg tattctgata tgtttttcct gatatgcatc aaaactctaa   1020

tctaaaacct gaatctccgc tatttttttt tttttnnnnn nngatgaccc cgttttcgtg   1080

acaaattaat ttccaacggg gtcttgtccg gataagagaa ttttgtttga ttatccgttc   1140

ggataaatgg acgcctgctc catatttttc cggttattac cccacctgga agtgcccaga   1200

attttccggg gattacggat aatacggtgg tctggattaa ttaatacgcc aagtcttaca   1260

ttttgttgca gtctcgtgcg agtatgtgca ataataaaca agatgagcca atttattgga   1320

ttagttgcag cttgaccccg ccatagctag gcatagccaa gtgctatggg tgttagatga   1380

tgcacttgga tgcagtgagt tttggagtat aaaagatcct taaaattcca ccctt        1435
```

<210> SEQ ID NO 80
<211> LENGTH: 1433
<212> TYPE: DNA
<213> ORGANISM: Artificial Sequence
<220> FEATURE:
<223> OTHER INFORMATION: pG1-4 promoter
<220> FEATURE:
<221> NAME/KEY: misc_feature
<222> LOCATION: (575)..(581)
<223> OTHER INFORMATION: n is t or absent
<220> FEATURE:
<221> NAME/KEY: misc_feature
<222> LOCATION: (1054)..(1060)
<223> OTHER INFORMATION: n is t or absent

<400> SEQUENCE: 80

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480
```

tcagggattc ccactatttg gtattctgat atgtttttcc tgatatgcat caaaactcta 540
atctaaaacc tgaatctccg cttttttttt ttttnnnnnn ngatgacccc gttttcgtga 600
caaattaatt tccaacgggg tcttgtccgg ataagagaat tttgtttgat tatccgttcg 660
gataaatgga cgcctgctcc atatttttcc ggttattacc ccacctggaa gtgcccagaa 720
ttttccgggg attacggata atacggtggt ctggattaat taatacgcca agtcttacat 780
tttgttgcag tctcgtgcga gtatgtgcaa taataaacaa gatgagccaa tttattggat 840
tagttgcagc ttgaccccgc catagctagg catagccaag tgctatgggt gttagatgat 900
gcacttggat gcagtgagtt ttggagtata aaagatcctt aaaattccac ccttagatct 960
cagggattcc cactatttgg tattctgata tgtttttcct gatatgcatc aaaactctaa 1020
tctaaaacct gaatctccgc tttttttttt tttnnnnnnn gatgaccccg ttttcgtgac 1080
aaattaattt ccaacggggt cttgtccgga taagagaatt ttgtttgatt atccgttcgg 1140
ataaatggac gcctgctcca tatttttccg gttattaccc cacctggaag tgcccagaat 1200
tttccgggga ttacggataa tacggtggtc tggattaatt aatacgccaa gtcttacatt 1260
ttgttgcagt ctcgtgcgag tatgtgcaat aataaacaag atgagccaat ttattggatt 1320
agttgcagct tgaccccgcc atagctaggc atagccaagt gctatgggtg ttagatgatg 1380
cacttggatg cagtgagttt tggagtataa aagatcctta aaattccacc ctt 1433

<210> SEQ ID NO 81
<211> LENGTH: 1423
<212> TYPE: DNA
<213> ORGANISM: Artificial Sequence
<220> FEATURE:
<223> OTHER INFORMATION: pG1-4 promoter

<400> SEQUENCE: 81
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttgatg accccgtttt cgtgacaaat 600
taatttccaa cggggtcttg tccggataag agaattttgt ttgattatcc gttcggataa 660
atggacgcct gctccatatt tttccggtta ttaccccacc tggaagtgcc cagaattttc 720
cggggattac ggataatacg gtggtctgga ttaattaata cgccaagtct tacattttgt 780
tgcagtctcg tgcgagtatg tgcaataata aacaagatga gccaatttat tggattagtt 840
gcagcttgac cccgccatag ctaggcatag ccaagtgcta tgggtgttag atgatgcact 900
tggatgcagt gagttttgga gtataaaaga tccttaaaat tccaccctta gatctcaggg 960
attcccacta tttggtattc tgatatgttt ttcctgatat gcatcaaaac tctaatctaa 1020
aacctgaatc tccgctattt tttttttttt gatgaccccg ttttcgtgac aaattaattt 1080
ccaacggggt cttgtccgga taagagaatt ttgtttgatt atccgttcgg ataaatggac 1140
gcctgctcca tatttttccg gttattaccc cacctggaag tgcccagaat tttccgggga 1200
ttacggataa tacggtggtc tggattaatt aatacgccaa gtcttacatt ttgttgcagt 1260
ctcgtgcgag tatgtgcaat aataaacaag atgagccaat ttattggatt agttgcagct 1320
tgaccccgcc atagctaggc atagccaagt gctatgggtg ttagatgatg cacttggatg 1380
cagtgagttt tggagtataa aagatcctta aaattccacc ctt 1423

<210> SEQ ID NO 82
<211> LENGTH: 1421
<212> TYPE: DNA
<213> ORGANISM: Artificial Sequence
<220> FEATURE:
<223> OTHER INFORMATION: pG1-4 promoter

<400> SEQUENCE: 82
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt ttttttgatg accccgtttt cgtgacaaat 600
taatttccaa cggggtcttg tccggataag agaattttgt ttgattatcc gttcggataa 660
atggacgcct gctccatatt tttccggtta ttaccccacc tggaagtgcc cagaattttc 720
cggggattac ggataatacg gtggtctgga ttaattaata cgccaagtct tacattttgt 780
tgcagtctcg tgcgagtatg tgcaataata aacaagatga gccaatttat tggattagtt 840
gcagcttgac cccgccatag ctaggcatag ccaagtgcta tgggtgttag atgatgcact 900
tggatgcagt gagttttgga gtataaaaga tccttaaaat tccaccctta gatctcaggg 960
attcccacta tttggtattc tgatatgttt ttcctgatat gcatcaaaac tctaatctaa 1020
aacctgaatc tccgcttttt ttttttttga tgaccccgtt ttcgtgacaa attaatttcc 1080
aacggggtct tgtccggata agagaatttt gtttgattat ccgttcggat aaatggacgc 1140
ctgctccata tttttccggt tattacccca cctggaagtg cccagaattt tccggggatt 1200
acggataata cggtggtctg gattaattaa tacgccaagt cttacatttt gttgcagtct 1260
cgtgcgagta tgtgcaataa taaacaagat gagccaattt attggattag ttgcagcttg 1320
accccgccat agctaggcat agccaagtgc tatgggtgtt agatgatgca cttggatgca 1380
gtgagttttg gagtataaaa gatccttaaa attccaccct t 1421

<210> SEQ ID NO 83
<211> LENGTH: 1421
<212> TYPE: DNA
<213> ORGANISM: Artificial Sequence
<220> FEATURE:
<223> OTHER INFORMATION: pG1-4 promoter

<400> SEQUENCE: 83

-continued

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttgatgac cccgttttcg tgacaaatta    600

atttccaacg gggtcttgtc cggataagag aattttgttt gattatccgt tcggataaat    660

ggacgcctgc tccatatttt tccggttatt accccacctg gaagtgccca gaattttccg    720

gggattacgg ataatacggt ggtctggatt aattaatacg ccaagtctta cattttgttg    780

cagtctcgtg cgagtatgtg caataataaa caagatgagc caatttattg gattagttgc    840

agcttgaccc cgccatagct aggcatagcc aagtgctatg ggtgttagat gatgcacttg    900

gatgcagtga gttttggagt ataaaagatc cttaaaattc caccccttaga tctcagggat    960

tcccactatt tggtattctg atatgttttt cctgatatgc atcaaaactc taatctaaaa   1020

cctgaatctc cgctattttt tttttttgga tgaccccgtt ttcgtgacaa attaatttcc   1080

aacggggtct tgtccggata agagaatttt gtttgattat ccgttcggat aaatggacgc   1140

ctgctccata tttttccggt tattacccca cctggaagtg cccagaattt tccggggatt   1200

acggataata cggtggtctg gattaattaa tacgccaagt cttacatttt gttgcagtct   1260

cgtgcgagta tgtgcaataa taaacaagat gagccaattt attggattag ttgcagcttg   1320

accccgccat agctaggcat agccaagtgc tatgggtgtt agatgatgca cttggatgca   1380

gtgagttttg gagtataaaa gatccttaaa attccaccct t                       1421
```

```
<210> SEQ ID NO 84
<211> LENGTH: 1419
<212> TYPE: DNA
<213> ORGANISM: Artificial Sequence
<220> FEATURE:
<223> OTHER INFORMATION: pG1-4 promoter

<400> SEQUENCE: 84

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttgatgac cccgttttcg tgacaaatta    600

atttccaacg gggtcttgtc cggataagag aattttgttt gattatccgt tcggataaat    660
```

ggacgcctgc tccatatttt tccggttatt accccacctg gaagtgccca gaattttccg 720
gggattacgg ataatacggt ggtctggatt aattaatacg ccaagtctta cattttgttg 780
cagtctcgtg cgagtatgtg caataataaa caagatgagc caatttattg gattagttgc 840
agcttgaccc cgccatagct aggcatagcc aagtgctatg ggtgttagat gatgcacttg 900
gatgcagtga gttttggagt ataaaagatc cttaaaattc caccccttaga tctcagggat 960 tcccactatt tggtattctg atatgttttt cctgatatgc atcaaaactc taatctaaaa 1020
cctgaatctc cgcttttttt ttttttgatg accccgtttt cgtgacaaat taatttccaa 1080
cggggtcttg tccggataag agaattttgt ttgattatcc gttcggataa atggacgcct 1140
gctccatatt tttccggtta ttaccccacc tggaagtgcc cagaattttc cggggattac 1200
ggataatacg gtggtctgga ttaattaata cgccaagtct tacattttgt tgcagtctcg 1260
tgcgagtatg tgcaataata aacaagatga gccaatttat tggattagtt gcagcttgac 1320
cccgccatag ctaggcatag ccaagtgcta tgggtgttag atgatgcact tggatgcagt 1380
gagttttgga gtataaaaga tccttaaaat tccacccctt 1419

<210> SEQ ID NO 85
<211> LENGTH: 1425
<212> TYPE: DNA
<213> ORGANISM: Artificial Sequence
<220> FEATURE:
<223> OTHER INFORMATION: pG1-4 promoter

<400> SEQUENCE: 85
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt ttttttgat gaccccgttt tcgtgacaaa 600
ttaatttcca acggggtctt gtccggataa gagaattttg tttgattatc cgttcggata 660
aatggacgcc tgctccatat ttttccggtt attaccccac ctggaagtgc ccagaatttt 720
ccggggatta cggataatac ggtggtctgg attaattaat acgccaagtc ttacattttg 780
ttgcagtctc gtgcgagtat gtgcaataat aaacaagatg agccaattta ttggattagt 840
tgcagcttga ccccgccata gctaggcata gccaagtgct atgggtgtta gatgatgcac 900
ttggatgcag tgagttttgg agtataaaag atccttaaaa ttccacccctt agatctcagg 960 gattcccact atttggtatt ctgatatgtt tttcctgata tgcatcaaaa ctctaatcta 1020
aaacctgaat ctccgctatt tttttttttt ttgatgaccc cgttttcgtg acaaattaat 1080
ttccaacggg gtcttgtccg gataagagaa ttttgtttga ttatccgttc ggataaatgg 1140
acgcctgctc catatttttc cggttattac cccacctgga agtgcccaga attttccggg 1200
gattacggat aatacggtgg tctggattaa ttaatacgcc aagtcttaca ttttgttgca 1260
gtctcgtgcg agtatgtgca ataataaaca agatgagcca atttattgga ttagttgcag 1320
cttgaccccg ccatagctag gcatagccaa gtgctatggg tgttagatga tgcacttgga 1380
tgcagtgagt tttggagtat aaaagatcct taaaattcca ccctt 1425

<210> SEQ ID NO 86
<211> LENGTH: 1423
<212> TYPE: DNA
<213> ORGANISM: Artificial Sequence
<220> FEATURE:
<223> OTHER INFORMATION: pG1-4 promoter

<400> SEQUENCE: 86
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttgat gaccccgttt tcgtgacaaa 600
ttaatttcca acggggtctt gtccggataa gagaattttg tttgattatc cgttcggata 660
aatggacgcc tgctccatat ttttccggtt attaccccac ctggaagtgc ccagaatttt 720
ccggggatta cggataatac ggtggtctgg attaattaat acgccaagtc ttacattttg 780
ttgcagtctc gtgcgagtat gtgcaataat aaacaagatg agccaattta ttggattagt 840
tgcagcttga ccccgccata gctaggcata gccaagtgct atgggtgtta gatgatgcac 900
ttggatgcag tgagttttgg agtataaaag atccttaaaa ttccaccctt agatctcagg 960
gattcccact atttggtatt ctgatatgtt tttcctgata tgcatcaaaa ctctaatcta 1020
aaacctgaat ctccgctttt tttttttttt gatgaccccg ttttcgtgac aaattaattt 1080
ccaacggggt cttgtccgga taagagaatt ttgtttgatt atccgttcgg ataaatggac 1140
gcctgctcca tatttttccg gttattaccc cacctggaag tgcccagaat tttccgggga 1200
ttacggataa tacggtggtc tggattaatt aatacgccaa gtcttacatt ttgttgcagt 1260
ctcgtgcgag tatgtgcaat aataaacaag atgagccaat ttattggatt agttgcagct 1320
tgaccccgcc atagctaggc atagccaagt gctatgggtg ttagatgatg cacttggatg 1380
cagtgagttt tggagtataa aagatcctta aaattccacc ctt 1423

<210> SEQ ID NO 87
<211> LENGTH: 1423
<212> TYPE: DNA
<213> ORGANISM: Artificial Sequence
<220> FEATURE:
<223> OTHER INFORMATION: pG1-4 promoter

<400> SEQUENCE: 87
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttgatga ccccgtttc gtgacaaatt 600 aatttccaac ggggtcttgt ccggataaga gaattttgtt tgattatccg ttcggataaa 660
tggacgcctg ctccatattt ttccggttat taccccacct ggaagtgccc agaattttcc 720
ggggattacg gataatacgg tggtctggat taattaatac gccaagtctt acattttgtt 780
gcagtctcgt gcgagtatgt gcaataataa acaagatgag ccaatttatt ggattagttg 840
cagcttgacc ccgccatagc taggcatagc caagtgctat gggtgttaga tgatgcactt 900
ggatgcagtg agttttggag tataaaagat ccttaaaatt ccacccttag atctcaggga 960
ttcccactat ttggtattct gatatgtttt tcctgatatg catcaaaact ctaatctaaa 1020
acctgaatct ccgctatttt tttttttttt gatgaccccg ttttcgtgac aaattaattt 1080
ccaacggggt cttgtccgga taagagaatt ttgtttgatt atccgttcgg ataaatggac 1140
gcctgctcca tatttttccg gttattaccc cacctggaag tgcccagaat tttccgggga 1200
ttacggataa tacggtggtc tggattaatt aatacgccaa gtcttacatt ttgttgcagt 1260
ctcgtgcgag tatgtgcaat aataaacaag atgagccaat ttattggatt agttgcagct 1320
tgaccccgcc atagctaggc atagccaagt gctatgggtg ttagatgatg cacttggatg 1380
cagtgagttt tggagtataa aagatcctta aaattccacc ctt 1423

<210> SEQ ID NO 88
<211> LENGTH: 1421
<212> TYPE: DNA
<213> ORGANISM: Artificial Sequence
<220> FEATURE:
<223> OTHER INFORMATION: pG1-4 promoter

<400> SEQUENCE: 88
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttgatga ccccgtttc gtgacaaatt 600 aatttccaac ggggtcttgt ccggataaga gaattttgtt tgattatccg ttcggataaa 660
tggacgcctg ctccatattt ttccggttat taccccacct ggaagtgccc agaattttcc 720
ggggattacg gataatacgg tggtctggat taattaatac gccaagtctt acattttgtt 780

-continued gcagtctcgt gcgagtatgt gcaataataa acaagatgag ccaatttatt ggattagttg 840
cagcttgacc ccgccatagc taggcatagc caagtgctat gggtgttaga tgatgcactt 900
ggatgcagtg agttttggag tataaaagat ccttaaaatt ccacccttag atctcaggga 960
ttcccactat ttggtattct gatatgtttt tcctgatatg catcaaaact ctaatctaaa 1020
acctgaatct ccgctttttt tttttttga tgaccccgtt ttcgtgacaa attaatttcc 1080
aacggggtct tgtccggata agagaatttt gtttgattat ccgttcggat aaatggacgc 1140
ctgctccata tttttccggt tattacccca cctggaagtg cccagaattt tccggggatt 1200
acggataata cggtggtctg gattaattaa tacgccaagt cttacatttt gttgcagtct 1260
cgtgcgagta tgtgcaataa taaacaagat gagccaattt attggattag ttgcagcttg 1320
accccgccat agctaggcat agccaagtgc tatgggtgtt agatgatgca cttggatgca 1380
gtgagttttg gagtataaaa gatccttaaa attccaccct t 1421

<210> SEQ ID NO 89
<211> LENGTH: 1427
<212> TYPE: DNA
<213> ORGANISM: Artificial Sequence
<220> FEATURE:
<223> OTHER INFORMATION: pG1-4 promoter

<400> SEQUENCE: 89
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttga tgaccccgtt ttcgtgacaa 600
attaatttcc aacggggtct tgtccggata agagaatttt gtttgattat ccgttcggat 660
aaatggacgc ctgctccata tttttccggt tattacccca cctggaagtg cccagaattt 720
tccggggatt acggataata cggtggtctg gattaattaa tacgccaagt cttacatttt 780
gttgcagtct cgtgcgagta tgtgcaataa taaacaagat gagccaattt attggattag 840
ttgcagcttg accccgccat agctaggcat agccaagtgc tatgggtgtt agatgatgca 900
cttggatgca gtgagttttg gagtataaaa gatccttaaa attccaccct tagatctcag 960
ggattcccac tatttggtat tctgatatgt ttttcctgat atgcatcaaa actctaatct 1020
aaaacctgaa tctccgctat tttttttttt ttttgatgac cccgttttcg tgacaaatta 1080
atttccaacg gggtcttgtc cggataagag aattttgttt gattatccgt tcggataaat 1140
ggacgcctgc tccatatttt tccggttatt accccacctg gaagtgccca gaattttccg 1200
gggattacgg ataatacggt ggtctggatt aattaatacg ccaagtctta cattttgttg 1260
cagtctcgtg cgagtatgtg caataataaa caagatgagc caatttattg gattagttgc 1320
agcttgaccc cgccatagct aggcatagcc aagtgctatg ggtgttagat gatgcacttg 1380
gatgcagtga gttttggagt ataaaagatc cttaaaattc caccctt 1427

<210> SEQ ID NO 90
<211> LENGTH: 1425
<212> TYPE: DNA
<213> ORGANISM: Artificial Sequence
<220> FEATURE:
<223> OTHER INFORMATION: pG1-4 promoter

<400> SEQUENCE: 90
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt ttttttttga tgaccccgtt ttcgtgacaa 600
attaatttcc aacggggtct tgtccggata agagaatttt gtttgattat ccgttcggat 660
aaatggacgc ctgctccata tttttccggt tattacccca cctggaagtg cccagaattt 720
tccggggatt acggataata cggtggtctg gattaattaa tacgccaagt cttacatttt 780
gttgcagtct cgtgcgagta tgtgcaataa taaacaagat gagccaattt attggattag 840
ttgcagcttg accccgccat agctaggcat agccaagtgc tatgggtgtt agatgatgca 900
cttggatgca gtgagttttg gagtataaaa gatccttaaa attccaccct tagatctcag 960
ggattcccac tatttggtat tctgatatgt ttttcctgat atgcatcaaa actctaatct 1020
aaaacctgaa tctccgcttt tttttttttt ttgatgaccc cgttttcgtg acaaattaat 1080
ttccaacggg gtcttgtccg gataagagaa ttttgtttga ttatccgttc ggataaatgg 1140
acgcctgctc catatttttc cggttattac cccacctgga agtgcccaga attttccggg 1200
gattacggat aatacggtgg tctggattaa ttaatacgcc aagtcttaca ttttgttgca 1260
gtctcgtgcg agtatgtgca ataataaaca agatgagcca atttattgga ttagttgcag 1320
cttgaccccg ccatagctag gcatagccaa gtgctatggg tgttagatga tgcacttgga 1380
tgcagtgagt tttggagtat aaaagatcct taaaattcca ccctt 1425

<210> SEQ ID NO 91
<211> LENGTH: 1425
<212> TYPE: DNA
<213> ORGANISM: Artificial Sequence
<220> FEATURE:
<223> OTHER INFORMATION: pG1-4 promoter

<400> SEQUENCE: 91
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300

```
ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttttgatg accccgtttt cgtgacaaat    600

taatttccaa cggggtcttg tccggataag agaattttgt ttgattatcc gttcggataa    660

atggacgcct gctccatatt tttccggtta ttaccccacc tggaagtgcc cagaattttc    720

cggggattac ggataatacg gtggtctgga ttaattaata cgccaagtct tacattttgt    780

tgcagtctcg tgcgagtatg tgcaataata aacaagatga gccaatttat tggattagtt    840

gcagcttgac ccgccatag ctaggcatag ccaagtgcta tgggtgttag atgatgcact    900

tggatgcagt gagttttgga gtataaaaga tccttaaaat tccaccctta gatctcaggg    960

attcccacta tttggtattc tgatatgttt ttcctgatat gcatcaaaac tctaatctaa   1020

aacctgaatc tccgctattt tttttttttt ttgatgaccc cgttttcgtg acaaattaat   1080

ttccaacggg gtcttgtccg gataagagaa ttttgtttga ttatccgttc ggataaatgg   1140

acgcctgctc catatttttc cggttattac cccacctgga agtgcccaga attttccggg   1200

gattacggat aatacggtgg tctggattaa ttaatacgcc aagtcttaca ttttgttgca   1260

gtctcgtgcg agtatgtgca ataataaaca agatgagcca atttattgga ttagttgcag   1320

cttgaccccg ccatagctag gcatagccaa gtgctatggg tgttagatga tgcacttgga   1380

tgcagtgagt tttggagtat aaaagatcct taaaattcca ccctt                   1425
```

```
<210> SEQ ID NO 92
<211> LENGTH: 1423
<212> TYPE: DNA
<213> ORGANISM: Artificial Sequence
<220> FEATURE:
<223> OTHER INFORMATION: pG1-4 promoter

<400> SEQUENCE: 92
```

```
caaacatttg ctcccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt ttttttgatg accccgtttt cgtgacaaat    600

taatttccaa cggggtcttg tccggataag agaattttgt ttgattatcc gttcggataa    660

atggacgcct gctccatatt tttccggtta ttaccccacc tggaagtgcc cagaattttc    720

cggggattac ggataatacg gtggtctgga ttaattaata cgccaagtct tacattttgt    780

tgcagtctcg tgcgagtatg tgcaataata aacaagatga gccaatttat tggattagtt    840

gcagcttgac ccgccatag ctaggcatag ccaagtgcta tgggtgttag atgatgcact    900

tggatgcagt gagttttgga gtataaaaga tccttaaaat tccaccctta gatctcaggg    960
```

attcccacta tttggtattc tgatatgttt ttcctgatat gcatcaaaac tctaatctaa 1020
aacctgaatc tccgcttttt tttttttttt gatgaccccg ttttcgtgac aaattaattt 1080
ccaacggggt cttgtccgga taagagaatt ttgtttgatt atccgttcgg ataaatggac 1140
gcctgctcca tatttttccg gttattaccc cacctggaag tgcccagaat tttccgggga 1200
ttacggataa tacggtggtc tggattaatt aatacgccaa gtcttacatt ttgttgcagt 1260
ctcgtgcgag tatgtgcaat aataaacaag atgagccaat ttattggatt agttgcagct 1320
tgaccccgcc atagctaggc atagccaagt gctatgggtg ttagatgatg cacttggatg 1380
cagtgagttt tggagtataa aagatcctta aaattccacc ctt 1423

<210> SEQ ID NO 93
<211> LENGTH: 1429
<212> TYPE: DNA
<213> ORGANISM: Artificial Sequence
<220> FEATURE:
<223> OTHER INFORMATION: pG1-4 promoter

<400> SEQUENCE: 93
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttttg atgaccccgt tttcgtgaca 600
aattaatttc caacggggtc ttgtccggat aagagaattt tgtttgatta tccgttcgga 660
taaatggacg cctgctccat atttttccgg ttattacccc acctggaagt gcccagaatt 720
ttccggggat tacggataat acggtggtct ggattaatta atacgccaag tcttacattt 780
tgttgcagtc tcgtgcgagt atgtgcaata ataaacaaga tgagccaatt tattggatta 840
gttgcagctt gaccccgcca tagctaggca tagccaagtg ctatgggtgt tagatgatgc 900
acttggatgc agtgagtttt ggagtataaa agatccttaa aattccaccc ttagatctca 960
gggattccca ctatttggta ttctgatatg tttttcctga tatgcatcaa aactctaatc 1020
taaaacctga atctccgcta tttttttttt tttttgatg accccgtttt cgtgacaaat 1080
taatttccaa cggggtcttg tccggataag agaattttgt ttgattatcc gttcggataa 1140
atggacgcct gctccatatt tttccggtta ttaccccacc tggaagtgcc cagaattttc 1200
cggggattac ggataatacg gtggtctgga ttaattaata cgccaagtct tacattttgt 1260
tgcagtctcg tgcgagtatg tgcaataata aacaagatga gccaatttat tggattagtt 1320
gcagcttgac cccgccatag ctaggcatag ccaagtgcta tgggtgttag atgatgcact 1380
tggatgcagt gagttttgga gtataaaaga tccttaaaat tccacccctt 1429

<210> SEQ ID NO 94
<211> LENGTH: 1427
<212> TYPE: DNA

<213> ORGANISM: Artificial Sequence
<220> FEATURE:
<223> OTHER INFORMATION: pG1-4 promoter

<400> SEQUENCE: 94
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttttg atgaccccgt tttcgtgaca 600
aattaatttc caacggggtc ttgtccggat aagagaattt tgtttgatta tccgttcgga 660
taaatggacg cctgctccat atttttccgg ttattacccc acctggaagt gcccagaatt 720
ttccggggat tacggataat acggtggtct ggattaatta atacgccaag tcttacattt 780
tgttgcagtc tcgtgcgagt atgtgcaata ataaacaaga tgagccaatt tattggatta 840
gttgcagctt gaccccgcca tagctaggca tagccaagtg ctatgggtgt tagatgatgc 900
acttggatgc agtgagtttt ggagtataaa agatccttaa aattccaccc ttagatctca 960
gggattccca ctatttggta ttctgatatg tttttcctga tatgcatcaa aactctaatc 1020
taaaacctga atctccgctt tttttttttt ttttgatgac cccgttttcg tgacaaatta 1080
atttccaacg gggtcttgtc cggataagag aattttgttt gattatccgt tcggataaat 1140
ggacgcctgc tccatatttt tccggttatt accccacctg gaagtgccca gaattttccg 1200
gggattacgg ataatacggt ggtctggatt aattaatacg ccaagtctta cattttgttg 1260
cagtctcgtg cgagtatgtg caataataaa caagatgagc caatttattg gattagttgc 1320
agcttgaccc cgccatagct aggcatagcc aagtgctatg ggtgttagat gatgcacttg 1380
gatgcagtga gttttggagt ataaaagatc cttaaaattc caccctt 1427

<210> SEQ ID NO 95
<211> LENGTH: 1427
<212> TYPE: DNA
<213> ORGANISM: Artificial Sequence
<220> FEATURE:
<223> OTHER INFORMATION: pG1-4 promoter

<400> SEQUENCE: 95
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttgat gaccccgttt tcgtgacaaa 600
ttaatttcca acggggtctt gtccggataa gagaattttg tttgattatc cgttcggata 660
aatggacgcc tgctccatat ttttccggtt attaccccac ctggaagtgc ccagaatttt 720
ccggggatta cggataatac ggtggtctgg attaattaat acgccaagtc ttacattttg 780
ttgcagtctc gtgcgagtat gtgcaataat aaacaagatg agccaattta ttggattagt 840
tgcagcttga ccccgccata gctaggcata gccaagtgct atgggtgtta gatgatgcac 900
ttggatgcag tgagttttgg agtataaaag atccttaaaa ttccaccctt agatctcagg 960
gattcccact atttggtatt ctgatatgtt tttcctgata tgcatcaaaa ctctaatcta 1020
aaacctgaat ctccgctatt tttttttttt ttttgatgac cccgttttcg tgacaaatta 1080
atttccaacg gggtcttgtc cggataagag aattttgttt gattatccgt tcggataaat 1140
ggacgcctgc tccatatttt tccggttatt accccacctg gaagtgccca gaattttccg 1200
gggattacgg ataatacggt ggtctggatt aattaatacg ccaagtctta cattttgttg 1260
cagtctcgtg cgagtatgtg caataataaa caagatgagc caatttattg gattagttgc 1320
agcttgaccc cgccatagct aggcatagcc aagtgctatg ggtgttagat gatgcacttg 1380
gatgcagtga gttttggagt ataaaagatc cttaaaattc cacccctt 1427

<210> SEQ ID NO 96
<211> LENGTH: 1425
<212> TYPE: DNA
<213> ORGANISM: Artificial Sequence
<220> FEATURE:
<223> OTHER INFORMATION: pG1-4 promoter

<400> SEQUENCE: 96
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttgat gaccccgttt tcgtgacaaa 600
ttaatttcca acggggtctt gtccggataa gagaattttg tttgattatc cgttcggata 660
aatggacgcc tgctccatat ttttccggtt attaccccac ctggaagtgc ccagaatttt 720
ccggggatta cggataatac ggtggtctgg attaattaat acgccaagtc ttacattttg 780
ttgcagtctc gtgcgagtat gtgcaataat aaacaagatg agccaattta ttggattagt 840
tgcagcttga ccccgccata gctaggcata gccaagtgct atgggtgtta gatgatgcac 900
ttggatgcag tgagttttgg agtataaaag atccttaaaa ttccaccctt agatctcagg 960
gattcccact atttggtatt ctgatatgtt tttcctgata tgcatcaaaa ctctaatcta 1020
aaacctgaat ctccgctttt tttttttttt ttgatgaccc cgttttcgtg acaaattaat 1080

-continued

```
ttccaacggg gtcttgtccg gataagagaa ttttgtttga ttatccgttc ggataaatgg   1140

acgcctgctc catatttttc cggttattac cccacctgga agtgcccaga attttccggg   1200

gattacggat aatacggtgg tctggattaa ttaatacgcc aagtcttaca ttttgttgca   1260

gtctcgtgcg agtatgtgca ataataaaca agatgagcca atttattgga ttagttgcag   1320

cttgaccccg ccatagctag gcatagccaa gtgctatggg tgttagatga tgcacttgga   1380

tgcagtgagt tttggagtat aaaagatcct taaaattcca ccctt                   1425
```

<210> SEQ ID NO 97
<211> LENGTH: 1431
<212> TYPE: DNA
<213> ORGANISM: Artificial Sequence
<220> FEATURE:
<223> OTHER INFORMATION: pG1-4 promoter

<400> SEQUENCE: 97

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt tttttttttt gatgaccccg ttttcgtgac    600

aaattaattt ccaacggggt cttgtccgga taagagaatt ttgtttgatt atccgttcgg    660

ataaatggac gcctgctcca tatttttccg gttattaccc cacctggaag tgcccagaat    720

tttccgggga ttacggataa tacggtggtc tggattaatt aatacgccaa gtcttacatt    780

ttgttgcagt ctcgtgcgag tatgtgcaat aataaacaag atgagccaat ttattggatt    840

agttgcagct tgaccccgcc atagctaggc atagccaagt gctatgggtg ttagatgatg    900

cacttggatg cagtgagttt tggagtataa aagatcctta aaattccacc cttagatctc    960

agggattccc actatttggt attctgatat gtttttcctg atatgcatca aaactctaat   1020

ctaaaacctg aatctccgct attttttttt tttttttga tgaccccgtt ttcgtgacaa   1080

attaatttcc aacggggtct tgtccggata agagaatttt gtttgattat ccgttcggat   1140

aaatggacgc ctgctccata tttttccggt tattacccca cctggaagtg cccagaattt   1200

tccggggatt acggataata cggtggtctg gattaattaa tacgccaagt cttacatttt   1260

gttgcagtct cgtgcgagta tgtgcaataa taaacaagat gagccaattt attggattag   1320

ttgcagcttg accccgccat agctaggcat agccaagtgc tatgggtgtt agatgatgca   1380

cttggatgca gtgagttttg gagtataaaa gatccttaaa attccaccct t            1431
```

<210> SEQ ID NO 98
<211> LENGTH: 1429
<212> TYPE: DNA
<213> ORGANISM: Artificial Sequence
<220> FEATURE:
<223> OTHER INFORMATION: pG1-4 promoter

<400> SEQUENCE: 98

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt taccccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg ctattttttt tttttttttt gatgaccccg ttttcgtgac    600
aaattaattt ccaacggggt cttgtccgga taagagaatt ttgtttgatt atccgttcgg    660
ataaatggac gcctgctcca tatttttccg gttattaccc cacctggaag tgcccagaat    720
tttccgggga ttacggataa tacggtggtc tggattaatt aatacgccaa gtcttacatt    780
ttgttgcagt ctcgtgcgag tatgtgcaat aataaacaag atgagccaat ttattggatt    840
agttgcagct tgaccccgcc atagctaggc atagccaagt gctatgggtg ttagatgatg    900
cacttggatg cagtgagttt tggagtataa aagatcctta aaattccacc cttagatctc    960
agggattccc actatttggt attctgatat gtttttcctg atatgcatca aaactctaat   1020
ctaaaacctg aatctccgct tttttttttt tttttgatg accccgtttt cgtgacaaat   1080
taatttccaa cggggtcttg tccggataag agaattttgt ttgattatcc gttcggataa   1140
atggacgcct gctccatatt tttccggtta ttaccccacc tggaagtgcc cagaattttc   1200
cggggattac ggataatacg gtggtctgga ttaattaata cgccaagtct tacattttgt   1260
tgcagtctcg tgcgagtatg tgcaataata aacaagatga gccaatttat tggattagtt   1320
gcagcttgac cccgccatag ctaggcatag ccaagtgcta tgggtgttag atgatgcact   1380
tggatgcagt gagttttgga gtataaaaga tccttaaaat tccacccctt               1429
```

<210> SEQ ID NO 99
<211> LENGTH: 1429
<212> TYPE: DNA
<213> ORGANISM: Artificial Sequence
<220> FEATURE:
<223> OTHER INFORMATION: pG1-4 promoter

<400> SEQUENCE: 99

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt taccccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg cttttttttt ttttttttga tgaccccgtt ttcgtgacaa    600
```

attaatttcc aacggggtct tgtccggata agagaatttt gtttgattat ccgttcggat 660
aaatggacgc ctgctccata tttttccggt tattacccca cctggaagtg cccagaattt 720
tccggggatt acggataata cggtggtctg gattaattaa tacgccaagt cttacatttt 780
gttgcagtct cgtgcgagta tgtgcaataa taaacaagat gagccaattt attggattag 840
ttgcagcttg accccgccat agctaggcat agccaagtgc tatgggtgtt agatgatgca 900
cttggatgca gtgagttttg gagtataaaa gatccttaaa attccaccct tagatctcag 960
ggattcccac tatttggtat tctgatatgt ttttcctgat atgcatcaaa actctaatct 1020
aaaacctgaa tctccgctat tttttttttt tttttgatg accccgtttt cgtgacaaat 1080
taatttccaa cggggtcttg tccggataag agaattttgt ttgattatcc gttcggataa 1140
atggacgcct gctccatatt tttccggtta ttaccccacc tggaagtgcc cagaattttc 1200
cggggattac ggataatacg gtggtctgga ttaattaata cgccaagtct tacattttgt 1260
tgcagtctcg tgcgagtatg tgcaataata aacaagatga gccaatttat tggattagtt 1320
gcagcttgac cccgccatag ctaggcatag ccaagtgcta tgggtgttag atgatgcact 1380
tggatgcagt gagttttgga gtataaaaga tccttaaaat tccaccctt 1429

<210> SEQ ID NO 100
<211> LENGTH: 1427
<212> TYPE: DNA
<213> ORGANISM: Artificial Sequence
<220> FEATURE:
<223> OTHER INFORMATION: pG1-4 promoter

<400> SEQUENCE: 100
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttga tgaccccgtt ttcgtgacaa 600
attaatttcc aacggggtct tgtccggata agagaatttt gtttgattat ccgttcggat 660
aaatggacgc ctgctccata tttttccggt tattacccca cctggaagtg cccagaattt 720
tccggggatt acggataata cggtggtctg gattaattaa tacgccaagt cttacatttt 780
gttgcagtct cgtgcgagta tgtgcaataa taaacaagat gagccaattt attggattag 840
ttgcagcttg accccgccat agctaggcat agccaagtgc tatgggtgtt agatgatgca 900
cttggatgca gtgagttttg gagtataaaa gatccttaaa attccaccct tagatctcag 960
ggattcccac tatttggtat tctgatatgt ttttcctgat atgcatcaaa actctaatct 1020
aaaacctgaa tctccgcttt tttttttttt ttttgatgac cccgttttcg tgacaaatta 1080
atttccaacg gggtcttgtc cggataagag aattttgttt gattatccgt tcggataaat 1140
ggacgcctgc tccatatttt tccggttatt accccacctg gaagtgccca gaattttccg 1200
gggattacgg ataatacggt ggtctggatt aattaatacg ccaagtctta cattttgttg 1260

```
cagtctcgtg cgagtatgtg caataataaa caagatgagc caatttattg gattagttgc   1320

agcttgaccc cgccatagct aggcatagcc aagtgctatg ggtgttagat gatgcacttg   1380

gatgcagtga gttttggagt ataaaagatc cttaaaattc caccctt                 1427
```

<210> SEQ ID NO 101
<211> LENGTH: 1433
<212> TYPE: DNA
<213> ORGANISM: Artificial Sequence
<220> FEATURE:
<223> OTHER INFORMATION: pG1-4 promoter

<400> SEQUENCE: 101

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt tttttttttt tgatgacccc gttttcgtga    600

caaattaatt tccaacgggg tcttgtccgg ataagagaat tttgtttgat tatccgttcg    660

gataaatgga cgcctgctcc atatttttcc ggttattacc ccacctggaa gtgcccagaa    720

ttttccgggg attacggata atacggtggt ctggattaat taatacgcca agtcttacat    780

tttgttgcag tctcgtgcga gtatgtgcaa taataaacaa gatgagccaa tttattggat    840

tagttgcagc ttgaccccgc catagctagg catagccaag tgctatgggt gttagatgat    900

gcacttggat gcagtgagtt ttggagtata aaagatcctt aaaattccac ccttagatct    960

cagggattcc cactatttgg tattctgata tgtttttcct gatatgcatc aaaactctaa   1020

tctaaaacct gaatctccgc tatttttttt tttttttttt gatgaccccg ttttcgtgac   1080

aaattaattt ccaacggggt cttgtccgga taagagaatt ttgtttgatt atccgttcgg   1140

ataaatggac gcctgctcca tatttttccg gttattaccc cacctggaag tgcccagaat   1200

tttccgggga ttacggataa tacggtggtc tggattaatt aatacgccaa gtcttacatt   1260

ttgttgcagt ctcgtgcgag tatgtgcaat aataaacaag atgagccaat ttattggatt   1320

agttgcagct tgaccccgcc atagctaggc atagccaagt gctatgggtg ttagatgatg   1380

cacttggatg cagtgagttt tggagtataa aagatcctta aaattccacc ctt          1433
```

<210> SEQ ID NO 102
<211> LENGTH: 1431
<212> TYPE: DNA
<213> ORGANISM: Artificial Sequence
<220> FEATURE:
<223> OTHER INFORMATION: pG1-4 promoter

<400> SEQUENCE: 102

```
caaacatttg ctccccctag tctccaggga aatgtaaaat atactgctaa tagaaaacag     60

taagacgctc agttgtcagg ataattacgt tcgactgtag taaaacagga atctgtattg    120
```

ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttttt tgatgacccc gttttcgtga 600
caaattaatt tccaacgggg tcttgtccgg ataagagaat tttgtttgat tatccgttcg 660
gataaatgga cgcctgctcc atatttttcc ggttattacc ccacctggaa gtgcccagaa 720
ttttccgggg attacggata atacggtggt ctggattaat taatacgcca agtcttacat 780
tttgttgcag tctcgtgcga gtatgtgcaa taataaacaa gatgagccaa tttattggat 840
tagttgcagc ttgaccccgc catagctagg catagccaag tgctatgggt gttagatgat 900
gcacttggat gcagtgagtt ttggagtata aaagatcctt aaaattccac ccttagatct 960
cagggattcc cactatttgg tattctgata tgtttttcct gatatgcatc aaaactctaa 1020
tctaaaacct gaatctccgc tttttttttt tttttttga tgaccccgtt ttcgtgacaa 1080
attaatttcc aacggggtct tgtccggata agagaatttt gtttgattat ccgttcggat 1140
aaatggacgc ctgctccata tttttccggt tattacccca cctggaagtg cccagaattt 1200
tccggggatt acggataata cggtggtctg gattaattaa tacgccaagt cttacatttt 1260
gttgcagtct cgtgcgagta tgtgcaataa taaacaagat gagccaattt attggattag 1320
ttgcagcttg accccgccat agctaggcat agccaagtgc tatgggtgtt agatgatgca 1380
cttggatgca gtgagttttg gagtataaaa gatccttaaa attccaccct t 1431

<210> SEQ ID NO 103
<211> LENGTH: 1431
<212> TYPE: DNA
<213> ORGANISM: Artificial Sequence
<220> FEATURE:
<223> OTHER INFORMATION: pG1-4 promoter

<400> SEQUENCE: 103
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt ttttttttg atgaccccgt tttcgtgaca 600
aattaatttc caacggggtc ttgtccggat aagagaattt tgtttgatta tccgttcgga 660
taaatggacg cctgctccat atttttccgg ttattacccc acctggaagt gcccagaatt 720
ttccggggat tacggataat acggtggtct ggattaatta atacgccaag tcttacattt 780
tgttgcagtc tcgtgcgagt atgtgcaata ataaacaaga tgagccaatt tattggatta 840
gttgcagctt gaccccgcca tagctaggca tagccaagtg ctatgggtgt tagatgatgc 900
acttggatgc agtgagtttt ggagtataaa agatccttaa aattccaccc ttagatctca 960
gggattccca ctatttggta ttctgatatg tttttcctga tatgcatcaa aactctaatc 1020
taaaacctga atctccgcta tttttttttt tttttttga tgaccccgtt ttcgtgacaa 1080
attaatttcc aacggggtct tgtccggata agagaatttt gtttgattat ccgttcggat 1140
aaatggacgc ctgctccata tttttccggt tattacccca cctggaagtg cccagaattt 1200
tccggggatt acggataata cggtggtctg gattaattaa tacgccaagt cttacatttt 1260
gttgcagtct cgtgcgagta tgtgcaataa taaacaagat gagccaattt attggattag 1320
ttgcagcttg accccgccat agctaggcat agccaagtgc tatgggtgtt agatgatgca 1380
cttggatgca gtgagttttg gagtataaaa gatccttaaa attccaccct t 1431

<210> SEQ ID NO 104
<211> LENGTH: 1429
<212> TYPE: DNA
<213> ORGANISM: Artificial Sequence
<220> FEATURE:
<223> OTHER INFORMATION: pG1-4 promoter

<400> SEQUENCE: 104
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttttg atgaccccgt tttcgtgaca 600
aattaatttc caacggggtc ttgtccggat aagagaattt tgtttgatta tccgttcgga 660
taaatggacg cctgctccat atttttccgg ttattacccc acctggaagt gcccagaatt 720
ttccggggat tacggataat acggtggtct ggattaatta atacgccaag tcttacattt 780
tgttgcagtc tcgtgcgagt atgtgcaata ataaacaaga tgagccaatt tattggatta 840
gttgcagctt gaccccgcca tagctaggca tagccaagtg ctatgggtgt tagatgatgc 900
acttggatgc agtgagtttt ggagtataaa agatccttaa aattccaccc ttagatctca 960
gggattccca ctatttggta ttctgatatg tttttcctga tatgcatcaa aactctaatc 1020
taaaacctga atctccgctt tttttttttt ttttttgatg accccgtttt cgtgacaaat 1080
taatttccaa cggggtcttg tccggataag agaattttgt ttgattatcc gttcggataa 1140
atggacgcct gctccatatt tttccggtta ttaccccacc tggaagtgcc cagaattttc 1200
cggggattac ggataatacg gtggtctgga ttaattaata cgccaagtct tacattttgt 1260
tgcagtctcg tgcgagtatg tgcaataata aacaagatga gccaatttat tggattagtt 1320
gcagcttgac cccgccatag ctaggcatag ccaagtgcta tgggtgttag atgatgcact 1380
tggatgcagt gagttttgga gtataaaaga tccttaaaat tccaccctt 1429

<210> SEQ ID NO 105
<211> LENGTH: 1435
<212> TYPE: DNA
<213> ORGANISM: Artificial Sequence
<220> FEATURE:
<223> OTHER INFORMATION: pG1-4 promoter

<400> SEQUENCE: 105
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttttt ttgatgaccc cgttttcgtg 600
acaaattaat ttccaacggg gtcttgtccg gataagagaa ttttgtttga ttatccgttc 660
ggataaatgg acgcctgctc catatttttc cggttattac cccacctgga agtgcccaga 720
attttccggg gattacggat aatacggtgg tctggattaa ttaatacgcc aagtcttaca 780
ttttgttgca gtctcgtgcg agtatgtgca ataataaaca agatgagcca atttattgga 840
ttagttgcag cttgaccccg ccatagctag gcatagccaa gtgctatggg tgttagatga 900
tgcacttgga tgcagtgagt tttggagtat aaaagatcct taaaattcca cccttagatc 960
tcagggattc ccactatttg gtattctgat atgtttttcc tgatatgcat caaaactcta 1020
atctaaaacc tgaatctccg ctattttttt tttttttttt ttgatgaccc cgttttcgtg 1080
acaaattaat ttccaacggg gtcttgtccg gataagagaa ttttgtttga ttatccgttc 1140
ggataaatgg acgcctgctc catatttttc cggttattac cccacctgga agtgcccaga 1200
attttccggg gattacggat aatacggtgg tctggattaa ttaatacgcc aagtcttaca 1260
ttttgttgca gtctcgtgcg agtatgtgca ataataaaca agatgagcca atttattgga 1320
ttagttgcag cttgaccccg ccatagctag gcatagccaa gtgctatggg tgttagatga 1380
tgcacttgga tgcagtgagt tttggagtat aaaagatcct taaaattcca ccctt 1435

<210> SEQ ID NO 106
<211> LENGTH: 1433
<212> TYPE: DNA
<213> ORGANISM: Artificial Sequence
<220> FEATURE:
<223> OTHER INFORMATION: pG1-4 promoter

<400> SEQUENCE: 106
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttttt ttgatgaccc cgttttcgtg 600
acaaattaat ttccaacggg gtcttgtccg gataagagaa ttttgtttga ttatccgttc 660
ggataaatgg acgcctgctc catatttttc cggttattac cccacctgga agtgcccaga 720
attttccggg gattacggat aatacggtgg tctggattaa ttaatacgcc aagtcttaca 780
ttttgttgca gtctcgtgcg agtatgtgca ataataaaca agatgagcca atttattgga 840
ttagttgcag cttgaccccg ccatagctag gcatagccaa gtgctatggg tgttagatga 900
tgcacttgga tgcagtgagt tttggagtat aaaagatcct taaaattcca cccttagatc 960
tcagggattc ccactatttg gtattctgat atgtttttcc tgatatgcat caaaactcta 1020
atctaaaacc tgaatctccg cttttttttt tttttttttt gatgaccccg ttttcgtgac 1080
aaattaattt ccaacggggt cttgtccgga taagagaatt ttgtttgatt atccgttcgg 1140
ataaatggac gcctgctcca tatttttccg gttattaccc cacctggaag tgcccagaat 1200
tttccgggga ttacggataa tacggtggtc tggattaatt aatacgccaa gtcttacatt 1260
ttgttgcagt ctcgtgcgag tatgtgcaat aataaacaag atgagccaat ttattggatt 1320
agttgcagct tgaccccgcc atagctaggc atagccaagt gctatgggtg ttagatgatg 1380
cacttggatg cagtgagttt tggagtataa aagatcctta aaattccacc ctt 1433

<210> SEQ ID NO 107
<211> LENGTH: 1433
<212> TYPE: DNA
<213> ORGANISM: Artificial Sequence
<220> FEATURE:
<223> OTHER INFORMATION: pG1-4 promoter

<400> SEQUENCE: 107
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttttt gatgaccccg ttttcgtgac 600
aaattaattt ccaacggggt cttgtccgga taagagaatt ttgtttgatt atccgttcgg 660
ataaatggac gcctgctcca tatttttccg gttattaccc cacctggaag tgcccagaat 720
tttccgggga ttacggataa tacggtggtc tggattaatt aatacgccaa gtcttacatt 780
ttgttgcagt ctcgtgcgag tatgtgcaat aataaacaag atgagccaat ttattggatt 840
agttgcagct tgaccccgcc atagctaggc atagccaagt gctatgggtg ttagatgatg 900

```
cacttggatg cagtgagttt tggagtataa aagatcctta aaattccacc cttagatctc    960
agggattccc actatttggt attctgatat gtttttcctg atatgcatca aaactctaat   1020
ctaaaacctg aatctccgct attttttttt ttttttttt gatgaccccg ttttcgtgac   1080
aaattaattt ccaacggggt cttgtccgga taagagaatt ttgtttgatt atccgttcgg   1140
ataaatggac gcctgctcca tatttttccg gttattaccc cacctggaag tgcccagaat   1200
tttccgggga ttacggataa tacggtggtc tggattaatt aatacgccaa gtcttacatt   1260
ttgttgcagt ctcgtgcgag tatgtgcaat aataaacaag atgagccaat ttattggatt   1320
agttgcagct tgaccccgcc atagctaggc atagccaagt gctatgggtg ttagatgatg   1380
cacttggatg cagtgagttt tggagtataa aagatcctta aaattccacc ctt          1433
```

<210> SEQ ID NO 108
<211> LENGTH: 1431
<212> TYPE: DNA
<213> ORGANISM: Artificial Sequence
<220> FEATURE:
<223> OTHER INFORMATION: pG1-4 promoter

<400> SEQUENCE: 108

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt taccccctct tttgtcaagc gcaaaatgcc tgtaagattt    420
ggtgggggtg tgagccgtta gctgaagtac aacaggctaa ttccctgaaa aaactgcagc    480
tcagggattc ccactatttg gtattctgat atgtttttcc tgatatgcat caaaactcta    540
atctaaaacc tgaatctccg cttttttttt ttttttttt gatgaccccg ttttcgtgac    600
aaattaattt ccaacggggt cttgtccgga taagagaatt ttgtttgatt atccgttcgg    660
ataaatggac gcctgctcca tatttttccg gttattaccc cacctggaag tgcccagaat    720
tttccgggga ttacggataa tacggtggtc tggattaatt aatacgccaa gtcttacatt    780
ttgttgcagt ctcgtgcgag tatgtgcaat aataaacaag atgagccaat ttattggatt    840
agttgcagct tgaccccgcc atagctaggc atagccaagt gctatgggtg ttagatgatg    900
cacttggatg cagtgagttt tggagtataa aagatcctta aaattccacc cttagatctc    960
agggattccc actatttggt attctgatat gtttttcctg atatgcatca aaactctaat   1020
ctaaaacctg aatctccgct tttttttttt tttttttga tgaccccgtt ttcgtgacaa   1080
attaatttcc aacggggtct tgtccggata agagaatttt gtttgattat ccgttcggat   1140
aaatggacgc ctgctccata tttttccggt tattacccca cctggaagtg cccagaattt   1200
tccggggatt acggataata cggtggtctg gattaattaa tacgccaagt cttacatttt   1260
gttgcagtct cgtgcgagta tgtgcaataa taaacaagat gagccaattt attggattag   1320
ttgcagcttg accccgccat agctaggcat agccaagtgc tatgggtgtt agatgatgca   1380
cttggatgca gtgagttttg gagtataaaa gatccttaaa attccaccct t            1431
```

<210> SEQ ID NO 109
<211> LENGTH: 1437

<212> TYPE: DNA
<213> ORGANISM: Artificial Sequence
<220> FEATURE:
<223> OTHER INFORMATION: pG1-4 promoter

<400> SEQUENCE: 109
caaacatttg ctcccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg ctattttttt tttttttttt tttgatgacc ccgttttcgt 600
gacaaattaa tttccaacgg ggtcttgtcc ggataagaga attttgtttg attatccgtt 660
cggataaatg gacgcctgct ccatattttt ccggttatta ccccacctgg aagtgcccag 720
aattttccgg ggattacgga taatacggtg gtctggatta attaatacgc caagtcttac 780
attttgttgc agtctcgtgc gagtatgtgc aataataaac aagatgagcc aatttattgg 840
attagttgca gcttgacccc gccatagcta ggcatagcca agtgctatgg gtgttagatg 900
atgcacttgg atgcagtgag ttttggagta taaaagatcc ttaaaattcc acccttagat 960
ctcagggatt cccactattt ggtattctga tatgtttttc ctgatatgca tcaaaactct 1020
aatctaaaac ctgaatctcc gctatttttt tttttttttt ttttgatgac cccgttttcg 1080
tgacaaatta atttccaacg gggtcttgtc cggataagag aattttgttt gattatccgt 1140
tcggataaat ggacgcctgc tccatatttt tccggttatt accccacctg gaagtgccca 1200
gaattttccg gggattacgg ataatacggt ggtctggatt aattaatacg ccaagtctta 1260
cattttgttg cagtctcgtg cgagtatgtg caataataaa caagatgagc caatttattg 1320
gattagttgc agcttgaccc cgccatagct aggcatagcc aagtgctatg ggtgttagat 1380
gatgcacttg gatgcagtga gttttggagt ataaaagatc cttaaaattc caccctt 1437

<210> SEQ ID NO 110
<211> LENGTH: 1435
<212> TYPE: DNA
<213> ORGANISM: Artificial Sequence
<220> FEATURE:
<223> OTHER INFORMATION: pG1-4 promoter

<400> SEQUENCE: 110
caaacatttg ctcccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420

-continued

```
ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg ctattttttt tttttttttt tttgatgacc ccgttttcgt    600

gacaaattaa tttccaacgg ggtcttgtcc ggataagaga attttgtttg attatccgtt    660

cggataaatg gacgcctgct ccatattttt ccggttatta ccccacctgg aagtgcccag    720

aattttccgg ggattacgga taatacggtg gtctggatta attaatacgc caagtcttac    780

attttgttgc agtctcgtgc gagtatgtgc aataataaac aagatgagcc aatttattgg    840

attagttgca gcttgacccc gccatagcta ggcatagcca agtgctatgg gtgttagatg    900

atgcacttgg atgcagtgag ttttggagta taaaagatcc ttaaaattcc acccttagat    960

ctcagggatt cccactattt ggtattctga tatgtttttc ctgatatgca tcaaaactct   1020

aatctaaaac ctgaatctcc gctttttttt tttttttttt ttgatgaccc cgttttcgtg   1080

acaaattaat ttccaacggg gtcttgtccg gataagagaa ttttgtttga ttatccgttc   1140

ggataaatgg acgcctgctc catatttttc cggttattac cccacctgga agtgcccaga   1200

attttccggg gattacggat aatacggtgg tctggattaa ttaatacgcc aagtcttaca   1260

ttttgttgca gtctcgtgcg agtatgtgca ataataaaca agatgagcca atttattgga   1320

ttagttgcag cttgaccccg ccatagctag gcatagccaa gtgctatggg tgttagatga   1380

tgcacttgga tgcagtgagt tttggagtat aaaagatcct taaaattcca ccctt        1435
```

```
<210> SEQ ID NO 111
<211> LENGTH: 1435
<212> TYPE: DNA
<213> ORGANISM: Artificial Sequence
<220> FEATURE:
<223> OTHER INFORMATION: pG1-4 promoter

<400> SEQUENCE: 111

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcagc    480

tcagggattc ccactatttg gtattctgat atgtttttcc tgatatgcat caaaactcta    540

atctaaaacc tgaatctccg cttttttttt tttttttttt tgatgacccc gttttcgtga    600

caaattaatt tccaacgggg tcttgtccgg ataagagaat tttgtttgat tatccgttcg    660

gataaatgga cgcctgctcc atatttttcc ggttattacc ccacctggaa gtgcccagaa    720

ttttccgggg attacggata atacggtggt ctggattaat taatacgcca agtcttacat    780

tttgttgcag tctcgtgcga gtatgtgcaa taataaacaa gatgagccaa tttattggat    840

tagttgcagc ttgaccccgc catagctagg catagccaag tgctatgggt gttagatgat    900

gcacttggat gcagtgagtt ttggagtata aaagatcctt aaaattccac ccttagatct    960

cagggattcc cactatttgg tattctgata tgtttttcct gatatgcatc aaaactctaa   1020

tctaaaacct gaatctccgc tatttttttt tttttttttt ttgatgaccc cgttttcgtg   1080
```

acaaattaat ttccaacggg gtcttgtccg gataagagaa ttttgtttga ttatccgttc 1140
ggataaatgg acgcctgctc catatttttc cggttattac cccacctgga agtgcccaga 1200
attttccggg gattacggat aatacggtgg tctggattaa ttaatacgcc aagtcttaca 1260
ttttgttgca gtctcgtgcg agtatgtgca ataataaaca agatgagcca atttattgga 1320
ttagttgcag cttgaccccg ccatagctag gcatagccaa gtgctatggg tgttagatga 1380
tgcacttgga tgcagtgagt tttggagtat aaaagatcct taaaattcca ccctt 1435

<210> SEQ ID NO 112
<211> LENGTH: 1433
<212> TYPE: DNA
<213> ORGANISM: Artificial Sequence
<220> FEATURE:
<223> OTHER INFORMATION: pG1-4 promoter

<400> SEQUENCE: 112
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcagc 480
tcagggattc ccactatttg gtattctgat atgtttttcc tgatatgcat caaaactcta 540
atctaaaacc tgaatctccg cttttttttt tttttttttt tgatgacccc gttttcgtga 600
caaattaatt tccaacgggg tcttgtccgg ataagagaat tttgtttgat tatccgttcg 660
gataaatgga cgcctgctcc atatttttcc ggttattacc ccacctggaa gtgcccagaa 720
ttttccgggg attacggata atacggtggt ctggattaat taatacgcca agtcttacat 780
tttgttgcag tctcgtgcga gtatgtgcaa taataaacaa gatgagccaa tttattggat 840
tagttgcagc ttgaccccgc catagctagg catagccaag tgctatgggt gttagatgat 900
gcacttggat gcagtgagtt ttggagtata aaagatcctt aaaattccac ccttagatct 960
cagggattcc cactatttgg tattctgata tgtttttcct gatatgcatc aaaactctaa 1020
tctaaaacct gaatctccgc tttttttttt tttttttttt gatgaccccg ttttcgtgac 1080
aaattaattt ccaacggggt cttgtccgga taagagaatt ttgtttgatt atccgttcgg 1140
ataaatggac gcctgctcca tatttttccg gttattaccc cacctggaag tgcccagaat 1200
tttccgggga ttacggataa tacggtggtc tggattaatt aatacgccaa gtcttacatt 1260
ttgttgcagt ctcgtgcgag tatgtgcaat aataaacaag atgagccaat ttattggatt 1320
agttgcagct tgaccccgcc atagctaggc atagccaagt gctatgggtg ttagatgatg 1380
cacttggatg cagtgagttt tggagtataa aagatcctta aaattccacc ctt 1433

<210> SEQ ID NO 113
<211> LENGTH: 1088
<212> TYPE: DNA
<213> ORGANISM: Artificial Sequence
<220> FEATURE:
<223> OTHER INFORMATION: pG1-5 promoter
<220> FEATURE:

<221> NAME/KEY: misc_feature
<222> LOCATION: (591)..(597)
<223> OTHER INFORMATION: n is t or absent

<400> SEQUENCE: 113

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgctattt tttttttttt nnnnnnngat    600
gaccccgttt tcgtgacaaa ttaatttcca acggggtctt gtccggataa gagaattttg    660
tttgattatc cgttcggata aatggacgcc tgctccatat ttttccggtt attaccccac    720
ctggaagtgc ccagaatttt ccggggatta cggataatac ccggataaga gaattttgtt    780
tgattatccg ttcggataaa tggacgcctg ctccatattt ttccggttat taccccacct    840
ggaagtgccc agaattttcc ggggattacg gataatacgg tggtctggat taattaatac    900
gccaagtctt acattttgtt gcagtctcgt gcgagtatgt gcaataataa acaagatgag    960
ccaatttatt ggattagttg cagcttgacc ccgccatagc taggcatagc caagtgctat   1020
gggtgttaga tgatgcactt ggatgcagtg agttttggag tataaaagat ccttaaaatt   1080
ccaccctt                                                            1088
```

<210> SEQ ID NO 114
<211> LENGTH: 1086
<212> TYPE: DNA
<213> ORGANISM: Artificial Sequence
<220> FEATURE:
<223> OTHER INFORMATION: pG1-5 promoter
<220> FEATURE:
<221> NAME/KEY: misc_feature
<222> LOCATION: (589)..(595)
<223> OTHER INFORMATION: n is t or absent

<400> SEQUENCE: 114

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgcttttt ttttttttnn nnnnngatga    600
ccccgttttc gtgacaaatt aatttccaac ggggtcttgt ccggataaga gaattttgtt    660
```

```
tgattatccg ttcggataaa tggacgcctg ctccatattt ttccggttat taccccacct    720

ggaagtgccc agaattttcc ggggattacg gataataccc ggataagaga attttgtttg    780

attatccgtt cggataaatg gacgcctgct ccatattttt ccggttatta ccccacctgg    840

aagtgcccag aattttccgg ggattacgga taatacggtg gtctggatta attaatacgc    900

caagtcttac attttgttgc agtctcgtgc gagtatgtgc aataataaac aagatgagcc    960

aatttattgg attagttgca gcttgacccc gccatagcta ggcatagcca agtgctatgg   1020

gtgttagatg atgcacttgg atgcagtgag ttttggagta taaaagatcc ttaaaattcc   1080

accctt                                                              1086
```

```
<210> SEQ ID NO 115
<211> LENGTH: 1081
<212> TYPE: DNA
<213> ORGANISM: Artificial Sequence
<220> FEATURE:
<223> OTHER INFORMATION: pG1-5 promoter

<400> SEQUENCE: 115

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt gatgaccccg    600

ttttcgtgac aaattaattt ccaacggggt cttgtccgga taagagaatt ttgtttgatt    660

atccgttcgg ataaatggac gcctgctcca tatttttccg gttattaccc cacctggaag    720

tgcccagaat tttccgggga ttacggataa tacccggata agagaatttt gtttgattat    780

ccgttcggat aaatggacgc ctgctccata tttttccggt tattacccca cctggaagtg    840

cccagaattt tccggggatt acggataata cggtggtctg gattaattaa tacgccaagt    900

cttacatttt gttgcagtct cgtgcgagta tgtgcaataa taaacaagat gagccaattt    960

attggattag ttgcagcttg accccgccat agctaggcat agccaagtgc tatgggtgtt   1020

agatgatgca cttggatgca gtgagttttg gagtataaaa gatccttaaa attccaccct   1080

t                                                                   1081
```

```
<210> SEQ ID NO 116
<211> LENGTH: 1079
<212> TYPE: DNA
<213> ORGANISM: Artificial Sequence
<220> FEATURE:
<223> OTHER INFORMATION: pG1-5 promoter

<400> SEQUENCE: 116

caaacatttg ctccccctag tctccaggga aatgtaaaat atactgctaa tagaaaacag     60

taagacgctc agttgtcagg ataattacgt tcgactgtag taaaacagga atctgtattg    120
```

```
ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttga tgaccccgtt    600

ttcgtgacaa attaatttcc aacggggtct tgtccggata agagaatttt gtttgattat    660

ccgttcggat aaatggacgc ctgctccata tttttccggt tattacccca cctggaagtg    720

cccagaattt tccggggatt acggataata cccggataag agaattttgt ttgattatcc    780

gttcggataa atggacgcct gctccatatt tttccggtta ttaccccacc tggaagtgcc    840

cagaattttc cggggattac ggataatacg gtggtctgga ttaattaata cgccaagtct    900

tacattttgt tgcagtctcg tgcgagtatg tgcaataata aacaagatga gccaatttat    960

tggattagtt gcagcttgac ccccgccatag ctaggcatag ccaagtgcta tgggtgttag   1020

atgatgcact tggatgcagt gagttttgga gtataaaaga tccttaaaat tccaccctt    1079
```

<210> SEQ ID NO 117
<211> LENGTH: 1082
<212> TYPE: DNA
<213> ORGANISM: Artificial Sequence
<220> FEATURE:
<223> OTHER INFORMATION: pG1-5 promoter

<400> SEQUENCE: 117

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt tgatgacccc    600

gttttcgtga caaattaatt tccaacgggg tcttgtccgg ataagagaat tttgtttgat    660

tatccgttcg gataaatgga cgcctgctcc atatttttcc ggttattacc ccacctggaa    720

gtgcccagaa ttttccgggg attacggata atacccggat aagagaattt tgtttgatta    780

tccgttcgga taaatggacg cctgctccat atttttccgg ttattacccc acctggaagt    840

gcccagaatt ttccggggat tacggataat acggtggtct ggattaatta atacgccaag    900

tcttacattt tgttgcagtc tcgtgcgagt atgtgcaata ataaacaaga tgagccaatt    960

tattggatta gttgcagctt gaccccgcca tagctaggca tagccaagtg ctatgggtgt   1020

tagatgatgc acttggatgc agtgagtttt ggagtataaa agatccttaa aattccaccc   1080

tt                                                                  1082
```

<210> SEQ ID NO 118
<211> LENGTH: 1080
<212> TYPE: DNA
<213> ORGANISM: Artificial Sequence
<220> FEATURE:
<223> OTHER INFORMATION: pG1-5 promoter

<400> SEQUENCE: 118

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt taccccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgcttttt tttttttttg atgaccccgt    600
tttcgtgaca aattaatttc caacggggtc ttgtccggat aagagaattt tgtttgatta    660
tccgttcgga taaatggacg cctgctccat atttttccgg ttattacccc acctggaagt    720
gcccagaatt ttccggggat tacggataat acccggataa gagaattttg tttgattatc    780
cgttcggata aatggacgcc tgctccatat ttttccggtt attaccccac ctggaagtgc    840
ccagaatttt ccggggatta cggataatac ggtggtctgg attaattaat acgccaagtc    900
ttacattttg ttgcagtctc gtgcgagtat gtgcaataat aaacaagatg agccaattta    960
ttggattagt tgcagcttga ccccgccata gctaggcata gccaagtgct atgggtgtta   1020
gatgatgcac ttggatgcag tgagttttgg agtataaaag atccttaaaa ttccaccctt   1080
```

<210> SEQ ID NO 119
<211> LENGTH: 1083
<212> TYPE: DNA
<213> ORGANISM: Artificial Sequence
<220> FEATURE:
<223> OTHER INFORMATION: pG1-5 promoter

<400> SEQUENCE: 119

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt taccccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgctattt tttttttttt ttgatgaccc    600
cgttttcgtg acaaattaat ttccaacggg gtcttgtccg gataagagaa ttttgtttga    660
```

```
ttatccgttc ggataaatgg acgcctgctc catatttttc cggttattac cccacctgga    720

agtgcccaga attttccggg gattacggat aatacccgga taagagaatt ttgtttgatt    780

atccgttcgg ataaatggac gcctgctcca tatttttccg gttattaccc cacctggaag    840

tgcccagaat tttccgggga ttacggataa tacggtggtc tggattaatt aatacgccaa    900

gtcttacatt ttgttgcagt ctcgtgcgag tatgtgcaat aataaacaag atgagccaat    960

ttattggatt agttgcagct tgaccccgcc atagctaggc atagccaagt gctatgggtg   1020

ttagatgatg cacttggatg cagtgagttt tggagtataa aagatcctta aaattccacc   1080

ctt                                                                 1083
```

<210> SEQ ID NO 120
<211> LENGTH: 1081
<212> TYPE: DNA
<213> ORGANISM: Artificial Sequence
<220> FEATURE:
<223> OTHER INFORMATION: pG1-5 promoter

<400> SEQUENCE: 120

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt gatgaccccg    600

ttttcgtgac aaattaattt ccaacggggt cttgtccgga taagagaatt ttgtttgatt    660

atccgttcgg ataaatggac gcctgctcca tatttttccg gttattaccc cacctggaag    720

tgcccagaat tttccgggga ttacggataa tacccggata agagaatttt gtttgattat    780

ccgttcggat aaatggacgc ctgctccata tttttccggt tattacccca cctggaagtg    840

cccagaattt tccggggatt acggataata cggtggtctg gattaattaa tacgccaagt    900

cttacatttt gttgcagtct cgtgcgagta tgtgcaataa taaacaagat gagccaattt    960

attggattag ttgcagcttg accccgccat agctaggcat agccaagtgc tatgggtgtt   1020

agatgatgca cttggatgca gtgagttttg gagtataaaa gatccttaaa attccaccct   1080

t                                                                   1081
```

<210> SEQ ID NO 121
<211> LENGTH: 1084
<212> TYPE: DNA
<213> ORGANISM: Artificial Sequence
<220> FEATURE:
<223> OTHER INFORMATION: pG1-5 promoter

<400> SEQUENCE: 121

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180
```

aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttgatgacc 600
ccgttttcgt gacaaattaa tttccaacgg ggtcttgtcc ggataagaga attttgtttg 660
attatccgtt cggataaatg gacgcctgct ccatattttt ccggttatta ccccacctgg 720
aagtgcccag aattttccgg ggattacgga taatacccgg ataagagaat tttgtttgat 780
tatccgttcg gataaatgga cgcctgctcc atatttttcc ggttattacc ccacctggaa 840
gtgcccagaa ttttccgggg attacggata atacggtggt ctggattaat taatacgcca 900
agtcttacat tttgttgcag tctcgtgcga gtatgtgcaa taataaacaa gatgagccaa 960
tttattggat tagttgcagc ttgaccccgc catagctagg catagccaag tgctatgggt 1020
gttagatgat gcacttggat gcagtgagtt ttggagtata aaagatcctt aaaattccac 1080
cctt 1084

<210> SEQ ID NO 122
<211> LENGTH: 1082
<212> TYPE: DNA
<213> ORGANISM: Artificial Sequence
<220> FEATURE:
<223> OTHER INFORMATION: pG1-5 promoter

<400> SEQUENCE: 122
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tgatgacccc 600
gttttcgtga caaattaatt tccaacgggg tcttgtccgg ataagagaat tttgtttgat 660
tatccgttcg gataaatgga cgcctgctcc atatttttcc ggttattacc ccacctggaa 720
gtgcccagaa ttttccgggg attacggata atacccggat aagagaattt tgtttgatta 780
tccgttcgga taaatggacg cctgctccat atttttccgg ttattacccc acctggaagt 840
gcccagaatt ttccggggat tacggataat acggtggtct ggattaatta atacgccaag 900
tcttacattt tgttgcagtc tcgtgcgagt atgtgcaata ataaacaaga tgagccaatt 960
tattggatta gttgcagctt gaccccgcca tagctaggca tagccaagtg ctatgggtgt 1020
tagatgatgc acttggatgc agtgagtttt ggagtataaa agatccttaa aattccaccc 1080
tt 1082

<210> SEQ ID NO 123
<211> LENGTH: 1085
<212> TYPE: DNA
<213> ORGANISM: Artificial Sequence
<220> FEATURE:
<223> OTHER INFORMATION: pG1-5 promoter

<400> SEQUENCE: 123
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttgatgac 600
cccgttttcg tgacaaatta atttccaacg gggtcttgtc cggataagag aattttgttt 660
gattatccgt tcggataaat ggacgcctgc tccatatttt tccggttatt accccacctg 720
gaagtgccca gaattttccg gggattacgg ataataccccg gataagagaa ttttgtttga 780
ttatccgttc ggataaatgg acgcctgctc catatttttc cggttattac cccacctgga 840
agtgcccaga attttccggg gattacggat aatacggtgg tctggattaa ttaatacgcc 900
aagtcttaca ttttgttgca gtctcgtgcg agtatgtgca ataataaaca agatgagcca 960
atttattgga ttagttgcag cttgaccccg ccatagctag gcatagccaa gtgctatggg 1020
tgttagatga tgcacttgga tgcagtgagt tttggagtat aaaagatcct taaaattcca 1080
ccctt 1085

<210> SEQ ID NO 124
<211> LENGTH: 1083
<212> TYPE: DNA
<213> ORGANISM: Artificial Sequence
<220> FEATURE:
<223> OTHER INFORMATION: pG1-5 promoter

<400> SEQUENCE: 124
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt ttgatgaccc 600
cgttttcgtg acaaattaat ttccaacggg gtcttgtccg gataagagaa ttttgtttga 660
ttatccgttc ggataaatgg acgcctgctc catatttttc cggttattac cccacctgga 720
agtgcccaga attttccggg gattacggat aatacccgga taagagaatt ttgtttgatt 780
atccgttcgg ataaatggac gcctgctcca tatttttccg gttattaccc cacctggaag 840
tgcccagaat tttccgggga ttacggataa tacggtggtc tggattaatt aatacgccaa 900
gtcttacatt ttgttgcagt ctcgtgcgag tatgtgcaat aataaacaag atgagccaat 960
ttattggatt agttgcagct tgaccccgcc atagctaggc atagccaagt gctatgggtg 1020
ttagatgatg cacttggatg cagtgagttt tggagtataa aagatcctta aaattccacc 1080
ctt 1083

<210> SEQ ID NO 125
<211> LENGTH: 1086
<212> TYPE: DNA
<213> ORGANISM: Artificial Sequence
<220> FEATURE:
<223> OTHER INFORMATION: pG1-5 promoter

<400> SEQUENCE: 125
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttttgatga 600
ccccgttttc gtgacaaatt aatttccaac ggggtcttgt ccggataaga gaattttgtt 660
tgattatccg ttcggataaa tggacgcctg ctccatattt ttccggttat taccccacct 720
ggaagtgccc agaattttcc ggggattacg gataataccc ggataagaga attttgtttg 780
attatccgtt cggataaatg gacgcctgct ccatattttt ccggttatta ccccacctgg 840
aagtgcccag aattttccgg ggattacgga taatacggtg gtctggatta attaatacgc 900
caagtcttac attttgttgc agtctcgtgc gagtatgtgc aataataaac aagatgagcc 960
aatttattgg attagttgca gcttgacccc gccatagcta ggcatagcca agtgctatgg 1020
gtgttagatg atgcacttgg atgcagtgag ttttggagta taaaagatcc ttaaaattcc 1080
accctt 1086

<210> SEQ ID NO 126
<211> LENGTH: 1084
<212> TYPE: DNA
<213> ORGANISM: Artificial Sequence
<220> FEATURE:
<223> OTHER INFORMATION: pG1-5 promoter

<400> SEQUENCE: 126
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tttgatgacc 600
ccgttttcgt gacaaattaa tttccaacgg ggtcttgtcc ggataagaga attttgtttg 660
attatccgtt cggataaatg gacgcctgct ccatattttt ccggttatta ccccacctgg 720
aagtgcccag aattttccgg ggattacgga taatacccgg ataagagaat tttgtttgat 780
tatccgttcg gataaatgga cgcctgctcc atatttttcc ggttattacc ccacctggaa 840
gtgcccagaa ttttccgggg attacggata atacggtggt ctggattaat taatacgcca 900
agtcttacat tttgttgcag tctcgtgcga gtatgtgcaa taataaacaa gatgagccaa 960
tttattggat tagttgcagc ttgaccccgc catagctagg catagccaag tgctatgggt 1020
gttagatgat gcacttggat gcagtgagtt ttggagtata aaagatcctt aaaattccac 1080
cctt 1084

<210> SEQ ID NO 127
<211> LENGTH: 1087
<212> TYPE: DNA
<213> ORGANISM: Artificial Sequence
<220> FEATURE:
<223> OTHER INFORMATION: pG1-5 promoter

<400> SEQUENCE: 127
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttttgatg 600
accccgtttt cgtgacaaat taatttccaa cggggtcttg tccggataag agaattttgt 660
ttgattatcc gttcggataa atggacgcct gctccatatt tttccggtta ttaccccacc 720
tggaagtgcc cagaattttc cggggattac ggataatacc cggataagag aattttgttt 780
gattatccgt tcggataaat ggacgcctgc tccatatttt tccggttatt accccacctg 840
gaagtgccca gaattttccg gggattacgg ataatacggt ggtctggatt aattaatacg 900
ccaagtctta cattttgttg cagtctcgtg cgagtatgtg caataataaa caagatgagc 960
caatttattg gattagttgc agcttgaccc cgccatagct aggcatagcc aagtgctatg 1020

```
ggtgttagat gatgcacttg gatgcagtga gttttggagt ataaaagatc cttaaaattc   1080

caccctt                                                              1087


<210> SEQ ID NO 128
<211> LENGTH: 1085
<212> TYPE: DNA
<213> ORGANISM: Artificial Sequence
<220> FEATURE:
<223> OTHER INFORMATION: pG1-5 promoter

<400> SEQUENCE: 128

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt ttttgatgac    600

cccgttttcg tgacaaatta atttccaacg gggtcttgtc cggataagag aattttgttt    660

gattatccgt tcggataaat ggacgcctgc tccatatttt tccggttatt accccacctg    720

gaagtgccca gaattttccg gggattacgg ataatacccg gataagagaa ttttgtttga    780

ttatccgttc ggataaatgg acgcctgctc catatttttc cggttattac cccacctgga    840

agtgcccaga attttccggg gattacggat aatacggtgg tctggattaa ttaatacgcc    900

aagtcttaca ttttgttgca gtctcgtgcg agtatgtgca ataataaaca agatgagcca    960

atttattgga ttagttgcag cttgaccccg ccatagctag gcatagccaa gtgctatggg   1020

tgttagatga tgcacttgga tgcagtgagt tttggagtat aaaagatcct taaaattcca   1080

ccctt                                                                1085


<210> SEQ ID NO 129
<211> LENGTH: 1088
<212> TYPE: DNA
<213> ORGANISM: Artificial Sequence
<220> FEATURE:
<223> OTHER INFORMATION: pG1-5 promoter

<400> SEQUENCE: 129

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480
```

tagacttcaa gatctcaggg attcccacta tttggtattc tgatatgttt ttcctgatat 540
gcatcaaaac tctaatctaa aacctgaatc tccgctattt tttttttttt tttttttgat 600
gaccccgttt tcgtgacaaa ttaatttcca acggggtctt gtccggataa gagaattttg 660
tttgattatc cgttcggata aatggacgcc tgctccatat tttccggtt attaccccac 720 ctggaagtgc ccagaatttt ccggggatta cggataatac ccggataaga gaattttgtt 780
tgattatccg ttcggataaa tggacgcctg ctccatattt ttccggttat taccccacct 840
ggaagtgccc agaattttcc ggggattacg gataatacgg tggtctggat taattaatac 900
gccaagtctt acattttgtt gcagtctcgt gcgagtatgt gcaataataa acaagatgag 960
ccaatttatt ggattagttg cagcttgacc ccgccatagc taggcatagc caagtgctat 1020
gggtgttaga tgatgcactt ggatgcagtg agttttggag tataaaagat ccttaaaatt 1080
ccacccctt 1088

<210> SEQ ID NO 130
<211> LENGTH: 1086
<212> TYPE: DNA
<213> ORGANISM: Artificial Sequence
<220> FEATURE:
<223> OTHER INFORMATION: pG1-5 promoter

<400> SEQUENCE: 130
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tttttgatga 600
ccccgttttc gtgacaaatt aatttccaac ggggtcttgt ccggataaga gaattttgtt 660
tgattatccg ttcggataaa tggacgcctg ctccatattt ttccggttat taccccacct 720
ggaagtgccc agaattttcc ggggattacg gataataccc ggataagaga attttgtttg 780
attatccgtt cggataaatg gacgcctgct ccatattttt ccggttatta ccccacctgg 840
aagtgcccag aattttccgg ggattacgga taatacggtg gtctggatta attaatacgc 900
caagtcttac attttgttgc agtctcgtgc gagtatgtgc aataataaac aagatgagcc 960
aatttattgg attagttgca gcttgacccc gccatagcta ggcatagcca agtgctatgg 1020
gtgttagatg atgcacttgg atgcagtgag ttttggagta taaaagatcc ttaaaattcc 1080
accctt 1086

<210> SEQ ID NO 131
<211> LENGTH: 1003
<212> TYPE: DNA
<213> ORGANISM: Artificial Sequence
<220> FEATURE:
<223> OTHER INFORMATION: pG1-6 promoter
<220> FEATURE:
<221> NAME/KEY: misc_feature
<222> LOCATION: (591)..(597)
<223> OTHER INFORMATION: n is t or absent

<400> SEQUENCE: 131
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt nnnnnnngat 600
gaccccgttt tcgtgacaaa ttaatttcca acggggtctt gtccggataa gagaattttg 660
tttgattatc cgttcggata aatggacgcc tgctccatat ttttccggtt ataaatggac 720
gcctgctcca tatttttccg gttattaccc cacctggaag tgcccagaat tttccgggga 780
ttacggataa tacggtggtc tggattaatt aatacgccaa gtcttacatt ttgttgcagt 840
ctcgtgcgag tatgtgcaat aataaacaag atgagccaat ttattggatt agttgcagct 900
tgaccccgcc atagctaggc atagccaagt gctatgggtg ttagatgatg cacttggatg 960
cagtgagttt tggagtataa aagatcctta aaattccacc ctt 1003

<210> SEQ ID NO 132
<211> LENGTH: 1001
<212> TYPE: DNA
<213> ORGANISM: Artificial Sequence
<220> FEATURE:
<223> OTHER INFORMATION: pG1-6 promoter
<220> FEATURE:
<221> NAME/KEY: misc_feature
<222> LOCATION: (589)..(595)
<223> OTHER INFORMATION: n is t or absent

<400> SEQUENCE: 132
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttnn nnnnngatga 600
ccccgttttc gtgacaaatt aatttccaac ggggtcttgt ccggataaga gaattttgtt 660
tgattatccg ttcggataaa tggacgcctg ctccatattt ttccggttat aaatggacgc 720
ctgctccata tttttccggt tattacccca cctggaagtg cccagaattt tccggggatt 780

```
acggataata cggtggtctg gattaattaa tacgccaagt cttacatttt gttgcagtct    840

cgtgcgagta tgtgcaataa taaacaagat gagccaattt attggattag ttgcagcttg    900

accccgccat agctaggcat agccaagtgc tatgggtgtt agatgatgca cttggatgca    960

gtgagttttg gagtataaaa gatccttaaa attccaccct t                       1001
```

<210> SEQ ID NO 133
<211> LENGTH: 996
<212> TYPE: DNA
<213> ORGANISM: Artificial Sequence
<220> FEATURE:
<223> OTHER INFORMATION: pG1-6 promoter

<400> SEQUENCE: 133

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt gatgaccccg    600

ttttcgtgac aaattaattt ccaacggggt cttgtccgga taagagaatt ttgtttgatt    660

atccgttcgg ataaatggac gcctgctcca tatttttccg gttataaatg gacgcctgct    720

ccatattttt ccggttatta ccccacctgg aagtgcccag aattttccgg ggattacgga    780

taatacggtg gtctggatta attaatacgc caagtcttac attttgttgc agtctcgtgc    840

gagtatgtgc aataataaac aagatgagcc aatttattgg attagttgca gcttgacccc    900

gccatagcta ggcatagcca agtgctatgg gtgttagatg atgcacttgg atgcagtgag    960

ttttggagta taaaagatcc ttaaaattcc accctt                              996
```

<210> SEQ ID NO 134
<211> LENGTH: 994
<212> TYPE: DNA
<213> ORGANISM: Artificial Sequence
<220> FEATURE:
<223> OTHER INFORMATION: pG1-6 promoter

<400> SEQUENCE: 134

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540
```

```
gcatcaaaac tctaatctaa aacctgaatc tccgcttttt ttttttttga tgaccccgtt    600

ttcgtgacaa attaatttcc aacggggtct tgtccggata agagaatttt gtttgattat    660

ccgttcggat aaatggacgc ctgctccata tttttccggt tataaatgga cgcctgctcc    720

atatttttcc ggttattacc ccacctggaa gtgcccagaa ttttccgggg attacggata    780

atacggtggt ctggattaat taatacgcca agtcttacat tttgttgcag tctcgtgcga    840

gtatgtgcaa taataaacaa gatgagccaa tttattggat tagttgcagc ttgaccccgc    900

catagctagg catagccaag tgctatgggt gttagatgat gcacttggat gcagtgagtt    960

ttggagtata aaagatcctt aaaattccac cctt                                994


<210> SEQ ID NO 135
<211> LENGTH: 997
<212> TYPE: DNA
<213> ORGANISM: Artificial Sequence
<220> FEATURE:
<223> OTHER INFORMATION: pG1-6 promoter

<400> SEQUENCE: 135

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt tgatgacccc    600

gttttcgtga caaattaatt tccaacgggg tcttgtccgg ataagagaat tttgtttgat    660

tatccgttcg gataaatgga cgcctgctcc atatttttcc ggttataaat ggacgcctgc    720

tccatatttt tccggttatt accccacctg gaagtgccca gaattttccg gggattacgg    780

ataatacggt ggtctggatt aattaatacg ccaagtctta cattttgttg cagtctcgtg    840

cgagtatgtg caataataaa caagatgagc caatttattg gattagttgc agcttgaccc    900

cgccatagct aggcatagcc aagtgctatg ggtgttagat gatgcacttg gatgcagtga    960

gttttggagt ataaaagatc cttaaaattc caccctt                             997


<210> SEQ ID NO 136
<211> LENGTH: 995
<212> TYPE: DNA
<213> ORGANISM: Artificial Sequence
<220> FEATURE:
<223> OTHER INFORMATION: pG1-6 promoter

<400> SEQUENCE: 136

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240
```

-continued

```
tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt ttttttttg atgaccccgt    600

tttcgtgaca aattaatttc caacggggtc ttgtccggat aagagaattt tgtttgatta    660

tccgttcgga taaatggacg cctgctccat atttttccgg ttataaatgg acgcctgctc    720

catatttttc cggttattac cccacctgga agtgcccaga attttccggg gattacggat    780

aatacggtgg tctggattaa ttaatacgcc aagtcttaca ttttgttgca gtctcgtgcg    840

agtatgtgca ataataaaca agatgagcca atttattgga ttagttgcag cttgaccccg    900

ccatagctag gcatagccaa gtgctatggg tgttagatga tgcacttgga tgcagtgagt    960

tttggagtat aaaagatcct taaaattcca ccctt                               995
```

```
<210> SEQ ID NO 137
<211> LENGTH: 998
<212> TYPE: DNA
<213> ORGANISM: Artificial Sequence
<220> FEATURE:
<223> OTHER INFORMATION: pG1-6 promoter

<400> SEQUENCE: 137

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt ttgatgaccc    600

cgttttcgtg acaaattaat ttccaacggg gtcttgtccg gataagagaa ttttgtttga    660

ttatccgttc ggataaatgg acgcctgctc catatttttc cggttataaa tggacgcctg    720

ctccatattt ttccggttat taccccacct ggaagtgccc agaattttcc ggggattacg    780

gataatacgg tggtctggat taattaatac gccaagtctt acattttgtt gcagtctcgt    840

gcgagtatgt gcaataataa acaagatgag ccaatttatt ggattagttg cagcttgacc    900

ccgccatagc taggcatagc caagtgctat gggtgttaga tgatgcactt ggatgcagtg    960

agttttggag tataaaagat ccttaaaatt ccaccctt                            998
```

```
<210> SEQ ID NO 138
<211> LENGTH: 996
<212> TYPE: DNA
<213> ORGANISM: Artificial Sequence
<220> FEATURE:
<223> OTHER INFORMATION: pG1-6 promoter

<400> SEQUENCE: 138
```

caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctctt tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt gatgaccccg 600
ttttcgtgac aaattaattt ccaacggggt cttgtccgga taagagaatt ttgtttgatt 660
atccgttcgg ataaatggac gcctgctcca tatttttccg gttataaatg gacgcctgct 720
ccatattttt ccggttatta ccccacctgg aagtgcccag aattttccgg ggattacgga 780
taatacggtg gtctggatta attaatacgc caagtcttac attttgttgc agtctcgtgc 840
gagtatgtgc aataataaac aagatgagcc aatttattgg attagttgca gcttgacccc 900
gccatagcta ggcatagcca agtgctatgg gtgttagatg atgcacttgg atgcagtgag 960
ttttggagta taaaagatcc ttaaaattcc accctt 996

<210> SEQ ID NO 139
<211> LENGTH: 999
<212> TYPE: DNA
<213> ORGANISM: Artificial Sequence
<220> FEATURE:
<223> OTHER INFORMATION: pG1-6 promoter

<400> SEQUENCE: 139
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctctt tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttgatgacc 600
ccgttttcgt gacaaattaa tttccaacgg ggtcttgtcc ggataagaga attttgtttg 660
attatccgtt cggataaatg gacgcctgct ccatattttt ccggttataa atggacgcct 720
gctccatatt tttccggtta ttaccccacc tggaagtgcc cagaattttc cggggattac 780
ggataatacg gtggtctgga ttaattaata cgccaagtct tacattttgt tgcagtctcg 840
tgcgagtatg tgcaataata aacaagatga gccaatttat tggattagtt gcagcttgac 900
cccgccatag ctaggcatag ccaagtgcta tgggtgttag atgatgcact tggatgcagt 960
gagttttgga gtataaaaga tccttaaaat tccaccctt 999

<210> SEQ ID NO 140
<211> LENGTH: 997
<212> TYPE: DNA
<213> ORGANISM: Artificial Sequence
<220> FEATURE:
<223> OTHER INFORMATION: pG1-6 promoter

<400> SEQUENCE: 140
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tgatgacccc 600
gttttcgtga caaattaatt tccaacgggg tcttgtccgg ataagagaat tttgtttgat 660
tatccgttcg gataaatgga cgcctgctcc atatttttcc ggttataaat ggacgcctgc 720
tccatatttt tccggttatt accccacctg gaagtgccca gaattttccg gggattacgg 780
ataatacggt ggtctggatt aattaatacg ccaagtctta cattttgttg cagtctcgtg 840
cgagtatgtg caataataaa caagatgagc caatttattg gattagttgc agcttgaccc 900
cgccatagct aggcatagcc aagtgctatg ggtgttagat gatgcacttg gatgcagtga 960
gttttggagt ataaaagatc cttaaaattc caccctt 997

<210> SEQ ID NO 141
<211> LENGTH: 1000
<212> TYPE: DNA
<213> ORGANISM: Artificial Sequence
<220> FEATURE:
<223> OTHER INFORMATION: pG1-6 promoter

<400> SEQUENCE: 141
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttgatgac 600
cccgttttcg tgacaaatta atttccaacg gggtcttgtc cggataagag aattttgttt 660
gattatccgt tcggataaat ggacgcctgc tccatatttt tccggttata aatggacgcc 720
tgctccatat ttttccggtt attaccccac ctggaagtgc ccagaatttt ccggggatta 780

```
cggataatac ggtggtctgg attaattaat acgccaagtc ttacattttg ttgcagtctc    840

gtgcgagtat gtgcaataat aaacaagatg agccaattta ttggattagt tgcagcttga    900

ccccgccata gctaggcata gccaagtgct atgggtgtta gatgatgcac ttggatgcag    960

tgagttttgg agtataaaag atccttaaaa ttccaccctt                         1000


<210> SEQ ID NO 142
<211> LENGTH: 998
<212> TYPE: DNA
<213> ORGANISM: Artificial Sequence
<220> FEATURE:
<223> OTHER INFORMATION: pG1-6 promoter

<400> SEQUENCE: 142

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt ttgatgaccc    600

cgttttcgtg acaaattaat ttccaacggg gtcttgtccg gataagagaa ttttgtttga    660

ttatccgttc ggataaatgg acgcctgctc catatttttc cggttataaa tggacgcctg    720

ctccatattt ttccggttat taccccacct ggaagtgccc agaattttcc ggggattacg    780

gataatacgg tggtctggat taattaatac gccaagtctt acattttgtt gcagtctcgt    840

gcgagtatgt gcaataataa acaagatgag ccaatttatt ggattagttg cagcttgacc    900

ccgccatagc taggcatagc caagtgctat gggtgttaga tgatgcactt ggatgcagtg    960

agttttggag tataaaagat ccttaaaatt ccaccctt                            998


<210> SEQ ID NO 143
<211> LENGTH: 1001
<212> TYPE: DNA
<213> ORGANISM: Artificial Sequence
<220> FEATURE:
<223> OTHER INFORMATION: pG1-6 promoter

<400> SEQUENCE: 143

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480
```

tagacttcaa gatctcaggg attcccacta tttggtattc tgatatgttt ttcctgatat 540
gcatcaaaac tctaatctaa aacctgaatc tccgctattt tttttttttt tttttgatga 600
ccccgttttc gtgacaaatt aatttccaac ggggtcttgt ccggataaga gaattttgtt 660
tgattatccg ttcggataaa tggacgcctg ctccatattt ttccggttat aaatggacgc 720
ctgctccata tttttccggt tattacccca cctggaagtg cccagaattt tccggggatt 780
acggataata cggtggtctg gattaattaa tacgccaagt cttacatttt gttgcagtct 840
cgtgcgagta tgtgcaataa taaacaagat gagccaattt attggattag ttgcagcttg 900
accccgccat agctaggcat agccaagtgc tatgggtgtt agatgatgca cttggatgca 960
gtgagttttg gagtataaaa gatccttaaa attccacccct t 1001

<210> SEQ ID NO 144
<211> LENGTH: 999
<212> TYPE: DNA
<213> ORGANISM: Artificial Sequence
<220> FEATURE:
<223> OTHER INFORMATION: pG1-6 promoter

<400> SEQUENCE: 144
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tttgatgacc 600
ccgttttcgt gacaaattaa tttccaacgg ggtcttgtcc ggataagaga attttgtttg 660
attatccgtt cggataaatg gacgcctgct ccatattttt ccggttataa atggacgcct 720
gctccatatt tttccggtta ttaccccacc tggaagtgcc cagaattttc cggggattac 780
ggataatacg gtggtctgga ttaattaata cgccaagtct tacattttgt tgcagtctcg 840
tgcgagtatg tgcaataata aacaagatga gccaatttat tggattagtt gcagcttgac 900
cccgccatag ctaggcatag ccaagtgcta tgggtgttag atgatgcact tggatgcagt 960
gagttttgga gtataaaaga tccttaaaat tccaccctt 999

<210> SEQ ID NO 145
<211> LENGTH: 1002
<212> TYPE: DNA
<213> ORGANISM: Artificial Sequence
<220> FEATURE:
<223> OTHER INFORMATION: pG1-6 promoter

<400> SEQUENCE: 145
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttttgatg 600
accccgtttt cgtgacaaat taatttccaa cggggtcttg tccggataag agaattttgt 660
ttgattatcc gttcggataa atggacgcct gctccatatt tttccggtta taaatggacg 720
cctgctccat atttttccgg ttattacccc acctggaagt gcccagaatt ttccggggat 780
tacggataat acggtggtct ggattaatta atacgccaag tcttacattt tgttgcagtc 840
tcgtgcgagt atgtgcaata ataaacaaga tgagccaatt tattggatta gttgcagctt 900
gaccccgcca tagctaggca tagccaagtg ctatgggtgt tagatgatgc acttggatgc 960
agtgagtttt ggagtataaa agatccttaa aattccaccc tt 1002

<210> SEQ ID NO 146
<211> LENGTH: 1000
<212> TYPE: DNA
<213> ORGANISM: Artificial Sequence
<220> FEATURE:
<223> OTHER INFORMATION: pG1-6 promoter

<400> SEQUENCE: 146
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt ttttgatgac 600
cccgttttcg tgacaaatta atttccaacg gggtcttgtc cggataagag aattttgttt 660
gattatccgt tcggataaat ggacgcctgc tccatatttt tccggttata aatggacgcc 720
tgctccatat ttttccggtt attaccccac ctggaagtgc ccagaatttt ccggggatta 780
cggataatac ggtggtctgg attaattaat acgccaagtc ttacattttg ttgcagtctc 840
gtgcgagtat gtgcaataat aaacaagatg agccaattta ttggattagt tgcagcttga 900
ccccgccata gctaggcata gccaagtgct atgggtgtta gatgatgcac ttggatgcag 960
tgagttttgg agtataaaag atccttaaaa ttccaccctt 1000

<210> SEQ ID NO 147
<211> LENGTH: 1003
<212> TYPE: DNA
<213> ORGANISM: Artificial Sequence
<220> FEATURE:
<223> OTHER INFORMATION: pG1-6 promoter

<400> SEQUENCE: 147
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttttgat 600 gaccccgttt tcgtgacaaa ttaatttcca acggggtctt gtccggataa gagaattttg 660
tttgattatc cgttcggata aatggacgcc tgctccatat ttttccggtt ataaatggac 720
gcctgctcca tatttttccg gttattaccc cacctggaag tgcccagaat tttccgggga 780
ttacggataa tacggtggtc tggattaatt aatacgccaa gtcttacatt ttgttgcagt 840
ctcgtgcgag tatgtgcaat aataaacaag atgagccaat ttattggatt agttgcagct 900
tgaccccgcc atagctaggc atagccaagt gctatgggtg ttagatgatg cacttggatg 960
cagtgagttt tggagtataa aagatcctta aaattccacc ctt 1003

<210> SEQ ID NO 148
<211> LENGTH: 1001
<212> TYPE: DNA
<213> ORGANISM: Artificial Sequence
<220> FEATURE:
<223> OTHER INFORMATION: pG1-6 promoter

<400> SEQUENCE: 148
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tttttgatga 600
ccccgttttc gtgacaaatt aatttccaac ggggtcttgt ccggataaga gaattttgtt 660
tgattatccg ttcggataaa tggacgcctg ctccatattt ttccggttat aaatggacgc 720
ctgctccata tttttccggt tattacccca cctggaagtg cccagaattt tccggggatt 780
acggataata cggtggtctg gattaattaa tacgccaagt cttacatttt gttgcagtct 840
cgtgcgagta tgtgcaataa taaacaagat gagccaattt attggattag ttgcagcttg 900
accccgccat agctaggcat agccaagtgc tatgggtgtt agatgatgca cttggatgca 960
gtgagttttg gagtataaaa gatccttaaa attccaccct t 1001

<210> SEQ ID NO 149
<211> LENGTH: 979
<212> TYPE: DNA
<213> ORGANISM: Artificial Sequence
<220> FEATURE:
<223> OTHER INFORMATION: pG1-7 promoter
<220> FEATURE:
<221> NAME/KEY: misc_feature
<222> LOCATION: (591)..(597)
<223> OTHER INFORMATION: n is t or absent

<400> SEQUENCE: 149
caaacatttg ctcccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt nnnnnnngat 600
gaccccgttt tcgtgacaaa ttaatttcca acggggtctt gtccggataa gagaattttg 660
tttgattatc cgttcggata aatggaataa atggacgcct gctccatatt tttccggtta 720
ttaccccacc tggaagtgcc cagaattttc cggggattac ggataatacg gtggtctgga 780
ttaattaata cgccaagtct tacattttgt tgcagtctcg tgcgagtatg tgcaataata 840
aacaagatga gccaatttat tggattagtt gcagcttgac cccgccatag ctaggcatag 900
ccaagtgcta tgggtgttag atgatgcact tggatgcagt gagttttgga gtataaaaga 960
tccttaaaat tccaccctt 979

<210> SEQ ID NO 150
<211> LENGTH: 977
<212> TYPE: DNA
<213> ORGANISM: Artificial Sequence
<220> FEATURE:
<223> OTHER INFORMATION: pG1-7 promoter
<220> FEATURE:
<221> NAME/KEY: misc_feature
<222> LOCATION: (589)..(595)
<223> OTHER INFORMATION: n is t or absent

<400> SEQUENCE: 150
caaacatttg ctcccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480

```
tagacttcaa gatctcaggg attcccacta tttggtattc tgatatgttt ttcctgatat    540

gcatcaaaac tctaatctaa aacctgaatc tccgcttttt ttttttttnn nnnnngatga    600

ccccgttttc gtgacaaatt aatttccaac ggggtcttgt ccggataaga gaattttgtt    660

tgattatccg ttcggataaa tggaataaat ggacgcctgc tccatatttt tccggttatt    720

accccacctg gaagtgccca gaattttccg gggattacgg ataatacggt ggtctggatt    780

aattaatacg ccaagtctta cattttgttg cagtctcgtg cgagtatgtg caataataaa    840

caagatgagc caatttattg gattagttgc agcttgaccc cgccatagct aggcatagcc    900

aagtgctatg ggtgttagat gatgcacttg gatgcagtga gttttggagt ataaaagatc    960

cttaaaattc caccctt                                                   977
```

<210> SEQ ID NO 151
<211> LENGTH: 972
<212> TYPE: DNA
<213> ORGANISM: Artificial Sequence
<220> FEATURE:
<223> OTHER INFORMATION: pG1-7 promoter

<400> SEQUENCE: 151

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt gatgaccccg    600

ttttcgtgac aaattaattt ccaacggggt cttgtccgga taagagaatt ttgtttgatt    660

atccgttcgg ataaatggaa taaatggacg cctgctccat atttttccgg ttattacccc    720

acctggaagt gcccagaatt ttccggggat tacggataat acggtggtct ggattaatta    780

atacgccaag tcttacattt tgttgcagtc tcgtgcgagt atgtgcaata ataaacaaga    840

tgagccaatt tattggatta gttgcagctt gaccccgcca tagctaggca tagccaagtg    900

ctatgggtgt tagatgatgc acttggatgc agtgagtttt ggagtataaa agatccttaa    960

aattccaccc tt                                                        972
```

<210> SEQ ID NO 152
<211> LENGTH: 970
<212> TYPE: DNA
<213> ORGANISM: Artificial Sequence
<220> FEATURE:
<223> OTHER INFORMATION: pG1-7 promoter

<400> SEQUENCE: 152

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240
```

tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttga tgaccccgtt 600 ttcgtgacaa attaatttcc aacggggtct tgtccggata agagaatttt gtttgattat 660
ccgttcggat aaatggaata aatggacgcc tgctccatat ttttccggtt attaccccac 720
ctggaagtgc ccagaatttt ccggggatta cggataatac ggtggtctgg attaattaat 780
acgccaagtc ttacattttg ttgcagtctc gtgcgagtat gtgcaataat aaacaagatg 840
agccaattta ttggattagt tgcagcttga ccccgccata gctaggcata gccaagtgct 900
atgggtgtta gatgatgcac ttggatgcag tgagttttgg agtataaaag atccttaaaa 960
ttccaccctt 970

<210> SEQ ID NO 153
<211> LENGTH: 973
<212> TYPE: DNA
<213> ORGANISM: Artificial Sequence
<220> FEATURE:
<223> OTHER INFORMATION: pG1-7 promoter

<400> SEQUENCE: 153
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tgatgacccc 600
gttttcgtga caaattaatt tccaacgggg tcttgtccgg ataagagaat tttgtttgat 660
tatccgttcg gataaatgga ataaatggac gcctgctcca tatttttccg gttattaccc 720
cacctggaag tgcccagaat tttccgggga ttacggataa tacggtggtc tggattaatt 780
aatacgccaa gtcttacatt ttgttgcagt ctcgtgcgag tatgtgcaat aataaacaag 840
atgagccaat ttattggatt agttgcagct tgaccccgcc atagctaggc atagccaagt 900
gctatgggtg ttagatgatg cacttggatg cagtgagttt tggagtataa aagatcctta 960
aaattccacc ctt 973

<210> SEQ ID NO 154
<211> LENGTH: 971
<212> TYPE: DNA
<213> ORGANISM: Artificial Sequence
<220> FEATURE:
<223> OTHER INFORMATION: pG1-7 promoter

<400> SEQUENCE: 154
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttg atgaccccgt 600
tttcgtgaca aattaatttc caacggggtc ttgtccggat aagagaattt tgtttgatta 660
tccgttcgga taaatggaat aaatggacgc ctgctccata tttttccggt tattacccca 720
cctggaagtg cccagaattt tccggggatt acggataata cggtggtctg gattaattaa 780
tacgccaagt cttacatttt gttgcagtct cgtgcgagta tgtgcaataa taaacaagat 840
gagccaattt attggattag ttgcagcttg accccgccat agctaggcat agccaagtgc 900
tatgggtgtt agatgatgca cttggatgca gtgagttttg gagtataaaa gatccttaaa 960
attccaccct t 971

<210> SEQ ID NO 155
<211> LENGTH: 974
<212> TYPE: DNA
<213> ORGANISM: Artificial Sequence
<220> FEATURE:
<223> OTHER INFORMATION: pG1-7 promoter

<400> SEQUENCE: 155
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttgatgaccc 600
cgttttcgtg acaaattaat ttccaacggg gtcttgtccg gataagagaa ttttgtttga 660
ttatccgttc ggataaatgg aataaatgga cgcctgctcc atatttttcc ggttattacc 720
ccacctggaa gtgcccagaa ttttccgggg attacggata atacggtggt ctggattaat 780
taatacgcca agtcttacat tttgttgcag tctcgtgcga gtatgtgcaa taataaacaa 840
gatgagccaa tttattggat tagttgcagc ttgaccccgc catagctagg catagccaag 900
tgctatgggt gttagatgat gcacttggat gcagtgagtt ttggagtata aaagatcctt 960
aaaattccac cctt 974

<210> SEQ ID NO 156
<211> LENGTH: 972
<212> TYPE: DNA
<213> ORGANISM: Artificial Sequence
<220> FEATURE:
<223> OTHER INFORMATION: pG1-7 promoter

<400> SEQUENCE: 156
caaacatttg ctcccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt ttttttttt gatgaccccg 600 ttttcgtgac aaattaattt ccaacggggt cttgtccgga taagagaatt ttgtttgatt 660
atccgttcgg ataaatggaa taaatggacg cctgctccat atttttccgg ttattacccc 720
acctggaagt gcccagaatt ttccggggat tacggataat acggtggtct ggattaatta 780
atacgccaag tcttacattt tgttgcagtc tcgtgcgagt atgtgcaata ataaacaaga 840
tgagccaatt tattggatta gttgcagctt gaccccgcca tagctaggca tagccaagtg 900
ctatgggtgt tagatgatgc acttggatgc agtgagtttt ggagtataaa agatccttaa 960
aattccaccc tt 972

<210> SEQ ID NO 157
<211> LENGTH: 975
<212> TYPE: DNA
<213> ORGANISM: Artificial Sequence
<220> FEATURE:
<223> OTHER INFORMATION: pG1-7 promoter

<400> SEQUENCE: 157
caaacatttg ctcccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt ttttttttt tttgatgacc 600 ccgttttcgt gacaaattaa tttccaacgg ggtcttgtcc ggataagaga attttgtttg 660
attatccgtt cggataaatg gaataaatgg acgcctgctc catatttttc cggttattac 720

-continued

```
cccacctgga agtgcccaga attttccggg gattacggat aatacggtgg tctggattaa    780

ttaatacgcc aagtcttaca ttttgttgca gtctcgtgcg agtatgtgca ataataaaca    840

agatgagcca atttattgga ttagttgcag cttgaccccg ccatagctag gcatagccaa    900

gtgctatggg tgttagatga tgcacttgga tgcagtgagt tttggagtat aaaagatcct    960

taaaattcca ccctt                                                     975
```

<210> SEQ ID NO 158
<211> LENGTH: 973
<212> TYPE: DNA
<213> ORGANISM: Artificial Sequence
<220> FEATURE:
<223> OTHER INFORMATION: pG1-7 promoter

<400> SEQUENCE: 158

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt tgatgacccc    600

gttttcgtga caaattaatt tccaacgggg tcttgtccgg ataagagaat tttgtttgat    660

tatccgttcg gataaatgga ataaatggac gcctgctcca tatttttccg gttattaccc    720

cacctggaag tgcccagaat tttccgggga ttacggataa tacggtggtc tggattaatt    780

aatacgccaa gtcttacatt ttgttgcagt ctcgtgcgag tatgtgcaat aataaacaag    840

atgagccaat ttattggatt agttgcagct tgaccccgcc atagctaggc atagccaagt    900

gctatgggtg ttagatgatg cacttggatg cagtgagttt tggagtataa aagatcctta    960

aaattccacc ctt                                                       973
```

<210> SEQ ID NO 159
<211> LENGTH: 976
<212> TYPE: DNA
<213> ORGANISM: Artificial Sequence
<220> FEATURE:
<223> OTHER INFORMATION: pG1-7 promoter

<400> SEQUENCE: 159

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccctct tttgtcaagc gcaaaatgcc tgtaagattt    420

ggtgggggtg tgagccgtta gctgaagtac aacaggctaa ttccctgaaa aaactgcaga    480
```

```
tagacttcaa gatctcaggg attcccacta tttggtattc tgatatgttt ttcctgatat    540

gcatcaaaac tctaatctaa aacctgaatc tccgctattt tttttttttt ttttgatgac    600

cccgttttcg tgacaaatta atttccaacg ggtcttgtc cggataagag aattttgttt     660

gattatccgt tcggataaat ggaataaatg gacgcctgct ccatattttt ccggttatta    720

ccccacctgg aagtgcccag aattttccgg ggattacgga taatacggtg gtctggatta    780

attaatacgc caagtcttac attttgttgc agtctcgtgc gagtatgtgc aataataaac    840

aagatgagcc aatttattgg attagttgca gcttgacccc gccatagcta ggcatagcca    900

agtgctatgg gtgttagatg atgcacttgg atgcagtgag ttttggagta taaaagatcc    960

ttaaaattcc accctt                                                    976
```

<210> SEQ ID NO 160
<211> LENGTH: 974
<212> TYPE: DNA
<213> ORGANISM: Artificial Sequence
<220> FEATURE:
<223> OTHER INFORMATION: pG1-7 promoter

<400> SEQUENCE: 160

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt tacccctct tttgtcaagc gcaaaatgcc tgtaagattt     420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt ttgatgaccc    600

cgttttcgtg acaaattaat ttccaacggg gtcttgtccg gataagagaa ttttgtttga    660

ttatccgttc ggataaatgg aataaatgga cgcctgctcc atatttttcc ggttattacc    720

ccacctggaa gtgcccagaa ttttccgggg attacggata atacggtggt ctggattaat    780

taatacgcca agtcttacat tttgttgcag tctcgtgcga gtatgtgcaa taataaacaa    840

gatgagccaa tttattggat tagttgcagc ttgaccccgc catagctagg catagccaag    900

tgctatgggt gttagatgat gcacttggat gcagtgagtt ttggagtata aaagatcctt    960

aaaattccac cctt                                                      974
```

<210> SEQ ID NO 161
<211> LENGTH: 977
<212> TYPE: DNA
<213> ORGANISM: Artificial Sequence
<220> FEATURE:
<223> OTHER INFORMATION: pG1-7 promoter

<400> SEQUENCE: 161

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180
```

aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttttgatga 600 ccccgtttttc gtgacaaatt aatttccaac ggggtcttgt ccggataaga gaattttgtt 660
tgattatccg ttcggataaa tggaataaat ggacgcctgc tccatatttt tccggttatt 720
accccacctg gaagtgccca gaattttccg gggattacgg ataatacggt ggtctggatt 780
aattaatacg ccaagtctta cattttgttg cagtctcgtg cgagtatgtg caataataaa 840
caagatgagc caatttattg gattagttgc agcttgaccc cgccatagct aggcatagcc 900
aagtgctatg ggtgttagat gatgcacttg gatgcagtga gttttggagt ataaaagatc 960
cttaaaattc caccctt 977

<210> SEQ ID NO 162
<211> LENGTH: 975
<212> TYPE: DNA
<213> ORGANISM: Artificial Sequence
<220> FEATURE:
<223> OTHER INFORMATION: pG1-7 promoter

<400> SEQUENCE: 162
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tttgatgacc 600
ccgttttcgt gacaaattaa tttccaacgg ggtcttgtcc ggataagaga attttgtttg 660
attatccgtt cggataaatg gaataaatgg acgcctgctc catatttttc cggttattac 720
cccacctgga agtgcccaga attttccggg gattacggat aatacggtgg tctggattaa 780
ttaatacgcc aagtcttaca ttttgttgca gtctcgtgcg agtatgtgca ataataaaca 840
agatgagcca atttattgga ttagttgcag cttgaccccg ccatagctag gcatagccaa 900
gtgctatggg tgttagatga tgcacttgga tgcagtgagt tttggagtat aaaagatcct 960
taaaattcca ccctt 975

<210> SEQ ID NO 163
<211> LENGTH: 978
<212> TYPE: DNA
<213> ORGANISM: Artificial Sequence
<220> FEATURE:
<223> OTHER INFORMATION: pG1-7 promoter

<400> SEQUENCE: 163
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttttgatg 600
accccgtttt cgtgacaaat taatttccaa cggggtcttg tccggataag agaattttgt 660
ttgattatcc gttcggataa atggaataaa tggacgcctg ctccatattt ttccggttat 720
taccccacct ggaagtgccc agaattttcc ggggattacg gataatacgg tggtctggat 780
taattaatac gccaagtctt acattttgtt gcagtctcgt gcgagtatgt gcaataataa 840
acaagatgag ccaatttatt ggattagttg cagcttgacc ccgccatagc taggcatagc 900
caagtgctat gggtgttaga tgatgcactt ggatgcagtg agttttggag tataaaagat 960
ccttaaaatt ccaccctt 978

<210> SEQ ID NO 164
<211> LENGTH: 976
<212> TYPE: DNA
<213> ORGANISM: Artificial Sequence
<220> FEATURE:
<223> OTHER INFORMATION: pG1-7 promoter

<400> SEQUENCE: 164
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt ttttgatgac 600
cccgttttcg tgacaaatta atttccaacg gggtcttgtc cggataagag aattttgttt 660
gattatccgt tcggataaat ggaataaatg gacgcctgct ccatattttt ccggttatta 720
ccccacctgg aagtgcccag aattttccgg ggattacgga taatacggtg gtctggatta 780
attaatacgc caagtcttac attttgttgc agtctcgtgc gagtatgtgc aataataaac 840
aagatgagcc aatttattgg attagttgca gcttgacccc gccatagcta ggcatagcca 900
agtgctatgg gtgttagatg atgcacttgg atgcagtgag ttttggagta taaaagatcc 960

-continued ttaaaattcc accctt 976

<210> SEQ ID NO 165
<211> LENGTH: 979
<212> TYPE: DNA
<213> ORGANISM: Artificial Sequence
<220> FEATURE:
<223> OTHER INFORMATION: pG1-7 promoter

<400> SEQUENCE: 165
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttttttgat 600
gaccccgttt tcgtgacaaa ttaatttcca acggggtctt gtccggataa gagaattttg 660
tttgattatc cgttcggata aatggaataa atggacgcct gctccatatt tttccggtta 720
ttaccccacc tggaagtgcc cagaattttc cggggattac ggataatacg gtggtctgga 780
ttaattaata cgccaagtct tacattttgt tgcagtctcg tgcgagtatg tgcaataata 840
aacaagatga gccaatttat tggattagtt gcagcttgac cccgccatag ctaggcatag 900
ccaagtgcta tgggtgttag atgatgcact tggatgcagt gagttttgga gtataaaaga 960
tccttaaaat tccaccctt 979

<210> SEQ ID NO 166
<211> LENGTH: 977
<212> TYPE: DNA
<213> ORGANISM: Artificial Sequence
<220> FEATURE:
<223> OTHER INFORMATION: pG1-7 promoter

<400> SEQUENCE: 166
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tttttgatga 600
ccccgttttc gtgacaaatt aatttccaac ggggtcttgt ccggataaga gaattttgtt 660
tgattatccg ttcggataaa tggaataaat ggacgcctgc tccatatttt tccggttatt 720

```
accccacctg gaagtgccca gaattttccg gggattacgg ataatacggt ggtctggatt    780

aattaatacg ccaagtctta cattttgttg cagtctcgtg cgagtatgtg caataataaa    840

caagatgagc caatttattg gattagttgc agcttgaccc cgccatagct aggcatagcc    900

aagtgctatg ggtgttagat gatgcacttg gatgcagtga gttttggagt ataaaagatc    960

cttaaaattc caccctt                                                   977


<210> SEQ ID NO 167
<211> LENGTH: 985
<212> TYPE: DNA
<213> ORGANISM: Artificial Sequence
<220> FEATURE:
<223> OTHER INFORMATION: pG1-8 promoter
<220> FEATURE:
<221> NAME/KEY: misc_feature
<222> LOCATION: (591)..(597)
<223> OTHER INFORMATION: n is t or absent

<400> SEQUENCE: 167

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt ttttttttt nnnnnnngat    600

gaccccgttt tcgtgacaaa ttaatttcca acggggtctt gtccggataa gagaattttg    660

tttgattatc cgttcggata aatggacgcc tgctccatat tttccggtt catatttttc    720

cggttattac cccacctgga agtgcccaga attttccggg gattacggat aatacggtgg    780

tctggattaa ttaatacgcc aagtcttaca ttttgttgca gtctcgtgcg agtatgtgca    840

ataataaaca agatgagcca atttattgga ttagttgcag cttgaccccg ccatagctag    900

gcatagccaa gtgctatggg tgttagatga tgcacttgga tgcagtgagt tttggagtat    960

aaaagatcct taaaattcca ccctt                                          985


<210> SEQ ID NO 168
<211> LENGTH: 983
<212> TYPE: DNA
<213> ORGANISM: Artificial Sequence
<220> FEATURE:
<223> OTHER INFORMATION: pG1-8 promoter
<220> FEATURE:
<221> NAME/KEY: misc_feature
<222> LOCATION: (589)..(595)
<223> OTHER INFORMATION: n is t or absent

<400> SEQUENCE: 168

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180
```

```
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt     420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgcttttt tttttttnn nnnnngatga    600
ccccgtttc gtgacaaatt aatttccaac ggggtcttgt ccggataaga gaattttgtt     660
tgattatccg ttcggataaa tggacgcctg ctccatattt ttccggttca tatttttccg    720
gttattaccc cacctggaag tgcccagaat tttccgggga ttacggataa tacggtggtc    780
tggattaatt aatacgccaa gtcttacatt ttgttgcagt ctcgtgcgag tatgtgcaat    840
aataaacaag atgagccaat ttattggatt agttgcagct tgaccccgcc atagctaggc    900
atagccaagt gctatgggtg ttagatgatg cacttggatg cagtgagttt tggagtataa    960
aagatcctta aaattccacc ctt                                             983
```

<210> SEQ ID NO 169
<211> LENGTH: 978
<212> TYPE: DNA
<213> ORGANISM: Artificial Sequence
<220> FEATURE:
<223> OTHER INFORMATION: pG1-8 promoter

<400> SEQUENCE: 169

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt     420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgctattt tttttttt gatgaccccg      600
ttttcgtgac aaattaattt ccaacggggt cttgtccgga taagagaatt ttgtttgatt    660
atccgttcgg ataaatggac gcctgctcca tatttttccg gttcatattt ttccggttat    720
taccccacct ggaagtgccc agaattttcc ggggattacg gataatacgg tggtctggat    780
taattaatac gccaagtctt acattttgtt gcagtctcgt gcgagtatgt gcaataataa    840
acaagatgag ccaatttatt ggattagttg cagcttgacc ccgccatagc taggcatagc    900
caagtgctat gggtgttaga tgatgcactt ggatgcagtg agttttggag tataaaagat    960
ccttaaaatt ccaccctt                                                   978
```

<210> SEQ ID NO 170
<211> LENGTH: 976
<212> TYPE: DNA
<213> ORGANISM: Artificial Sequence
<220> FEATURE:
<223> OTHER INFORMATION: pG1-8 promoter

<400> SEQUENCE: 170

```
caaacatttg ctcccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgcttttt tttttttga tgaccccgtt    600
ttcgtgacaa attaatttcc aacggggtct tgtccggata agagaatttt gtttgattat    660
ccgttcggat aaatggacgc ctgctccata tttttccggt tcatattttt ccggttatta    720
ccccacctgg aagtgcccag aattttccgg ggattacgga taatacggtg gtctggatta    780
attaatacgc caagtcttac attttgttgc agtctcgtgc gagtatgtgc aataataaac    840
aagatgagcc aatttattgg attagttgca gcttgacccc gccatagcta ggcatagcca    900
agtgctatgg gtgttagatg atgcacttgg atgcagtgag ttttggagta taaaagatcc    960
ttaaaattcc accctt                                                    976
```

<210> SEQ ID NO 171
<211> LENGTH: 979
<212> TYPE: DNA
<213> ORGANISM: Artificial Sequence
<220> FEATURE:
<223> OTHER INFORMATION: pG1-8 promoter

<400> SEQUENCE: 171

```
caaacatttg ctcccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgctattt tttttttttt tgatgacccc    600
gttttcgtga caaattaatt tccaacgggg tcttgtccgg ataagagaat tttgtttgat    660
tatccgttcg gataaatgga cgcctgctcc atatttttcc ggttcatatt tttccggtta    720
ttaccccacc tggaagtgcc cagaattttc cggggattac ggataatacg gtggtctgga    780
ttaattaata cgccaagtct tacattttgt tgcagtctcg tgcgagtatg tgcaataata    840
aacaagatga gccaatttat tggattagtt gcagcttgac cccgccatag ctaggcatag    900
ccaagtgcta tgggtgttag atgatgcact tggatgcagt gagttttgga gtataaaaga    960
```

tccttaaaat tccacccctt 979

<210> SEQ ID NO 172
<211> LENGTH: 977
<212> TYPE: DNA
<213> ORGANISM: Artificial Sequence
<220> FEATURE:
<223> OTHER INFORMATION: pG1-8 promoter

<400> SEQUENCE: 172
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttg atgaccccgt 600
tttcgtgaca aattaatttc caacggggtc ttgtccggat aagagaattt tgtttgatta 660
tccgttcgga taaatggacg cctgctccat atttttccgg ttcatatttt tccggttatt 720
accccacctg gaagtgccca gaattttccg gggattacgg ataatacggt ggtctggatt 780
aattaatacg ccaagtctta cattttgttg cagtctcgtg cgagtatgtg caataataaa 840
caagatgagc caatttattg gattagttgc agcttgaccc cgccatagct aggcatagcc 900
aagtgctatg ggtgttagat gatgcacttg gatgcagtga gttttggagt ataaaagatc 960
cttaaaattc caccctt 977

<210> SEQ ID NO 173
<211> LENGTH: 980
<212> TYPE: DNA
<213> ORGANISM: Artificial Sequence
<220> FEATURE:
<223> OTHER INFORMATION: pG1-8 promoter

<400> SEQUENCE: 173
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttgatgaccc 600
cgttttcgtg acaaattaat ttccaacggg gtcttgtccg gataagagaa ttttgtttga 660
ttatccgttc ggataaatgg acgcctgctc catatttttc cggttcatat ttttccggtt 720
attaccccac ctggaagtgc ccagaatttt ccggggatta cggataatac ggtggtctgg 780
attaattaat acgccaagtc ttacattttg ttgcagtctc gtgcgagtat gtgcaataat 840
aaacaagatg agccaattta ttggattagt tgcagcttga ccccgccata gctaggcata 900
gccaagtgct atgggtgtta gatgatgcac ttggatgcag tgagttttgg agtataaaag 960
atccttaaaa ttccaccctt 980

<210> SEQ ID NO 174
<211> LENGTH: 978
<212> TYPE: DNA
<213> ORGANISM: Artificial Sequence
<220> FEATURE:
<223> OTHER INFORMATION: pG1-8 promoter

<400> SEQUENCE: 174
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt gatgaccccg 600
ttttcgtgac aaattaattt ccaacggggt cttgtccgga taagagaatt ttgtttgatt 660
atccgttcgg ataaatggac gcctgctcca tatttttccg gttcatattt ttccggttat 720
taccccacct ggaagtgccc agaattttcc ggggattacg gataatacgg tggtctggat 780
taattaatac gccaagtctt acattttgtt gcagtctcgt gcgagtatgt gcaataataa 840
acaagatgag ccaatttatt ggattagttg cagcttgacc ccgccatagc taggcatagc 900
caagtgctat gggtgttaga tgatgcactt ggatgcagtg agttttggag tataaaagat 960
ccttaaaatt ccaccctt 978

<210> SEQ ID NO 175
<211> LENGTH: 981
<212> TYPE: DNA
<213> ORGANISM: Artificial Sequence
<220> FEATURE:
<223> OTHER INFORMATION: pG1-8 promoter

<400> SEQUENCE: 175
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttgatgacc 600
ccgttttcgt gacaaattaa tttccaacgg ggtcttgtcc ggataagaga attttgtttg 660
attatccgtt cggataaatg gacgcctgct ccatattttt ccggttcata tttttccggt 720
tattacccca cctggaagtg cccagaattt tccggggatt acggataata cggtggtctg 780
gattaattaa tacgccaagt cttacatttt gttgcagtct cgtgcgagta tgtgcaataa 840
taaacaagat gagccaattt attggattag ttgcagcttg accccgccat agctaggcat 900
agccaagtgc tatgggtgtt agatgatgca cttggatgca gtgagttttg gagtataaaa 960
gatccttaaa attccaccct t 981

<210> SEQ ID NO 176
<211> LENGTH: 979
<212> TYPE: DNA
<213> ORGANISM: Artificial Sequence
<220> FEATURE:
<223> OTHER INFORMATION: pG1-8 promoter

<400> SEQUENCE: 176
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tgatgacccc 600
gttttcgtga caaattaatt tccaacgggg tcttgtccgg ataagagaat tttgtttgat 660
tatccgttcg gataaatgga cgcctgctcc atatttttcc ggttcatatt tttccggtta 720
ttaccccacc tggaagtgcc cagaattttc cggggattac ggataatacg gtggtctgga 780
ttaattaata cgccaagtct tacattttgt tgcagtctcg tgcgagtatg tgcaataata 840
aacaagatga gccaatttat tggattagtt gcagcttgac cccgccatag ctaggcatag 900
ccaagtgcta tgggtgttag atgatgcact tggatgcagt gagttttgga gtataaaaga 960
tccttaaaat tccaccctt 979

<210> SEQ ID NO 177
<211> LENGTH: 982
<212> TYPE: DNA
<213> ORGANISM: Artificial Sequence
<220> FEATURE:
<223> OTHER INFORMATION: pG1-8 promoter

<400> SEQUENCE: 177
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttgatgac 600
cccgttttcg tgacaaatta atttccaacg gggtcttgtc cggataagag aattttgttt 660
gattatccgt tcggataaat ggacgcctgc tccatatttt tccggttcat atttttccgg 720
ttattacccc acctggaagt gcccagaatt ttccggggat tacggataat acggtggtct 780
ggattaatta atacgccaag tcttacattt tgttgcagtc tcgtgcgagt atgtgcaata 840
ataaacaaga tgagccaatt tattggatta gttgcagctt gaccccgcca tagctaggca 900
tagccaagtg ctatgggtgt tagatgatgc acttggatgc agtgagtttt ggagtataaa 960
agatccttaa aattccaccc tt 982

<210> SEQ ID NO 178
<211> LENGTH: 980
<212> TYPE: DNA
<213> ORGANISM: Artificial Sequence
<220> FEATURE:
<223> OTHER INFORMATION: pG1-8 promoter

<400> SEQUENCE: 178
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt ttgatgaccc 600
cgttttcgtg acaaattaat ttccaacggg gtcttgtccg gataagagaa ttttgtttga 660
ttatccgttc ggataaatgg acgcctgctc catatttttc cggttcatat ttttccggtt 720
attaccccac ctggaagtgc ccagaatttt ccggggatta cggataatac ggtggtctgg 780
attaattaat acgccaagtc ttacattttg ttgcagtctc gtgcgagtat gtgcaataat 840
aaacaagatg agccaattta ttggattagt tgcagcttga ccccgccata gctaggcata 900
gccaagtgct atgggtgtta gatgatgcac ttggatgcag tgagttttgg agtataaaag 960
atccttaaaa ttccaccctt 980

<210> SEQ ID NO 179
<211> LENGTH: 983
<212> TYPE: DNA
<213> ORGANISM: Artificial Sequence
<220> FEATURE:

<223> OTHER INFORMATION: pG1-8 promoter

<400> SEQUENCE: 179
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttttgatga 600
ccccgttttc gtgacaaatt aatttccaac ggggtcttgt ccggataaga gaattttgtt 660
tgattatccg ttcggataaa tggacgcctg ctccatattt ttccggttca tatttttccg 720
gttattaccc cacctggaag tgcccagaat tttccgggga ttacggataa tacggtggtc 780
tggattaatt aatacgccaa gtcttacatt ttgttgcagt ctcgtgcgag tatgtgcaat 840
aataaacaag atgagccaat ttattggatt agttgcagct tgaccccgcc atagctaggc 900
atagccaagt gctatgggtg ttagatgatg cacttggatg cagtgagttt tggagtataa 960
aagatcctta aaattccacc ctt 983

<210> SEQ ID NO 180
<211> LENGTH: 981
<212> TYPE: DNA
<213> ORGANISM: Artificial Sequence
<220> FEATURE:
<223> OTHER INFORMATION: pG1-8 promoter

<400> SEQUENCE: 180
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tttgatgacc 600
ccgttttcgt gacaaattaa tttccaacgg ggtcttgtcc ggataagaga attttgtttg 660
attatccgtt cggataaatg gacgcctgct ccatattttt ccggttcata tttttccggt 720
tattacccca cctggaagtg cccagaattt tccggggatt acggataata cggtggtctg 780
gattaattaa tacgccaagt cttacatttt gttgcagtct cgtgcgagta tgtgcaataa 840
taaacaagat gagccaattt attggattag ttgcagcttg accccgccat agctaggcat 900
agccaagtgc tatgggtgtt agatgatgca cttggatgca gtgagttttg gagtataaaa 960
gatccttaaa attccaccct t 981

<210> SEQ ID NO 181
<211> LENGTH: 984
<212> TYPE: DNA
<213> ORGANISM: Artificial Sequence
<220> FEATURE:
<223> OTHER INFORMATION: pG1-8 promoter

<400> SEQUENCE: 181
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttttgatg 600
accccgtttt cgtgacaaat taatttccaa cggggtcttg tccggataag agaattttgt 660
ttgattatcc gttcggataa atggacgcct gctccatatt tttccggttc atatttttcc 720
ggttattacc ccacctggaa gtgcccagaa ttttccgggg attacggata atacggtggt 780
ctggattaat taatacgcca agtcttacat tttgttgcag tctcgtgcga gtatgtgcaa 840
taataaacaa gatgagccaa tttattggat tagttgcagc ttgaccccgc catagctagg 900
catagccaag tgctatgggt gttagatgat gcacttggat gcagtgagtt ttggagtata 960
aaagatcctt aaaattccac cctt 984

<210> SEQ ID NO 182
<211> LENGTH: 982
<212> TYPE: DNA
<213> ORGANISM: Artificial Sequence
<220> FEATURE:
<223> OTHER INFORMATION: pG1-8 promoter

<400> SEQUENCE: 182
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt ttttgatgac 600
cccgttttcg tgacaaatta atttccaacg gggtcttgtc cggataagag aattttgttt 660
gattatccgt tcggataaat ggacgcctgc tccatatttt tccggttcat atttttccgg 720
ttattacccc acctggaagt gcccagaatt ttccggggat tacggataat acggtggtct 780
ggattaatta atacgccaag tcttacattt tgttgcagtc tcgtgcgagt atgtgcaata 840
ataaacaaga tgagccaatt tattggatta gttgcagctt gaccccgcca tagctaggca 900
tagccaagtg ctatgggtgt tagatgatgc acttggatgc agtgagtttt ggagtataaa 960
agatccttaa aattccaccc tt 982

<210> SEQ ID NO 183
<211> LENGTH: 985
<212> TYPE: DNA
<213> ORGANISM: Artificial Sequence
<220> FEATURE:
<223> OTHER INFORMATION: pG1-8 promoter

<400> SEQUENCE: 183
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttttttgat 600
gaccccgttt tcgtgacaaa ttaatttcca acggggtctt gtccggataa gagaattttg 660
tttgattatc cgttcggata aatggacgcc tgctccatat ttttccggtt catatttttc 720
cggttattac cccacctgga agtgcccaga attttccggg gattacggat aatacggtgg 780
tctggattaa ttaatacgcc aagtcttaca ttttgttgca gtctcgtgcg agtatgtgca 840
ataataaaca agatgagcca atttattgga ttagttgcag cttgaccccg ccatagctag 900
gcatagccaa gtgctatggg tgttagatga tgcacttgga tgcagtgagt tttggagtat 960
aaaagatcct taaaattcca ccctt 985

<210> SEQ ID NO 184
<211> LENGTH: 983
<212> TYPE: DNA
<213> ORGANISM: Artificial Sequence
<220> FEATURE:
<223> OTHER INFORMATION: pG1-8 promoter

<400> SEQUENCE: 184
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420

```
ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt tttttgatga    600

ccccgttttc gtgacaaatt aatttccaac ggggtcttgt ccggataaga gaattttgtt    660

tgattatccg ttcggataaa tggacgcctg ctccatattt ttccggttca tatttttccg    720

gttattaccc cacctggaag tgcccagaat tttccgggga ttacggataa tacggtggtc    780

tggattaatt aatacgccaa gtcttacatt ttgttgcagt ctcgtgcgag tatgtgcaat    840

aataaacaag atgagccaat ttattggatt agttgcagct tgacccccgcc atagctaggc    900

atagccaagt gctatgggtg ttagatgatg cacttggatg cagtgagttt tggagtataa    960

aagatcctta aaattccacc ctt                                            983
```

<210> SEQ ID NO 185
<211> LENGTH: 1039
<212> TYPE: DNA
<213> ORGANISM: Artificial Sequence
<220> FEATURE:
<223> OTHER INFORMATION: pG1-9 promoter
<220> FEATURE:
<221> NAME/KEY: misc_feature
<222> LOCATION: (591)..(597)
<223> OTHER INFORMATION: n is t or absent

<400> SEQUENCE: 185

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt nnnnnnngat    600

gaccccgttt tcgtgacaaa ttaatttcca acggggtctt gtccggataa gagaattttg    660

tttgattatc cgttcggata aatggacgcc tgctccatat ttttccggtt attaccccac    720

ctggaagtgt ttgattatcc gttcggataa atggacgcct gctccatatt tttccggtta    780

ttaccccacc tggaagtgcc cagaattttc cggggattac ggataatacg gtggtctgga    840

ttaattaata cgccaagtct tacattttgt tgcagtctcg tgcgagtatg tgcaataata    900

aacaagatga gccaatttat tggattagtt gcagcttgac ccccgccatag ctaggcatag    960

ccaagtgcta tgggtgttag atgatgcact tggatgcagt gagttttgga gtataaaaga   1020

tccttaaaat tccaccctt                                                1039
```

<210> SEQ ID NO 186
<211> LENGTH: 1037
<212> TYPE: DNA
<213> ORGANISM: Artificial Sequence
<220> FEATURE:
<223> OTHER INFORMATION: pG1-9 promoter
<220> FEATURE:

<221> NAME/KEY: misc_feature
<222> LOCATION: (589)..(595)
<223> OTHER INFORMATION: n is t or absent

<400> SEQUENCE: 186
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt ttttttttnn nnnnngatga 600
ccccgttttc gtgacaaatt aatttccaac ggggtcttgt ccggataaga gaattttgtt 660
tgattatccg ttcggataaa tggacgcctg ctccatattt ttccggttat taccccacct 720
ggaagtgttt gattatccgt tcggataaat ggacgcctgc tccatatttt tccggttatt 780
accccacctg gaagtgccca gaattttccg ggattacgg ataatacggt ggtctggatt 840
aattaatacg ccaagtctta cattttgttg cagtctcgtg cgagtatgtg caataataaa 900
caagatgagc caatttattg gattagttgc agcttgaccc cgccatagct aggcatagcc 960
aagtgctatg ggtgttagat gatgcacttg gatgcagtga gttttggagt ataaaagatc 1020
cttaaaattc caccctt 1037

<210> SEQ ID NO 187
<211> LENGTH: 1032
<212> TYPE: DNA
<213> ORGANISM: Artificial Sequence
<220> FEATURE:
<223> OTHER INFORMATION: pG1-9 promoter

<400> SEQUENCE: 187
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt gatgaccccg 600
ttttcgtgac aaattaattt ccaacggggt cttgtccgga taagagaatt ttgtttgatt 660
atccgttcgg ataaatggac gcctgctcca tatttttccg gttattaccc cacctggaag 720
tgtttgatta tccgttcgga taaatggacg cctgctccat atttttccgg ttattacccc 780
acctggaagt gcccagaatt ttccggggat tacggataat acggtggtct ggattaatta 840
atacgccaag tcttacattt tgttgcagtc tcgtgcgagt atgtgcaata ataaacaaga 900
tgagccaatt tattggatta gttgcagctt gaccccgcca tagctaggca tagccaagtg 960
ctatgggtgt tagatgatgc acttggatgc agtgagtttt ggagtataaa agatccttaa 1020
aattccaccc tt 1032

<210> SEQ ID NO 188
<211> LENGTH: 1030
<212> TYPE: DNA
<213> ORGANISM: Artificial Sequence
<220> FEATURE:
<223> OTHER INFORMATION: pG1-9 promoter

<400> SEQUENCE: 188
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttga tgaccccgtt 600 ttcgtgacaa attaatttcc aacggggtct tgtccggata agagaatttt gtttgattat 660
ccgttcggat aaatggacgc ctgctccata tttttccggt tattacccca cctggaagtg 720
tttgattatc cgttcggata aatggacgcc tgctccatat ttttccggtt attaccccac 780
ctggaagtgc ccagaatttt ccggggatta cggataatac ggtggtctgg attaattaat 840
acgccaagtc ttacattttg ttgcagtctc gtgcgagtat gtgcaataat aaacaagatg 900
agccaattta ttggattagt tgcagcttga ccccgccata gctaggcata gccaagtgct 960
atgggtgtta gatgatgcac ttggatgcag tgagttttgg agtataaaag atccttaaaa 1020
ttccaccctt 1030

<210> SEQ ID NO 189
<211> LENGTH: 1033
<212> TYPE: DNA
<213> ORGANISM: Artificial Sequence
<220> FEATURE:
<223> OTHER INFORMATION: pG1-9 promoter

<400> SEQUENCE: 189
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt ttttttttt tgatgacccc 600 gttttcgtga caaattaatt tccaacgggg tcttgtccgg ataagagaat tttgtttgat 660
tatccgttcg gataaatgga cgcctgctcc atatttttcc ggttattacc ccacctggaa 720
gtgtttgatt atccgttcgg ataaatggac gcctgctcca tatttttccg gttattaccc 780
cacctggaag tgcccagaat tttccgggga ttacggataa tacggtggtc tggattaatt 840
aatacgccaa gtcttacatt ttgttgcagt ctcgtgcgag tatgtgcaat aataaacaag 900
atgagccaat ttattggatt agttgcagct tgaccccgcc atagctaggc atagccaagt 960
gctatgggtg ttagatgatg cacttggatg cagtgagttt tggagtataa aagatcctta 1020
aaattccacc ctt 1033

<210> SEQ ID NO 190
<211> LENGTH: 1031
<212> TYPE: DNA
<213> ORGANISM: Artificial Sequence
<220> FEATURE:
<223> OTHER INFORMATION: pG1-9 promoter

<400> SEQUENCE: 190
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttg atgaccccgt 600
tttcgtgaca aattaatttc caacggggtc ttgtccggat aagagaattt tgtttgatta 660
tccgttcgga taaatggacg cctgctccat atttttccgg ttattacccc acctggaagt 720
gtttgattat ccgttcggat aaatggacgc ctgctccata tttttccggt tattacccca 780
cctggaagtg cccagaattt tccggggatt acggataata cggtggtctg gattaattaa 840
tacgccaagt cttacatttt gttgcagtct cgtgcgagta tgtgcaataa taaacaagat 900
gagccaattt attggattag ttgcagcttg accccgccat agctaggcat agccaagtgc 960
tatgggtgtt agatgatgca cttggatgca gtgagttttg gagtataaaa gatccttaaa 1020
attccaccct t 1031

<210> SEQ ID NO 191
<211> LENGTH: 1034
<212> TYPE: DNA
<213> ORGANISM: Artificial Sequence
<220> FEATURE:
<223> OTHER INFORMATION: pG1-9 promoter

<400> SEQUENCE: 191
caaacatttg ctccccctag tctccaggga aatgtaaaat atactgctaa tagaaaacag 60

-continued

```
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgctattt ttttttttt ttgatgaccc    600
cgttttcgtg acaaattaat ttccaacggg gtcttgtccg gataagagaa ttttgtttga    660
ttatccgttc ggataaatgg acgcctgctc catatttttc cggttattac cccacctgga    720
agtgtttgat tatccgttcg gataaatgga cgcctgctcc atatttttcc ggttattacc    780
ccacctggaa gtgcccagaa ttttccgggg attacggata atacggtggt ctggattaat    840
taatacgcca agtcttacat tttgttgcag tctcgtgcga gtatgtgcaa taataaacaa    900
gatgagccaa tttattggat tagttgcagc ttgaccccgc catagctagg catagccaag    960
tgctatgggt gttagatgat gcacttggat gcagtgagtt ttggagtata aaagatcctt   1020
aaaattccac cctt                                                     1034
```

<210> SEQ ID NO 192
<211> LENGTH: 1032
<212> TYPE: DNA
<213> ORGANISM: Artificial Sequence
<220> FEATURE:
<223> OTHER INFORMATION: pG1-9 promoter

<400> SEQUENCE: 192

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgcttttt ttttttttt gatgaccccg    600
ttttcgtgac aaattaattt ccaacggggt cttgtccgga taagagaatt ttgtttgatt    660
atccgttcgg ataaatggac gcctgctcca tatttttccg gttattaccc cacctggaag    720
tgtttgatta tccgttcgga taaatggacg cctgctccat atttttccgg ttattacccc    780
acctggaagt gcccagaatt ttccggggat tacggataat acggtggtct ggattaatta    840
atacgccaag tcttacattt tgttgcagtc tcgtgcgagt atgtgcaata ataaacaaga    900
tgagccaatt tattggatta gttgcagctt gaccccgcca tagctaggca tagccaagtg    960
ctatgggtgt tagatgatgc acttggatgc agtgagtttt ggagtataaa agatccttaa   1020
```

aattccaccc tt 1032

<210> SEQ ID NO 193
<211> LENGTH: 1035
<212> TYPE: DNA
<213> ORGANISM: Artificial Sequence
<220> FEATURE:
<223> OTHER INFORMATION: pG1-9 promoter

<400> SEQUENCE: 193
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt tttgatgacc 600
ccgttttcgt gacaaattaa tttccaacgg ggtcttgtcc ggataagaga attttgtttg 660
attatccgtt cggataaatg gacgcctgct ccatattttt ccggttatta ccccacctgg 720
aagtgtttga ttatccgttc ggataaatgg acgcctgctc catatttttc cggttattac 780
cccacctgga agtgcccaga attttccggg gattacggat aatacggtgg tctggattaa 840
ttaatacgcc aagtcttaca ttttgttgca gtctcgtgcg agtatgtgca ataataaaca 900
agatgagcca atttattgga ttagttgcag cttgaccccg ccatagctag gcatagccaa 960
gtgctatggg tgttagatga tgcacttgga tgcagtgagt tttggagtat aaaagatcct 1020
taaaattcca ccctt 1035

<210> SEQ ID NO 194
<211> LENGTH: 1033
<212> TYPE: DNA
<213> ORGANISM: Artificial Sequence
<220> FEATURE:
<223> OTHER INFORMATION: pG1-9 promoter

<400> SEQUENCE: 194
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tgatgacccc 600
gttttcgtga caaattaatt tccaacgggg tcttgtccgg ataagagaat tttgtttgat 660
tatccgttcg gataaatgga cgcctgctcc atatttttcc ggttattacc ccacctggaa 720
gtgtttgatt atccgttcgg ataaatggac gcctgctcca tatttttccg gttattaccc 780
cacctggaag tgcccagaat tttccgggga ttacggataa tacggtggtc tggattaatt 840
aatacgccaa gtcttacatt ttgttgcagt ctcgtgcgag tatgtgcaat aataaacaag 900
atgagccaat ttattggatt agttgcagct tgaccccgcc atagctaggc atagccaagt 960
gctatgggtg ttagatgatg cacttggatg cagtgagttt tggagtataa aagatcctta 1020
aaattccacc ctt 1033

<210> SEQ ID NO 195
<211> LENGTH: 1036
<212> TYPE: DNA
<213> ORGANISM: Artificial Sequence
<220> FEATURE:
<223> OTHER INFORMATION: pG1-9 promoter

<400> SEQUENCE: 195
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt tacccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgctattt tttttttttt ttttgatgac 600
cccgttttcg tgacaaatta atttccaacg gggtcttgtc cggataagag aattttgttt 660
gattatccgt tcggataaat ggacgcctgc tccatatttt tccggttatt accccacctg 720
gaagtgtttg attatccgtt cggataaatg gacgcctgct ccatattttt ccggttatta 780
ccccacctgg aagtgcccag aattttccgg ggattacgga taatacggtg gtctggatta 840
attaatacgc caagtcttac attttgttgc agtctcgtgc gagtatgtgc aataataaac 900
aagatgagcc aatttattgg attagttgca gcttgacccc gccatagcta ggcatagcca 960
agtgctatgg gtgttagatg atgcacttgg atgcagtgag ttttggagta taaaagatcc 1020
ttaaaattcc accctt 1036

<210> SEQ ID NO 196
<211> LENGTH: 1034
<212> TYPE: DNA
<213> ORGANISM: Artificial Sequence
<220> FEATURE:
<223> OTHER INFORMATION: pG1-9 promoter

<400> SEQUENCE: 196
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240

```
tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt ttgatgaccc    600

cgttttcgtg acaaattaat ttccaacggg gtcttgtccg gataagagaa ttttgtttga    660

ttatccgttc ggataaatgg acgcctgctc catatttttc cggttattac cccacctgga    720

agtgtttgat tatccgttcg gataaatgga cgcctgctcc atatttttcc ggttattacc    780

ccacctggaa gtgcccagaa ttttccgggg attacggata atacggtggt ctggattaat    840

taatacgcca agtcttacat tttgttgcag tctcgtgcga gtatgtgcaa taataaacaa    900

gatgagccaa tttattggat tagttgcagc ttgaccccgc catagctagg catagccaag    960

tgctatgggt gttagatgat gcacttggat gcagtgagtt ttggagtata aaagatcctt   1020

aaaattccac cctt                                                     1034
```

<210> SEQ ID NO 197
<211> LENGTH: 1037
<212> TYPE: DNA
<213> ORGANISM: Artificial Sequence
<220> FEATURE:
<223> OTHER INFORMATION: pG1-9 promoter

<400> SEQUENCE: 197

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgctattt tttttttttt tttttgatga    600

ccccgttttc gtgacaaatt aatttccaac ggggtcttgt ccggataaga gaattttgtt    660

tgattatccg ttcggataaa tggacgcctg ctccatattt ttccggttat taccccacct    720

ggaagtgttt gattatccgt tcggataaat ggacgcctgc tccatatttt tccggttatt    780

accccacctg gaagtgccca gaattttccg gggattacgg ataatacggt ggtctggatt    840

aattaatacg ccaagtctta cattttgttg cagtctcgtg cgagtatgtg caataataaa    900

caagatgagc caatttattg gattagttgc agcttgaccc cgccatagct aggcatagcc    960

aagtgctatg ggtgttagat gatgcacttg gatgcagtga gttttggagt ataaaagatc   1020

cttaaaattc caccctt                                                  1037
```

<210> SEQ ID NO 198
<211> LENGTH: 1035
<212> TYPE: DNA
<213> ORGANISM: Artificial Sequence
<220> FEATURE:
<223> OTHER INFORMATION: pG1-9 promoter

<400> SEQUENCE: 198

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgcttttt tttttttttt tttgatgacc    600
ccgttttcgt gacaaattaa tttccaacgg ggtcttgtcc ggataagaga attttgtttg    660
attatccgtt cggataaatg gacgcctgct ccatattttt ccggttatta ccccacctgg    720
aagtgtttga ttatccgttc ggataaatgg acgcctgctc catatttttc cggttattac    780
cccacctgga agtgcccaga attttccggg gattacggat aatacggtgg tctggattaa    840
ttaatacgcc aagtcttaca ttttgttgca gtctcgtgcg agtatgtgca ataataaaca    900
agatgagcca atttattgga ttagttgcag cttgaccccg ccatagctag gcatagccaa    960
gtgctatggg tgttagatga tgcacttgga tgcagtgagt tttggagtat aaaagatcct   1020
taaaattcca ccctt                                                    1035
```

<210> SEQ ID NO 199
<211> LENGTH: 1038
<212> TYPE: DNA
<213> ORGANISM: Artificial Sequence
<220> FEATURE:
<223> OTHER INFORMATION: pG1-9 promoter

<400> SEQUENCE: 199

```
caaacatttg ctccccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa aacagcttga    180
aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt tacccccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgctattt tttttttttt tttttgatg    600
accccgtttt cgtgacaaat taatttccaa cggggtcttg tccggataag agaattttgt    660
ttgattatcc gttcggataa atggacgcct gctccatatt tttccggtta ttaccccacc    720
tggaagtgtt tgattatccg ttcggataaa tggacgcctg ctccatattt ttccggttat    780
taccccacct ggaagtgccc agaattttcc ggggattacg gataatacgg tggtctggat    840
```

taattaatac gccaagtctt acattttgtt gcagtctcgt gcgagtatgt gcaataataa 900
acaagatgag ccaatttatt ggattagttg cagcttgacc ccgccatagc taggcatagc 960
caagtgctat gggtgttaga tgatgcactt ggatgcagtg agttttggag tataaaagat 1020
ccttaaaatt ccacccctt 1038

<210> SEQ ID NO 200
<211> LENGTH: 1036
<212> TYPE: DNA
<213> ORGANISM: Artificial Sequence
<220> FEATURE:
<223> OTHER INFORMATION: pG1-9 promoter

<400> SEQUENCE: 200
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt ttttgatgac 600
cccgttttcg tgacaaatta atttccaacg gggtcttgtc cggataagag aattttgttt 660
gattatccgt tcggataaat ggacgcctgc tccatatttt tccggttatt accccacctg 720
gaagtgtttg attatccgtt cggataaatg gacgcctgct ccatattttt ccggttatta 780
ccccacctgg aagtgcccag aattttccgg ggattacgga taatacggtg gtctggatta 840
attaatacgc caagtcttac attttgttgc agtctcgtgc gagtatgtgc aataataaac 900
aagatgagcc aatttattgg attagttgca gcttgacccc gccatagcta ggcatagcca 960
agtgctatgg gtgttagatg atgcacttgg atgcagtgag ttttggagta taaaagatcc 1020
ttaaaattcc accctt 1036

<210> SEQ ID NO 201
<211> LENGTH: 1039
<212> TYPE: DNA
<213> ORGANISM: Artificial Sequence
<220> FEATURE:
<223> OTHER INFORMATION: pG1-9 promoter

<400> SEQUENCE: 201
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480

-continued

```
tagacttcaa gatctcaggg attcccacta tttggtattc tgatatgttt ttcctgatat    540

gcatcaaaac tctaatctaa aacctgaatc tccgctattt tttttttttt ttttttttgat    600

gaccccgttt tcgtgacaaa ttaatttcca acggggtctt gtccggataa gagaattttg    660

tttgattatc cgttcggata aatggacgcc tgctccatat ttttccggtt attaccccac    720

ctggaagtgt ttgattatcc gttcggataa atggacgcct gctccatatt tttccggtta    780

ttaccccacc tggaagtgcc cagaattttc cggggattac ggataatacg gtggtctgga    840

ttaattaata cgccaagtct tacattttgt tgcagtctcg tgcgagtatg tgcaataata    900

aacaagatga gccaatttat tggattagtt gcagcttgac cccgccatag ctaggcatag    960

ccaagtgcta tgggtgttag atgatgcact tggatgcagt gagttttgga gtataaaaga   1020

tccttaaaat tccacccctt                                               1039
```

<210> SEQ ID NO 202
<211> LENGTH: 1037
<212> TYPE: DNA
<213> ORGANISM: Artificial Sequence
<220> FEATURE:
<223> OTHER INFORMATION: pG1-9 promoter

<400> SEQUENCE: 202

```
caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt tttttgatga    600

ccccgttttc gtgacaaatt aatttccaac ggggtcttgt ccggataaga gaattttgtt    660

tgattatccg ttcggataaa tggacgcctg ctccatattt ttccggttat taccccacct    720

ggaagtgttt gattatccgt tcggataaat ggacgcctgc tccatatttt tccggttatt    780

accccacctg gaagtgccca gaattttccg gggattacgg ataatacggt ggtctggatt    840

aattaatacg ccaagtctta cattttgttg cagtctcgtg cgagtatgtg caataataaa    900

caagatgagc caatttattg gattagttgc agcttgaccc cgccatagct aggcatagcc    960

aagtgctatg ggtgttagat gatgcacttg gatgcagtga gttttggagt ataaaagatc   1020

cttaaaattc caccctt                                                  1037
```

<210> SEQ ID NO 203
<211> LENGTH: 497
<212> TYPE: DNA
<213> ORGANISM: Artificial Sequence
<220> FEATURE:
<223> OTHER INFORMATION: pG1-10 promoter
<220> FEATURE:
<221> NAME/KEY: misc_feature
<222> LOCATION: (118)..(124)
<223> OTHER INFORMATION: n is t or absent

<400> SEQUENCE: 203
ctgcagatag acttcaagat ctcagggatt cccactattt ggtattctga tatgtttttc 60
ctgatatgca tcaaaactct aatctaaaac ctgaatctcc gctatttttt ttttttnnn 120 nnnngatgac cccgttttcg tgacaaatta atttccaacg ggtcttgtc cggataagag 180 aattttgttt gattatccgt tcggataaat ggacgcctgc tccatatttt tccggttatt 240
accccacctg gaagtgccca gaattttccg ggattacgg ataatacggt ggtctggatt 300
aattaatacg ccaagtctta cattttgttg cagtctcgtg cgagtatgtg caataataaa 360
caagatgagc caatttattg gattagttgc agcttgaccc cgccatagct aggcatagcc 420
aagtgctatg ggtgttagat gatgcacttg gatgcagtga gttttggagt ataaaagatc 480
cttaaaattc caccctt 497

<210> SEQ ID NO 204
<211> LENGTH: 495
<212> TYPE: DNA
<213> ORGANISM: Artificial Sequence
<220> FEATURE:
<223> OTHER INFORMATION: pG1-10 promoter
<220> FEATURE:
<221> NAME/KEY: misc_feature
<222> LOCATION: (116)..(122)
<223> OTHER INFORMATION: n is t or absent

<400> SEQUENCE: 204
ctgcagatag acttcaagat ctcagggatt cccactattt ggtattctga tatgtttttc 60
ctgatatgca tcaaaactct aatctaaaac ctgaatctcc gcttttttt tttttnnnnn 120 nngatgaccc cgttttcgtg acaaattaat ttccaacggg gtcttgtccg gataagagaa 180
ttttgtttga ttatccgttc ggataaatgg acgcctgctc catatttttc cggttattac 240
cccacctgga agtgcccaga attttccggg gattacggat aatacggtgg tctggattaa 300
ttaatacgcc aagtcttaca ttttgttgca gtctcgtgcg agtatgtgca ataataaaca 360
agatgagcca atttattgga ttagttgcag cttgaccccg ccatagctag gcatagccaa 420
gtgctatggg tgttagatga tgcacttgga tgcagtgagt tttggagtat aaaagatcct 480
taaaattcca ccctt 495

<210> SEQ ID NO 205
<211> LENGTH: 490
<212> TYPE: DNA
<213> ORGANISM: Artificial Sequence
<220> FEATURE:
<223> OTHER INFORMATION: pG1-10 promoter

<400> SEQUENCE: 205
ctgcagatag acttcaagat ctcagggatt cccactattt ggtattctga tatgtttttc 60
ctgatatgca tcaaaactct aatctaaaac ctgaatctcc gctatttttt tttttttgat 120
gaccccgttt tcgtgacaaa ttaatttcca acggggtctt gtccggataa gagaattttg 180
tttgattatc cgttcggata aatggacgcc tgctccatat ttttccggtt attaccccac 240
ctggaagtgc ccagaatttt ccggggatta cggataatac ggtggtctgg attaattaat 300
acgccaagtc ttacattttg ttgcagtctc gtgcgagtat gtgcaataat aaacaagatg 360
agccaattta ttggattagt tgcagcttga ccccgccata gctaggcata gccaagtgct 420
atgggtgtta gatgatgcac ttggatgcag tgagttttgg agtataaaag atccttaaaa 480
ttccaccctt 490

<210> SEQ ID NO 206
<211> LENGTH: 488
<212> TYPE: DNA
<213> ORGANISM: Artificial Sequence
<220> FEATURE:
<223> OTHER INFORMATION: pG1-10 promoter

<400> SEQUENCE: 206
ctgcagatag acttcaagat ctcagggatt cccactattt ggtattctga tatgtttttc 60
ctgatatgca tcaaaactct aatctaaaac ctgaatctcc gctttttttt tttttgatga 120
ccccgttttc gtgacaaatt aatttccaac ggggtcttgt ccggataaga gaattttgtt 180
tgattatccg ttcggataaa tggacgcctg ctccatattt ttccggttat taccccacct 240
ggaagtgccc agaattttcc ggggattacg gataatacgg tggtctggat taattaatac 300
gccaagtctt acattttgtt gcagtctcgt gcgagtatgt gcaataataa acaagatgag 360
ccaatttatt ggattagttg cagcttgacc ccgccatagc taggcatagc caagtgctat 420
gggtgttaga tgatgcactt ggatgcagtg agttttggag tataaaagat ccttaaaatt 480
ccaccctt 488

<210> SEQ ID NO 207
<211> LENGTH: 491
<212> TYPE: DNA
<213> ORGANISM: Artificial Sequence
<220> FEATURE:
<223> OTHER INFORMATION: pG1-10 promoter

<400> SEQUENCE: 207
ctgcagatag acttcaagat ctcagggatt cccactattt ggtattctga tatgtttttc 60
ctgatatgca tcaaaactct aatctaaaac ctgaatctcc gctatttttt tttttttga 120 tgaccccgtt ttcgtgacaa attaatttcc aacggggtct tgtccggata agagaatttt 180
gtttgattat ccgttcggat aaatggacgc ctgctccata tttttccggt tattacccca 240
cctggaagtg cccagaattt tccggggatt acggataata cggtggtctg gattaattaa 300
tacgccaagt cttacatttt gttgcagtct cgtgcgagta tgtgcaataa taaacaagat 360
gagccaattt attggattag ttgcagcttg accccgccat agctaggcat agccaagtgc 420
tatgggtgtt agatgatgca cttggatgca gtgagttttg gagtataaaa gatccttaaa 480
attccaccct t 491

<210> SEQ ID NO 208
<211> LENGTH: 489
<212> TYPE: DNA
<213> ORGANISM: Artificial Sequence
<220> FEATURE:
<223> OTHER INFORMATION: pG1-10 promoter

<400> SEQUENCE: 208
ctgcagatag acttcaagat ctcagggatt cccactattt ggtattctga tatgtttttc 60
ctgatatgca tcaaaactct aatctaaaac ctgaatctcc gctttttttt ttttttgatg 120
accccgtttt cgtgacaaat taatttccaa cggggtcttg tccggataag agaattttgt 180
ttgattatcc gttcggataa atggacgcct gctccatatt tttccggtta ttaccccacc 240
tggaagtgcc cagaattttc cggggattac ggataatacg gtggtctgga ttaattaata 300
cgccaagtct tacattttgt tgcagtctcg tgcgagtatg tgcaataata aacaagatga 360

```
gccaatttat tggattagtt gcagcttgac cccgccatag ctaggcatag ccaagtgcta    420

tgggtgttag atgatgcact tggatgcagt gagttttgga gtataaaaga tccttaaaat    480

tccacccctt                                                           489


<210> SEQ ID NO 209
<211> LENGTH: 492
<212> TYPE: DNA
<213> ORGANISM: Artificial Sequence
<220> FEATURE:
<223> OTHER INFORMATION: pG1-10 promoter

<400> SEQUENCE: 209

ctgcagatag acttcaagat ctcagggatt cccactattt ggtattctga tatgtttttc     60

ctgatatgca tcaaaactct aatctaaaac ctgaatctcc gctatttttt ttttttttttg    120

atgaccccgt tttcgtgaca aattaatttc caacggggtc ttgtccggat aagagaattt    180

tgtttgatta tccgttcgga taaatggacg cctgctccat atttttccgg ttattacccc    240

acctggaagt gcccagaatt ttccggggat tacggataat acggtggtct ggattaatta    300

atacgccaag tcttacattt tgttgcagtc tcgtgcgagt atgtgcaata ataaacaaga    360

tgagccaatt tattggatta gttgcagctt gaccccgcca tagctaggca tagccaagtg    420

ctatgggtgt tagatgatgc acttggatgc agtgagtttt ggagtataaa agatccttaa    480

aattccaccc tt                                                        492


<210> SEQ ID NO 210
<211> LENGTH: 490
<212> TYPE: DNA
<213> ORGANISM: Artificial Sequence
<220> FEATURE:
<223> OTHER INFORMATION: pG1-10 promoter

<400> SEQUENCE: 210

ctgcagatag acttcaagat ctcagggatt cccactattt ggtattctga tatgtttttc     60

ctgatatgca tcaaaactct aatctaaaac ctgaatctcc gctttttttt tttttttgat    120

gaccccgttt tcgtgacaaa ttaatttcca acggggtctt gtccggataa gagaattttg    180

tttgattatc cgttcggata aatggacgcc tgctccatat ttttccggtt attaccccac    240

ctggaagtgc ccagaatttt ccggggatta cggataatac ggtggtctgg attaattaat    300

acgccaagtc ttacattttg ttgcagtctc gtgcgagtat gtgcaataat aaacaagatg    360

agccaattta ttggattagt tgcagcttga ccccgccata gctaggcata gccaagtgct    420

atgggtgtta gatgatgcac ttggatgcag tgagttttgg agtataaaag atccttaaaa    480

ttccaccctt                                                           490


<210> SEQ ID NO 211
<211> LENGTH: 947
<212> TYPE: DNA
<213> ORGANISM: Artificial Sequence
<220> FEATURE:
<223> OTHER INFORMATION: TAT motif

<400> SEQUENCE: 211

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240
```

```
tttgacttga ctgaagtcat cggttaacaa tcaagtaccc tagtctgtct gaatgctcct    300

ttccatattc agtaggtgtt tcttgcactt ttgcatgcca atagcgcgtt tcatatgcgc    360

ttttacccc tcttttgtca agcgcaaaat gcctgtaaga tttggtgggg gtgtgagccg    420

ttagctgaag tacaacaggc taattccctg aaaaaactgc agatagactt caagatctca    480

gggattccca ctatttggta ttctgatatg tttttcctga tatgcatcaa aactctaatc    540

taaaacctga atctccgcta ttttttttt ttttgatgac cccgttttcg tgacaaatta    600

atttccaacg gggtcttgtc cggataagag aattttgttt gattatccgt tcggataaat    660

ggacgcctgc tccatatttt tccggttatt accccacctg gaagtgccca gaattttccg    720

gggattacgg ataatacggt ggtctggatt aattaatacg ccaagtctta cattttgttg    780

cagtctcgtg cgagtatgtg caataataaa caagatgagc caatttattg gattagttgc    840

agcttgaccc cgccatagct aggcatagcc aagtgctatg ggtgttagat gatgcacttg    900

gatgcagtga gttttggagt ataaaagatc cttaaaattc caccctt                947
```

<210> SEQ ID NO 212
<211> LENGTH: 491
<212> TYPE: DNA
<213> ORGANISM: Artificial Sequence
<220> FEATURE:
<223> OTHER INFORMATION: pG1-10 promoter

<400> SEQUENCE: 212

```
ctgcagatag acttcaagat ctcagggatt cccactattt ggtattctga tatgtttttc     60

ctgatatgca tcaaaactct aatctaaaac ctgaatctcc gctttttttt tttttttga    120

tgaccccgtt ttcgtgacaa attaatttcc aacggggtct tgtccggata agagaatttt    180

gtttgattat ccgttcggat aaatggacgc ctgctccata tttttccggt tattacccca    240

cctggaagtg cccagaattt tccggggatt acggataata cggtggtctg gattaattaa    300

tacgccaagt cttacatttt gttgcagtct cgtgcgagta tgtgcaataa taaacaagat    360

gagccaattt attggattag ttgcagcttg accccgccat agctaggcat agccaagtgc    420

tatgggtgtt agatgatgca cttggatgca gtgagttttg gagtataaaa gatccttaaa    480

attccaccct t                                                        491
```

<210> SEQ ID NO 213
<211> LENGTH: 494
<212> TYPE: DNA
<213> ORGANISM: Artificial Sequence
<220> FEATURE:
<223> OTHER INFORMATION: pG1-10 promoter

<400> SEQUENCE: 213

```
ctgcagatag acttcaagat ctcagggatt cccactattt ggtattctga tatgtttttc     60

ctgatatgca tcaaaactct aatctaaaac ctgaatctcc gctatttttt tttttttttt    120

tgatgacccc gttttcgtga caaattaatt tccaacgggg tcttgtccgg ataagagaat    180

tttgtttgat tatccgttcg gataaatgga cgcctgctcc atatttttcc ggttattacc    240

ccacctggaa gtgcccagaa ttttccgggg attacggata atacggtggt ctggattaat    300

taatacgcca agtcttacat tttgttgcag tctcgtgcga gtatgtgcaa taataaacaa    360

gatgagccaa tttattggat tagttgcagc ttgaccccgc catagctagg catagccaag    420

tgctatgggt gttagatgat gcacttggat gcagtgagtt ttggagtata aaagatcctt    480
```

aaaattccac cctt 494

<210> SEQ ID NO 214
<211> LENGTH: 492
<212> TYPE: DNA
<213> ORGANISM: Artificial Sequence
<220> FEATURE:
<223> OTHER INFORMATION: pG1-10 promoter

<400> SEQUENCE: 214
ctgcagatag acttcaagat ctcagggatt cccactattt ggtattctga tatgtttttc 60
ctgatatgca tcaaaactct aatctaaaac ctgaatctcc gctttttttt tttttttttg 120
atgaccccgt tttcgtgaca aattaatttc caacggggtc ttgtccggat aagagaattt 180
tgtttgatta tccgttcgga taaatggacg cctgctccat atttttccgg ttattacccc 240
acctggaagt gcccagaatt ttccggggat tacggataat acggtggtct ggattaatta 300
atacgccaag tcttacattt tgttgcagtc tcgtgcgagt atgtgcaata ataaacaaga 360
tgagccaatt tattggatta gttgcagctt gaccccgcca tagctaggca tagccaagtg 420
ctatgggtgt tagatgatgc acttggatgc agtgagtttt ggagtataaa agatccttaa 480
aattccaccc tt 492

<210> SEQ ID NO 215
<211> LENGTH: 495
<212> TYPE: DNA
<213> ORGANISM: Artificial Sequence
<220> FEATURE:
<223> OTHER INFORMATION: pG1-10 promoter

<400> SEQUENCE: 215
ctgcagatag acttcaagat ctcagggatt cccactattt ggtattctga tatgtttttc 60
ctgatatgca tcaaaactct aatctaaaac ctgaatctcc gctatttttt tttttttttt 120
ttgatgaccc cgttttcgtg acaaattaat ttccaacggg gtcttgtccg gataagagaa 180
ttttgtttga ttatccgttc ggataaatgg acgcctgctc catatttttc cggttattac 240
cccacctgga agtgcccaga attttccggg gattacggat aatacggtgg tctggattaa 300
ttaatacgcc aagtcttaca ttttgttgca gtctcgtgcg agtatgtgca ataataaaca 360
agatgagcca atttattgga ttagttgcag cttgaccccg ccatagctag gcatagccaa 420
gtgctatggg tgttagatga tgcacttgga tgcagtgagt tttggagtat aaaagatcct 480
taaaattcca ccctt 495

<210> SEQ ID NO 216
<211> LENGTH: 493
<212> TYPE: DNA
<213> ORGANISM: Artificial Sequence
<220> FEATURE:
<223> OTHER INFORMATION: pG1-10 promoter

<400> SEQUENCE: 216
ctgcagatag acttcaagat ctcagggatt cccactattt ggtattctga tatgtttttc 60
ctgatatgca tcaaaactct aatctaaaac ctgaatctcc gctttttttt tttttttttt 120
gatgaccccg ttttcgtgac aaattaattt ccaacggggt cttgtccgga taagagaatt 180
ttgtttgatt atccgttcgg ataaatggac gcctgctcca tatttttccg gttattaccc 240
cacctggaag tgcccagaat tttccgggga ttacggataa tacggtggtc tggattaatt 300
aatacgccaa gtcttacatt ttgttgcagt ctcgtgcgag tatgtgcaat aataaacaag 360
atgagccaat ttattggatt agttgcagct tgaccccgcc atagctaggc atagccaagt 420
gctatgggtg ttagatgatg cacttggatg cagtgagttt tggagtataa aagatcctta 480
aaattccacc ctt 493

<210> SEQ ID NO 217
<211> LENGTH: 496
<212> TYPE: DNA
<213> ORGANISM: Artificial Sequence
<220> FEATURE:
<223> OTHER INFORMATION: pG1-10 promoter

<400> SEQUENCE: 217
ctgcagatag acttcaagat ctcagggatt cccactattt ggtattctga tatgtttttc 60
ctgatatgca tcaaaactct aatctaaaac ctgaatctcc gctatttttt tttttttttt 120
tttgatgacc ccgttttcgt gacaaattaa tttccaacgg ggtcttgtcc ggataagaga 180
attttgtttg attatccgtt cggataaatg gacgcctgct ccatattttt ccggttatta 240
ccccacctgg aagtgcccag aattttccgg ggattacgga taatacggtg gtctggatta 300
attaatacgc caagtcttac attttgttgc agtctcgtgc gagtatgtgc aataataaac 360
aagatgagcc aatttattgg attagttgca gcttgacccc gccatagcta ggcatagcca 420
agtgctatgg gtgttagatg atgcacttgg atgcagtgag ttttggagta taaaagatcc 480
ttaaaattcc accctt 496

<210> SEQ ID NO 218
<211> LENGTH: 494
<212> TYPE: DNA
<213> ORGANISM: Artificial Sequence
<220> FEATURE:
<223> OTHER INFORMATION: pG1-10 promoter

<400> SEQUENCE: 218
ctgcagatag acttcaagat ctcagggatt cccactattt ggtattctga tatgtttttc 60
ctgatatgca tcaaaactct aatctaaaac ctgaatctcc gctttttttt tttttttttt 120
tgatgacccc gttttcgtga caaattaatt tccaacgggg tcttgtccgg ataagagaat 180
tttgtttgat tatccgttcg gataaatgga cgcctgctcc atatttttcc ggttattacc 240
ccacctggaa gtgcccagaa ttttccgggg attacggata atacggtggt ctggattaat 300
taatacgcca agtcttacat tttgttgcag tctcgtgcga gtatgtgcaa taataaacaa 360
gatgagccaa tttattggat tagttgcagc ttgaccccgc catagctagg catagccaag 420
tgctatgggt gttagatgat gcacttggat gcagtgagtt ttggagtata aaagatcctt 480
aaaattccac cctt 494

<210> SEQ ID NO 219
<211> LENGTH: 497
<212> TYPE: DNA
<213> ORGANISM: Artificial Sequence
<220> FEATURE:
<223> OTHER INFORMATION: pG1-10 promoter

<400> SEQUENCE: 219
ctgcagatag acttcaagat ctcagggatt cccactattt ggtattctga tatgtttttc 60
ctgatatgca tcaaaactct aatctaaaac ctgaatctcc gctatttttt tttttttttt 120
ttttgatgac cccgttttcg tgacaaatta atttccaacg gggtcttgtc cggataagag 180

```
aattttgttt gattatccgt tcggataaat ggacgcctgc tccatatttt tccggttatt    240

accccacctg gaagtgccca gaattttccg gggattacgg ataatacggt ggtctggatt    300

aattaatacg ccaagtctta cattttgttg cagtctcgtg cgagtatgtg caataataaa    360

caagatgagc caatttattg gattagttgc agcttgaccc cgccatagct aggcatagcc    420

aagtgctatg ggtgttagat gatgcacttg gatgcagtga gttttggagt ataaaagatc    480

cttaaaattc caccctt                                                   497
```

<210> SEQ ID NO 220
<211> LENGTH: 495
<212> TYPE: DNA
<213> ORGANISM: Artificial Sequence
<220> FEATURE:
<223> OTHER INFORMATION: pG1-10 promoter

<400> SEQUENCE: 220

```
ctgcagatag acttcaagat ctcagggatt cccactattt ggtattctga tatgtttttc     60

ctgatatgca tcaaaactct aatctaaaac ctgaatctcc gctttttttt tttttttttt    120

ttgatgaccc cgttttcgtg acaaattaat ttccaacggg gtcttgtccg gataagagaa    180

ttttgtttga ttatccgttc ggataaatgg acgcctgctc catatttttc cggttattac    240

cccacctgga agtgcccaga attttccggg gattacggat aatacggtgg tctggattaa    300

ttaatacgcc aagtcttaca ttttgttgca gtctcgtgcg agtatgtgca ataataaaca    360

agatgagcca atttattgga ttagttgcag cttgaccccg ccatagctag gcatagccaa    420

gtgctatggg tgttagatga tgcacttgga tgcagtgagt tttggagtat aaaagatcct    480

taaaattcca ccctt                                                     495
```

<210> SEQ ID NO 221
<211> LENGTH: 668
<212> TYPE: DNA
<213> ORGANISM: Artificial Sequence
<220> FEATURE:
<223> OTHER INFORMATION: pG1-11 promoter
<220> FEATURE:
<221> NAME/KEY: misc_feature
<222> LOCATION: (289)..(295)
<223> OTHER INFORMATION: n is t or absent

<400> SEQUENCE: 221

```
ccatattcag taggtgtttc ttgcactttt gcatgcactg cggaagaatt agccaatagc     60

gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgctattttt ttttttttnn nnnnngatga    300

ccccgttttc gtgacaaatt aatttccaac ggggtcttgt ccggataaga gaattttgtt    360

tgattatccg ttcggataaa tggacgcctg ctccatattt ttccggttat taccccacct    420

ggaagtgccc agaattttcc ggggattacg gataatacgg tggtctggat taattaatac    480

gccaagtctt acattttgtt gcagtctcgt gcgagtatgt gcaataataa acaagatgag    540

ccaatttatt ggattagttg cagcttgacc ccgccatagc taggcatagc caagtgctat    600

gggtgttaga tgatgcactt ggatgcagtg agttttggag tataaaagat ccttaaaatt    660

ccaccctt                                                             668
```

<210> SEQ ID NO 222
<211> LENGTH: 666
<212> TYPE: DNA
<213> ORGANISM: Artificial Sequence
<220> FEATURE:
<223> OTHER INFORMATION: pG1-11 promoter
<220> FEATURE:
<221> NAME/KEY: misc_feature
<222> LOCATION: (287)..(293)
<223> OTHER INFORMATION: n is t or absent

<400> SEQUENCE: 222
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgcttttttt tttttnnnn nnngatgacc 300 ccgttttcgt gacaaattaa tttccaacgg ggtcttgtcc ggataagaga attttgtttg 360
attatccgtt cggataaatg gacgcctgct ccatattttt ccggttatta ccccacctgg 420
aagtgcccag aattttccgg ggattacgga taatacggtg gtctggatta attaatacgc 480
caagtcttac attttgttgc agtctcgtgc gagtatgtgc aataataaac aagatgagcc 540
aatttattgg attagttgca gcttgacccc gccatagcta ggcatagcca agtgctatgg 600
gtgttagatg atgcacttgg atgcagtgag ttttggagta taaaagatcc ttaaaattcc 660
accctt 666

<210> SEQ ID NO 223
<211> LENGTH: 661
<212> TYPE: DNA
<213> ORGANISM: Artificial Sequence
<220> FEATURE:
<223> OTHER INFORMATION: pG1-11 promoter

<400> SEQUENCE: 223
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgctattttt ttttttttga tgaccccgtt 300
ttcgtgacaa attaatttcc aacggggtct tgtccggata agagaatttt gtttgattat 360
ccgttcggat aaatggacgc ctgctccata tttttccggt tattacccca cctggaagtg 420
cccagaattt tccggggatt acggataata cggtggtctg gattaattaa tacgccaagt 480
cttacatttt gttgcagtct cgtgcgagta tgtgcaataa taaacaagat gagccaattt 540
attggattag ttgcagcttg accccgccat agctaggcat agccaagtgc tatgggtgtt 600
agatgatgca cttggatgca gtgagttttg gagtataaaa gatccttaaa attccaccct 660
t 661

<210> SEQ ID NO 224
<211> LENGTH: 659
<212> TYPE: DNA
<213> ORGANISM: Artificial Sequence
<220> FEATURE:
<223> OTHER INFORMATION: pG1-11 promoter

<400> SEQUENCE: 224
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgcttttttt tttttgatg accccgtttt 300 cgtgacaaat taatttccaa cggggtcttg tccggataag agaattttgt ttgattatcc 360
gttcggataa atggacgcct gctccatatt tttccggtta ttaccccacc tggaagtgcc 420
cagaattttc cggggattac ggataatacg gtggtctgga ttaattaata cgccaagtct 480
tacattttgt tgcagtctcg tgcgagtatg tgcaataata aacaagatga gccaatttat 540
tggattagtt gcagcttgac ccgcccatag ctaggcatag ccaagtgcta tgggtgttag 600
atgatgcact tggatgcagt gagttttgga gtataaaaga tccttaaaat tccaccctt 659

<210> SEQ ID NO 225
<211> LENGTH: 662
<212> TYPE: DNA
<213> ORGANISM: Artificial Sequence
<220> FEATURE:
<223> OTHER INFORMATION: pG1-11 promoter

<400> SEQUENCE: 225
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgctattttt tttttttttg atgaccccgt 300
tttcgtgaca aattaatttc caacggggtc ttgtccggat aagagaattt tgtttgatta 360
tccgttcgga taaatggacg cctgctccat atttttccgg ttattacccc acctggaagt 420
gcccagaatt ttccggggat tacggataat acggtggtct ggattaatta atacgccaag 480
tcttacattt tgttgcagtc tcgtgcgagt atgtgcaata ataaacaaga tgagccaatt 540
tattggatta gttgcagctt gacccgcgca tagctaggca tagccaagtg ctatgggtgt 600
tagatgatgc acttggatgc agtgagtttt ggagtataaa agatccttaa aattccaccc 660
tt 662

<210> SEQ ID NO 226
<211> LENGTH: 660
<212> TYPE: DNA
<213> ORGANISM: Artificial Sequence
<220> FEATURE:
<223> OTHER INFORMATION: pG1-11 promoter

<400> SEQUENCE: 226
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgcttttttt ttttttgat gaccccgttt 300 tcgtgacaaa ttaatttcca acggggtctt gtccggataa gagaattttg tttgattatc 360

```
cgttcggata aatggacgcc tgctccatat ttttccggtt attaccccac ctggaagtgc    420

ccagaatttt ccggggatta cggataatac ggtggtctgg attaattaat acgccaagtc    480

ttacattttg ttgcagtctc gtgcgagtat gtgcaataat aaacaagatg agccaattta    540

ttggattagt tgcagcttga ccccgccata gctaggcata gccaagtgct atgggtgtta    600

gatgatgcac ttggatgcag tgagttttgg agtataaaag atccttaaaa ttccaccctt    660
```

```
<210> SEQ ID NO 227
<211> LENGTH: 663
<212> TYPE: DNA
<213> ORGANISM: Artificial Sequence
<220> FEATURE:
<223> OTHER INFORMATION: pG1-11 promoter

<400> SEQUENCE: 227

ccatattcag taggtgtttc ttgcactttt gcatgcactg cggaagaatt agccaatagc     60

gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgctattttt ttttttttt gatgaccccg    300

ttttcgtgac aaattaattt ccaacggggt cttgtccgga taagagaatt ttgtttgatt    360

atccgttcgg ataaatggac gcctgctcca tatttttccg gttattaccc cacctggaag    420

tgcccagaat tttccgggga ttacggataa tacggtggtc tggattaatt aatacgccaa    480

gtcttacatt ttgttgcagt ctcgtgcgag tatgtgcaat aataaacaag atgagccaat    540

ttattggatt agttgcagct tgaccccgcc atagctaggc atagccaagt gctatgggtg    600

ttagatgatg cacttggatg cagtgagttt tggagtataa aagatcctta aaattccacc    660

ctt                                                                  663
```

```
<210> SEQ ID NO 228
<211> LENGTH: 661
<212> TYPE: DNA
<213> ORGANISM: Artificial Sequence
<220> FEATURE:
<223> OTHER INFORMATION: pG1-11 promoter

<400> SEQUENCE: 228

ccatattcag taggtgtttc ttgcactttt gcatgcactg cggaagaatt agccaatagc     60

gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgcttttttt ttttttttga tgaccccgtt    300

ttcgtgacaa attaatttcc aacggggtct tgtccggata agagaatttt gtttgattat    360

ccgttcggat aaatggacgc ctgctccata tttttccggt tattacccca cctggaagtg    420

cccagaattt tccggggatt acggataata cggtggtctg gattaattaa tacgccaagt    480

cttacatttt gttgcagtct cgtgcgagta tgtgcaataa taaacaagat gagccaattt    540

attggattag ttgcagcttg accccgccat agctaggcat agccaagtgc tatgggtgtt    600

agatgatgca cttggatgca gtgagttttg gagtataaaa gatccttaaa attccaccct    660

t                                                                    661
```

<210> SEQ ID NO 229
<211> LENGTH: 664
<212> TYPE: DNA
<213> ORGANISM: Artificial Sequence
<220> FEATURE:
<223> OTHER INFORMATION: pG1-11 promoter

<400> SEQUENCE: 229
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgctattttt tttttttttt tgatgacccc 300
gttttcgtga caaattaatt tccaacgggg tcttgtccgg ataagagaat tttgtttgat 360
tatccgttcg gataaatgga cgcctgctcc atatttttcc ggttattacc ccacctggaa 420
gtgcccagaa ttttccgggg attacggata atacggtggt ctggattaat taatacgcca 480
agtcttacat tttgttgcag tctcgtgcga gtatgtgcaa taataaacaa gatgagccaa 540
tttattggat tagttgcagc ttgaccccgc catagctagg catagccaag tgctatgggt 600
gttagatgat gcacttggat gcagtgagtt ttggagtata aaagatcctt aaaattccac 660
cctt 664

<210> SEQ ID NO 230
<211> LENGTH: 662
<212> TYPE: DNA
<213> ORGANISM: Artificial Sequence
<220> FEATURE:
<223> OTHER INFORMATION: pG1-11 promoter

<400> SEQUENCE: 230
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgcttttttt tttttttttg atgaccccgt 300
tttcgtgaca aattaatttc caacggggtc ttgtccggat aagagaattt tgtttgatta 360
tccgttcgga taaatggacg cctgctccat atttttccgg ttattacccc acctggaagt 420
gcccagaatt ttccggggat tacggataat acggtggtct ggattaatta atacgccaag 480
tcttacattt tgttgcagtc tcgtgcgagt atgtgcaata ataaacaaga tgagccaatt 540
tattggatta gttgcagctt gaccccgcca tagctaggca tagccaagtg ctatgggtgt 600
tagatgatgc acttggatgc agtgagtttt ggagtataaa agatccttaa aattccaccc 660
tt 662

<210> SEQ ID NO 231
<211> LENGTH: 665
<212> TYPE: DNA
<213> ORGANISM: Artificial Sequence
<220> FEATURE:
<223> OTHER INFORMATION: pG1-11 promoter

<400> SEQUENCE: 231
ccatattcag taggtgtttc ttgcactttt gcatgcactg cggaagaatt agccaatagc 60

```
gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgctattttt tttttttttt ttgatgaccc    300

cgttttcgtg acaaattaat ttccaacggg gtcttgtccg gataagagaa ttttgtttga    360

ttatccgttc ggataaatgg acgcctgctc catatttttc cggttattac cccacctgga    420

agtgcccaga attttccggg gattacggat aatacggtgg tctggattaa ttaatacgcc    480

aagtcttaca ttttgttgca gtctcgtgcg agtatgtgca ataataaaca agatgagcca    540

atttattgga ttagttgcag cttgaccccg ccatagctag gcatagccaa gtgctatggg    600

tgttagatga tgcacttgga tgcagtgagt tttggagtat aaaagatcct taaaattcca    660

ccctt                                                                665
```

```
<210> SEQ ID NO 232
<211> LENGTH: 663
<212> TYPE: DNA
<213> ORGANISM: Artificial Sequence
<220> FEATURE:
<223> OTHER INFORMATION: pG1-11 promoter

<400> SEQUENCE: 232

ccatattcag taggtgtttc ttgcactttt gcatgcactg cggaagaatt agccaatagc     60

gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgcttttttt tttttttttt gatgaccccg    300

ttttcgtgac aaattaattt ccaacggggt cttgtccgga taagagaatt ttgtttgatt    360

atccgttcgg ataaatggac gcctgctcca tatttttccg gttattaccc cacctggaag    420

tgcccagaat tttccgggga ttacggataa tacggtggtc tggattaatt aatacgccaa    480

gtcttacatt ttgttgcagt ctcgtgcgag tatgtgcaat aataaacaag atgagccaat    540

ttattggatt agttgcagct tgaccccgcc atagctaggc atagccaagt gctatgggtg    600

ttagatgatg cacttggatg cagtgagttt tggagtataa aagatcctta aaattccacc    660

ctt                                                                  663
```

```
<210> SEQ ID NO 233
<211> LENGTH: 666
<212> TYPE: DNA
<213> ORGANISM: Artificial Sequence
<220> FEATURE:
<223> OTHER INFORMATION: pG1-11 promoter

<400> SEQUENCE: 233

ccatattcag taggtgtttc ttgcactttt gcatgcactg cggaagaatt agccaatagc     60

gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgctattttt tttttttttt tttgatgacc    300

ccgttttcgt gacaaattaa tttccaacgg ggtcttgtcc ggataagaga attttgtttg    360
```

```
attatccgtt cggataaatg gacgcctgct ccatattttt ccggttatta ccccacctgg    420

aagtgcccag aattttccgg ggattacgga taatacggtg gtctggatta attaatacgc    480

caagtcttac attttgttgc agtctcgtgc gagtatgtgc aataataaac aagatgagcc    540

aatttattgg attagttgca gcttgacccc gccatagcta ggcatagcca agtgctatgg    600

gtgttagatg atgcacttgg atgcagtgag ttttggagta taaaagatcc ttaaaattcc    660

accctt                                                               666


<210> SEQ ID NO 234
<211> LENGTH: 664
<212> TYPE: DNA
<213> ORGANISM: Artificial Sequence
<220> FEATURE:
<223> OTHER INFORMATION: pG1-11 promoter

<400> SEQUENCE: 234

ccatattcag taggtgtttc ttgcactttt gcatgcactg cggaagaatt agccaatagc     60

gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgcttttttt tttttttttt tgatgacccc    300

gttttcgtga caaattaatt tccaacgggg tcttgtccgg ataagagaat tttgtttgat    360

tatccgttcg gataaatgga cgcctgctcc atatttttcc ggttattacc ccacctggaa    420

gtgcccagaa ttttccgggg attacggata atacggtggt ctggattaat taatacgcca    480

agtcttacat tttgttgcag tctcgtgcga gtatgtgcaa taataaacaa gatgagccaa    540

tttattggat tagttgcagc ttgaccccgc catagctagg catagccaag tgctatgggt    600

gttagatgat gcacttggat gcagtgagtt ttggagtata aaagatcctt aaaattccac    660

cctt                                                                 664


<210> SEQ ID NO 235
<211> LENGTH: 667
<212> TYPE: DNA
<213> ORGANISM: Artificial Sequence
<220> FEATURE:
<223> OTHER INFORMATION: pG1-11 promoter

<400> SEQUENCE: 235

ccatattcag taggtgtttc ttgcactttt gcatgcactg cggaagaatt agccaatagc     60

gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgctattttt tttttttttt ttttgatgac    300

cccgttttcg tgacaaatta atttccaacg gggtcttgtc cggataagag aattttgttt    360

gattatccgt tcggataaat ggacgcctgc tccatatttt tccggttatt accccacctg    420

gaagtgccca gaattttccg gggattacgg ataatacggt ggtctggatt aattaatacg    480

ccaagtctta cattttgttg cagtctcgtg cgagtatgtg caataataaa caagatgagc    540

caatttattg gattagttgc agcttgaccc cgccatagct aggcatagcc aagtgctatg    600

ggtgttagat gatgcacttg gatgcagtga gttttggagt ataaaagatc cttaaaattc    660

caccctt                                                              667
```

<210> SEQ ID NO 236
<211> LENGTH: 665
<212> TYPE: DNA
<213> ORGANISM: Artificial Sequence
<220> FEATURE:
<223> OTHER INFORMATION: pG1-11 promoter

<400> SEQUENCE: 236
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgcttttttt tttttttttt ttgatgaccc 300
cgttttcgtg acaaattaat ttccaacggg gtcttgtccg gataagagaa ttttgtttga 360
ttatccgttc ggataaatgg acgcctgctc catatttttc cggttattac cccacctgga 420
agtgcccaga attttccggg gattacggat aatacggtgg tctggattaa ttaatacgcc 480
aagtcttaca ttttgttgca gtctcgtgcg agtatgtgca ataataaaca agatgagcca 540
atttattgga ttagttgcag cttgaccccg ccatagctag gcatagccaa gtgctatggg 600
tgttagatga tgcacttgga tgcagtgagt tttggagtat aaaagatcct taaaattcca 660
ccctt 665

<210> SEQ ID NO 237
<211> LENGTH: 668
<212> TYPE: DNA
<213> ORGANISM: Artificial Sequence
<220> FEATURE:
<223> OTHER INFORMATION: pG1-11 promoter

<400> SEQUENCE: 237
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgctattttt tttttttttt tttttgatga 300
ccccgttttc gtgacaaatt aatttccaac ggggtcttgt ccggataaga gaattttgtt 360
tgattatccg ttcggataaa tggacgcctg ctccatattt ttccggttat taccccacct 420
ggaagtgccc agaattttcc ggggattacg gataatacgg tggtctggat taattaatac 480
gccaagtctt acattttgtt gcagtctcgt gcgagtatgt gcaataataa acaagatgag 540
ccaatttatt ggattagttg cagcttgacc ccgccatagc taggcatagc caagtgctat 600
gggtgttaga tgatgcactt ggatgcagtg agttttggag tataaaagat ccttaaaatt 660
ccaccctt 668

<210> SEQ ID NO 238
<211> LENGTH: 666
<212> TYPE: DNA
<213> ORGANISM: Artificial Sequence
<220> FEATURE:
<223> OTHER INFORMATION: pG1-11 promoter

<400> SEQUENCE: 238

```
ccatattcag taggtgtttc ttgcactttt gcatgcactg cggaagaatt agccaatagc     60

gcgtttcata tgcgctttta ccccctcttt tgtcaagcgc aaaatgcctg taagatttgg    120

tgggggtgtg agccgttagc tgaagtacaa caggctaatt ccctgaaaaa actgcagata    180

gacttcaaga tctcagggat tcccactatt tggtattctg atatgttttt cctgatatgc    240

atcaaaactc taatctaaaa cctgaatctc cgcttttttt ttttttttt tttgatgacc    300

ccgttttcgt gacaaattaa tttccaacgg ggtcttgtcc ggataagaga attttgtttg    360

attatccgtt cggataaatg gacgcctgct ccatattttt ccggttatta ccccacctgg    420

aagtgcccag aattttccgg ggattacgga taatacggtg gtctggatta attaatacgc    480

caagtcttac attttgttgc agtctcgtgc gagtatgtgc aataataaac aagatgagcc    540

aatttattgg attagttgca gcttgacccc gccatagcta ggcatagcca agtgctatgg    600

gtgttagatg atgcacttgg atgcagtgag ttttggagta taaaagatcc ttaaaattcc    660

accctt                                                               666
```

<210> SEQ ID NO 239
<211> LENGTH: 863
<212> TYPE: DNA
<213> ORGANISM: Artificial Sequence
<220> FEATURE:
<223> OTHER INFORMATION: pG1-12 promotor
<220> FEATURE:
<221> NAME/KEY: misc_feature
<222> LOCATION: (484)..(490)
<223> OTHER INFORMATION: n is t or absent

<400> SEQUENCE: 239

```
ggaatctgta ttgttagaaa gaacgagagt tttttacggc gccgccatat tgggccgtgt     60

gaaaacagct tgaaacccca ctactttcaa aggttctgtt gctatacacg aaccatgttt    120

aaccaacctc gcttttgact tgactgaagt catcggttaa caatcaagta ccctagtctg    180

tctgaatgct cctttccata ttcagtaggt gtttcttgca cttttgcatg cactgcggaa    240

gaattagcca atagcgcgtt tcatatgcgc ttttaccccc tcttttgtca agcgcaaaat    300

gcctgtaaga tttggtgggg gtgtgagccg ttagctgaag tacaacaggc taattccctg    360

aaaaaactgc agatagactt caagatctca gggattccca ctatttggta ttctgatatg    420

tttttcctga tatgcatcaa aactctaatc taaaacctga atctccgcta tttttttttt    480

tttnnnnnnn gatgaccccg ttttcgtgac aaattaattt ccaacggggt cttgtccgga    540

taagagaatt ttgtttgatt atccgttcgg ataaatggac gcctgctcca tatttttccg    600

gttattaccc cacctggaag tgcccagaat tttccgggga ttacggataa tacggtggtc    660

tggattaatt aatacgccaa gtcttacatt ttgttgcagt ctcgtgcgag tatgtgcaat    720

aataaacaag atgagccaat ttattggatt agttgcagct tgaccccgcc atagctaggc    780

atagccaagt gctatgggtg ttagatgatg cacttggatg cagtgagttt tggagtataa    840

aagatcctta aaattccacc ctt                                            863
```

<210> SEQ ID NO 240
<211> LENGTH: 861
<212> TYPE: DNA
<213> ORGANISM: Artificial Sequence
<220> FEATURE:
<223> OTHER INFORMATION: pG1-12 promotor
<220> FEATURE:
<221> NAME/KEY: misc_feature
<222> LOCATION: (482)..(488)
<223> OTHER INFORMATION: n is t or absent

<400> SEQUENCE: 240
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgctt tttttttttt 480
tnnnnnnnga tgaccccgtt ttcgtgacaa attaatttcc aacggggtct tgtccggata 540
agagaatttt gtttgattat ccgttcggat aaatggacgc ctgctccata tttttccggt 600
tattacccca cctggaagtg cccagaattt tccggggatt acggataata cggtggtctg 660
gattaattaa tacgccaagt cttacatttt gttgcagtct cgtgcgagta tgtgcaataa 720
taaacaagat gagccaattt attggattag ttgcagcttg accccgccat agctaggcat 780
agccaagtgc tatgggtgtt agatgatgca cttggatgca gtgagttttg gagtataaaa 840
gatccttaaa attccaccct t 861

<210> SEQ ID NO 241
<211> LENGTH: 856
<212> TYPE: DNA
<213> ORGANISM: Artificial Sequence
<220> FEATURE:
<223> OTHER INFORMATION: pG1-12 promoter

<400> SEQUENCE: 241
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgcta tttttttttt 480
tttgatgacc ccgttttcgt gacaaattaa tttccaacgg ggtcttgtcc ggataagaga 540
attttgtttg attatccgtt cggataaatg gacgcctgct ccatattttt ccggttatta 600
ccccacctgg aagtgcccag aattttccgg ggattacgga taatacggtg gtctggatta 660
attaatacgc caagtcttac attttgttgc agtctcgtgc gagtatgtgc aataataaac 720
aagatgagcc aatttattgg attagttgca gcttgacccc gccatagcta ggcatagcca 780
agtgctatgg gtgttagatg atgcacttgg atgcagtgag ttttggagta taaaagatcc 840
ttaaaattcc accctt 856

<210> SEQ ID NO 242
<211> LENGTH: 854
<212> TYPE: DNA
<213> ORGANISM: Artificial Sequence
<220> FEATURE:

<223> OTHER INFORMATION: pG1-12 promoter

<400> SEQUENCE: 242
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgctt tttttttttt 480
tgatgacccc gttttcgtga caaattaatt tccaacgggg tcttgtccgg ataagagaat 540
tttgtttgat tatccgttcg gataaatgga cgcctgctcc atatttttcc ggttattacc 600
ccacctggaa gtgcccagaa ttttccgggg attacggata atacggtggt ctggattaat 660
taatacgcca agtcttacat tttgttgcag tctcgtgcga gtatgtgcaa taataaacaa 720
gatgagccaa tttattggat tagttgcagc ttgaccccgc catagctagg catagccaag 780
tgctatgggt gttagatgat gcacttggat gcagtgagtt ttggagtata aaagatcctt 840
aaaattccac cctt 854

<210> SEQ ID NO 243
<211> LENGTH: 857
<212> TYPE: DNA
<213> ORGANISM: Artificial Sequence
<220> FEATURE:
<223> OTHER INFORMATION: pG1-12 promoter

<400> SEQUENCE: 243
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgcta tttttttttt 480
ttttgatgac cccgttttcg tgacaaatta atttccaacg gggtcttgtc cggataagag 540
aattttgttt gattatccgt tcggataaat ggacgcctgc tccatatttt tccggttatt 600
accccacctg gaagtgccca gaattttccg gggattacgg ataatacggt ggtctggatt 660
aattaatacg ccaagtctta cattttgttg cagtctcgtg cgagtatgtg caataataaa 720
caagatgagc caatttattg gattagttgc agcttgaccc cgccatagct aggcatagcc 780
aagtgctatg ggtgttagat gatgcacttg gatgcagtga gttttggagt ataaaagatc 840
cttaaaattc caccctt 857

<210> SEQ ID NO 244
<211> LENGTH: 855
<212> TYPE: DNA
<213> ORGANISM: Artificial Sequence
<220> FEATURE:
<223> OTHER INFORMATION: pG1-12 promoter

<400> SEQUENCE: 244

```
ggaatctgta ttgttagaaa gaacgagagt tttttacggc gccgccatat tgggccgtgt     60

gaaaacagct tgaaacccca ctactttcaa aggttctgtt gctatacacg aaccatgttt    120

aaccaacctc gcttttgact tgactgaagt catcggttaa caatcaagta ccctagtctg    180

tctgaatgct cctttccata ttcagtaggt gtttcttgca cttttgcatg cactgcggaa    240

gaattagcca atagcgcgtt tcatatgcgc ttttaccccc tcttttgtca agcgcaaaat    300

gcctgtaaga tttggtgggg gtgtgagccg ttagctgaag tacaacaggc taattccctg    360

aaaaaactgc agatagactt caagatctca gggattccca ctatttggta ttctgatatg    420

tttttcctga tatgcatcaa aactctaatc taaaacctga atctccgctt tttttttttt    480

ttgatgaccc cgttttcgtg acaaattaat ttccaacggg gtcttgtccg gataagagaa    540

ttttgtttga ttatccgttc ggataaatgg acgcctgctc catatttttc cggttattac    600

cccacctgga agtgcccaga attttccggg gattacggat aatacggtgg tctggattaa    660

ttaatacgcc aagtcttaca ttttgttgca gtctcgtgcg agtatgtgca ataataaaca    720

agatgagcca atttattgga ttagttgcag cttgaccccg ccatagctag gcatagccaa    780

gtgctatggg tgttagatga tgcacttgga tgcagtgagt tttggagtat aaaagatcct    840

taaaattcca ccctt                                                     855
```

<210> SEQ ID NO 245
<211> LENGTH: 858
<212> TYPE: DNA
<213> ORGANISM: Artificial Sequence
<220> FEATURE:
<223> OTHER INFORMATION: pG1-12 promoter

<400> SEQUENCE: 245

```
ggaatctgta ttgttagaaa gaacgagagt tttttacggc gccgccatat tgggccgtgt     60

gaaaacagct tgaaacccca ctactttcaa aggttctgtt gctatacacg aaccatgttt    120

aaccaacctc gcttttgact tgactgaagt catcggttaa caatcaagta ccctagtctg    180

tctgaatgct cctttccata ttcagtaggt gtttcttgca cttttgcatg cactgcggaa    240

gaattagcca atagcgcgtt tcatatgcgc ttttaccccc tcttttgtca agcgcaaaat    300

gcctgtaaga tttggtgggg gtgtgagccg ttagctgaag tacaacaggc taattccctg    360

aaaaaactgc agatagactt caagatctca gggattccca ctatttggta ttctgatatg    420

tttttcctga tatgcatcaa aactctaatc taaaacctga atctccgcta tttttttttt    480

tttttgatga ccccgttttc gtgacaaatt aatttccaac ggggtcttgt ccggataaga    540

gaattttgtt tgattatccg ttcggataaa tggacgcctg ctccatattt ttccggttat    600

taccccacct ggaagtgccc agaattttcc ggggattacg gataatacgg tggtctggat    660

taattaatac gccaagtctt acattttgtt gcagtctcgt gcgagtatgt gcaataataa    720

acaagatgag ccaatttatt ggattagttg cagcttgacc ccgccatagc taggcatagc    780

caagtgctat gggtgttaga tgatgcactt ggatgcagtg agttttggag tataaaagat    840

ccttaaaatt ccaccctt                                                  858
```

<210> SEQ ID NO 246
<211> LENGTH: 856
<212> TYPE: DNA

<213> ORGANISM: Artificial Sequence
<220> FEATURE:
<223> OTHER INFORMATION: pG1-12 promoter

<400> SEQUENCE: 246
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttacccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgctt ttttttttt 480 tttgatgacc ccgttttcgt gacaaattaa tttccaacgg ggtcttgtcc ggataagaga 540
attttgtttg attatccgtt cggataaatg gacgcctgct ccatattttt ccggttatta 600
ccccacctgg aagtgcccag aattttccgg ggattacgga taatacggtg gtctggatta 660
attaatacgc caagtcttac attttgttgc agtctcgtgc gagtatgtgc aataataaac 720
aagatgagcc aatttattgg attagttgca gcttgacccc gccatagcta ggcatagcca 780
agtgctatgg gtgttagatg atgcacttgg atgcagtgag ttttggagta taaaagatcc 840
ttaaaattcc accctt 856

<210> SEQ ID NO 247
<211> LENGTH: 859
<212> TYPE: DNA
<213> ORGANISM: Artificial Sequence
<220> FEATURE:
<223> OTHER INFORMATION: pG1-12 promoter

<400> SEQUENCE: 247
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgcta ttttttttt 480 tttttgatg accccgtttt cgtgacaaat taatttccaa cggggtcttg tccggataag 540
agaattttgt ttgattatcc gttcggataa atggacgcct gctccatatt tttccggtta 600
ttaccccacc tggaagtgcc cagaattttc cggggattac ggataatacg gtggtctgga 660
ttaattaata cgccaagtct tacattttgt tgcagtctcg tgcgagtatg tgcaataata 720
aacaagatga gccaatttat tggattagtt gcagcttgac cccgccatag ctaggcatag 780
ccaagtgcta tgggtgttag atgatgcact tggatgcagt gagttttgga gtataaaaga 840
tccttaaaat tccaccctt 859

<210> SEQ ID NO 248
<211> LENGTH: 857

<212> TYPE: DNA
<213> ORGANISM: Artificial Sequence
<220> FEATURE:
<223> OTHER INFORMATION: pG1-12 promoter

<400> SEQUENCE: 248
ggaatctgta ttgttagaaa gaacgagagt tttttacggc gccgccatat tgggccgtgt 60
gaaaacagct tgaaaccccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttacccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgctt tttttttttt 480
ttttgatgac cccgttttcg tgacaaatta atttccaacg gggtcttgtc cggataagag 540
aattttgttt gattatccgt tcggataaat ggacgcctgc tccatatttt tccggttatt 600
accccacctg gaagtgccca gaattttccg gggattacgg ataatacggt ggtctggatt 660
aattaatacg ccaagtctta cattttgttg cagtctcgtg cgagtatgtg caataataaa 720
caagatgagc caatttattg gattagttgc agcttgaccc cgccatagct aggcatagcc 780
aagtgctatg ggtgttagat gatgcacttg gatgcagtga gttttggagt ataaaagatc 840
cttaaaattc caccctt 857

<210> SEQ ID NO 249
<211> LENGTH: 860
<212> TYPE: DNA
<213> ORGANISM: Artificial Sequence
<220> FEATURE:
<223> OTHER INFORMATION: pG1-12 promoter

<400> SEQUENCE: 249
ggaatctgta ttgttagaaa gaacgagagt tttttacggc gccgccatat tgggccgtgt 60
gaaaacagct tgaaaccccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttacccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgcta tttttttttt 480
tttttttgat gaccccgttt tcgtgacaaa ttaatttcca acggggtctt gtccggataa 540
gagaattttg tttgattatc cgttcggata aatggacgcc tgctccatat ttttccggtt 600
attaccccac ctggaagtgc ccagaatttt ccggggatta cggataatac ggtggtctgg 660
attaattaat acgccaagtc ttacattttg ttgcagtctc gtgcgagtat gtgcaataat 720
aaacaagatg agccaattta ttggattagt tgcagcttga ccccgccata gctaggcata 780
gccaagtgct atgggtgtta gatgatgcac ttggatgcag tgagttttgg agtataaaag 840
atccttaaaa ttccaccctt 860

<210> SEQ ID NO 250

<211> LENGTH: 858
<212> TYPE: DNA
<213> ORGANISM: Artificial Sequence
<220> FEATURE:
<223> OTHER INFORMATION: pG1-12 promoter

<400> SEQUENCE: 250

```
ggaatctgta ttgttagaaa gaacgagagt tttttacggc gccgccatat tgggccgtgt     60
gaaaacagct tgaaacccca ctactttcaa aggttctgtt gctatacacg aaccatgttt    120
aaccaacctc gcttttgact tgactgaagt catcggttaa caatcaagta ccctagtctg    180
tctgaatgct cctttccata ttcagtaggt gtttcttgca cttttgcatg cactgcggaa    240
gaattagcca atagcgcgtt tcatatgcgc ttttaccccc tcttttgtca agcgcaaaat    300
gcctgtaaga tttggtgggg gtgtgagccg ttagctgaag tacaacaggc taattccctg    360
aaaaaactgc agatagactt caagatctca gggattccca ctatttggta ttctgatatg    420
tttttcctga tatgcatcaa aactctaatc taaaacctga atctccgctt tttttttttt    480
tttttgatga ccccgttttc gtgacaaatt aatttccaac ggggtcttgt ccggataaga    540
gaattttgtt tgattatccg ttcggataaa tggacgcctg ctccatattt ttccggttat    600
taccccacct ggaagtgccc agaattttcc ggggattacg gataatacgg tggtctggat    660
taattaatac gccaagtctt acattttgtt gcagtctcgt gcgagtatgt gcaataataa    720
acaagatgag ccaatttatt ggattagttg cagcttgacc ccgccatagc taggcatagc    780
caagtgctat gggtgttaga tgatgcactt ggatgcagtg agttttggag tataaaagat    840
ccttaaaatt ccaccctt                                                  858
```

<210> SEQ ID NO 251
<211> LENGTH: 861
<212> TYPE: DNA
<213> ORGANISM: Artificial Sequence
<220> FEATURE:
<223> OTHER INFORMATION: pG1-12 promoter

<400> SEQUENCE: 251

```
ggaatctgta ttgttagaaa gaacgagagt tttttacggc gccgccatat tgggccgtgt     60
gaaaacagct tgaaacccca ctactttcaa aggttctgtt gctatacacg aaccatgttt    120
aaccaacctc gcttttgact tgactgaagt catcggttaa caatcaagta ccctagtctg    180
tctgaatgct cctttccata ttcagtaggt gtttcttgca cttttgcatg cactgcggaa    240
gaattagcca atagcgcgtt tcatatgcgc ttttaccccc tcttttgtca agcgcaaaat    300
gcctgtaaga tttggtgggg gtgtgagccg ttagctgaag tacaacaggc taattccctg    360
aaaaaactgc agatagactt caagatctca gggattccca ctatttggta ttctgatatg    420
tttttcctga tatgcatcaa aactctaatc taaaacctga atctccgcta tttttttttt    480
ttttttttga tgaccccgtt ttcgtgacaa attaatttcc aacggggtct tgtccggata    540
agagaatttt gtttgattat ccgttcggat aaatggacgc ctgctccata tttttccggt    600
tattacccca cctggaagtg cccagaattt tccggggatt acggataata cggtggtctg    660
gattaattaa tacgccaagt cttacatttt gttgcagtct cgtgcgagta tgtgcaataa    720
taaacaagat gagccaattt attggattag ttgcagcttg accccgccat agctaggcat    780
agccaagtgc tatgggtgtt agatgatgca cttggatgca gtgagttttg gagtataaaa    840
gatccttaaa attccaccct t                                              861
```

<210> SEQ ID NO 252
<211> LENGTH: 859
<212> TYPE: DNA
<213> ORGANISM: Artificial Sequence
<220> FEATURE:
<223> OTHER INFORMATION: pG1-12 promoter

<400> SEQUENCE: 252
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgctt tttttttttt 480
ttttttgatg accccgtttt cgtgacaaat taatttccaa cggggtcttg tccggataag 540
agaattttgt ttgattatcc gttcggataa atggacgcct gctccatatt tttccggtta 600
ttaccccacc tggaagtgcc cagaattttc cggggattac ggataatacg gtggtctgga 660
ttaattaata cgccaagtct tacattttgt tgcagtctcg tgcgagtatg tgcaataata 720
aacaagatga gccaatttat tggattagtt gcagcttgac ccgccatag ctaggcatag 780 ccaagtgcta tgggtgttag atgatgcact tggatgcagt gagttttgga gtataaaaga 840
tccttaaaat tccacccctt 859

<210> SEQ ID NO 253
<211> LENGTH: 862
<212> TYPE: DNA
<213> ORGANISM: Artificial Sequence
<220> FEATURE:
<223> OTHER INFORMATION: pG1-12 promoter

<400> SEQUENCE: 253
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgcta tttttttttt 480
tttttttttg atgaccccgt tttcgtgaca aattaatttc caacggggtc ttgtccggat 540
aagagaattt tgtttgatta tccgttcgga taaatggacg cctgctccat atttttccgg 600
ttattacccc acctggaagt gcccagaatt ttccggggat tacggataat acggtggtct 660
ggattaatta atacgccaag tcttacattt tgttgcagtc tcgtgcgagt atgtgcaata 720
ataaacaaga tgagccaatt tattggatta gttgcagctt gaccccgcca tagctaggca 780
tagccaagtg ctatgggtgt tagatgatgc acttggatgc agtgagtttt ggagtataaa 840
agatccttaa aattccaccc tt 862

<210> SEQ ID NO 254
<211> LENGTH: 860
<212> TYPE: DNA
<213> ORGANISM: Artificial Sequence
<220> FEATURE:
<223> OTHER INFORMATION: pG1-12 promoter

<400> SEQUENCE: 254
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgctt tttttttttt 480
tttttttgat gaccccgttt tcgtgacaaa ttaatttcca acggggtctt gtccggataa 540
gagaattttg tttgattatc cgttcggata aatggacgcc tgctccatat ttttccggtt 600
attaccccac ctggaagtgc ccagaatttt ccggggatta cggataatac ggtggtctgg 660
attaattaat acgccaagtc ttacattttg ttgcagtctc gtgcgagtat gtgcaataat 720
aaacaagatg agccaattta ttggattagt tgcagcttga ccccgccata gctaggcata 780
gccaagtgct atgggtgtta gatgatgcac ttggatgcag tgagttttgg agtataaaag 840
atccttaaaa ttccaccctt 860

<210> SEQ ID NO 255
<211> LENGTH: 863
<212> TYPE: DNA
<213> ORGANISM: Artificial Sequence
<220> FEATURE:
<223> OTHER INFORMATION: pG1-12 promoter

<400> SEQUENCE: 255
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgcta tttttttttt 480
tttttttttt gatgaccccg ttttcgtgac aaattaattt ccaacggggt cttgtccgga 540
taagagaatt ttgtttgatt atccgttcgg ataaatggac gcctgctcca tatttttccg 600
gttattaccc cacctggaag tgcccagaat tttccgggga ttacggataa tacggtggtc 660
tggattaatt aatacgccaa gtcttacatt ttgttgcagt ctcgtgcgag tatgtgcaat 720
aataaacaag atgagccaat ttattggatt agttgcagct tgaccccgcc atagctaggc 780
atagccaagt gctatgggtg ttagatgatg cacttggatg cagtgagttt tggagtataa 840
aagatcctta aaattccacc ctt 863

<210> SEQ ID NO 256
<211> LENGTH: 861
<212> TYPE: DNA
<213> ORGANISM: Artificial Sequence
<220> FEATURE:
<223> OTHER INFORMATION: pG1-12 promoter

<400> SEQUENCE: 256
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgctt tttttttttt 480
ttttttttga tgaccccgtt ttcgtgacaa attaatttcc aacggggtct tgtccggata 540
agagaatttt gtttgattat ccgttcggat aaatggacgc ctgctccata tttttccggt 600
tattacccca cctggaagtg cccagaattt tccggggatt acggataata cggtggtctg 660
gattaattaa tacgccaagt cttacatttt gttgcagtct cgtgcgagta tgtgcaataa 720
taaacaagat gagccaattt attggattag ttgcagcttg accccgccat agctaggcat 780
agccaagtgc tatgggtgtt agatgatgca cttggatgca gtgagttttg gagtataaaa 840
gatccttaaa attccaccct t 861

<210> SEQ ID NO 257
<211> LENGTH: 964
<212> TYPE: DNA
<213> ORGANISM: Artificial Sequence
<220> FEATURE:
<223> OTHER INFORMATION: pG1-x promoter

<400> SEQUENCE: 257
caaacatttg ctccccctag tctccaggga aatgtaaaat atactgctaa tagaaaacag 60
taagacgctc agttgtcagg ataattacgt tcgactgtag taaaacagga atctgtattg 120
ttagaaagaa cgagagtttt ttacggcgcc gccatattgg gccgtgtgaa aacagcttga 180
aaccccacta ctttcaaagg ttctgttgct atacacgaac catgtttaac caacctcgct 240
tttgacttga ctgaagtcat cggttaacaa tcaagtaccc tagtctgtct gaatgctcct 300
ttccatattc agtaggtgtt tcttgcactt ttgcatgcac tgcggaagaa ttagccaata 360
gcgcgtttca tatgcgcttt taccccctct tttgtcaagc gcaaaatgcc tgtaagattt 420
ggtgggggtg tgagccgtta gctgaagtac aacaggctaa ttccctgaaa aaactgcaga 480
tagacttcaa gatctcaggg attcccacta tttggtattc tgatatgttt ttcctgatat 540
gcatcaaaac tctaatctaa aacctgaatc tccgcttttt tttttttttt tgatgacccc 600
gttttcgtga caaattaatt tccaacgggg tcttgtccgg ataagagaat tttgtttgat 660
tatccgttcg gataaatgga cgcctgctcc atatttttcc ggttattacc ccacctggaa 720
gtgcccagaa ttttccgggg attacggata atacggtggt ctggattaat taatacgcca 780
agtcttacat tttgttgcag tctcgtgcga gtatgtgcaa taataaacaa gatgagccaa 840

```
tttattggat tagttgcagc ttgaccccgc catagctagg catagccaag tgctatgggt    900

gttagatgat gcacttggat gcagtgagtt ttggagtata aaagatcctt aaaattccac    960

cctt                                                                 964


<210> SEQ ID NO 258
<211> LENGTH: 966
<212> TYPE: DNA
<213> ORGANISM: Artificial Sequence
<220> FEATURE:
<223> OTHER INFORMATION: pG1-x promoter

<400> SEQUENCE: 258

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt tttgatgacc    600

ccgttttcgt gacaaattaa tttccaacgg ggtcttgtcc ggataagaga attttgtttg    660

attatccgtt cggataaatg gacgcctgct ccatattttt ccggttatta ccccacctgg    720

aagtgcccag aattttccgg ggattacgga taatacggtg gtctggatta attaatacgc    780

caagtcttac attttgttgc agtctcgtgc gagtatgtgc aataataaac aagatgagcc    840

aatttattgg attagttgca gcttgacccc gccatagcta ggcatagcca agtgctatgg    900

gtgttagatg atgcacttgg atgcagtgag ttttggagta taaaagatcc ttaaaattcc    960

accctt                                                               966


<210> SEQ ID NO 259
<211> LENGTH: 968
<212> TYPE: DNA
<213> ORGANISM: Artificial Sequence
<220> FEATURE:
<223> OTHER INFORMATION: pG1-x promoter

<400> SEQUENCE: 259

caaacatttg ctccccctag tctccaggga aatgtaaaat atactgctaa tagaaaacag     60

taagacgctc agttgtcagg ataattacgt tcgactgtag taaaacagga atctgtattg    120

ttagaaagaa cgagagtttt ttacggcgcc gccatattgg gccgtgtgaa aacagcttga    180

aaccccacta ctttcaaagg ttctgttgct atacacgaac catgtttaac caacctcgct    240

tttgacttga ctgaagtcat cggttaacaa tcaagtaccc tagtctgtct gaatgctcct    300

ttccatattc agtaggtgtt tcttgcactt ttgcatgcac tgcggaagaa ttagccaata    360

gcgcgtttca tatgcgcttt taccccctct tttgtcaagc gcaaaatgcc tgtaagattt    420

ggtgggggtg tgagccgtta gctgaagtac aacaggctaa ttccctgaaa aaactgcaga    480

tagacttcaa gatctcaggg attcccacta tttggtattc tgatatgttt ttcctgatat    540

gcatcaaaac tctaatctaa aacctgaatc tccgcttttt tttttttttt tttttgatga    600
```

```
ccccgttttc gtgacaaatt aatttccaac ggggtcttgt ccggataaga gaattttgtt    660

tgattatccg ttcggataaa tggacgcctg ctccatattt ttccggttat taccccacct    720

ggaagtgccc agaattttcc ggggattacg gataatacgg tggtctggat taattaatac    780

gccaagtctt acattttgtt gcagtctcgt gcgagtatgt gcaataataa acaagatgag    840

ccaatttatt ggattagttg cagcttgacc ccgccatagc taggcatagc caagtgctat    900

gggtgttaga tgatgcactt ggatgcagtg agttttggag tataaaagat ccttaaaatt    960

ccaccctt                                                             968
```

<210> SEQ ID NO 260
<211> LENGTH: 1000
<212> TYPE: DNA
<213> ORGANISM: Pichia pastoris

<400> SEQUENCE: 260

```
ctgctactct ggtcccaagt gaaccacctt ttggacccta ttgaccggac cttaacttgc     60

caaacctaaa cgcttaatgc ctcagacgtt ttaatgcctc tcaacacctc caaggttgct    120

ttcttgagca tgcctactag gaactttaac gaactgtggg gttgcagaca gtttcaggcg    180

tgtcccgacc aatatggcct actagactct ctgaaaaatc acagttttcc agtagttccg    240

atcaaattac catcgaaatg gtcccataaa cggacatttg acatccgttc ctgaattata    300

gtcttccacc gtggatcatg gtgttccttt ttttcccaaa gaatatcagc atcccttaac    360

tacgttaggt cagtgatgac aatggaccaa attgttgcaa ggtttttctt tttctttcat    420

cggcacattt cagcctcaca tgcgactatt atcgatcaat gaaatccatc aagattgaaa    480

tcttaaaatt gcccctttca cttgacagga tcctttttttg tagaaatgtc ttggtgtcct    540

cgtccaatca ggtagccatc tctgaaatat ctggctccgt tgcaactccg aacgacctgc    600

tggcaacgta aaattctccg gggtaaaact taaatgtgga gtaatggaac cagaaacgtc    660

tcttcccttc tctctccttc caccgcccgt taccgtccct aggaaatttt actctgctgg    720

agagcttctt ctacggcccc cttgcagcaa tgctcttccc agcattacgt tgcgggtaaa    780

acggaggtcg tgtacccgac ctagcagccc agggatggaa aagtcccggc cgtcgctggc    840

aataatagcg ggcggacgca tgtcatgaga ttattggaaa ccaccagaat cgaatataaa    900

aggcgaacac ctttcccaat tttggtttct cctgacccaa agactttaaa tttaatttat    960

ttgtccctat ttcaatcaat tgaacaacta tcaaaacaca                         1000
```

<210> SEQ ID NO 261
<211> LENGTH: 756
<212> TYPE: PRT
<213> ORGANISM: Pichia pastoris

<400> SEQUENCE: 261

```
Met Ile Pro Thr Ile Asp Pro Lys Asp Pro Glu Leu Val Ser Glu Asp
1               5                   10                  15

Thr Ala Gln Ser Ala Ser Ala Arg Lys Arg Ser Lys Val Ser Arg Ala
            20                  25                  30

Cys Asp Glu Cys Arg Arg Lys Lys Ile Lys Cys Asp Ala Thr Phe Leu
        35                  40                  45

Ala Asn Ser Asn Thr Leu Leu Lys Pro Cys Thr Asn Cys Tyr Lys Tyr
    50                  55                  60

Asn Cys Ser Cys Ser Phe Thr Arg Val Pro Leu Lys Arg Gly Pro Ser
65                  70                  75                  80
```

```
Lys Gly Phe Ala Arg Asp Gly Ser Gly Tyr Glu Arg Arg Arg Ser Ser
                85                  90                  95

Ser Val His Ser Val Ser Ser Ser Gln Ser Val Thr Ser Pro Val Pro
            100                 105                 110

Ser His Ala Ser Leu Pro Ile Pro Pro Ala Asn Pro Val Ser Leu Pro
        115                 120                 125

Arg Leu Asn Val Pro Gly Asp Gly Leu Leu Ser Pro Lys Ala Val Pro
    130                 135                 140

Pro Thr Asn Leu Phe Trp Lys Val Pro Tyr Glu Leu Pro Ser Phe Ser
145                 150                 155                 160

Asp Arg Arg Ser Ser Val Ala Ser Ala Asp Ser Phe Arg Arg Pro Ser
                165                 170                 175

Ile Tyr Gln Ser Asp Ser Glu Asp Asp Phe Tyr Ser Ala Thr Gly Ser
            180                 185                 190

Gln Arg Asn Ser Ile Ser Gln Ala Pro Arg Gln Arg Asn Leu Ser Pro
        195                 200                 205

Ala Leu Ser Val Ser Ser Thr Ser Ser Leu Asn Asn Arg Ile Lys Ser
    210                 215                 220

Leu Asn Met Val Ala Ser Thr Leu Glu Ser Asn Ile His Asn Tyr Tyr
225                 230                 235                 240

Ser Gln Gly Phe Asn Ser Ser Leu Pro Ile Leu Pro Leu Asp Glu Arg
                245                 250                 255

Ile Leu Ser Thr Leu Leu Ser Asn Val Ser Asn Gly Ser Ser Ser Ala
            260                 265                 270

Ser Trp Asp Ala Ile Arg Ser Pro Ile Leu Glu Leu Phe Asp Lys Ser
        275                 280                 285

Ile Leu Met Leu Leu Arg Ser Tyr Glu Ser Gln Phe Asn Phe Asn Asp
    290                 295                 300

Leu Leu Asp His Val Thr Glu Met Gln Ser Ile Tyr Pro Arg Ile Arg
305                 310                 315                 320

Ser His Leu Leu Ser Asp Glu Leu Leu Lys Leu Ile Phe Leu Met Ser
                325                 330                 335

Gly Val Leu Thr Asp Tyr Ala Leu Ile Leu Thr Gly Gln Pro Tyr Ser
            340                 345                 350

Thr Gly Leu Ser Ile Thr Val Ser Val Phe Asn Asp Trp Lys Thr Tyr
        355                 360                 365

Glu Asn Val Gln Arg Val Leu Val Ile Asn Arg Ala Gly Ser Leu Asp
    370                 375                 380

Leu Asp Tyr Asp Ser Leu Pro Phe Leu Phe Ala Arg Cys Tyr Leu Ser
385                 390                 395                 400

Leu Ala Thr Leu Asp Leu Ile Tyr Ser Leu Ser Phe Ser Ser Pro Arg
                405                 410                 415

Leu Ile Ser Ser Phe Ala Asn Leu Pro Ile Leu Asp Ile Val Gln Lys
            420                 425                 430

Cys Gly Ile Thr Lys Asp Ala Lys Leu Asp Glu Thr Pro Leu Pro Val
        435                 440                 445

Leu Asp Gln Phe Leu Asn Cys Phe Leu Pro Gly Asp Thr Tyr Pro Thr
    450                 455                 460

Ala Leu Asn Thr Leu Lys Thr Gly Leu Val Leu Leu Asp Phe Thr Asn
465                 470                 475                 480

Asn Arg Ser Thr Thr Leu Arg Phe Pro Phe Ile Asn Ile His Asp Asp
                485                 490                 495
```

```
Asn His Met Thr Gly Leu Ser His Leu Leu Ser Asn Val Ser Asp Phe
            500                 505                 510

Met Ser Gln Phe Thr Glu Val His Ser Asp Ser Lys Asp Ser Gln Leu
        515                 520                 525

Leu Phe Leu Arg Cys Ile Trp Ala Phe Trp Glu Ile Gly Ser Val Leu
    530                 535                 540

Ser Glu Leu Ile Asp His Phe Ile Ser Ser Ser Ala Asn Ser Gln Val
545                 550                 555                 560

Gly Asp Lys Asp Ala Ser Phe Phe Tyr Glu His Gln Leu Lys Val Thr
                565                 570                 575

Thr Leu Leu Gly Thr Phe Ser Asn Ile Ala Ser Ala Phe Leu Thr Ser
            580                 585                 590

Ser Thr Thr Ala Ala Ser His Pro Pro Pro Ser Ile Ser Pro Phe His
        595                 600                 605

Ile Ile Ser Met Val Glu Ser Phe Lys Met Val Gln Phe Leu Asn Lys
    610                 615                 620

Leu Ile Ala Ser Phe Ile Ser Leu Asn Glu Lys Leu Glu Lys Arg Glu
625                 630                 635                 640

Leu Glu Asp Glu Leu Ser Lys Cys Lys Glu Glu Leu Asn Asn Leu Asn
                645                 650                 655

Glu Arg Phe Gln Ala Val Ser Ser Val Gln Thr Leu Pro Val Val His
            660                 665                 670

Val Leu Phe Arg Asp Leu Val Phe Ser Ser Asn Arg Leu Asp Thr Gln
        675                 680                 685

Arg Asp Arg Ala Ser Ser Val Val Ser Ala Thr Thr Thr Thr Ser Thr
    690                 695                 700

Ala Thr Thr Thr Ala Thr Thr Lys Lys Ser Ser Phe Gly Asn Leu Leu
705                 710                 715                 720

His Ser Asp Glu Glu Asn Ile Leu Pro Thr Val Ile Asp Trp Cys Lys
                725                 730                 735

Glu Gln Lys His Ser Ala Glu Met Phe Leu Asn Lys Asn Asp Leu Asn
            740                 745                 750

Gly Trp Leu Tyr
        755


<210> SEQ ID NO 262
<211> LENGTH: 1036
<212> TYPE: PRT
<213> ORGANISM: Pichia pastoris

<400> SEQUENCE: 262

Met Met Pro Glu Glu Gln Val Thr Ser Pro Gln Arg Lys His Gln Lys
1               5                   10                  15

Ser Lys Ala Lys Thr Ile Arg Ala Pro Gly Ser Ser Ile Glu Arg Val
            20                  25                  30

Ala Gln Ala Cys Asp Arg Cys Arg Ser Lys Lys Thr Arg Cys Asp Gly
        35                  40                  45

Lys Arg Pro Gln Cys Ser Gln Cys Ala Ala Val Gly Phe Glu Cys Lys
    50                  55                  60

Ile Ser Asp Lys Leu Ser Arg Arg Ala Phe Pro Arg Gly Tyr Thr Glu
65                  70                  75                  80

Thr Leu Glu Glu Arg Ile Arg Glu Leu Glu Phe Glu Asn Lys Lys Leu
                85                  90                  95

His Lys Leu Ile Asp Leu Lys Asn Glu Gln Val Glu Ile Lys Asn Arg
            100                 105                 110
```

-continued

```
Ile Asp Gln Glu Ser Thr Leu Thr Asn Glu Asn Leu Thr Leu Leu Asn
        115                 120                 125

Lys Glu Gln Glu Val Ser His Ser Gly Asn Ile His His His Ala Asp
    130                 135                 140

Gly Glu Pro Cys Asn Cys Ala Asn Ser Val Ser Ala Arg Pro Val Ser
145                 150                 155                 160

Ile Ala Gly Ser Val Asp Ile Asp Thr Thr Asp Leu Ser Asp Glu Asp
                165                 170                 175

Asp Ser Leu Tyr Ser Ala Ala Ser Tyr Asn Ala Lys Tyr His Gln Thr
            180                 185                 190

Gly Thr Ser Gly Pro Glu Met Val Arg Leu Ser Gln Arg Tyr Ser Ser
        195                 200                 205

Gly Asn Phe Asn Asp Pro Leu Ser Phe Glu Gln Ser Asn Ala Pro Gly
    210                 215                 220

Ala Ala Ala Ala Ile Ser Ile Gln Asn Lys Met Arg Thr Gln Thr Phe
225                 230                 235                 240

Val Asn Leu Ala Asn Leu Val Ala Met Ser Ile Pro Arg Thr Thr Glu
                245                 250                 255

Glu Thr Leu Phe Ile Ala Ser Leu Leu Ala Lys Ile Cys Asn Val His
            260                 265                 270

Gly Phe Gln Ser Lys Ala Pro Ile Leu Thr Ala Lys Ser Ile Ala Leu
        275                 280                 285

Leu Lys Asp Lys Tyr Asn Tyr Gly Asn Asp Glu Val Phe Ala Asn Ile
    290                 295                 300

Thr Leu Lys Asn Val Asn Phe Asn Lys Leu Thr Ser Gln Gln Ser Gln
305                 310                 315                 320

Gln Phe Phe Gln Ser Leu Asn Leu Pro Asn Gln Val Asn Leu Asp Leu
                325                 330                 335

Phe Ile Thr Thr Phe Phe Asn Thr Trp Asn Asn Phe Ile Pro Ile Ile
            340                 345                 350

Asn Arg His Ile Phe Met Ser Ser Tyr Ile Lys Phe Asn Lys Ser Arg
        355                 360                 365

Glu Thr Met Phe Thr Asp Asn Ser Met Phe Gly Asn Glu Lys Phe Gly
    370                 375                 380

Glu Ile Leu Leu Leu Ile Thr Thr Met Val Met Leu Ser Gln Glu Arg
385                 390                 395                 400

Asn Asn Asn Arg Glu Ala Val Pro Ser Ser Ser Tyr Lys Lys Asp Ser
                405                 410                 415

Thr Pro His Pro His Arg Pro Asp Ala Ser Ser Gln Ser Asn Val Glu
            420                 425                 430

Ile Leu Gln Tyr Tyr Asp His Leu Ile His Glu Phe Ile Lys Ser Asn
        435                 440                 445

Ile Ser Asp Asp Cys Ser Leu Pro Thr Leu Glu Ser Leu Ser Leu Gln
    450                 455                 460

Leu Leu Tyr Cys Leu Ala Ile Gly Asp Leu Thr Thr Ser Tyr Glu Leu
465                 470                 475                 480

Arg Gly Lys Ile Ile Thr Met Gly Gln Gln Leu Arg Leu His Arg Cys
                485                 490                 495

Pro Ser Ala Val Leu Gly Thr Asn Gly Ser Lys Val Ser Gln Met Gln
            500                 505                 510

Gln Gly Glu Arg Arg Ile Leu Phe Trp Cys Ile Tyr Ile Leu Asp Thr
        515                 520                 525
```

-continued

```
Phe Ser Ala Leu Ile Leu Gly Val Pro Arg Leu Leu Lys Asp Tyr Glu
    530                 535                 540

Ile Glu Cys Ala Leu Pro Phe Ser Asn Glu Ser Asn Asn Ala Asn Val
545                 550                 555                 560

Lys Gly Ser Ile Glu Asn Thr Thr Asn Thr Val Ile Ile Asn Asn Ile
                565                 570                 575

Lys Leu Ser Leu Ala Gly Lys Val Ser Asp Cys Ala Leu Ala Val Met
            580                 585                 590

Arg Tyr Ser Lys Val Leu Gly Asn Ile Leu Asp Ser Ile Phe Gln Arg
        595                 600                 605

Ser Ser Ile Asn Asn Pro Ser Val Val Ser Lys Ser Thr Asn Ile Thr
    610                 615                 620

Glu Glu Thr Cys Leu Leu His Glu His Ala Leu Asp Leu Trp Arg Arg
625                 630                 635                 640

Glu Leu Ser Pro His Ile Asn Val Asp Leu Asp Lys Ser Pro Gly Gly
                645                 650                 655

Val Glu Tyr Glu Arg Leu Ser Asp Asn Gln Leu Thr Ile Leu Phe Leu
            660                 665                 670

Tyr Tyr His Ala Lys Ile Leu Ile Tyr Leu Pro Leu Met Ala Asn Glu
        675                 680                 685

Ser Ser Gln Ser Arg Ser Ser Ala Ser Tyr Ile Asn Ile Gln Gln Ser
    690                 695                 700

Thr Thr Ser Ile Leu Ala Ile Ala Asn Thr Leu Ala Thr Lys Glu Arg
705                 710                 715                 720

Asn Phe Tyr Phe Leu Pro Leu Pro Val Asn Leu Ser Arg Glu Lys Val
                725                 730                 735

Arg Leu Ala Phe Leu Ser Ala Lys Gly Ser Leu Glu Tyr Ala Arg Gly
            740                 745                 750

Gly Ala Leu Phe Gln Glu Ser Lys Ile Leu Leu Ala Ser Val Ile Asn
        755                 760                 765

Glu Leu Lys Ile Glu Thr Ser Ile Gly Met Leu Gly Cys Leu Ser Val
    770                 775                 780

Pro Cys Met Glu Ala Val Asp Asn Ala Met Glu Gln Ile Met Ala Leu
785                 790                 795                 800

Pro Gly Lys Val Ser Ser Val Asn Gly Ser Asn Ser Glu Met Lys Arg
                805                 810                 815

Ser Ser Ser Lys Arg Lys Ser Ser Pro Leu Arg Gln Asp Ile Ser Gly
            820                 825                 830

Asp Glu Arg Lys Ser His Asn Ile Glu Val Ser Asp Ser Arg Thr Pro
        835                 840                 845

Ser Val Gln Ser Ser Leu Tyr Pro Gln Pro Asn Gln Met His His Pro
    850                 855                 860

Asn Ile Ile Lys Ser Glu Asn Asn Glu Gln Met Ile Pro Glu Asn Asp
865                 870                 875                 880

Thr Pro Gly Ala Ile Asn Asp Ile Phe Thr Ser His Ser Pro Pro Gly
                885                 890                 895

Thr Val Thr Ser Met Lys Glu Glu Asp Leu Pro Ile Lys Val Pro Ile
            900                 905                 910

Leu Leu Gln Thr Gln Gln Arg Gln Ile Tyr Asn Asn Asn Pro Asn His
        915                 920                 925

Ser Leu Phe Ser Gln Gln Pro Gly Thr Gln Val Leu Ser Gly Gln Gln
    930                 935                 940

Met Pro Gly Pro Ser Ser Thr Asp Gln Gln Phe Lys Arg Ile Thr Thr
```

945 950 955 960

Pro Asp Gly Leu Asp Ser Leu Met Met Gln Asp Phe Gly Val Asp Ala
965 970 975

Ser Leu Gly Leu Pro Met Leu Asp Phe Asp Phe Asn Phe Asp Phe Glu
980 985 990

Asn Val Gln Asn Asn Tyr Ser Gln Ser Asn Val Ser Pro Pro Asn Ser
995 1000 1005

Glu Ser Val Pro Ser Ser Ile Gln Gly Thr His Ser Asn Asp Pro
1010 1015 1020

Lys Asp Ser Gln Val Ser Ala Gly Ser Leu Phe Gly Leu
1025 1030 1035

<210> SEQ ID NO 263
<211> LENGTH: 887
<212> TYPE: PRT
<213> ORGANISM: Pichia pastoris

<400> SEQUENCE: 263

Met Lys Glu Asn Gln Ala Ser Asn Lys Phe Asn Leu Ile Lys Asn Pro
1 5 10 15

Ile Thr Gly Lys Pro Arg Ile Ser Gln Ala Cys Asp Arg Cys Arg Ile
20 25 30

Lys Lys Ile Lys Cys Asp Gly Thr Leu Pro Ser Cys Thr Asn Cys Ser
35 40 45

Lys Ile Gly Phe Val Cys Lys Ile Ser Asp Arg Leu Thr Arg Ser Ser
50 55 60

Phe Pro Lys Gly Tyr Thr Lys Asn Leu Glu Gln Lys Leu Ile Asp Met
65 70 75 80

Glu Leu Asp Arg Asn Arg Leu Met Leu Glu Leu Asn Arg Ile Lys Lys
85 90 95

Glu Gly Phe Asp Gly Thr Asn Asn Asn Ile Ala Met Ala Ser Ser Val
100 105 110

Ser Ser Ser Glu Asn Leu Lys Ser Asp Asp Ser Ser Glu Cys Gln Ser
115 120 125

Val Thr Val Ser Leu Ser Ser Thr Ser Gly Pro Ser Leu Ser Pro Glu
130 135 140

Pro Lys Gln Asp Asp Phe Arg Phe Arg Val Gly Met Asp Gly Ser Phe
145 150 155 160

Val Leu Asn Gln Phe Leu Gln Ser Pro Leu Met Asp Tyr Ile Lys Ser
165 170 175

Leu Asn Val Leu Gln Phe Asn Gly Cys Ala Asn Phe Asp Gln Ser Phe
180 185 190

Asn Asp Asp Pro Leu Val Leu Asn Lys Tyr His Met Asn Leu Asn Arg
195 200 205

Phe Leu Asn Leu Ile Phe Tyr Lys Leu Leu Leu Pro Leu Ile His Arg
210 215 220

Asn Ser Asn Thr Leu Asn Glu Lys Phe Ala Glu Asp Asn Asn Ser Leu
225 230 235 240

Asp Ser Leu Ile Trp Lys Phe Phe Thr Asn Tyr Asn Lys Leu Ile Pro
245 250 255

Ile Leu Glu Phe Asp Ser Phe Tyr Lys Asp Tyr Leu Gln Phe Ile His
260 265 270

Lys Tyr Tyr Ser Asn Asn Gln Val Phe Val Asp Gly Phe Arg Lys Tyr
275 280 285

Phe Glu Phe Ser Glu Phe Glu Gln Cys Phe Ile Val Lys Leu Ile Leu
    290                 295                 300

Ile Leu Lys Phe Thr Leu Pro Val Ile His Asp Thr Ser Val Pro Ser
305                 310                 315                 320

Glu Ile Tyr Arg Leu Ile Ser Met Asp Ser Leu Gln Arg Leu Phe Gly
                325                 330                 335

Asn Ile Asp Phe Leu Lys Pro Ser Thr Asp Lys Val Ser Ile Leu Leu
            340                 345                 350

Leu Val Leu His Tyr Met Val Leu Tyr Glu Ser Pro Lys Ser Leu Leu
        355                 360                 365

Asp Thr Gln Asp Glu Ala Gln Lys Tyr Asp Glu Phe Ile Gly Asn Leu
    370                 375                 380

Leu Ser Thr Ala Val His His Ile Thr Ser Leu Arg Leu His Ile Asp
385                 390                 395                 400

Pro Arg Lys Leu Gln Phe Pro Arg Pro Leu Pro Ser Asn Gly Asn Arg
                405                 410                 415

Leu Arg Ile Lys Leu Ser Trp Cys Tyr Lys Leu Ile Ser Lys Leu Phe
            420                 425                 430

Arg Val Ile Tyr Asn Ile Asp Asn Asp Ser Leu Tyr Ser Leu Asp Asp
        435                 440                 445

Ser His Leu Pro Glu Leu Gln Ser Ile Ser Ile Leu His Glu Glu Leu
    450                 455                 460

Asp Val Thr Ile Gln Phe Asn Asn Leu Leu Asn Leu Ile Pro Asn Asn
465                 470                 475                 480

Phe His Ser Leu Arg Asp Lys Gln Ser Leu Ser Lys Ile Lys Thr Gln
                485                 490                 495

Leu Leu Glu Trp His Lys Asn Phe Asn Thr Glu Phe Val Glu His Phe
            500                 505                 510

Asn Leu Asn Asp Thr Asp Ser Asp Glu Leu Ser Ala Glu Lys Ile Asn
        515                 520                 525

Val Leu Arg Ser Lys Leu Ile Ser Leu Asn Arg Leu Asn Cys Tyr Asn
    530                 535                 540

Ser Tyr Phe Gln Leu Val Ile Glu Leu Gln Leu Lys Glu Asn Leu Asp
545                 550                 555                 560

Ser Val Val Ser Gly Ile Phe Gly Leu Ser Asn Glu Met Leu Ile Asp
                565                 570                 575

Asn Lys Ser Ser Thr Glu Leu Leu Asn Thr Leu Gln Gln Thr Pro Ile
            580                 585                 590

Ile His Gln Ser Ser Ile Leu Val Ser Leu Cys Tyr Arg Ile Gln Thr
        595                 600                 605

Gly Asn Leu Gln Asp Glu Ile Cys Ser Ile Leu Val Asn Asn Tyr Glu
    610                 615                 620

Lys Leu Leu Gln Cys Asn Asp Ala Gly Leu Pro Ile Lys Ile Leu Pro
625                 630                 635                 640

Gln Leu Val His Tyr Phe Lys Gly Lys Ile Ser Thr Asn Leu Ser Asn
                645                 650                 655

Ser Ala Ala His Glu Asp Leu Met Asn Met Phe Thr Leu Asn Asp Asn
            660                 665                 670

Leu Ser Thr Thr Thr Thr Asp Leu Asp Ser Phe Ile Ile Pro Pro Lys
        675                 680                 685

Arg Lys Gln Asp Gln Thr Leu Pro Ile Gly Thr Lys Arg Ser Lys Ser
    690                 695                 700

Ala Ser Thr Ser Ser Val Ile Ser Ser Asp Asp Cys Ser Leu Phe Ser 705 710 715 720

Asn Ser Leu Ser Val Pro Thr Thr Phe Ser Gly Ser Ser Ile Ser Val
725 730 735

Gly Met Asp Asn Pro Pro Ser Ser Leu Phe Gly Ser Tyr Lys Arg Pro
740 745 750

Ser Ser Ile Val Lys Gln Glu Pro Thr Ile Asn Pro Arg Ser Asn Gly
755 760 765

Thr Asn Thr Asp Ser Asn Leu Phe Asp Thr Phe Asn Asp Ser Ile Lys
770 775 780

Gly Ser Leu Asn Asn Gly Leu Lys Lys Leu Lys Asp Ile Arg Cys Asn
785 790 795 800

Ser Val Val Glu Arg Ser His Ser Ser Gln Arg Asn Asp Phe Leu Met
805 810 815

Asp Gln Glu Asp Ser Ile Thr Lys Glu Thr Ile Asn Phe Ser Glu Leu
820 825 830

Phe Thr Cys Gly Thr Pro Thr Ala Ser Gln Ser Ile Asp Arg Ser Pro
835 840 845

Lys Ser Leu Leu Leu Asn Asp Leu Ala Ile Ala Pro Asp Thr Leu Val
850 855 860

Ile Lys Pro Asp Ala Glu Asp Leu Asp Arg Leu Lys Asn Lys Ile Arg
865 870 875 880

Ser Val Lys Ser Thr Val His
885

<210> SEQ ID NO 264
<211> LENGTH: 1001
<212> TYPE: DNA
<213> ORGANISM: Artificial Sequence
<220> FEATURE:
<223> OTHER INFORMATION: pG1 promoter

<400> SEQUENCE: 264
atttccaccc ccatcccagt agaatgtagg gtccccaaac atttgctccc cctagtctcc 60
agggaaatgt aaaatatact gctaatagaa aacagtaaga cgctcagttg tcaggataat 120
tacgttcgac tgtagtaaaa caggaatctg tattgttaga aagaacgaga gtttttacg 180 gcgccgccat attgggccgt gtgaaaacag cttgaaaccc cactactttc aaaggttctg 240
ttgctataca cgaaccatgt ttaaccaacc tcgcttttga cttgactgaa gtcatcggtt 300
aacaatcaag taccctagtc tgtctgaatg ctcctttcca tattcagtag gtgtttcttg 360
cacttttgca tgcactgcgg aagaattagc caatagcgcg tttcatatgc gcttttaccc 420
cctcttttgt caagcgcaaa atgcctgtaa gatttggtgg gggtgtgagc cgttagctga 480
agtacaacag gctaattccc tgaaaaaact gcagatagac ttcaagatct cagggattcc 540
cactatttgg tattctgata tgtttttcct gatatgcatc aaaactctaa tctaaaacct 600
gaatctccgc tattttttt ttttttttga tgaccccgtt ttcgtgacaa attaatttcc 660
aacggggtct tgtccggata agagaatttt gtttgattat ccgttcggat aaatggacgc 720
ctgctccata tttttccggt tattacccca cctggaagtg cccagaattt tccggggatt 780
acggataata cggtggtctg gattaattaa tacgccaagt cttacatttt gttgcagtct 840
cgtgcgagta tgtgcaataa taaacaagat gagccaattt attggattag ttgcagcttg 900
accccgccat agctaggcat agccaagtgc tatgggtgtt agatgatgca cttggatgca 960
gtgagttttg gagtataaaa gatccttaaa attccaccct t 1001

<210> SEQ ID NO 265
<211> LENGTH: 859
<212> TYPE: DNA
<213> ORGANISM: Artificial Sequence
<220> FEATURE:
<223> OTHER INFORMATION: pG1-a promoter

<400> SEQUENCE: 265
ggaatctgta ttgttagaaa gaacgagagt tttttacggc gccgccatat tgggccgtgt 60
gaaaacagct tgaaacccca ctactttcaa aggttctgtt gctatacacg aaccatgttt 120
aaccaacctc gcttttgact tgactgaagt catcggttaa caatcaagta ccctagtctg 180
tctgaatgct cctttccata ttcagtaggt gtttcttgca cttttgcatg cactgcggaa 240
gaattagcca atagcgcgtt tcatatgcgc ttttaccccc tcttttgtca agcgcaaaat 300
gcctgtaaga tttggtgggg gtgtgagccg ttagctgaag tacaacaggc taattccctg 360
aaaaaactgc agatagactt caagatctca gggattccca ctatttggta ttctgatatg 420
tttttcctga tatgcatcaa aactctaatc taaaacctga atctccgcta ttttttttt 480 ttttttgatg accccgtttt cgtgacaaat taatttccaa cggggtcttg tccggataag 540
agaattttgt ttgattatcc gttcggataa atggacgcct gctccatatt tttccggtta 600
ttaccccacc tggaagtgcc cagaattttc cggggattac ggataatacg gtggtctgga 660
ttaattaata cgccaagtct tacattttgt tgcagtctcg tgcgagtatg tgcaataata 720
aacaagatga gccaatttat tggattagtt gcagcttgac cccgccatag ctaggcatag 780
ccaagtgcta tgggtgttag atgatgcact tggatgcagt gagttttgga gtataaaaga 840
tccttaaaat tccaccctt 859

<210> SEQ ID NO 266
<211> LENGTH: 664
<212> TYPE: DNA
<213> ORGANISM: Artificial Sequence
<220> FEATURE:
<223> OTHER INFORMATION: pG1-b promoter

<400> SEQUENCE: 266
ccatattcag taggtgtttc ttgcactttt gcatgcactg cggaagaatt agccaatagc 60
gcgtttcata tgcgctttta ccccctcttt tgtcaagcgc aaaatgcctg taagatttgg 120
tgggggtgtg agccgttagc tgaagtacaa caggctaatt ccctgaaaaa actgcagata 180
gacttcaaga tctcagggat tcccactatt tggtattctg atatgttttt cctgatatgc 240
atcaaaactc taatctaaaa cctgaatctc cgctattttt tttttttttt tgatgacccc 300
gttttcgtga caaattaatt tccaacgggg tcttgtccgg ataagagaat tttgtttgat 360
tatccgttcg gataaatgga cgcctgctcc atatttttcc ggttattacc ccacctggaa 420
gtgcccagaa ttttccgggg attacggata atacggtggt ctggattaat taatacgcca 480
agtcttacat tttgttgcag tctcgtgcga gtatgtgcaa taataaacaa gatgagccaa 540
tttattggat tagttgcagc ttgaccccgc catagctagg catagccaag tgctatgggt 600
gttagatgat gcacttggat gcagtgagtt ttggagtata aaagatcctt aaaattccac 660
cctt 664

<210> SEQ ID NO 267
<211> LENGTH: 493
<212> TYPE: DNA
<213> ORGANISM: Artificial Sequence
<220> FEATURE:
<223> OTHER INFORMATION: pG1-c promoter

<400> SEQUENCE: 267
ctgcagatag acttcaagat ctcagggatt cccactattt ggtattctga tatgtttttc 60
ctgatatgca tcaaaactct aatctaaaac ctgaatctcc gctatttttt ttttttttt 120 gatgaccccg ttttcgtgac aaattaattt ccaacggggt cttgtccgga taagagaatt 180
ttgtttgatt atccgttcgg ataaatggac gcctgctcca tatttttccg gttattaccc 240
cacctggaag tgcccagaat tttccgggga ttacggataa tacggtggtc tggattaatt 300
aatacgccaa gtcttacatt ttgttgcagt ctcgtgcgag tatgtgcaat aataaacaag 360
atgagccaat ttattggatt agttgcagct tgaccccgcc atagctaggc atagccaagt 420
gctatgggtg ttagatgatg cacttggatg cagtgagttt tggagtataa aagatcctta 480
aaattccacc ctt 493

<210> SEQ ID NO 268
<211> LENGTH: 370
<212> TYPE: DNA
<213> ORGANISM: Artificial Sequence
<220> FEATURE:
<223> OTHER INFORMATION: pG1-d promoter

<400> SEQUENCE: 268
gaccccgttt tcgtgacaaa ttaatttcca acggggtctt gtccggataa gagaattttg 60
tttgattatc cgttcggata aatggacgcc tgctccatat ttttccggtt attaccccac 120
ctggaagtgc ccagaatttt ccggggatta cggataatac ggtggtctgg attaattaat 180
acgccaagtc ttacattttg ttgcagtctc gtgcgagtat gtgcaataat aaacaagatg 240
agccaattta ttggattagt tgcagcttga ccccgccata gctaggcata gccaagtgct 300
atgggtgtta gatgatgcac ttggatgcag tgagttttgg agtataaaag atccttaaaa 360
ttccaccctt 370

<210> SEQ ID NO 269
<211> LENGTH: 328
<212> TYPE: DNA
<213> ORGANISM: Artificial Sequence
<220> FEATURE:
<223> OTHER INFORMATION: pG1-e promoter

<400> SEQUENCE: 269
ccggataaga gaattttgtt tgattatccg ttcggataaa tggacgcctg ctccatattt 60
ttccggttat taccccacct ggaagtgccc agaattttcc ggggattacg gataatacgg 120
tggtctggat taattaatac gccaagtctt acattttgtt gcagtctcgt gcgagtatgt 180
gcaataataa acaagatgag ccaatttatt ggattagttg cagcttgacc ccgccatagc 240
taggcatagc caagtgctat gggtgttaga tgatgcactt ggatgcagtg agttttggag 300
tataaaagat ccttaaaatt ccaccctt 328

<210> SEQ ID NO 270
<211> LENGTH: 283
<212> TYPE: DNA
<213> ORGANISM: Artificial Sequence
<220> FEATURE:
<223> OTHER INFORMATION: pG1-f promoter

<400> SEQUENCE: 270

-continued

```
gcctgctcca tatttttccg gttattaccc cacctggaag tgcccagaat tttccgggga     60

ttacggataa tacggtggtc tggattaatt aatacgccaa gtcttacatt ttgttgcagt    120

ctcgtgcgag tatgtgcaat aataaacaag atgagccaat ttattggatt agttgcagct    180

tgaccccgcc atagctaggc atagccaagt gctatgggtg ttagatgatg cacttggatg    240

cagtgagttt tggagtataa aagatcctta aaattccacc ctt                      283


<210> SEQ ID NO 271
<211> LENGTH: 17
<212> TYPE: DNA
<213> ORGANISM: Artificial Sequence
<220> FEATURE:
<223> OTHER INFORMATION: TFBS

<400> SEQUENCE: 271

accctacatt ctactgg                                                    17


<210> SEQ ID NO 272
<211> LENGTH: 13
<212> TYPE: DNA
<213> ORGANISM: Artificial Sequence
<220> FEATURE:
<223> OTHER INFORMATION: TFBS

<400> SEQUENCE: 272

tgtagggtcc cca                                                        13


<210> SEQ ID NO 273
<211> LENGTH: 15
<212> TYPE: DNA
<213> ORGANISM: Artificial Sequence
<220> FEATURE:
<223> OTHER INFORMATION: TFBS

<400> SEQUENCE: 273

gagactaggg ggagc                                                      15


<210> SEQ ID NO 274
<211> LENGTH: 9
<212> TYPE: DNA
<213> ORGANISM: Artificial Sequence
<220> FEATURE:
<223> OTHER INFORMATION: TFBS

<400> SEQUENCE: 274

tccctggag                                                              9


<210> SEQ ID NO 275
<211> LENGTH: 13
<212> TYPE: DNA
<213> ORGANISM: Artificial Sequence
<220> FEATURE:
<223> OTHER INFORMATION: TFBS

<400> SEQUENCE: 275

gggaaatgta aaa                                                        13


<210> SEQ ID NO 276
<211> LENGTH: 19
<212> TYPE: DNA
<213> ORGANISM: Artificial Sequence
<220> FEATURE:
<223> OTHER INFORMATION: TFBS

<400> SEQUENCE: 276
```

gttttctatt agcagtata 19

<210> SEQ ID NO 277
<211> LENGTH: 11
<212> TYPE: DNA
<213> ORGANISM: Artificial Sequence
<220> FEATURE:
<223> OTHER INFORMATION: TFBS

<400> SEQUENCE: 277
gctcagttgt c 11

<210> SEQ ID NO 278
<211> LENGTH: 15
<212> TYPE: DNA
<213> ORGANISM: Artificial Sequence
<220> FEATURE:
<223> OTHER INFORMATION: TFBS

<400> SEQUENCE: 278
ttatcctgac aactg 15

<210> SEQ ID NO 279
<211> LENGTH: 15
<212> TYPE: DNA
<213> ORGANISM: Artificial Sequence
<220> FEATURE:
<223> OTHER INFORMATION: TFBS

<400> SEQUENCE: 279
aacgtaatta tcctg 15

<210> SEQ ID NO 280
<211> LENGTH: 15
<212> TYPE: DNA
<213> ORGANISM: Artificial Sequence
<220> FEATURE:
<223> OTHER INFORMATION: TFBS

<400> SEQUENCE: 280
aggataatta cgttc 15

<210> SEQ ID NO 281
<211> LENGTH: 21
<212> TYPE: DNA
<213> ORGANISM: Artificial Sequence
<220> FEATURE:
<223> OTHER INFORMATION: TFBS

<400> SEQUENCE: 281
acagtcgaac gtaattatcc t 21

<210> SEQ ID NO 282
<211> LENGTH: 21
<212> TYPE: DNA
<213> ORGANISM: Artificial Sequence
<220> FEATURE:
<223> OTHER INFORMATION: TFBS

<400> SEQUENCE: 282
actacagtcg aacgtaatta t 21

<210> SEQ ID NO 283
<211> LENGTH: 19
<212> TYPE: DNA

<213> ORGANISM: Artificial Sequence
<220> FEATURE:
<223> OTHER INFORMATION: TFBS

<400> SEQUENCE: 283
tctttctaac aatacagat 19

<210> SEQ ID NO 284
<211> LENGTH: 13
<212> TYPE: DNA
<213> ORGANISM: Artificial Sequence
<220> FEATURE:
<223> OTHER INFORMATION: TFBS

<400> SEQUENCE: 284
ctgtattgtt aga 13

<210> SEQ ID NO 285
<211> LENGTH: 11
<212> TYPE: DNA
<213> ORGANISM: Artificial Sequence
<220> FEATURE:
<223> OTHER INFORMATION: TFBS

<400> SEQUENCE: 285
tgtattgtta g 11

<210> SEQ ID NO 286
<211> LENGTH: 15
<212> TYPE: DNA
<213> ORGANISM: Artificial Sequence
<220> FEATURE:
<223> OTHER INFORMATION: TFBS

<400> SEQUENCE: 286
gcggcgccgt aaaaa 15

<210> SEQ ID NO 287
<211> LENGTH: 15
<212> TYPE: DNA
<213> ORGANISM: Artificial Sequence
<220> FEATURE:
<223> OTHER INFORMATION: TFBS

<400> SEQUENCE: 287
acggcgccgc catat 15

<210> SEQ ID NO 288
<211> LENGTH: 9
<212> TYPE: DNA
<213> ORGANISM: Artificial Sequence
<220> FEATURE:
<223> OTHER INFORMATION: TFBS

<400> SEQUENCE: 288 aaccccact 9

<210> SEQ ID NO 289
<211> LENGTH: 15
<212> TYPE: DNA
<213> ORGANISM: Artificial Sequence
<220> FEATURE:
<223> OTHER INFORMATION: TFBS

<400> SEQUENCE: 289
cgtgtatagc aacag 15

<210> SEQ ID NO 290
<211> LENGTH: 13
<212> TYPE: DNA
<213> ORGANISM: Artificial Sequence
<220> FEATURE:
<223> OTHER INFORMATION: TFBS

<400> SEQUENCE: 290
tatacacgaa cca 13

<210> SEQ ID NO 291
<211> LENGTH: 15
<212> TYPE: DNA
<213> ORGANISM: Artificial Sequence
<220> FEATURE:
<223> OTHER INFORMATION: TFBS

<400> SEQUENCE: 291
ctgaagtcat cggtt 15

<210> SEQ ID NO 292
<211> LENGTH: 17
<212> TYPE: DNA
<213> ORGANISM: Artificial Sequence
<220> FEATURE:
<223> OTHER INFORMATION: TFBS

<400> SEQUENCE: 292
tcatcggtta acaatca 17

<210> SEQ ID NO 293
<211> LENGTH: 13
<212> TYPE: DNA
<213> ORGANISM: Artificial Sequence
<220> FEATURE:
<223> OTHER INFORMATION: TFBS

<400> SEQUENCE: 293
ttgattgtta acc 13

<210> SEQ ID NO 294
<211> LENGTH: 13
<212> TYPE: DNA
<213> ORGANISM: Artificial Sequence
<220> FEATURE:
<223> OTHER INFORMATION: TFBS

<400> SEQUENCE: 294
cttgattgtt aac 13

<210> SEQ ID NO 295
<211> LENGTH: 11
<212> TYPE: DNA
<213> ORGANISM: Artificial Sequence
<220> FEATURE:
<223> OTHER INFORMATION: TFBS

<400> SEQUENCE: 295
ttgattgtta a 11

<210> SEQ ID NO 296
<211> LENGTH: 33
<212> TYPE: DNA
<213> ORGANISM: Artificial Sequence
<220> FEATURE:

<223> OTHER INFORMATION: TFBS

<400> SEQUENCE: 296
aacacctact gaatatggaa aggagcattc aga 33

<210> SEQ ID NO 297
<211> LENGTH: 13
<212> TYPE: DNA
<213> ORGANISM: Artificial Sequence
<220> FEATURE:
<223> OTHER INFORMATION: TFBS

<400> SEQUENCE: 297
gcagtgcatg caa 13

<210> SEQ ID NO 298
<211> LENGTH: 17
<212> TYPE: DNA
<213> ORGANISM: Artificial Sequence
<220> FEATURE:
<223> OTHER INFORMATION: TFBS

<400> SEQUENCE: 298
cactgcggaa gaattag 17

<210> SEQ ID NO 299
<211> LENGTH: 15
<212> TYPE: DNA
<213> ORGANISM: Artificial Sequence
<220> FEATURE:
<223> OTHER INFORMATION: TFBS

<400> SEQUENCE: 299
ctaattcttc cgcag 15

<210> SEQ ID NO 300
<211> LENGTH: 21
<212> TYPE: DNA
<213> ORGANISM: Artificial Sequence
<220> FEATURE:
<223> OTHER INFORMATION: TFBS

<400> SEQUENCE: 300
tagccaatag cgcgtttcat a 21

<210> SEQ ID NO 301
<211> LENGTH: 13
<212> TYPE: DNA
<213> ORGANISM: Artificial Sequence
<220> FEATURE:
<223> OTHER INFORMATION: TFBS

<400> SEQUENCE: 301
gaaacgcgct att 13

<210> SEQ ID NO 302
<211> LENGTH: 13
<212> TYPE: DNA
<213> ORGANISM: Artificial Sequence
<220> FEATURE:
<223> OTHER INFORMATION: TFBS

<400> SEQUENCE: 302
atagcgcgtt tca 13

<210> SEQ ID NO 303
<211> LENGTH: 9
<212> TYPE: DNA
<213> ORGANISM: Artificial Sequence
<220> FEATURE:
<223> OTHER INFORMATION: TFBS

<400> SEQUENCE: 303 catatgcgc 9

<210> SEQ ID NO 304
<211> LENGTH: 13
<212> TYPE: DNA
<213> ORGANISM: Artificial Sequence
<220> FEATURE:
<223> OTHER INFORMATION: TFBS

<400> SEQUENCE: 304
catatgcgct ttt 13

<210> SEQ ID NO 305
<211> LENGTH: 13
<212> TYPE: DNA
<213> ORGANISM: Artificial Sequence
<220> FEATURE:
<223> OTHER INFORMATION: TFBS

<400> SEQUENCE: 305
cttttacccc ctc 13

<210> SEQ ID NO 306
<211> LENGTH: 19
<212> TYPE: DNA
<213> ORGANISM: Artificial Sequence
<220> FEATURE:
<223> OTHER INFORMATION: TFBS

<400> SEQUENCE: 306
ttgacaaaag agggggtaa 19

<210> SEQ ID NO 307
<211> LENGTH: 15
<212> TYPE: DNA
<213> ORGANISM: Artificial Sequence
<220> FEATURE:
<223> OTHER INFORMATION: TFBS

<400> SEQUENCE: 307
caaaagaggg ggtaa 15

<210> SEQ ID NO 308
<211> LENGTH: 21
<212> TYPE: DNA
<213> ORGANISM: Artificial Sequence
<220> FEATURE:
<223> OTHER INFORMATION: TFBS

<400> SEQUENCE: 308
taccccctct tttgtcaagc g 21

<210> SEQ ID NO 309
<211> LENGTH: 13
<212> TYPE: DNA
<213> ORGANISM: Artificial Sequence
<220> FEATURE:
<223> OTHER INFORMATION: TFBS

<400> SEQUENCE: 309
ctcttttgtc aag 13

<210> SEQ ID NO 310
<211> LENGTH: 9
<212> TYPE: DNA
<213> ORGANISM: Artificial Sequence
<220> FEATURE:
<223> OTHER INFORMATION: TFBS

<400> SEQUENCE: 310 attttgcgc 9

<210> SEQ ID NO 311
<211> LENGTH: 19
<212> TYPE: DNA
<213> ORGANISM: Artificial Sequence
<220> FEATURE:
<223> OTHER INFORMATION: TFBS

<400> SEQUENCE: 311
taagatttgg tgggggtgt 19

<210> SEQ ID NO 312
<211> LENGTH: 23
<212> TYPE: DNA
<213> ORGANISM: Artificial Sequence
<220> FEATURE:
<223> OTHER INFORMATION: TFBS

<400> SEQUENCE: 312
gctaacggct cacaccccca cca 23

<210> SEQ ID NO 313
<211> LENGTH: 15
<212> TYPE: DNA
<213> ORGANISM: Artificial Sequence
<220> FEATURE:
<223> OTHER INFORMATION: TFBS

<400> SEQUENCE: 313
cggctcacac cccca 15

<210> SEQ ID NO 314
<211> LENGTH: 17
<212> TYPE: DNA
<213> ORGANISM: Artificial Sequence
<220> FEATURE:
<223> OTHER INFORMATION: TFBS

<400> SEQUENCE: 314
ttgtacttca gctaacg 17

<210> SEQ ID NO 315
<211> LENGTH: 17
<212> TYPE: DNA
<213> ORGANISM: Artificial Sequence
<220> FEATURE:
<223> OTHER INFORMATION: TFBS

<400> SEQUENCE: 315
tgcagttttt tcaggga 17

<210> SEQ ID NO 316
<211> LENGTH: 17

<212> TYPE: DNA
<213> ORGANISM: Artificial Sequence
<220> FEATURE:
<223> OTHER INFORMATION: TFBS

<400> SEQUENCE: 316
atatcaggaa aaacata 17

<210> SEQ ID NO 317
<211> LENGTH: 15
<212> TYPE: DNA
<213> ORGANISM: Artificial Sequence
<220> FEATURE:
<223> OTHER INFORMATION: TFBS

<400> SEQUENCE: 317
tcctgatatg catca 15

<210> SEQ ID NO 318
<211> LENGTH: 13
<212> TYPE: DNA
<213> ORGANISM: Artificial Sequence
<220> FEATURE:
<223> OTHER INFORMATION: TFBS

<400> SEQUENCE: 318
gatatgcatc aaa 13

<210> SEQ ID NO 319
<211> LENGTH: 13
<212> TYPE: DNA
<213> ORGANISM: Artificial Sequence
<220> FEATURE:
<223> OTHER INFORMATION: TFBS

<400> SEQUENCE: 319
ttttgatgca tat 13

<210> SEQ ID NO 320
<211> LENGTH: 21
<212> TYPE: DNA
<213> ORGANISM: Artificial Sequence
<220> FEATURE:
<223> OTHER INFORMATION: TFBS

<400> SEQUENCE: 320
taaaacctga atctccgcta t 21

<210> SEQ ID NO 321
<211> LENGTH: 17
<212> TYPE: DNA
<213> ORGANISM: Artificial Sequence
<220> FEATURE:
<223> OTHER INFORMATION: TFBS

<400> SEQUENCE: 321
aatagcggag attcagg 17

<210> SEQ ID NO 322
<211> LENGTH: 11
<212> TYPE: DNA
<213> ORGANISM: Artificial Sequence
<220> FEATURE:
<223> OTHER INFORMATION: TFBS

<400> SEQUENCE: 322
tagcggagat t 11

<210> SEQ ID NO 323
<211> LENGTH: 15
<212> TYPE: DNA
<213> ORGANISM: Artificial Sequence
<220> FEATURE:
<223> OTHER INFORMATION: TFBS

<400> SEQUENCE: 323
ttgtcacgaa aacgg 15

<210> SEQ ID NO 324
<211> LENGTH: 13
<212> TYPE: DNA
<213> ORGANISM: Artificial Sequence
<220> FEATURE:
<223> OTHER INFORMATION: TFBS

<400> SEQUENCE: 324
ttgtcacgaa aac 13

<210> SEQ ID NO 325
<211> LENGTH: 21
<212> TYPE: DNA
<213> ORGANISM: Artificial Sequence
<220> FEATURE:
<223> OTHER INFORMATION: TFBS

<400> SEQUENCE: 325
tggaaattaa tttgtcacga a 21

<210> SEQ ID NO 326
<211> LENGTH: 17
<212> TYPE: DNA
<213> ORGANISM: Artificial Sequence
<220> FEATURE:
<223> OTHER INFORMATION: TFBS

<400> SEQUENCE: 326
aattaatttg tcacgaa 17

<210> SEQ ID NO 327
<211> LENGTH: 13
<212> TYPE: DNA
<213> ORGANISM: Artificial Sequence
<220> FEATURE:
<223> OTHER INFORMATION: TFBS

<400> SEQUENCE: 327
ttaatttgtc acg 13

<210> SEQ ID NO 328
<211> LENGTH: 15
<212> TYPE: DNA
<213> ORGANISM: Artificial Sequence
<220> FEATURE:
<223> OTHER INFORMATION: TFBS

<400> SEQUENCE: 328
aaattaattt gtcac 15

<210> SEQ ID NO 329
<211> LENGTH: 15
<212> TYPE: DNA
<213> ORGANISM: Artificial Sequence

<220> FEATURE:
<223> OTHER INFORMATION: TFBS

<400> SEQUENCE: 329
tgacaaatta atttc 15

<210> SEQ ID NO 330
<211> LENGTH: 21
<212> TYPE: DNA
<213> ORGANISM: Artificial Sequence
<220> FEATURE:
<223> OTHER INFORMATION: TFBS

<400> SEQUENCE: 330
tgacaaatta atttccaacg g 21

<210> SEQ ID NO 331
<211> LENGTH: 17
<212> TYPE: DNA
<213> ORGANISM: Artificial Sequence
<220> FEATURE:
<223> OTHER INFORMATION: TFBS

<400> SEQUENCE: 331
cccgttggaa attaatt 17

<210> SEQ ID NO 332
<211> LENGTH: 17
<212> TYPE: DNA
<213> ORGANISM: Artificial Sequence
<220> FEATURE:
<223> OTHER INFORMATION: TFBS

<400> SEQUENCE: 332
tccggacaag accccgt 17

<210> SEQ ID NO 333
<211> LENGTH: 17
<212> TYPE: DNA
<213> ORGANISM: Artificial Sequence
<220> FEATURE:
<223> OTHER INFORMATION: TFBS

<400> SEQUENCE: 333
ttatccggac aagaccc 17

<210> SEQ ID NO 334
<211> LENGTH: 17
<212> TYPE: DNA
<213> ORGANISM: Artificial Sequence
<220> FEATURE:
<223> OTHER INFORMATION: TFBS

<400> SEQUENCE: 334
ttgtccggat aagagaa 17

<210> SEQ ID NO 335
<211> LENGTH: 11
<212> TYPE: DNA
<213> ORGANISM: Artificial Sequence
<220> FEATURE:
<223> OTHER INFORMATION: TFBS

<400> SEQUENCE: 335
gtccggataa g 11

<210> SEQ ID NO 336
<211> LENGTH: 15
<212> TYPE: DNA
<213> ORGANISM: Artificial Sequence
<220> FEATURE:
<223> OTHER INFORMATION: TFBS

<400> SEQUENCE: 336
tccggataag agaat 15

<210> SEQ ID NO 337
<211> LENGTH: 13
<212> TYPE: DNA
<213> ORGANISM: Artificial Sequence
<220> FEATURE:
<223> OTHER INFORMATION: TFBS

<400> SEQUENCE: 337
taatcaaaca aaa 13

<210> SEQ ID NO 338
<211> LENGTH: 15
<212> TYPE: DNA
<213> ORGANISM: Artificial Sequence
<220> FEATURE:
<223> OTHER INFORMATION: TFBS

<400> SEQUENCE: 338
aacggataat caaac 15

<210> SEQ ID NO 339
<211> LENGTH: 17
<212> TYPE: DNA
<213> ORGANISM: Artificial Sequence
<220> FEATURE:
<223> OTHER INFORMATION: TFBS

<400> SEQUENCE: 339
ccgaacggat aatcaaa 17

<210> SEQ ID NO 340
<211> LENGTH: 21
<212> TYPE: DNA
<213> ORGANISM: Artificial Sequence
<220> FEATURE:
<223> OTHER INFORMATION: TFBS

<400> SEQUENCE: 340
ttatccgaac ggataatcaa a 21

<210> SEQ ID NO 341
<211> LENGTH: 25
<212> TYPE: DNA
<213> ORGANISM: Artificial Sequence
<220> FEATURE:
<223> OTHER INFORMATION: TFBS

<400> SEQUENCE: 341
cgtccattta tccgaacgga taatc 25

<210> SEQ ID NO 342
<211> LENGTH: 17
<212> TYPE: DNA
<213> ORGANISM: Artificial Sequence
<220> FEATURE:
<223> OTHER INFORMATION: TFBS

<400> SEQUENCE: 342
ccgttcggat aaatgga 17

<210> SEQ ID NO 343
<211> LENGTH: 25
<212> TYPE: DNA
<213> ORGANISM: Artificial Sequence
<220> FEATURE:
<223> OTHER INFORMATION: TFBS

<400> SEQUENCE: 343
agcaggcgtc catttatccg aacgg 25

<210> SEQ ID NO 344
<211> LENGTH: 15
<212> TYPE: DNA
<213> ORGANISM: Artificial Sequence
<220> FEATURE:
<223> OTHER INFORMATION: TFBS

<400> SEQUENCE: 344
tccatttatc cgaac 15

<210> SEQ ID NO 345
<211> LENGTH: 11
<212> TYPE: DNA
<213> ORGANISM: Artificial Sequence
<220> FEATURE:
<223> OTHER INFORMATION: TFBS

<400> SEQUENCE: 345
gttcggataa a 11

<210> SEQ ID NO 346
<211> LENGTH: 25
<212> TYPE: DNA
<213> ORGANISM: Artificial Sequence
<220> FEATURE:
<223> OTHER INFORMATION: TFBS

<400> SEQUENCE: 346
gttcggataa atggacgcct gctcc 25

<210> SEQ ID NO 347
<211> LENGTH: 17
<212> TYPE: DNA
<213> ORGANISM: Artificial Sequence
<220> FEATURE:
<223> OTHER INFORMATION: TFBS

<400> SEQUENCE: 347
taaccggaaa aatatgg 17

<210> SEQ ID NO 348
<211> LENGTH: 15
<212> TYPE: DNA
<213> ORGANISM: Artificial Sequence
<220> FEATURE:
<223> OTHER INFORMATION: TFBS

<400> SEQUENCE: 348
catatttttc cggtt 15

<210> SEQ ID NO 349

<211> LENGTH: 17
<212> TYPE: DNA
<213> ORGANISM: Artificial Sequence
<220> FEATURE:
<223> OTHER INFORMATION: TFBS

<400> SEQUENCE: 349
ataaccggaa aaatatg 17

<210> SEQ ID NO 350
<211> LENGTH: 21
<212> TYPE: DNA
<213> ORGANISM: Artificial Sequence
<220> FEATURE:
<223> OTHER INFORMATION: TFBS

<400> SEQUENCE: 350
aggtggggta ataaccggaa a 21

<210> SEQ ID NO 351
<211> LENGTH: 13
<212> TYPE: DNA
<213> ORGANISM: Artificial Sequence
<220> FEATURE:
<223> OTHER INFORMATION: TFBS

<400> SEQUENCE: 351
ttattacccc acc 13

<210> SEQ ID NO 352
<211> LENGTH: 17
<212> TYPE: DNA
<213> ORGANISM: Artificial Sequence
<220> FEATURE:
<223> OTHER INFORMATION: TFBS

<400> SEQUENCE: 352
cttccaggtg gggtaat 17

<210> SEQ ID NO 353
<211> LENGTH: 19
<212> TYPE: DNA
<213> ORGANISM: Artificial Sequence
<220> FEATURE:
<223> OTHER INFORMATION: TFBS

<400> SEQUENCE: 353
cacttccagg tggggtaat 19

<210> SEQ ID NO 354
<211> LENGTH: 9
<212> TYPE: DNA
<213> ORGANISM: Artificial Sequence
<220> FEATURE:
<223> OTHER INFORMATION: TFBS

<400> SEQUENCE: 354 taccccacc 9

<210> SEQ ID NO 355
<211> LENGTH: 17
<212> TYPE: DNA
<213> ORGANISM: Artificial Sequence
<220> FEATURE:
<223> OTHER INFORMATION: TFBS

<400> SEQUENCE: 355
atccccggaa aattctg 17

<210> SEQ ID NO 356
<211> LENGTH: 19
<212> TYPE: DNA
<213> ORGANISM: Artificial Sequence
<220> FEATURE:
<223> OTHER INFORMATION: TFBS

<400> SEQUENCE: 356
cagaattttc cggggatta 19

<210> SEQ ID NO 357
<211> LENGTH: 21
<212> TYPE: DNA
<213> ORGANISM: Artificial Sequence
<220> FEATURE:
<223> OTHER INFORMATION: TFBS

<400> SEQUENCE: 357
attatccgta atccccggaa a 21

<210> SEQ ID NO 358
<211> LENGTH: 17
<212> TYPE: DNA
<213> ORGANISM: Artificial Sequence
<220> FEATURE:
<223> OTHER INFORMATION: TFBS

<400> SEQUENCE: 358
atccgtaatc cccggaa 17

<210> SEQ ID NO 359
<211> LENGTH: 9
<212> TYPE: DNA
<213> ORGANISM: Artificial Sequence
<220> FEATURE:
<223> OTHER INFORMATION: TFBS

<400> SEQUENCE: 359 tccccggaa 9

<210> SEQ ID NO 360
<211> LENGTH: 17
<212> TYPE: DNA
<213> ORGANISM: Artificial Sequence
<220> FEATURE:
<223> OTHER INFORMATION: TFBS

<400> SEQUENCE: 360
tccggggatt acggata 17

<210> SEQ ID NO 361
<211> LENGTH: 9
<212> TYPE: DNA
<213> ORGANISM: Artificial Sequence
<220> FEATURE:
<223> OTHER INFORMATION: TFBS

<400> SEQUENCE: 361 tccggggat 9

<210> SEQ ID NO 362
<211> LENGTH: 15
<212> TYPE: DNA

<213> ORGANISM: Artificial Sequence
<220> FEATURE:
<223> OTHER INFORMATION: TFBS

<400> SEQUENCE: 362
ccggggatta cggat 15

<210> SEQ ID NO 363
<211> LENGTH: 21
<212> TYPE: DNA
<213> ORGANISM: Artificial Sequence
<220> FEATURE:
<223> OTHER INFORMATION: TFBS

<400> SEQUENCE: 363
ggggattacg gataatacgg t 21

<210> SEQ ID NO 364
<211> LENGTH: 17
<212> TYPE: DNA
<213> ORGANISM: Artificial Sequence
<220> FEATURE:
<223> OTHER INFORMATION: TFBS

<400> SEQUENCE: 364
gattacggat aatacgg 17

<210> SEQ ID NO 365
<211> LENGTH: 15
<212> TYPE: DNA
<213> ORGANISM: Artificial Sequence
<220> FEATURE:
<223> OTHER INFORMATION: TFBS

<400> SEQUENCE: 365
acggataata cggtg 15

<210> SEQ ID NO 366
<211> LENGTH: 21
<212> TYPE: DNA
<213> ORGANISM: Artificial Sequence
<220> FEATURE:
<223> OTHER INFORMATION: TFBS

<400> SEQUENCE: 366
tggtctggat taattaatac g 21

<210> SEQ ID NO 367
<211> LENGTH: 21
<212> TYPE: DNA
<213> ORGANISM: Artificial Sequence
<220> FEATURE:
<223> OTHER INFORMATION: TFBS

<400> SEQUENCE: 367
cttggcgtat taattaatcc a 21

<210> SEQ ID NO 368
<211> LENGTH: 15
<212> TYPE: DNA
<213> ORGANISM: Artificial Sequence
<220> FEATURE:
<223> OTHER INFORMATION: TFBS

<400> SEQUENCE: 368
gtattaatta atcca 15

<210> SEQ ID NO 369
<211> LENGTH: 15
<212> TYPE: DNA
<213> ORGANISM: Artificial Sequence
<220> FEATURE:
<223> OTHER INFORMATION: TFBS

<400> SEQUENCE: 369
ggattaatta atacg 15

<210> SEQ ID NO 370
<211> LENGTH: 19
<212> TYPE: DNA
<213> ORGANISM: Artificial Sequence
<220> FEATURE:
<223> OTHER INFORMATION: TFBS

<400> SEQUENCE: 370
ggattaatta atacgccaa 19

<210> SEQ ID NO 371
<211> LENGTH: 17
<212> TYPE: DNA
<213> ORGANISM: Artificial Sequence
<220> FEATURE:
<223> OTHER INFORMATION: TFBS

<400> SEQUENCE: 371
atacgccaag tcttaca 17

<210> SEQ ID NO 372
<211> LENGTH: 13
<212> TYPE: DNA
<213> ORGANISM: Artificial Sequence
<220> FEATURE:
<223> OTHER INFORMATION: TFBS

<400> SEQUENCE: 372
gactgcaaca aaa 13

<210> SEQ ID NO 373
<211> LENGTH: 17
<212> TYPE: DNA
<213> ORGANISM: Artificial Sequence
<220> FEATURE:
<223> OTHER INFORMATION: TFBS

<400> SEQUENCE: 373
gcaataataa acaagat 17

<210> SEQ ID NO 374
<211> LENGTH: 13
<212> TYPE: DNA
<213> ORGANISM: Artificial Sequence
<220> FEATURE:
<223> OTHER INFORMATION: TFBS

<400> SEQUENCE: 374
ctaatccaat aaa 13

<210> SEQ ID NO 375
<211> LENGTH: 25
<212> TYPE: DNA
<213> ORGANISM: Artificial Sequence
<220> FEATURE:

-continued

<223> OTHER INFORMATION: TFBS

<400> SEQUENCE: 375
cggggtcaag ctgcaactaa tccaa 25

<210> SEQ ID NO 376
<211> LENGTH: 17
<212> TYPE: DNA
<213> ORGANISM: Artificial Sequence
<220> FEATURE:
<223> OTHER INFORMATION: TFBS

<400> SEQUENCE: 376
gcagcttgac cccgcca 17

<210> SEQ ID NO 377
<211> LENGTH: 19
<212> TYPE: DNA
<213> ORGANISM: Artificial Sequence
<220> FEATURE:
<223> OTHER INFORMATION: TFBS

<400> SEQUENCE: 377
ctagctatgg cggggtcaa 19

<210> SEQ ID NO 378
<211> LENGTH: 23
<212> TYPE: DNA
<213> ORGANISM: Artificial Sequence
<220> FEATURE:
<223> OTHER INFORMATION: TFBS

<400> SEQUENCE: 378
tgcatcatct aacacccata gca 23

<210> SEQ ID NO 379
<211> LENGTH: 13
<212> TYPE: DNA
<213> ORGANISM: Artificial Sequence
<220> FEATURE:
<223> OTHER INFORMATION: TFBS

<400> SEQUENCE: 379
caagtgcatc atc 13

<210> SEQ ID NO 380
<211> LENGTH: 17
<212> TYPE: DNA
<213> ORGANISM: Artificial Sequence
<220> FEATURE:
<223> OTHER INFORMATION: TFBS

<400> SEQUENCE: 380
gagtataaaa gatcctt 17

<210> SEQ ID NO 381
<211> LENGTH: 17
<212> TYPE: DNA
<213> ORGANISM: Artificial Sequence
<220> FEATURE:
<223> OTHER INFORMATION: TFBS

<400> SEQUENCE: 381
aagggtggaa ttttaag 17

<210> SEQ ID NO 382
<211> LENGTH: 34
<212> TYPE: DNA
<213> ORGANISM: Artificial Sequence
<220> FEATURE:
<223> OTHER INFORMATION: Primer

<400> SEQUENCE: 382
gatagggccc caaacatttg ctccccctag tctc 34

<210> SEQ ID NO 383
<211> LENGTH: 39
<212> TYPE: DNA
<213> ORGANISM: Artificial Sequence
<220> FEATURE:
<223> OTHER INFORMATION: Primer

<400> SEQUENCE: 383
gatacctgca ggaagggtgg aattttaagg atcttttat 39

<210> SEQ ID NO 384
<211> LENGTH: 39
<212> TYPE: DNA
<213> ORGANISM: Artificial Sequence
<220> FEATURE:
<223> OTHER INFORMATION: Primer

<400> SEQUENCE: 384
gatagggccc ggaatctgta ttgttagaaa gaacgagag 39

<210> SEQ ID NO 385
<211> LENGTH: 36
<212> TYPE: DNA
<213> ORGANISM: Artificial Sequence
<220> FEATURE:
<223> OTHER INFORMATION: Primer

<400> SEQUENCE: 385
gatagggccc ccatattcag taggtgtttc ttgcac 36

<210> SEQ ID NO 386
<211> LENGTH: 36
<212> TYPE: DNA
<213> ORGANISM: Artificial Sequence
<220> FEATURE:
<223> OTHER INFORMATION: Primer

<400> SEQUENCE: 386
gatagggccc ctgcagatag acttcaagat ctcagg 36

<210> SEQ ID NO 387
<211> LENGTH: 32
<212> TYPE: DNA
<213> ORGANISM: Artificial Sequence
<220> FEATURE:
<223> OTHER INFORMATION: Primer

<400> SEQUENCE: 387
gatagggccc gaccccgttt tcgtgacaaa tt 32

<210> SEQ ID NO 388
<211> LENGTH: 37
<212> TYPE: DNA
<213> ORGANISM: Artificial Sequence
<220> FEATURE:
<223> OTHER INFORMATION: Primer

<400> SEQUENCE: 388
gatagggccc ccggataaga gaattttgtt tgattat 37

<210> SEQ ID NO 389
<211> LENGTH: 31
<212> TYPE: DNA
<213> ORGANISM: Artificial Sequence
<220> FEATURE:
<223> OTHER INFORMATION: Primer

<400> SEQUENCE: 389
gatagggccc gcctgctcca tatttttccg g 31

<210> SEQ ID NO 390
<211> LENGTH: 34
<212> TYPE: DNA
<213> ORGANISM: Artificial Sequence
<220> FEATURE:
<223> OTHER INFORMATION: Primer

<400> SEQUENCE: 390
gatagggccc cggtggtctg gattaattaa tacg 34

<210> SEQ ID NO 391
<211> LENGTH: 34
<212> TYPE: DNA
<213> ORGANISM: Artificial Sequence
<220> FEATURE:
<223> OTHER INFORMATION: Primer

<400> SEQUENCE: 391
gatagggccc gtgttagatg atgcacttgg atgc 34

<210> SEQ ID NO 392
<211> LENGTH: 44
<212> TYPE: DNA
<213> ORGANISM: Artificial Sequence
<220> FEATURE:
<223> OTHER INFORMATION: Primer

<400> SEQUENCE: 392
gaaaacagct tgaactttca aaggttctgt tgctatacac gaac 44

<210> SEQ ID NO 393
<211> LENGTH: 52
<212> TYPE: DNA
<213> ORGANISM: Artificial Sequence
<220> FEATURE:
<223> OTHER INFORMATION: Primer

<400> SEQUENCE: 393
gttcgtgtat agcaacagaa cctttgaaag ttcaagctgt tttcacacgg cc 52

<210> SEQ ID NO 394
<211> LENGTH: 47
<212> TYPE: DNA
<213> ORGANISM: Artificial Sequence
<220> FEATURE:
<223> OTHER INFORMATION: Primer

<400> SEQUENCE: 394
gtaggtgttt cttgcacttt tgcatgccaa tagcgcgttt catatgc 47

<210> SEQ ID NO 395
<211> LENGTH: 47

-continued

<212> TYPE: DNA
<213> ORGANISM: Artificial Sequence
<220> FEATURE:
<223> OTHER INFORMATION: Primer

<400> SEQUENCE: 395
gcatatgaaa cgcgctattg gcatgcaaaa gtgcaagaaa cacctac 47

<210> SEQ ID NO 396
<211> LENGTH: 41
<212> TYPE: DNA
<213> ORGANISM: Artificial Sequence
<220> FEATURE:
<223> OTHER INFORMATION: Primer

<400> SEQUENCE: 396
cgcgtttcat atgcgcttgc gcaaaatgcc tgtaagattt g 41

<210> SEQ ID NO 397
<211> LENGTH: 41
<212> TYPE: DNA
<213> ORGANISM: Artificial Sequence
<220> FEATURE:
<223> OTHER INFORMATION: Primer

<400> SEQUENCE: 397
caaatcttac aggcattttg cgcaagcgca tatgaaacgc g 41

<210> SEQ ID NO 398
<211> LENGTH: 43
<212> TYPE: DNA
<213> ORGANISM: Artificial Sequence
<220> FEATURE:
<223> OTHER INFORMATION: Primer

<400> SEQUENCE: 398
gtcaagcgca aaatgcctgg agccgttagc tgaagtacaa cag 43

<210> SEQ ID NO 399
<211> LENGTH: 43
<212> TYPE: DNA
<213> ORGANISM: Artificial Sequence
<220> FEATURE:
<223> OTHER INFORMATION: Primer

<400> SEQUENCE: 399
ctgttgtact tcagctaacg gctccaggca ttttgcgctt gac 43

<210> SEQ ID NO 400
<211> LENGTH: 58
<212> TYPE: DNA
<213> ORGANISM: Artificial Sequence
<220> FEATURE:
<223> OTHER INFORMATION: Primer

<400> SEQUENCE: 400
gggattccca ctatttggta ttctgagcat caaaactcta atctaaaacc tgaatctc 58

<210> SEQ ID NO 401
<211> LENGTH: 58
<212> TYPE: DNA
<213> ORGANISM: Artificial Sequence
<220> FEATURE:
<223> OTHER INFORMATION: Primer

<400> SEQUENCE: 401
gagattcagg ttttagatta gagttttgat gctcagaata ccaaatagtg ggaatccc 58

<210> SEQ ID NO 402
<211> LENGTH: 49
<212> TYPE: DNA
<213> ORGANISM: Artificial Sequence
<220> FEATURE:
<223> OTHER INFORMATION: Primer

<400> SEQUENCE: 402
gttttcgtga caaattaatt tccaacgttt tgtttgatta tccgttcgg 49

<210> SEQ ID NO 403
<211> LENGTH: 49
<212> TYPE: DNA
<213> ORGANISM: Artificial Sequence
<220> FEATURE:
<223> OTHER INFORMATION: Primer

<400> SEQUENCE: 403
ccgaacggat aatcaaacaa aacgttggaa attaatttgt cacgaaaac 49

<210> SEQ ID NO 404
<211> LENGTH: 38
<212> TYPE: DNA
<213> ORGANISM: Artificial Sequence
<220> FEATURE:
<223> OTHER INFORMATION: Primer

<400> SEQUENCE: 404
ccggataaga gaattttgtt cggataaatg gacgcctg 38

<210> SEQ ID NO 405
<211> LENGTH: 46
<212> TYPE: DNA
<213> ORGANISM: Artificial Sequence
<220> FEATURE:
<223> OTHER INFORMATION: Primer

<400> SEQUENCE: 405
caggcgtcca tttatccgaa caaaattctc ttatccggac aagacc 46

<210> SEQ ID NO 406
<211> LENGTH: 46
<212> TYPE: DNA
<213> ORGANISM: Artificial Sequence
<220> FEATURE:
<223> OTHER INFORMATION: Primer

<400> SEQUENCE: 406
gaattttgtt tgattatccg ttcggcgcct gctccatatt tttccg 46

<210> SEQ ID NO 407
<211> LENGTH: 46
<212> TYPE: DNA
<213> ORGANISM: Artificial Sequence
<220> FEATURE:
<223> OTHER INFORMATION: Primer

<400> SEQUENCE: 407
cggaaaaata tggagcaggc gccgaacgga taatcaaaca aaattc 46

<210> SEQ ID NO 408
<211> LENGTH: 42
<212> TYPE: DNA
<213> ORGANISM: Artificial Sequence
<220> FEATURE:
<223> OTHER INFORMATION: Primer

<400> SEQUENCE: 408
cggataaatg gacgcctgct cattacccca cctggaagtg cc 42

<210> SEQ ID NO 409
<211> LENGTH: 42
<212> TYPE: DNA
<213> ORGANISM: Artificial Sequence
<220> FEATURE:
<223> OTHER INFORMATION: Primer

<400> SEQUENCE: 409
ggcacttcca ggtggggtaa tgagcaggcg tccatttatc cg 42

<210> SEQ ID NO 410
<211> LENGTH: 39
<212> TYPE: DNA
<213> ORGANISM: Artificial Sequence
<220> FEATURE:
<223> OTHER INFORMATION: Primer

<400> SEQUENCE: 410
gcctgctcca tatttttccg gttatcccag aattttccg 39

<210> SEQ ID NO 411
<211> LENGTH: 39
<212> TYPE: DNA
<213> ORGANISM: Artificial Sequence
<220> FEATURE:
<223> OTHER INFORMATION: Primer

<400> SEQUENCE: 411
cggaaaattc tgggataacc ggaaaaatat ggagcaggc 39

<210> SEQ ID NO 412
<211> LENGTH: 48
<212> TYPE: DNA
<213> ORGANISM: Artificial Sequence
<220> FEATURE:
<223> OTHER INFORMATION: Primer

<400> SEQUENCE: 412
tattacccca cctggaagtg cccggataat acggtggtct ggattaat 48

<210> SEQ ID NO 413
<211> LENGTH: 48
<212> TYPE: DNA
<213> ORGANISM: Artificial Sequence
<220> FEATURE:
<223> OTHER INFORMATION: Primer

<400> SEQUENCE: 413
attaatccag accaccgtat tatccgggca cttccaggtg gggtaata 48

<210> SEQ ID NO 414
<211> LENGTH: 48
<212> TYPE: DNA
<213> ORGANISM: Artificial Sequence
<220> FEATURE:
<223> OTHER INFORMATION: Primer

<400> SEQUENCE: 414
ccagaatttt ccggggatta tggtctggat taattaatac gccaagtc 48

<210> SEQ ID NO 415
<211> LENGTH: 48
<212> TYPE: DNA
<213> ORGANISM: Artificial Sequence
<220> FEATURE:
<223> OTHER INFORMATION: Primer

<400> SEQUENCE: 415
gacttggcgt attaattaat ccagaccata atccccggaa aattctgg 48

<210> SEQ ID NO 416
<211> LENGTH: 51
<212> TYPE: DNA
<213> ORGANISM: Artificial Sequence
<220> FEATURE:
<223> OTHER INFORMATION: Primer

<400> SEQUENCE: 416
caaaactcta atctaaaacc tgaatctccg cgatgacccc gttttcgtga c 51

<210> SEQ ID NO 417
<211> LENGTH: 51
<212> TYPE: DNA
<213> ORGANISM: Artificial Sequence
<220> FEATURE:
<223> OTHER INFORMATION: Primer

<400> SEQUENCE: 417
gtcacgaaaa cggggtcatc gcggagattc aggttttaga ttagagtttt g 51

<210> SEQ ID NO 418
<211> LENGTH: 41
<212> TYPE: DNA
<213> ORGANISM: Artificial Sequence
<220> FEATURE:
<223> OTHER INFORMATION: Primer

<400> SEQUENCE: 418
cctgaatctc cgcttttttt tttttttttt tgatgacccc g 41

<210> SEQ ID NO 419
<211> LENGTH: 41
<212> TYPE: DNA
<213> ORGANISM: Artificial Sequence
<220> FEATURE:
<223> OTHER INFORMATION: Primer

<400> SEQUENCE: 419
cggggtcatc aaaaaaaaaa aaaaaaaagc ggagattcag g 41

<210> SEQ ID NO 420
<211> LENGTH: 43
<212> TYPE: DNA
<213> ORGANISM: Artificial Sequence
<220> FEATURE:
<223> OTHER INFORMATION: Primer

<400> SEQUENCE: 420
cctgaatctc cgcttttttt tttttttttt tttgatgacc ccg 43

<210> SEQ ID NO 421
<211> LENGTH: 43
<212> TYPE: DNA
<213> ORGANISM: Artificial Sequence -continued

```
<220> FEATURE:
<223> OTHER INFORMATION: Primer

<400> SEQUENCE: 421

cggggtcatc aaaaaaaaaa aaaaaaaaaa gcggagattc agg                         43


<210> SEQ ID NO 422
<211> LENGTH: 45
<212> TYPE: DNA
<213> ORGANISM: Artificial Sequence
<220> FEATURE:
<223> OTHER INFORMATION: Primer

<400> SEQUENCE: 422

cctgaatctc cgcttttttt tttttttttt tttttgatga ccccg                       45


<210> SEQ ID NO 423
<211> LENGTH: 45
<212> TYPE: DNA
<213> ORGANISM: Artificial Sequence
<220> FEATURE:
<223> OTHER INFORMATION: Primer

<400> SEQUENCE: 423

cggggtcatc aaaaaaaaaa aaaaaaaaaa aagcggagat tcagg                       45


<210> SEQ ID NO 424
<211> LENGTH: 37
<212> TYPE: DNA
<213> ORGANISM: Artificial Sequence
<220> FEATURE:
<223> OTHER INFORMATION: Primer

<400> SEQUENCE: 424

gatactgcag ctcagggatt cccactattt ggtattc                                37


<210> SEQ ID NO 425
<211> LENGTH: 33
<212> TYPE: DNA
<213> ORGANISM: Artificial Sequence
<220> FEATURE:
<223> OTHER INFORMATION: Primer

<400> SEQUENCE: 425

gatagatctc gtattaatta atccagacca ccg                                    33


<210> SEQ ID NO 426
<211> LENGTH: 36
<212> TYPE: DNA
<213> ORGANISM: Artificial Sequence
<220> FEATURE:
<223> OTHER INFORMATION: Primer

<400> SEQUENCE: 426

gatagatcta agggtggaat tttaaggatc ttttat                                 36
```